(12) United States Patent
Stierli et al.

(10) Patent No.: US 10,899,724 B2
(45) Date of Patent: Jan. 26, 2021

(54) MICROBIOCIDAL OXADIAZOLE DERIVATIVES

(71) Applicant: SYNGENTA PARTICIPATIONS AG, Basel (CH)

(72) Inventors: Daniel Stierli, Stein (CH); Thomas James Hoffman, Stein (CH); Renaud Beaudegnies, Stein (CH); Martin Pouliot, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 15/765,138

(22) PCT Filed: Sep. 29, 2016

(86) PCT No.: PCT/EP2016/073295
§ 371 (c)(1),
(2) Date: Mar. 30, 2018

(87) PCT Pub. No.: WO2017/055473
PCT Pub. Date: Apr. 6, 2017

(65) Prior Publication Data
US 2018/0273494 A1    Sep. 27, 2018

(30) Foreign Application Priority Data

Oct. 2, 2015 (EP) ..................... 15188238
Jan. 7, 2016 (EP) ..................... 16150491

(51) Int. Cl.
| | |
|---|---|
| *C07D 413/04* | (2006.01) |
| *C07D 413/12* | (2006.01) |
| *C07D 271/06* | (2006.01) |
| *C07D 417/12* | (2006.01) |
| *A01N 43/82* | (2006.01) |

(52) U.S. Cl.
CPC .......... *C07D 271/06* (2013.01); *A01N 43/82* (2013.01); *C07D 413/04* (2013.01); *C07D 413/12* (2013.01); *C07D 417/12* (2013.01)

(58) Field of Classification Search
CPC .. C07D 413/04; C07D 413/12; C07D 271/06; C07D 417/12; A01N 43/82
USPC ....... 548/131; 546/269.4; 544/238, 333, 405
See application file for complete search history.

(56) References Cited

U.S. PATENT DOCUMENTS

| | | | | |
|---|---|---|---|---|
| 9,278,910 | B2 * | 3/2016 | Boehm | C07C 255/57 |
| 9,700,543 | B2 * | 7/2017 | Boehm | C07C 255/57 |
| 2018/0368410 | A1 * | 12/2018 | Hoffman | A01N 43/82 |
| 2018/0370927 | A1 * | 12/2018 | Hoffman | A01N 43/82 |

FOREIGN PATENT DOCUMENTS

| | | |
|---|---|---|
| CN | 1927860 A | 3/2007 |
| EP | 0 276 432 A2 | 8/1988 |
| EP | 3 187 497 A1 | 5/2015 |
| EP | 3 165 093 A1 | 5/2017 |
| EP | 3 165 094 A1 | 5/2017 |
| JP | 2017-190296 A | 10/2017 |
| WO | 2003028729 A2 | 4/2003 |
| WO | 2008/037789 A1 | 4/2008 |
| WO | 2011/088181 A1 | 7/2011 |
| WO | 2011/088192 A1 | 7/2011 |
| WO | 2012/052490 A1 | 4/2012 |
| WO | 2013/006408 A1 | 1/2013 |
| WO | 2013/008162 A1 | 1/2013 |
| WO | 2013/009810 A1 | 1/2013 |
| WO | 2013/009827 A1 | 1/2013 |
| WO | 2013/009830 A1 | 1/2013 |
| WO | 2013/064079 A1 | 5/2013 |
| WO | 2013/066835 A2 | 5/2013 |
| WO | 2013/066839 A2 | 5/2013 |
| WO | 2013/080120 A1 | 6/2013 |
| WO | 2015/055706 A2 | 4/2015 |
| WO | 2015/185845 A1 | 12/2015 |
| WO | 2017/033946 A1 | 3/2017 |
| WO | 2017/076739 A1 | 5/2017 |
| WO | 2017/076740 A1 | 5/2017 |
| WO | 2017/076742 A1 | 5/2017 |
| WO | 2017/076757 A1 | 5/2017 |
| WO | 2017/076935 A1 | 5/2017 |
| WO | 2017/081309 A1 | 5/2017 |
| WO | 2017/081310 A1 | 5/2017 |
| WO | 2017/081311 A1 | 5/2017 |
| WO | 2017/081312 A1 | 5/2017 |
| WO | 2017/085098 A1 | 5/2017 |
| WO | 2017/085100 A1 | 5/2017 |
| WO | 2017/093019 A1 | 6/2017 |

(Continued)

OTHER PUBLICATIONS

CN1927860, machine translation of foreign patent CN1927860, 2007 (publication No. CN100556905).*

(Continued)

*Primary Examiner* — Sun Jae Yoo
(74) *Attorney, Agent, or Firm* — BakerHostetler; Toni-Junell Herbert

(57) ABSTRACT

Compounds of the formula (I) wherein the substituents are as defined in claim 1, useful as a pesticides, especially fungicides.

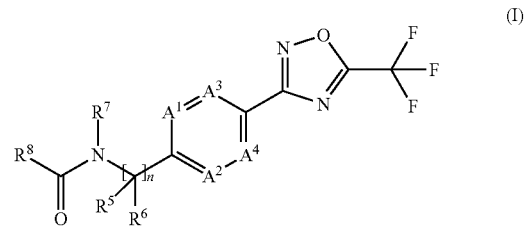

13 Claims, No Drawings

(56) References Cited

FOREIGN PATENT DOCUMENTS

| WO | 2017/110861 A1 | 6/2017 |
|---|---|---|
| WO | 2017/110862 A1 | 6/2017 |
| WO | 2017/110864 A1 | 6/2017 |
| WO | 2017/110865 A1 | 6/2017 |
| WO | 2017/111152 A1 | 6/2017 |
| WO | 2017/169893 A1 | 10/2017 |
| WO | 2017/178245 A1 | 10/2017 |
| WO | 2017/211649 A1 | 12/2017 |
| WO | 2017/211650 A1 | 12/2017 |
| WO | 2017/211652 A1 | 12/2017 |
| WO | 2017/213252 A1 | 12/2017 |
| WO | 2017/222951 A1 | 12/2017 |
| WO | 2018/030460 A1 | 2/2018 |

OTHER PUBLICATIONS

International Search Report and Written Opinion for PCT/EP2016/073295, dated Oct. 26, 2016.

* cited by examiner

MICROBIOCIDAL OXADIAZOLE DERIVATIVES

CROSS-REFERENCE TO RELATED APPLICATIONS

This application is a 371 National Stage application of International Application No. PCT/EP2016/073295, filed Sep. 29, 2016, which claims priority to European Patent Application No. 15188238.8, filed Oct. 2, 2015 and European Patent Application No. 16150491.5, filed Jan. 7, 2016, the entire contents of which are hereby incorporated by reference.

The present invention relates to microbiocidal oxadiazole derivatives, eg, as active ingredients, which have microbiocidal activity, in particular, fungicidal activity. The invention also relates to agrochemical compositions which comprise at least one of the oxadiazole derivatives, to processes of preparation of these compounds and to uses of the oxadiazole derivatives or compositions in agriculture or horticulture for controlling or preventing infestation of plants, harvested food crops, seeds or non-living materials by phytopathogenic microorganisms, preferably fungi.

Microbiocidal oxadiazole derivatives are known as insecticidal and acaricidal agents, eg, from CN 1927860. WO 2013/064079, EP 0 276 432 and WO 2015/185485 describe the use of substituted oxadiazoles for combating phytopathogenic fungi.

According to the present invention, there is provided a compound of formula (I):

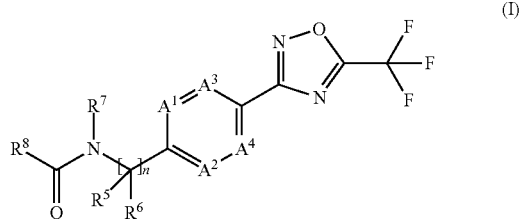

wherein
n is 1 or 2

$A^1$ represents N or $CR^1$, wherein $R^1$ is hydrogen, halogen, methyl, ethyl, difluoromethyl, trifluoromethyl, methoxy, ethoxy, or difluoromethoxy;

$A^2$ represents N or $CR^2$, wherein $R^2$ is hydrogen, halogen, methyl, ethyl, difluoromethyl, trifluoromethyl, methoxy, ethoxy, or difluoromethoxy;

$A^3$ represents N or $CR^3$, wherein $R^3$ is hydrogen or halogen;

$A^4$ represents N or $CR^4$, wherein $R^4$ is hydrogen or halogen; and wherein 0, 1 or 2 of $A^1$, $A^2$, $A^3$ and $A^4$ are N;

$R^5$ and $R^6$ are independently selected from hydrogen, $C_{1-4}$alkyl, halogen, cyano, trifluoromethyl and difluoromethyl, or $R^5$ and $R^6$ together with the carbon atom they share form a cyclopropyl;

$R^7$ is hydroxy, $C_{1-4}$alkyl, $C_{1-4}$ haloalkyl, $C_{1-4}$alkoxy, hydroxy$C_{1-4}$alkyl, $C_{1-2}$alkoxy$C_{1-4}$alkyl, $C_{1-2}$haloalkoxy$C_{1-4}$alkyl, $C_{3-6}$alkenyl, $C_{3-4}$alkynyl, $C_{3-6}$alkenyloxy, $C_{3-6}$alkynyloxy, $C_{3-6}$ haloalkenyl, $C_{3-6}$haloalkenyloxy, $C_{1-4}$alkylcarbonyloxy, $C_{1-4}$ haloalkylcarbonyloxy, $C_{1-4}$alkoxycarbonyloxy, $C_{1-4}$alkylcarbonyloxy$C_{1-4}$alkyl, $C_{1-4}$ haloalkylcarbonyloxy$C_{1-4}$alkyl or $C_{1-4}$alkoxycarbonyloxy$C_{1-4}$alkyl; or $R^7$ is $C_{3-6}$cycloalkyl, $C_{3-6}$cycloalkyl$C_{1-2}$alkyl, $C_{3-6}$cycloalkyl$C_{1-2}$alkoxy, phenyl, phenyl$C_{1-2}$alkyl, phenyl$C_{1-2}$alkoxy, heteroaryl, heteroaryl$C_{1-2}$alkyl, heteroaryl$C_{1-2}$alkoxy, heterocyclyl, heterocyclyl$C_{1-2}$alkyl, heterocyclyl$C_{1-2}$ alkoxy, $C_{3-6}$cycloalkylcarbonyloxy, heterocyclylcarbonyloxy phenylcarbonyloxy, $C_{3-6}$cycloalkylcarbonyloxy$C_{1-4}$alkyl, heterocyclylcarbonyloxy$C_{1-4}$alkyl or phenylcarbonyloxy$C_{1-4}$alkyl, wherein the heteroaryl moiety is a 5- or 6-membered monocyclic aromatic ring which comprises 1, 2, 3 or 4 heteroatoms individually selected from N, O and S, the heterocyclyl moiety is a 4- to 6-membered non-aromatic ring which comprises 1 or 2 heteroatoms individually selected from N, O and S, and wherein any of said cycloalkyl, phenyl, heteroaryl and heterocyclyl moieties are optionally substituted by 1 or 2 substituents selected from cyano, fluoro, chloro, bromo, methyl, difluoromethyl, trifluoromethyl, methoxy, ethoxy, or difluoromethoxy;

$R^8$ is hydrogen, $C_{1-6}$alkyl, $C_{2-6}$alkenyl, $C_{2-6}$alkynyl, cyano$C_{1-6}$alkyl, $C_{1-6}$ haloalkyl, $C_{2-6}$haloalkenyl, hydroxy$C_{1-6}$alkyl, $C_{1-4}$alkoxy$C_{1-6}$alkyl, $C_{1-4}$ haloalkoxy$C_{1-6}$alkyl, $C_{1-4}$alkoxy$C_{1-4}$alkoxy$C_{1-6}$alkyl, $C_{2-4}$alkynyloxy$C_{1-6}$alkyl, amino$C_{1-6}$alkyl, N—$C_{1-4}$alkylamino$C_{1-6}$alkyl, N,N-di$C_{1-4}$alkylamino$C_{1-6}$alkyl, $C_{1-6}$alkylcarbonyl$C_{1-6}$alkyl, $C_{1-6}$alkylcarbonyl$C_{2-6}$alkenyl, $C_{1-6}$alkoxycarbonyl$C_{1-6}$alkyl, $C_{1-6}$alkylcarbonyloxy$C_{1-6}$alkyl, N—$C_{1-4}$alkylaminocarbonyl$C_{1-6}$alkyl, N,N-di$C_{1-4}$alkylaminocarbonyl$C_{1-6}$alkyl, $C_{1-6}$alkylsulfanyl$C_{1-6}$alkyl, $C_{1-6}$alkylsulfonyl$C_{1-6}$alkyl, $C_{1-6}$alkylsulfonylamino$C_{1-6}$alkyl, $C_{1-6}$ alkylsulfonylamino$C_{2-6}$alkynyl, $C_{2-6}$alkynyloxycarbonylamino$C_{1-6}$alkyl, $C_{1-4}$alkylcarbonylamino$C_{1-6}$alkyl or $C_{1-4}$alkoxycarbonylamino$C_{1-6}$alkyl; or $R^8$ is $C_{3-8}$cycloalkyl, $C_{3-8}$cycloalkyl$C_{1-6}$alkyl, wherein the cycloalkyl moiety is optionally partially unsaturated, phenyl, phenyl$C_{1-6}$alkyl, phenyl$C_{2-6}$alkenyl, napthyl, napthyl$C_{1-6}$alkyl, heteroaryl, heteroaryl$C_{1-6}$alkyl, wherein the heteroaryl moiety is a 5- or 6-membered monocyclic aromatic ring which comprises 1, 2, 3 or 4 heteroatoms individually selected from N, O and S, heterodiaryl, heterodiaryl$C_{1-6}$alkyl wherein the heterodiaryl moiety is a 9- or 10-membered bicyclic aromatic system which comprises 1, 2, 3 or 4 heteroatoms individually selected from N, O and S, heterocyclyl, heterocyclyl$C_{1-6}$alkyl wherein the heterocyclyl moiety is a 4- to 6-membered non-aromatic ring which comprises 1, 2 or 3 heteroatoms individually selected from N, O and S, or $C_{3-6}$cycloalkylcarbonylamino$C_{1-6}$alkyl, wherein for $R^8$, any cycloalkyl, phenyl, napthyl, heteroaryl, heterodiaryl or heterocyclyl moiety is optionally substituted by 1, 2 or 3 substituents, which may be the same or different, selected from $R^9$; or, additionally, when $R^8$ is cyclopropyl, the cyclopropyl moiety is substituted by 4 substituents, which may be the same or different, selected from $R^9$, with the proviso that at least 2 $R^9$ substituents are the same; wherein $R^9$ is cyano, halogen, hydroxy, $C_{1-4}$alkyl, $C_{2-4}$alkenyl, $C_{2-4}$alkynyl, $C_{1-4}$ haloalkyl, $C_{2-4}$ haloalkenyl, $C_{1-4}$alkoxy, $C_{1-4}$ haloalkoxy, $C_{3-4}$alkynyloxy, N—$C_{1-4}$alkylamino, N,N-di$C_{1-4}$alkylamino, $C_{1-4}$alkylcarbonyl, $C_{3-6}$cycloalkylcarbonyl, $C_{1-4}$alkoxycarbonyl, carbonylamino, N—$C_{1-4}$alkylaminocarbonyl, N,N-di$C_{1-4}$alkylaminocarbonyl or $C_{1-4}$alkoxycarbonylamino, and wherein when $R_8$ is substituted $C_{3-8}$cycloalkyl, $C_{3-8}$cycloalkyl$C_{1-6}$alkyl, heterocyclyl, or heterocyclyl$C_{1-6}$alkyl, $R^9$ may also represent oxo on the $C_{3-8}$cycloalkyl or heterocyclyl moiety; or wherein for $R^8$, any cycloalkyl, phenyl, napthyl, heteroaryl, heterodiaryl or heterocyclyl moiety is optionally substituted by 1 substituent selected from $R^{10}$ and further optionally substituted by 1 or 2 substituents selected from $R^9$; wherein $R^{10}$ is $C_{3-8}$cycloalkyl, $C_{3-8}$cycloalkyl$C_{1-2}$alkyl, phenyl, phenyl$C_{1-2}$alkyl, heteroaryl, heteroaryl$C_{1-2}$alkyl wherein the heteroaryl moiety is a 5- or 6-membered monocyclic aromatic ring which comprises 1, 2, 3 or 4 heteroatoms individually selected from N, O and S, heterocyclyl or heterocyclyl$C_{1-6}$alkyl wherein the heterocyclyl moiety is a 4- to 6-membered non-aromatic ring which comprises 1, 2 or 3 heteroatoms individually selected from N, O and S, and wherein any of said cycloalkyl, phenyl, heteroaryl and heterocyclyl moieties are optionally substituted by 1, 2 or 3 substituents, which may be the same or different, selected from $R^{11}$; wherein $R^{11}$ is hydrogen, cyano, fluoro, chloro, bromo, methyl, trifluoromethyl, methoxy and ethoxy;

or $R^8$ represents —$OR^{12}$, wherein $R^{12}$ is hydrogen, $C_{1-6}$alkyl, $C_{3-6}$alkenyl, $C_{3-6}$alkynyl, cyano$C_{1-6}$alkyl, $C_{1-6}$ haloalkyl, $C_{3-6}$ haloalkenyl, hydroxy$C_{1-6}$alkyl, $C_{1-4}$alkoxy$C_{1-6}$alkyl, $C_{1-4}$ haloalkoxy$C_{1-6}$alkyl, $C_{1-4}$alkoxy$C_{1-4}$alkoxy$C_{1-6}$alkyl, amino$C_{1-6}$alkyl, $C_{1-6}$alkylcarbonyl$C_{1-6}$alkyl, $C_{1-6}$alkylcarbonyl$C_{2-6}$alkenyl, $C_{1-6}$alkoxycarbonyl$C_{1-6}$alkyl, $C_{1-6}$alkylcarbonyloxy$C_{1-6}$alkyl, N—$C_{1-4}$alkylaminocarbonyl$C_{1-6}$alkyl, N,N-di$C_{1-4}$alkylaminocarbonyl$C_{1-6}$alkyl, $C_{1-4}$alkylsulfanyl$C_{1-6}$alkyl, $C_{1-6}$alkylsulfonyl$C_{1-6}$alkyl or $C_{1-6}$alkylsulfonylamino$C_{1-6}$alkyl; or $R^{12}$ is $C_{3-8}$cycloalkyl, $C_{3-8}$cycloalkyl$C_{1-6}$alkyl, wherein the cycloalkyl moiety is optionally partially unsaturated, phenyl, phenyl$C_{1-6}$alkyl, heteroaryl, heteroaryl$C_{1-6}$alkyl, wherein the heteroaryl moiety is a 5- or 6-membered monocyclic aromatic ring which comprises 1, 2, 3 or 4 heteroatoms individually selected from N, O and S, heterocyclyl or heterocyclyl$C_{1-6}$alkyl, wherein the heterocyclyl moiety is a 4-to 6-membered non-aromatic ring which comprises 1, 2 or 3 heteroatoms individually selected from N, O and S;

wherein for $R^{12}$, any cycloalkyl, phenyl, heteroaryl or heterocyclyl moiety is optionally substituted by 1, 2 or 3 substituents, which may be the same or different, selected from $R^{13}$; wherein $R^{13}$ is cyano, halogen, hydroxy, $C_{1-4}$alkyl, $C_{2-4}$alkenyl, $C_{2-4}$alkynyl, $C_{1-4}$ haloalkyl, $C_{2-4}$haloalkenyl, $C_{1-4}$alkoxy, $C_{1-4}$ haloalkoxy, $C_{3-4}$alkenyloxy, $C_{3-4}$alkynyloxy, N—$C_{1-4}$alkylamino, N,N-di$C_{1-4}$alkylamino, $C_{1-4}$alkylcarbonyl, $C_{1-4}$alkoxycarbonyl, carbonylamino, N—$C_{1-4}$alkylaminocarbonyl, N,N-di$C_{1-4}$alkylaminocarbonyl or $C_{1-4}$alkoxycarbonylamino;

and wherein when $R^{12}$ is substituted $C_{3-8}$cycloalkyl, $C_{3-8}$cycloalkyl$C_{1-6}$alkyl, heterocyclyl, or heterocyclyl$C_{1-6}$alkyl, $R^{13}$ may also represent oxo on the $C_{3-8}$cycloalkyl or heterocyclyl moiety;

or $R^8$ represents —$NR^{14}R^{15}$, wherein $R^{14}$ is hydrogen, cyano, $C_{1-6}$alkyl, $C_{1-6}$alkoxy, $C_{2-6}$alkenyl, $C_{2-6}$alkynyl, $C_{3-6}$alkenyloxy, $C_{3-6}$alkynyloxy, cyano$C_{1-6}$alkyl, $C_{1-6}$ haloalkyl, $C_{1-6}$ haloalkenyl, hydroxy$C_{1-6}$alkyl, $C_{1-4}$alkoxy$C_{1-6}$alkyl, $C_{1-4}$ haloalkoxy$C_{1-6}$alkyl, $C_{1-4}$alkoxy$C_{1-4}$alkoxy$C_{1-6}$alkyl, amino$C_{1-6}$alkyl, N—$C_{1-4}$alkylamino$C_{1-6}$alkyl, N,N-di$C_{1-4}$alkylamino$C_{1-6}$alkyl, $C_{1-6}$alkylcarbonyl$C_{1-6}$alkyl, $C_{1-6}$alkylcarbonyl$C_{2-6}$alkenyl, $C_{1-6}$alkoxycarbonyl$C_{1-6}$alkyl, $C_{1-6}$alkylcarbonyloxy$C_{1-6}$alkyl, N—$C_{1-4}$alkylaminocarbonyl$C_{1-6}$alkyl, N,N-di$C_{1-4}$alkylaminocarbonyl$C_{1-6}$alkyl, $C_{1-6}$alkylsulfonyl$C_{1-6}$alkyl or $C_{1-6}$alkylsulfonylamino$C_{1-6}$alkyl; or $R^{14}$ is $C_{3-8}$cycloalkyl, $C_{3-8}$cycloalkyl$C_{1-6}$alkyl, $C_{3-8}$cycloalkyl$C_{1-6}$alkoxy, $C_{3-6}$cycloalkyloxy, wherein the cycloalkyl moiety is optionally partially unsaturated, phenyl, phenyl$C_{1-6}$alkyl, phenyl$C_{1-6}$alkoxy, heteroaryl, heteroaryl$C_{1-6}$alkyl, heteroaryl$C_{1-6}$alkoxy, wherein the heteroaryl moiety is a 5- or 6-membered monocyclic aromatic ring which comprises 1, 2, 3 or 4 heteroatoms individually selected from N, O and S, heterocyclyl, heterocyclyl$C_{1-6}$alkyl or heterocyclyl$C_{1-6}$alkoxy wherein the heterocyclyl moiety is a 4- to 6-membered non-aromatic ring which comprises 1, 2 or 3 heteroatoms individually selected from N, O and S;

wherein for $R^{14}$, any cycloalkyl, phenyl, heteroaryl, heterocyclyl moiety is optionally substituted by 1, 2 or 3 substituents, which may be the same or different, selected from $R^{16}$; wherein $R^{16}$ is cyano, halogen, hydroxy, $C_{1-4}$alkyl, $C_{2-4}$alkenyl, $C_{2-4}$alkynyl, $C_{1-4}$ haloalkyl, $C_{2-4}$haloalkenyl, $C_{1-4}$alkoxy, $C_{1-2}$alkoxy$C_{1-2}$alkyl, $C_{1-4}$ haloalkoxy, $C_{3-4}$alkenyloxy, $C_{3-4}$alkynyloxy, N—$C_{1-4}$alkylamino, N,N-di$C_{1-4}$alkylamino, $C_{1-4}$alkylcarbonyl, $C_{1-4}$alkoxycarbonyl, carbonylamino, N—$C_{1-4}$alkylaminocarbonyl, N,N-di$C_{1-4}$alkylaminocarbonyl and $C_{1-4}$alkoxycarbonylamino;

and wherein when $R^{14}$ is substituted $C_{3-8}$cycloalkyl, $C_{3-8}$cycloalkyl$C_{1-6}$alkyl, $C_{3-8}$cycloalkyl$C_{1-6}$alkoxy, heterocyclyl, heterocyclyl$C_{1-6}$alkyl or heterocyclyl$C_{1-6}$alkoxy, $R^{16}$ may also represent oxo on the $C_{3-8}$cycloalkyl or heterocyclyl moiety;

$R^{15}$ is hydrogen, $C_{1-4}$alkyl, $C_{3-4}$alkynyl, $C_{1-4}$alkoxy$C_{1-4}$alkyl, cyano$C_{1-4}$alkyl, $C_{3-6}$cycloalkyl, $C_{3-6}$cycloalkyl$C_{1-2}$alkyl; or $R^{14}$ and $R^{15}$, together with the nitrogen atom to which they are bonded, form a 4-, 5- or 6-membered cycle optionally containing an additional heteroatom or group selected from O, S, $S(O)_2$, oxo (=O) and $NR^{17}$; wherein $R^{17}$ is hydrogen, methyl, methoxy, formyl or acyl; or a salt or an N-oxide thereof.

Surprisingly, it has been found that the novel compounds of formula (I) have, for practical purposes, a very advantageous level of biological activity for protecting plants against diseases that are caused by fungi.

According to a second aspect of the invention, there is provided an agrochemical composition comprising a fungicidally effective amount of a compound of formula (I). The composition may further comprise at least one additional active ingredient and/or an agrochemically-acceptable diluent or carrier.

According to a third aspect of the invention, there is provided a method of controlling or preventing infestation of useful plants by phytopathogenic microorganisms, wherein a fungicidally effective amount of a compound of formula (I), or a composition comprising this compound as active ingredient, is applied to the plants, to parts thereof or the locus thereof.

According to a fourth aspect of the invention, there is provided the use of a compound of formula (I) as a fungicide. According to this particular aspect of the invention, the use may or may not include methods for the treatment of the human or animal body by surgery or therapy.

As used herein, the term "halogen" or "halo" refers to fluorine (fluoro), chlorine (chloro), bromine (bromo) or iodine (iodo), preferably fluorine, chlorine or bromine.

As used herein, cyano means a —CN group.

As used herein, amino means an —$NH_2$ group.

As used herein, hydroxy means an —OH group.

As used herein, carbonylamino means an —N(H)C(O)H group.

As used herein, formyl means an —C(O)H group.

As used herein, acyl means an —C(O)$CH_3$ group.

As used herein, the term "$C_{1-6}$alkyl" refers to a straight or branched hydrocarbon chain radical consisting solely of carbon and hydrogen atoms, containing no unsaturation, having from one to six carbon atoms, and which is attached to the rest of the molecule by a single bond. The terms "$C_{1-4}$alkyl" and "$C_{1-2}$alkyl" are to be construed accordingly. Examples of $C_{1-6}$alkyl include, but are not limited to, methyl, ethyl, n-propyl, 1-methylethyl (iso-propyl), n-butyl, 1,1-dimethylethyl (tert-butyl) and n-pentyl. A "$C_1$-$C_6$alkylene" group refers to the corresponding definition of $C_1$-$C_6$alkyl (and $C_{1-4}$alkyl and $C_{1-2}$alkyl), except that such radical is attached to the rest of the molecule by two single bonds. Examples of $C_1$-$C_6$alkylene, include, but are not limited to, —$CH_2$—, —$CH_2CH_2$— and —$(CH_2)_3$—.

As used herein, the term "$C_{2-6}$alkenyl" refers to a straight or branched hydrocarbon chain radical group consisting solely of carbon and hydrogen atoms, containing at least one double bond that can be of either the (E)- or (Z)-configuration, having from two to six carbon atoms, which is attached to the rest of the molecule by a single bond. The term "$C_{3-6}$alkenyl" is to be construed accordingly. Examples of $C_{2-6}$alkenyl include, but are not limited to, ethenyl, prop-1-enyl, but-1-enyl.

As used herein, the term "$C_{2-6}$alkynyl" refers to a straight or branched hydrocarbon chain radical group consisting solely of carbon and hydrogen atoms, containing at least one triple bond, having from two to six carbon atoms, and which is attached to the rest of the molecule by a single bond. The term "$C_{3-4}$alkynyl" is to be construed accordingly. Examples of $C_{2-6}$alkynyl include, but are not limited to, ethynyl, prop-1-ynyl, but-1-ynyl.

As used herein, oxo means an =O group, eg, a ketonyl (—C(O)—), sulfinyl (—S(O)—) or sulfonyl (—S(O)$_2$—) oxygen.

As used herein, the term "N—$C_{1-4}$alkylamino" refers to a radical of the formula —NH—$R_a$ where $R_a$ is a $C_{1-4}$alkyl radical as defined above.

As used herein, the term "N,N-di$C_{1-4}$alkylamino" refers to a radical of the formula —N($R_a$)—$R_a$ where each $R_a$ is a $C_{1-4}$alkyl radical, which may be the same or different, as defined above.

As used herein, the term "$C_{1-6}$alkoxy" refers to a radical of the formula —$OR_a$ where $R_a$ is a $C_{1-6}$alkyl radical as generally defined above. The terms "$C_{1-4}$alkoxy" and "$C_{1-2}$alkoxy" are to be construed accordingly. Examples of $C_{1-6}$alkoxy include, but are not limited to, methoxy, ethoxy, propoxy, iso-propoxy, butoxy.

As used herein, the term "$C_{1-4}$alkoxycarbonyloxy" refers to a radical of the formula —OC(O)$R_a$ where $R_a$ is a $C_{1-4}$alkoxy radical as generally defined above.

As used herein, the term "$C_{1-4}$alkoxycarbonyloxy$C_{1-4}$alkyl" refers to a $C_{1-4}$alkyl radical as generally defined above substituted by a $C_{1-4}$alkoxycarbonyloxy radical as generally defined above.

As used herein, the term "hydroxy$C_{1-4}$alkyl" refers to a $C_{1-4}$alkyl radical as generally defined above substituted by one or more hydroxy groups as defined above.

As used herein, the term "$C_{1-6}$alkylcarbonyl" refers to a radical of the formula —C(O)$R_a$ where $R_a$ is a $C_{1-6}$alkyl radical as generally defined above. The term "$C_{1-4}$alkylcarbonyl" is to be construed accordingly.

As used herein, the term "$C_{1-6}$alkoxycarbonyl" refers to a radical of the formula —C(O)O$R_a$ where $R_a$ is a $C_{1-6}$alkyl radical as generally defined above. The term "$C_{1-4}$alkoxycarbonyl" is to be construed accordingly.

As used herein, the term "$C_{1-6}$alkylcarbonyloxy" refers to a radical of the formula —OC(O)$R_a$ where $R_a$ is a $C_{1-6}$alkyl radical as generally defined above. The term "$C_{1-4}$alkylcarbonyloxy" is to be construed accordingly.

As used herein, the term "N—$C_{1-4}$alkylaminocarbonyl" refers to a radical of the formula —C(O)NH$R_a$ where $R_a$ is a $C_{1-4}$alkyl radical as generally defined above.

As used herein, the term "N,N-di$C_{1-4}$alkylaminocarbonyl" refers to a radical of the formula —C(O)N$R_a$($R_a$) where each $R_a$ is a $C_{1-4}$alkyl radical as generally defined above.

As used herein, the term "$C_{1-4}$alkylcarbonylamino" refers to a radical of the formula —NHC(O)$R_a$ where $R_a$ is a $C_{1-4}$alkyl radical as generally defined above.

As used herein, the term "$C_{1-4}$alkylcarbonylamino$C_{1-6}$alkyl" refers to a $C_{1-6}$alkyl radical as generally defined above substituted by a $C_{1-4}$alkylcarbonylamino group as defined above.

As used herein, the term "$C_{1-4}$alkoxycarbonylamino" refers to a radical of the formula —NHC(O)O$R_a$ where $R_a$ is a $C_{1-4}$alkyl radical as generally defined above.

As used herein, the term "$C_{1-4}$alkoxycarbonylamino$C_{1-6}$alkyl" refers to a $C_{1-6}$alkyl radical as generally defined above substituted by a $C_{1-4}$alkoxycarbonylamino group as defined above.

As used herein, the term "$C_{1-6}$alkylsulfanyl" refers to a radical of the formula —S$R_a$ where $R_a$ is a $C_{1-6}$alkyl radical as generally defined above. The term "$C_{1-4}$alkylsulfanyl" is to be construed accordingly.

As used herein, the term "$C_{1-6}$alkylsulfinyl" refers to a radical of the formula —S(O)$R_a$ where $R_a$ is a $C_{1-6}$alkyl radical as generally defined above. The term "$C_{1-4}$alkylsulfonyl" is to be construed accordingly.

As used herein, the term "$C_{1-6}$alkylsulfonyl" refers to a radical of the formula —S(O)$_2R_a$ where $R_a$ is a $C_{1-6}$alkyl radical as generally defined above. The term "$C_{1-4}$alkylsulfonyl" is to be construed accordingly.

As used herein, the term "$C_{1-6}$alkylsulfonylamino" refers to a radical of the formula —NHS(O)$_2R_a$ where $R_a$ is a $C_{1-6}$alkyl radical as generally defined above. The term "$C_{1-4}$alkylsulfonylamino" is to be construed accordingly.

As used herein, the term "$C_{3-6}$alkenyloxy" refers to a radical of the formula —$OR_a$ where $R_a$ is a $C_{3-6}$alkenyl radical as generally defined above.

As used herein, the term "$C_{2-6}$alkynloxy" refers to a radical of the formula —$OR_a$ where $R_a$ is a $C_{2-6}$alkynyl radical as generally defined above. The terms "$C_{2-4}$alkynloxy" and "$C_{3-6}$alkynyloxy" are to be construed accordingly.

As used herein, the term "$C_{3-6}$ haloalkenyloxy" refers to a $C_{3-6}$alkenyloxy radical as generally defined above substituted by one or more of the same or different halogen atoms.

As used herein, the term "$C_{2-6}$alkynyloxycarbonylamino" refers to a radical of the formula —NHC(O)O$R_a$ where $R_a$ is a $C_{2-6}$alkynyl radical as generally defined above. The term "$C_{2-4}$alkynyloxycarbonylamino" is to be construed accordingly.

As used herein, the term "$C_{1-4}$ haloalkoxy" refers to a $C_{1-4}$alkoxy group as defined above substituted by one or more of the same or different halogen atoms. Examples of $C_{1-4}$ haloalkoxy include, but are not limited to, fluoromethoxy, fluoroethoxy, trifluoromethoxy, trifluoroethoxy.

As used herein, the term "cyano$C_{1-6}$alkyl" refers to a $C_{1-6}$alkyl radical as generally defined above substituted by one or more cyano groups as defined above. The term "cyano$C_{1-4}$alkyl" is to be construed accordingly. Examples of cyano$C_{1-6}$alkyl include, but are not limited to cyanomethyl, cyanoethyl.

As used herein, the term "$C_{1-6}$ haloalkyl" refers to a $C_{1-6}$alkyl radical as generally defined above substituted by one or more of the same or different halogen atoms. The term "$C_{1-4}$ haloalkyl" is to be construed accordingly. Examples of $C_{1-6}$ haloalkyl include, but are not limited to fluoromethyl, fluoroethyl, trifluoromethyl, 2,2,2-trifluoroethyl.

As used herein, the term "$C_{2-6}$ haloalkenyl" refers to a $C_{2-6}$alkenyl radical as generally defined above substituted by one or more of the same or different halogen atoms. The terms "$C_{2-4}$ haloalkenyl" and "$C_{3-6}$ haloalkenyl" are to be construed accordingly.

As used herein, the term "$C_{1-4}$ haloalkylcarbonyloxy" refers to a radical of the formula —OC(O)$R_a$ where $R_a$ is a $C_{1-4}$ haloalkyl radical as generally defined above.

As used herein, the term "$C_{1-4}$ haloalkylcarbonyloxy$C_{1-4}$alkyl" refers to a $C_{1-4}$alkyl radical as generally defined above substituted by a $C_{1-4}$ haloalkylcarbonyloxy radical as generally defined above.

As used herein, the term "hydroxy$C_{1-6}$alkyl" refers to a $C_{1-6}$alkyl radical as generally defined above substituted by one or more hydroxy groups as defined above. The term "hydroxy$C_{1-4}$alkyl" is to be construed accordingly.

As used herein, the term "$C_{1-4}$alkoxy$C_{1-6}$alkyl" refers to a $C_{1-6}$alkyl radical as generally defined above substituted by a $C_{1-4}$alkoxy group as defined above. The terms "$C_{1-4}$alkoxy$C_{1-4}$alkyl" and "$C_{1-2}$alkoxy$C_{1-4}$alkyl" are to be construed accordingly. Examples of $C_{1-4}$alkoxy$C_{1-6}$alkyl include, but are not limited to methoxymethyl, 2-methoxyethyl.

As used herein, the term "$C_{1-4}$ haloalkoxy$C_{1-6}$alkyl" refers to a $C_{1-6}$alkyl radical as generally defined above substituted by a $C_{1-4}$ haloalkoxy group as defined above. The terms "$C_{1-4}$ halolalkoxy$C_{1-4}$alkyl" and "$C_{1-2}$ haloalkoxy$C_{1-4}$alkyl" are to be construed accordingly.

As used herein, the term "$C_{1-4}$alkoxy$C_{1-4}$alkoxy$C_{1-6}$alkyl" refers to a $C_{1-6}$alkyl radical as generally defined above substituted by a $C_{1-4}$alkoxy group as defined above, the $C_{1-4}$alkoxy group itself substituted by a $C_{1-4}$alkoxy group as defined above.

As used herein, the term "$C_{2-6}$alkynyloxy$C_{1-6}$alkyl" refers to a $C_{1-6}$alkyl radical as generally defined above substituted by a $C_{2-6}$alkynyloxy group as defined above.

As used herein, the term "amino$C_{1-6}$alkyl" refers to a $C_{1-6}$alkyl radical as generally defined above substituted by one or more amino groups as defined above. The term "amino$C_{1-4}$alkyl" is to be construed accordingly.

As used herein, the term "N—$C_{1-4}$alkylamino$C_{1-6}$alkyl" refers to a $C_{1-6}$alkyl radical as generally defined above substituted by a N—$C_{1-4}$alkylamino group as defined above. The term "N—$C_{1-4}$alkylamino$C_{1-4}$alkyl" is to be construed accordingly.

As used herein, the term "N,N-di$C_{1-4}$alkylamino$C_{1-6}$alkyl" refers to a $C_{1-6}$alkyl radical as generally defined above substituted by a N,N-di$C_{1-4}$alkylamino group as defined above. The term "N,N-di$C_{1-4}$alkylamino$C_{1-4}$alkyl" is to be construed accordingly.

As used herein, the term "$C_{1-6}$alkylcarbonyl$C_{1-6}$alkyl" refers to a $C_{1-6}$alkyl radical as generally defined above substituted by a $C_{1-6}$alkylcarbonyl group as defined above. The term "$C_{1-6}$alkylcarbonyl$C_{1-4}$alkyl" is to be construed accordingly.

As used herein, the term "$C_{1-6}$alkylcarbonyl$C_{2-6}$alkenyl" refers to a $C_{2-6}$alkenyl radical as generally defined above substituted by a $C_{1-6}$alkylcarbonyl group as defined above. The term "$C_{1-6}$alkylcarbonyl$C_{2-4}$alkenyl" is to be construed accordingly.

As used herein, the term "$C_{1-6}$alkoxycarbonyl$C_{1-6}$alkyl" refers to a $C_{1-6}$alkyl radical as generally defined above substituted by a $C_{1-6}$alkoxycarbonyl group as defined above. The term "$C_{1-6}$alkoxycarbonyl$C_{1-4}$alkyl" is to be construed accordingly.

As used herein, the term "$C_{1-6}$alkylcarbonyloxy$C_{1-6}$alkyl" refers to a $C_{1-6}$alkyl radical as generally defined above substituted by a $C_{1-6}$alkylcarbonyloxy group as defined above. The term "$C_{1-6}$alkylcarbonyloxy$C_{1-4}$alkyl" is to be construed accordingly.

As used herein, the term "N—$C_{1-4}$alkylaminocarbonyl$C_{1-6}$ alkyl", refers to a $C_{1-6}$alkyl radical as generally defined above substituted by a N—$C_{1-4}$alkylaminocarbonyl group as defined above. The term "N—$C_{1-4}$alkylaminocarbonyl$C_{1-4}$ alkyl" is to be construed accordingly.

As used herein, the term "N,N-di$C_{1-4}$alkylaminocarbonyl$C_{1-6}$alkyl", refers to a $C_{1-6}$alkyl radical as generally defined above substituted by a N,N-di$C_{1-4}$alkylaminocarbonyl$C_{1-6}$alkyl group as defined above. The term "N,N-di$C_{1-4}$ alkylaminocarbonyl$C_{1-4}$alkyl" is to be construed accordingly.

As used herein, the term "$C_{1-6}$alkylsulfanyl$C_{1-6}$alkyl", refers to a $C_{1-6}$alkyl radical as generally defined above substituted by a $C_{1-6}$alkylsulfanyl group as defined above. The term "$C_{1-6}$alkylsulfanyl$C_{1-4}$alkyl" is to be construed accordingly.

As used herein, the term "$C_{1-6}$alkylsulfonyl$C_{1-6}$alkyl", refers to a $C_{1-6}$alkyl radical as generally defined above substituted by a $C_{1-6}$alkylsulfonyl group as defined above. The term "$C_{1-6}$alkylsulfonyl$C_{1-4}$alkyl" is to be construed accordingly.

As used herein, the term "$C_{1-6}$alkylsulfonylamino$C_{1-6}$alkyl", refers to a $C_{1-6}$alkyl radical as generally defined above substituted by a $C_{1-6}$alkylsulfonylamino group as defined above. The term "$C_{1-6}$alkylsulfonylamino$C_{1-4}$alkyl" is to be construed accordingly.

As used herein, the term "$C_{1-6}$alkylsulfonylamino$C_{2-6}$alkynyl", refers to a $C_{2-6}$alkynyl radical as generally defined above substituted by a $C_{1-6}$alkylsulfonylamino group as defined above. The term "$C_{1-6}$alkylsulfonylamino$C_{2-4}$alkynyl" is to be construed accordingly.

As used herein, $C_{2-6}$alkynyloxycarbonylamino$C_{1-6}$alkyl refers to a $C_{1-6}$alkyl radical as generally defined above substituted by a $C_{2-6}$alkynyloxycarbonylamino group as defined above. The term "$C_{2-4}$alkynyloxycarbonylamino$C_{1-4}$ alkyl" is to be construed accordingly.

As used herein, the term "$C_{3-8}$cycloalkyl" may be mono- or bi-cyclic and contains 3 to 8 carbon atoms. "$C_{3-6}$cycloalkyl" is to be construed accordingly. Examples of $C_{3-8}$cycloalkyl include, but are not limited to, cyclopropyl, 1-methylcyclopropyl, 2-methylcyclopropyl, cyclobutyl, cyclopentyl and cyclohexyl.

As used herein, the term "aryl" refers to an aromatic ring system consisting solely of carbon and hydrogen atoms which may be mono-, bi- or tricyclic. Examples of such ring systems include phenyl, naphthalenyl, anthracenyl, indenyl or phenanthrenyl.

As used herein, the term "heteroaryl" refers to a 5- or 6-membered aromatic monocyclic ring radical which comprises 1, 2, 3 or 4 heteroatoms individually selected from nitrogen, oxygen and sulfur. The heteroaryl radical may be bonded via a carbon atom or heteroatom. Examples of heteroaryl include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

As used herein, the term "heterodiaryl" refers to a stable 9- or 10-membered bicyclic aromatic ring system which comprises 1, 2, 3 or 4 heteroatoms individually selected from nitrogen, oxygen and sulfur. The heteroaryl radical may be bonded via a carbon atom or heteroatom.

As used herein, the term "heterocyclyl" or "heterocyclic" refers to a stable 4-, 5- or 6-membered non-aromatic monocyclic ring radical which comprises 1, 2, or 3, heteroatoms individually selected from nitrogen, oxygen and sulfur. The heterocyclyl radical may be bonded to the rest of the molecule via a carbon atom or heteroatom. Examples of heterocyclyl include, but are not limited to, azetidinyl, oxetanyl, pyrrolinyl, pyrrolidyl, thietanyl, tetrahydrofuryl, tetrahydrothienyl, tetrahydrothiopyranyl, piperidyl, piperazinyl, tetrahydropyranyl, morpholinyl or perhydroazepinyl.

As used herein, the term "$C_{3-8}$cycloalkyl$C_{0-6}$alkyl" refers to a $C_{3-8}$cycloalkyl ring as defined above attached to the rest of the molecule by a single bond or by a $C_1$-$C_6$alkylene radical as defined above. "$C_{3-6}$cycloalkyl$C_{1-2}$alkyl" is to be construed accordingly. Examples of $C_{3-8}$cycloalkyl$C_{0-6}$alkyl include, but are not limited to, cyclopropyl, cyclopropylmethyl, cyclopropylethyl, cyclobutyl, cyclopentyl or cyclohexyl.

As used herein, the term "$C_{3-6}$cycloalkyl$C_{1-2}$alkoxy" refers to a $C_{1-2}$alkoxy radical as generally defined above substituted by a $C_{3-6}$cycloalkyl ring as defined above.

As used herein, the term "$C_{3-6}$cycloalkylcarbonyl" refers to a —C(O)$R^a$ radical, wherein $R^a$ is a $C_{3-6}$cycloalkyl ring as defined above.

As used herein, the term "$C_{3-6}$cycloalkylcarbonyloxy" refers to a —OC(O)$R^a$ radical wherein $R^a$ is a $C_{3-6}$cycloalkyl ring as described above.

As used herein, the term "$C_{3-6}$cycloalkylcarbonyloxy$C_{1-4}$ alkyl" refers to a $C_{3-6}$cycloalkylcarbonyloxy group as described above attached to the rest of the molecule by a $C_{1-4}$alkylene radical as defined above.

As used herein, the term "phenyl$C_{0-6}$alkyl" refers to a phenyl ring attached to the rest of the molecule by a single bond or by a $C_{1-6}$alkylene radical as defined above. "phenyl$C_{1-6}$alkyl" and "phenyl$C_{1-2}$alkyl" are to be construed accordingly. Examples of phenyl$C_{0-6}$alkyl include, but are not limited to, phenyl, benzyl or 2-phenylethyl.

As used herein, the term "phenyl$C_{1-2}$alkoxy" refers to a $C_{1-2}$alkoxy radical as generally defined above substituted by a phenyl ring.

As used herein, the term "phenyl$C_{2-6}$alkenyl" refers to a $C_{2-6}$alkenyl radical as generally defined above substituted by a phenyl ring.

As used herein, the term "phenylcarbonyloxy" refers to a —OC(O)$R^a$ radical wherein $R^a$ is a phenyl ring.

As used herein, the term "phenylcarbonyloxy$C_{1-4}$alkyl" refers to a phenylcarbonyloxy group as described above attached to the rest of the molecule by a $C_{1-4}$alkylene radical as defined above.

As used herein, the term "naphthyl$C_{0-6}$alkyl" refers to a naphthalene ring attached to the rest of the molecule by a single bond or by a $C_{1-6}$alkylene radical as defined above.

As used herein, the term "heteroaryl$C_{0-6}$alkyl" refers to a heteroaryl ring as described above attached to the rest of the molecule by a single bond or by a $C_{1-6}$alkylene radical as defined above. "Heteroaryl$C_{1-6}$alkyl" and "heteroaryl$C_{1-2}$alkyl" are to be construed accordingly.

As used herein, the term "heteroaryl$C_{1-6}$alkoxy" refers to a $C_{1-6}$alkoxy radical as generally defined above substituted by a heteroaryl group as generally defined above. Heteroaryl$C_{1-2}$alkoxy" is to be construed accordingly.

As used herein, the term "heterodiaryl$C_{0-6}$ alkyl" refers to a heterodiaryl ring as described above attached to the rest of the molecule by a single bond or by a $C_{1-6}$alkylene radical as defined above. "Heterodiaryl$C_{1-6}$alkyl" and "heterodiaryl$C_{1-2}$alkyl" are to be construed accordingly.

As used herein, the term "heterocyclyl$C_{0-6}$alkyl" refers to a heterocyclyl ring as described above attached to the rest of the molecule by a single bond or by a $C_{1-6}$alkylene radical as defined above. "Heterocyclyl$C_{1-6}$alkyl" and "heterocyclyl$C_{1-2}$alkyl" are to be construed accordingly.

As used herein, the term "heterocyclyl$C_{1-6}$alkoxy" refers to a $C_{1-6}$alkoxy radical as generally defined above substituted by a heterocyclyl group as generally defined above. "Heterocyclyl$C_{1-2}$alkoxy" is to be construed accordingly.

As used herein, the term "heterocyclylcarbonyloxy" refers to a —OC(O)$R^a$ radical wherein $R^a$ is a heteroaryl ring as described above.

As used herein, the term "heterocyclylcarbonyloxy$C_{1-4}$ alkyl" refers to a heterocyclylcarbonyloxy group as described above attached to the rest of the molecule by a $C_{1-4}$alkylene radical as defined above.

As used herein, the term "$C_{3-6}$cycloalkylcarbonylamino$C_{1-6}$alkyl" refers to a a radical of the formula —$R_a$NHC(O)$R_b$, wherein $R_a$ is a $C_{1-6}$alkyl radical as defined above and $R_b$ is a $C_{3-6}$cycloalkyl ring as described above.

The presence of one or more possible asymmetric carbon atoms in a compound of formula (I) means that the compounds may occur in chiral isomeric forms, i.e., enantiomeric or diastereomeric forms. Also atropisomers may occur as a result of restricted rotation about a single bond. Formula (I) is intended to include all those possible isomeric forms and mixtures thereof. The present invention includes all those possible isomeric forms and mixtures thereof for a compound of formula (I). Likewise, formula (I) is intended to include all possible tautomers (including lactam-lactim tautomerism and keto-enol tautomerism) where present. The present invention includes all possible tautomeric forms for a compound of formula (I).

In each case, the compounds of formula (I) according to the invention are in free form, in covalently hydrated form, in oxidized form as an N-oxide or in salt form, e.g., an agronomically usable or agrochemically acceptable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

The following list provides definitions, including preferred definitions, for substituents n, $A^1$, $A^2$, $A^3$, $A^4$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ with reference to the compounds of formula (I). For any one of these substituents, any of the definitions given below may be combined with any definition of any other substituent given below or elsewhere in this document.

n represents 1 or 2. In some embodiments of the invention, n is 1, In other embodiments of the invention, n is 2. Preferably, n is 1.

$A^1$ represents N or $CR^1$, wherein $R^1$ is hydrogen, halogen, methyl, ethyl, difluoromethyl, trifluoromethyl, methoxy, ethoxy, or difluoromethoxy.

$A^2$ represents N or $CR^2$, wherein $R^2$ is hydrogen, halogen, methyl, ethyl, difluoromethyl, trifluoromethyl, methoxy, ethoxy, or difluoromethoxy.

$A^3$ represents N or $CR^3$, wherein $R^3$ is hydrogen or halogen.

$A^4$ represents N or $CR^4$, wherein $R^4$ is hydrogen or halogen. and wherein 0, 1 or 2 of $A^1$, $A^2$, $A^3$ and $A^4$ are N;

$R^1$ and $R^2$ are independently selected from hydrogen, halogen, methyl, ethyl. difluoromethyl, trifluoromethyl, methoxy, ethoxy, or difluoromethoxy. Preferably, $R^1$ and $R^2$ are independently selected from hydrogen and halogen. More preferably, $R^1$ and $R^2$ are hydrogen.

$R^3$ and $R^4$ are independently selected from hydrogen and halogen. Preferably, $R^3$ and $R^4$ are independently selected from hydrogen and fluoro. More preferably, $R^3$ and $R^4$ are hydrogen.

$A^3$ may represent $CR^3$, wherein $R^3$ is hydrogen or halogen.

$A^4$ may represent $CR^4$, wherein $R^4$ is hydrogen or halogen.

In the compounds according to Formula (I), at least two of $R^1$, $R^2$, $R^3$ and $R^4$ may be hydrogen. Preferably, three of $R^1$, $R^2$, $R^3$ and $R^4$ may be hydrogen, wherein more preferably $R^2$, $R^3$ and $R^4$ are hydrogen.

In some embodiments of the invention, the 6-membered ring comprising $A^1$ to $A^4$ is a phenyl (where $A^1$ to $A^4$ are C—H), pyridinyl (where $A^1$ or $A^3$ is N and the other A positions are C—H), pyrimidinyl (where $A^1$ and $A^3$ are N and the other A positions are C—H), fluorophenyl (where $A^1$ or $A^3$ are C—F (preferably $A^3$ is C—F) and the other A positions are C—H) or difluorophenyl (where $A^1$ and $A^3$ are C—F and the $A^2$ and $A^4$ positions are C—H) group.

In the compounds according to Formula (I), when $R^8$ is not —$OR^{12}$ or —$NR^{14}R^{15}$, preferably $A^1$, $A^2$, $A^3$ and $A^4$ are C—H; $A^2$, $A^3$ and $A^4$ are C—H and $A^1$ is N; $A^1$, $A^2$ and $A^4$ are C—H and $A^3$ is N; $A^1$, $A^2$ and $A^4$ are C—H and $A^3$ is C-halogen (preferably fluoro); $A^2$, $A^3$ and $A^4$ are C—H and $A^1$ is C-halogen (preferably fluoro) or $A^2$, $A^3$ and $A^4$ are C—H and $A^1$ is C-halogen (preferably fluoro); $A^2$ and $A^4$ are C—H and $A^1$ and $A^3$ are C-halogen (preferably fluoro); or $A^3$ and $A^4$ are C—H and $A^1$ and $A^2$ are C-halogen (preferably fluoro). More preferably, $A^1$, $A^2$, $A^3$, and $A^4$ are C—H.

In the compounds according to Formula (I), when $R^8$ is —$OR^{12}$, preferably $A^1$, $A^2$, $A^3$ and $A^4$ are C—H.

In the compounds according to Formula (I), when $R^8$ is —$NR^{14}R^{15}$, preferably $A^1$, $A^2$, $A^3$ and $A^4$ are C—H; $A^1$, $A^2$ and $A^4$ are C—H and $A^3$ is C-halogen (preferably fluoro); or $A^2$, $A^3$ and $A^4$ are C—H and $A^1$ is C-halogen (preferably fluoro). More preferably, $A^1$, $A^2$, $A^3$ and $A^4$ are C—H.

$R^5$ and $R^6$ independently represent hydrogen, $C_{1-4}$alkyl, halogen, cyano, trifluoromethyl and difluoromethyl, or $R^5$ and $R^6$ together with the carbon atom they share form a cyclopropyl. Preferably, $R^5$ and $R^6$ may be independently selected from hydrogen, $C_{1-4}$alkyl, halogen, cyano, trifluoromethyl and difluoromethyl, or $R^5$ and $R^6$ together with the carbon atom they share form a cyclopropyl. More preferably, $R^5$ and $R^6$ are independently selected from hydrogen, $C_{1-4}$alkyl (in particular methyl) and cyano.

In the compounds according to Formula (I), when $R^8$ is not —OR or —$NR^{14}R^{15}$, preferably $R^5$ and $R^6$ are hydrogen; $R^5$ is hydrogen and $R^6$ is methyl; or $R^5$ is hydrogen and $R^6$ is cyano. More preferably, $R^5$ and $R^6$ are hydrogen and n is 1.

In the compounds according to Formula (I), when $R^8$ is —$OR^{12}$, preferably $R^5$ and $R^6$ are hydrogen and n is 1.

In the compounds according to Formula (I), when $R^8$ is —$NR^{14}R^{15}$, preferably $R^5$ and $R^6$ are hydrogen and n is 1.

$R^7$ is hydroxy, $C_{1-4}$alkyl, $C_{2-4}$ haloalkyl, $C_{1-4}$alkoxy, hydroxy$C_{1-4}$alkyl, $C_{1-2}$alkoxy$C_{1-4}$alkyl, $C_{1-2}$haloalkoxy$C_{1-4}$alkyl, $C_{3-4}$alkynyl, $C_{3-6}$alkenyl, $C_{3-6}$alkenyloxy, $C_{3-6}$alkynyloxy, $C_{3-6}$ haloalkenyl, $C_{3-6}$haloalkenyloxy, $C_{1-4}$alkylcarbonyloxy, $C_{1-4}$ haloalkylcarbonyloxy, $C_{1-4}$alkoxycarbonyloxy, $C_{1-4}$alkylcarbonyloxy$C_1$alkyl, $C_{1-4}$haloalkylcarbonyloxy$C_1$alkyl, $C_{1-4}$alkoxycarbonyloxy$C_{1-4}$alkyl; or $R^7$ is $C_{3-6}$cycloalkyl, $C_{3-6}$cycloalkyl$C_{1-2}$alkyl, $C_{3-6}$cycloalkyl$C_{1-2}$alkoxy, phenyl, phenyl$C_{1-2}$alkyl, phenyl$C_{1-2}$alkoxy, heteroaryl, heteroaryl$C_{1-2}$alkyl, heteroaryl$C_{1-2}$alkoxy, heterocyclyl, heterocyclyl$C_{1-2}$alkyl, heterocyclyl$C_{1-2}$alkoxy, $C_{3-6}$cycloalkylcarbonyloxy, heterocyclylcarbonyloxy, phenylcarbonyloxy, $C_{3-6}$cycloalkylcarbonyloxy$C_{1-4}$alkyl, heterocyclylcarbonyloxy$C_{1-4}$alkyl or phenylcarbonyloxy$C_{1-4}$alkyl; wherein the heteroaryl moiety is a 5- or 6-membered monocyclic aromatic ring which comprises 1, 2, 3 or 4 heteroatoms individually selected from N, O and S, the heterocyclyl moiety is a 4- to 6-membered non-aromatic ring which comprises 1 or 2 heteroatoms individually selected from N, O and S, and wherein any of said cycloalkyl, phenyl, heteroaryl and heterocyclyl moieties are optionally substituted by 1 or 2 substituents selected from cyano, fluoro, chloro, bromo, methyl, difluoromethyl, trifluoromethyl, methoxy, ethoxy, or difluoromethoxy.

Preferably, $R^7$ is $C_{1-4}$alkyl, $C_{1-4}$alkoxy, $C_{1-2}$alkoxy$C_{1-4}$alkyl, $C_{1-2}$ haloalkoxy$C_{1-4}$alkyl, $C_{3-6}$alkenyl, $C_{3-4}$alkynyl, $C_{3-6}$alkenyloxy, $C_{3-6}$alkynyloxy, $C_{3-6}$ haloalkenyl, $C_{3-6}$ haloalkenyloxy, $C_{3-6}$cycloalkyl, $C_{3-6}$cycloalkyl$C_{1-2}$alkyl, $C_{3-6}$cycloalkyl$C_{1-2}$alkoxy, phenyl, phenyl$C_{1-2}$alkyl, phenyl$C_{1-2}$alkoxy, heteroaryl, heteroaryl$C_{1-2}$alkyl, heteroaryl$C_{1-2}$alkoxy, heterocyclyl, heterocyclyl$C_{1-2}$alkyl, or heterocyclyl$C_{1-2}$alkoxy.

More preferably, $R^7$ is $C_{1-4}$alkyl, $C_{1-4}$alkoxy, $C_{1-2}$alkoxy$C_{1-4}$alkyl, $C_{3-6}$alkenyl, $C_{3-4}$alkynyl, $C_{3-6}$alkenyloxy, $C_{3-6}$ haloalkenyl, $C_{3-6}$ haloalkenyloxy, $C_{3-6}$cycloalkyl, $C_{3-6}$cycloalkyl$C_{1-2}$alkyl, phenyl$C_{1-2}$alkoxy, heteroaryl$C_{1-2}$alkyl, or heterocyclyl$C_{1-2}$alkyl.

In the compounds according to Formula (I), when $R^8$ is not —$OR^{12}$ or —$NR^{14}R^{15}$, preferably $R^7$ is hydroxy, $C_{1-4}$alkyl, $C_{2-4}$ haloalkyl, $C_{1-4}$alkoxy, hydroxy$C_{1-4}$alkyl, $C_{1-2}$alkoxy$C_{1-4}$alkyl, $C_{3-6}$alkenyl, $C_{3-4}$alkynyl, $C_{3-6}$ haloalkenyloxy, $C_{3-6}$cycloalkyl, $C_{3-6}$cycloalkyl$C_{1-2}$alkyl, phenyl$C_{1-2}$alkoxy, heterocyclyl, heterocyclyl$C_{1-2}$alkyl, heteroaryl or heteroaryl$C_{1-2}$alkyl, wherein the heteroaryl moiety is a 5-membered monocyclic aromatic ring which comprises 1 or 2 heteroatoms individually selected from N, O and S, the heterocyclyl moiety is a 5-membered non-aromatic ring which comprises 1 or 2 heteroatoms individually selected from N, O and S, and wherein any of said cycloalkyl, phenyl, heteroaryl and heterocyclyl moieties are optionally substituted by 1 or 2 substituents selected from cyano, fluoro, chloro, bromo, methyl, difluoromethyl, trifluoromethyl, methoxy, ethoxy, or difluoromethoxy. More preferably, $R^7$ is hydroxy, $C_{1-4}$alkyl, $C_{2-4}$fluoroalkyl, $C_{1-4}$alkoxy, hydroxy$C_{1-4}$alkyl, $C_{1-2}$alkoxy$C_{1-4}$alkyl, $C_{3-4}$alkenyl, $C_{3-4}$alkynyl, $C_{3-6}$ haloalkenyloxy, cyclopropyl, (cyclopropyl)methyl, phenyl$C_{1-2}$alkoxy, (tetrahydrofuran-2-yl)methyl or (2-furyl)methyl, wherein any of said cyclopropyl, phenyl, tetrahydrofuran-2-yl and 2-furyl moieties are optionally substituted by 1 or 2 substituents selected from cyano, fluoro, chloro, bromo, methyl, difluoromethyl, trifluoromethyl, methoxy, ethoxy, or difluoromethoxy.

In the compounds according to Formula (I), when $R^8$ is not —$OR^{12}$ or —$NR^{14}R^{15}$, still more preferably $R^7$ is $C_{1-4}$alkyl, $C_{2-4}$ haloalkyl, $C_{1-4}$alkoxy or $C_{3-6}$cycloalkyl. Further more preferably, $R^7$ is $C_{1-4}$alkyl, $C_{2-4}$fluoroalkyl, methoxy, ethoxy or cyclopropyl. Most preferably, $R^7$ is methyl, ethyl, n-propyl, iso-propyl, 2,2,2-fluoroethyl, methoxy, ethoxy or cyclopropyl.

In the compounds according to Formula (I), when $R^8$ is —$OR^{12}$, preferably $R^7$ is hydroxy, $C_{1-4}$alkyl, $C_{2-4}$ haloalkyl, $C_{1-4}$alkoxy, $C_{3-6}$alkenyl, $C_{3-4}$alkynyl, $C_{1-4}$alkoxycarbonyloxy. More preferably, $R^7$ is hydroxy, $C_{1-4}$alkyl, $C_{2-4}$ haloalkyl, $C_{1-4}$alkoxy, $C_{3-4}$alkenyl, $C_{3-4}$alkynyl, $C_{1-4}$alkoxycarbonyloxy. Even more preferably, $R^7$ is $C_{1-4}$alkoxy, in particular, methoxy.

In the compounds according to Formula (I), when $R^8$ is —$NR^{14}R^{15}$, preferably $R^7$ is hydroxy, $C_{1-4}$alkyl, $C_{2-4}$ haloalkyl, $C_{1-4}$alkoxy, $C_{3-4}$alkenyl, $C_{3-4}$alkynyl, $C_{3-6}$cycloalkyl. More preferably, $R^7$ is hydroxy, $C_{1-4}$alkyl, $C_2$ haloalkyl, $C_{1-2}$alkoxy, $C_{3-4}$alkenyl, $C_{3-4}$alkynyl, cyclopropyl. Even more preferably, $R^7$ is $C_{1-4}$alkyl or $C_{1-4}$alkoxy, and in particular, methyl, ethyl or methoxy.

$R^8$ is hydrogen, $C_{1-6}$alkyl, $C_{2-6}$alkenyl, $C_{2-6}$alkynyl, cyano$C_{1-6}$alkyl, $C_{1-6}$haloalkyl, $C_{2-6}$haloalkenyl, hydroxy$C_{1-6}$alkyl, $C_{1-4}$alkoxy$C_{1-6}$alkyl, $C_{1-4}$ haloalkoxy$C_{1-6}$alkyl, $C_{1-4}$alkoxy$C_{1-4}$alkoxy$C_{1-6}$alkyl, $C_{2-4}$alkynyloxy$C_{1-6}$alkyl, amino$C_{1-6}$alkyl, N—$C_{1-4}$alkylamino$C_{1-6}$alkyl, N,N-di$C_{1-4}$alkylamino$C_{1-6}$alkyl, $C_{1-6}$alkylcarbonyl$C_{1-6}$alkyl, $C_{1-6}$alkylcarbonyl$C_{2-6}$alkenyl, $C_{1-6}$alkoxycarbonyl$C_{1-6}$alkyl, $C_{1-6}$alkylcarbonyloxy$C_{1-6}$alkyl, N—$C_{1-4}$alkylaminocarbonyl$C_{1-6}$alkyl, N,N-di$C_{1-4}$alkylaminocarbonyl$C_{1-6}$alkyl, $C_{1-6}$alkylsulfanyl$C_{1-6}$alkyl, $C_{1-6}$alkylsulfonyl$C_{1-6}$alkyl, $C_{1-6}$alkylsulfonylamino$C_{1-6}$alkyl, $C_{1-6}$alkylsulfonylamino$C_{2-6}$alkynyl, $C_{2-6}$alkynyloxycarbonylamino$C_{1-6}$alkyl, $C_{1-4}$alkylcarbonylamino$C_{1-6}$alkyl, $C_{1-4}$alkoxycarbonylamino$C_{1-6}$alkyl; or $R^8$ is $C_{3-8}$cycloalkyl, $C_{3-8}$cycloalkyl$C_{1-6}$alkyl, wherein the cycloalkyl moiety is optionally partially unsaturated, phenyl, phenyl$C_{1-6}$alkyl, phenyl$C_{2-6}$alkenyl, napthyl, naphthyl$C_{1-6}$alkyl, heteroaryl, heteroaryl$C_{1-6}$alkyl, wherein the heteroaryl moiety is a 5- or 6-membered monocyclic aromatic ring which comprises 1, 2, 3 or 4 heteroatoms individually selected from N, O and S, heterodiaryl, heterodiaryl$C_{1-6}$alkyl wherein the heterodiaryl moiety is a 9- or 10-membered bicyclic aromatic system which comprises 1, 2, 3 or 4 heteroatoms individually selected from N, O and S, heterocyclyl, heterocyclyl$C_{1-6}$alkyl wherein the heterocyclyl moiety is a 4- to 6-membered non-aromatic ring which comprises 1, 2 or 3 heteroatoms individually selected from N, O and S, or $C_{3-6}$cycloalkylcarbonylamino$C_{1-6}$alkyl, wherein for $R^8$, any cycloalkyl, phenyl, napthyl, heteroaryl, heterodiaryl, heterocyclyl moiety is optionally substituted by 1, 2 or 3 substituents, which may be the same or different, selected from $R^9$; or, additionally, when $R^8$ is cyclopropyl, the cyclopropyl moiety is substituted by 4 substituents, which may be the same or different, selected from $R^9$, with the proviso that at least 2 $R^9$ substituents are the same; wherein $R^9$ is cyano, halogen, hydroxy, $C_{1-4}$alkyl, $C_{2-4}$alkenyl, $C_{2-4}$alkynyl, $C_{1-4}$ haloalkyl, $C_{2-4}$ haloalkenyl, $C_{1-4}$alkoxy, $C_{1-4}$ haloalkoxy, $C_{3-4}$alkynyloxy, N—$C_{1-4}$alkylamino, N,N-di$C_{1-4}$alkylamino, $C_{1-4}$alkylcarbonyl, $C_{3-6}$cycloalkylcarbonyl, $C_{1-4}$alkoxycarbonyl, carbonylamino, N—$C_{1-4}$alkylaminocarbonyl, N,N-di$C_{1-4}$alkylaminocarbonyl or $C_{1-4}$alkoxycarbonylamino, and wherein when $R_8$ is substituted $C_{3-8}$cycloalkyl, $C_{3-8}$cycloalkyl$C_{1-6}$alkyl, heterocyclyl, or heterocyclyl$C_{1-6}$alkyl, $R^9$ may also represent oxo on the $C_{3-8}$cycloalkyl or heterocyclyl moiety; or wherein for $R^8$, any cycloalkyl, phenyl, napthyl, heteroaryl, heterodiaryl, heterocyclyl, moiety is optionally substituted by 1 substituent selected from $R^{10}$ and further optionally substituted by 1 or 2 substituents selected from $R^9$; wherein $R^{10}$ is $C_{3-8}$cycloalkyl, $C_{3-8}$cycloalkyl$C_{1-2}$alkyl, phenyl, phenyl$C_{1-2}$alkyl, heteroaryl, heteroaryl$C_{1-2}$alkyl wherein the heteroaryl moiety is a 5- or 6-membered monocyclic aromatic ring which comprises 1, 2, 3 or 4 heteroatoms individually selected from N, O and S, heterocyclyl, heterocyclyl$C_{1-6}$alkyl wherein the heterocyclyl moiety is a 4- to 6-membered non-aromatic ring which comprises 1, 2 or 3 heteroatoms individually selected from N, O and S, and wherein any of said cycloalkyl, phenyl, heteroaryl and heterocyclyl moieties are optionally substituted by 1, 2 or 3 substituents, which may be the same or different, selected from $R^{11}$; wherein $R^{11}$ is hydrogen, cyano, fluoro, chloro, bromo, methyl, trifluoromethyl, methoxy and ethoxy.

In some embodiments of the compounds according to Formula (I), $R^8$ is hydrogen, $C_{1-6}$alkyl, $C_{2-6}$alkenyl, $C_{2-6}$alkynyl, cyano$C_{1-6}$alkyl, $C_{1-6}$ haloalkyl, $C_{1-6}$ haloalkenyl, hydroxy$C_{1-6}$alkyl, $C_{1-4}$alkoxy$C_{1-6}$alkyl, $C_{1-4}$ haloalkoxy$C_{1-6}$alkyl, $C_{1-4}$alkoxy$C_{1-4}$alkoxy$C_{1-6}$alkyl, $C_{2-4}$alkynyloxy$C_{1-6}$alkyl, amino$C_{1-6}$alkyl, N—$C_{1-4}$alkylamino$C_{1-6}$alkyl, N,N-di$C_{1-4}$alkylamino$C_{1-6}$alkyl, $C_{1-6}$alkylcarbonyl$C_{1-6}$alkyl, $C_{1-6}$alkylcarbonyl$C_{2-6}$alkenyl, $C_{1-6}$alkoxycarbonyl$C_{1-6}$alkyl, $C_{1-6}$alkylcarbonyloxy$C_{1-6}$alkyl, N—$C_{1-4}$alkylaminocarbonyl$C_{1-6}$alkyl, N,N-di$C_{1-4}$alkylaminocarbonyl$C_{1-6}$alkyl, $C_{1-6}$alkylsulfanyl$C_{1-6}$alkyl, $C_{1-6}$alkylsulfonyl$C_{1-6}$alkyl, $C_{1-6}$alkylsulfonylamino$C_{1-6}$alkyl, $C_{1-6}$alkylsulfonylamino$C_{2-6}$alkynyl, or $C_{2-6}$alkynyloxycarbonylamino$C_{1-6}$alkyl.

In some embodiments of the compounds according to Formula (I), $R^8$ is $C_{3-8}$cycloalkyl, $C_{3-8}$cycloalkyl$C_{1-6}$alkyl, wherein the cycloalkyl moiety is optionally partially unsaturated, phenyl, phenyl$C_{1-6}$alkyl, phenyl$C_{2-6}$alkenyl, napthyl, naphthyl$C_{1-6}$alkyl, heteroaryl, heteroaryl$C_{1-6}$alkyl, wherein the heteroaryl moiety is a 5- or 6-membered monocyclic aromatic ring which comprises 1, 2, 3 or 4 heteroatoms individually selected from N, O and S, heterodiaryl, heterodiaryl$C_{1-6}$alkyl wherein the heterodiaryl moiety is a 9- or 10-membered bicyclic aromatic system which comprises 1, 2, 3 or 4 heteroatoms individually selected from N, O and S, heterocyclyl, heterocyclyl$C_{1-6}$alkyl wherein the heterocyclyl moiety is a 4- to 6-membered non-aromatic ring which comprises 1, 2 or 3 heteroatoms individually selected from N, O and S, and $C_{3-6}$cycloalkylcarbonylamino$C_{1-6}$alkyl. At least one of $C_{3-8}$cycloalkyl, $C_{3-8}$cycloalkyl$C_{1-6}$alkyl, phenyl, phenyl$C_{1-6}$alkyl, phenyl$C_{2-6}$alkenyl, napthyl, naphthyl$C_{1-6}$alkyl, heteroaryl, heteroaryl$C_{1-6}$alkyl, heterodiaryl, heterodiaryl$C_{1-6}$alkyl, heterocyclyl, heterocyclyl$C_{1-6}$alkyl and $C_{3-6}$cycloalkylcarbonylamino$C_{1-6}$alkyl moieties may be substituted by 1, 2 or 3 substituents selected from cyano, halogen, hydroxy, $C_{1-4}$alkyl, $C_{2-4}$alkenyl, $C_{2-4}$alkynyl, $C_{1-4}$ haloalkyl, $C_{2-4}$haloalkenyl, $C_{1-4}$alkoxy, $C_{1-4}$ haloalkoxy, $C_{3-4}$alkynyloxy, N—$C_{1-4}$alkylamino, N,N-di$C_{1-4}$alkylamino, $C_{1-4}$alkylcarbonyl, $C_{1-4}$alkoxycarbonyl, carbonylamino, N—$C_{1-4}$alkylaminocarbonyl, N,N-di$C_{1-4}$alkylaminocarbonyl and $C_{1-4}$alkoxycarbonylamino.

Preferably, $R^8$ is hydrogen, $C_{1-6}$alkyl, $C_{2-6}$alkenyl, $C_{2-6}$alkynyl, cyano$C_{1-6}$alkyl, $C_{1-6}$ haloalkyl, $C_{2-6}$haloalkenyl, hydroxy$C_{1-6}$alkyl, $C_{1-4}$alkoxy$C_{1-6}$alkyl, $C_{1-4}$ haloalkoxy$C_{1-6}$alkyl, $C_{1-4}$alkoxy$C_{1-4}$alkoxy$C_{1-6}$alkyl, $C_{2-4}$alkynyloxy$C_{1-6}$alkyl, amino$C_{1-6}$alkyl, $C_{1-6}$alkylcarbonyl$C_{1-6}$alkyl, $C_{1-6}$alkylcarbonyl$C_{2-6}$alkenyl, $C_{1-6}$alkylcarbonyloxy$C_{1-6}$alkyl, $C_{1-6}$alkylsulfonylamino$C_{2-6}$alkynyl, $C_{2-6}$alkynyloxycarbonylamino$C_{1-6}$alkyl, $C_{1-4}$alkylcarbonylamino$C_{1-6}$alkyl, $C_{1-4}$alkoxycarbonylamino$C_{1-6}$alkyl; or $R^8$ is $C_{3-8}$cycloalkyl, $C_{3-8}$cycloalkyl$C_{1-6}$alkyl, wherein the cycloalkyl moiety is optionally partially unsaturated, phenyl, phenyl$C_{1-6}$alkyl, phenyl$C_{2-6}$alkenyl, napthyl, heteroaryl, heteroaryl$C_{1-6}$alkyl, wherein the heteroaryl moiety is a 5- or 6-membered monocyclic aromatic ring which comprises 1, 2, 3 or 4 heteroatoms individually selected from N, O and S, heterocyclyl, heterocyclyl$C_{1-6}$alkyl wherein the heterocyclyl moiety is a 4- to 6-membered non-aromatic ring which comprises 1, 2 or 3 heteroatoms individually selected from N, O and S, or $C_{3-6}$cycloalkylcarbonylamino$C_{1-6}$alkyl, wherein for $R^8$, any of $C_{3-8}$cycloalkyl, $C_{3-8}$cycloalkyl$C_{1-6}$alkyl, phenyl, phenyl$C_{1-6}$alkyl, phenyl$C_{2-6}$alkenyl, napthyl, heteroaryl, heteroaryl$C_{1-6}$alkyl, heterocyclyl and heterocyclyl$C_{1-6}$alkyl moieties are optionally substituted by 1, 2 or 3 substituents, which may be the same or different, selected from $R^9$; wherein $R^9$ is cyano, halogen, hydroxy, $C_{2-4}$ haloalkenyl, $C_{1-4}$alkoxy, $C_{1-4}$ haloalkoxy, $C_{3-4}$alkynyloxy, $C_{1-4}$alkylcarbonyl, $C_{3-6}$cycloalkylcarbonyl, $C_{1-4}$alkoxycarbonyl, carbonylamino; or wherein for $R^8$, any of $C_{3-8}$cycloalkyl, phenyl moieties are optionally substituted by 1 substituent selected from $R^{10}$ and are further optionally substituted by 1 or 2 substituents selected from $R^9$; wherein $R^{10}$ is phenyl, heteroaryl wherein the heteroaryl moiety is a 5- or 6-membered monocyclic aromatic ring which comprises 1, 2, 3 or 4 heteroatoms individually selected from N, O and S, and wherein any of said phenyl and heteroaryl moieties are optionally substituted by a single substituents selected from $R^{11}$; wherein $R^{11}$ is cyano, fluoro, chloro, bromo, methyl, trifluoromethyl, methoxy and ethoxy.

More preferably, $R^8$ is $C_{1-6}$alkyl, $C_{2-4}$alkenyl, $C_{2-4}$alkynyl, cyano$C_{1-4}$alkyl, $C_{1-6}$ haloalkyl, $C_{2-4}$haloalkenyl, hydroxy$C_{1-4}$alkyl, $C_{1-2}$alkoxy$C_{1-4}$alkyl, $C_{1-2}$haloalkoxy$C_{1-4}$ alkyl, $C_{1-2}$alkoxy$C_{1-2}$alkoxy$C_{1-4}$alkyl, $C_{2-4}$alkynyloxy$C_{1-4}$ alkyl, amino$C_{1-4}$alkyl, $C_{1-4}$alkylcarbonyl$C_{1-4}$alkyl, $C_{1-4}$alkylcarbonyl$C_{2-4}$alkenyl, $C_{1-4}$alkylcarbonyloxy$C_{1-4}$alkyl, $C_{1-4}$alkylsulfonylamino$C_{2-4}$alkynyl, $C_{2-4}$alkynyloxycarbonylamino$C_{1-4}$alkyl, $C_{1-2}$alkylcarbonylamino$C_{1-4}$alkyl, $C_{1-2}$alkoxycarbonylamino$C_{1-4}$alkyl; or $R^8$ is $C_{3-6}$cycloalkyl, $C_{3-6}$cycloalkyl$C_{1-2}$alkyl, wherein the cycloalkyl moiety is optionally partially unsaturated, phenyl, phenyl$C_{1-4}$alkyl, phenyl$C_{2-4}$alkenyl, napthyl, heteroaryl, heteroaryl$C_{1-2}$alkyl, wherein the heteroaryl moiety is a 5- or 6-membered monocyclic aromatic ring which comprises 1, 2 or 3 heteroatoms individually selected from N, O and S, heterocyclyl, heterocyclyl$C_{1-2}$alkyl wherein the heterocyclyl moiety is a 4- to 6-membered non-aromatic ring which comprises 1, 2 or 3 heteroatoms individually selected from N, O and S, or $C_{3-6}$cycloalkylcarbonylamino$C_{1-4}$alkyl, wherein for $R^8$, any of $C_{3-6}$cycloalkyl, $C_{3-6}$cycloalkyl$C_{1-2}$alkyl, phenyl, phenyl$C_{1-2}$alkyl, phenyl$C_{2-4}$alkenyl, napthyl, heteroaryl, heteroaryl$C_{1-2}$alkyl, heterocyclyl and heterocyclyl$C_{1-2}$alkyl moieties are optionally substituted by 1, 2 or 3 substituents, which may be the same or different, selected from $R^9$; wherein $R^9$ is cyano, halogen, hydroxy, $C_{1-4}$alkyl, $C_{1-4}$ haloalkyl, $C_{2-4}$ haloalkenyl, $C_{1-4}$alkoxy, $C_{1-4}$ haloalkoxy, $C_{3-4}$alkynyloxy, $C_{1-4}$alkylcarbonyl, $C_{3-6}$cycloalkylcarbonyl, $C_{1-4}$alkoxycarbonyl, carbonylamino; or wherein for $R^8$, any of $C_{3-6}$cycloalkyl, phenyl moieties are optionally substituted by 1 substituent selected from $R^{10}$ and are further optionally substituted by 1 or 2 substituents selected from $R^9$; wherein $R^{10}$ is phenyl, heteroaryl wherein the heteroaryl moiety is a 5- or 6-membered monocyclic aromatic ring which comprises 1, 2, 3 or 4 heteroatoms individually selected from N, O and S, and wherein any of said phenyl and heteroaryl moieties are optionally substituted by a single substituents selected from $R^{11}$; wherein $R^{11}$ is cyano, fluoro, chloro, bromo, methyl, trifluoromethyl, methoxy and ethoxy.

Even more preferably, $R^8$ is $C_{1-6}$alkyl, $C_{2-4}$alkenyl, $C_{2-4}$alkynyl, cyano$C_{1-4}$alkyl, $C_{1-6}$ haloalkyl, $C_{2-4}$haloalkenyl, hydroxy$C_{1-4}$alkyl, $C_{1-2}$alkoxy$C_{1-4}$alkyl, $C_{1-2}$haloalkoxy$C_{1-4}$ alkyl, $C_{1-2}$alkoxy$C_{1-2}$alkoxy$C_{1-4}$alkyl, amino$C_{1-4}$alkyl, $C_{1-2}$alkylcarbonyl$C_{1-4}$alkyl, $C_{1-4}$alkylcarbonyl$C_{2-4}$alkenyl, $C_{1-4}$alkylcarbonyloxy$C_{1-4}$alkyl, $C_{1-4}$alkylsulfonylamino$C_{2-4}$alkynyl, $C_{1-2}$alkylcarbonylamino$C_{1-4}$alkyl, $C_{2-4}$alkynyloxycarbonylamino$C_{1-4}$alkyl, $C_{1-2}$alkoxycarbonylamino$C_{1-4}$alkyl; or $R^8$ is $C_{3-6}$cycloalkyl, $C_{3-6}$cycloalkyl$C_{1-2}$alkyl, phenyl, phenyl$C_{1-4}$alkyl, phenyl$C_{2-4}$alkenyl, napthyl, a heteroaryl-containing moiety selected from furanyl (including furan-2-yl, furan-3-yl), pyrazolyl (including pyrazol-1-yl, pyrazol-3-yl, pyrazol-4-yl, pyrazol-5-yl), imidazolyl (including imidazol-1-yl, imidazol-2-yl, imidazol-4-yl, imidazol-5-yl), triazolyl (including 1,2,3-triazol-1-yl), 1,2,3-benzothiadiazole, (pyridinyl)methyl (including pyridin-2-methyl, pyridin-3-methyl, pyridin-4-methyl), or a heterocyclyl-containing moiety selected from oxetanyl (including oxetan-2-yl, oxetan-3-yl), pyrrolidinyl (including pyrrolidin-2-yl, pyrrolidin-3-yl), azetidinyl (including azetidin-2-yl, azetidin-3-yl), tetrahydrofuranyl (including tetrahydrofuran-2-yl, tetrahydrofuran-3-yl), 1,3-dioxolanyl (including 1,3-dioxolan-2-yl), thietanyl (including thietan-2-yl, thietan-3-yl), 1-oxo-thietan-3-yl, 1,1-dioxo-thietan-3-yl, tetrahydropyranyl (including tetrahydropyran-2-yl, tetrahydropyran-3-yl, tetrahydropyran-4-yl), tetrahydrothiopyranyl (including tetrahydrothiopyran-2-yl, tetrahydrothiopyran-3-yl, tetrahydrothiopyran-4-yl), $C_{3-6}$cycloalkylcarbonylamino$C_{1-4}$alkyl, wherein the cycle of each heteroaryl-containing moiety or heterocyclyl-containing moiety is optionally substituted by 1 or 2 or 3 substituents, which may be the same of different, selected from $R^9$; wherein $R^9$ is cyano, methyl, chloro, fluoro, hydroxyl, methoxy, trifluoromethyl, $C_2$-haloalkenyl, methylcarbonyl, ethylcarbonyl, carbonylamino; or wherein the cycle of each heteroaryl-containing moiety or heterocyclyl-containing moiety is optionally substituted by 1 substituent selected from $R^{10}$ and further optionally substituted by 1 or 2 substituents selected from $R^9$, wherein $R^{10}$ is phenyl or pyridinyl (including pyridin-2-yl), wherein phenyl or pyridinyl is optionally substituted by 1, 2 or 3 substituents, which may be the same or different, selected from $R^{11}$; wherein $R^{11}$ is fluoro, chloro, bromo and methoxy.

In some embodiments of the compounds according to Formula (I), preferably, $R^8$ is $C_{1-6}$alkyl, $C_{1-2}$ haloalkyl, hydroxy$C_{1-6}$alkyl, $C_{1-2}$alkoxy$C_{1-4}$alkyl, $C_{3-6}$cycloalkyl or heterocyclyl, wherein the heterocyclyl moiety is a 4- or 5-membered non-aromatic ring which comprises 1 or 2 heteroatoms individually selected from N and O, wherein $C_{3-6}$cycloalkyl and heterocyclyl are optionally substituted by 1, 2 or 3 substituents, which may be the same or different, selected from $R^9$; wherein $R^9$ is cyano, halogen, hydroxy, $C_{1-4}$alkyl, $C_{2-4}$alkenyl, $C_{2-4}$alkynyl, $C_{1-4}$ haloalkyl or $C_{1-4}$alkoxy.

More preferably, R $C_{1-4}$alkyl, $C_{1-2}$ haloalkyl, hydroxy$C_{1-4}$ alkyl, $C_{1-2}$alkoxy$C_{1-4}$alkyl, $C_{3-6}$cycloalkyl or heterocyclyl, wherein the heterocyclyl moiety is a 4- or 5-membered non-aromatic ring which comprises 1 or 2 heteroatoms which are oxygen, wherein $C_{3-6}$cycloalkyl and heterocyclyl are optionally substituted by 1 or 2 substituents, which may be the same or different, selected from $R^9$; wherein $R^9$ is cyano, fluoro, chloro, hydroxy, methyl, ethyl, trifluoromethyl and methoxy.

Even more preferably, $R^8$ is $C_{1-4}$alkyl, $C_{1-2}$ haloalkyl, hydroxy$C_{1-4}$alkyl, $C_{1-2}$alkoxy$C_{1-2}$alkyl, $C_{3-6}$cycloalkyl or heterocyclyl, wherein the heterocyclyl moiety is a 4- or 5-membered non-aromatic ring which comprises 1 or 2 heteroatoms which are oxygen, wherein $C_{3-6}$cycloalkyl and heterocyclyl are optionally substituted by 1 or 2 substituents, which may be the same or different, selected from $R^9$; wherein $R^9$ is fluoro, chloro, methyl.

Still more preferably, $R^9$ is $C_{1-4}$alkyl(methyl, ethyl, n-propyl, iso-propyl, n-butyl, sec-butyl, iso-butyl, t-butyl), 2,2,2-trifluoroethyl, hydroxy$C_{1-4}$alkyl, $C_{1-2}$alkoxy$C_{1-2}$alkyl, cyclopropyl or heterocyclyl, wherein the heterocyclyl moiety is tetrahydrofuran-2-yl, oxetan-3-yl or 1,3-dioxolan-2-yl, wherein cyclopropyl and heterocyclyl are each optionally substituted by 1 or 2 substituents selected from $R^9$, wherein $R^9$ is fluoro, chloro, methyl.

$R^8$ may represent —$OR^{12}$, wherein $R^{12}$ is hydrogen, $C_{1-6}$alkyl, $C_{3-6}$alkenyl, $C_{3-6}$alkynyl, cyano$C_{1-6}$alkyl, $C_{1-6}$ haloalkyl, $C_{3-6}$ haloalkenyl, hydroxy$C_{1-6}$alkyl, $C_{1-4}$alkoxy$C_{1-6}$alkyl, $C_{1-4}$ haloalkoxy$C_{1-6}$alkyl, $C_{1-4}$alkoxy$C_{1-4}$alkoxy$C_{1-6}$alkyl, amino$C_{1-6}$alkyl, N—$C_{1-4}$alkylamino$C_{1-6}$alkyl, N,N-di$C_{1-4}$alkylamino$C_{1-6}$alkyl, $C_{1-6}$alkylcarbonyl$C_{1-6}$alkyl, $C_{1-6}$alkylcarbonyl$C_{2-6}$alkenyl, $C_{1-6}$alkoxycarbonyl$C_{1-6}$alkyl, $C_{1-6}$alkylcarbonyloxy$C_{1-6}$alkyl, N—$C_{1-4}$alkylaminocarbonyl$C_{1-6}$alkyl, N,N-di$C_{1-4}$alkylaminocarbonyl$C_{1-6}$alkyl, $C_{1-4}$alkylsulfanyl$C_{1-6}$alkyl, $C_{1-6}$alkylsulfonyl$C_{1-6}$alkyl, $C_{1-6}$alkylsulfonylamino$C_{1-6}$alkyl; or $R^{12}$ is $C_{3-8}$cycloalkyl, $C_{3-8}$cycloalkyl$C_{1-6}$alkyl, wherein the cycloalkyl moiety is optionally partially unsaturated, phenyl, phenyl$C_{1-6}$alkyl, heteroaryl, heteroaryl$C_{1-6}$alkyl, wherein the heteroaryl moiety is a 5- or 6-membered monocyclic aromatic ring which comprises 1, 2, 3 or 4 heteroatoms individually selected from N, O and S, heterocyclyl, heterocyclyl$C_{1-6}$alkyl, wherein the heterocyclyl moiety is a 4- to 6-membered non-aromatic ring which comprises 1, 2 or 3 heteroatoms individually selected from N, O and S;

wherein for $R^{12}$, any cycloalkyl, phenyl, heteroaryl, heterocyclyl moiety is optionally substituted by 1, 2 or 3 substituents, which may be the same or different, selected from $R^{13}$; wherein $R^{13}$ is cyano, halogen, hydroxy, $C_{1-4}$alkyl, $C_{2-4}$alkenyl, $C_{2-4}$alkynyl, $C_{1-4}$ haloalkyl, $C_{2-4}$haloalkenyl, $C_{1-4}$alkoxy, $C_{1-4}$ haloalkoxy, $C_{3-4}$alkenyloxy, $C_{3-4}$alkynyloxy, N—$C_{1-4}$alkylamino, N,N-di$C_{1-4}$alkylamino, $C_{1-4}$alkylcarbonyl, $C_{1-4}$alkoxycarbonyl, carbonylamino, N—$C_{1-4}$alkylaminocarbonyl, N,N-di$C_{1-4}$alkylaminocarbonyl or $C_{1-4}$alkoxycarbonylamino;

and wherein when $R^{12}$ is substituted $C_{3-8}$cycloalkyl, $C_{3-8}$cycloalkyl$C_{1-6}$alkyl, heterocyclyl, or heterocyclyl$C_{1-6}$alkyl, $R^{13}$ may also represent oxo on the $C_{3-8}$cycloalkyl or heterocyclyl moiety;

Preferably, $R^{12}$ is hydrogen, $C_{1-6}$alkyl, $C_{3-6}$alkenyl, $C_{3-6}$alkynyl, cyano$C_{1-6}$alkyl, $C_{1-6}$ haloalkyl, $C_{3-6}$haloalkenyl, hydroxy$C_{1-6}$alkyl, $C_{1-4}$alkoxy$C_{1-6}$alkyl, $C_{1-4}$haloalkoxy$C_{1-6}$alkyl, $C_{1-4}$alkoxy$C_{1-4}$alkoxy$C_{1-6}$alkyl, amino$C_{1-6}$alkyl, N—$C_{1-4}$alkylamino$C_{1-6}$alkyl, N,N-di$C_{1-4}$alkylamino$C_{1-6}$alkyl, $C_{1-6}$alkylcarbonyl$C_{1-6}$alkyl, $C_{1-6}$alkylcarbonyl$C_{2-6}$alkenyl, $C_{1-6}$alkoxycarbonyl$C_{1-6}$alkyl, $C_{1-6}$alkylcarbonyloxy$C_{1-6}$alkyl, N—$C_{1-4}$alkylaminocarbonyl$C_{1-6}$alkyl, N,N-di$C_{1-4}$alkylaminocarbonyl$C_{1-6}$alkyl, $C_{1-4}$alkylsulfanyl$C_{1-6}$alkyl, $C_{1-6}$alkylsulfonyl$C_{1-6}$alkyl, $C_{1-6}$alkylsulfonylamino$C_{1-6}$alkyl, phenyl, phenyl$C_{1-6}$alkyl, $C_{3-8}$cycloalkyl or $C_{3-8}$cycloalkyl$C_{1-6}$alkyl. More preferably, $R^{12}$ is hydrogen, $C_{1-6}$alkyl, $C_{3-6}$alkenyl, $C_{3-6}$alkynyl, $C_{1-6}$ haloalkyl, $C_{1-4}$alkoxy$C_{1-6}$alkyl, phenyl, phenyl$C_{1-6}$alkyl. Even more preferably, $R^{12}$ is $C_{1-6}$alkyl, $C_{3-4}$alkenyl, $C_{3-4}$alkynyl, $C_{1-4}$ haloalkyl, $C_{1-2}$alkoxy$C_{1-4}$alkyl, phenyl, phenyl$C_{1-2}$alkyl. Still more preferably, $R^{12}$ is $C_{1-6}$alkyl, $C_{3-4}$alkenyl, $C_{3-4}$alkynyl, $C_{1-4}$fluoroalkyl, $C_{1-4}$chloroalkyl, $C_{1-2}$alkoxy$C_{1-2}$alkyl, phenyl, benzyl.

$R^8$ represents —$NR^{14}R^{15}$, wherein $R^{14}$ is hydrogen, cyano, $C_{1-6}$alkyl, $C_{1-6}$alkoxy, $C_{2-6}$alkenyl, $C_{2-6}$alkynyl, $C_{3-6}$alkenyloxy, $C_{3-6}$alkynyloxy, cyano$C_{1-6}$alkyl, $C_{1-6}$ haloalkyl, $C_{1-6}$ haloalkenyl, hydroxy$C_{1-6}$alkyl, $C_{1-4}$alkoxy$C_{1-6}$alkyl, $C_{1-4}$ haloalkoxy$C_{1-6}$alkyl, $C_{1-4}$alkoxy$C_{1-4}$alkoxy$C_{1-6}$alkyl, amino$C_{1-6}$alkyl, N—$C_{1-4}$alkylamino$C_{1-6}$alkyl, N,N-di$C_{1-4}$alkylamino$C_{1-6}$alkyl, N,N-di$C_{1-4}$alkylamino$C_{1-6}$alkyl, $C_{1-6}$alkylcarbonyl$C_{1-6}$alkyl, $C_{1-6}$alkylcarbonyl$C_{2-6}$alkenyl, $C_{1-6}$alkoxycarbonyl$C_{1-6}$alkyl, $C_{1-6}$alkylcarbonyloxy$C_{1-6}$alkyl, N—$C_{1-4}$alkylaminocarbonyl$C_{1-6}$alkyl, N,N-di$C_{1-4}$alkylaminocarbonyl$C_{1-6}$alkyl, $C_{1-4}$alkylsulfanyl$C_{1-6}$alkyl, $C_{1-6}$alkylsulfonyl$C_{1-6}$alkyl, $C_{1-6}$alkylsulfonylamino$C_{1-6}$alkyl; or $R^{14}$ is $C_{3-8}$cycloalkyl, $C_{3-8}$cycloalkyl$C_{1-6}$alkyl, $C_{3-8}$cycloalkyl$C_{1-6}$alkoxy, $C_{3-6}$cycloalkyloxy, wherein the cycloalkyl moiety is optionally partially unsaturated, phenyl, phenyl$C_{1-6}$alkyl, phenyl$C_{1-6}$alkoxy, heteroaryl, heteroaryl$C_{1-6}$alkyl, heteroaryl$C_{1-6}$alkoxy, wherein the heteroaryl moiety is a 5- or 6-membered monocyclic aromatic ring which comprises 1, 2, 3 or 4 heteroatoms individually selected from N, O and S, heterocyclyl, heterocyclyl$C_{1-6}$alkyl, heterocyclyl$C_{1-6}$alkoxy wherein the heterocyclyl moiety is a 4- to 6-membered non-aromatic ring which comprises 1, 2 or 3 heteroatoms individually selected from N, O and S;

wherein for $R^{14}$, any cycloalkyl, phenyl, heteroaryl, heterocyclyl moiety is optionally substituted by 1, 2 or 3 substituents, which may be the same or different, selected from $R^{16}$; wherein $R^{16}$ is cyano, halogen, hydroxy, $C_{1-4}$alkyl, $C_{2-4}$alkenyl, $C_{2-4}$alkynyl, $C_{1-4}$ haloalkyl, $C_{2-4}$haloalkenyl, $C_{1-4}$alkoxy, $C_{1-2}$alkoxy$C_{1-2}$alkyl, $C_{1-4}$ haloalkoxy, $C_{3-4}$alkenyloxy, $C_{3-4}$alkynyloxy, N—$C_{1-4}$alkylamino, N,N-di$C_{1-4}$alkylamino, $C_{1-4}$alkylcarbonyl, $C_{1-4}$alkoxycarbonyl, carbonylamino, N—$C_{1-4}$alkylaminocarbonyl, N,N-di$C_{1-4}$alkylaminocarbonyl or $C_{1-4}$alkoxycarbonylamino;

and wherein when $R^{14}$ is substituted $C_{3-8}$cycloalkyl, $C_{3-8}$cycloalkyl$C_{1-6}$alkyl, $C_{3-8}$cycloalkyl$C_{1-6}$alkoxy, heterocyclyl, or heterocyclyl$C_{1-6}$alkyl, heterocyclyl$C_{1-6}$alkoxy, $R^{16}$ may also represent oxo on 35 the $C_{3-8}$cycloalkyl or heterocyclyl moiety;

$R^{15}$ is hydrogen, $C_{1-4}$alkyl, $C_{3-4}$alkynyl, $C_{1-4}$alkoxy$C_{1-4}$alkyl, cyano$C_{1-4}$alkyl, $C_{3-6}$cycloalkyl, $C_{3-6}$cycloalkyl$C_{1-2}$alkyl; or $R^{14}$ and $R^{15}$, together with the nitrogen atom to which they are bonded, form a 4-, 5- or 6-membered cycle optionally containing an additional heteroatom selected from 0, S and $NR^{17}$; wherein $R^{17}$ is hydrogen, methyl, methoxy, formyl or acyl.

Preferably, $R^8$ represents —$NR^{14}R^{15}$, wherein $R^{14}$ is hydrogen, $C_{1-6}$alkyl, $C_{1-6}$alkoxy, $C_{2-6}$alkenyl, $C_{2-6}$alkynyl, cyano$C_{1-6}$alkyl, $C_{1-6}$haloalkyl, $C_{1-6}$haloalkenyl, hydroxy$C_{1-6}$ alkyl, $C_{1-4}$alkoxy$C_{1-6}$alkyl, $C_{1-4}$haloalkoxy$C_{1-6}$ alkyl, $C_{1-4}$alkoxy$C_{1-4}$alkoxy$C_{1-6}$alkyl, amino$C_{1-6}$alkyl, N—$C_{1-4}$alkylamino$C_{1-6}$alkyl, N,N-di$C_{1-4}$alkylamino$C_{1-6}$alkyl, $C_{1-6}$alkylcarbonyl$C_{1-6}$alkyl, $C_{1-6}$alkylcarbonyl$C_{2-6}$alkenyl, $C_{1-6}$alkoxycarbonyl$C_{1-6}$alkyl, $C_{1-6}$alkylcarbonyloxy$C_{1-6}$alkyl, N—$C_{1-4}$alkylaminocarbonyl$C_{1-6}$alkyl, N,N-di$C_{1-4}$alkylaminocarbonyl$C_{1-6}$alkyl, $C_{1-4}$alkylsulfanyl$C_{1-6}$alkyl, $C_{1-6}$alkylsulfonyl$C_{1-6}$alkyl, $C_{1-6}$alkylsulfonylamino$C_{1-6}$alkyl or $C_{3-8}$cycloalkyl and $R^{15}$ is hydrogen, $C_{1-4}$alkyl, $C_{1-4}$alkoxy$C_{1-4}$alkyl or cyano$C_{1-4}$alkyl.

More preferably, $R^{14}$ is hydrogen, cyano, $C_{1-6}$alkyl, $C_{1-6}$alkoxy, $C_{2-6}$alkenyl, $C_{2-6}$alkynyl, cyano$C_{1-6}$alkyl, $C_{1-6}$ haloalkyl, $C_{1-4}$alkoxy$C_{1-6}$alkyl, $C_{1-6}$alkoxycarbonyl$C_{1-6}$alkyl, or $C_{3-8}$cycloalkyl, $C_{3-8}$cycloalkyl$C_{1-6}$alkyl, phenyl or heteroaryl$C_{1-6}$alkyl, wherein the heteroaryl moiety is a 5-membered monocyclic aromatic ring which comprises 1, 2, 3 or 4 heteroatoms individually selected from N, O and S, wherein any of $C_{3-8}$cycloalkyl, phenyl or heteroaryl, are optionally substituted by 1 or 2 substituents selected from $R^{16}$, wherein $R^{16}$ is cyano, halogen, hydroxy, $C_{1-4}$alkyl, $C_{1-4}$ haloalkyl, $C_{1-4}$alkoxy, $C_{1-4}$ haloalkoxy or $C_{1-4}$alkoxycarbonyl. Even more preferably, $R^{14}$ is hydrogen, $C_{1-6}$alkyl, $C_{1-6}$alkoxy, $C_{2-4}$alkenyl, $C_{2-4}$alkynyl, $C_{1-2}$ haloalkyl, $C_{3-6}$cycloalkyl. Still more preferably, $R^{14}$ is hydrogen, methyl, ethyl, propyl, iso-propyl, sec-butyl, methoxy, ethoxy, allyl, propyn-2-yl, 2,2,2-trifluoromethyl, cyclopropyl or cyclobutyl.

Preferably, $R^{15}$ is hydrogen, methyl, ethyl, $C_{3-4}$alkynyl or methoxyethyl. More preferably, $R^{15}$ is hydrogen, methyl or ethyl, in particular, hydrogen.

In other embodiments, $R^{15}$ may be hydrogen, $C_{1-4}$alkyl, $C_{1-4}$alkoxy$C_{1-4}$alkyl or cyano$C_{1-4}$alkyl.

$R^{14}$ and $R^{15}$, together with the nitrogen atom to which they are bonded, may form a 5- or 6-membered cycle optionally containing an additional heteroatom which is oxygen.

In some embodiments, for the compounds of Formula (I), preferably n is 1;
- $A^1$ to $A^4$ are C—H, $A^1$ is C—F and $A^2$ to $A^4$ are C—H, $A^1$ and $A^2$ are C—F and $A^3$ and $A^4$ are C—H, $A^1$ and $A^3$ are C—F and $A^2$ and $A^4$ are C—H or $A^1$ is N and $A^2$ to $A^4$ are C—H;
- $R^5$ and $R^6$ are independently selected from hydrogen, $C_{1-4}$alkyl and cyano;
- $R^7$ is hydroxy, $C_{1-4}$alkyl, $C_{2-4}$fluoroalkyl, $C_{1-4}$alkoxy, hydroxy$C_{1-4}$alkyl, $C_{1-2}$alkoxy$C_{1-4}$alkyl, $C_{3-4}$alkenyl, $C_{3-4}$alkynyl, $C_{3-6}$ haloalkenyloxy, cyclopropyl, (cyclopropyl)methyl, phenyl$C_{1-2}$alkoxy, (tetrahydrofuran-2-yl)methyl or (2-furyl)methyl, wherein any of said cyclopropyl, phenyl, tetrahydrofuran-2-yl and 2-furyl moieties are optionally substituted by 1 or 2 substituents selected from cyano, fluoro, chloro, bromo, methyl, difluoromethyl, trifluoromethyl, methoxy, ethoxy, or difluoromethoxy;
- $R^8$ is $C_{1-6}$alkyl, $C_{1-2}$ haloalkyl, hydroxy$C_{1-6}$alkyl, $C_{1-2}$alkoxy$C_{1-4}$alkyl, $C_{3-6}$cycloalkyl or heterocyclyl, wherein the heterocyclyl moiety is a 4- or 5-membered non-aromatic ring which comprises 1 or 2 heteroatoms individually selected from N and O, wherein $C_{3-6}$cycloalkyl and heterocyclyl are optionally substituted by 1, 2 or 3 substituents, which may be the same or different, selected from $R^9$; and
- $R^9$ is cyano, halogen, hydroxy, $C_{1-4}$alkyl, $C_{2-4}$alkenyl, $C_{2-4}$alkynyl, $C_{1-4}$ haloalkyl or $C_{1-4}$alkoxy.

More preferably in the compounds of Formula (I), n is 1;
- $A^1$ to $A^4$ are C—H;
- $R^5$ and $R^6$ are independently selected from hydrogen and $C_{1-4}$alkyl;
- $R^7$ is $C_{1-4}$alkyl, $C_{2-4}$fluoroalkyl, methoxy, ethoxy or cyclopropyl;
- $R^8$ is $C_{1-6}$alkyl, $C_{1-2}$ haloalkyl, hydroxy$C_{1-6}$alkyl, $C_{1-2}$alkoxy$C_{1-4}$alkyl, $C_{3-6}$cycloalkyl or heterocyclyl, wherein the heterocyclyl moiety is a 4- or 5-membered non-aromatic ring which comprises 1 or 2 heteroatoms individually selected from N and O, wherein $C_{3-6}$cycloalkyl and heterocyclyl are optionally substituted by 1, 2 or 3 substituents, which may be the same or different, selected from $R^9$; and
- $R^9$ is cyano, halogen, hydroxy, $C_{1-4}$alkyl, $C_{2-4}$alkenyl, $C_{2-4}$alkynyl, $C_{1-4}$ haloalkyl or $C_{1-4}$alkoxy.

Even more preferably in the compounds of Formula (I), n is 1;
- $A^1$ to $A^4$ are C—H;
- $R^5$ and $R^6$ are independently selected from hydrogen and methyl, preferably hydrogen;
- $R^7$ is methyl, ethyl, n-propyl, iso-propyl, 2,2,2-fluoroethyl, methoxy, ethoxy or cyclopropyl;
- $R^8$ is $C_{1-4}$alkyl, $C_{1-2}$ haloalkyl, hydroxy$C_{1-4}$alkyl, $C_{1-2}$alkoxy$C_{1-2}$alkyl, $C_{3-6}$cycloalkyl or heterocyclyl, wherein the heterocyclyl moiety is a 4- or 5-membered non-aromatic ring which comprises 1 or 2 heteroatoms which are oxygen, wherein $C_{3-6}$cycloalkyl and heterocyclyl are optionally substituted by 1 or 2 substituents, which may be the same or different, selected from $R^9$; and
- $R^9$ is fluoro, chloro, methyl.

In other embodiments, for the compounds of Formula (I), preferably n is 1;
- $A^1$ to $A^4$ are C—H;
- $R^5$ and $R^6$ are independently selected from hydrogen and methyl;
- $R^7$ is hydroxy, $C_{2-4}$haloalkyl, $C_{3-6}$alkenyl, $C_{3-4}$alkynyl or $C_{1-4}$alkoxycarbonyloxy;
- $R^8$ is —$OR^{12}$; and
- $R^{12}$ is hydrogen, $C_{1-6}$alkyl, $C_{3-6}$alkenyl, $C_{3-6}$alkynyl, $C_{1-4}$alkoxy$C_{1-6}$alkyl, phenyl, phenyl$C_{1-6}$alkyl.

More preferably in the compounds of Formula (I), n is 1;
- $A^1$ to $A^4$ are C—H;
- $R^5$ and $R^6$ are hydrogen;
- $R^7$ is methoxy;
- $R^8$ is —$OR^{12}$; and
- $R^{12}$ is hydrogen, $C_{1-6}$alkyl, $C_{3-6}$alkenyl, $C_{3-6}$alkynyl, $C_{1-6}$ haloalkyl, $C_{1-4}$alkoxy$C_{1-6}$alkyl, phenyl, phenyl$C_{1-6}$alkyl.

In still other embodiments, for the compounds of Formula (I), preferably n is 1;
- $A^1$ to $A^4$ are C—H or $A^1$, $A^2$ and $A^4$ are C—H and $A^3$ is C—F;
- $R^5$ and $R^6$ are hydrogen;
- $R^7$ is hydroxy, $C_{1-4}$alkyl, $C_{2-4}$ haloalkyl, $C_{1-4}$alkoxy, $C_{3-6}$alkenyl, $C_{3-4}$alkynyl, $C_{3-6}$cycloalkyl;
- $R^8$ is —$NR^{14}R^{15}$;
- $R^{14}$ is hydrogen, cyano, $C_{1-6}$alkyl, $C_{1-6}$alkoxy, $C_{2-6}$alkenyl, $C_{2-6}$alkynyl, cyano$C_{1-6}$alkyl, $C_{1-6}$haloalkyl, $C_{1-4}$alkoxy$C_{1-6}$alkyl, $C_{1-6}$alkoxycarbonyl$C_{1-6}$alkyl, or $C_{3-8}$cycloalkyl, $C_{3-8}$cycloalkyl$C_{1-6}$alkyl, phenyl or heteroaryl$C_{1-6}$alkyl, wherein the heteroaryl moiety is a 5-membered monocyclic aromatic ring which comprises 1, 2, 3 or 4 heteroatoms individually selected from N, O and S, wherein any of $C_{3-8}$cycloalkyl, phenyl or heteroaryl, are optionally substituted by 1 or 2 substituents selected from $R^{16}$, wherein $R^{16}$ is cyano, halogen, hydroxy, $C_{1-4}$alkoxy, $C_{1-4}$ haloalkoxy or $C_{1-4}$alkoxycarbonyl; and
- $R^{15}$ is hydrogen, methyl, ethyl, $C_{3-4}$alkynyl or methoxyethyl.

More preferably in the compounds of Formula (I), n is 1;
- $A^1$ to $A^4$ are C—H;
- $R^5$ and $R^6$ are hydrogen;
- $R^7$ is hydroxy, $C_{1-4}$alkyl, $C_{2-4}$ haloalkyl, $C_{1-2}$alkoxy, $C_{3-4}$alkenyl, $C_{3-4}$alkynyl or cyclopropyl;
- $R^8$ is —$NR^{14}R^{15}$;
- $R^{14}$ is hydrogen, methyl, ethyl, propyl, iso-propyl, sec-butyl, methoxy, ethoxy, allyl, propyn-2-yl, 2,2,2-trifluoromethyl, cyclopropyl or cyclobutyl; and
- $R^{15}$ is hydrogen, methyl or ethyl.

Even more preferably in the compounds of Formula (I), n is 1;
- $A^1$ to $A^4$ are C—H;
- $R^5$ and $R^6$ are hydrogen;
- $R^7$ is $C_{1-4}$alkyl or $C_{1-2}$alkoxy;
- $R^8$ is —$NR^{14}R^{15}$;
- $R^{14}$ is hydrogen, methyl, ethyl, propyl, iso-propyl, sec-butyl, methoxy, ethoxy, allyl, propyn-2-yl, 2,2,2-trifluoromethyl, cyclopropyl or cyclobutyl; and
- $R^{15}$ is hydrogen.

The compound according to Formula (I) may be selected from compound 1.1 to 1.811 listed in Table T1 below, from compound 2.1 to 2.26 listed in Table T2 below, and from compound 3.1 to 3.140 listed in Table T3 below.

The compound of Formula (I) may be a compound according to Formula (IA):

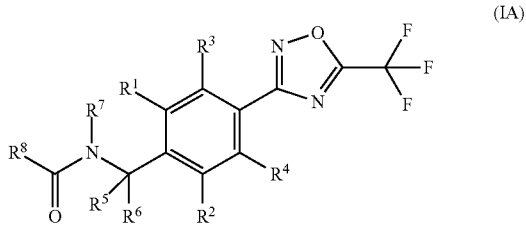

(IA)

wherein
$R^1$ and $R^2$ are independently selected from hydrogen, chloro, fluoro, methyl, methoxy and trifluoromethyl; and
$R^3$ and $R^4$ are independently selected from hydrogen and halogen;
wherein at least two of $R^1$, $R^2$, $R^3$ and $R^4$ are hydrogen;
$R^5$ and $R^6$ are independently selected from hydrogen and $C_{1-4}$alkyl;
$R^7$ is $C_{1-4}$alkyl or $C_{1-4}$alkoxy; and
$R^8$ hydrogen, $C_{1-6}$alkyl, $C_{2-6}$alkenyl, $C_{2-6}$alkynyl, cyano$C_{1-6}$alkyl, $C_{1-6}$haloalkyl, $C_{2-6}$haloalkenyl, hydroxy$C_{1-6}$alkyl, $C_{1-4}$alkoxy$C_{1-6}$alkyl, $C_{1-4}$ haloalkoxy$C_{1-6}$alkyl, $C_{1-4}$alkoxy$C_{1-4}$alkoxy$C_{1-6}$alkyl, $C_{2-4}$alkynyloxy$C_{1-6}$alkyl, amino$C_{1-6}$alkyl, N—$C_{1-4}$alkylamino$C_{1-6}$alkyl, N,N-di$C_{1-4}$alkylamino$C_{1-6}$alkyl, $C_{1-6}$alkylcarbonyl$C_{1-6}$alkyl, $C_{1-6}$alkylcarbonyl$C_{2-6}$alkenyl, $C_{1-6}$alkoxycarbonyl$C_{1-6}$alkyl, $C_{1-6}$alkylcarbonyloxy$C_{1-6}$alkyl, N—$C_{1-4}$alkylaminocarbonyl$C_{1-6}$alkyl, N,N-di$C_{1-4}$alkylaminocarbonyl$C_{1-6}$alkyl, $C_{1-6}$alkylsulfanyl$C_{1-6}$alkyl, $C_{1-6}$alkylsulfonyl$C_{1-6}$alkyl, $C_{1-6}$alkylsulfonylamino$C_{1-6}$alkyl, $C_{1-6}$ alkylsulfonylamino$C_{2-6}$alkynyl, $C_{2-6}$alkynyloxycarbonylamino$C_{1-6}$alkyl; or
$R^8$ is $C_{3-8}$cycloalkyl$C_{0-6}$alkyl, wherein the cycloalkyl moiety is optionally partially unsaturated, phenyl$C_{0-6}$alkyl, phenyl$C_{2-6}$alkenyl, naphthyl$C_{0-6}$alkyl, heteroaryl$C_{0-6}$alkyl wherein the heteroaryl moiety is a 5- or 6-membered monocyclic aromatic ring which comprises 1, 2, 3 or 4 heteroatoms individually selected from N, O and S, heterodiaryl$C_{0-6}$alkyl wherein the heterodiaryl moiety is a 9- or 10-membered bicyclic aromatic system which comprises 1, 2, 3 or 4 heteroatoms individually selected from N, O and S, heterocyclyl$C_{0-6}$alkyl wherein the heterocyclyl moiety is a 4- to 6-membered non-aromatic ring which comprises 1, 2 or 3 heteroatoms individually selected from N, O and S, or $C_{3-6}$cycloalkylcarbonylamino$C_{1-6}$alkyl,
wherein for $R^8$, any of $C_{3-8}$cycloalkyl$C_{0-6}$alkyl, phenyl$C_{0-6}$alkyl, phenyl$C_{2-6}$alkenyl, naphthyl$C_{0-6}$alkyl, heteroaryl$C_{0-6}$alkyl, heterodiaryl$C_{0-6}$alkyl, heterocyclyl$C_{0-6}$alkyl and $C_{3-6}$cycloalkylcarbonylamino$C_{1-6}$alkyl moieties are optionally substituted by 1, 2 or 3 substituents, which may be the same or different, selected from $R^9$; wherein
$R^9$ is cyano, halogen, hydroxy, $C_{2-4}$alkenyl, $C_{2-4}$alkynyl, $C_{1-4}$ haloalkyl, $C_{2-4}$ haloalkenyl, $C_{1-4}$alkoxy, $C_{1-4}$ haloalkoxy, $C_{3-4}$alkynyloxy, $C_{1-4}$alkylcarbonyl, $C_{1-4}$alkoxycarbonyl, carbonylamino, N—$C_{1-4}$alkylaminocarbonyl, N,N-di$C_{1-4}$alkylaminocarbonyl or $C_{1-4}$alkoxycarbonylamino, and wherein $R_8$ is substituted $C_{3-8}$cycloalkyl$C_{0-6}$alkyl or heterocyclyl$C_{0-6}$alkyl, $R^9$ may also represent oxo on the $C_{3-8}$cycloalkyl or heterocyclyl moiety; or wherein for $R^8$, any of $C_{3-8}$cycloalkyl$C_{0-6}$alkyl, phenyl$C_{0-6}$alkyl, phenyl$C_{2-6}$alkenyl, naphthyl$C_{0-6}$alkyl, heteroaryl$C_{0-6}$alkyl, heterodiaryl$C_{0-6}$alkyl, heterocyclyl$C_{0-6}$alkyl and $C_{3-6}$cycloalkylcarbonylamino$C_{1-6}$alkyl moieties are optionally substituted by 1 substituent selected from $R^{10}$; wherein
$R^{10}$ is $C_{3-8}$cycloalkyl$C_{0-2}$alkyl, phenyl$C_{0-2}$alkyl, heteroaryl$C_{0-2}$alkyl wherein the heteroaryl moiety is a 5- or 6-membered monocyclic aromatic ring which comprises 1, 2, 3 or 4 heteroatoms individually selected from N, O and S, heterocyclyl$C_{0-6}$alkyl wherein the heterocyclyl moiety is a 4- to 6-membered non-aromatic ring which comprises 1, 2 or 3 heteroatoms individually selected from N, O and S, and wherein any of said cycloalkyl, phenyl, heteroaryl and heterocyclyl moieties are optionally substituted by 1, 2 or 3 substituents, which may be the same or different, selected from $R^{11}$; wherein
$R^{11}$ is hydrogen, cyano, fluoro, chloro, bromo, methyl, trifluoromethyl, methoxy and ethoxy; or
a salt or an N-oxide thereof.

For the compounds of Formula (IA), when $R^8$ as a $C_{3-8}$cycloalkyl$C_{0-6}$alkyl, phenyl$C_{0-6}$alkyl, phenyl$C_{2-6}$alkenyl, naphthyl$C_{0-6}$alkyl, heteroaryl$C_{0-6}$alkyl, heterodiaryl$C_{0-6}$alkyl, heterocyclyl$C_{0-6}$alkyl or $C_{3-6}$cycloalkylcarbonylamino$C_{1-6}$alkyl moiety is indicated as optionally substituted by $R^9$ or $R^{10}$, the cycloalkyl, phenyl, naphthyl, heteroaryl, heterodiaryl, heterocyclyl fragment only may be substituted.

In the compounds of Formula (IA), preferably $R^1$ and $R^2$ are independently selected from hydrogen and fluoro. More preferably, $R^1$ and $R^2$ are hydrogen.

In the compounds of Formula (IA), preferably $R^3$ and $R^4$ are independently selected from hydrogen and fluoro. More preferably, Wand $R^4$ are hydrogen.

In the compounds of Formula (IA), preferably three of $R^1$, $R^2$, $R^3$ and $R^4$ are hydrogen, wherein more preferably $R^2$, $R^3$ and $R^4$ are hydrogen.

In the compounds of Formula (IA), preferably $R^5$ and $R^6$ are hydrogen, or $R^5$ is hydrogen and $R^6$ is $C_{1-4}$alkyl, preferably methyl or ethyl. More preferably, $R^5$ and $R^6$ are hydrogen.

In the compounds of Formula (IA), preferably $R^7$ is methyl, ethyl, propyl, isopropyl, butyl, sec-butyl, methoxy, ethoxy, propoxy, isopropoxy, butoxy, or sec-butoxy. More preferably, $R^7$ is methyl, ethyl, sec-butyl, methoxy, ethoxy, or propoxy. Most preferably, $R^7$ is sec-butyl, methoxy or propoxy.

In the compounds of Formula (IA), preferably $R^8$ is hydrogen, $C_{1-6}$alkyl, $C_{2-6}$alkenyl, $C_{2-6}$alkynyl, cyano$C_{1-6}$alkyl, $C_{1-6}$ haloalkyl, $C_{2-6}$ haloalkenyl, hydroxy$C_{1-6}$alkyl, $C_{1-4}$alkoxy$C_{1-6}$alkyl, $C_{1-4}$ haloalkoxy$C_{1-6}$alkyl, $C_{1-4}$alkoxy$C_{1-4}$alkoxy$C_{1-6}$alkyl, $C_{2-4}$alkynyloxy$C_{1-6}$alkyl, $C_{1-6}$alkylcarbonyl$C_{2-6}$alkenyl, $C_{1-6}$alkylcarbonyloxy$C_{1-6}$alkyl, $C_{1-6}$alkylsulfonylamino$C_{2-6}$alkynyl, $C_{2-6}$alkynyloxycarbonylamino$C_{1-6}$alkyl;  or $C_{3-8}$cycloalkyl$C_{0-2}$alkyl, wherein the cycloalkyl moiety is optionally partially unsaturated, phenyl$C_{0-2}$alkyl, heteroaryl$C_{0-2}$alkyl wherein the heteroaryl moiety is a 5- or 6-membered monocyclic aromatic ring which comprises 1, 2, 3 or 4 heteroatoms individually selected from N, O and S, or heterocyclyl$C_{0-2}$alkyl wherein the heterocyclyl moiety is a 4- to 6-membered non-aromatic ring which comprises 1, 2 or 3 heteroatoms individually selected from N, O and S; wherein any of said $C_{3-8}$cycloalkyl$C_{0-2}$alkyl, phenyl$C_{0-2}$alkyl, heteroaryl$C_{0-2}$alkyl and heterocyclyl$C_{0-2}$alkyl moieties are optionally substituted by 1, 2 or 3 substituents, which may be the same or different, selected from $R^9$; and $R^9$ is cyano, halogen, hydroxy, $C_{1-4}$alkyl, $C_{1-4}$ haloalkyl, $C_{1-4}$alkoxy, $C_{2-4}$ haloalkenyl, $C_{3-4}$alkynyloxy, $C_{1-4}$alkylcarbonyl and $C_{1-4}$alkoxycarbonyl.

More preferably, $R^8$ is $C_{1-6}$alkyl, $C_{2-6}$alkenyl, $C_{2-6}$alkynyl, $C_{1-6}$fluoroalkyl, $C_{1-6}$chloroalkyl, $C_{1-4}$alkoxyC$_{1-6}$alkyl, $C_{1-4}$alkoxyC$_{1-4}$alkoxyC$_{1-6}$alkyl, $C_{1-6}$alkylcarbonylC$_{2-6}$alkenyl, $C_{1-6}$alkylcarbonyloxyC$_{1-6}$alkyl, $C_{1-6}$ alkylsulfonylaminoC$_{2-6}$alkynyl or $C_{2-6}$alkynyloxycarbonylaminoC$_{1-6}$alkyl; $C_{3-8}$cycloalkylC$_{0-6}$alkyl, phenylC$_{0-6}$alkyl, or heterocyclylC$_{0-6}$alkyl, wherein any of said cycloalkyl, phenyl, and heterocyclyl moieties are optionally substituted by 1, 2 or 3 substituents which may be the same or different, selected from $R^9$, wherein $R^9$ is cyano, halogen, hydroxy, $C_{1-4}$alkyl, $C_{1-4}$ haloalkyl, $C_{2-4}$ haloalkenyl, $C_{3-4}$alkynyloxy, $C_{1-4}$alkylcarbonyl, $C_{1-4}$alkoxycarbonyl; or wherein any of said cycloalkyl, phenyl, and heterocyclyl moieties are optionally substituted by 1 substituent selected from $R^{10}$ which is a phenyl.

Even more preferably, $R^8$ is $C_{1-6}$alkyl, $C_{2-4}$alkenyl, $C_{2-4}$alkynyl, $C_{1-6}$fluoroalkyl, $C_{1-4}$chloroalkyl, $C_{1-4}$alkoxyC$_{1-4}$alkyl, $C_{1-4}$alkoxyC$_{1-2}$alkoxyC$_{1-4}$alkyl, $C_{1-4}$alkylcarbonylC$_{2-4}$alkenyl, $C_{1-2}$alkylcarbonyloxyC$_{1-4}$alkyl, $C_{1-4}$alkylsulfonylaminoC$_{2-4}$alkynyl or $C_{2-4}$alkynyloxycarbonylaminoC$_{1-4}$alkyl; $C_{3-6}$cycloalkylC$_{0-1}$alkyl, phenylC$_{0-1}$alkyl or heterocyclylC$_{0-1}$alkyl, wherein any of said cycloalkyl, phenyl, and heterocyclyl moieties are optionally substituted by 1, 2 or 3 substituents which may be the same or different, selected from $R^9$, wherein $R^9$ is cyano, fluoro, chloro, hydroxy, methyl, ethyl, trifluoromethyl, 2,2-dichloroethenyl, propynyloxy, acetyl, methoxycarbonyl; or wherein any of said cycloalkyl, phenyl, and heterocyclyl moieties are optionally substituted by 1 substituent selected from $R^{10}$ which is a phenyl.

In some embodiments of the invention according to Formula (IA) where $R^8$ is a group selected from $C_{3-8}$cycloalkylC$_{0-6}$alkyl, phenylC$_{0-6}$alkyl, phenylC$_{2-6}$alkenyl, naphthylC$_{0-6}$alkyl, heteroarylC$_{0-6}$alkyl, heterodiarylC$_{0-6}$alkyl, heterocyclylC$_{0-6}$alkyl, preferably $R^8$ is $C_{3-8}$cycloalkylC$_{0-2}$alkyl, phenylC$_{0-2}$alkyl, phenylC$_{2-4}$alkenyl, naphthylC$_{0-2}$alkyl, heteroarylC$_{0-2}$alkyl, heterodiarylC$_{0-2}$alkyl or heterocyclylC$_{0-2}$alkyl.

In some embodiments of the invention according to Formula (IA) where $R^8$ is a group selected from $C_{3-8}$cycloalkylC$_{0-6}$alkyl, preferably $C_{3-8}$cycloalkyl is cyclopropyl, cyclobutyl, cyclopentyl or cyclohexyl.

In some embodiments of the invention according to Formula (IA) where $R^8$ is a group selected from phenylC$_{0-6}$alkyl, preferably, $R^8$ is phenyl or benzyl.

In some embodiments of the invention according to Formula (IA) where $R^8$ is a group selected from heterocyclylC$_{0-6}$alkyl, preferably the heterocyclyl group has 1 or 2 heteroatoms selected from N, O and S. More preferably, the heterocyclyl group has a single heteroatom selected from O and S. Most preferable for $R^8$ as a heterocyclylC$_{0-6}$alkyl are oxetanyl, tetrahydrofuranyl, tetrahydropyranyl, thietanyl or tetrahydrothiopyranyl.

In the compounds of Formula (IA), preferably $R^1$ and $R^2$ are independently selected from hydrogen and fluoro;

$R^3$ and $R^4$ are independently selected from hydrogen and fluoro;

wherein at least two of $R^1$, $R^2$, $R^3$ and $R^4$ are hydrogen, $R^5$ and $R^6$ are hydrogen, or $R^5$ is hydrogen and $R^6$ is methyl;

$R^7$ is $C_{1-4}$alkyl or $C_{1-4}$alkoxy; and $R^8$ is $C_{1-6}$alkyl, $C_{2-6}$alkenyl, $C_{2-6}$alkynyl, $C_{1-6}$fluoroalkyl, $C_{1-6}$chloroalkyl, $C_{1-4}$alkoxyC$_{1-6}$alkyl, $C_{1-4}$alkoxyC$_{1-4}$ alkoxyC$_{1-6}$alkyl, $C_{1-6}$alkylcarbonylC$_{2-6}$alkenyl, $C_{1-6}$alkylcarbonyloxyC$_{1-6}$alkyl, $C_{1-6}$ alkylsulfonylaminoC$_{2-6}$alkynyl or $C_{2-6}$alkynyloxycarbonylaminoC$_{1-6}$alkyl; $C_{3-8}$cycloalkylC$_{0-6}$alkyl, phenylC$_{0-6}$alkyl, or heterocyclylC$_{0-6}$alkyl, wherein any of said cycloalkyl, phenyl, and heterocyclyl moieties are optionally substituted by 1, 2 or 3 substituents which may be the same or different, selected from $R^9$, wherein $R^9$ is cyano, halogen, hydroxy, $C_{1-4}$alkyl, $C_{1-4}$haloalkyl, $C_{2-4}$ haloalkenyl, $C_{3-4}$alkynyloxy, $C_{1-4}$alkylcarbonyl, $C_{1-4}$alkoxycarbonyl; or wherein any of said cycloalkyl, phenyl, and heterocyclyl moieties are optionally substituted by 1 substituent selected from $R^{10}$ which is a phenyl.

In the compounds of Formula (IA), more preferably $R^1$ and $R^2$ are independently selected from hydrogen and fluoro;

$R^3$ and $R^4$ are independently selected from hydrogen and fluoro;

wherein at least two of $R^1$, $R^2$, $R^3$ and $R^4$ are hydrogen $R^5$ and $R^6$ are hydrogen, or $R^5$ is hydrogen and $R^6$ is methyl;

$R^7$ is methoxy, propoxy or sec-butyl; and $R^8$ is $C_{1-6}$alkyl, $C_{2-4}$alkenyl, $C_{2-4}$alkynyl, $C_{1-6}$fluoroalkyl, $C_{1-4}$chloroalkyl, $C_{1-4}$alkoxyC$_{1-4}$alkyl, $C_{1-4}$alkoxyC$_{1-2}$ alkoxyC$_{1-4}$alkyl, $C_{1-4}$alkylcarbonylC$_{2-4}$alkenyl, $C_{1-2}$alkylcarbonyloxyC$_{1-4}$alkyl, $C_{1-4}$alkylsulfonylaminoC$_{2-4}$ alkynyl or $C_{2-4}$alkynyloxycarbonylaminoC$_{1-4}$alkyl; $C_{3-6}$cycloalkylC$_{0-1}$ alkyl, phenylC$_{0-1}$alkyl or heterocyclylC$_{0-1}$alkyl, wherein any of said cycloalkyl, phenyl, and heterocyclyl moieties are optionally substituted by 1, 2 or 3 substituents which may be the same or different, selected from $R^9$, wherein $R^9$ is cyano, fluoro, chloro, hydroxy, methyl, ethyl, trifluoromethyl, 2,2-dichloroethenyl, propynyloxy, acetyl, methoxycarbonyl; or wherein any of said cycloalkyl, phenyl, and heterocyclyl moieties are optionally substituted by 1 substituent selected from $R^{10}$ which is a phenyl.

In the compounds of Formula (IA), even more preferably, $R^1$ and $R^2$ are hydrogen;

$R^3$ and $R^4$ are hydrogen;

$R^5$ and $R^6$ are hydrogen;

$R^7$ is methoxy, propoxy or sec-butyl; and $R^8$ is $C_{1-6}$alkyl, $C_{2-4}$alkenyl, $C_{2-4}$alkynyl, $C_{1-6}$fluoroalkyl, $C_{1-4}$chloroalkyl, $C_{1-4}$alkoxyC$_{1-4}$alkyl, $C_{1-4}$alkoxyC$_{1-2}$ alkoxyC$_{1-4}$alkyl, $C_{1-4}$alkylcarbonylC$_{2-4}$alkenyl, $C_{1-2}$alkylcarbonyloxyC$_{1-4}$alkyl, $C_{1-4}$alkylsulfonylaminoC$_{2-4}$ alkynyl or $C_{2-4}$alkynyloxycarbonylaminoC$_{1-4}$alkyl; $C_{3-6}$cycloalkylC$_{0-1}$alkyl, phenylC$_{0-1}$alkyl or heterocyclylC$_{0-1}$alkyl, wherein any of said cycloalkyl, phenyl, and heterocyclyl moieties are optionally substituted by 1, 2 or 3 substituents which may be the same or different, selected from $R^9$, wherein $R^9$ is cyano, fluoro, chloro, hydroxy, methyl, ethyl, trifluoromethyl, 2,2-dichloroethenyl, propynyloxy, acetyl, methoxycarbonyl; or wherein any of said cycloalkyl, phenyl, and heterocyclyl moieties are optionally substituted by 1 substituent selected from $R^{10}$ which is a phenyl.

The compounds of the present invention may be enantiomers of the compound of Formula (I) as represented by a Formula (Ia) or a Formula (Ib) when n is 1, wherein $R^5$ and $R^6$ are different (see below), or indeed when n is 2 and at only one of the two carbon positions bound to $R^5$ and $R^6$, $R^5$ and $R^6$ are different.

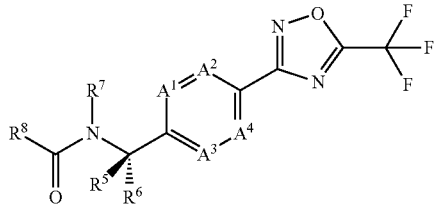

(Ia)

$R^8, R^9, R^{10}, R^{11}, R^{12}, R^{13}, R^{14}, R^{15}, R^{16}$ and $R^{17}$ with reference to the compounds of formula (I) of the present invention apply generally to the compounds of Formula (I-I) and Formula (I-II), as well as to the specific disclosures of combinations of n, $A^1, A^2, A^3, A^4, R^1, R^2, R^3, R^4, R^5, R^6, R^7, R^8, R^9, R^{10}, R^{11}, R^{12}, R^{13}, R^{14}, R^{15}, R^{16}$ and $R^{17}$ as represented in Tables 1.1 to 1.29, 2.1 to 2.5, 3.1 to 3.14 and 4.1 to 4.4 below or the compounds 1.1 to 1.811 described in Table T1 (below), the compounds 2.1 to 2.26 described in Table T2 (below), and the compounds 3.1 to 3.140 described in Table T3 (below).

-continued (Ib)

Likewise, the compounds of the present invention may be diastereomers of the compound of Formula (I) when n is 2, and wherein at each of the two carbon positions bound to $R^5$ and $R^6$, $R^5$ and $R^6$ are different.

It is understood that when in aqueous media, the compounds of formula (I) according to the invention may be present in a reversible equilibrium with the corresponding covalently hydrated forms (ie, the compounds of formula (I-I) and formula (I-II) as shown below) at the $CF_3$-oxadiazole motif. This dynamic equilibrium may be important for the biological activity of the compounds of Formula (I). The designations of n, $A^1, A^2, A^3, A^4, R^1, R^2, R^3, R^4, R^5, R^6, R^7,$ Compounds of the present invention can be made as shown in the following schemes 1 to 14, in which, unless otherwise stated, the definition of each variable is as defined above for a compound of formula (I).

The compounds of formula (I) can be obtained by an amide coupling transformation with compounds of formula (II) and compounds of formula (III) by activating the carboxylic acid function of the compounds of formula (III), a process that usually takes place by converting the —OH of the carboxylic acid into a good leaving group, such as a chloride group, for example by using $(COCl)_2$ or $SOCl_2$, prior to treatment with the compounds of formula (II), preferably in a suitable solvent (eg, dimethylformamide, dichloromethane or tetrahydrofuran), preferably at a temperature of between 25° C. and 100° C., and optionally in the presence of a base such as triethylamine or N,N-diisopropylethylamine, or under conditions described in the literature for an amide coupling. For examples, see WO 2003/028729. Compounds of formula (III) are commercially available or prepared using known methods. For related examples, see: Nelson, T. D et al *Tetrahedron Lett.* (2004), 45, 8917; Senthil, K. et al *Pest. Res. Journal* (2009), 21, 133; and Crich, D., Zou, Y. *J. Org. Chem.* (2005), 70, 3309. This reaction is shown in Scheme 1.

Scheme 1

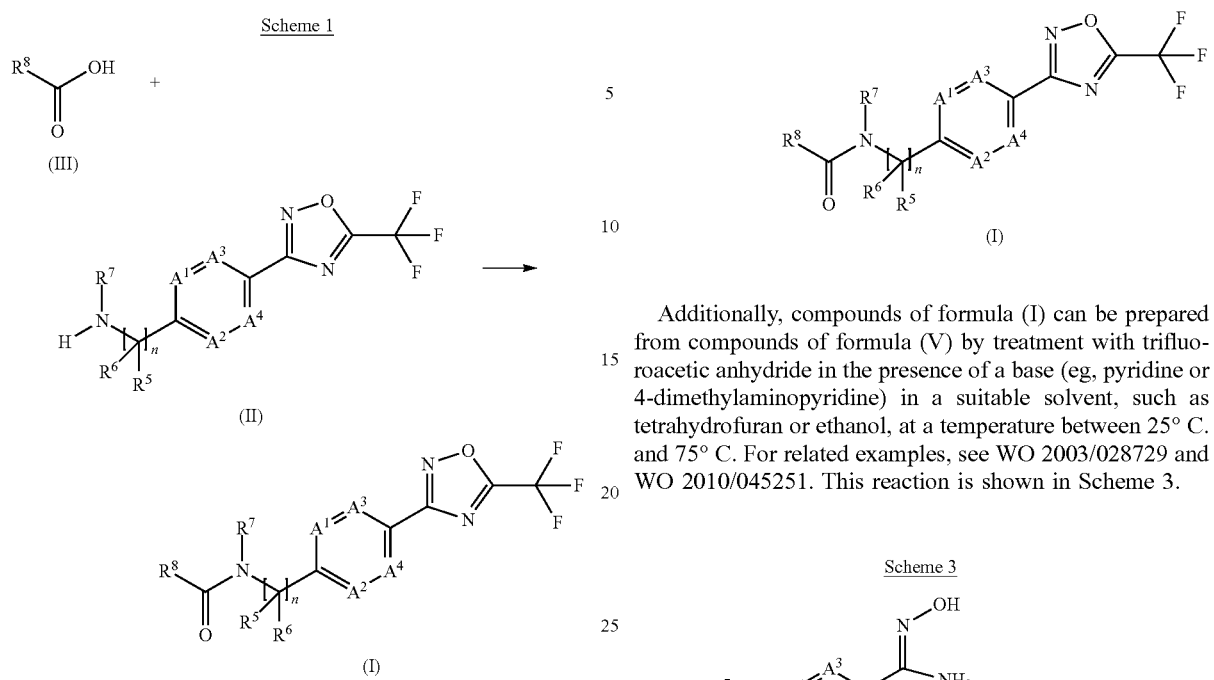

Alternatively, compounds of formula (I) can be prepared from compounds of formula (II) via treatment with triphosgene, in a suitable solvent (eg, ethyl acetate, CHCl$_3$, or toluene) with heating between 65° C. and 100° C. followed by the addition of suitable nucleophiles of formula (IV), wherein R$^8$—Nu is an organometallic (eg, an organomagnesium, organozinc, or organolithium) reagent in a suitable solvent (eg, toluene, diethyl ether or tetrahydrofuran) at a temperature between −78° C. and 25° C. For related examples, see Charalambides, Y. C., Moratti, S. C. *Synth. Commun.* (2007), 37, 1037; Schaefer, G. et al *Angew. Chem., Int. Ed.* (2012) 51, 9173; Lengyel, I. et al *Heterocycles* (2007), 73, 349; and Benalil, A et al *Synthesis* (1991), 9, 787. Furthermore, compounds of formula (I) can be prepared from compounds of formula (II) via treatment with triphosgene, in a suitable solvent (eg, 1,2-dichloroethane, CHCl$_3$, or toluene) followed by the addition of suitable nucleophiles of formula (IV), wherein R$^8$—Nu represents HOR$^{10}$ or HN(R$^{11}$)R$^{12}$ in the presence of a suitable base such as triethylamine. This reaction is shown in Scheme 2

Scheme 2

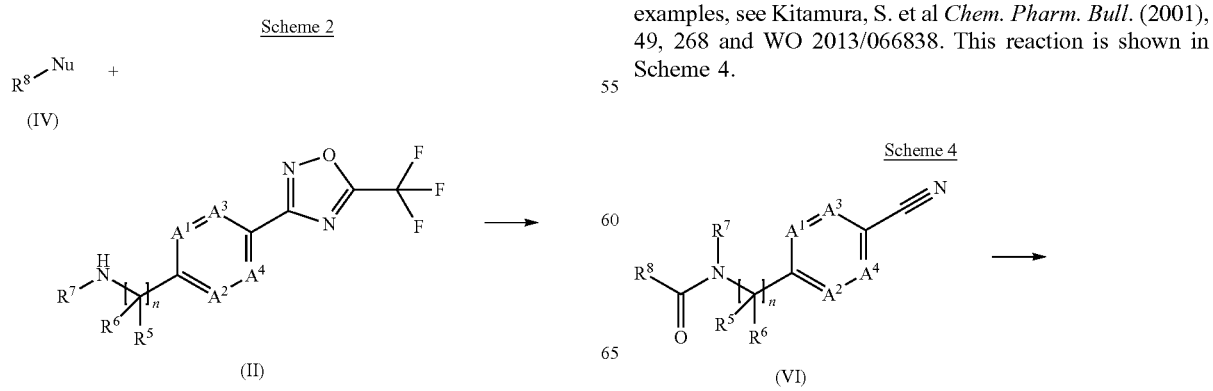

Additionally, compounds of formula (I) can be prepared from compounds of formula (V) by treatment with trifluoroacetic anhydride in the presence of a base (eg, pyridine or 4-dimethylaminopyridine) in a suitable solvent, such as tetrahydrofuran or ethanol, at a temperature between 25° C. and 75° C. For related examples, see WO 2003/028729 and WO 2010/045251. This reaction is shown in Scheme 3.

Scheme 3

Compounds of formula (V) can be prepared from compounds of formula (VI) by treatment with a hydroxylamine hydrochloride salt in the presence of a base, such as triethylamine, in a suitable solvent, such as methanol, at a temperature between 0° C. and 100° C. For related examples, see Kitamura, S. et al *Chem. Pharm. Bull.* (2001), 49, 268 and WO 2013/066838. This reaction is shown in Scheme 4.

Scheme 4

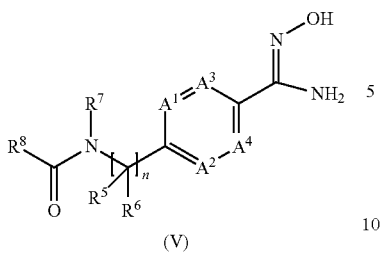

(V)

Compounds of formula (VI) can be prepared from compounds of formula (VII), wherein Z is Br or I, via metal-promoted reaction with a suitable cyanide reagent, such as Pd(0)/Zn(CN)$_2$ or CuCN, in a suitable solvent (eg, dimethylformamide or N-methylpyrrolidone) at elevated temperature between 100° C. and 120° C. For related examples, see US 2007/0155739 and WO 2009/022746. This reaction is shown in Scheme 5.

Scheme 5

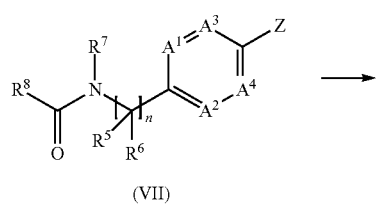

(VII)

↓

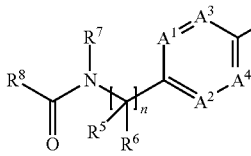

(VI)

Compounds of formula (VII), wherein the N—R$^7$ bond contains a directly linked —CH$_2$ segment, can be prepared from compounds of formula (VIII), wherein Z is Br or I, via a base-promoted reaction (eg, sodium hydride) with a suitable alkylating reagent (eg, methyl iodide or propyl iodide), in a suitable solvent (eg, dimethylformamide or N-methylpyrrolidone) at elevated temperature between 100° C. and 120° C. This reaction is shown in Scheme 6.

Scheme 6

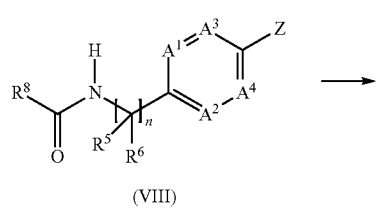

(VIII)

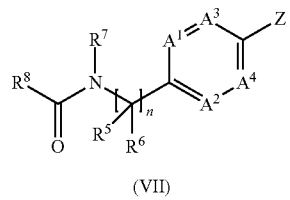

(VII)

Compounds of formula (II), wherein n is preferably 0 and R$^6$ is hydrogen, can be prepared from carbonyl compounds of formula (IX), starting with treatment by compounds of formula (X), wherein R$^{PG}$ is tert-butylsulfinamide, optionally in the presence of an activating reagent (eg, Ti(OEt)$_4$), in a suitable solvent, (eg, tetrahydrofuran) at a temperature between 60° C. and 75° C. and followed by the addition of a reagent of formula (XI), such as an alkyl Grignard reagent (eg. alkylMgBr), Me$_3$SiCN, or a metal hydride (eg, NaBH$_4$, NaBH$_3$CN, or LiAlH$_4$), in a suitable solvent, (eg, tetrahydrofuran or ethanol) at temperatures between 0° C. and 25° C. Removal of the tert-butanesulfinyl group with concomitant liberation of amine compounds of formula (II) occurs upon treatment with methanolic HCl. For related examples, see Cogan, D., Ellman J. A. *J. Am. Chem. Soc.* (1999), 121, 268. This reaction is shown in Scheme 7.

Scheme 7

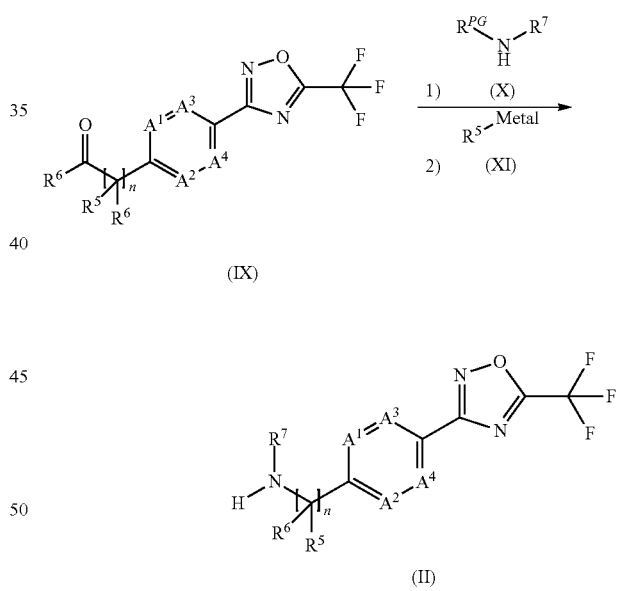

(II)

Alternatively, compounds of formula (II), wherein n is preferably 1, can be prepared from compounds of formula (XIII), wherein X is Cl or Br, by treatment with amines of formula (XII), wherein Y is tert-butylcarboxylate, in a suitable solvent (eg, tetrahydrofuran) at a temperature between 25° C. and 60° C. Removal of the tert-butylcarboxylate groups with concomitant liberation of benzylamines of formula (II) occurs upon treatment with HCl or trifluoroacetic acid in a suitable solvent (eg, dioxane or MeOH). For related examples, see Miyawaki, K. et al *Heterocycles* (2001), 54, 887, WO 2003/028729, and WO 2013/066839. This reaction is shown in Scheme 8.

Scheme 8

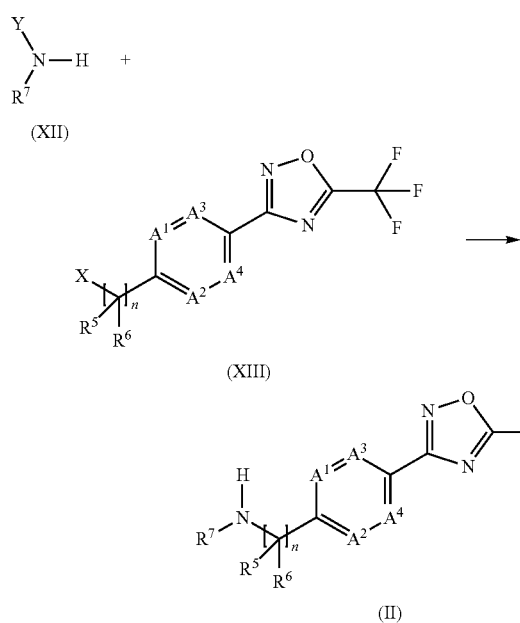

Compounds of formula (XIII), wherein n is 1, can be prepared from compounds of formula (XIV), wherein X is Cl or Br, by treatment with a halogen source (eg, N-bromosuccinimide (NBS) or N-chlorosuccinimide (NCS)) and a radical initiator (eg, (PhCO$_2$)$_2$ or azobisisobutyronitrile (AIBN)) in a suitable solvent, such as tetrachloromethane, at temperatures between 55° and 100° C. in the presence of ultraviolet light. For related examples, see Liu, S. et al *Synthesis* (2001), 14, 2078 and Kompella, A. et al *Org. Proc. Res. Dev.* (2012), 16, 1794. This reaction is shown in Scheme 9.

Scheme 9

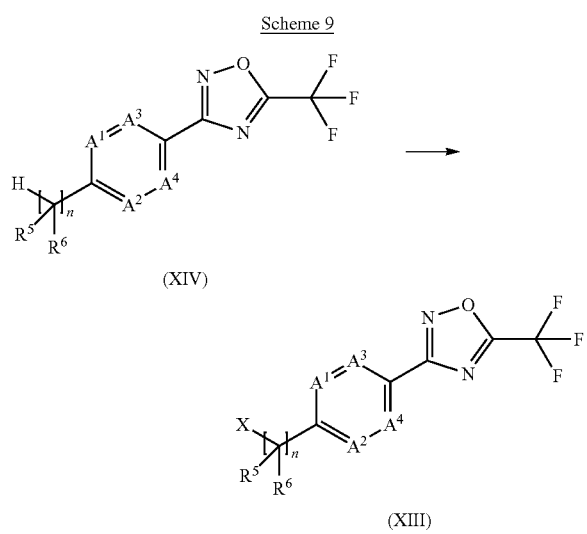

The compounds of formula (VII) can be obtained by an amide coupling transformation with compounds of formula (XV) and compounds of formula (III) by activating the carboxylic acid function of the compounds of formula (III), a process that usually takes place by converting the —OH of the carboxylic acid into a good leaving group, such as a chloride group, for example by using (COCl)$_2$ or SOCl$_2$, prior to treatment with the compounds of formula (XV), preferably in a suitable solvent (eg, dimethylformamide, dichloromethane or tetrahydrofuran), preferably at a temperature of between 25° C. and 100° C., and optionally in the presence of a base such as triethylamine or N,N-diisopropylethylamine, or under conditions described in the literature for an amide coupling. For examples, see WO 2003/028729. Compounds of formula (III) are commercially available or prepared using known methods. For related examples, see: Nelson, T. D et al *Tetrahedron Lett.* (2004), 45, 8917; Senthil, K. et al *Pest. Res. Journal* (2009), 21, 133; and Crich, D., Zou, Y. *J. Org. Chem.* (2005), 70, 3309. This reaction is shown in Scheme 10.

Scheme 10

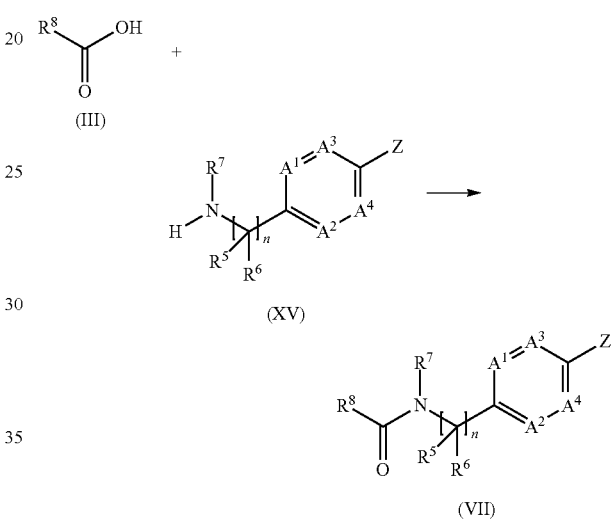

Furthermore, compounds of formula (VII), wherein Z is Br, I, or CN and R$^8$ may also be OR$^{12}$ or NR$^{14}$R$^{15}$ where R$^{15}$ is not hydrogen and n is preferably 1, can be prepared from compounds of formula (XVIII), wherein X is Cl, Br or I, via treatment with amides of formula (XVII), wherein Y is tert-butylcarboxylate, in the presence of a suitable base, such as NaH, in a suitable solvent, such as dimethylformamide, at a temperature between 0° C. and 100° C. In some cases, a better reaction performance may be gained from the use of a catalyst (eg, NaI or 4-dimethylaminopyridine) and with microwave irradiation. Removal of the tert-butylcarboxylate groups with concomitant liberation of benzylamides of formula (VIII) occurs upon treatment with HCl or trifluoroacetic acid in a suitable solvent (eg, dioxane, dichloromethane or MeOH). For related examples, see Miyawaki, K. et al *Heterocycles* (2001), 54, 887. This reaction is shown in Scheme 11.

Scheme 11

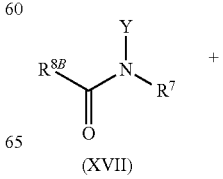

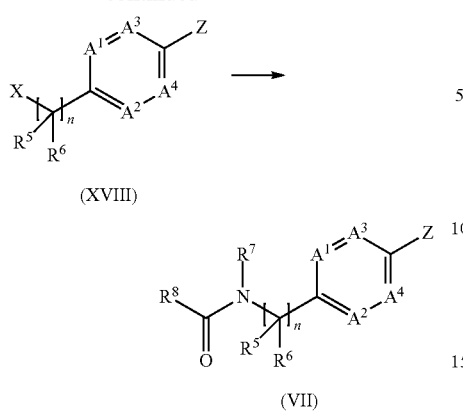

(XVIII)

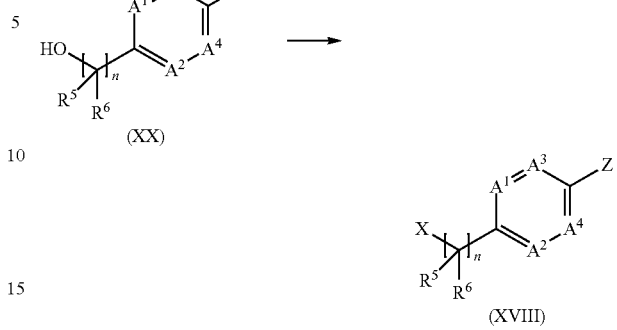

Compounds of formula (XVIII), wherein Z is Br, I, or CN and X is Cl or Br and n is preferably 1, are either commercially available or can be prepared from compounds of formula (XIX), by treatment with a halogen source, (eg, N-bromosuccinimide (NBS) or N-chlorosuccinimide (NCS)) and a radical initiator, such as $(PhCO_2)_2$ or azobisisobutyronitrile (AIBN), in the presence of ultraviolet light, in a suitable solvent, such as tetrachloromethane, at temperatures between 55° C. and 100° C. For related examples, see Liu, S. et al *Synthesis* (2001), 14, 2078 and Kompella, A. et al *Org. Proc. Res. Dev.* (2012), 16, 1794. This reaction is shown in Scheme 12.

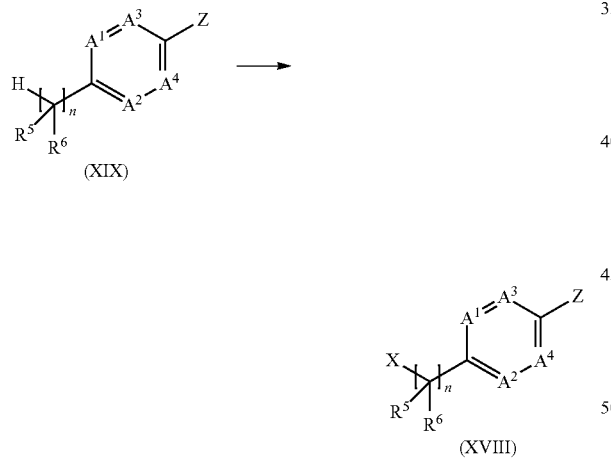

Alternatively, compounds of formula (XVIII), wherein X is Cl, Br, I, or $OSO_2Me$ and Z is Br, I and n is preferably 1, or CN are either commercially available or can be prepared from compounds of formula (XX), by treatment with a halogen source (eg $CBr_4$, $CCl_4$ or $I_2$) in the presence of triphenylphosphine, or with methanesulfonyl chloride ($ClSO_2Me$), in a suitable solvent, (eg, dichloromethane) at a temperature between 0° C. and 100° C. For related examples, see Liu, H. et al *Bioorg. Med. Chem.* (2008), 16, 10013, WO 2014/020350 and Kompella, A. et al *Bioorg. Med. Chem. Lett.* (2001), 1, 3161. Compounds of formula (XIX) are commercially available. This reaction is shown in Scheme 13.

Compounds of formula (XV), wherein n is 0 or 1, and $R^6$ is preferably hydrogen, can be prepared from compounds of formula (XXI), starting with treatment by compounds of formula (X), wherein $R^{PG}$ is a tert-butylsulfinamides or hydrogen, optionally in the presence of an activating reagent (eg, $Ti(OEt)_4$), in a suitable solvent, (eg, tetrahydrofuran) at a temperature between 60° C. and 75° C. and followed by the addition of an organometallic compound of formula (XI), such as an alkyl Grignard reagent (eg. alkylMgBr) and $Me_3SiCN$, or a metal hydride of formula (XI), wherein the metal is B or Al (eg, $NaBH_4$, $NaBH_3CN$, or $LiAlH_4$), in a suitable solvent, (eg, tetrahydrofuran or ethanol) at temperatures between 0° C. and 25° C. Removal of the tert-butanesulfinyl group with concomitant liberation of benzylamines of formula (XV) occurs upon treatment with methanolic HCl. For related examples, see Cogan, D., Ellman J. A. *J. Am. Chem. Soc.* (1999), 121, 268. This reaction is shown in Scheme 14.

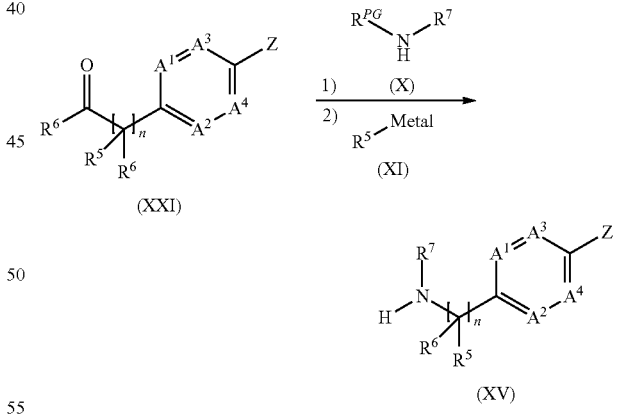

As already indicated, surprisingly, it has now been found that the novel compounds of formula (I) according to the invention have, for practical purposes, a very advantageous level of biological activity for protecting plants against diseases that are caused by fungi.

The compounds of formula (I) can be used in the agricultural sector and related fields of use, e.g., as active ingredients for controlling plant pests or on non-living materials for the control of spoilage microorganisms or organisms potentially harmful to man. The novel compounds are distinguished by excellent activity at low rates of application, by being well tolerated by plants and by being environmentally safe. They have very useful curative, preventive and systemic properties and can be used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later, e.g., from phytopathogenic microorganisms.

The present invention further relates to a method for controlling or preventing infestation of plants or plant propagation material and/or harvested food crops susceptible to microbial attack by treating plants or plant propagation material and/or harvested food crops wherein an effective amount a compound of formula (I) is applied to the plants, to parts thereof or the locus thereof.

It is also possible to use compounds of formula (I) as fungicide. The term "fungicide" as used herein means a compound that controls, modifies, or prevents the growth of fungi. The term "fungicidally effective amount" means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

It may also be possible to use compounds of formula (I) as dressing agents for the treatment of plant propagation material, e.g., seed, such as fruits, tubers or grains, or plant cuttings, for the protection against fungal infections as well as against phytopathogenic fungi occurring in the soil. The propagation material can be treated with a composition comprising a compound of formula (I) before planting: seed, for example, can be dressed before being sown. The active compounds of formula (I) can also be applied to grains (coating), either by impregnating the seeds in a liquid formulation or by coating them with a solid formulation. The composition can also be applied to the planting site when the propagation material is being planted, for example, to the seed furrow during sowing. The invention relates also to such methods of treating plant propagation material and to the plant propagation material so treated.

Furthermore, the compounds of formula (I) can be used for controlling fungi in related areas, for example in the protection of technical materials, including wood and wood related technical products, in food storage, in hygiene management.

In addition, the invention could be used to protect non-living materials from fungal attack, e.g. lumber, wall boards and paint.

The compounds of formula (I) are for example, effective against fungi and fungal vectors of disease as well as phytopathogenic bacteria and viruses. These fungi and fungal vectors of disease as well as phytopathogenic bacteria and viruses are for example:

*Absidia corymbifera, Alternaria* spp, *Aphanomyces* spp, *Ascochyta* spp, *Aspergillus* spp. including *A. flavus, A. fumigatus, A. nidulans, A. niger, A. terrus, Aureobasidium* spp. including *A. pullulans, Blastomyces dermatitidis, Blumeria graminis, Bremia lactucae, Botryosphaeria* spp. including *B. dothidea, B. obtusa, Botrytis* spp. inclusing *B. cinerea, Candida* spp. including *C. albicans, C. glabrata, C. krusei, C. lusitaniae, C. parapsilosis, C. tropicalis, Cephaloascus fragrans, Ceratocystis* spp, *Cercospora* spp. including *C. arachidicola, Cercosporidium personatum, Cladosporium* spp, *Claviceps purpurea, Coccidioides immitis, Cochliobolus* spp, *Colletotrichum* spp. including *C. musae, Cryptococcus neoformans, Diaporthe* spp, *Didymella* spp, *Drechslera* spp, *Elsinoe* spp, *Epidermophyton* spp, *Erwinia amylovora, Erysiphe* spp. including *E. cichoracearum, Eutypa lata, Fusarium* spp. including *F. culmorum, F. graminearum, F. langsethiae, F. moniliforme, F. oxysporum, F. proliferatum, F. subglutinans, F. solani, Gaeumannomyces graminis, Gibberella fujikuroi, Gloeodes pomigena, Gloeosporium musarum, Glomerella cingulate, Guignardia bidwellii, Gymnosporangium juniperi-virginianae, Helminthosporium* spp, *Hemileia* spp, *Histoplasma* spp. including *H. capsulatum, Laetisaria fuciformis, Leptographium lindbergi, Leveillula taurica, Lophodermium seditiosum, Microdochium nivale, Microsporum* spp, *Monilinia* spp, *Mucor* spp, *Mycosphaerella* spp. including *M. graminicola, M. pomi, Oncobasidium theobromaeon, Ophiostoma piceae, Paracoccidioides* spp, *Penicillium* spp. including *P. digitatum, P. italicum, Petriellidium* spp, *Peronosclerospora* spp. Including *P. maydis, P. philippinensis* and *P. sorghi, Peronospora* spp, *Phaeosphaeria nodorum, Phakopsora pachyrhizi, Phellinus igniarus, Phialophora* spp, *Phoma* spp, *Phomopsis viticola, Phytophthora* spp. including *P. infestans, Plasmopara* spp. including *P. halstedii, P. viticola, Pleospora* spp., *Podosphaera* spp. including *P. leucotricha, Polymyxa graminis, Polymyxa betae, Pseudocercosporella herpotrichoides, Pseudomonas* spp, *Pseudoperonospora* spp. including *P. cubensis, P. humuli, Pseudopeziza tracheiphila, Puccinia* Spp. including *P. hordei, P. recondita, P. striiformis, P. triticina, Pyrenopeziza* spp, *Pyrenophora* spp, *Pyricularia* spp. including *P. oryzae, Pythium* spp. including *P. ultimum, Ramularia* spp, *Rhizoctonia* spp, *Rhizomucor pusillus, Rhizopus arrhizus, Rhynchosporium* spp, *Scedosporium* spp. including *S. apiospermum* and *S. prolificans, Schizothyrium pomi, Sclerotinia* spp, *Sclerotium* spp, *Septoria* spp, including *S. nodorum, S. tritici, Sphaerotheca macularis, Sphaerotheca fusca (Sphaerotheca fuliginea), Sporothorix* spp, *Stagonospora nodorum, Stemphylium* spp., *Stereum hirsutum, Thanatephorus cucumeris, Thielaviopsis basicola, Tilletia* spp, *Trichoderma* spp. including *T. harzianum, T. pseudokoningii, T. viride, Trichophyton* spp, *Typhula* spp, *Uncinula necator, Urocystis* spp, *Ustilago* spp, *Venturia* spp. including *V. inaequalis, Verticillium* spp, and *Xanthomonas* spp.

The compounds of formula (I) may be used for example on turf, ornamentals, such as flowers, shrubs, broad-leaved trees or evergreens, for example conifers, as well as for tree injection, pest management and the like.

Within the scope of present invention, target crops and/or useful plants to be protected typically comprise perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

The term "useful plants" is to be understood as also including useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as also including useful plants which have been so transformed by the use of recombinant DNA techniques that they are capable of synthesising one or more selectively acting toxins, such as are known, for example, from toxin-producing bacteria, especially those of the genus *Bacillus.*

Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard 11® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus.*

Toxins that can be expressed by such transgenic plants include, for example, insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

Further, in the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO93/07278, WO95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" is understood to denote generative parts of the plant, such as seeds, which can be used for the multiplication of the latter, and vegetative material, such as cuttings or tubers, for example potatoes. There can be mentioned for example seeds (in the strict sense), roots, fruits, tubers, bulbs, rhizomes and parts of plants. Germinated plants and young plants which are to be transplanted after germination or after emergence from the soil, may also be mentioned. These young plants can be protected before transplantation by a total or partial treatment by immersion. Preferably "plant propagation material" is understood to denote seeds.

The compounds of formula I may be used in unmodified form or, preferably, together with the adjuvants conventionally employed in the art of formulation. To this end they may be conveniently formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants, e.g. for agricultural use, can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

Suspension concentrates are aqueous formulations in which finely divided solid particles of the active compound are suspended. Such formulations include anti-settling agents and dispersing agents and may further include a wetting agent to enhance activity as well an anti-foam and a crystal growth inhibitor. In use, these concentrates are diluted in water and normally applied as a spray to the area to be treated. The amount of active ingredient may range from 0.5% to 95% of the concentrate.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain from 5% to 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from 0.5% to 95% of the concentrate.

Granular formulations include both extrudates and relatively coarse particles and are usually applied without dilution to the area in which treatment is required. Typical carriers for granular formulations include sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Granular formulations normally contain 5% to 25% of active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically 1 to 50 microns in diameter. The enclosed liquid typically constitutes 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimetre to 1 centimetre and preferably 1 to 2 millimetres in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Suitable agricultural adjuvants and carriers that are useful in formulating the compositions of the invention in the formulation types described above are well known to those skilled in the art.

Liquid carriers that can be employed include, for example, water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc., ethylene glycol, propylene glycol, glycerine and N-methyl-2-pyrrolidinone. Water is generally the carrier of choice for the dilution of concentrates.

Suitable solid carriers include, for example, talc, titanium dioxide, pyrophyllite clay, silica, attapulgite clay, kieselguhr, chalk, diatomaxeous earth, lime, calcium carbonate, bentonite clay, fuller's earth, cotton seed hulls, wheat flour, soybean flour, pumice, wood flour, walnut shell flour and lignin.

A broad range of surface-active agents are advantageously employed in both said liquid and solid compositions, especially those designed to be diluted with carrier before application. These agents, when used, normally comprise from 0.1% to 15% by weight of the formulation. They can be anionic, cationic, non-ionic or polymeric in character and can be employed as emulsifying agents, wetting agents, suspending agents or for other purposes. Typical surface active agents include salts of alkyl sulfates, such as diethanolammonium lauryl sulphate; alkylarylsulfonate salts, such as calcium dodecylbenzenesulfonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, anti-foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants and sticking agents.

In addition, further, other biocidally active ingredients or compositions may be combined with the compositions of the invention and used in the methods of the invention and applied simultaneously or sequentially with the compositions of the invention. When applied simultaneously, these further active ingredients may be formulated together with the compositions of the invention or mixed in, for example, the spray tank. These further biocidally active ingredients may be fungicides, herbicides, insecticides, bactericides, acaricides, nematicides and/or plant growth regulators.

Pesticidal agents are referred to herein using their common name are known, for example, from "The Pesticide Manual", 15th Ed., British Crop Protection Council 2009.

In addition, the compositions of the invention may also be applied with one or more systemically acquired resistance inducers ("SAR" inducer). SAR inducers are known and described in, for example, U.S. Pat. No. 6,919,298 and include, for example, salicylates and the commercial SAR inducer acibenzolar-S-methyl.

The compounds of formula (I) are normally used in the form of agrochemical compositions and can be applied to the crop area or plant to be treated, simultaneously or in succession with further compounds. These further compounds can be e.g. fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) may be used in the form of (fungicidal) compositions for controlling or protecting against phytopathogenic microorganisms, comprising as active ingredient at least one compound of formula (I) or of at least one preferred individual compound as defined herein, in free form or in agrochemically usable salt form, and at least one of the above-mentioned adjuvants.

The invention therefore provides a composition, preferably a fungicidal composition, comprising at least one compound formula (I) an agriculturally acceptable carrier and optionally an adjuvant. An agricultural acceptable carrier is for example a carrier that is suitable for agricultural use. Agricultural carriers are well known in the art. Preferably said composition may comprise at least one or more pesticidally-active compounds, for example an additional fungicidal active ingredient in addition to the compound of formula (I).

The compound of formula (I) may be the sole active ingredient of a composition or it may be admixed with one or more additional active ingredients such as a pesticide, fungicide, synergist, herbicide or plant growth regulator where appropriate. An additional active ingredient may, in some cases, result in unexpected synergistic activities.

Examples of suitable additional active ingredients include the following: acycloamino acid fungicides, aliphatic nitrogen fungicides, amide fungicides, anilide fungicides, antibiotic fungicides, aromatic fungicides, arsenical fungicides, aryl phenyl ketone fungicides, benzamide fungicides, benzanilide fungicides, benzimidazole fungicides, benzothiazole fungicides, botanical fungicides, bridged diphenyl fungicides, carbamate fungicides, carbanilate fungicides, conazole fungicides, copper fungicides, dicarboximide fungicides, dinitrophenol fungicides, dithiocarbamate fungicides, dithiolane fungicides, furamide fungicides, furanilide fungicides, hydrazide fungicides, imidazole fungicides, mercury fungicides, morpholine fungicides, organophosphorous fungicides, organotin fungicides, oxathiin fungicides, oxazole fungicides, phenylsulfamide fungicides, polysulfide fungicides, pyrazole fungicides, pyridine fungicides, pyrimidine fungicides, pyrrole fungicides, quaternary ammonium fungicides, quinoline fungicides, quinone fungicides, quinoxaline fungicides, strobilurin fungicides, sulfonanilide fungicides, thiadiazole fungicides, thiazole fungicides, thiazolidine fungicides, thiocarbamate fungicides, thiophene fungicides, triazine fungicides, triazole fungicides, triazolopyrimidine fungicides, urea fungicides, valinamide fungicides, and zinc fungicides.

Examples of suitable additional active ingredients also include the following: 3-difluoromethyl-1-methyl-1H-pyrazole-4-carboxylic acid (9-dichloromethylene-1,2,3,4-tetrahydro-1,4-methano-naphthalen-5-yl)-amide, 3-difluoromethyl-1-methyl-1H-pyrazole-4-carboxylic acid methoxy-[1-methyl-2-(2,4,6-trichlorophenyl)-ethyl]-amide, 1-methyl-3-difluoromethyl-1H-pyrazole-4-carboxylic acid (2-dichloromethylene-3-ethyl-1-methyl-indan-4-yl)-amide (1072957-71-1), 1-methyl-3-difluoromethyl-1H-pyrazole-4-carboxylic acid (4'-methylsulfanyl-biphenyl-2-yl)-amide, 1-methyl-3-difluoromethyl-4H-pyrazole-4-carboxylic acid [2-(2,4-dichloro-phenyl)-2-methoxy-1-methyl-ethyl]amide, (5-chloro-2,4-dimethyl-pyridin-3-yl)-(2,3,4-trimethoxy-6-methyl-phenyl)-methanone, (5-Bromo-4-chloro-2-methoxy-pyridin-3-yl)-(2,3,4-trimethoxy-6-methyl-phenyl)-methanone, 2-{2-[(E)-3-(2,6-Dichloro-phenyl)-1-methyl-prop-2-en-(E)-ylideneaminooxymethyl]-phenyl}-2-[(Z)-methoxyimino]-N-methyl-acetamide, 3-[5-(4-chloro-phenyl)-2,3-dimethyl-isoxazolidin-3-yl]-pyridine, (E)-N-methyl-2-[2-(2,5-dimethylphenoxymethyl) phenyl]-2-methoxy-iminoacetamide, 4-bromo-2-cyano-N,N-dimethyl-6-trifluoromethylbenzimidazole-1-sulphonamide, a-[N-(3-chloro-2,6-xylyl)-2-methoxyacetamido]-y-butyrolactone, 4-chloro-2-cyano-N,-dimethyl-5-p-tolylimidazole-1-sulfonamide, N-allyl-4,5,-dimethyl-2-trimethylsilylthiophene-3-carboxamide, N-(1-cyano-1,2-dimethylpropyl)-2-(2,4-dichlorophenoxy) propionamide, N-(2-methoxy-5-pyridyl)-cyclopropane carboxamide, (.+-.)-cis-1-(4-chlorophenyl)-2-(1H-1,2,4-triazol-1-yl)-cycloheptanol, 2-(1-tert-butyl)-1-(2-chlorophenyl)-3-(1,2,4-triazol-1-yl)-propan-2-ol, 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one, methyl (E)-2-[2-[6-(2-cyanophenoxy)pyrimidin-4-yloxy]phenyl]3-methoxyacrylate, methyl (E)-2-[2-[6-(2-thioamidophenoxy) pyrimidin-4-yloxy]phenyl]-3-methoxyacrylate, methyl (E)-2-[2-[6-(2-fluorophenoxy)pyrimidin-4-yloxy]phenyl]-3-methoxyacrylate, methyl (E)-2-[2-[6-(2,6-difluorophenoxy) pyrimidin-4-yloxy]phenyl]-3-methoxyacrylate, methyl (E)-2-[2-[3-(pyrimidin-2-yloxy)phenoxy]phenyl]-3-methoxyacrylate, methyl (E)-2-[2-[3-(5-methylpyrimidin-2-yloxy)-phenoxy]phenyl]-3-methoxyacrylate, methyl (E)-2-[2-[3-(phenyl-sulphonyloxy)phenoxy]phenyl-3-methoxyacrylate, methyl (E)-2-[2-[3-(4-nitrophenoxy) phenoxy]phenyl]-3-methoxyacrylate, methyl (E)-2-[2-phenoxyphenyl]-3-methoxyacrylate, methyl (E)-2-[2-(3,5-dimethyl-benzoyl)pyrrol-1-yl]-3-methoxyacrylate, methyl (E)-2-[2-(3-methoxyphenoxy)phenyl]-3-methoxyacrylate, methyl (E)-2-[2-(2-phenylethen-1-yl)-phenyl]-3-methoxy-acrylate, methyl (E)-2-[2-(3,5-dichlorophenoxy)pyridin-3-yl]-3-methoxyacrylate, methyl (E)-2-(2-(3-(1,1,2,2-tetrafluoroethoxy)phenoxy)phenyl)-3-methoxyacrylate,
methyl (E)-2-(2-[3-(alpha-hydroxybenzyl)phenoxy]phenyl)-3-methoxyacrylate, methyl (E)-2-(2-(4-phenoxypyridin-2-yloxy)phenyl)-3-methoxyacrylate, methyl (E)-2-[2-(3-n-propyloxy-phenoxy)phenyl]3-methoxyacrylate, methyl (E)-2-[2-(3-isopropyloxyphenoxy)phenyl]-3-methoxyacrylate, methyl (E)-2-[2-[3-(2-fluorophenoxy)phenyl]-3-methoxyacrylate, methyl (E)-2-[2-(3-ethoxyphenoxy)phenyl]-3-methoxyacrylate, methyl (E)-2-[2-(4-tert-butyl-pyridin-2-yloxy)phenyl]-3-methoxyacrylate, methyl (E)-2-[2-[3-(3-cyanophenoxy)phenoxy]phenyl]-3-methoxyacrylate, methyl (E)-2-[2-[(3-methyl-pyridin-2-yloxymethyl)phenyl]-3-methoxyacrylate, methyl (E)-2-[2-[6-(2-methyl-phenoxy)pyrimidin-4-yloxy]phenyl]-3-methoxyacrylate, methyl (E)-2-[2-(5-bromo-pyridin-2-yloxymethyl)phenyl]-3-methoxyacrylate, methyl (E)-2-[2-(3-(3-iodopyridin-2-yloxy)phenoxy)phenyl]-3-methoxyacrylate, methyl (E)-2-[2-[6-(2-chloropyridin-3-yloxy)pyrimidin-4-yloxy]phenyl]-3-methoxyacrylate,
methyl (E),(E)-2-[2-(5,6-dimethylpyrazin-2-ylmethyloxy)iminomethyl)phenyl]-3-methoxyacrylate, methyl (E)-2-{2-[6-(6-methylpyridin-2-yloxy)pyrimidin-4-yloxy]phenyl}-3-methoxy-acrylate, methyl (E),(E)-{2-(3-methoxyphenyl) methyloximinomethyl]-phenyl}-3-methoxyacrylate, methyl (E)-2-{2-(6-(2-azidophenoxy)-pyrimidin-4-yloxy]phenyl}-3-methoxyacrylate, methyl (E),(E)-2-{2-[6-phenylpyrimidin-4-yl)-methyloximinomethyl]phenyl}-3-methoxyacrylate, methyl (E),(E)-2-{2-[(4-chlorophenyl)-methyloximinomethyl]-phenyl}-3-methoxyacrylate, methyl (E)-2-{2-[6-(2-n-propylphenoxy)-1,3,5-triazin-4-yloxy] phenyl}-3-methoxyacrylate, methyl (E),(E)-2-{2-[(3-nitrophenyl)methyloximinomethyl]phenyl}-3-methoxyacrylate, 3-chloro-7-(2-aza-2,7,7-trimethyl-oct-3-en-5-ine), 2,6-dichloro-N-(4-trifluoromethylbenzyl)-benzamide, 3-iodo-2-propinyl alcohol, 4-chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbamate, 3-iodo-2-propinyl phenylcarbamate; phenol derivatives, such as tribromophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol, 5-hydroxy-2 (5H)-furanone; 4,5-dichlorodithiazolinone, 4,5-benzodithiazolinone, 4,5-trimethylenedithiazolinone, 4,5-dichloro-(3H)-1,2-dithiol-3-one, 3,5-dimethyl-tetrahydro-1,3,5-thiadiazine-2-thione, N-(2-p-chlorobenzoylethyl)-hexaminium chloride, acibenzolar, acypetacs, alanycarb, albendazole, aldimorph, allicin, allyl alcohol, ametoctradin, amisulbrom, amobam, ampropylfos, anilazine, asomate, aureofungin, azaconazole, azafendin, azithiram, azoxystrobin, barium polysulfide, benalaxyl, benalaxyl-M, benodanil, benomyl, benquinox, bentaluron, benthiavalicarb, benthiazole, benzalkonium chloride, benzamacril, benzamorf, benzohydroxamic acid, benzovindiflupyr, berberine, bethoxazin, biloxazol, binapacryl, biphenyl, bitertanol, bithionol, bixafen, blasticidin-S, boscalid, bromothalonil, bromuconazole, bupirimate, buthiobate, butylamine calcium polysulfide, captafol, captan, carbamorph, carbendazim, carbendazim chlorhydrate, carboxin, carpropamid, carvone, CGA41396, CGA41397, chinomethionate, chitosan, chlobenthiazone, chloraniformethan, chloranil, chlorfenazole, chloroneb, chloropicrin, chlorothalonil, chlorozolinate, chlozolinate, climbazole, clotrimazole, clozylacon, copper containing compounds such as copper acetate, copper carbonate, copper hydroxide, copper naphthenate, copper oleate, copper oxychloride, copper oxyquinolate, copper silicate, copper sulphate, copper tallate, copper zinc chromate and Bordeaux mixture, cresol, cufraneb, cuprobam, cuprous oxide, cyazofamid, cyclafuramid, cycloheximide, cyflufenamid, cymoxanil, cypendazole, cyproconazole, cyprodinil, dazomet, debacarb, decafentin, dehydroacetic acid, di-2-pyridyl disulphide 1,1'-dioxide, dichlofluanid, diclomezine, dichlone, dicloran, dichlorophen, dichlozoline, diclobutrazol, diclocymet, diethofencarb, difenoconazole, difenzoquat, diflumetorim, O, O-di-iso-propyl-S-benzyl thiophosphate, dimefluazole, dimetachlone, dimetconazole, dimethomorph, dimethirimol, diniconazole, diniconazole-M, dinobuton, dinocap, dinocton, dinopenton, dinosulfon, dinoterbon, diphenylamine, dipyrithione, disulfiram, ditalimfos, dithianon, dithioether, dodecyl dimethyl ammonium chloride, dodemorph, dodicin, dodine, doguadine, drazoxolon, edifenphos, enestroburin, epoxiconazole, etaconazole, etem, ethaboxam, ethirimol, ethoxyquin, ethilicin, ethyl (Z)—N-benzyl-N ([methyl(methyl-thioethylideneaminooxycarbonyl) amino]thio)-β-alaninate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fenpyrazamine, fentin acetate, fentin hydroxide, ferbam, ferimzone, fluazinam, fludioxonil, flumetover, flumorph, flupicolide, fluopyram, fluoroimide, fluotrimazole, fluoxastrobin, fluquinconazole, flusilazole, flusulfamide, flutanil, flutolanil, flutriafol, fluxapyroxad, folpet, formaldehyde, fosetyl, fuberidazole, furalaxyl, furametpyr, furcarbanil, furconazole, furfural, furmecyclox, furophanate, glyodin, griseofulvin, guazatine, halacrinate, hexa chlorobenzene, hexachlorobutadiene, hexachlorophene, hexaconazole, hexylthiofos, hydrargaphen, hydroxyisoxazole, hymexazole, imazalil, imazalil sulphate, imibenconazole, iminoctadine, iminoctadine triacetate, inezin, iodocarb, ipconazole, ipfentrifluconazole, iprobenfos, iprodione, iprovalicarb, isopropanyl butyl carbamate, isoprothiolane, isopyrazam, isotianil, isovaledione, izopamfos, kasugamycin, kresoxim-methyl, LY186054, LY211795, LY248908, mancozeb, mandipropamid, maneb, mebenil, mecarbinzid, mefenoxam, mefentrifluconazole, mepanipyrim, mepronil, mercuric chloride, mercurous chloride, meptyldinocap, metalaxyl, metalaxyl-M, metam, metazoxolon, metconazole, methasulfocarb, methfuroxam, methyl bromide, methyl iodide, methyl isothiocyanate, metiram, metiram-zinc, metominostrobin, metrafenone, metsulfovax, milneb, moroxydine, myclobutanil, myclozolin, nabam, natamycin, neoasozin, nickel dimethyldithiocarbamate, nitrostyrene, nitrothal-iso-propyl, nuarimol, octhilinone, ofurace, organomercury compounds, orysastrobin, osthol, oxadixyl, oxasulfuron, oxine-copper, oxolinic acid, oxpoconazole, oxycarboxin, parinol, pefurazoate, penconazole, pencycuron, penflufen, pentachlorophenol, penthiopyrad, phenamacril, phenazin oxide, phosdiphen, phosetyl-Al, phosphorus acids, phthalide, picoxystrobin, piperalin, polycarbamate, polyoxin D, polyoxrim, polyram, probenazole, prochloraz, procymidone, propamidine, propamocarb, propiconazole, propineb, propionic acid, proquinazid, prothiocarb, prothioconazole, pydiflumetofen, pyracarbolid, pyraclostrobin, pyrametrostrobin, pyraoxystrobin, pyrazophos, pyribencarb, pyridinitril, pyrifenox, pyrimethanil, pyriofenone, pyroquilon, pyroxychlor, pyroxyfur, pyrrolnitrin, quaternary ammonium compounds, quinacetol, quinazamid, quinconazole, quinomethionate, quinoxyfen, quintozene, rabenzazole, santonin, sedaxane, silthiofam, simeconazole, sipconazole, sodium pentachlorophenate, solatenol, spiroxamine, streptomycin, sulphur, sultropen, tebuconazole, tebfloquin, tecloftalam, tecnazene, tecoram, tetraconazole, thiabendazole, thiadifluor, thicyofen, thifluzamide, 2-(thiocyanomethylthio) benzothiazole, thiophanate-methyl, thioquinox, thiram, tiadinil, timibenconazole, tioxymid, tolclofos-methyl, tolylfluanid, triadimefon, triadimenol, triamiphos, triarimol, triazbutil, triazoxide, tricyclazole, tridemorph, trifloxystrobin, triflumazole, triforine, triflumizole, triticonazole, uniconazole, urbacide, validamycin, valifenalate, vapam, vinclozolin, zarilamid, zineb, ziram, and zoxamide.

The compounds of the invention may also be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in US-5015630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. Nos. 5,478,855, 4,639,771 and DE-19520936.

The compounds of the invention may be used in combination with derivatives and analogues of the general class of dioxomorpholine antiparasitic agents as described in WO 96/15121 and also with anthelmintic active cyclic depsipeptides such as those described in WO 96/11945, WO 93/19053, WO 93/25543, EP 0 626 375, EP 0 382 173, WO 94/19334, EP 0 382 173, and EP 0 503 538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO 95/19363 or WO 04/72086, particularly the compounds disclosed therein.

Other examples of such biologically active compounds that the compounds of the invention may be used in combination with include but are not restricted to the following:

Organophosphates: acephate, azamethiphos, azinphosethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathionmethyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1 R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195, RH-0345, RH-2485, RYI-210, S-1283, S-1833, S1-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Biological agents: *Bacillus thuringiensis* ssp *aizawai, kurstaki, Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

Another aspect of invention is related to the use of a compound of formula (I) or of a preferred individual compound as defined herein, of a composition comprising at least one compound of formula (I) or at least one preferred individual compound as above-defined, or of a fungicidal or insecticidal mixture comprising at least one compound of formula (I) or at least one preferred individual compound as above-defined, in admixture with other fungicides or insecticides as described above, for controlling or preventing infestation of plants, e.g. useful plants such as crop plants, propagation material thereof, e.g. seeds, harvested crops, e.g. harvested food crops, or non-living materials by insects or by phytopathogenic microorganisms, preferably fungal organisms.

A further aspect of invention is related to a method of controlling or preventing an infestation of plants, e.g., useful plants such as crop plants, propagation material thereof, e.g. seeds, harvested crops, e.g., harvested food crops, or of non-living materials by insects or by phytopathogenic or spoilage microorganisms or organisms potentially harmful to man, especially fungal organisms, which comprises the application of a compound of formula (I) or of a preferred individual compound as above-defined as active ingredient to the plants, to parts of the plants or to the locus thereof, to the propagation material thereof, or to any part of the non-living materials.

Controlling or preventing means reducing infestation by phytopathogenic or spoilage microorganisms or organisms potentially harmful to man, especially fungal organisms, to such a level that an improvement is demonstrated.

A preferred method of controlling or preventing an infestation of crop plants by phytopathogenic microorganisms, especially fungal organisms, or insects which comprises the application of a compound of formula (I), or an agrochemical composition which contains at least one of said compounds, is foliar application. The frequency of application and the rate of application will depend on the risk of infestation by the corresponding pathogen or insect. However, the compounds of formula (I) can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, e.g. a composition containing the compound of formula (I), and, if desired, a solid or liquid adjuvant or monomers for encapsulating the compound of formula (I), may be prepared in a known manner, typically by intimately mixing and/or grinding the compound with extenders, for example solvents, solid carriers and, optionally, surface active compounds (surfactants).

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

When the combinations of the present invention are used for treating seed, rates of 0.001 to 50 g of a compound of formula I per kg of seed, preferably from 0.01 to 10 g per kg of seed are generally sufficient.

Suitably, a composition comprising a compound of formula (I) according to the present invention is applied either preventative, meaning prior to disease development or curative, meaning after disease development.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the ondensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula (I) optionally together with other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

Whereas, it is preferred to formulate commercial products as concentrates, the end user will normally use dilute formulations.

Table 1.1: This table discloses 149 specific compounds of the formula (T-1):

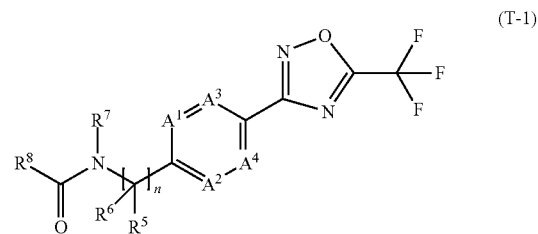

(T-1)

wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$ and $R^6$ are hydrogen, $R^7$ is methoxy and $R^8$ is as defined below in the Table 1.

Each of Tables 1.2 to 1.29 (which follow Table 1.1) make available 149 individual compounds of the formula (T-1) in which n, $A^1$, $A^2$, $A^3$, $A^4$, $R^1$, $R^2$, $R^3$, $R^4$, $R^5$, $R^6$, and $R^7$ are as specifically defined in Tables 1.2 to 1.29, which refer to Table 1 wherein $R^8$ is specifically defined.

TABLE 1

| Compound no. | $R^8$ |
| --- | --- |
| 1.001 | methyl |
| 1.002 | ethyl |
| 1.003 | propyl |
| 1.004 | isopropyl |
| 1.005 | butyl |
| 1.006 | sec-butyl |
| 1.007 | 2-methylbutyl |
| 1.008 | tert-butyl |
| 1.009 | isobutyl |
| 1.010 | pentyl |
| 1.011 | 1-ethylpropyl |
| 1.012 | 2-ethylbutyl |
| 1.013 | 2,2-dimethylpropyl |
| 1.014 | 1,1-dimethylbutyl |
| 1.015 | 2,2-dimethylbutyl |
| 1.016 | 1-ethyl-1-methylpropyl |
| 1.017 | but-2-enyl |
| 1.018 | 2-methylpropenyl |
| 1.019 | ethenyl |
| 1.020 | propen-2-yl |

TABLE 1-continued

| Compound no. | R⁸ |
|---|---|
| 1.021 | allyl |
| 1.022 | 1-methylallyl |
| 1.023 | 2-methylallyl |
| 1.024 | 1,1-dimethylallyl |
| 1.025 | 1-methylprop-1-enyl |
| 1.026 | but-1-enyl |
| 1.027 | 3-methylbut-2-enyl |
| 1.028 | (E)-1,1-dimethylbut-2-enyl |
| 1.029 | but-3-enyl |
| 1.030 | prop-2-ynyl |
| 1.031 | but-3-ynyl |
| 1.032 | but-2-ynyl |
| 1.033 | 1-methylprop-2-ynyl |
| 1.034 | 1-methylbut-2-ynyl |
| 1.035 | 1,1-dimethylprop-2-ynyl |
| 1.036 | cyanomethyl |
| 1.037 | 2-cyanoethyl |
| 1.038 | 3-cyanopropyl |
| 1.039 | 1-ethoxymethyl |
| 1.040 | 1-methoxymethyl |
| 1.041 | difluoromethoxymethyl |
| 1.042 | 1-difluoromethoxyethyl |
| 1.043 | 1-methoxyethyl |
| 1.044 | 1-methoxyisopropyl |
| 1.045 | 1-ethyloxyisopropyl |
| 1.046 | 1-difluoromethoxyisopropyl |
| 1.047 | 2-methoxyethyl |
| 1.048 | 2-(difluoromethoxy)ethyl |
| 1.049 | 3-methoxypropyl |
| 1.050 | 4-methoxybutyl |
| 1.051 | 2-ethoxyethyl |
| 1.052 | 1-ethoxyethyl |
| 1.053 | 2-methoxypropyl |
| 1.054 | 1-(methoxymethyl)propyl |
| 1.055 | 2-methoxy-1,1-dimethyl-ethyl |
| 1.056 | 2-methoxyethoxymethyl |
| 1.057 | 1-acetoxymethyl |
| 1.058 | 2-acetoxyethyl |
| 1.059 | 2-acetoxy-1,1-dimethyl-ethyl |
| 1.060 | 2,2-diethoxyethyl |
| 1.061 | 2,2-dimethoxyethyl |
| 1.062 | hydroxymethyl |
| 1.063 | 1-hydroxyethyl |
| 1.064 | 1-hydroxyisopropyl |
| 1.065 | 2-hydroxyethyl |
| 1.066 | 2-hydroxypropyl |
| 1.067 | 3-hydroxypropyl |
| 1.068 | 2-hydroxy-1,1-dimethyl-ethyl |
| 1.069 | 2-hydroxy-2-methyl-propyl |
| 1.070 | trifluoromethyl |
| 1.071 | 2,2,2-trifluoroethyl |
| 1.072 | 3,3,3-trifluoropropyl |
| 1.073 | 4,4,4-trifluorobutyl |
| 1.074 | fluoromethyl |
| 1.075 | difluoromethyl |
| 1.076 | 2-fluoroethyl |
| 1.077 | 1-fluoroethyl |
| 1.078 | chloromethyl |
| 1.079 | 2-chloroethyl |
| 1.080 | 2-chloro-1,1-dimethylethyl |
| 1.081 | 2-(methylamino)-2-oxo-ethyl |
| 1.082 | 2-(ethylamino)-2-oxo-ethyl |
| 1.083 | 2-(tert-butylamino)-2-oxo-ethyl |
| 1.084 | 2-(isopropylamino)-2-oxo-ethyl |
| 1.085 | acetamidomethyl |
| 1.086 | acetamidoethyl |
| 1.087 | 1-methyl-3-oxo-butyl |
| 1.088 | 3-hydroxy-1-methyl-3-oxo-propyl |
| 1.089 | 3-methoxy-3-oxo-propyl |
| 1.090 | phenyl |
| 1.091 | 2-chlorophenyl |
| 1.092 | 2-fluorophenyl |
| 1.093 | 3-fluorophenyl |
| 1.094 | 4-fluorophenyl |
| 1.095 | 3,5-difluorophenyl |
| 1.096 | 4-pyrimidinyl |
| 1.097 | thiazol-5-yl |
| 1.098 | oxazol-5-yl |
| 1.099 | isoxazol-3-yl |
| 1.100 | 2-pyridyl |
| 1.101 | benzyl |
| 1.102 | 3-chlorophenylmethyl |
| 1.103 | 3-fluorophenylmethyl |
| 1.104 | 2-pyridylmethyl |
| 1.105 | cyclopentyl |
| 1.106 | cyclohexyl |
| 1.107 | cyclopentylmethyl |
| 1.108 | cyclohexylmethyl |
| 1.109 | cyclopropylmethyl |
| 1.110 | cyclopropyl |
| 1.111 | 1-chlorocycloprop-1-yl |
| 1.112 | 1-cyanocycloprop-1-yl |
| 1.113 | 1-fluorocycloprop-1-yl |
| 1.114 | 1-methylcyclopropyl |
| 1.115 | 1-trifluoromethylcycloprop-1-yl |
| 1.116 | 2-cyanocyclopropyl |
| 1.117 | 2-fluorocyclopropyl |
| 1.118 | 2-methylcyclopropyl |
| 1.119 | 2,2-dichlorocyclopropyl |
| 1.120 | 2,2-difluorocyclopropyl |
| 1.121 | 2,2-dimethylcyclopropyl |
| 1.122 | 2,2,3,3-tetramethylcyclopropyl |
| 1.123 | 2,2-dichloro-1-methyl-cyclopropyl |
| 1.124 | cyclobutyl |
| 1.125 | 1-methylcyclobutyl |
| 1.126 | 1-(trifluoromethyl)cyclobutyl |
| 1.127 | 1-cyanocyclobut-1-yl |
| 1.128 | cyclobutylmethyl |
| 1.129 | 2,2-difluorocyclopropylmethyl |
| 1.130 | tetrahydrothiopyran-2-yl |
| 1.131 | tetrahydrothiopyran-3-yl |
| 1.132 | tetrahydrothiopyran-4-yl |
| 1.133 | oxetan-3-yl |
| 1.134 | 3-cyanooxetan-3-yl |
| 1.135 | 3-methyloxetan-3-yl |
| 1.136 | 3-trifluoromethyloxetan-3-yl |
| 1.137 | oxetan-2-yl |
| 1.138 | oxetan-3-ylmethyl |
| 1.139 | oxetan-2-ylmethyl |
| 1.140 | tetrahydrofuran-2-yl |
| 1.141 | tetrahydrofuran-3-yl |
| 1.142 | tetrahydrofuran-2-ylmethyl |
| 1.143 | tetrahydropyran-2-yl |
| 1.144 | tetrahydropyran-3-yl |
| 1.145 | tetrahydropyran-4-yl |
| 1.146 | 2-methyl-1,3-dioxolan-2-yl |
| 1.147 | 1,3-dioxolan-2-yl |
| 1.148 | 1-acetylpyrrolidin-2-yl |
| 1.149 | 1-imidazoyl |

Table 1.2: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^2$, $R^3$, $R^4$, $R^5$, and $R^6$ are hydrogen, $R^7$ is methoxy, $R^1$ is fluorine, and $R^8$ is as defined above in Table 1.

Table 1.3: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^2$, $R^3$, $R^4$, $R^5$, and $R^6$ are hydrogen, $R^7$ is methoxy, $R^1$ is chlorine, and $R^8$ is as defined above in Table 1.

Table 1.4: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^2$, $R^3$, $R^4$, $R^5$, and $R^6$ are hydrogen, $R^7$ is methoxy, $R^1$ is methyl, and $R^8$ is as defined above in Table 1.

Table 1.5: This table discloses 149 specific compounds of formula (T-1) wherein n is 1, $A^1$ is N, $A^2$ is C—$R^2$, $A^3$ is C—$R^3$, $A^4$ is C—$R^4$ and $R^2$, $R^3$, $R^4$, $R^5$, and $R^6$ are hydrogen, $R^7$ is methoxy, and $R^8$ is as defined above in Table 1.

Table 1.6: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^4$, $R^5$, and $R^6$ are hydrogen, $R^7$ is methoxy, $R^3$ is fluorine, and $R^8$ is as defined above in Table 1.

Table 1.7: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^2$, $R^4$, $R^5$, and $R^6$ are hydrogen, $R^7$ is methoxy, $R^1$ and $R^3$ are fluorine, and $R^8$ is as defined above in Table 1.

Table 1.8: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^3$, $R^4$, $R^5$, and $R^6$ are hydrogen, $R^7$ is methoxy, $R^1$ and $R^2$ are fluorine, and $R^8$ is as defined above in Table 1.

Table 1.9: This table discloses 149 specific compounds of formula (T-1) wherein n is 2, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is methoxy, and $R^8$ is as defined above in Table 1.

Table 1.10: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, and $R^5$ are hydrogen, $R^7$ is methoxy, $R^6$ is methyl, and $R^8$ is as defined above in Table 1.

Table 1.11: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$ $R^4$, and $R^5$ are hydrogen, $R^7$ is methyl, $R^6$ is cyano, and $R^8$ is as defined above in Table 1.

Table 1.13: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is methyl, and $R^8$ is as defined above in Table 1.

Table 1.14: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is ethyl, and $R^8$ is as defined above in Table 1.

Table 1.15: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is propyl, and $R^8$ is as defined above in Table 1.

Table 1.16: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is isopropyl, and $R^8$ is as defined above in Table 1.

Table 1.17: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is allyl, and $R^8$ is as defined above in Table 1.

Table 1.18: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is isobutyl, and $R^8$ is as defined above in Table 1.

Table 1.19: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is 2-methoxyethyl, and $R^8$ is as defined above in Table 1.

Table 1.20: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is propyloxy, and $R^8$ is as defined above in Table 1.

Table 1.21: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is 2-propynl, and $R^8$ is as defined above in Table 1.

Table 1.22: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is 2-furylmethyl, and $R^8$ is as defined above in Table 1.

Table 1.23: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is tetrahydrofuran-2-ylmethyl, and $R^8$ is as defined above in Table 1.

Table 1.24: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is cyclopropylmethyl, and $R^8$ is as defined above in Table 1.

Table 1.25: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is cyclopropyl, and $R^8$ is as defined above in Table 1.

Table 1.26: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is ethoxy, and $R^8$ is as defined above in Table 1.

Table 1.27: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is hydroxy, and $R^8$ is as defined above in Table 1.

Table 1.28: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is 2,2,2-trifluoroethyl, and $R^8$ is as defined above in Table 1.

Table 1.29: This table discloses 149 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is 2-hydroxyethyl, and $R^8$ is as defined above in Table 1.

Table 2.1: This table discloses 26 specific compounds of the formula (T-2):

(T-2)

wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$ and $R^6$ are hydrogen, $R^7$ is methoxy and $R^{12}$ is as defined below in Table 2.

Each of Tables 2.2 to 2.5 (which follow Table 2.1) make available 26 individual compounds of the formula (T-2) in which n, $A^1$, $A^2$, $A^3$, $A^4$, $R^1$, $R^2$, $R^3$, $R^4$, $R^5$, $R^6$ and $R^7$ are as specifically defined in Tables 2.2 to 2.5, which refer to Table 2 wherein $R^{12}$ is specifically defined.

TABLE 2

| Compound no. | $R^{12}$ |
|---|---|
| 2.001 | methyl |
| 2.002 | ethyl |
| 2.003 | propyl |
| 2.004 | isopropyl |
| 2.005 | butyl |
| 2.006 | sec-butyl |
| 2.007 | tert-butyl |
| 2.008 | isobutyl |
| 2.009 | allyl |
| 2.010 | but-3-ynyl |
| 2.011 | but-2-ynyl |
| 2.012 | prop-2-ynyl |
| 2.013 | 2-acetoxyethyl |
| 2.014 | 2-hydroxyethyl |
| 2.015 | 2-hydroxypropyl |
| 2.016 | 2-chloroethyl |
| 2.017 | 2-fluoroethyl |
| 2.018 | 3-chloropropyl |
| 2.019 | 3-fluoropropyl |
| 2.020 | 4-chlorobutyl |
| 2.021 | 2-cyanoethyl |
| 2.022 | 2-methoxyethyl |
| 2.023 | 2-ethoxyethyl |
| 2.024 | 2-methoxypropyl |
| 2.025 | phenyl |
| 2.026 | phenylmethyl |

Table 2.2: This table discloses 26 specific compounds of formula (T-2) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is allyl, and $R^{12}$ is as defined above in Table 2.

Table 2.3: This table discloses 26 specific compounds of formula (T-2) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is ethoxy, and $R^{12}$ is as defined above in Table 2.

Table 2.4: This table discloses 26 specific compounds of formula (T-2) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is hydroxy, and $R^{12}$ is as defined above in Table 2.

Table 2.5: This table discloses 26 specific compounds of formula (T-2) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is 2,2,2-trifluoroethyl, and $R^{12}$ is as defined above in Table 2.

Table 3.1: This table discloses 100 specific compounds of the formula (T-3):

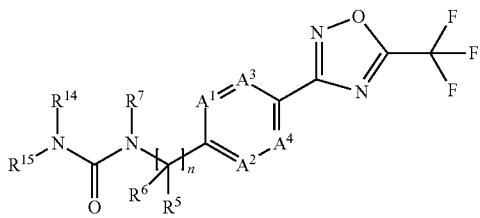

(T-3)

wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, $R^6$, and $R^{15}$ are hydrogen, $R^7$ is methoxy and $R^{14}$ is as defined below in Table 3.

Each of Tables 3.2 to 3.14 (which follow Table 3.1) make available 100 individual compounds of the formula (T-3) in which n, $A^1$, $A^2$, $A^3$, $A^4$, $R^1$, $R^2$, $R^3$, $R^4$, $R^5$, $R^6$, $R^7$ and $R^{15}$ are as specifically defined in Tables 3.2 to 3.14, which refer to Table 3 wherein $R^{14}$ is specifically defined.

TABLE 3

| Compound no. | $R^{14}$ |
|---|---|
| 3.001 | methyl |
| 3.002 | ethyl |
| 3.003 | propyl |
| 3.004 | isopropyl |
| 3.005 | butyl |
| 3.006 | sec-butyl |
| 3.007 | tert-butyl |
| 3.008 | isobutyl |
| 3.009 | pentyl |
| 3.010 | allyl |
| 3.011 | 2-methylallyl |
| 3.012 | 1,1-dimethylallyl |
| 3.013 | prop-2-ynyl |
| 3.014 | 2-acetoxyethyl |
| 3.015 | 2-hydroxyethyl |
| 3.016 | 2-hydroxypropyl |
| 3.017 | 3-hydroxypropyl |
| 3.018 | 2,2-difluoroethyl |
| 3.019 | 2,2,2-trifluoroethyl |
| 3.020 | 3,3,3-trifluoropropyl |
| 3.021 | 4,4,4-trifluorobutyl |
| 3.022 | but-3-ynyl |
| 3.023 | but-2-ynyl |
| 3.024 | 2-cyanoethyl |
| 3.025 | 2-methoxyethyl |
| 3.026 | 2-ethoxyethyl |
| 3.027 | 2-methoxypropyl |
| 3.028 | 1-methoxy-4-piperidyl |
| 3.029 | oxetan-3-yl |
| 3.030 | phenyl |
| 3.031 | pyrid-2-yl |
| 3.032 | pyrid-3-yl |
| 3.033 | pyrid-4-yl |
| 3.034 | phenylmethyl |
| 3.035 | pyrid-2-ylmethyl |
| 3.036 | cyclopropyl |
| 3.037 | 1-cyanocyclopropyl |
| 3.038 | 1-fluorocyclopropyl |
| 3.039 | 1-methylcyclopropyl |
| 3.040 | cyclobutyl |
| 3.041 | cyclopentyl |
| 3.042 | cyclohexyl |
| 3.043 | cyclopropylmethyl |
| 3.044 | cyclobutylmethyl |
| 3.045 | cyclopentylmethyl |
| 3.046 | cyclohexylmethyl |
| 3.047 | tetrahydrofuran-3-yl |
| 3.048 | tetrahydropyran-3-yl |
| 3.049 | tetrahydropyran-4-yl |
| 3.050 | tetrahydrofuran-2-ylmethyl |
| 3.051 | tetrahydrofuran-3-ylmethyl |
| 3.052 | tetrahydropyran-2-ylmethyl |
| 3.053 | tetrahydropyran-3-ylmethyl |
| 3.054 | benzyl |
| 3.055 | furylmethyl |
| 3.056 | 1-methoxymethylcyclopropyl |
| 3.057 | 1-ethoxycarbonylcyclopropyl |
| 3.058 | 1-hydroxycyclopropylmethyl |
| 3.059 | cyclopropyl-1-ethyl |
| 3.060 | 2,2-dimethylpropyl |
| 3.061 | cyano |
| 3.062 | 1-methylprop-2-ynyl |
| 3.063 | 1-methylbut-2-ynyl |
| 3.064 | 1,1-dimethylprop-2-ynyl |
| 3.065 | cyanomethyl |
| 3.066 | 2-cyanoethyl |

TABLE 3-continued

| Compound no. | $R^{14}$ |
|---|---|
| 3.067 | 3-cyanopropyl |
| 3.068 | 1-methoxymethyl |
| 3.069 | 2-methoxyethyl |
| 3.070 | 3-methoxypropyl |
| 3.071 | 4-methoxybutyl |
| 3.072 | 1-methoxyethyl |
| 3.073 | 1-(methoxymethyl)propyl |
| 3.074 | 2-methoxy-1,1-dimethylethyl |
| 3.075 | 2-methoxyethoxymethyl |
| 3.076 | 1-acetoxymethyl |
| 3.077 | 2-acetoxy-1,1-dimethylethyl |
| 3.078 | 2,2-diethoxyethyl |
| 3.079 | 2,2-dimethoxyethyl |
| 3.08 | hydroxymethyl |
| 3.081 | 2-hydroxypropyl |
| 3.082 | 2-hydroxy-1,1-dimethylethyl |
| 3.083 | 2-hydroxy-2-methylpropyl |
| 3.084 | trifluoromethyl |
| 3.085 | fluoromethyl |
| 3.086 | difluoromethyl |
| 3.087 | 2-fluoroethyl |
| 3.088 | 2-chloroethyl |
| 3.089 | 3-chloropropyl |
| 3.090 | methoxy |
| 3.091 | ethoxy |
| 3.092 | propoxy |
| 3.093 | isopropoxy |
| 3.094 | butoxy |
| 3.095 | sec-butoxy |
| 3.096 | isobutoxy |
| 3.097 | allyloxy |
| 3.098 | prop-2-ynyloxy |
| 3.099 | ethoxycarbonylmethyl |
| 3.100 | methylaminocarbonylmethyl |

Table 3.2: This table discloses 100 specific compounds of formula (T-3) wherein $A^1$ is C—$R^1$, $A^2$ is C—$R^2$, $A^3$ is C—$R^3$, $A^4$ is C—$R^4$ and $R^2$, $R^3$, $R^4$, $R^5$, $R^6$, and $R^{15}$ are hydrogen, $R^7$ is methoxy, $R^1$ is fluorine, n is 1, and $R^{14}$ is as defined above in Table 3.

Table 3.3: This table discloses 100 specific compounds of formula (T-3) wherein $A^1$ is N, $A^2$ is C—$R^2$, $A^3$ is C—$R^3$, $A^4$ is C—$R^4$ and $R^2$, $R^3$, $R^4$, $R^5$, $R^6$, and $R^{15}$ are hydrogen, $R^7$ is methoxy, n is 1, and $R^{14}$ is as defined above in Table 3.

Table 3.4: This table discloses 100 specific compounds of formula (T-3) wherein $A^1$ is C—$R^1$, $A^2$ is C—$R^2$, $A^3$ is C—$R^3$, $A^4$ is C—$R^4$ and $R^1$, $R^2$, $R^4$, $R^5$, $R^6$, and $R^{15}$ are hydrogen, $R^7$ is methoxy, $R^3$ is fluorine, n is 1, and $R^{14}$ is as defined above in Table 3.

Table 3.5: This table discloses 100 specific compounds of formula (T-3) wherein $A^1$ is C—$R^1$, $A^2$ is C—$R^2$, $A^3$ is C—$R^3$, $A^4$ is C—$R^4$ and $R^3$, $R^4$, $R^5$, $R^6$, and $R^{15}$ are hydrogen, $R^7$ is methoxy, $R^1$ and $R^2$ are fluorine, n is 1, and $R^{14}$ is as defined above in Table 3.

Table 3.6: This table discloses 100 specific compounds of formula (T-3) wherein $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, $R^6$ and $R^{15}$ are hydrogen, $R^7$ is isopropyl, n is 2, and $R^{14}$ is as defined above in Table 3.

Table 3.7: This table discloses 100 specific compounds of formula (T-3) wherein $A^1$ is C—$R^1$, $A^2$ is C—$R^2$, $A^3$ is C—$R^3$, $A^4$ is C—$R^4$ and $R^1$, $R^2$, $R^3$, $R^4$, and $R^6$, are hydrogen, $R^7$ is methoxy, $R^{15}$ is methyl, n is 1, and $R^{14}$ is as defined above in Table 3.

Table 3.8: This table discloses 100 specific compounds of formula (T-3) wherein $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is methoxy, $R^1$ is fluorine, $R^{15}$ is methyl, n is 1, and $R^{14}$ is as defined above in Table 3.

Table 3.9: This table discloses 100 specific compounds of formula (T-3) wherein $A^1$ is C—$R^1$, $A^2$ is C—$R^2$, $A^3$ is C—$R^3$, $A^4$ is C—$R^4$ and $R^1$, $R^2$, $R^4$, $R^5$, and $R^6$ are hydrogen, $R^7$ is methoxy, $R^3$ is fluorine, $R^{15}$ is methyl, n is 1, and $R^{14}$ is as defined above in Table 3.

Table 3.10: This table discloses 100 specific compounds of formula (T-3) wherein $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, $R^6$ and $R^{15}$ are hydrogen, $R^7$ is methyl, n is 1, and $R^{14}$ is as defined above in Table 3.

Table 3.11: This table discloses 100 specific compounds of formula (T-3) wherein $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, $R^6$ and $R^{15}$ are hydrogen, $R^7$ is ethyl, n is 1, and $R^{14}$ is as defined above in Table 3.

Table 3.12: This table discloses 100 specific compounds of formula (T-3) wherein $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, $R^6$ and $R^{15}$ are hydrogen, $R^7$ is isopropyl, n is 1, and $R^{14}$ is as defined above in Table 3.

Table 3.13: This table discloses 100 specific compounds of formula (T-3) wherein $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, $R^6$ and $R^{15}$ are hydrogen, $R^7$ is cyclopropyl, n is 1, and $R^{14}$ is as defined above in Table 3.

Table 3.14: This table discloses 100 specific compounds of formula (T-3) wherein $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, $R^6$ and $R^{15}$ are hydrogen, $R^7$ is hydroxy, n is 1, and $R^{14}$ is as defined above in Table 3.

Table 4.1: This table discloses 4 specific compounds of the formula (T-4):

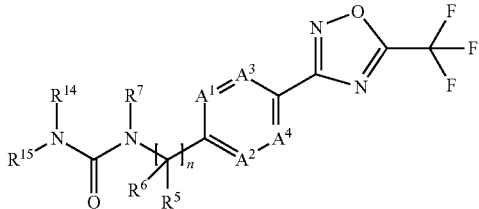

(T-4)

wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is methoxy, and $R^{14}$—N—$R^{15}$ is as defined below in the Table 4.

Each of Tables 4.2 to 4.4 (which follow Table 4.1) make available 4 individual compounds of the formula (T-4) in which n, $A^1$, $A^2$, $A^3$, $A^4$, $R^1$, $R^2$, $R^3$, $R^4$, $R^5$, $R^6$, and $R^7$ are as specifically defined in Tables 4.2 to 4.4, which refer to Table 4 wherein $R^{14}$—N—$R^{15}$ is specifically defined.

TABLE 4

| Compound no. | $R^{14}$—N—$R^{15}$ |
|---|---|
| 4.001 | pyrolidine |
| 4.002 | piperidine |
| 4.003 | morpholine |
| 4.004 | isooxazolidine |

Table 4.2: This table discloses 4 specific compounds of formula (T-4) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is methyl, and $R^{14}$—N—$R^{15}$ is as defined above in Table 4.

Table 4.3: This table discloses 4 specific compounds of formula (T-4) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, $R^7$ is ethyl and $R^{14}$—N—$R^{15}$ is as defined above in Table 4.

Table 4.4: This table discloses 4 specific compounds of formula (T-4) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, $R^6$ are hydrogen, $R^7$ is isopropyl, and $R^{14}$—N—$R^{15}$ is as defined above in Table 4.

EXAMPLES

The Examples which follow serve to illustrate the invention. The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, δppm, 3 ppm, 1.5 ppm or 0.2 ppm.

Compounds of Formula (I) (including those according to the invention) may possess any number of benefits including, inter alia, advantageous levels of biological activity for protecting plants against diseases that are caused by fungi or superior properties for use as agrochemical active ingredients (for example, greater biological activity, an advantageous spectrum of activity, an increased safety profile (including improved crop tolerance), improved physicochemical properties, or increased biodegradability).

Throughout this description, temperatures are given in degrees Celsius (° C.) and "mp." means melting point. LC/MS means Liquid Chromatography Mass Spectrometry and the description of the apparatus and the method (Methods A and B) is as follows:

The Description of the LC/MS Apparatus and the Method A is:
SQ Detector 2 from Waters
Ionisation method: Electrospray
Polarity: positive and negative ions
Capillary (kV) 3.0, Cone (V) 30.00, Extractor (V) 2.00, Source Temperature (° C.) 150, Desolvation
Temperature (° C.) 350, Cone Gas Flow (L/Hr) 0, Desolvation Gas Flow (L/Hr) 650
Mass range: 100 to 900 Da
DAD Wavelength range (nm): 210 to 500
Method Waters ACQUITY UPLC with the following HPLC gradient conditions:
(Solvent A: Water/Methanol 20:1+0.05% formic acid and Solvent B: acetonitrile+0.05% formic acid)

| Time (minutes) | A (%) | B (%) | Flow rate (ml/min) |
|---|---|---|---|
| 0 | 100 | 0 | 0.85 |
| 1.2 | 0 | 100 | 0.85 |
| 1.5 | 0 | 100 | 0.85 |

Type of column: Waters ACQUITY UPLC HSS T3; Column length: 30 mm; Internal diameter of column: 2.1 mm; Particle Size: 1.8 micron; Temperature: 60° C.

The description of the LC/MS apparatus and the method B is:
SQ Detector 2 from Waters
Ionisation method: Electrospray
Polarity: positive ions
Capillary (kV) 3.5, Cone (V) 30.00, Extractor (V) 3.00, Source Temperature (° C.) 150, Desolvation
Temperature (° C.) 400, Cone Gas Flow (L/Hr) 60, Desolvation Gas Flow (L/Hr) 700
Mass range: 140 to 800 Da
DAD Wavelength range (nm): 210 to 400
Method Waters ACQUITY UPLC with the following HPLC gradient conditions
(Solvent A: Water/Methanol 9:1+0.1% formic acid and Solvent B: acetonitrile+0.1% formic acid)

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.

Where necessary, enantiomerically pure final compounds may be obtained from racemic materials as appropriate via standard physical separation techniques, such as reverse phase chiral chromatography, or through stereoselective synthetic techniques, eg, by using chiral starting materials.

FORMULATION EXAMPLES

Wettable Powders

| | a) | b) | c) |
|---|---|---|---|
| active ingredient [compound of formula (I)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

Powders for Dry Seed Treatment

| | a) | b) | c) |
|---|---|---|---|
| active ingredient [compound of formula (I)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The active ingredient is thoroughly mixed with the adjuvants and the mixture is thoroughly ground in a suitable mill, affording powders that can be used directly for seed treatment.

Emulsifiable Concentrate

| active ingredient [compound of formula (I)] | 10% |
|---|---|
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

Dusts

|  | a) | b) | c) |
|---|---|---|---|
| Active ingredient [compound of formula (I)] | 5% | 6% | 4% |
| Talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

Extruder Granules

| Active ingredient [compound of formula (I)] | 15% |
|---|---|
| sodium lignosulfonate | 2% |
| Carboxymethylcellulose | 1% |
| Kaolin | 82% |

The active ingredient is mixed and ground with the adjuvants, and the mixture is moistened with water. The mixture is extruded and then dried in a stream of air.

Coated Granules

| Active ingredient [compound of formula (I)] | 8% |
|---|---|
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

Suspension Concentrate

| active ingredient [compound of formula (I)] | 40% |
|---|---|
| propylene glycol | 10% |
| nonylphenol polyethylene glycol ether (15 mol of ethylene oxide) | 6% |
| Sodium lignosulfonate | 10% |
| Carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| active ingredient [compound of formula (I)] | 40% |
|---|---|
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow-Release Capsule Suspension 28 parts of a combination of the compound of formula I are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

List of Abbreviations:
AIBN=azobisisobutyronitrile
BOP-Cl=phosphoric acid bis(2-oxooxazolidide) chloride
CDI=carbonyl diimidazole
DCE=1,2-dichloroethane
DCM=dichloromethane
DIBAL-H=diisobutylaluminium hydride
DIPEA=N,N-diisopropylethylamine
DMA=dimethylacetamide
DMF=dimethylformamide
EdCl=3-(ethyliminomethyleneamino)-N,N-dimethylpropan-1-amine
EtOAc=ethyl acetate
EtOH=ethyl alcohol
HCl=hydrochloric acid
HOAt=1-hydroxy-7-azabenzotriazole
HATU=1-[bis(dimethylamino)methylene]-1H-1,2,3-triazolo[4,5-b]pyridinium 3-oxid-hexafluorophosphate
min=minutes
mp=melting point
MeOH=methyl alcohol
NaOH=sodium hydroxide
NBS=N-bromosuccinimide
TFAA=trifluoroacetic acid anhydride
THF=tetrahydrofuran

PREPARATION EXAMPLES

Using the synthetic techniques described both above and below, compounds of formula (I) may be prepared accordingly.

Example 1

This example illustrates the preparation of N-methoxy-N-[[4-[5-(trifluoromethyl)-1,2,4-oxadiazol-3-yl]phenyl]methyl]-acetamide (Compound 1.1 of Table T1 below).

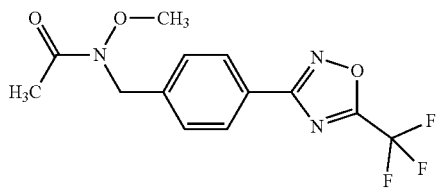 [SMILES: CON(Cc1ccc(-c2noc(C(F)(F)F)n2)cc1)C(C)=O]

Step 1: Preparation of 4-[5-(trifluoromethyl)-1,2,4-oxadiazol-3-yl]benzoyl chloride

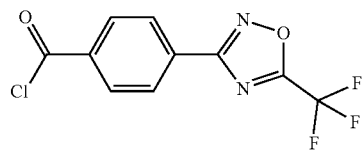 [SMILES: O=C(Cl)c1ccc(-c2noc(C(F)(F)F)n2)cc1]

4-[5-(trifluoromethyl)-1,2,4-oxadiazol-3-yl]benzoic acid (4.00 g, 15.0 mmol) was suspended in dichloromethane (90 mL) DMF (0.01 mL, 0.150 mmol) was added followed by oxalyl chloride (1.46 mL, 16.5 mmol). The mixture was heated at reflux for 2 hours. The mixture was evaporated under reduced pressure to afford 4.15 g of 4-[5-(trifluoromethyl)-1,2,4-oxadiazol-3-yl]benzoyl chloride as a yellow solid.

Step 2: Preparation of N-methoxy-N-methyl-4-[5-(trifluoromethyl)-1,2,4-oxadiazol-3-yl]benzamide

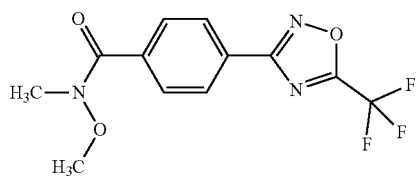 [SMILES: CON(C)C(=O)c1ccc(-c2noc(C(F)(F)F)n2)cc1]

A solution of 4-[5-(trifluoromethyl)-1,2,4-oxadiazol-3-yl]benzoyl chloride from Step 1 (4.15 g, 14.6 mmol) in dichloromethane (20 mL) was added drop wise at room temperature to a stirred solution of N-methoxymethanamine (1.10 g, 17.5 mmol) and triethylamine (3.10 ml, 21.8 mmol) in dichloromethane (80 mL). The mixture was stirred at room temperature for 18 hours. The reaction mixture was poured into water extracted twice with dichloromethane. The combined organic layers were washed with brine, dried over sodium sulfate, and filtered. The solvent was removed under reduced pressure and the resultant crude residue was subjected to flash chromatography over silica gel (heptane: EtOAc eluent gradient 9:1 to 65:35) to afford 4.12 g of N-methoxy-N-methyl-4-[5-(trifluoromethyl)-1,2,4-oxadiazol-3-yl]benzamide as a solid. LC/MS (Method A) retention time=0.97 minutes, 302 (M+H).

$^1$H NMR (400 MHz, CDCl$_3$) δppm: 8.18 (d, 2H), 7.84 (d, 2H), 3.56 (s, 3H), 3.40 (s, 3H).

Step 3: Preparation of 4-[5-(trifluoromethyl)-1,2,4-oxadiazol-3-yl]benzaldehyde

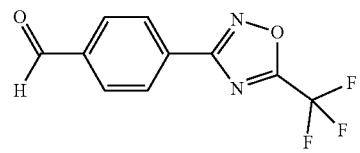 [SMILES: O=Cc1ccc(-c2noc(C(F)(F)F)n2)cc1]

In a 75-mL multi neck flask equipped with stirrer, thermometer at −78° C. under argon, DIBAL-H, 1.0 M in toluene (16 mL, 16.0 mmol) was added drop-wise to a solution of N-methoxy-N-methyl-4-[5-(trifluoromethyl)-1,2,4-oxadiazol-3-yl]benzamide (4.10 g, 13.3 mmol) in 2-methyltetrahydrofuran (90 mL). The mixture was stirred two hours at −78° C. and for one hour temperature was let increase to 0° C. Complete conversion observed by LC-MS. The mixture was quenched by drop wise addition of sat. ammonium chloride solution. Precipitation of a white solid occurred. 4 M HCl was added until full solubilisation. The mixture was extracted thrice with ethyl acetate. Combined organics were dried over magnesium sulfate and evaporated to afford the crude as beige solid. The crude was subject to flash chromatography over silicagel (heptane: EtOAc eluent gradient 99:1 to 90:10) to afford 2.93 g of 4-[5-(trifluoromethyl)-1,2,4-oxadiazol-3-yl]benzaldehyde as a white solid mp: 40-50° C.

$^1$H NMR (400 MHz, CDCl$_3$) δppm: 10.12 (s, 1H), 8.31 (d, 2H), 8.05 (d, 2H).

$^{19}$F NMR (400 MHz, CDCl$_3$) δppm: −65.29 (s).

Step 4: Preparation of N-methoxy-1-[4-[5-(trifluoromethyl)-1,2,4-oxadiazol-3-yl]phenyl]methanimine

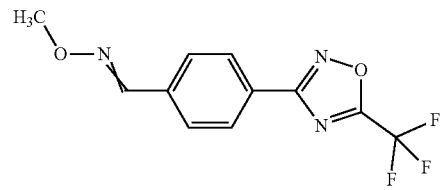 [SMILES: CON=Cc1ccc(-c2noc(C(F)(F)F)n2)cc1]

A solution of 4-[5-(trifluoromethyl)-1,2,4-oxadiazol-3-yl]benzaldehyde (0.30 g, 1.1 mmol) in methanol (11 mL) was treated at room temperature with pyridine (0.15 mL, 1.9 mmol) followed by addition of O-methylhydroxylamine hydrochloride (0.15 g, 1.8 mmol). The mixture was stirred at room temperature over the weekend, poured on water, acidified with 1 M HCl and extracted trice with ethyl acetate. Combined organics were washed with water, dried over magnesium sulfate and evaporated to afford a resin. The crude was subject to flash chromatography over silicagel (heptane: EtOAc eluent gradient 100:0 to 95:5) to afford the title compound as a white solid mp: 55-65° C.

$^1$H NMR (400 MHz, CDCl$_3$) δppm: 8.14 (s, 1H), 8.11 (d, 2H), 7.73 (d, 2H).

$^{19}$F NMR (400 MHz, CDCl$_3$) δppm: −65.40 (s).

Step 5: Preparation of N-methoxy-1-[4-[5-(trifluoromethyl)-1,2,4-oxadiazol-3-yl]phenyl]methanamine

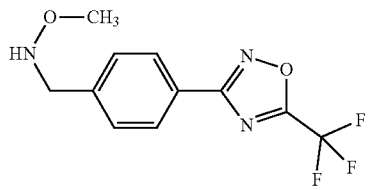 [SMILES: CONCc1ccc(-c2noc(C(F)(F)F)n2)cc1]

A solution of N-methoxy-1-[4-[5-(trifluoromethyl)-1,2,4-oxadiazol-3-yl]phenyl]methanimine (0.81 g, 2.89 mmol) in acetic acid (11 mL) was treated at 15° C. with sodium cyano borohydride (0.4 g, 6.1 mmol). The mixture was stirred at 22° C. for 18 hours until complete consumption of starting material was observed. The reaction mixture was carefully poured in 0.1 M NaOH solution. By addition of 1 M NaOH pH was adjusted to 12-13. The mixture was extracted four times with TBME. Combined organics were washed twice with water and once with brine then dried over magnesium sulfate and concentrated under reduced. The resultant green oil was purified by flash chromatography over silica gel (heptane: EtOAc eluent gradient 99:1 to 70:30) to give 0.60 g of the title compound as an oil.

$^1$H NMR (400 MHz, CDCl$_3$) δppm: 8.09 (d, 2H), 7.53 (d, 2H), 5.33 (S$_{br}$, 1H), 4.12 (s, 2H), 3.50 (s, 3H).

$^{19}$F NMR (400 MHz, CDCl$_3$) δppm: −65.32 (s).

Step 6: Preparation of N-methoxy-N-[[4-[5-(trifluoromethyl)-1,2,4-oxadiazol-3-yl]phenyl]methyl]-acetamide

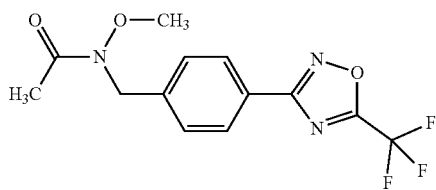 [SMILES: CON(Cc1ccc(-c2noc(C(F)(F)F)n2)cc1)C(C)=O]

To a stirred solution of acetic acid (0.03 g, 0.49 mmol), EDCl (0.15 g, 0.76 mmol), HOAt (0.03 g, 0.19 mmol) and triethylamine (0.16 mL, 1.14 mmol) in dry dichloromethane (2.9 mL) under an atmosphere of nitrogen at room temperature was added N-methoxy-1-[4-[5-(trifluoromethyl)-1,2,4-oxadiazol-3-yl]phenyl]methanamine (0.11 g, 0.38 mmol). The reaction mixture was stirred at room temperature for 18 hours and then 1 M HCl and dichloromethane were added. The resultant mixture was shaken and the layers were separated. The aqueous layer was extracted trice with dichloromethane and the combined organic layers were washed with brine, dried over sodium sulfate, filtered and evaporated to dryness. The crude oil was purified by flash chromatography over silica gel (heptane: EtOAc eluent gradient 99:1 to 80:20) to give 0.08 g of the title compound as a clear oil.

LC/MS (Method A) retention time=0.98 minutes, 316.3 (M+H).

$^1$H NMR (400 MHz, CDCl$_3$) δppm: 8.09 (d, 2H), 7.47 (d, 2H), 4.86 (s, 2H), 3.68 (s, 3H).

$^{19}$F NMR (400 MHz, CDCl$_3$) δppm: −65.34 (s).

Example 2

This example illustrates the preparation of Intermediate 3-[4-(bromomethyl)phenyl]-5-(trifluoromethyl)-1,2,4-oxadiazole

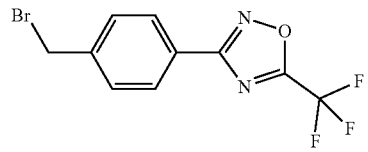 [SMILES: FC(F)(F)c1nc(-c2ccc(CBr)cc2)no1]

Step 1: Preparation of N'-hydroxy-4-methyl-benzamidine

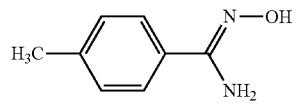

To a stirred suspension of 4-methylbenzonitrile (35 g, 0.29 mol) in ethanol (220 mL) and water (440 mL) was added at room temperature hydroxylamine hydrochloride (41.1 g, 0.58 mol), potassium carbonate (65.4 g, 0.47 mol) and 8-hydroxyquinoline (0.22 g, 1.5 mmol). The reaction mixture was heated at 80° C. for 4 hours. The mixture was cooled to room temperature and diluted with 2N HCl until pH 8. Ethanol was evaporated under reduced pressure. The mixture was filtered, washed with water and dried under vacuum to afford 39.1 g of the title compound. LC/MS (Method A) retention time=0.23 minutes, 151.0 (M+H).

Step 2: Preparation of 3-(p-tolyl)-5-(trifluoromethyl)-1,2,4-oxadiazole

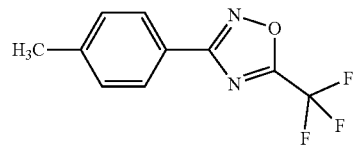 [SMILES: Cc1ccc(-c2noc(C(F)(F)F)n2)cc1]

To a stirred solution of N'-hydroxy-4-methyl-benzamidine (38.7 g, 0.25 mol) in 2-methyltetrahydrofuran (750 mL) was added TFAA at 0° C. The reaction mixture was stirred at 15° C. for two hours and diluted with water. The organic layer was separated, washed successively with sodium bicarbonate solution, ammonium chloride solution and water, dried over sodium sulfate, filtered and evaporated to dryness. The crude was subject to flash chromatography over silica gel (750 g prepacked column) with heptane/EtOAc 99:1 to 90:10 to afford 54.1 g of the title compound as clear oil, which solidified after storage.

LC/MS (Method A) retention time=1.15 minutes, mass not detected.

¹H NMR (400 MHz, CDCl₃) δppm: 8.00 (d, 2H), 7.32 (d, 2H), 2.45 (s, 3H).
¹⁹F NMR (400 MHz, CDCl₃) δppm: −65.41 (s).

Step 3a: Preparation of 3-[4-(bromomethyl)phenyl]-5-(trifluoromethyl)-1,2,4-oxadiazole

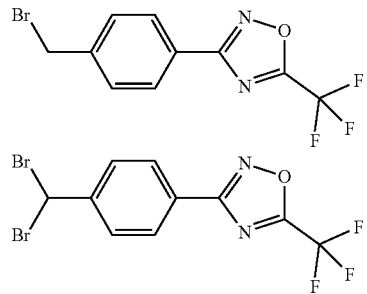

A stirred mixture of 3-(p-tolyl)-5-(trifluoromethyl)-1,2,4-oxadiazole (56.0 g, 0.24 mol) and NBS (45.4 g, 0.25 mol) in tetrachloromethane (480 mL) under argon was heated to 70° C. AIBN (4.03 g, 24 mmol) was added and the reaction mixture was stirred at 65° C. for 18 hours. The mixture was cooled to room temperature and diluted with dichloromethane and water. Layers were separated. The organic layer was washed with sodium bicarbonate solution, dried over sodium sulfate, filtered and evaporated to dryness. The crude was subject to flash chromatography over silicagel (750 g pre packed column) with cyclohehane/EtOAc 100:0 to 95:5 to afford 44.7 g of the title compound as a white solid mp: 58-63° C.
¹H NMR (400 MHz, CDCl₃) δppm: 8.11 (d, 2H), 7.55 (d, 2H), 4.53 (s, 2H).
¹⁹F NMR (400 MHz, CDCl₃) δppm: −65.32 (s).
3-[4-(dibromomethyl)phenyl]-5-(trifluoromethyl)-1,2,4-oxadiazole was isolated as by-product as white solid mp: 61-66° C.
¹H NMR (400 MHz, CDCl₃) δppm: 8.15 (d, 2H), 7.73 (d, 2H), 6.68 (s, 1H).
¹⁹F NMR (400 MHz, CDCl₃) δppm: −65.34 (s).

Step 3b: Preparation of 3-[4-(bromomethyl)phenyl]-5-(trifluoromethyl)-1,2,4-oxadiazole from 3-[4-(dibromomethyl)phenyl]-5-(trifluoromethyl)-1,2,4-oxadiazole

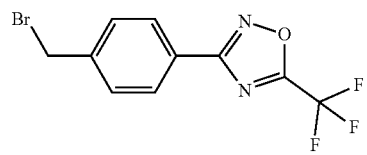 [SMILES: FC(F)(F)c1nc(-c2ccc(CBr)cc2)no1]

To a 1:9 ratio mixture of 3-[4-(bromomethyl)phenyl]-5-(trifluoromethyl)-1,2,4-oxadiazole and 3-[4-(dibromomethyl)phenyl]-5-(trifluoromethyl)-1,2,4-oxadiazole (10.2 g) in acetonitrile (95 mL), water (1.9 mL) and DIPEA (6.20 ml, 35.7 mmol) was added diethylphosphite (4.7 ml, 35.7 mmol) at 5° C. The mixture was stirred at 5-10° C. for two hours, water and 1 M HCl was added and acetonitrile was evaporated under reduced pressure. The white slurry was extracted thrice with dichloromethane. The combined organic layers were dried over sodium sulfate, and filtered. The solvent was removed under reduced pressure and the resultant crude was subject to flash chromatography over silicagel (40 g prepacked column) with cyclohexane/EtOAc 99:1 to 9:1 to afford 7.10 g of 3-[4-(bromomethyl)phenyl]-5-(trifluoromethyl)-1,2,4-oxadiazole.
¹H NMR (400 MHz, CDCl₃) δppm: 8.11 (d, 2H), 7.55 (d, 2H), 4.53 (s, 2H).
¹⁹F NMR (400 MHz, CDCl₃) δppm: −65.32 (s).

Example 3

This example illustrates the preparation of intermediate N-propoxy-1-[4-[5-(trifluoromethyl)-1,2,4-oxadiazol-3-yl]phenyl]methanamine

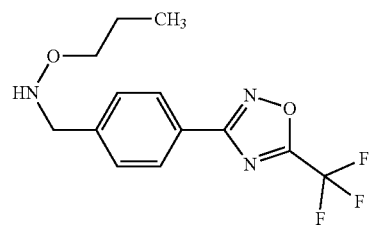 [SMILES: CCCONCc1ccc(-c2noc(C(F)(F)F)n2)cc1]

A solution of 3-[4-(bromomethyl)phenyl]-5-(trifluoromethyl)-1,2,4-oxadiazole (1.30 g, 4.06 mmol) in dichloromethane (10 mL) was added drop wise at room temperature to a stirred solution of O-propylhydroxylamine hydrochloride (3.74 g, 32.5 mmol) and DIEA (6.40 ml, 36.6 mmol) in dichloromethane (6 mL). The mixture was stirred at room temperature for 24 hours. The reaction mixture was poured onto water and the layers were separated. The aqueous layer was extracted trice with dichloromethane. The combined organic layers were washed with brine, dried over sodium sulfate, and filtered. The solvent was removed under reduced pressure and the resultant crude was purified by flash chromatography over silica gel (cyclohexane: EtOAc eluent gradient 1:0 to 1:1) to give 0.92 g of the title compound as a clear oil. LC/MS (Method A) retention time=1.12 minutes, 302 (M+H).
¹H NMR (400 MHz, CDCl₃) δppm: 8.09 (d, 2H), 7.02 (d, 2H), 5.70 (s_{br}, 1H), 4.11 (s, 2H), 3.59 (m, 2H), 1.52 (m, 2H), 0.86 (s, 3H).
¹⁹F NMR (400 MHz, CDCl₃) δppm: −65.33 (s).

Example 4

This example illustrates the preparation of intermediate N-[[4-[5-(trifluoromethyl)-1,2,4-oxadiazol-3-yl]phenyl]methyl]ethanamine.

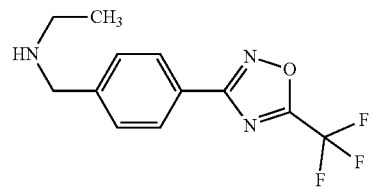 [SMILES: CCNCc1ccc(-c2noc(C(F)(F)F)n2)cc1]

A solution of 3-[4-(bromomethyl)phenyl]-5-(trifluoromethyl)-1,2,4-oxadiazole (1.50 g, 4.69 mmol) in dichloromethane (9.4 mL) was added drop-wise at room temperature to a stirred solution of ethylamine 2 M in MeOH (12 mL, 24.0 mmol). The mixture was stirred at room temperature for 24 hours. The reaction mixture was poured into water and the layers were separated. The aqueous layer was extracted trice with dichloromethane. The combined organic layers were washed with brine, dried over sodium sulfate and filtered. The solvent was removed under reduced pressure and the resultant crude was purified by flash chromatography over silica gel (cyclohexane: EtOAc eluent gradient 1:0 to 1:1) to give 0.92 g of the title compound as a white solid mp: 102-112° C., LC/MS (Method A) retention time=0.66 minutes, 272 (M+H).

$^1$H NMR (400 MHz, DMSO) δppm: 8.01 (d, 2H), 7.57 (d, 2H), 3.86 (q, 2H), 3.29 ($s_{br}$, 1H), 2.53 (q, 2H), 1.05 (t, 3H).

$^{19}$F NMR (400 MHz, CDCl$_3$) δppm: −64.77 (s).

Example 5

This example illustrates the preparation of the intermediate N-[[4-[5-(trifluoromethyl)-1,2,4-oxadiazol-3-yl]phenyl]methyl]ethanamine.

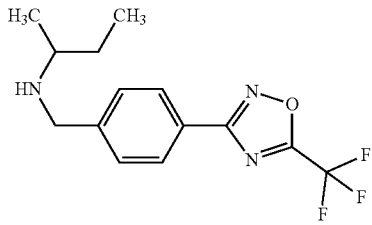 [SMILES: CCC(C)NCc1ccc(-c2noc(C(F)(F)F)n2)cc1]

A solution of 3-[4-(bromomethyl)phenyl]-5-(trifluoromethyl)-1,2,4-oxadiazole (1.50 g, 4.69 mmol) in dichloromethane (9.4 mL) was added drop wise at room temperature to a stirred solution of sec-butylamine (2.4 mL, 23.4 mmol) in dichloromethane (5 mL). The mixture was stirred at room temperature for 24 hours. The reaction mixture was poured into water and extracted trice with dichloromethane. The combined organic layers were washed with brine, dried over sodium sulfate, and filtered. The solvent was removed under reduced pressure and the resultant crude residue was purified by flash chromatography over silica gel (cyclohexane: EtOAc eluent gradient 1:0 to 1:1) to give 1.18 g of the title compound as a clear oil, LC/MS (Method A) retention time=0.71 minutes, 300 (M+H).

$^1$H NMR (400 MHz, CDCl$_3$) δppm: 8.06 (d, 2H), 7.49 (d, 2H), 3.86 (q, 2H), 2.62 (m, 1H), 1.53 (m, 1H), 1.49 (m, 1H), 1.09 (d, 3H), 0.91 (m, 3H).

$^{19}$F NMR (400 MHz, CDCl$_3$) δppm: −65.39 (s).

Example 6

This example illustrates the preparation of the intermediate N-methoxy-1-[4-[5-(trifluoromethyl)-1,2,4-oxadiazol-3-yl]phenyl]ethanamine.

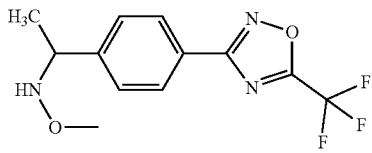 [SMILES: CONC(C)c1ccc(-c2noc(C(F)(F)F)n2)cc1]

Step 1: Preparation of 4-[(E)-N-methoxy-C-methyl-carbonimidoyl]benzonitrile

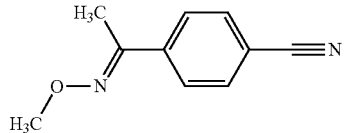

A solution of 4-acetyl benzonitrile (5.0 g, 33.8 mmol) in EtOH (270 mL) was treated at room temperature with 0-methylhydroxylamine hydrochloride (4.32 g, 50.6 mmol). The mixture was stirred at room temperature for 70 hours, poured on water and extracted thrice with dichloromethane. Combined organics were washed with water, dried over magnesium sulfate and evaporated to afford 5.95 g of the title compound as clear oil. No further purification was required. LC/MS (Method A) retention time=0.93 minutes, 175 (M+H).

$^1$H NMR (400 MHz, CDCl$_3$) δppm: 7.78 (d, 2H), 7.65 (d, 2H), 4.03 (s, 3H), 2.22 (s, 3H).

Step 2: Preparation of N'-hydroxy-4-[(E)-N-methoxy-C-methyl-carbonimidoyl]benzamidine

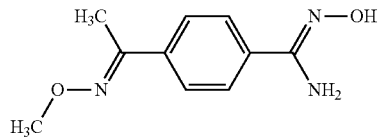

To a stirred suspension of 4-[(E)-N-methoxy-C-methyl-carbonimidoyl]benzonitrile (5.95 g, 33.5 mmol) in ethanol (50 mL) and water (100 mL) was added at room temperature hydroxylamine hydrochloride (4.7 g, 66.9 mmol), potassium carbonate (7.48 g, 53.6 mmol) and 8-hydroxyquinoline (0.025 g, 0.17 mmol). The reaction mixture was heated at 80° C. for 3 hours. The mixture was cooled to room temperature and 1 M HCl was added until pH 8-9. Ethanol was removed under reduced pressure at 50° C. The mixture was stirred 30 minutes at 5° C., filtered, washed with water and dried under vacuum to afford 6.6 g of the title compound as a white solid mp: 134-139° C., LC/MS (Method A) retention time=0.43 minutes, 208 (M+H).

$^1$H NMR (400 MHz, CDCl$_3$) δppm: 8.23 ($s_{br}$, 1H), 7.69 (d, 2H), 7.62 (d, 2H), 4.88 ($s_{br}$, 2H), 4.00 (s, 3H), 2.23 (s, 3H).

Step 3: Preparation of N-methoxy-1-[4-[5-(trifluoromethyl)-1,2,4-oxadiazol-3-yl]phenyl]ethanimine

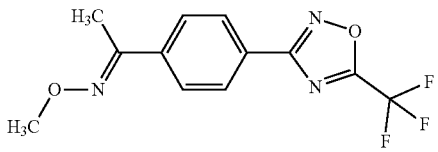 [SMILES: CO/N=C(\C)c1ccc(-c2noc(C(F)(F)F)n2)cc1]

To a stirred solution of N'-hydroxy-4-[(E)-N-methoxy-C-methyl-carbonimidoyl]benzamidine (6.46 g, 31.2 mmol) in 2-methyltetrahydrofuran (93 mL) was added TFAA (6.24 mL, 43.7 mmol) at 15° C. The reaction mixture was stirred at 15° C. for two hours and diluted with water. The organic layer was separated and washed successively with sodium bicarbonate solution, ammonium chloride solution and water, dried over sodium sulfate, filtered and evaporated to dryness to afford 8.9 g of the title compound as beige solid mp: 56-61° C., LC/MS (Method A) retention time=1.19 minutes, 286 (M+H).

$^1$H NMR (400 MHz, CDCl$_3$) δppm: 8.13 (d, 2H), 7.81 (d, 2H), 4.03 (s, 3H), 2.25 (s, 3H).

$^{19}$F NMR (400 MHz, CDCl$_3$) δppm: −65.34 (s).

Step 4: Preparation of N-methoxy-1-[4-[5-(trifluoromethyl)-1,2,4-oxadiazol-3-yl]phenyl]ethanamine

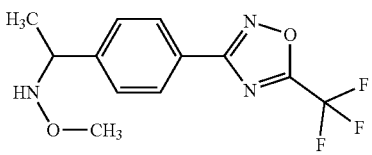 [SMILES: CONC(C)c1ccc(-c2noc(C(F)(F)F)n2)cc1]

A solution of N-methoxy-1-[4-[5-(trifluoromethyl)-1,2,4-oxadiazol-3-yl]phenyl]ethanimine (8.9 g, 29.6 mmol) in acetic acid (119 mL) was treated at 15° C. portion wise with sodium cyano borohydride (4.12 g, 62.3 mmol). The mixture was stirred at 23° C. for 18 hours. Partial consumption of starting material was observed. Additional cyano borohydride (4.12 g, 62.3 mmol) was added portion wise. The reaction mixture was carefully poured in 0.1 M sodium hydroxide solution. By addition of 4 M NaOH pH was adjusted to 9-12. The mixture was extracted four times with TBME. Combined organics were washed twice with water and once with brine then dried over magnesium sulfate and concentrated under reduced. The resultant green oil was purified by flash chromatography over silica gel (heptane: EtOAc eluent gradient 99:1 to 70:30) to give 5.0 g of the title compound as an oil. LC/MS retention time=1.05 minutes, 288 (M+H).

$^1$H NMR (400 MHz, CDCl$_3$) δppm: 8.10 (d, 2H), 7.51 (d, 2H), 5.65 (S$_{br}$, 1H), 4.22 (q, 1H), 3.47 (s, 3H), 1.38 (d, 3H).

$^{19}$F NMR (400 MHz, CDCl$_3$) δppm: −65.37 (s).

Example 7

This example illustrates the preparation of the 1-[cyano-[4-[5-(trifluoromethyl)-1,2,4-oxadiazol-3-yl]phenyl]methyl]-3-methoxy-1,3-dimethyl-urea (Compound 3.31 of Table T3)

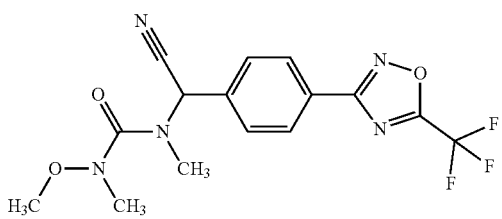 [SMILES: CON(C)C(=O)N(C)C(C#N)c1ccc(-c2noc(C(F)(F)F)n2)cc1]

Step 1: Preparation of 2-(methylamino)-2-[4-[5-(trifluoromethyl)-1,2,4-oxadiazol-3-yl]phenyl]acetonitrile

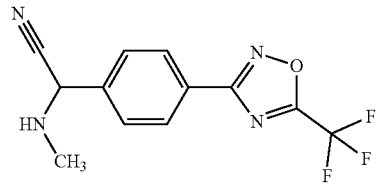 [SMILES: CNC(C#N)c1ccc(-c2noc(C(F)(F)F)n2)cc1]

To a stirred solution of 4-[5-(trifluoromethyl)-1,2,4-oxadiazol-3-yl]benzaldehyde (2.5 g, 10.3 mmol) in THF (16 mL) was added at room temperature methylamine (0.38 g, 12.4 mmol). After 10 minutes water (51.6 ml) and acetone cyanohydrin (0.8 g, 10.3 mmol) was added. The mixture was stirred overnight, poured on water and extracted twice with ethyl acetate. The organic layer was washed successively with brine, dried over sodium sulfate, filtered and evaporated to dryness. The crude was subject to flash chromatography over silica gel with cyclohexane/t-butylmethylether 9:1 to afford 2.1 g of the title compound as white solid.

$^1$H NMR (400 MHz, CDCl$_3$) δppm: 8.17 (d, 2H), 7.72 (d, 2H), 4.87 (s, 1H), 2.61 (s, 3H), 1.62 (S$_{br}$, 1H).

Step 2: Preparation of 1-[cyano-[4-[5-(trifluoromethyl)-1,2,4-oxadiazol-3-yl]phenyl]methyl]-3-methoxy-1,3-dimethyl-urea

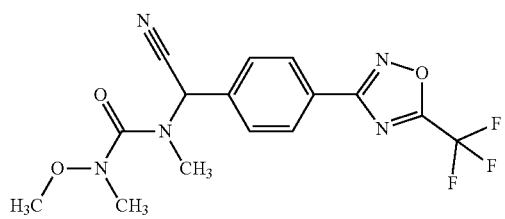 [SMILES: CON(C)C(=O)N(C)C(C#N)c1ccc(-c2noc(C(F)(F)F)n2)cc1]

To a stirred solution of 2-(methylamino)-2-[4-[5-(trifluoromethyl)-1,2,4-oxadiazol-3-yl]phenyl]acetonitrile (0.17 g, 0.60 mmol) in dichloromethane (5 mL) under an atmosphere of nitrogen was added at 0° C. triethylamine (0.17 mL, 1.20 mmol), N,N-dimethylpyridin-4-amine (0.07 g, 0.60 mmol) followed by N,N-dimethylcarbamoyl chloride (0.09 g, 0.72 mmol). The reaction mixture was stirred for 18 hours at room temperature, poured on HCl 1 M solution and extracted with dichloromethane. The combined organic layers were washed with 1 M NaOH, brine, dried over sodium sulfate, and filtered. The solvent was removed under reduced pressure and the resultant crude residue was subjected to flash chromatography over silica gel (cyclohexane: EtOAc eluent gradient 7:1 to 5:1) to afford 0.085 g of 1-[cyano-[4-[5-(trifluoromethyl)-1,2,4-oxadiazol-3-yl]phenyl]methyl]-3-methoxy-1,3-dimethyl-urea as a white solid mp: 106-107° C.

$^1$H NMR (400 MHz, CDCl$_3$) δppm: 8.20 (d, 2H), 7.67 (d, 2H), 6.57 (s, 1H), 3.67 (s, 3H), 3.11 (s, 3H), 2.86 (s, 3H).

Example 8

Preparation of N-(oxetan-3-yl)-N-[[4-[5-(trifluoromethyl)-1,2,4-oxadiazol-3-yl]phenyl]methyl]propanamide (Compound 1.604 of Table T1)

Step 1: Preparation of N-[[4-[5-(trifluoromethyl)-1,2,4-oxadiazol-3-yl]phenyl]methyl]oxetan-3-amine

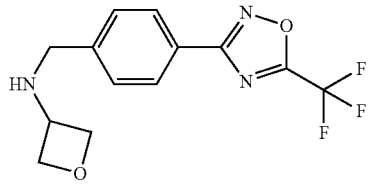 [SMILES: FC(F)(F)c1nc(-c2ccc(CNC3COC3)cc2)no1]

To a stirred solution of 3-[4-(bromomethyl)phenyl]-5-(trifluoromethyl)-1,2,4-oxadiazole (2.0 g, 6.25 mmol) in dichloromethane (13 mL) was added drop wise at room temperature N-ethyl-N-isopropyl-propan-2-amine (1.1 mL) followed by the addition of oxetan-3-amine (3.5 g, 50 mmol). The mixture was stirred at room temperature for 24 hours. The reaction mixture was poured into water and extracted trice with dichloromethane. The combined organic layers were washed with brine, dried over sodium sulfate, and filtered. The solvent was removed under reduced pressure and the resultant crude residue was purified by flash chromatography over silica gel (cyclohexane: EtOAc eluent gradient 1:0 to 0:1) to give the title compound as a clear oil.

$^1$H NMR (400 MHz, CDCl$_3$) δppm: 8.08 (d, 2H), 7.48 (d, 2H), 4.80 (t, 2H), 4.44 (t, 2H), 4.04 (m, 1H), 3.83 (s, 2H), 2.01 (s, 1H).

Step 2: Preparation of N-(oxetan-3-yl)-N-[[4-[5-(trifluoromethyl)-1,2,4-oxadiazol-3-yl]phenyl]methyl]propanamide

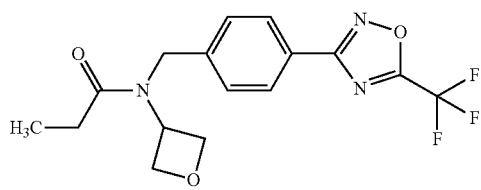 [SMILES: CCC(=O)N(Cc1ccc(-c2noc(C(F)(F)F)n2)cc1)C1COC1]

To a stirred suspension of N-[[4-[5-(trifluoromethyl)-1,2,4-oxadiazol-3-yl]phenyl]methyl]oxetan-3-amine (0.10 g, 0.33 mmol) in dichloromethane (6 mL) under an atmosphere of nitrogen was added triethylamine (0.09 mL, 0.66 mmol) at 0° C. followed by propanoyl chloride (0.03 mL, 0.35 mmol). The reaction mixture was evaporated under reduced pressure and the resultant crude residue was subjected to flash chromatography over silica gel (heptane: EtOAc eluent gradient 9:1 to 1:9) to afford the desired product as a white solid mp: 88.8°-93.5° C.

Example 8

N-(2,2,2-trifluoroethyl)-N-[[4-[5-(trifluoromethyl)-1,2,4-oxadiazol-3-yl]phenyl]methyl]tetrahydrofuran-2-carboxamide (Compound 1.587 of Table T1)

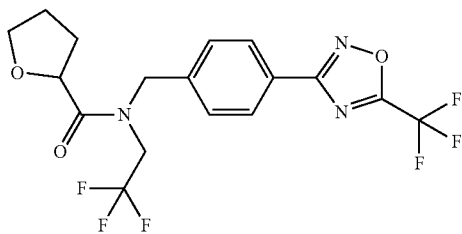 [SMILES: O=C(C1CCCO1)N(Cc1ccc(-c2noc(C(F)(F)F)n2)cc1)CC(F)(F)F]

Step 1: Preparation of 2,2,2-trifluoro-N-[[4-[5-(trifluoromethyl)-1,2,4-oxadiazol-3-yl]phenyl]methyl]ethanamine

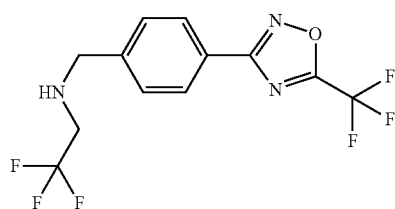 [SMILES: FC(F)(F)CNCc1ccc(-c2noc(C(F)(F)F)n2)cc1]

To a stirred solution of 3-[4-(bromomethyl)phenyl]-5-(trifluoromethyl)-1,2,4-oxadiazole (1.5 g, 4.69 mmol) in dichloromethane (10 mL) was added drop wise at room temperature N-ethyl-N-isopropyl-propan-2-amine (0.82 mL, 4.69 mmol) followed by the addition of 2,2,2-trifluoroethanamine (2.94 mL, 37.5 mmol). The mixture was stirred at room temperature for 24 hours. The reaction mixture was poured into water and extracted trice with dichloromethane. The combined organic layers were dried over sodium sulfate, and filtered. The solvent was removed under reduced pressure and the resultant crude residue was purified by flash chromatography over silica gel (cyclohexane: EtOAc eluent gradient 1:0 to 0:1) to give the title compound as a clear oil.

$^1$H NMR (400 MHz, CDCl$_3$) δppm: 8.09 (d, 2H), 7.51 (d, 2H), 4.00 (s, 2H), 3.22 (q, 2H), 1.71 (s, 1H).

Step 2: Preparation of N-(2,2,2-trifluoroethyl)-N-[[4-[5-(trifluoromethyl)-1,2,4-oxadiazol-3-yl]phenyl]methyl]tetrahydrofuran-2-carboxamide

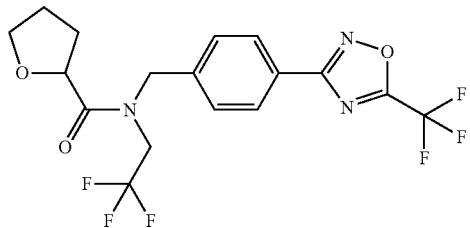 [SMILES: O=C(C1CCCO1)N(Cc1ccc(-c2noc(C(F)(F)F)n2)cc1)CC(F)(F)F]

To a stirred suspension of 2,2,2-trifluoro-N-[[4-[5-(trifluoromethyl)-1,2,4-oxadiazol-3-yl]phenyl]methyl]ethanamine (0.09 g, 0.27 mmol) in dichloromethane (6 mL) under an atmosphere of nitrogen was added triethylamine (0.08 mL, 0.55 mmol) at 0° C. followed by tetrahydrofuran-2-carbonyl chloride (0.04 g, 0.29 mmol). The reaction mixture was evaporated under reduced pressure and the resultant crude residue was subjected to combiflash chromatography over 12 g pre packed silica gel (heptane: EtOAc eluent gradient 9:1 to 1:9) to afford the desired product as a clear yellowish oil. LC/MS (Method A) retention time=1.14 minutes, 424.3 (M+H).

Example 9

This example illustrates the preparation N-[[3-fluoro-4-[5-(trifluoromethyl)-1,2,4-oxadiazol-3-yl]phenyl]methyl]-N, 2-dimethoxy-propanamide (Compound 1.783 of Table T1)

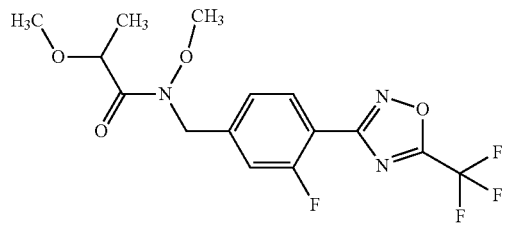 [SMILES: COC(C)C(=O)N(Cc1ccc(-c2noc(C(F)(F)F)n2)c(F)c1)OC]

Step 1: Preparation of 2-fluoro-N'-hydroxy-4-methyl-benzamidine

To a suspension of 2-fluoro-4-methylbenzonitrile (5 g, 37.0 mmol) in ethanol (125 mL) at 25° C. was added hydroxylamine hydrochloride (7.7 g, 111 mmol). The reaction mixture was heated at 80° C. for 2 h. After cooling to room temperature the volatiles were removed under reduced pressure thus affording a white solid that was used in the next step without any purification. LC/MS (Method A) retention time=1.14 minutes, 169.2 (M+H).

$^1$H NMR (400 MHz, CDCl$_3$) δppm: 7.96 (t, 1H), 7.11 (m, 2H), 2.45 (s, 3H).

Step 2: Preparation of 3-(2-fluoro-4-methyl-phenyl)-5-(trifluoromethyl)-1,2,4-oxadiazole

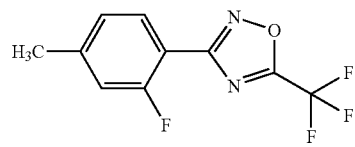 [SMILES: Cc1ccc(-c2noc(C(F)(F)F)n2)c(F)c1]

To a solution of 2-fluoro-N'-hydroxy-4-methyl-benzamidine (37 mmol) in tetrahydrofuran (122 mL) cooled via an ice bath was added TFAA (7.71 mL, 55.5 mmol). The reaction mixture was stirred at 25° C. overnight and then diluted with water. The organic layer was separated, washed successively with sodium bicarbonate solution, ammonium chloride solution, and water then dried over sodium sulfate, filtered and evaporated to dryness. The crude product was subjected to flash chromatography over silica gel with cyclohexane/EtOAc 99:1 to 1:1 to afford the title compound (6.6 g, 72% yield) as an amorphous white solid. LC/MS (Method A) retention time=1.14 minutes, 247 (M+H).

$^1$H NMR (400 MHz, CDCl$_3$) δppm: 8.00 (d, 1H), 7.32 (d, 2H), 2.45 (s, 3H).

$^{19}$F NMR (400 MHz, CDCl$_3$) δppm: −65.3 (s), 108.1 (s).

Step 3a: Preparation of 3-[4-(bromomethyl)phenyl]-5-(trifluoromethyl)-1,2,4-oxadiazole

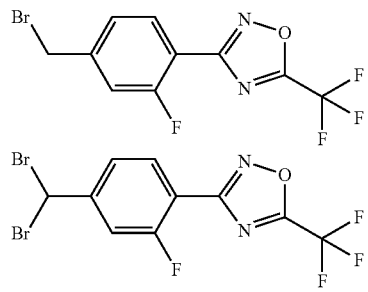

A stirred mixture of 3-(2-fluoro-4-methyl-phenyl)-5-(trifluoromethyl)-1,2,4-oxadiazole (4.2 g, 17.1 mmol) and NBS (3.11 g, 17.1 mmol) in tetrachloromethane (34.3 mL) under argon was heated to 70° C. AIBN (0.29 g, 1.71 mmol) was added and the reaction mixture stirred at 65° C. for 18 h. The mixture was cooled to 25° C. then diluted with dichloromethane and water after which the layers were separated. The succinimide by-product was filtrated off, and the solvent was removed under reduced pressure to afford a brown gum. This crude residue was subjected to flash chromatography over silica gel (with cyclohexane/EtOAc 100:0 to 4:1 to afford the title compound as a white solid (1.7 g, 31% yield. LC/MS (Method A) retention time=1.13 minutes, (M+H) not detected.

$^1$H NMR (400 MHz, CDCl$_3$) δppm: 8.09 (t, 1H), 7.34 (m, 2H), 4.49 (s, 2H).

$^{19}$F NMR (400 MHz, CDCl$_3$) δppm: −65.18 (s), −106.2 (s).

3-[4-(dibromomethyl)phenyl]-5-(trifluoromethyl)-1,2,4-oxadiazole was isolated as by-product in the form of a beige solid (4.0 g, 58% yield) LC/MS (Method A) retention time=1.20 minutes, (M+H) not detected.

$^1$H NMR (400 MHz, CDCl$_3$) δppm: 8.14 (d, 1H), 7.52 (dd, 2H), 6.63 (s, 1H).

Step 3b: Preparation of 3-[4-(bromomethyl)-2-fluoro-phenyl]-5-(trifluoromethyl)-1,2,4-oxadiazole from 33-[4-(dibromomethyl)-2-fluoro-phenyl]-5-(trifluoromethyl)-1,2,4-oxadiazole

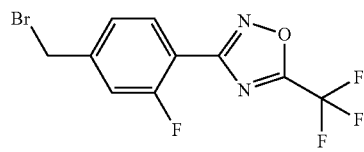 [SMILES: Fc1cc(CBr)ccc1-c1noc(C(F)(F)F)n1]

To a 1:20 ratio mixture of 3-[4-(bromomethyl)-2-fluoro-phenyl]-5-(trifluoromethyl)-1,2,4-oxadiazole and 3-[4-(dibromomethyl)-2-fluoro-phenyl]-5-(trifluoromethyl)-1,2,4-oxadiazole (4.0 g, 9.9 mmol) in acetonitrile (37 mL), water (0.8 mL) and DIPEA (2.59 mL, 14.8 mmol) at 5° C. was added diethylphosphite (2.0 mL, 14.8 mmol). The mixture was stirred at 5-10° C. for 2 h, water and 1 M HCl were added, and volatiles were removed under reduced pressure. The white slurry was extracted three times with dichloromethane and the combined organic layers were dried over sodium sulfate and filtered. The solvent was removed under reduced pressure and the resultant light orange colored crude residue was subjected to flash chromatography over silica gel with cyclohexane/EtOAc 99:1 to 1:1 to afford 3-[4-(bromomethyl)-2-fluoro-phenyl]-5-(trifluoromethyl)-1,2,4-oxadiazole (2.2 g, 68% yield). LC/MS (Method A) retention time=1.13 minutes, (M+H) not detected.

$^1$H NMR (400 MHz, CDCl$_3$) δppm: 8.09 (t, 1H), 7.34 (m, 2H), 4.49 (s, 2H).

$^{19}$F NMR (400 MHz, CDCl$_3$) δppm: −65.18 (s), −106.2 (s).

Step 4: Preparation of 1-[3-fluoro-4-[5-(trifluoromethyl)-1,2,4-oxadiazol-3-yl]phenyl]-N-methoxy-methanamine

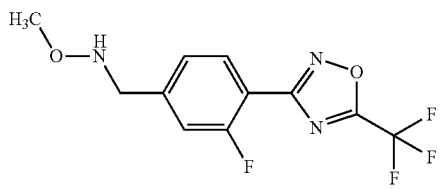

A solution of 0-methylhydroxylamine hydrochloride (4.9 g, 59 mmol) in dichloromethane (15 mL) was treated dropwise with DIPEA (12 mL, 66 mmol) followed by a solution of 3-[4-(bromomethyl)-2-flurorphenyl]-5-(trifluoromethyl)-1,2,4-oxadiazole (1.2 g, 3.7 mmol) in dichloromethane (5 mL). After 18 h, water was introduced (10 mL) and the reaction contents were extracted twice with dichloromethane and the combined organic layers were dried over sodium sulfate and filtered. The resultant residue was purified by flash chromatography over silica gel (cyclohexane/EtOAc eluent gradient 1:0 to 1:1) to afford 1-[3-fluoro-4-[5-(trifluoromethyl)-1,2,4-oxadiazol-3-yl]phenyl]-N-methoxy-methanamine as a colorless oil (410 mg, 38% yield). LC/MS (Method A) retention time=1.01 minutes, (M+H) not detected.

$^1$H NMR (400 MHz, CDCl$_3$) δppm: 8.05 (t, 1H), 7.45 (m, 2H), 5.85 (brs, 1H), 4.12 (s, 2H), 3.50 (s, 3H).

$^{19}$F NMR (400 MHz, CDCl$_3$) δppm: −65.21 (s), −107.33 (s).

Step 4: Preparation of N-[[3-fluoro-4-[5-(trifluoromethyl)-1,2,4-oxadiazol-3-yl]phenyl]methyl]-N,2-dimethoxy-propanamide

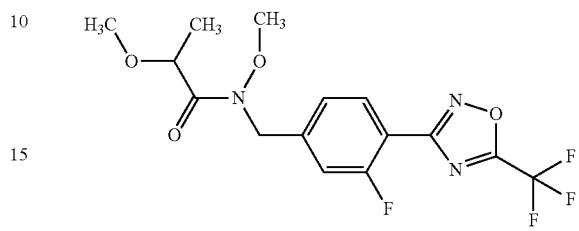

To a stirring solution of 2-methoxy propanoic acid (0.01 g, 0.08 mmol) and HATU (0.03 g, 0.08 mmol in DMF (0.35 mL) under an atmosphere of nitrogen at room temperature was introduced N-ethyl-N-isopropyl-propan-2-amine (0.2 mL, 1.03 mmol). After 5 minutes, 1-[3-fluoro-4-[5-(trifluoromethyl)-1,2,4-oxadiazol-3-yl]phenyl]-N-methoxy-methanamine (0.02 g, 0.07 mmol) was added. After 2 hours, ethyl acetate and water were introduced and the layers were separated. The aqueous layer was extracted with EtOAc and the combined organic phase was washed with brine, dried over sodium sulfate, filtered and evaporated to dryness. A crude white gum was purified by flash chromatography over silica gel (cycloheptane: EtOAc eluent gradient 99:1 to 1:1) to give N-[[3-fluoro-4-[5-(trifluoromethyl)-1,2,4-oxadiazol-3-yl]phenyl]methyl]-N,2-dimethoxy-propanamide (0.08 g, 35%) as a clear oil. LC/MS (Method A) retention time=1.02 minutes, 378 (M+H).

$^1$H NMR (400 MHz, CDCl$_3$) δppm: 8.06 (t, 1H), 7.25 (m, 2H), 4.96 (m, 1H), 4.83 (m, 1H), 4.28 (q, 1H), 3.71 (s, 3H), 3.38 (s, 3H), 1.26 (d, 3H).

$^{19}$F NMR (400 MHz, CDCl$_3$) δppm: −65.21 (s), −106.58 (s).

Example 10

This example illustrates the preparation 1-[[3-fluoro-4-[5-(trifluoromethyl)-1,2,4-oxadiazol-3-yl]phenyl]methyl]-1-methoxy-3-methyl-urea (Compound 3.45 of Table T1)

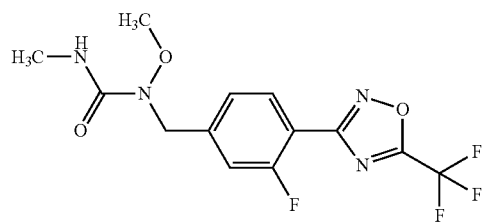

To a solution of 1-[3-fluoro-4-[5-(trifluoromethyl)-1,2,4-oxadiazol-3-yl]phenyl]-N-methoxy-methanamine (20 mg, 0.07 mmol) in DCM (0.23 mL, 0.07 mmol) was added N-methylcarbamoyl chloride (0.012 g, 0.14 mmol) followed by triethylamine (0.02 mL, 0.02 mmol). After 1 hour, the reaction mixture was concentrated under reduced pressure and the residue was purified by flash chromatography over silica gel (cyclohexane: EtOAc eluent gradient 99:1 to 1:1)

to provide 1-[[3-fluoro-4-[5-(trifluoromethyl)-1,2,4-oxadiazol-3-yl]phenyl]methyl]-1-methoxy-3-methyl-urea (12 mg, 50% yield) as a gum. LC/MS (Method A) retention time=0.97 minutes, 349 (M+H).

$^1$H NMR (400 MHz, CDCl$_3$) δppm: 8.04 (t, 1H), 7.31 (m, 2H), 5.81 (m, 1H), 4.71 (s, 2H), 3.60 (s, 3H), 2.87 (d, 3H).

$^{19}$F NMR (400 MHz, CDCl$_3$) δppm: −65.17 (s), −107.10 (s).

Example 11

This example illustrates the preparation 2-chloro-N-[[2,3-difluoro-4-[5-(trifluoromethyl)-1,2,4-oxadiazol-3-yl]phenyl]methyl]-N-methoxy-benzamide (Compound 1.576 of Table T1)

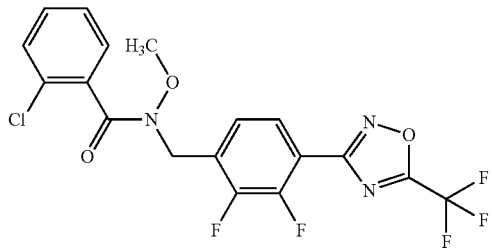 [SMILES: CON(Cc1ccc(-c2noc(C(F)(F)F)n2)c(F)c1F)C(=O)c1ccccc1Cl]

Step 1: Preparation of 2,3-difluoro-N'-hydroxy-4-methyl-benzamidine

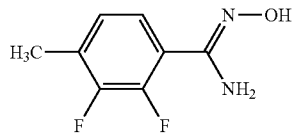

To a suspension of 2,3-difluoro-4-methylbenzonitrile (5.0 g, 32.6 mmol) in ethanol (111 mL) at 25° C. was added hydroxylamine hydrochloride (4.5 g, 65.3 mmol). The reaction mixture was heated at 80° C. for 2 h. After cooling to room temperature the volatiles were removed under reduced pressure thus affording a white solid that was used in the next step without purification.

$^1$H NMR (400 MHz, CDCl$_3$) δppm: 7.30 (m, 1H), 6.95 (m, 1H), 6.50 (brs, 1H), 5.05 (brs, 2H), 2.30 (s, 3H).

Step 2: Preparation of 3-(2,3-difluoro-4-methyl-phenyl)-5-(trifluoromethyl)-1,2,4-oxadiazole

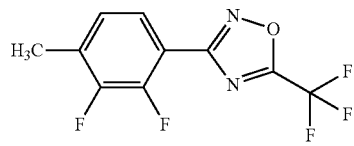 [SMILES: Cc1ccc(-c2noc(C(F)(F)F)n2)c(F)c1F]

To a solution of 2,3-difluoro-N'-hydroxy-4-methyl-benzamidine (2.6 mmol) in tetrahydrofuran (108 mL) cooled using an ice bath was added TFAA (6.9 mL, 49 mmol). The reaction mixture was stirred at 25° C. overnight and then diluted with water. The organic layer was separated, washed successively with sodium bicarbonate solution, ammonium chloride solution, and water then dried over sodium sulfate, filtered and evaporated to dryness. The crude title compound (6.6 g, 72% yield) was isolated as a light brown solid that was used in the next transformation without further purification. LC/MS (Method A) retention time=1.16 minutes, 265 (M+H).

$^1$H NMR (400 MHz, CDCl$_3$) δppm: 7.76 (d, 1H), 7.12 (d, 1H), 2.41 (s, 3H).

$^{19}$F NMR (400 MHz, CDCl$_3$) δppm: −65.41 (s), −133.3 (s), −140.1 (s).

Step 3: Preparation of 3-[4-(bromomethyl)-2,3-difluoro-phenyl]-5-(trifluoromethyl)-1,2,4-oxadiazole

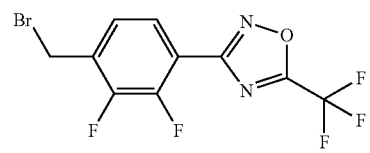 [SMILES: Fc1c(CBr)ccc(-c2noc(C(F)(F)F)n2)c1F]

A mixture of 3-(2,3-difluoro-4-methyl-phenyl)-5-(trifluoromethyl)-1,2,4-oxadiazole (6.0 g, 22.6 mmol) and NBS (7.17 g, 10.0 mmol) in tetrachloromethane (79 mL) under argon was heated to 70° C. AIBN (0.68 g, 3.95 mmol) was added and the reaction mixture stirred at 65° C. for 36 h. The mixture was cooled to 25° C., diluted with dichloromethane and water, and the layers were separated. The succinimide by-product was filtered off, and the solvent was removed under vacuum, to afford a brown gum. This crude residue was subjected to flash chromatography over silica gel (cyclohexane/EtOAc eluent gradient 100:0 to 4:1) to afford the title compound as a white solid (4.8 g, 72% yield). LC/MS (Method A) retention time=1.16 minutes, 344 (M+H).

$^1$H NMR (400 MHz, CDCl$_3$) δppm: 7.80 (m, 1H), 7.37 (m, 1H), 4.55 (s, 2H).

$^{19}$F NMR (400 MHz, CDCl$_3$) δppm: −65.1 (s), −131.2 (s), −139.1 (s).

Step 4: Preparation of 1-[2,3-difluoro-4-[5-(trifluoromethyl)-1,2,4-oxadiazol-3-yl]phenyl]-N-methoxy-methanamine

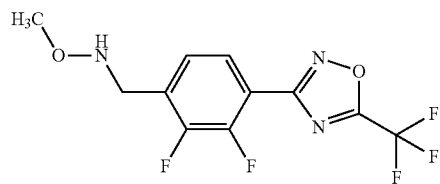

A solution of O-methylhydroxylamine hydrochloride (3.5 g, 42 mmol) in dichloromethane (8 mL) was treated dropwise with DIPEA (8.3 mL, 47 mmol) followed by a solution of 3-[4-(bromomethyl)-2,3-difluoro-phenyl]-5-(trifluoromethyl)-1,2,4-oxadiazole (2 g, 5.2 mmol) in dichloromethane (5 mL). After 18 h, water was introduced (10 mL) and the reaction contents were extracted twice with dichloromethane and the combined organic layers were dried over sodium sulfate and filtered. The resultant residue was purified by flash chromatography over silica gel (cyclohexane/EtOAc eluent gradient 1:0 to 1:1) to afford 1-[2,3-difluoro-4-[5-

(trifluoromethyl)-1,2,4-oxadiazol-3-yl]phenyl]-N-methoxy-methanamine as a pale yellow oil (1.1 g, 68% yield). LC/MS (Method A) retention time=1.03 minutes, 310 (M+H).

$^1$H NMR (400 MHz, CDCl$_3$) δppm: 7.84 (t, 1H), 7.38 (t, 1H), 5.87 (brs, 1H), 4.20 (s, 2H), 3.52 (s, 3H).

$^{19}$F NMR (400 MHz, CDCl$_3$) δppm: −65.21 (s), −132.53 (s), −147.50 (s).

Step 5: Preparation 2-chloro-N-[[2,3-difluoro-4-[5-(trifluoromethyl)-1,2,4-oxadiazol-3-yl]phenyl]methyl]-N-methoxy-benzamide

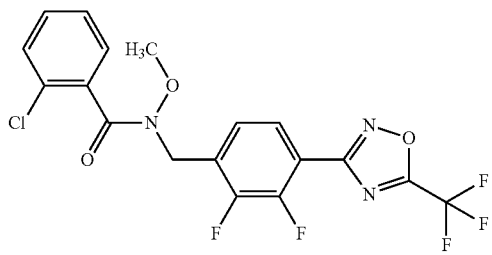 [SMILES: CON(Cc1ccc(-c2noc(C(F)(F)F)n2)c(F)c1F)C(=O)c1ccccc1Cl]

A clear solution of 1-[2,3-difluoro-4-[5-(trifluoromethyl)-1,2,4-oxadiazol-3-yl]phenyl]-N-methoxy-methanamine (0.150 g, 0.485 mmol) and DCM (3 mL) was treated with triethylamine (0.13 mL, 0.970 mmol) followed by 2-chlorobenzoyl chloride (80 mg, 0.51 mmol). After 2 hr, isolute was added to the reaction mixture and volatiles were removed under reduced pressure. The crude product was subjected to flash chromatography over silica gel with cyclohexane/EtOAc 99:1 to 1:1 to afford 2-chloro-N-[[2,3-difluoro-4-[5-(trifluoromethyl)-1,2,4-oxadiazol-3-yl]phenyl]methyl]-N-methoxy-benzamide (212 mg, 98% yield) as a colourless oil. LC/MS (Method A) retention time=1.16 minutes, 448 (M+H).

$^1$H NMR (400 MHz, CDCl$_3$) δppm: 7.88 (m, 1H), 7.54 (m, 1H), 7.40 (m, 4H), 5.14 (brs, 2H), 3.52 (brs, 3H).

$^{19}$F NMR (400 MHz, CDCl$_3$) δppm: −65.21 (s), −131.98 (s), −141.10 (s).

Example 12

This example illustrates the preparation N-methoxy-N-[[5-[5-(trifluoromethyl)-1,2,4-oxadiazol-3-yl]-2-pyridyl]methyl]cyclopropanecarboxamide (Compound 1.570 of Table T1)

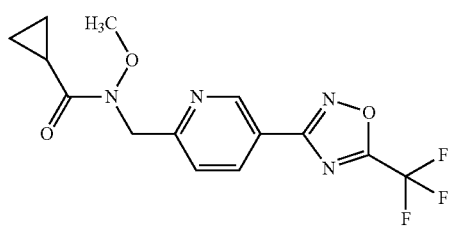 [SMILES: CON(Cc1ccc(-c2noc(C(F)(F)F)n2)cn1)C(=O)C1CC1]

Step 1: Preparation of N'-hydroxy-6-methyl-pyridine-3-carboxamidine

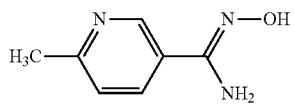

To a suspension of 5-cyano-2-picoline (3 g, 25.0 mmol) in ethanol (86 mL) at 25° C. was added hydroxylamine hydrochloride (5.3 g, 76 mmol). The reaction mixture was heated at 80° C. for 2 h. After cooling to room temperature the volatiles were removed under reduced pressure thus affording a white solid that was used in the next step without any purification. LC/MS (Method A) retention time=0.17 minutes, 152 (M+H).

$^1$H NMR (400 MHz, CDCl$_3$) δppm: 8.75 (s, 1H), 7.83 (d, 1H), 7.19 (d, 1H), 4.86 (brs, 2H), 2.63 (s, 3H).

Step 2: Preparation of 3-(6-methyl-3-pyridyl)-5-(trifluoromethyl)-1,2,4-oxadiazole

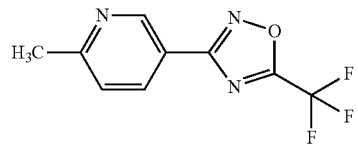 [SMILES: Cc1ccc(-c2noc(C(F)(F)F)n2)cn1]

To a solution of N'-hydroxy-6-methyl-pyridine-3-carboxamidine (25 mmol) in tetrahydrofuran (84 mL) cooled via an ice bath was added TFAA (5.28 mL, 38.0 mmol). The reaction mixture was stirred at 25° C. overnight and then diluted with water. The organic layer was separated, washed successively with sodium bicarbonate solution, ammonium chloride solution, and water then dried over sodium sulfate, filtered and evaporated to dryness to afford 3-(6-methyl-3-pyridyl)-5-(trifluoromethyl)-1,2,4-oxadiazole (5.8 g, 84% yield) as an amorphous white solid. LC/MS (Method A) retention time=1.14 minutes, 247 (M+H).

$^1$H NMR (400 MHz, CDCl$_3$) δppm: 9.23 (d, 1H), 8.27 (dd, 1H), 7.33 (d, 1H), 2.63 (s, 3H).

$^{19}$F NMR (400 MHz, CDCl$_3$) δppm: −65.3 (s).

Step 3: Preparation of 3-[6-(bromomethyl)-3-pyridyl]-5-(trifluoromethyl)-1,2,4-oxadiazole

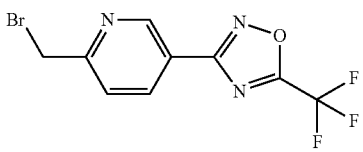 [SMILES: FC(F)(F)c1nc(-c2ccc(CBr)nc2)no1]

A solution of 3-(6-methyl-3-pyridyl)-5-(trifluoromethyl)-1,2,4-oxadiazole (4.4 g, 19 mmol), AIBN (0.32 g, 1.9 mmol), and tetrachloromethane (38 mL) under argon was heated to 65° C. NBS (3.11 g, 17.1 mmol) was added portionwise and the reaction mixture stirred at 65° C. for 5 h and then a second equivalent of NBS (3.11 g, 17.1 mmol) and stirring continued overnight. The mixture was cooled to 25° C. then diluted with dichloromethane and water after which the layers were separated. The succinimide by-product was filtrated off, and the solvent was removed under reduced pressure to afford a brown gum. This crude residue was subjected to flash chromatography over silica gel (cyclohexane/EtOAc eluent gradient 100:0 to 4:1) to afford 3-[6-(bromomethyl)-3-pyridyl]-5-(trifluoromethyl)-1,2,4-oxadiazole as a white solid (5.9 g, 37% yield. LC/MS (Method A) retention time=1.01 minutes, 308 (M+H).

¹H NMR (400 MHz, CDCl₃) δppm: 9.30 (d, 1H), 8.40 (dd, 1H), 7.63 (d, 1H), 4.62 (s, 2H).

¹⁹F NMR (400 MHz, CDCl₃) δppm: −65.2 (s).

Step 4: Preparation of N-methoxy-1-[5-[5-(trifluoromethyl)-1,2,4-oxadiazol-3-yl]-2-pyridyl]methanamine

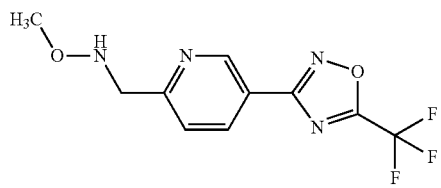 [SMILES: CONCc1ccc(-c2noc(C(F)(F)F)n2)cn1]

A solution of O-methylhydroxylamine hydrochloride (4.4 g, 52 mmol) in dichloromethane (26 mL) was treated dropwise with DIPEA (10.3 mL, 58 mmol) followed by a solution of 3346-(bromomethyl)-3-pyridyl]-5-(trifluoromethyl)-1,2,4-oxadiazole (2 g, 6.5 mmol) in dichloromethane (10 mL). After 18 h, additional equivalents O-methylhydroxylamine hydrochloride (4.4 g, 52 mmol) and DIPEA (10.3 mL, 58 mmol) were introduced and the reaction was heated at 40° C. for 48 hr. of water was introduced (50 mL) and the reaction contents were extracted twice with dichloromethane and the combined organic layers were dried over sodium sulfate and filtered. The resultant residue was purified by flash chromatography over silica gel (cyclohexane/EtOAc eluent gradient 1:0 to 1:1) to afford 1-[2,3-difluoro-4-[5-(trifluoromethyl)-1,2,4-oxadiazol-3-yl]phenyl]-N-methoxy-methanamine as a pale yellow solid (1.4 g, 79% yield). LC/MS (Method A) retention time=0.87 minutes, 275 (M+H).

¹H NMR (400 MHz, CDCl₃) δppm: 9.31 (s, 1H), 8.37 (d, 1H), 7.52 (d, 1H), 6.42 (brs, 1H), 4.24 (s, 2H), 3.56 (s, 3H).

¹⁹F NMR (400 MHz, CDCl₃) δppm: −65.25 (s).

Step 5: Preparation of N-methoxy-N-[[5-[5-(trifluoromethyl)-1,2,4-oxadiazol-3-yl]-2-pyridyl]methyl]cyclopropanecarboxamide

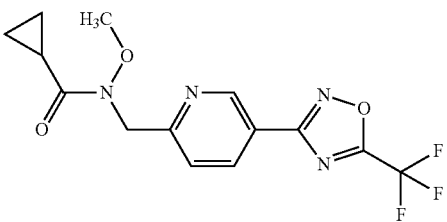 [SMILES: CON(Cc1ccc(-c2noc(C(F)(F)F)n2)cn1)C(=O)C1CC1]

A clear solution of N-methoxy-1-[5-[5-(trifluoromethyl)-1,2,4-oxadiazol-3-yl]-2-pyridyl]methanamine (0.10 g, 0.36 mmol) and DCM (2 mL) cooled to 0° C. was treated with triethylamine (0.10 mL, 0.73 mmol) followed by cyclopropanecarbonyl chloride (38 mg, 0.36 mmol). After 2 hr, isolute was added to the reaction mixture and volatiles were removed under reduced pressure. The crude product was subjected to flash chromatography over silica gel (cyclohexane/EtOAc eluent gradient 99:1 to 1:1) to afford N-methoxy-N-[[5-[5-(trifluoromethyl)-1,2,4-oxadiazol-3-yl]-2-pyridyl]methyl]cyclopropanecarboxamide (212 mg, 98% yield) as a colourless oil. LC/MS (Method A) retention time=1.16 minutes, 448 (M+H).

¹H NMR (400 MHz, CDCl₃) δppm: 7.88 (m, 1H), 7.54 (m, 1H), 7.40 (m, 4H), 5.14 (brs, 2H), 3.52 (brs, 3H).

¹⁹F NMR (400 MHz, CDCl₃) δppm: −65.21 (s), −131.98 (s), −141.10 (s).

Example 13

This example illustrates the preparation methyl N-methoxy-N-[[4-[5-(trifluoromethyl)-1,2,4-oxadiazol-3-yl]phenyl]methyl]carbamate (Compound 2.3 of Table T2)

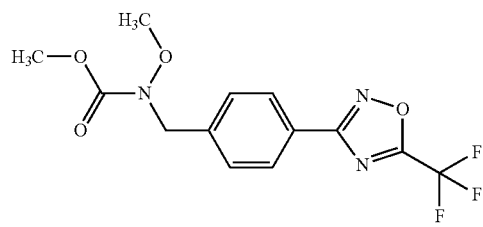 [SMILES: COC(=O)N(Cc1ccc(-c2noc(C(F)(F)F)n2)cc1)OC]

To a solution of N-methoxy-1-[4-[5-(trifluoromethyl)-1,2,4-oxadiazol-3-yl]phenyl]methanamine (0.10 g, 0.37 mmol) in DCM (1.2 mL) was added methyl chloroformate (0.06 mL, 0.732 mmol) and triethylamine (0.10 mL, 0.73 mmol). The reaction mixture was stirred for 1 h 30 min at room temperature after which time the solvent was removed under reduced pressure and the resultant crude residue was purified by combiflash chromatography over silica gel (cyclohexane/EtOAc eluent gradient 1:0 to 1:1) give methyl N-methoxy-N-[[4-[5-(trifluoromethyl)-1,2,4-oxadiazol-3-yl]phenyl]methyl]carbamate (0.105 g, 87% Yield) as a yellow oil. LC/MS (Method A) retention time=1.06 minutes, 332 (M+H).

¹H NMR (400 MHz, CDCl₃) δppm: 8.04 (d, 2H), 7.42 (d, 2H), 4.64 (s, 2H), 3.75 (s, 3H), 3.57 (s, 3H).

¹⁹F NMR (400 MHz, CDCl₃) δppm: −65.33 (s).

Example 14

Preparation of N-Isopropyl-N-[2-[4-[5-(trifluoromethyl)-1,2,4-oxadiazol-3-yl]phenyl]ethyl]cyclopropanecarboxamide (Compound 1.810 of Table T1)

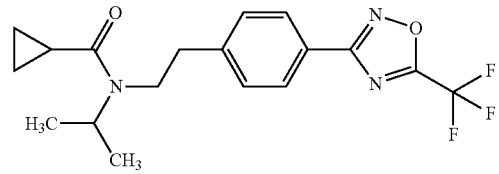

Step 1: Preparation of 4-(2-bromoethyl)-N'-hydroxy-benzamidine

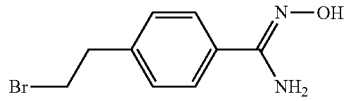

To a stirring solution of 4-(2-bromoethyl)benzonitrile (5 g, 24 mmol) in ethanol (80 mL) was added at room temperature triethylamine (15 mL, 110 mmol) and hydroxylamine hydrochloride (3.3 g, 48 mmol). After 6 hours the solvent was evaporated under reduced pressure to afford the title compound as crude solid that was used without further purification.

Step 2: Preparation of 3-[4-(2-bromoethyl)phenyl]-5-(trifluoromethyl)-1,2,4-oxadiazole

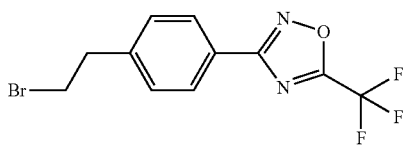 [SMILES: FC(F)(F)c1nc(-c2ccc(CCBr)cc2)no1]

To a stirring suspension of crude 4-(2-bromoethyl)-N'-hydroxy-benzamidine (24 mmol) in 2-methyltetrahydrofuran (150 mL) was added TFAA (10 mL, 71 mmol) at 0° C. The reaction mixture was stirred at 25° C. for 15 hours and then diluted with water (100 mL), followed by extraction with EtOAc. The organic layers were separated, washed successively with saturated aqueous sodium bicarbonate solution and water, dried over sodium sulfate, filtered and evaporated to dryness under reduced pressure. The crude residue was subject to flash chromatography over silicagel (cyclohexane/EtOAc eluent gradient 95:5) to afford 3-[4-(2-bromoethyl)phenyl]-5-(trifluoromethyl)-1,2,4-oxadiazole (4.93 g, 65% yield) as white solid m.p 39-40° C. LC/MS (Method A) retention time=1.19 minutes, mass not detected.
$^1$H NMR (400 MHz, CDCl$_3$) δppm: 8.07 (d, 2H), 7.37 (d, 2H), 3.61 (t, 2H), 3.25 (t, 2H).

Step 3: Preparation of N-[2-[4-[5-(trifluoromethyl)-1,2,4-oxadiazol-3-yl]phenyl]ethyl]propan-2-amine

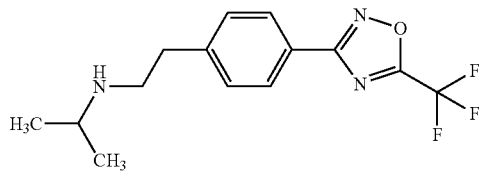 [SMILES: CC(C)NCCc1ccc(-c2noc(C(F)(F)F)n2)cc1]

To a stirring solution of 3-[4-(2-bromoethyl)phenyl]-5-(trifluoromethyl)-1,2,4-oxadiazole (1.5 g, 4.40 mmol) in dichloromethane (10 mL) was added dropwise N-ethyl-N-isopropyl-propan-2-amine (0.76 mL, 4.40 mmol) at room temperature followed by the addition of isopropylamine (9.2 mL, 110 mmol). The mixture was stirred at room temperature for 37 hours then poured into water and extracted three times with EtOAc. The combined organic layers were washed with brine, dried over sodium sulfate, and filtered. The solvent was removed under reduced pressure and the resultant crude residue was purified by flash chromatography over silica gel (cyclohexane: EtOAc eluent gradient 98:2 to 95:5) to give N-[2-[4-[5-(trifluoromethyl)-1,2,4-oxadiazol-3-yl]phenyl]ethyl]propan-2-amine (530 mg, 44% yield) as a clear oil. LC/MS (Method A) retention time=0.75 minutes, minutes, 300.5 (M+H).
$^1$H NMR (400 MHz, CDCl$_3$) δppm: 8.05 (d, 2H), 7.37 (d, 2H), 2.91 (m, 4H), 2.85 (m, 1H), 1.06 (d, 6H).

Step 4: Preparation of N-isopropyl-N-[2-[4-[5-(trifluoromethyl)-1,2,4-oxadiazol-3-yl]phenyl]ethyl]cyclopropanecarboxamide

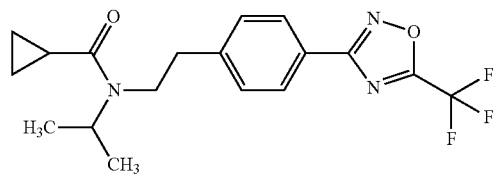 [SMILES: CC(C)N(CCc1ccc(-c2noc(C(F)(F)F)n2)cc1)C(=O)C1CC1]

To a stirring suspension of N-[2-[4-[5-(trifluoromethyl)-1,2,4-oxadiazol-3-yl]phenyl]ethyl]propan-2-amine (0.075 g, 0.25 mmol) in dichloromethane (5 mL) under an atmosphere of nitrogen was added triethylamine (0.04 mL, 0.30 mmol) at 0° C. followed by cyclopropanecarbonyl chloride (0.024 mL, 0.26 mmol). The reaction mixture was stirred at room temperature for 17 hours, poured into water, and extracted twice with EtOAc. The combined organic layers were washed with brine, dried over sodium sulfate, and filtered. The solvent was evaporated under reduced pressure and the resultant crude residue was subjected to flash chromatography over silica gel (cyclohexane: EtOAc eluent gradient 3:1 to 2:1) to afford N-isopropyl-N-[2-[4-[5-(trifluoromethyl)-1,2,4-oxadiazol-3-yl]phenyl]ethyl]cyclopropanecarboxamide (89 mg, 96% yield) as a white solid. LC/MS (Method A) retention time=1.17 minutes, minutes, 368.5 (M+H).
$^1$H NMR (400 MHz, CDCl$_3$) δppm: 8.06 (m, 2H), 7.38 (m, 2H), 4.79 (m, 0.5H), 4.47 (m, 0.5H), 3.58 (m, 1H), 3.40 (m, 1H), 3.05 (m, 1H), 2.95 (m, 1H), 1.76 (m, 1H), 1.29 (m, 3H), 1.13 (d, 3H), 1.04 (m, 1H), 0.83 (m, 2H).

The following procedure was used in a combinatorial fashion using appropriate building blocks (compounds (II) and (III)) to provide the compounds of Formula (I) wherein R$^8$ is —C(O)R$^9$. The compounds prepared via the following combinatorial protocol were analyzed using LC/MS Method B.

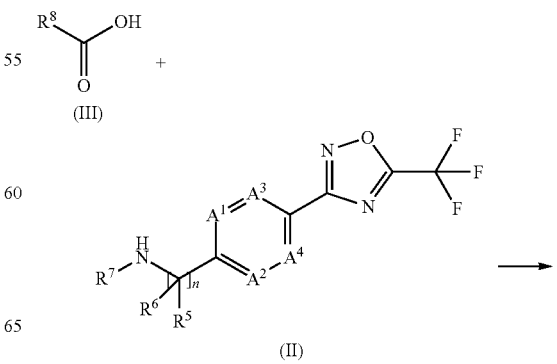

-continued

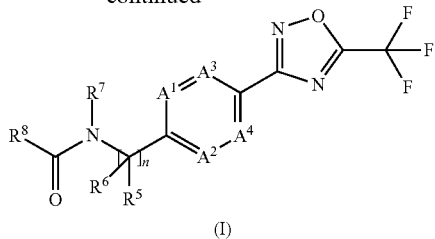

(I)

-continued

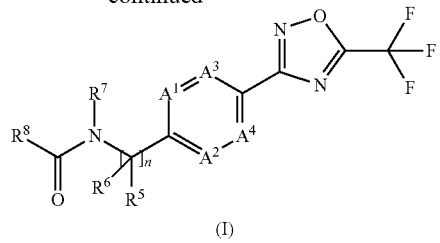

(I)

By way of exemplification, acid derivatives of formula (III) (0.0375 mmol in 375 µL DMA) were transferred to a 96 slot deep well plate (DWP96) containing the [4-[5-(trifluoromethyl)-1,2,4-oxadiazol-3-yl]aryl]methanamine derivative of formula (II) (0.03 mmol) and DIPEA (0.09 mmol) in 250 µL DMA, followed by the addition of BOP-Cl (0.06 mmol) dissolved in DMA (250 µL). The DWP was sealed and stirred at 50° C. for 18 hours. The solvent was removed under a stream of nitrogen. The resultant crude residues were solubilized in a mixture of MeOH (250 µL) and DMA (500 µL) and directly submitted for preparative LC/MS purification which provided the compounds of formula (I) in 10-85% yields.

Alternatively, the following procedures (protocol A and protocol B) were used in a combinatorial fashion using appropriate building blocks (compounds (II) and (IV)) to provide the compounds of Formula (I) wherein $R^8$ is —C(O)$OR^{10}$ or —C(O)$NR^{11}R^{12}$. The compounds prepared via the following combinatorial protocol were analyzed using LC/MS Method B.

Protocol A: Portions of triphosgene (6 mg) in DCE (0.3 mL) were transferred at 0° C. to a 96 slot deep well plate (DWP96) containing the alcohol derivative [$HOR^{10}$] or amine derivative [$HN(R^{11})R^{12}$] of formula (IV) (0.05 mmol) and triethylamine (0.12 mmol) in 200 µL DMA. The reaction mixtures were stirred at room temperature for 30 minutes. [4-[5-(trifluoromethyl)-1,2,4-oxadiazol-3-yl]aryl]methanamine derivatives of formula (II) (0.05 mmol) and triethylamine (0.12 mmol) in 200 µL DMA were added. The DWP was sealed and stirred at room temperature for 18 hours. DCE was removed under the Barkey station. The crude residues were solubilized in a mixture of MeOH (200 µL) and DMA (600 µL) and directly submitted for preparative LC/MS purification which provided the compounds of formula (I) in 3-45% yields.

Protocol B: The alcohol derivative [$HOR^{10}$] or amine derivative [$HNR^{11}R^{12}$] of formula (IV) (0.05 mmol) and DIPEA (0.25 mmol) in 300 µL DMA were transferred at room temperature to a 96 slot deep well plate (DWP96). CDI (0.10 mmol) in DMA (300 µL) was added and stirred until solubilization. 4-[5-(trifluoromethyl)-1,2,4-oxadiazol-3-yl]aryl]methanamine derivatives of formula (II) (0.05 mmol) and triethylamine (0.12 mmol) in 200 µL DMA were added. The DWP was sealed and stirred at room temperature for 18 hours. The DCE was removed under the Barkey station. The crude residues were solubilized in a mixture of MeOH (200 µL) and DMA (600 µL) and directly submitted for preparative LC/MS purification which provided the compounds of formula (I) in 5-47% yields.

Where necessary, enantiomerically pure final compounds may be obtained from racemic materials as appropriate via standard physical separation techniques, such as reverse phase chiral chromatography, or through stereoselective synthetic techniques, (eg, by using chiral starting materials).

TABLE T1

Melting point (mp) data and/or retention times (RT) for compounds according to Formula (I):

| Entry | Name | Structure | RT (min) | [M + H] | Method | MP (° C.) |
|---|---|---|---|---|---|---|
| 1.1 | N-methoxy-N-[[4-[5-(trifluoromethyl)-1,2,4-oxadiazol-3-yl]phenyl]methyl]-acetamide | 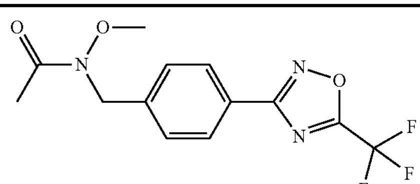 | 0.99 | 316.3 | A | |
| 1.2 | N-methoxy-N-[[4-[5-(trifluoromethyl)-1,2,4-oxadiazol-3-yl]phenyl]methyl]-cyclopropane-carboxamide | 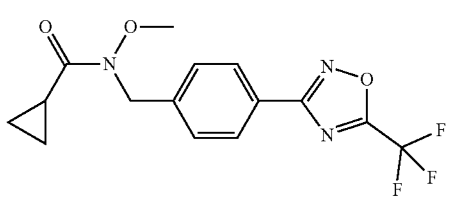 [SMILES: CON(Cc1ccc(-c2noc(C(F)(F)F)n2)cc1)C(=O)C1CC1] | 1.07 | 342.3 | A | 35-40 |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.3 | N-methoxy-N-[[4-[5-(trifluoromethyl)-1,2,4-oxadiazol-3-yl]phenyl]methyl]-benzamide | 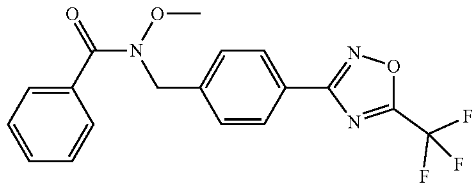 [SMILES: CON(Cc1ccc(-c2noc(C(F)(F)F)n2)cc1)C(=O)c1ccccc1] | 1.1 | 378.3 | A | |
| 1.4 | N-methoxy-2-phenyl-N-[[4-[5-(trifluoromethyl)-1,2,4-oxadiazol-3-yl]phenyl]methyl]-acetamide | 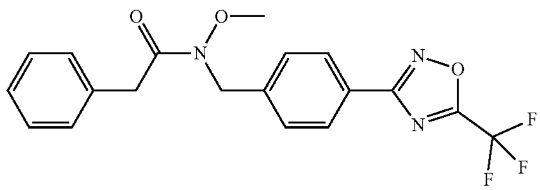 [SMILES: CON(Cc1ccc(-c2noc(C(F)(F)F)n2)cc1)C(=O)Cc1ccccc1] | 1.13 | 392.4 | A | |
| 1.5 | (E)-N-methoxy-3-phenyl-N-[[4-[5-(trifluoromethyl)-1,2,4-oxadiazol-3-yl]phenyl]methyl]-prop-2-enamide | 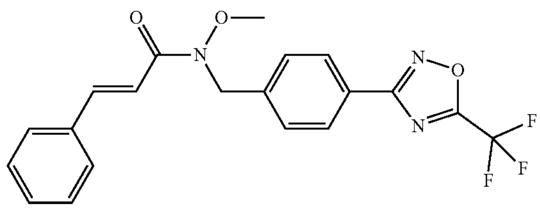 [SMILES: CON(Cc1ccc(-c2noc(C(F)(F)F)n2)cc1)C(=O)/C=C/c1ccccc1] | 1.17 | 404.4 | A | 94-99 |
| 1.6 | N-methoxy-1-(trifluoromethyl)-N-[[4-[5-(trifluoromethyl)-1,2,4-oxadiazol-3-yl]phenyl]methyl]-cyclopropane-carboxamide | 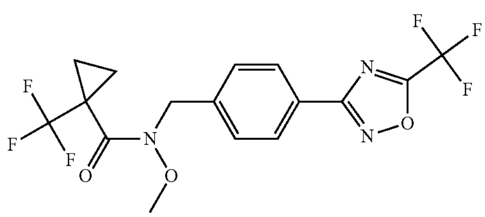 [SMILES: CON(Cc1ccc(-c2noc(C(F)(F)F)n2)cc1)C(=O)C1(C(F)(F)F)CC1] | 1.89 | 410.2 | B | |
| 1.7 | N,2-dimethoxy-N-[[4-[5-(trifluoromethyl)-1,2,4-oxadiazol-3-yl]phenyl]methyl]-benzamide | 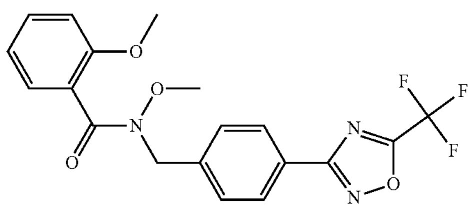 [SMILES: COc1ccccc1C(=O)N(Cc1ccc(-c2noc(C(F)(F)F)n2)cc1)OC] | 1.79 | 408.2 | B | |
| 1.8 | 2-cyclopentyl-N-methoxy-N-[[4-[5-(trifluoromethyl)-1,2,4-oxadiazol-3-yl]phenyl]methyl]-acetamide | 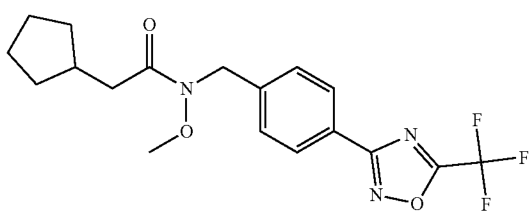 [SMILES: CON(Cc1ccc(-c2noc(C(F)(F)F)n2)cc1)C(=O)CC1CCCC1] | 2.05 | 384.2 | B | |
| 1.9 | 2,4-dichloro-N-methoxy-N-[[4-[5-(trifluoromethyl)-1,2,4-oxadiazol-3-yl]phenyl]methyl]-benzamide | 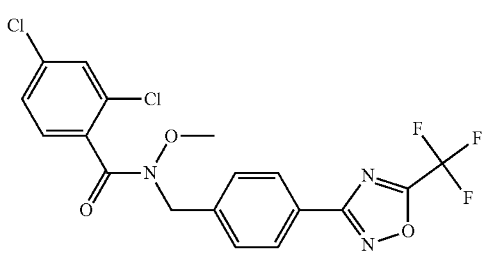 [SMILES: CON(Cc1ccc(-c2noc(C(F)(F)F)n2)cc1)C(=O)c1ccc(Cl)cc1Cl] | 2.03 | 446.1 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.10 | N-methoxy-2,2-dimethyl-N-[[4-[5-(trifluoromethyl)-1,2,4-oxadiazol-3-yl]phenyl]methyl]-pentanamide | 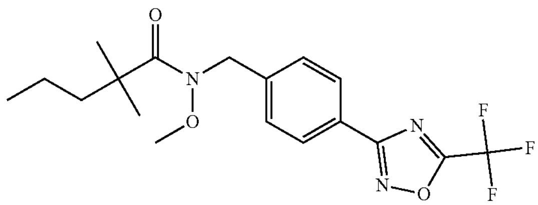 [SMILES: CCCC(C)(C)C(=O)N(Cc1ccc(-c2noc(C(F)(F)F)n2)cc1)OC] | 2.16 | 386.3 | B | |
| 1.11 | N-methoxy-N-[[4-[5-(trifluoromethyl)-1,2,4-oxadiazol-3-yl]phenyl]methyl]-pent-4-ynamide | 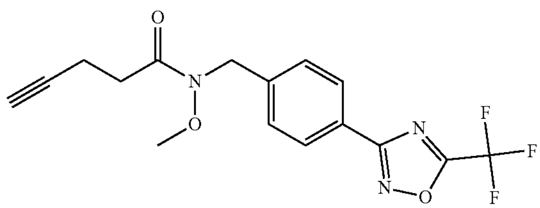 [SMILES: C#CCCC(=O)N(Cc1ccc(-c2noc(C(F)(F)F)n2)cc1)OC] | 1.73 | 354.2 | B | |
| 1.12 | N-methoxy-2-methyl-N-[[4-[5-(trifluoromethyl)-1,2,4-oxadiazol-3-yl]phenyl]methyl]-propanamide | 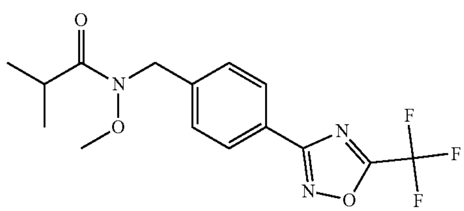 [SMILES: CON(Cc1ccc(-c2noc(C(F)(F)F)n2)cc1)C(=O)C(C)C] | 1.82 | 344.2 | B | |
| 1.13 | N-methoxy-3-(trifluoromethyl)-N-[[4-[5-(trifluoromethyl)-1,2,4-oxadiazol-3-yl]phenyl]methyl]-benzamide | 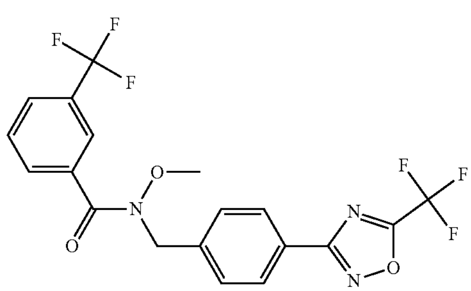 [SMILES: CON(Cc1ccc(-c2noc(C(F)(F)F)n2)cc1)C(=O)c1cccc(C(F)(F)F)c1] | 2.01 | 446.2 | B | |
| 1.14 | N-methoxy-2,2,3,3-tetramethyl-N-[[4-[5-(trifluoromethyl)-1,2,4-oxadiazol-3-yl]phenyl]methyl]-cyclopropane-carboxamide | 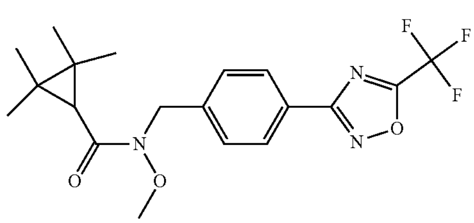 [SMILES: CON(Cc1ccc(-c2noc(C(F)(F)F)n2)cc1)C(=O)C1C(C)(C)C1(C)C] | 2.18 | 398.3 | B | |
| 1.15 | 2,2-difluoro-N-methoxy-N-[[4-[5-(trifluoromethyl)-1,2,4-oxadiazol-3-yl]phenyl]methyl]-cyclopropane-carboxamide | 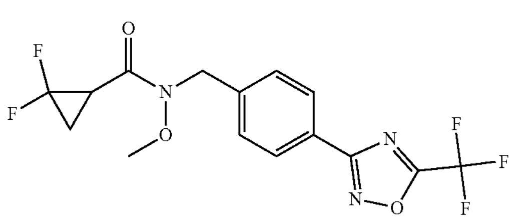 [SMILES: CON(Cc1ccc(-c2noc(C(F)(F)F)n2)cc1)C(=O)C1CC1(F)F] | 1.79 | 378.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.16 | N-methoxy-N-[[4-[5-(trifluoromethyl)-1,2,4-oxadiazol-3-yl]phenyl]methyl]-cyclohexane-carboxamide | 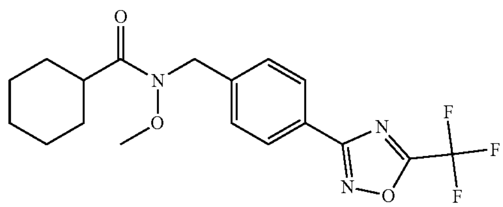 [SMILES: CON(Cc1ccc(-c2noc(C(F)(F)F)n2)cc1)C(=O)C1CCCCC1] | 2.04 | 384.2 | B | |
| 1.17 | N-methoxy-N-[[4-[5-(trifluoromethyl)-1,2,4-oxadiazol-3-yl]phenyl]methyl]-pent-4-enamide | 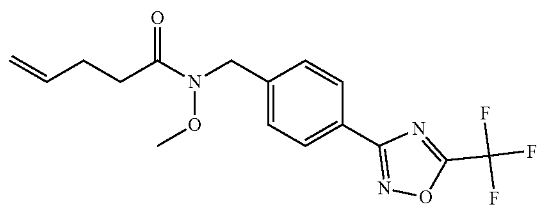 [SMILES: C=CCCC(=O)N(Cc1ccc(-c2noc(C(F)(F)F)n2)cc1)OC] | 1.85 | 356.2 | B | |
| 1.18 | 3-(4-chlorophenyl)-N-methoxy-N-[[4-[5-(trifluoromethyl)-1,2,4-oxadiazol-3-yl]phenyl]methyl]-propanamide | 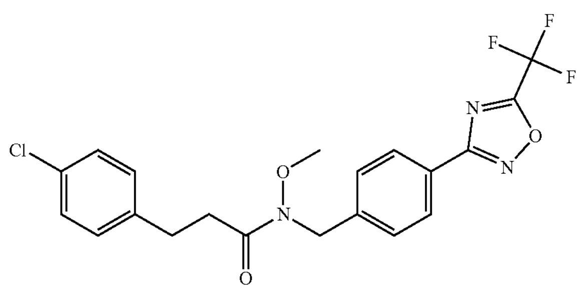 [SMILES: CON(Cc1ccc(-c2noc(C(F)(F)F)n2)cc1)C(=O)CCc1ccc(Cl)cc1] | 2.07 | 440.2 | B | |
| 1.19 | N-methoxy-1-(trifluoromethyl)-N-[[4-[5-(trifluoromethyl)-1,2,4-oxadiazol-3-yl]phenyl]methyl]-cyclobutane-carboxamide | 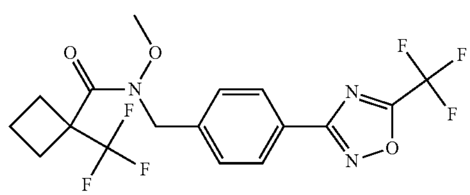 [SMILES: CON(Cc1ccc(-c2noc(C(F)(F)F)n2)cc1)C(=O)C1(C(F)(F)F)CCC1] | 2.01 | 424.2 | B | |
| 1.20 | N-methoxy-N-[[4-[5-(trifluoromethyl)-1,2,4-oxadiazol-3-yl]phenyl]methyl]-hexanamide | 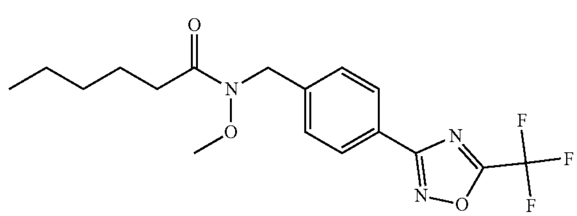 [SMILES: CCCCCC(=O)N(Cc1ccc(-c2noc(C(F)(F)F)n2)cc1)OC] | 2.03 | 372.2 | B | |
| 1.21 | 1-(4-chlorophenyl)-N-methoxy-N-[[4-[5-(trifluoromethyl)-1,2,4-oxadiazol-3-yl]phenyl]methyl]-cyclobutane-carboxamide | 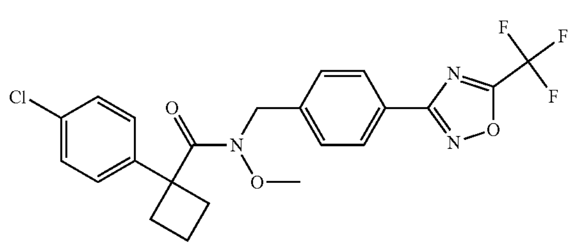 [SMILES: CON(Cc1ccc(-c2noc(C(F)(F)F)n2)cc1)C(=O)C1(c2ccc(Cl)cc2)CCC1] | 2.23 | 466.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.22 | N-methoxy-2-methyl-4-oxo-N-[[4-[5-(trifluoromethyl)-1,2,4-oxadiazol-3-yl]phenyl]methyl]-pentanamide | 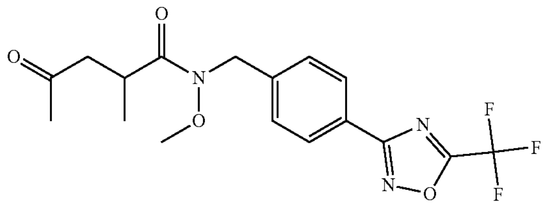 [SMILES: CON(Cc1ccc(-c2noc(C(F)(F)F)n2)cc1)C(=O)C(C)CC(C)=O] | 1.70 | 386.2 | B | |
| 1.23 | N-methoxy-1-phenyl-N-[[4-[5-(trifluoromethyl)-1,2,4-oxadiazol-3-yl]phenyl]methyl]-cyclopropane-carboxamide | 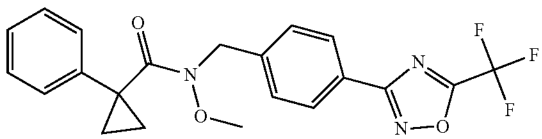 [SMILES: CON(Cc1ccc(-c2noc(C(F)(F)F)n2)cc1)C(=O)C1(c2ccccc2)CC1] | 2.00 | 418.2 | B | |
| 1.24 | N-methoxy-N-[[4-[5-(trifluoromethyl)-1,2,4-oxadiazol-3-yl]phenyl]methyl]-butanamide | 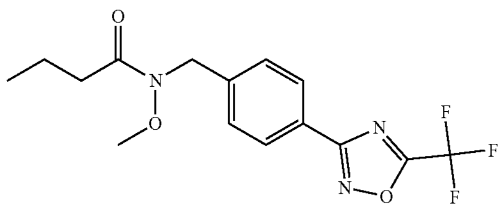 [SMILES: CCCC(=O)N(Cc1ccc(-c2noc(C(F)(F)F)n2)cc1)OC] | 1.82 | 344.2 | B | |
| 1.25 | N-methoxy-2-phenyl-N-[[4-[5-(trifluoromethyl)-1,2,4-oxadiazol-3-yl]phenyl]methyl]-cyclopropane-carboxamide | 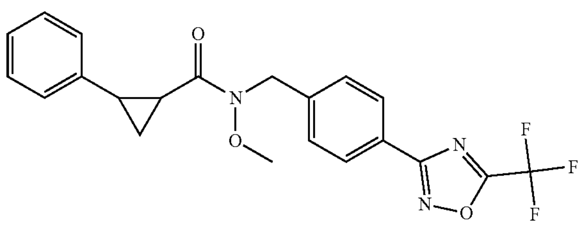 [SMILES: CON(Cc1ccc(-c2noc(C(F)(F)F)n2)cc1)C(=O)C1CC1c1ccccc1] | 2.02 | 418.2 | B | |
| 1.26 | 2-cyclopropyl-N-methoxy-N-[[4-[5-(trifluoromethyl)-1,2,4-oxadiazol-3-yl]phenyl]methyl]-acetamide | 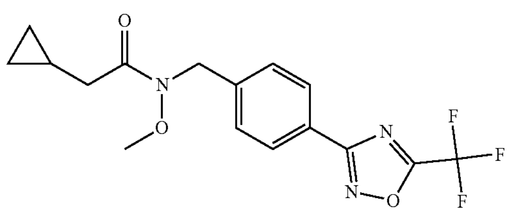 [SMILES: CON(Cc1ccc(-c2noc(C(F)(F)F)n2)cc1)C(=O)CC1CC1] | 1.81 | 356.2 | B | |
| 1.27 | N-methoxy-N-[[4-[5-(trifluoromethyl)-1,2,4-oxadiazol-3-yl]phenyl]methyl]-cyclopentane-carboxamide | 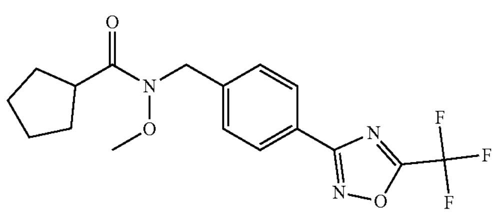 [SMILES: CON(Cc1ccc(-c2noc(C(F)(F)F)n2)cc1)C(=O)C1CCCC1] | 1.96 | 370.2 | B | |
| 1.28 | N-methoxy-2-(3-pyridyl)-N-[[4-[5-(trifluoromethyl)-1,2,4-oxadiazol-3-yl]phenyl]methyl]-acetamide | 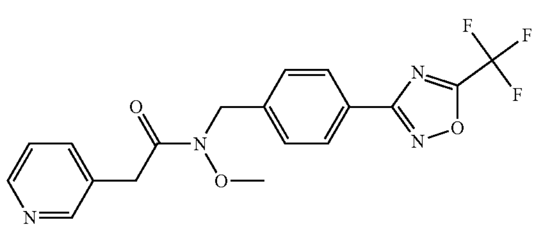 [SMILES: CON(Cc1ccc(-c2noc(C(F)(F)F)n2)cc1)C(=O)Cc1cccnc1] | 1.25 | 393.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.29 | N-methoxy-N-[[4-[5-(trifluoromethyl)-1,2,4-oxadiazol-3-yl]phenyl]methyl]-tetrahydrofuran-3-carboxamide | 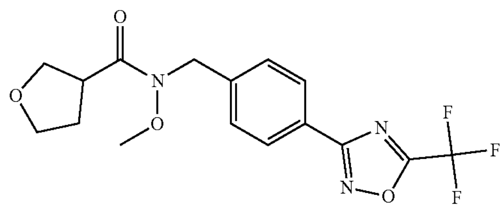 [SMILES: CON(Cc1ccc(-c2noc(C(F)(F)F)n2)cc1)C(=O)C1CCOC1] | 1.62 | 372.2 | B | |
| 1.30 | N-methoxy-N-[[4-[5-(trifluoromethyl)-1,2,4-oxadiazol-3-yl]phenyl]methyl]-thietane-3-carboxamide | 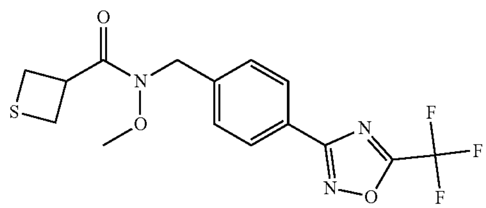 [SMILES: CON(Cc1ccc(-c2noc(C(F)(F)F)n2)cc1)C(=O)C1CSC1] | 1.80 | 374.2 | B | |
| 1.31 | N,3-dimethoxy-N-[[4-[5-(trifluoromethyl)-1,2,4-oxadiazol-3-yl]phenyl]methyl]-propanamide | 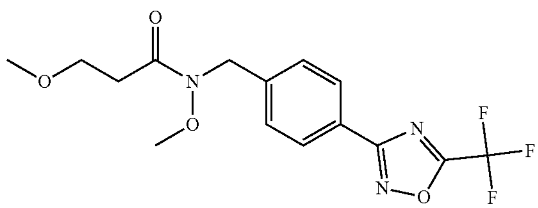 [SMILES: COCCC(=O)N(Cc1ccc(-c2noc(C(F)(F)F)n2)cc1)OC] | 1.62 | 360.2 | B | |
| 1.32 | 2,2-dichloro-N-methoxy-1-methyl-N-[[4-[5-(trifluoromethyl)-1,2,4-oxadiazol-3-yl]phenyl]methyl]-cyclopropane-carboxamide | 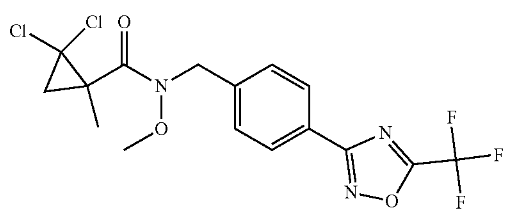 [SMILES: CON(Cc1ccc(-c2noc(C(F)(F)F)n2)cc1)C(=O)C1(C)CC1(Cl)Cl] | 2.01 | 424.1 | B | |
| 1.33 | N-methoxy-1-methyl-N-[[4-[5-(trifluoromethyl)-1,2,4-oxadiazol-3-yl]phenyl]methyl]-cyclohexane-carboxamide | 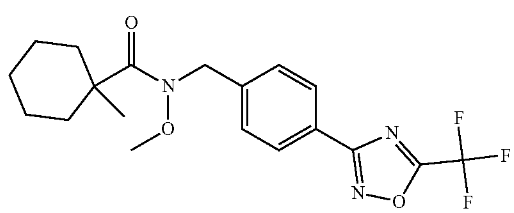 [SMILES: CON(Cc1ccc(-c2noc(C(F)(F)F)n2)cc1)C(=O)C1(C)CCCCC1] | 2.21 | 398.3 | B | |
| 1.34 | N-methoxy-3-methyl-N-[[4-[5-(trifluoromethyl)-1,2,4-oxadiazol-3-yl]phenyl]methyl]-butanamide | 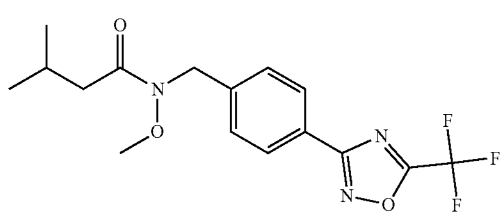 [SMILES: CON(Cc1ccc(-c2noc(C(F)(F)F)n2)cc1)C(=O)CC(C)C] | 1.92 | 358.2 | B | |
| 1.35 | 3-chloro-N-methoxy-2,2-dimethyl-N-[[4-[5-(trifluoromethyl)-1,2,4-oxadiazol-3-yl]phenyl]methyl]-propanamide | 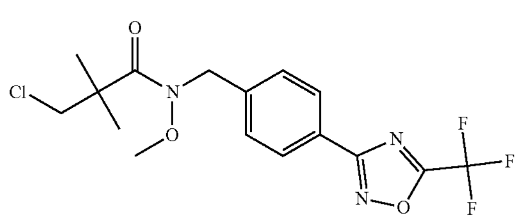 [SMILES: CON(Cc1ccc(-c2noc(C(F)(F)F)n2)cc1)C(=O)C(C)(C)CCl] | 1.96 | 392.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.36 | 3,3,3-trifluoro-N-methoxy-N-[[4-[5-(trifluoromethyl)-1,2,4-oxadiazol-3-yl]phenyl]methyl]-propanamide | 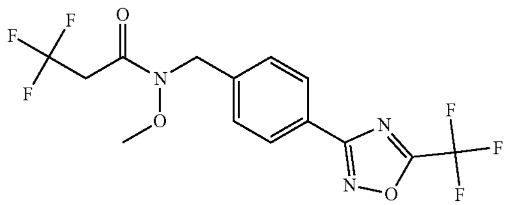 [SMILES: CON(Cc1ccc(-c2noc(C(F)(F)F)n2)cc1)C(=O)CC(F)(F)F] | 1.78 | 384.2 | B | |
| 1.37 | N-methoxy-N-[[4-[5-(trifluoromethyl)-1,2,4-oxadiazol-3-yl]phenyl]methyl]-naphthalene-1-carboxamide | 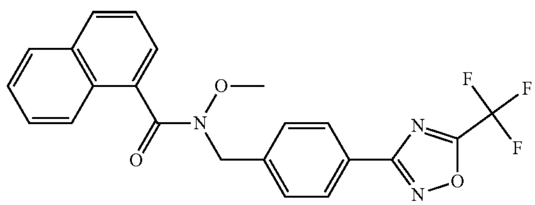 [SMILES: CON(Cc1ccc(-c2noc(C(F)(F)F)n2)cc1)C(=O)c1cccc2ccccc12] | 1.96 | 428.2 | B | |
| 1.38 | N-methoxy-N-[[4-[5-(trifluoromethyl)-1,2,4-oxadiazol-3-yl]phenyl]methyl]-cyclobutane-carboxamide | 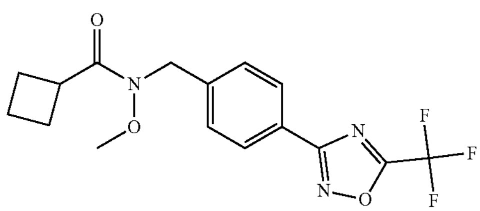 [SMILES: CON(Cc1ccc(-c2noc(C(F)(F)F)n2)cc1)C(=O)C1CCC1] | 1.86 | 356.2 | B | |
| 1.39 | N-methoxy-2-(4-phenylphenyl)-N-[[4-[5-(trifluoromethyl)-1,2,4-oxadiazol-3-yl]phenyl]methyl]-acetamide | 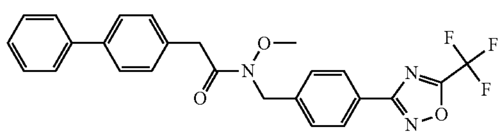 [SMILES: CON(Cc1ccc(-c2noc(C(F)(F)F)n2)cc1)C(=O)Cc1ccc(-c2ccccc2)cc1] | 2.13 | 468.3 | B | |
| 1.40 | N-methoxy-2-methyl-N-[[4-[5-(trifluoromethyl)-1,2,4-oxadiazol-3-yl]phenyl]methyl]-cyclopropane-carboxamide | 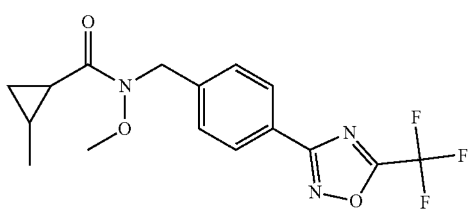 [SMILES: CON(Cc1ccc(-c2noc(C(F)(F)F)n2)cc1)C(=O)C1CC1C] | 1.85 | 356.2 | B | |
| 1.41 | N-methoxy-3,3-dimethyl-N-[[4-[5-(trifluoromethyl)-1,2,4-oxadiazol-3-yl]phenyl]methyl]-butanamide | 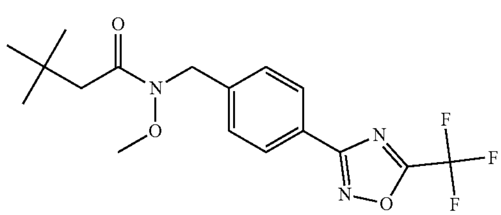 [SMILES: CON(Cc1ccc(-c2noc(C(F)(F)F)n2)cc1)C(=O)CC(C)(C)C] | 2.03 | 372.2 | B | |
| 1.42 | N-methoxy-2,2-dimethyl-N-[[4-[5-(trifluoromethyl)-1,2,4-oxadiazol-3-yl]phenyl]methyl]-propanamide | 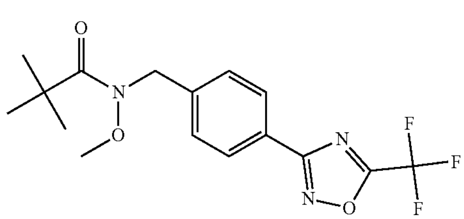 [SMILES: CON(Cc1ccc(-c2noc(C(F)(F)F)n2)cc1)C(=O)C(C)(C)C] | 1.97 | 358.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.43 | N-methoxy-1-methyl-N-[[4-[5-(trifluoromethyl)-1,2,4-oxadiazol-3-yl]phenyl]methyl]-cyclopropane-carboxamide | 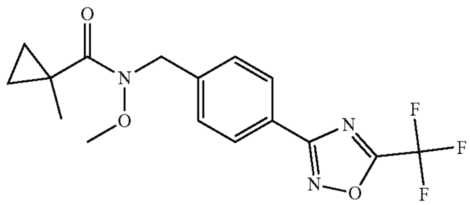 [SMILES: CON(Cc1ccc(-c2noc(C(F)(F)F)n2)cc1)C(=O)C1(C)CC1] | 1.81 | 356.2 | B | |
| 1.44 | 2-chloro-N-methoxy-N-[[4-[5-(trifluoromethyl)-1,2,4-oxadiazol-3-yl]phenyl]methyl]-benzamide | 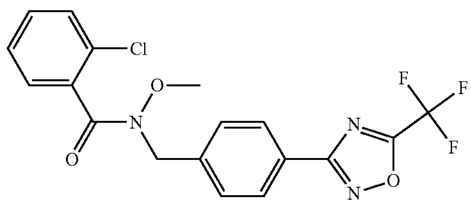 [SMILES: CON(Cc1ccc(-c2noc(C(F)(F)F)n2)cc1)C(=O)c1ccccc1Cl] | 1.88 | 412.1 | B | |
| 1.45 | N-methoxy-2-methyl-N-[[4-[5-(trifluoromethyl)-1,2,4-oxadiazol-3-yl]phenyl]methyl]-prop-2-enamide | 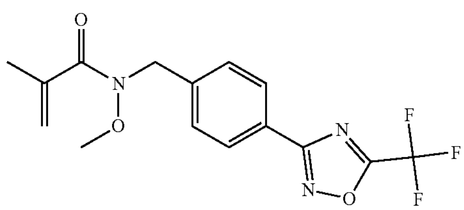 [SMILES: C=C(C)C(=O)N(Cc1ccc(-c2noc(C(F)(F)F)n2)cc1)OC] | 1.74 | 342.2 | B | |
| 1.46 | N-methoxy-N-[[4-[5-(trifluoromethyl)-1,2,4-oxadiazol-3-yl]phenyl]methyl] tetrahydrothiopyran-4-carboxamide | 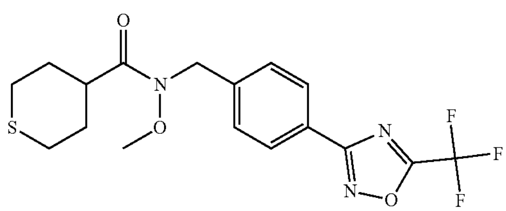 [SMILES: CON(Cc1ccc(-c2noc(C(F)(F)F)n2)cc1)C(=O)C1CCSCC1] | 1.85 | 402.0 | B | |
| 1.47 | N-methoxy-2,2-dimethyl-N-[[4-[5-(trifluoromethyl)-1,2,4-oxadiazol-3-yl]phenyl]methyl]-cyclopropane-carboxamide | 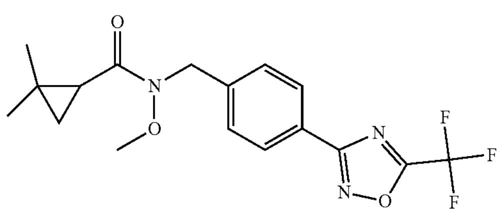 [SMILES: CON(Cc1ccc(-c2noc(C(F)(F)F)n2)cc1)C(=O)C1CC1(C)C] | 1.96 | 370.2 | B | |
| 1.48 | N-methoxy-2-methyl-N-[[4-[5-(trifluoromethyl)-1,2,4-oxadiazol-3-yl]phenyl]methyl]-butanamide | 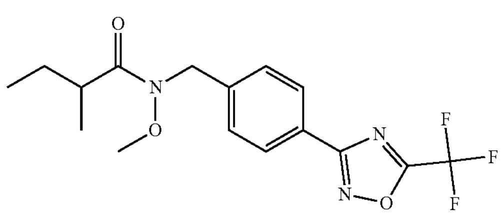 [SMILES: CCC(C)C(=O)N(Cc1ccc(-c2noc(C(F)(F)F)n2)cc1)OC] | 1.92 | 358.2 | B | |
| 1.49 | 2-(4-chlorophenyl)-N-methoxy-N-[[4-[5-(trifluoromethyl)-1,2,4-oxadiazol-3-yl]phenyl]methyl]-acetamide | 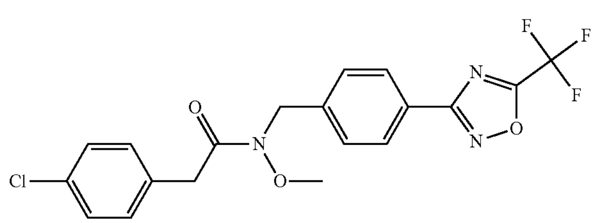 [SMILES: CON(Cc1ccc(-c2noc(C(F)(F)F)n2)cc1)C(=O)Cc1ccc(Cl)cc1] | 2.00 | 426.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.50 | N-methoxy-3-methyl-N-[[4-[5-(trifluoromethyl)-1,2,4-oxadiazol-3-yl]phenyl]methyl]-oxetane-3-carboxamide | 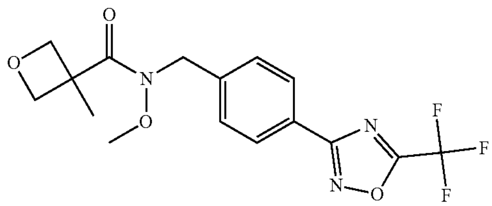 [SMILES: CON(Cc1ccc(-c2noc(C(F)(F)F)n2)cc1)C(=O)C1(C)COC1] | 1.61 | 372.2 | B | |
| 1.51 | 3-fluoro-N-methoxy-4-prop-2-ynoxy-N-[[4-[5-(trifluoromethy)-1,2,4-oxadiazol-3-yl]phenyl]methyl]-benzamide | 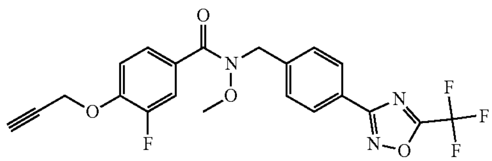 [SMILES: C#CCOc1ccc(C(=O)N(Cc2ccc(-c3noc(C(F)(F)F)n3)cc2)OC)cc1F] | 1.88 | 450.2 | B | |
| 1.52 | 2-(4-cyanophenyl)-N-methoxy-N-[[4-[5-(trifluoromethyl)-1,2,4-oxadiazol-3-yl]phenyl]methyl]-acetamide | 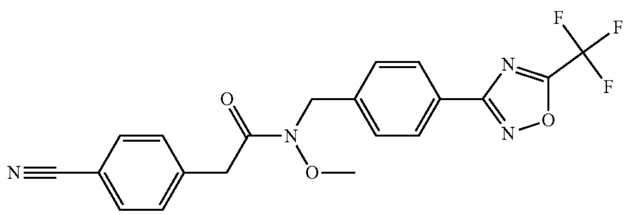 [SMILES: CON(Cc1ccc(-c2noc(C(F)(F)F)n2)cc1)C(=O)Cc1ccc(C#N)cc1] | 1.80 | 417.2 | B | |
| 1.53 | 6,6,6-trifluoro-N-methoxy-N-[[4-[5-(trifluoromethyl)-1,2,4-oxadiazol-3-yl]phenyl]methyl]-hexanamide | 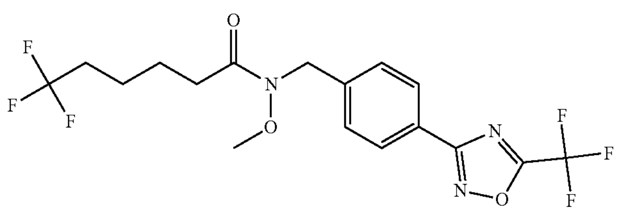 [SMILES: CON(Cc1ccc(-c2noc(C(F)(F)F)n2)cc1)C(=O)CCCCC(F)(F)F] | 1.96 | 426.2 | B | |
| 1.54 | N-[1-(methoxy-[[4-[5-(trifluoromethyl)-1,2,4-oxadiazol-3-yl]phenyl]methyl]carbamoyl]-2-methyl-propyl]-cyclopropane-carboxamide | 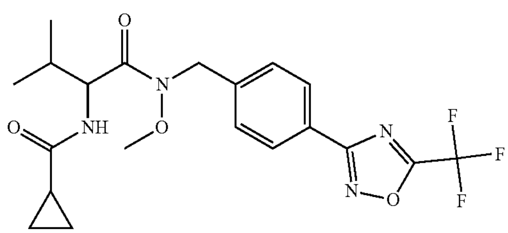 [SMILES: CON(Cc1ccc(-c2noc(C(F)(F)F)n2)cc1)C(=O)C(NC(=O)C1CC1)C(C)C] | 1.77 | 441.3 | B | 104.4-109 |
| 1.55 | 6-bromo-N-methoxy-N-[[4-[5-(trifluoromethyl)-1,2,4-oxadiazol-3-yl]phenyl]methyl]-1,3-benzoxlioxole-5-carboxamide | 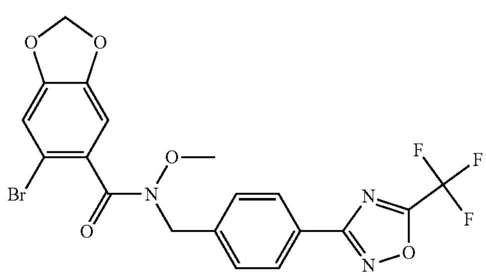 [SMILES: CON(Cc1ccc(-c2noc(C(F)(F)F)n2)cc1)C(=O)c1cc2c(cc1Br)OCO2] | 1.88 | 500.1 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.56 | 3-(2,2-dibromovinyl)-N-methoxy-2,2-dimethyl-N-[[4-[5-(trifluoromethyl)-1,2,4-oxadiazol-3-yl]phenyl]methyl]-cyclopropane-carboxamide | 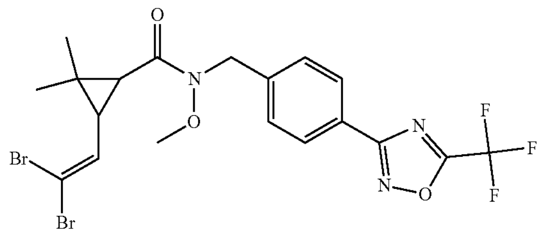 [SMILES: CON(Cc1ccc(-c2noc(C(F)(F)F)n2)cc1)C(=O)C1C(C=C(Br)Br)C1(C)C] | 2.24 | 552.1 | B | |
| 1.57 | N-methoxy-2-(methoxymethyl)-N-[[4-[5-(trifluoromethyl)-1,2,4-oxadiazol-3-yl]phenyl]methyl]-butanamide | 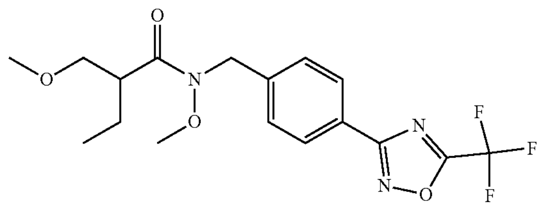 [SMILES: CCC(COC)C(=O)N(Cc1ccc(-c2noc(C(F)(F)F)n2)cc1)OC] | 1.85 | 388.2 | B | |
| 1.58 | 2-ethyl-N-methoxy-2-methyl-N-[[4-[5-(trifluoromethyl)-1,2,4-oxadiazol-3-yl]phenyl]methyl]-butanamide | 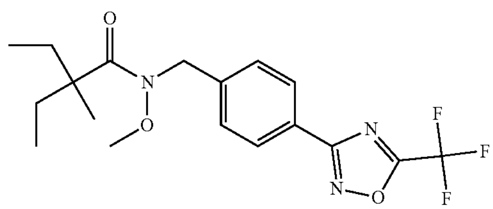 [SMILES: CCC(C)(CC)C(=O)N(Cc1ccc(-c2noc(C(F)(F)F)n2)cc1)OC] | 2.15 | 386.3 | B | |
| 1.59 | N,4-dimethoxy-N-[[4-(5-(trifluoromethyl)-1,2,4-oxadiazol-3-yl]phenyl]methyl]-butanamide | 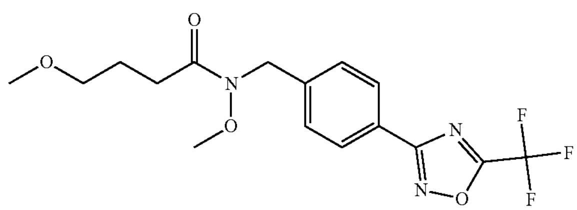 [SMILES: COCCCC(=O)N(Cc1ccc(-c2noc(C(F)(F)F)n2)cc1)OC] | 1.69 | 374.2 | B | |
| 1.60 | 2-(ethylsulfonylamino)-N-methoxy-N-[[4-[5-(trifluoromethyl)-1,2,4-oxadiazol-3-yl]phenyl]methyl]-pent-4-ynamide | 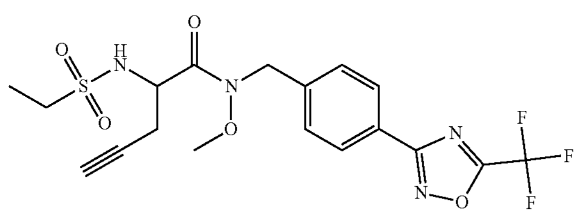 [SMILES: C#CCC(NS(=O)(=O)CC)C(=O)N(Cc1ccc(-c2noc(C(F)(F)F)n2)cc1)OC] | 1.82 | 461.2 | B | |
| 1.61 | 2,2-dichloro-1-ethyl-N-methoxy-3-methyl-N-[[4-[5-(trifluoromethyl)-1,2,4-oxadiazol-3-yl]phenyl]methyl]-cyclopropane-carboxamide | 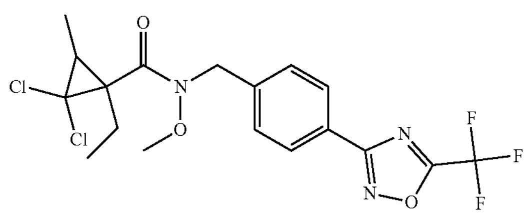 [SMILES: CCC1(C(=O)N(Cc2ccc(-c3noc(C(F)(F)F)n3)cc2)OC)C(C)C1(Cl)Cl] | 2.17 | 452.2 | B | |
| 1.62 | 3-(2,2-dichlorovinyl)-N-methoxy-2,2-dimethyl-N-[[4-[5-(trifluoromethyl)-1,2,4-oxadiazol-3-yl]phenyl]methyl]-cyclopropane-carboxamide | 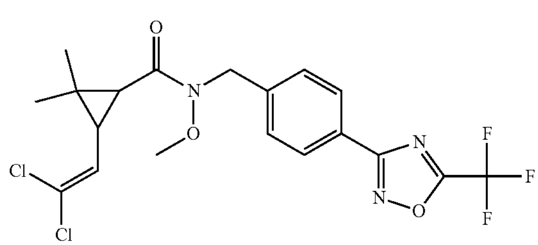 [SMILES: CON(Cc1ccc(-c2noc(C(F)(F)F)n2)cc1)C(=O)C1C(C=C(Cl)Cl)C1(C)C] | 2.22 | 464.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.63 | 3-(2,2-dichlorovinyl)-N-methoxy-2,2-dimethyl-N-[[4-[5-(trifluoromethyl)-1,2,4-oxadiazol-3-yl]phenyl]methyl]-cyclopropane-carboxamide | 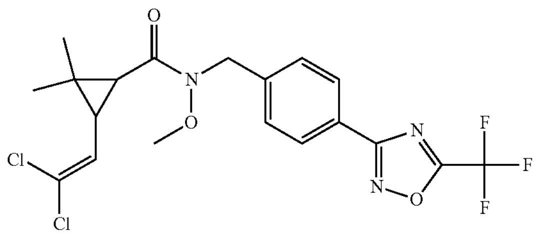 [SMILES: CON(Cc1ccc(-c2noc(C(F)(F)F)n2)cc1)C(=O)C1C(C=C(Cl)Cl)C1(C)C] | 2.29 | 464.2 | B | |
| 1.64 | 2-(2,2-difluorocyclopropyl)-N-methoxy-N-[[4-[5-(trifluoromethyl)-1,2,4-oxadiazol-3-yl]phenyl]methyl]-acetamide | 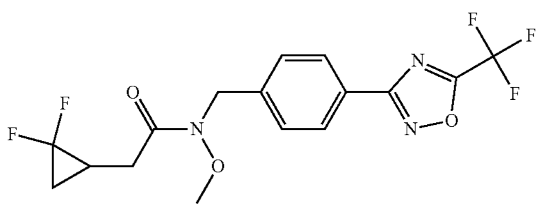 [SMILES: CON(Cc1ccc(-c2noc(C(F)(F)F)n2)cc1)C(=O)CC1CC1(F)F] | 1.82 | 392.2 | B | |
| 1.65 | 1-(3-chlorophenyl)-N-methoxy-N-[[4-[5-(trifluoromethyl)-1,2,4-oxadiazol-3-yl]phenyl]methyl]-cyclopropane-carboxamide | 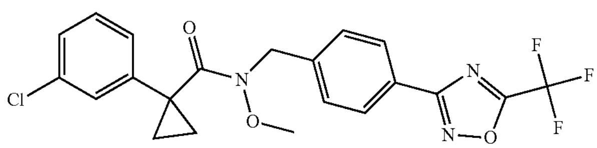 [SMILES: CON(Cc1ccc(-c2noc(C(F)(F)F)n2)cc1)C(=O)C1(c2cccc(Cl)c2)CC1] | 2.09 | 452.2 | B | |
| 1.66 | 1-(2,4-difluorophenyl)-N-methoxy-N-[[4-[5-(trifluoromethyl)-1,2,4-oxadiazol-3-yl]phenyl]methyl]-cyclopropane-carboxamide | 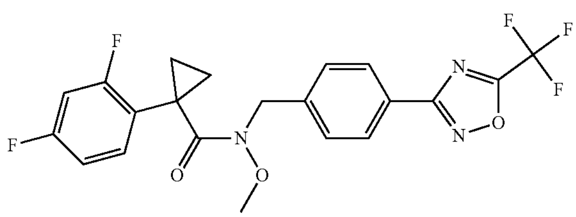 [SMILES: CON(Cc1ccc(-c2noc(C(F)(F)F)n2)cc1)C(=O)C1(c2ccc(F)cc2F)CC1] | 2.01 | 454.2 | B | |
| 1.67 | N-methoxy-N-[[4-[5-(trifluoromethyl)-1,2,4-oxadiazol-3-yl]phenyl]methyl]-1,2,3-benzothiadiazole-7-carboxamide | 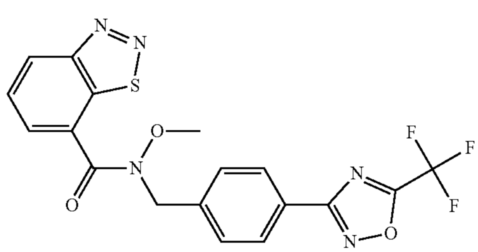 [SMILES: CON(Cc1ccc(-c2noc(C(F)(F)F)n2)cc1)C(=O)c1cccc2nnsc12] | 1.93 | 436.2 | B | |
| 1.68 | N-methoxy-N-[[4-[5-(trifluoromethyl)-1,2,4-oxadiazol-3-yl]phenyl]methyl]-2-[4-(trifluoromethyl)-phenyl]acetamide | 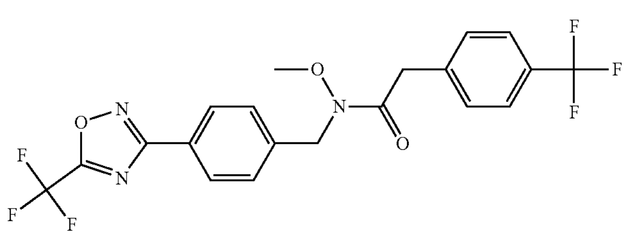 [SMILES: CON(Cc1ccc(-c2noc(C(F)(F)F)n2)cc1)C(=O)Cc1ccc(C(F)(F)F)cc1] | 2.03 | 460.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.69 | 2-(4-chlorophenyl)-N-methoxy-2-prop-2-ynoxy-N-[[4-[5-(trifluoromethyl)-1,2,4-oxadiazol-3-yl]phenyl]methyl]-acetamide | 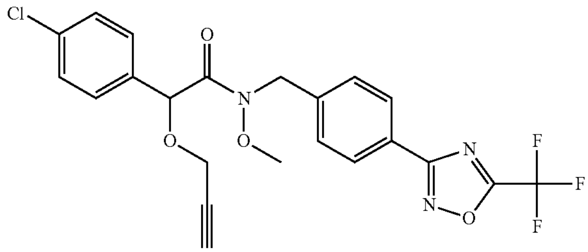 [SMILES: C#CCOC(C(=O)N(Cc1ccc(-c2noc(C(F)(F)F)n2)cc1)OC)c1ccc(Cl)cc1] | 1.98 | 480.2 | B | |
| 1.70 | 1-(4-ethoxyphenyl)-2,2-difluoro-N-methoxy-N-[[4-[5-(trifluoromethyl)-1,2,4-oxadiazol-3-yl]phenyl]methyl]-cyclopropane-carboxamide | 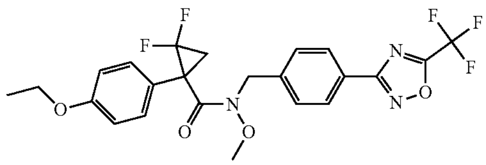 [SMILES: CCOc1ccc(C2(C(=O)N(Cc3ccc(-c4noc(C(F)(F)F)n4)cc3)OC)CC2(F)F)cc1] | 2.11 | 498.2 | B | |
| 1.71 | 4-chloro-N-methoxy-N-[[4-[5-(trifluoromethyl)-1,2,4-oxadiazol-3-yl]phenyl]methyl]-benzamide | 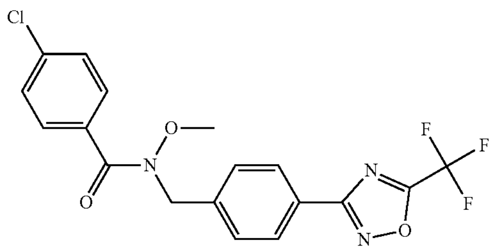 [SMILES: CON(Cc1ccc(-c2noc(C(F)(F)F)n2)cc1)C(=O)c1ccc(Cl)cc1] | 1.98 | 412.1 | B | |
| 1.72 | N-methoxy-1-(3-methoxyphenyl)-N-[[4-[5-(trifluoromethyl)-1,2,4-oxadiazol-3-yl]phenyl]methyl]-cyclopropane-carboxamide | 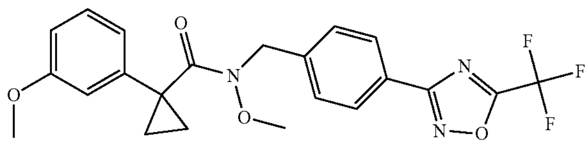 [SMILES: COc1cccc(C2(C(=O)N(Cc3ccc(-c4noc(C(F)(F)F)n4)cc3)OC)CC2)c1] | 1.97 | 448.2 | B | |
| 1.156 | N-isopropyl-2-methoxy-N-[2-[4-[5-(trifluoromethyl)-1,2,4-oxadiazol-3-yl]phenyl]ethyl]-acetamide | 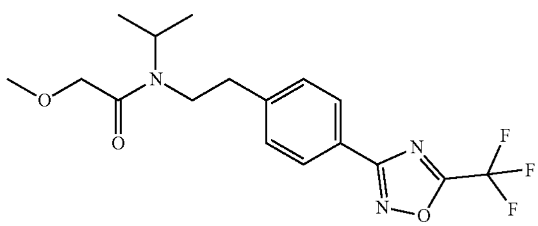 [SMILES: COCC(=O)N(CCc1ccc(-c2noc(C(F)(F)F)n2)cc1)C(C)C] | 1.08 | 372 | A | |
| 1.74 | N-methoxy-1-(4-methoxyphenyl)-N-[[4-[5-(trifluoromethyl)-1,2,4-oxadiazol-3-yl]phenyl]methyl]-cyclopropane-carboxamide | 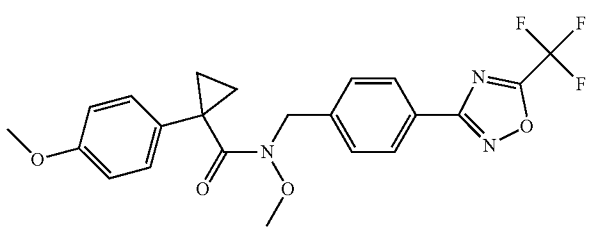 [SMILES: COc1ccc(C2(C(=O)N(Cc3ccc(-c4noc(C(F)(F)F)n4)cc3)OC)CC2)cc1] | 1.96 | 448.2 | B | |
| 1.75 | 1-(4-chlorophenyl)-N-methoxy-N-[[4-[5-(trifluoromethyl)-1,2,4-oxadiazol-3-yl]phenyl]methyl]-cyclopropane-carboxamide | 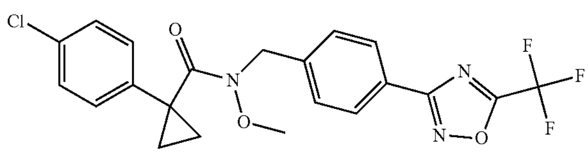 [SMILES: CON(Cc1ccc(-c2noc(C(F)(F)F)n2)cc1)C(=O)C1(c2ccc(Cl)cc2)CC1] | 2.10 | 452.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.76 | N-methoxy-2,2-dimethyl-3-phenyl-N-[[4-[5-(trifluoromethyl)-1,2,4-oxadiazol-3-yl]phenyl]methyl]-propanamide | 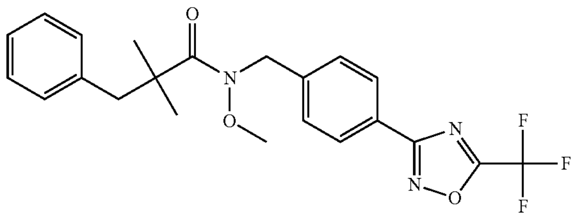 [SMILES: CON(Cc1ccc(-c2noc(C(F)(F)F)n2)cc1)C(=O)C(C)(C)Cc1ccccc1] | 2.18 | 434.3 | B | |
| 1.77 | prop-2-ynyl N-[1-[methoxy-[[4-[5-(trifluoromethyl)-1,2,4-oxadiazol-3-yl]phenyl]methyl]carbamoyl]-2-methyl-propyl]carbamate | 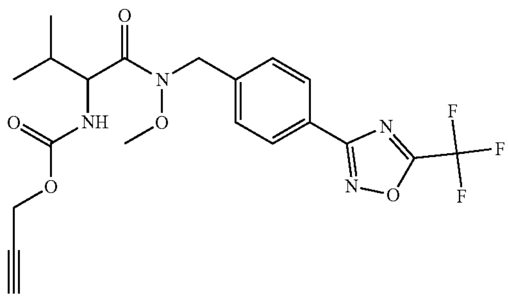 [SMILES: C#CCOC(=O)NC(C(=O)N(Cc1ccc(-c2noc(C(F)(F)F)n2)cc1)OC)C(C)C] | 1.85 | 455.3 | B | |
| 1.78 | 1-(3-bromo-5-chloro-2-pyridyl)-N-methoxy-N-[[4-[5-(trifluoromethyl)-1,2,4-oxadiazol-3-yl]phenyl]methyl]-cyclopropane-carboxamide | 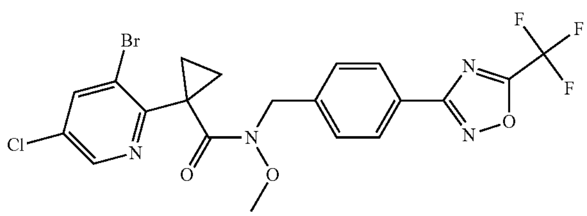 [SMILES: CON(Cc1ccc(-c2noc(C(F)(F)F)n2)cc1)C(=O)C1(c2ncc(Cl)cc2Br)CC1] | 2.13 | 531.1 | B | |
| 1.79 | N-methoxy-N-[[4-[5-(trifluoromethyl)-1,2,4-oxadiazol-3-yl]phenyl]methyl]-2-(2,4,6-trimethylphenyl)-acetamide | 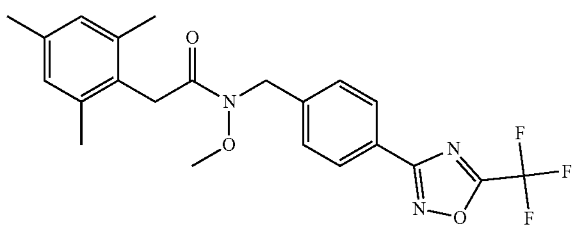 [SMILES: CON(Cc1ccc(-c2noc(C(F)(F)F)n2)cc1)C(=O)Cc1c(C)cc(C)cc1C] | 2.16 | 434.3 | B | |
| 1.80 | N-methoxy-2-methyl-3-phenyl-N-[[4-[5-(trifluoromethyl)-1,2,4-oxadiazol-3-yl]phenyl]methyl]-propanamide | 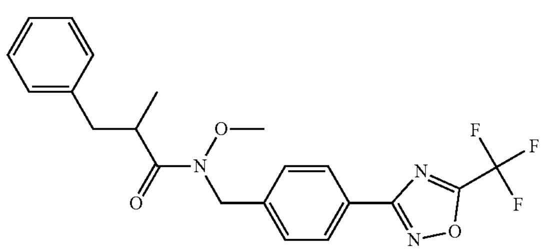 [SMILES: CON(Cc1ccc(-c2noc(C(F)(F)F)n2)cc1)C(=O)C(C)Cc1ccccc1] | 2.14 | 420.2 | B | |
| 1.81 | N,2-dimethoxy-N-[[4-[5-(trifluoromethyl)-1,2,4-oxadiazol-3-yl]phenyl]methyl]-propanamide | 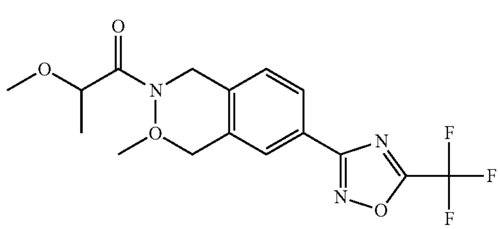 | 1.62 | 360.2 | B | 62-65 |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.82 | N-methoxy-3-(trifluoromethyl)-N-[[4-[5-(trifluoromethyl)-1,2,4-oxadiazol-3-yl]phenyl]methyl]-pentamide | 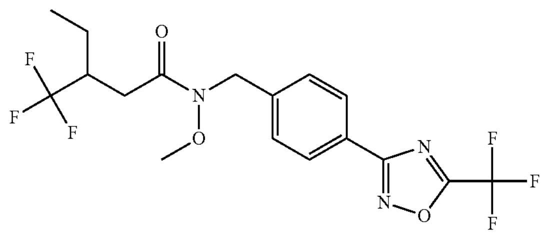 [SMILES: CCC(CC(=O)N(Cc1ccc(-c2noc(C(F)(F)F)n2)cc1)OC)C(F)(F)F] | 2.05 | 426.2 | B | |
| 1.83 | N-cyclopropyl-1-(trifluoromethyl)-N-[4-[5-(trifluoromethyl)-1,2,4-oxadiazol-3-yl]phenyl]methyl]-cyclopropane-carboxamide | 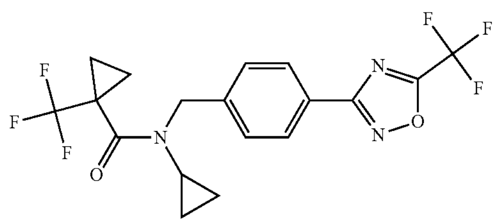 [SMILES: O=C(N(Cc1ccc(-c2noc(C(F)(F)F)n2)cc1)C1CC1)C1(C(F)(F)F)CC1] | 1.93 | 419.1 | B | |
| 1.84 | 2-cyclopentyl-N-cyclopropyl-N-[[4-[5-(trifluoromethyl)-1,2,4-oxadiazol-3-yl]phenyl]methyl]-acetamide | 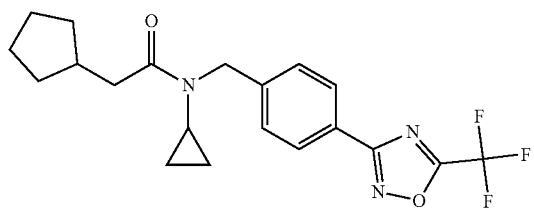 [SMILES: O=C(CC1CCCC1)N(Cc1ccc(-c2noc(C(F)(F)F)n2)cc1)C1CC1] | 2.13 | 394.3 | B | |
| 1.85 | N-cyclopropyl-2,2-dimethyl-N-[[4-[5-(trifluoromethyl)-1,2,4-oxadiazol-3-yl]phenyl]methyl]-pentanamide | 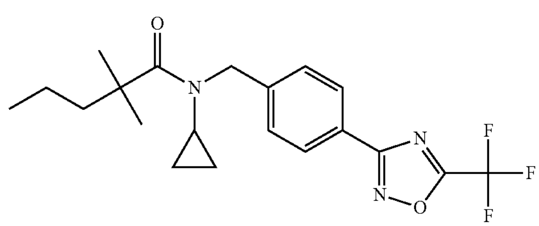 [SMILES: CCCC(C)(C)C(=O)N(Cc1ccc(-c2noc(C(F)(F)F)n2)cc1)C1CC1] | 2.18 | 396.3 | B | |
| 1.86 | N-cyclopropyl-N-[[4-[5-(trifluoromethyl)-1,2,4-oxadiazol-3-yl]phenyl]methyl]-pent-4-ynamide | 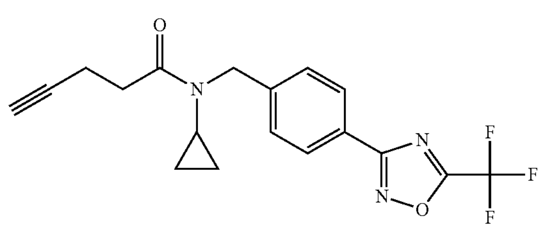 [SMILES: C#CCCC(=O)N(Cc1ccc(-c2noc(C(F)(F)F)n2)cc1)C1CC1] | 1.8 | 364.2 | B | |
| 1.87 | N-cyclopropyl-2-methyl-N-[[4-[5-(trifluoromethyl)-1,2,4-oxadiazol-3-yl]phenyl]methyl]-propanamide | 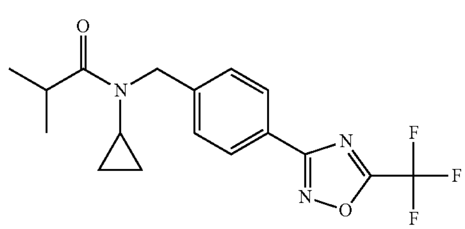 [SMILES: CC(C)C(=O)N(Cc1ccc(-c2noc(C(F)(F)F)n2)cc1)C1CC1] | 1.88 | 354.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.88 | N-cyclopropyl-3-(trifluoromethyl)-N-[[4-[5-(trifluoromethyl)-1,2,4-oxadiazol-3-yl]phenyl]methyl]-benzamide | 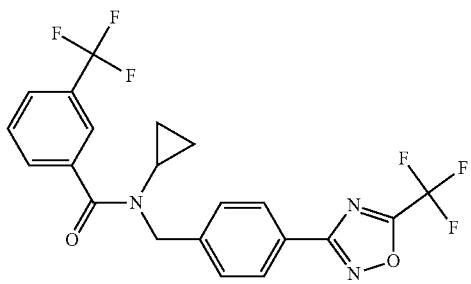 [SMILES: O=C(c1cccc(C(F)(F)F)c1)N(Cc1ccc(-c2noc(C(F)(F)F)n2)cc1)C1CC1] | 2.06 | 456.2 | B | |
| 1.89 | N-cyclopropyl-2,2-difluoro-N-[[4-[5-(trifluoromethyl)-1,2,4-oxadiazol-3-yl]phenyl]methyl]-cyclopropane-carboxamide | 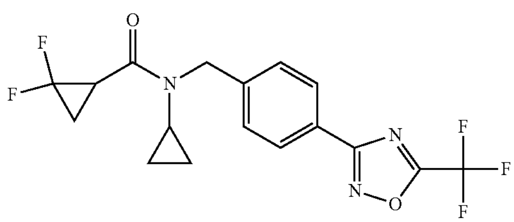 [SMILES: O=C(C1CC1(F)F)N(Cc1ccc(-c2noc(C(F)(F)F)n2)cc1)C1CC1] | 1.87 | 388.2 | B | |
| 1.90 | N-cyclopropyl-N-[[4-[5-(trifluoromethyl)-1,2,4-oxadiazol-3-yl]phenyl]methyl]-cyclohexane-carboxamide | 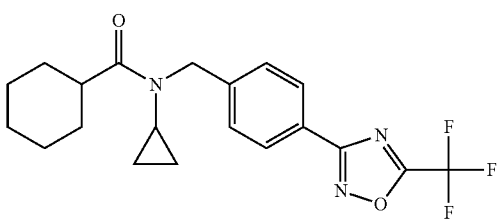 [SMILES: O=C(C1CCCCC1)N(Cc1ccc(-c2noc(C(F)(F)F)n2)cc1)C1CC1] | 2.1 | 394.3 | B | |
| 1.91 | N-cyclopropyl-N-[[4-[5-(trifluoromethyl)-1,2,4-oxadiazol-3-yl]phenyl]methyl]-pent-4-enamide | 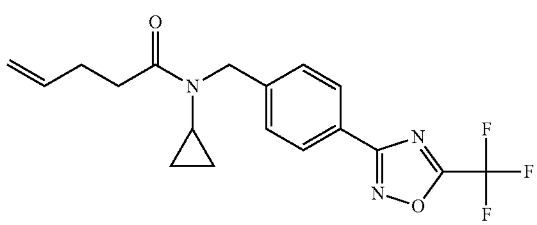 [SMILES: C=CCCC(=O)N(Cc1ccc(-c2noc(C(F)(F)F)n2)cc1)C1CC1] | 1.92 | 366.2 | B | |
| 1.92 | N-cyclopropyl-1-(trifluoromethyl)-N-[[4-[5-(trifluoromethyl)-1,2,4-oxadiazol-3-yl]phenyl]methyl]-cyclobutane-carboxamide | 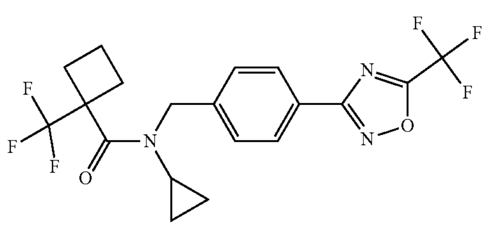 [SMILES: O=C(N(Cc1ccc(-c2noc(C(F)(F)F)n2)cc1)C1CC1)C1(C(F)(F)F)CCC1] | 2.03 | 434.2 | B | |
| 1.93 | N-cyclopropyl-N-[[4-[5-(trifluoromethyl)-1,2,4-oxadiazol-3-yl]phenyl]methyl]-hexanamide | 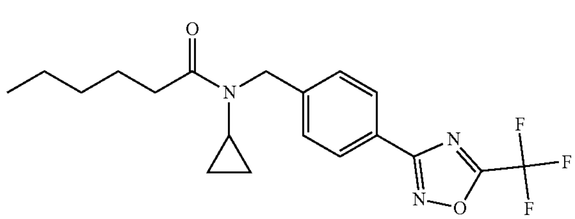 [SMILES: CCCCCC(=O)N(Cc1ccc(-c2noc(C(F)(F)F)n2)cc1)C1CC1] | 2.1 | 382.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.94 | 2-(2-chlorophenyl)-N-cyclopropyl-N-[[4-[5-(trifluoromethyl)-1,2,4-oxadiazol-3-yl]phenyl]methyl]-acetamide | 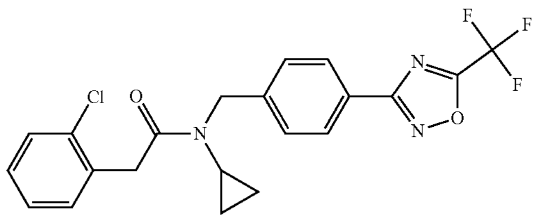 [SMILES: O=C(Cc1ccccc1Cl)N(Cc1ccc(-c2noc(C(F)(F)F)n2)cc1)C1CC1] | 2.07 | 436.2 | B | |
| 1.95 | N-cyclopropyl-2-methyl-4-oxo-N-[[4-[5-(trifluoromethyl)-1,2,4-oxadiazol-3-yl]phenyl]methyl]-pentanamide | 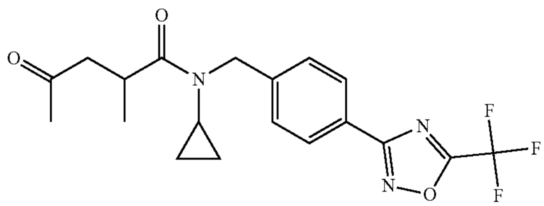 [SMILES: CC(=O)CC(C)C(=O)N(Cc1ccc(-c2noc(C(F)(F)F)n2)cc1)C1CC1] | 1.78 | 396.2 | B | |
| 1.96 | N-cyclopropyl-1-phenyl-N-[[4-[5-(trifluoromethyl)-1,2,4-oxadiazol-3-yl]phenyl]methyl]-cyclopropanecarboxamide | 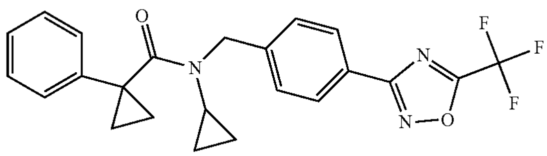 [SMILES: O=C(N(Cc1ccc(-c2noc(C(F)(F)F)n2)cc1)C1CC1)C1(c2ccccc2)CC1] | 2.09 | 428.2 | B | |
| 1.97 | N-cyclopropyl-N-[[4-[5-(trifluoromethyl)-1,2,4-oxadiazol-3-yl]phenyl]methyl]-butanamide | 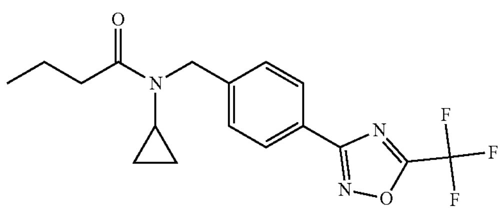 [SMILES: CCCC(=O)N(Cc1ccc(-c2noc(C(F)(F)F)n2)cc1)C1CC1] | 1.89 | 354.2 | B | |
| 1.98 | N-cyclopropyl-2-phenyl-N-[[4-[5-(trifluoromethyl)-1,2,4-oxadiazol-3-yl]phenyl]methyl]-cyclopropanecarboxamide | 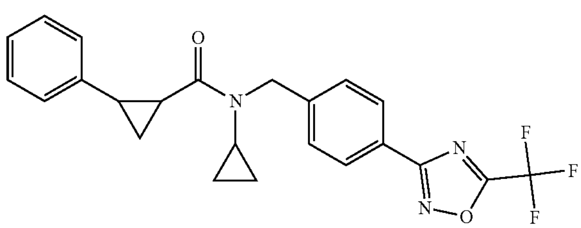 [SMILES: O=C(C1CC1c1ccccc1)N(Cc1ccc(-c2noc(C(F)(F)F)n2)cc1)C1CC1] | 2.09 | 428.2 | B | |
| 1.99 | N,2-dicyclopropyl-N-[[4-[5-(trifluoromethyl)-1,2,4-oxadiazol-3-yl]phenyl]methyl]-acetamide | 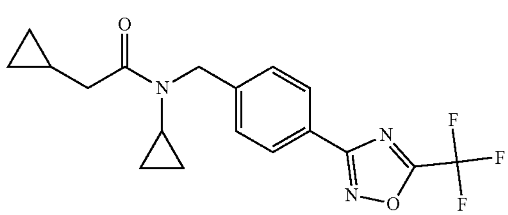 [SMILES: O=C(CC1CC1)N(Cc1ccc(-c2noc(C(F)(F)F)n2)cc1)C1CC1] | 1.88 | 366.2 | B | |
| 1.100 | N-cyclopropyl-N-[[4-[5-(trifluoromethyl)-1,2,4-oxadiazol-3-yl]phenyl]methyl]-cyclopentanecarboxamide | 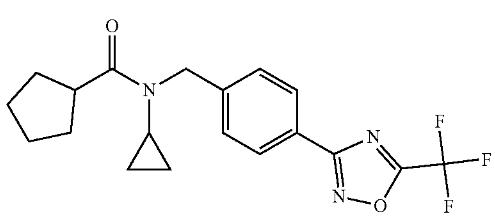 [SMILES: O=C(C1CCCC1)N(Cc1ccc(-c2noc(C(F)(F)F)n2)cc1)C1CC1] | 2.04 | 380.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.101 | N-cyclopropyl-4,4,4-trifluoro-N-[[4-[5-(trifluoromethyl)-1,2,4-oxadiazol-3-yl]phenyl]methyl]-butanamide | 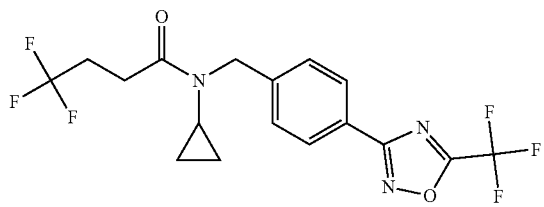 [SMILES: O=C(CCC(F)(F)F)N(Cc1ccc(-c2noc(C(F)(F)F)n2)cc1)C1CC1] | 1.94 | 408.2 | B | |
| 1.102 | N-cyclopropyl-2-(3-pyridyl)-N-[[4-[5-(trifluoromethyl)-1,2,4-oxadiazol-3-yl]phenyl]methyl]-acetamide | 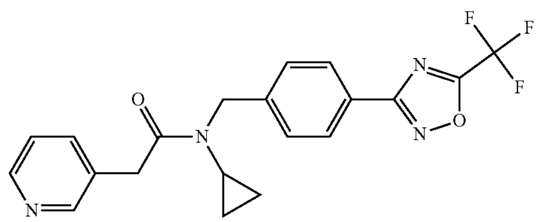 [SMILES: O=C(Cc1cccnc1)N(Cc1ccc(-c2noc(C(F)(F)F)n2)cc1)C1CC1] | 1.3 | 403.2 | B | |
| 1.103 | N-cyclopropyl-N-[[4-[5-(trifluoromethyl)-1,2,4-oxadiazol-3-yl]phenyl]methyl]-tetrahydrofuran-3-carboxamide | 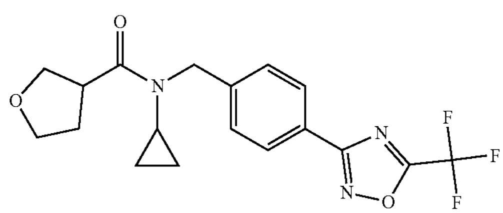 [SMILES: O=C(C1CCOC1)N(Cc1ccc(-c2noc(C(F)(F)F)n2)cc1)C1CC1] | 1.68 | 382.2 | B | |
| 1.104 | N-cyclopropyl-N-[[4-[5-(trifluoromethyl)-1,2,4-oxadiazol-3-yl]phenyl]methyl]-thietane-3-carboxamide | 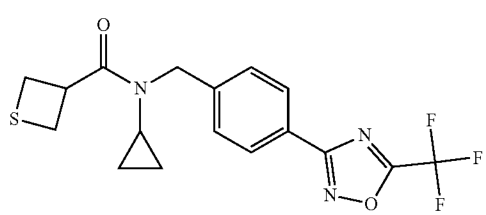 [SMILES: O=C(C1CSC1)N(Cc1ccc(-c2noc(C(F)(F)F)n2)cc1)C1CC1] | 1.85 | 384.2 | B | |
| 1.105 | N-cyclopropyl-2,6-dimethyl-N-[[4-[5-(trifluoromethyl)-1,2,4-oxadiazol-3-yl]phenyl]methyl]-benzamide | 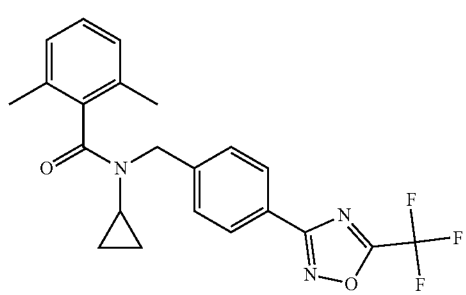 [SMILES: Cc1cccc(C)c1C(=O)N(Cc1ccc(-c2noc(C(F)(F)F)n2)cc1)C1CC1] | 2.07 | 416.2 | B | |
| 1.106 | N-cyclopropyl-3-methoxy-N-[[4-[5-(trifluoromethyl)-1,2,4-oxadiazol-3-yl]phenyl]methyl]-propanamide | 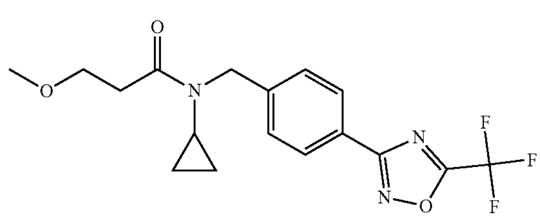 [SMILES: COCCC(=O)N(Cc1ccc(-c2noc(C(F)(F)F)n2)cc1)C1CC1] | 1.71 | 370.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.107 | 2,2-dichloro-N-cyclopropyl-1-methyl-N-[[4-[5-(trifluoromethyl)-1,2,4-oxadiazol-3-yl]phenyl]methyl]-cyclopropane-carboxamide | 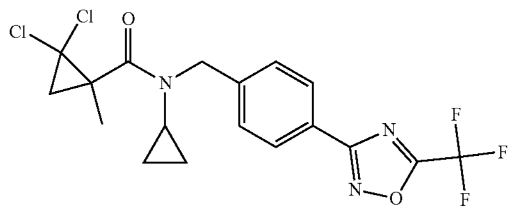 [SMILES: CC1(C(=O)N(Cc2ccc(-c3noc(C(F)(F)F)n3)cc2)C2CC2)CC1(Cl)Cl] | 2.07 | 434.2 | B | |
| 1.108 | N-cyclopropyl-1-methyl-N-[[4-[5-(trifluoromethyl)-1,2,4-oxadiazol-3-yl]phenyl]methyl]-cyclohexane-carboxamide | 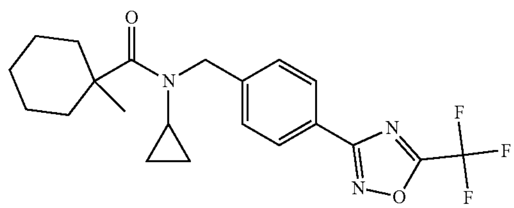 [SMILES: CC1(C(=O)N(Cc2ccc(-c3noc(C(F)(F)F)n3)cc2)C2CC2)CCCCC1] | 2.23 | 408.3 | B | |
| 1.109 | N-cyclopropyl-3-methyl-N-[[4-[5-(trifluoromethyl)-1,2,4-oxadiazol-3-yl]phenyl]methyl]-butanamide | 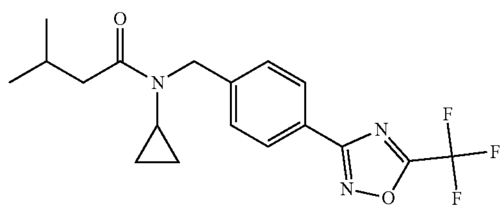 [SMILES: CC(C)CC(=O)N(Cc1ccc(-c2noc(C(F)(F)F)n2)cc1)C1CC1] | 2 | 368.2 | B | |
| 1.110 | 3-chloro-N-cyclopropyl-2,2-dimethyl-N-[[4-[5-(trifluoromethyl)-1,2,4-oxadiazol-3-yl]phenyl]methyl]-propanamide | 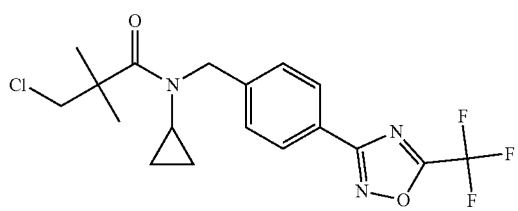 [SMILES: CC(C)(CCl)C(=O)N(Cc1ccc(-c2noc(C(F)(F)F)n2)cc1)C1CC1] | 2 | 402.2 | B | |
| 1.111 | N-cyclopropyl-3,3,3-trifluoro-N-[[4-[5-(trifluoromethyl)-1,2,4-oxadiazol-3-yl]phenyl]methyl]-propanamide | 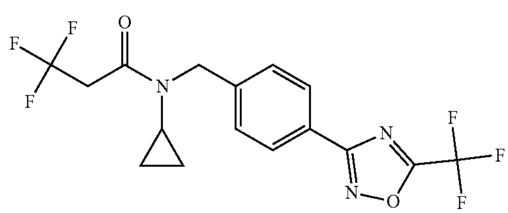 [SMILES: O=C(CC(F)(F)F)N(Cc1ccc(-c2noc(C(F)(F)F)n2)cc1)C1CC1] | 1.84 | 394.2 | B | |
| 1.112 | N-cyclopropyl-N-[[4-[5-(trifluoromethyl)-1,2,4-oxadiazol-3-yl]phenyl]methyl]-cyclobutane-carboxamide | 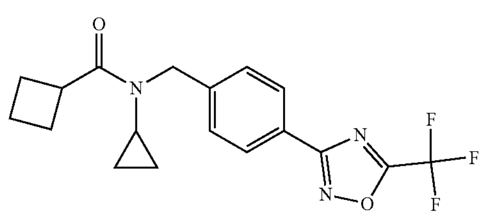 [SMILES: O=C(C1CCC1)N(Cc1ccc(-c2noc(C(F)(F)F)n2)cc1)C1CC1] | 1.94 | 366.2 | B | |
| 1.113 | N-cyclopropyl-2-(2-methoxyphenyl)-N-[[4-[5-(trifluoromethyl)-1,2,4-oxadiazol-3-yl]phenyl]methyl]-acetamide | 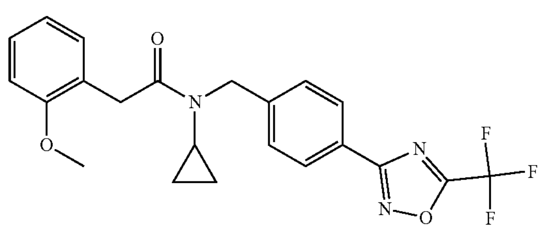 [SMILES: COc1ccccc1CC(=O)N(Cc1ccc(-c2noc(C(F)(F)F)n2)cc1)C1CC1] | 2 | 432.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.114 | N-cyclopropyl-N-[[4-[5-(trifluoromethyl)-1,2,4-oxadiazol-3-yl]phenyl]methyl]pent-3-enamide | 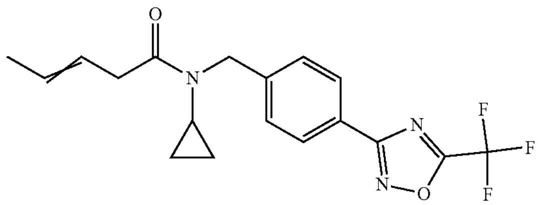 [SMILES: CC=CCC(=O)N(Cc1ccc(-c2noc(C(F)(F)F)n2)cc1)C1CC1] | 1.92 | 366.2 | B | |
| 1.115 | N-cyclopropyl-2-methyl-N-[[4-[5-(trifluoromethyl)-1,2,4-oxadiazol-3-yl]phenyl]methyl]-cyclopropane-carboxamide | 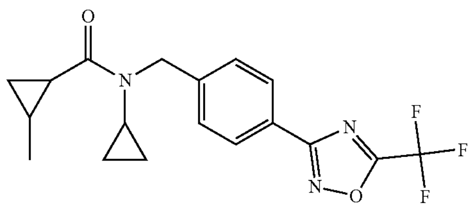 [SMILES: CC1CC1C(=O)N(Cc1ccc(-c2noc(C(F)(F)F)n2)cc1)C1CC1] | 1.93 | 366.2 | B | |
| 1.116 | N-cyclopropy 1-3,3-dimethyl-N-[[4-[5-(trifluoromethyl)-1,2,4-oxadiazol-3-yl]phenyl]methyl]-butanamide | 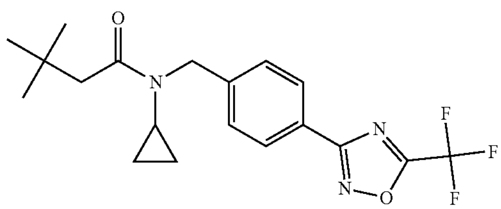 [SMILES: CC(C)(C)CC(=O)N(Cc1ccc(-c2noc(C(F)(F)F)n2)cc1)C1CC1] | 2.11 | 382.3 | B | |
| 1.117 | N-cyclopropyl-2,2-dimethyl-N-[[4-[5-(trifluoromethyl)-1,2,4-oxadiazol-3-yl]phenyl]methyl]-propanamide | 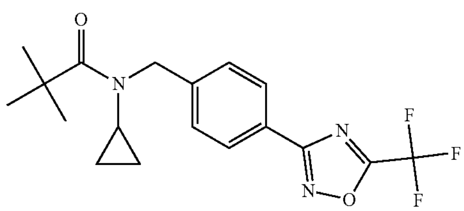 [SMILES: CC(C)(C)C(=O)N(Cc1ccc(-c2noc(C(F)(F)F)n2)cc1)C1CC1] | 1.98 | 368.3 | B | |
| 1.118 | N-cyclopropyl-1-methyl-N-[[4-[5-(trifluoromethyl)-1,2,4-oxadiazol-3-yl]phenyl]methyl]-cyclopropane-carboxamide | 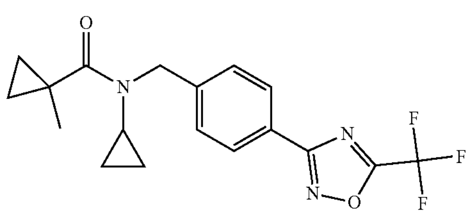 [SMILES: CC1(C(=O)N(Cc2ccc(-c3noc(C(F)(F)F)n3)cc2)C2CC2)CC1] | 1.86 | 366.2 | B | |
| 1.119 | N-cyclopropyl-N-[[4-[5-(trifluoromethyl)-1,2,4-oxadiazol-3-yl]phenyl]methyl]-propanamide | 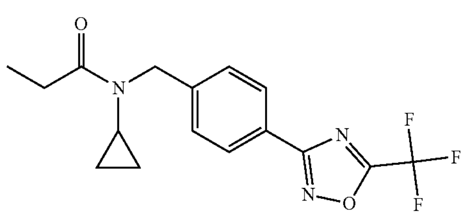 [SMILES: CCC(=O)N(Cc1ccc(-c2noc(C(F)(F)F)n2)cc1)C1CC1] | 1.79 | 340.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.120 | 2-chloro-N-cyclopropyl-N-[[4-[5-(trifluoromethyl)-1,2,4-oxadiazol-3-yl]phenyl]methyl]-benzamide | 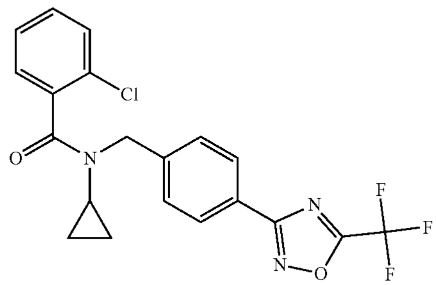 [SMILES: O=C(c1ccccc1Cl)N(Cc1ccc(-c2noc(C(F)(F)F)n2)cc1)C1CC1] | 1.99 | 422.2 | B | |
| 1.121 | N-cyclopropyl-2-phenyl-N-[[4-[5-(trifluoromethyl)-1,2,4-oxadiazol-3-yl]phenyl]methyl]-acetamide | 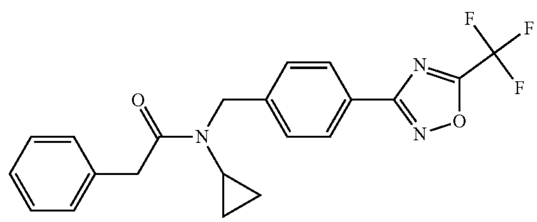 [SMILES: O=C(Cc1ccccc1)N(Cc1ccc(-c2noc(C(F)(F)F)n2)cc1)C1CC1] | 1.97 | 402.2 | B | |
| 1.122 | N-cyclopropyl-2-methyl-N-[[4-[5-(trifluoromethyl)-1,2,4-oxadiazol-3-yl]phenyl]methyl]prop-2-enamide | 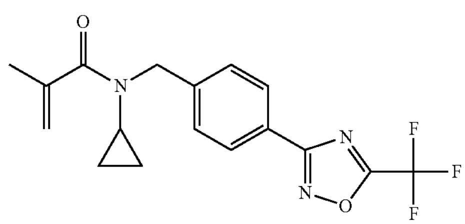 [SMILES: C=C(C)C(=O)N(Cc1ccc(-c2noc(C(F)(F)F)n2)cc1)C1CC1] | 1.82 | 352.2 | B | |
| 1.123 | N-cyclopropyl-N-[[4-[5-(trifluoromethyl)-1,2,4-oxadiazol-3-yl]phenyl]methyl]-tetrahydrothiopyran-4-carboxamide | 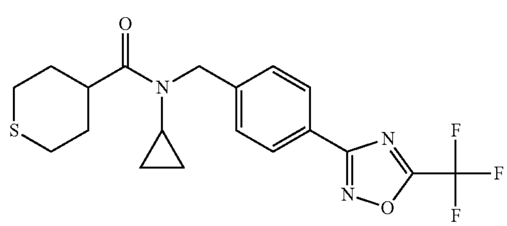 [SMILES: O=C(C1CCSCC1)N(Cc1ccc(-c2noc(C(F)(F)F)n2)cc1)C1CC1] | 1.91 | 412.2 | B | |
| 1.124 | N-cyclopropyl-2,2-dimethyl-N-[[4-[5-(trifluoromethyl)-1,2,4-oxadiazol-3-yl]phenyl]methyl]-cyclopropane-carboxamide | 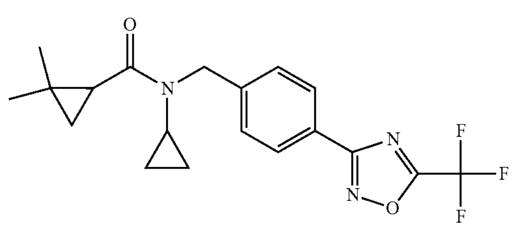 [SMILES: CC1(C)CC1C(=O)N(Cc1ccc(-c2noc(C(F)(F)F)n2)cc1)C1CC1] | 2.04 | 380.2 | B | |
| 1.125 | 2,2-dichloro-N-cyclopropyl-N-[[4-[5-(trifluoromethyl)-1,2,4-oxadiazol-3-yl]phenyl]methyl]-cyclopropane-carboxamide | 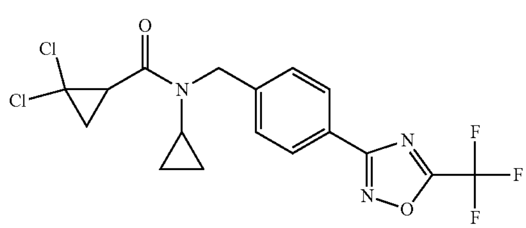 [SMILES: O=C(C1CC1(Cl)Cl)N(Cc1ccc(-c2noc(C(F)(F)F)n2)cc1)C1CC1] | 2.02 | 420.1 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.126 | N-cyclopropyl-2-methyl-N-[[4-[5-(trifluoromethyl)-1,2,4-oxadiazol-3-yl]phenyl]methyl]-butanamide | 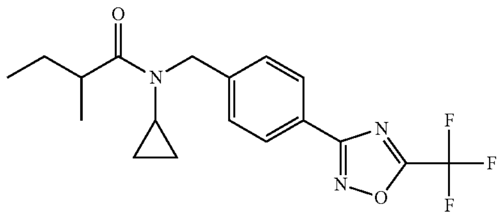 [SMILES: CCC(C)C(=O)N(Cc1ccc(-c2noc(C(F)(F)F)n2)cc1)C1CC1] | 1.98 | 368.2 | B | |
| 1.127 | 2-(4-chlorophenyl)-N-cyclopropyl-N-[[4-[5-(trifluoromethyl)-1,2,4-oxadiazol-3-yl]phenyl]methyl]-acetamide | 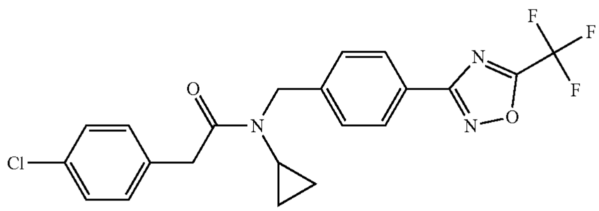 [SMILES: O=C(Cc1ccc(Cl)cc1)N(Cc1ccc(-c2noc(C(F)(F)F)n2)cc1)C1CC1] | 2.07 | 436.2 | B | |
| 1.128 | N-cyclopropyl-3-methyl-N-[[4-[5-(trifluoromethyl)-1,2,4-oxadiazol-3-yl]phenyl]methyl]-oxetane-3-carboxamide | 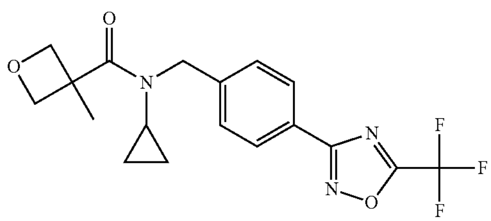 [SMILES: CC1(C(=O)N(Cc2ccc(-c3noc(C(F)(F)F)n3)cc2)C2CC2)COC1] | 1.64 | 382.2 | B | |
| 1.129 | N-cyclopropyl-3-fluoro-4-prop-2-ynoxy-N-[[4-[5-(trifluoromethyl)-1,2,4-oxadiazol-3-yl]phenyl]methyl]-benzamide | 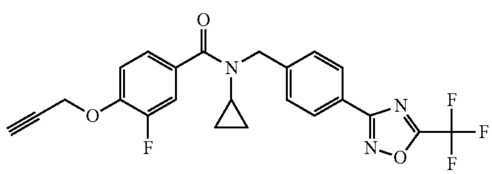 [SMILES: C#CCOc1ccc(C(=O)N(Cc2ccc(-c3noc(C(F)(F)F)n3)cc2)C2CC2)cc1F] | 1.92 | 460.2 | B | |
| 1.130 | 2-(4-cyanophenyl)-N-cyclopropyl-N-[[4-[5-(trifluoromethyl)-1,2,4-oxadiazol-3-yl]phenyl]methyl]-acetamide | 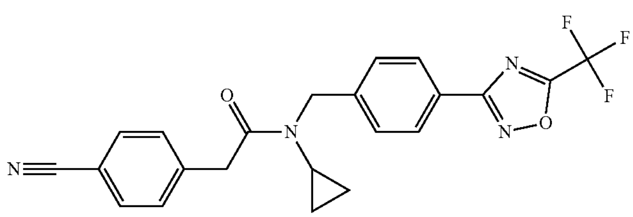 [SMILES: N#Cc1ccc(CC(=O)N(Cc2ccc(-c3noc(C(F)(F)F)n3)cc2)C2CC2)cc1] | 1.87 | 427.2 | B | |
| 1.131 | N-cyclopropyl-6,6,6-trifluoro-N-[[4-[5-(trifluoromethyl)-1,2,4-oxadiazol-3-yl]phenyl]methyl]-hexanamide | 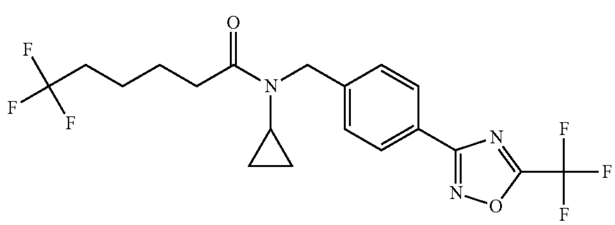 [SMILES: O=C(CCCCC(F)(F)F)N(Cc1ccc(-c2noc(C(F)(F)F)n2)cc1)C1CC1] | 2.02 | 436.2 | B | |
| 1.132 | N-[1-[cyclopropyl-[[4-[5-(trifluoromethyl)-1,2,4-oxadiazol-3-yl]phenyl]methyl]-carbamoyl]-2-methyl-propyl]-cyclopropane-carboxamide | 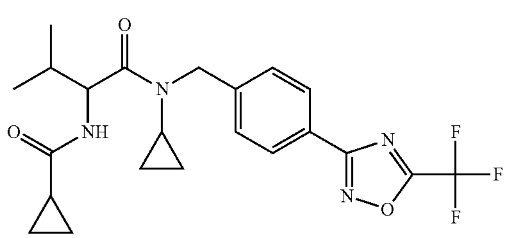 [SMILES: CC(C)C(NC(=O)C1CC1)C(=O)N(Cc1ccc(-c2noc(C(F)(F)F)n2)cc1)C1CC1] | 1.84 | 451.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.133 | 6-bromo-N-cyclopropyl-N-[[4-[5-(trifluoromethyl)-1,2,4-oxadiazol-3-yl]phenyl]methyl]-1,3-benzodioxole-5-carboxamide | 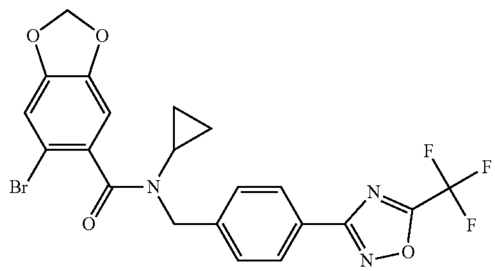 [SMILES: O=C(c1cc2c(cc1Br)OCO2)N(Cc1ccc(-c2noc(C(F)(F)F)n2)cc1)C1CC1] | 1.98 | 510.1 | B | |
| 1.134 | N-cyclopropyl-2-(methoxymethyl)-N-[[4-[5-(trifluoromethyl)-1,2,4-oxadiazol-3-yl]phenyl]methyl]-butanamide | 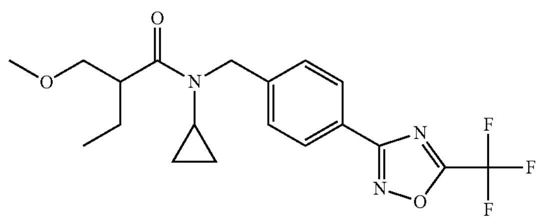 [SMILES: CCC(COC)C(=O)N(Cc1ccc(-c2noc(C(F)(F)F)n2)cc1)C1CC1] | 1.95 | 398.3 | B | |
| 1.135 | N-cyclopropyl-2-ethyl-2-methyl-N-[[4-[5-(trifluoromethyl)-1,2,4-oxadiazol-3-yl]phenyl]methyl]-butanamide | 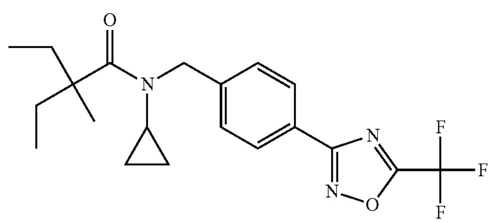 [SMILES: CCC(C)(CC)C(=O)N(Cc1ccc(-c2noc(C(F)(F)F)n2)cc1)C1CC1] | 2.17 | 396.3 | B | |
| 1.136 | N-cyclopropyl-4-methoxy-N-[[4-[5-(trifluoromethyl)-1,2,4-oxadiazol-3-yl]phenyl]methyl]-butanamide | 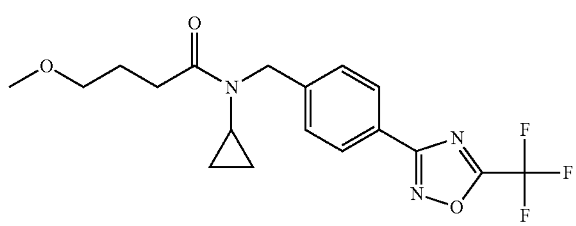 [SMILES: COCCCC(=O)N(Cc1ccc(-c2noc(C(F)(F)F)n2)cc1)C1CC1] | 1.77 | 384.2 | B | |
| 1.137 | N-cyclopropyl-2-(ethylsulfonylamino)-N-[[4-[5-(trifluoromethyl)-1,2,4-oxadiazol-3-yl]phenyl]methyl]pent-4-ynamide | 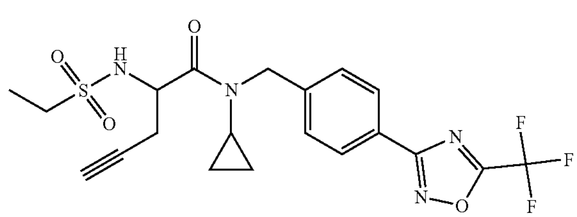 [SMILES: C#CCC(NS(=O)(=O)CC)C(=O)N(Cc1ccc(-c2noc(C(F)(F)F)n2)cc1)C1CC1] | 1.72 | 471.2 | B | |
| 1.138 | N-cyclopropyl-2-(2,2-difluorocyclopropyl)-N-[[4-[5-(trifluoromethyl)-1,2,4-oxadiazol-3-yl]phenyl]methyl]-acetamide | 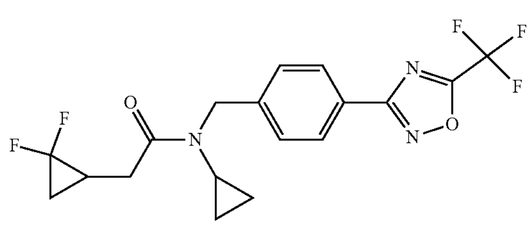 [SMILES: O=C(CC1CC1(F)F)N(Cc1ccc(-c2noc(C(F)(F)F)n2)cc1)C1CC1] | 1.88 | 402.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.139 | N-cyclopropyl-N-[[4-[5-(trifluoromethyl)-1,2,4-oxadiazol-3-yl]phenyl]methyl]-1,2,3-benzothiadiazole-7-carboxamide | 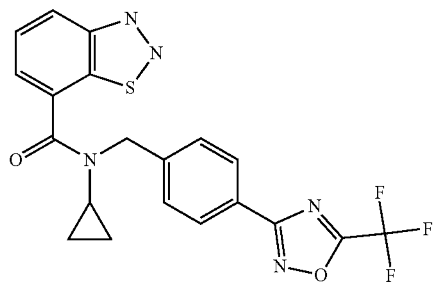 [SMILES: O=C(c1cccc2c1SNN2)N(Cc1ccc(-c2noc(C(F)(F)F)n2)cc1)C1CC1] | 1.95 | 446.2 | B | |
| 1.140 | N-cyclopropyl-N-[[4-[5-(trifluoromethyl)-1,2,4-oxadiazol-3-yl]phenyl]methyl]-2-[4-(trifluoromethyl)-phenyl]acetamide | 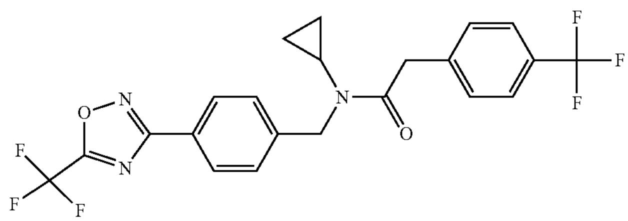 [SMILES: O=C(Cc1ccc(C(F)(F)F)cc1)N(Cc1ccc(-c2noc(C(F)(F)F)n2)cc1)C1CC1] | 2.1 | 470.2 | B | |
| 1.141 | 2-(4-chlorophenyl)-N-cyclopropyl-2-prop-2-ynoxy-N-[[4-[5-(trifluoromethyl)-1,2,4-oxadiazol-3-yl]phenyl]methyl]-acetamide | 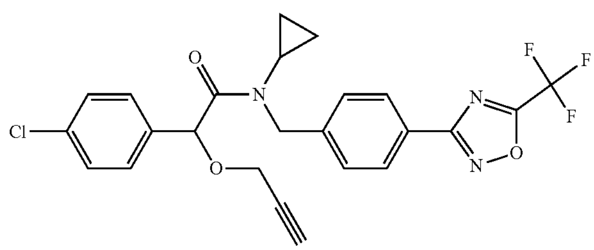 [SMILES: C#CCOC(C(=O)N(Cc1ccc(-c2noc(C(F)(F)F)n2)cc1)C1CC1)c1ccc(Cl)cc1] | 2.05 | 490.2 | B | |
| 1.142 | 4-chloro-N-cyclopropyl-N-[[4-[5-(trifluoromethyl)-1,2,4-oxadiazol-3-yl]phenyl]methyl]-benzamide | 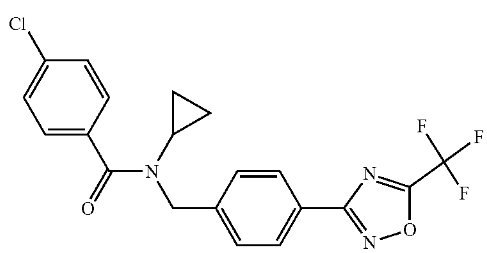 [SMILES: O=C(c1ccc(Cl)cc1)N(Cc1ccc(-c2noc(C(F)(F)F)n2)cc1)C1CC1] | 2.03 | 422.2 | B | |
| 1.143 | N-cyclopropyl-1-(4-methoxyphenyl)-N-[[4-[5-(trifluoromethyl)-1,2,4-oxadiazol-3-yl]phenyl]methyl]-cyclopropane-carboxamide | 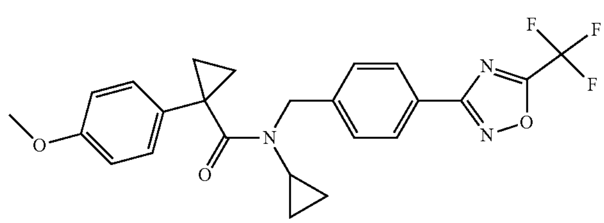 [SMILES: COc1ccc(C2(C(=O)N(Cc3ccc(-c4noc(C(F)(F)F)n4)cc3)C3CC3)CC2)cc1] | 2.05 | 458.3 | B | |
| 1.144 | prop-2-ynyl N-[1-[cyclopropyl-[[4-[5-(trifluoromethyl)-1,2,4-oxadiazol-3-yl]phenyl]methyl]-carbamoyl]-2-methyl-propyl]carbamate | 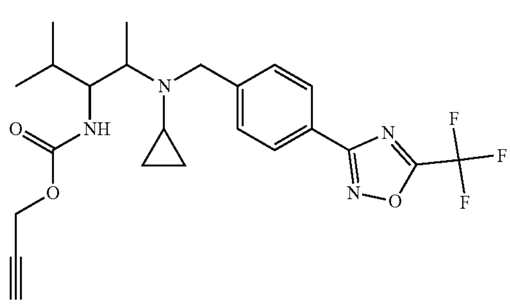 [SMILES: C#CCOC(=O)NC(C(C)C)C(C)N(Cc1ccc(-c2noc(C(F)(F)F)n2)cc1)C1CC1] | 1.91 | 465.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.145 | N-cyclopropyl-N-[[4-[5-(trifluoromethyl)-1,2,4-oxadiazol-3-yl]phenyl]methyl]-tetrahydrofuran-2-carboxamide | 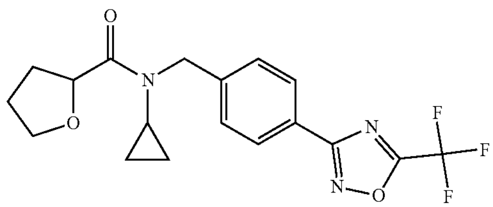 [SMILES: O=C(C1CCCO1)N(Cc1ccc(-c2noc(C(F)(F)F)n2)cc1)C1CC1] | 1.71 | 382.2 | B | |
| 1.146 | 2-cyano-N-cyclopropyl-N-[[4-[5-(trifluoromethyl)-1,2,4-oxadiazol-3-yl]phenyl]methyl]-acetamide | 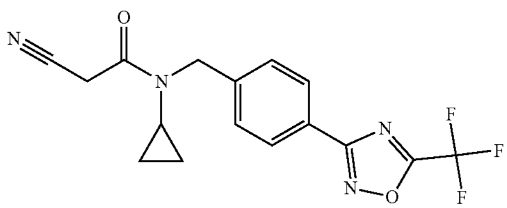 [SMILES: N#CCC(=O)N(Cc1ccc(-c2noc(C(F)(F)F)n2)cc1)C1CC1] | 1.62 | 351.2 | B | |
| 1.147 | N-cyclopropyl-2-methoxy-N-[[4-[5-(trifluoromethyl)-1,2,4-oxadiazol-3-yl]phenyl]methyl]-propanamide | 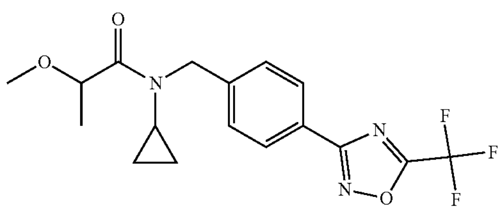 [SMILES: COC(C)C(=O)N(Cc1ccc(-c2noc(C(F)(F)F)n2)cc1)C1CC1] | 1.68 | 370.2 | B | |
| 1.148 | N-cyclopropyl-3-(trifluoromethyl)-N-[[4-[5-(trifluoromethyl)-1,2,4-oxadiazol-3-yl]phenyl]methyl]-pentanamide | 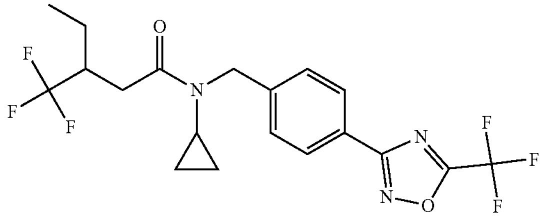 [SMILES: CCC(CC(=O)N(Cc1ccc(-c2noc(C(F)(F)F)n2)cc1)C1CC1)C(F)(F)F] | 2.12 | 436.2 | B | |
| 1.149 | N-cyclopropyl-N-[[4-[5-(trifluoromethyl)-1,2,4-oxadiazol-3-yl]phenyl]methyl]-cyclopropane-carboxamide | 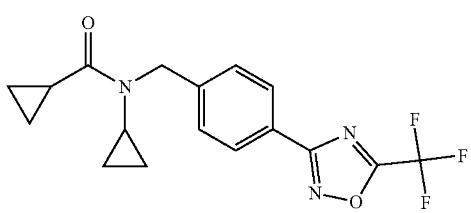 [SMILES: O=C(C1CC1)N(Cc1ccc(-c2noc(C(F)(F)F)n2)cc1)C1CC1] | 1.83 | 352.2 | B | |
| 1.150 | N-cyclopropyl-N-[[4-[5-(trifluoromethyl)-1,2,4-oxadiazol-3-yl]phenyl]methyl]-benzamide | 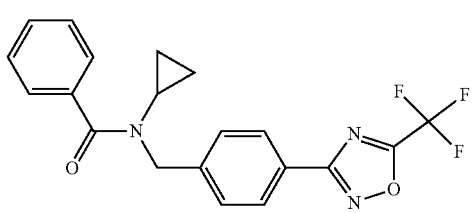 [SMILES: O=C(c1ccccc1)N(Cc1ccc(-c2noc(C(F)(F)F)n2)cc1)C1CC1] | 1.91 | 388.2 | B | |
| 1.151 | N-prop-2-ynyl-1-(trifluoromethyl)-N-[[4-[5-(trifluoromethyl)-1,2,4-oxadiazol-3-yl]phenyl]methyl]-cyclopropane-carboxamide | 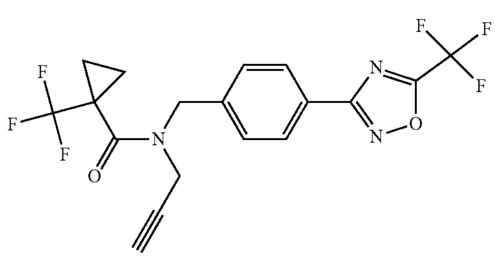 [SMILES: C#CCN(Cc1ccc(-c2noc(C(F)(F)F)n2)cc1)C(=O)C1(C(F)(F)F)CC1] | 1.9 | 418.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.152 | 2-cyclopentyl-N-prop-2-ynyl-N-[[4-[5-(trifluoromethyl)-1,2,4-oxadiazol-3-yl]phenyl]methyl]-acetamide | 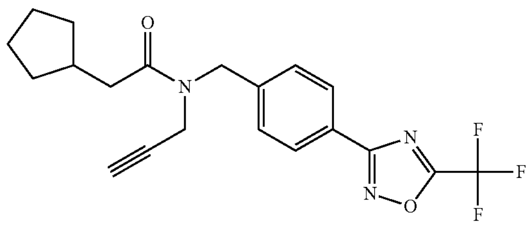 [SMILES: C#CCN(Cc1ccc(-c2noc(C(F)(F)F)n2)cc1)C(=O)CC1CCCC1] | 2.01 | 392.2 | B | |
| 1.153 | 2,2-dimethyl-N-prop-2-ynyl-N-[[4-[5-(trifluoromethyl)-1,2,4-oxadiazol-3-yl]phenyl]methyl]-pentanamide | 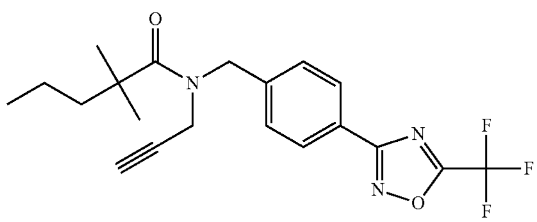 [SMILES: C#CCN(Cc1ccc(-c2noc(C(F)(F)F)n2)cc1)C(=O)C(C)(C)CCC] | 2.11 | 394.3 | B | |
| 1.154 | N-prop-2-ynyl-N-[[4-[5-(trifluoromethyl)-1,2,4-oxadiazol-3-yl]phenyl]methyl]-pent-4-ynamide | 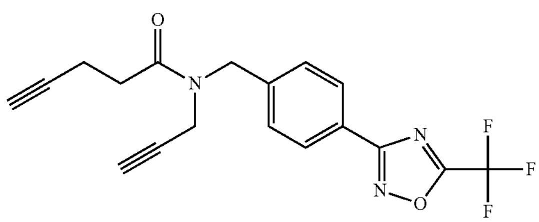 [SMILES: C#CCCC(=O)N(CC#C)Cc1ccc(-c2noc(C(F)(F)F)n2)cc1] | 1.72 | 362.2 | B | |
| 1.155 | 2-methyl-N-prop-2-ynyl-N-[[4-[5-(trifluoromethyl)-1,2,4-oxadiazol-3-yl]phenyl]methyl]-propanamide | 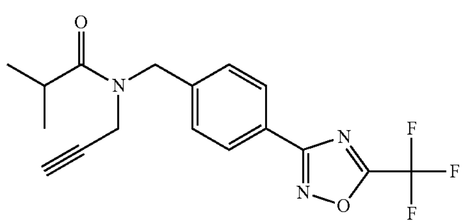 [SMILES: C#CCN(Cc1ccc(-c2noc(C(F)(F)F)n2)cc1)C(=O)C(C)C] | 1.79 | 352.2 | B | |
| 1.156 | N-isopropyl-2-methoxy-N-[2-[4-[5-(trifluoromethyl)-1,2,4-oxadiazol-3-yl]phenyl]ethyl]-acetamide | 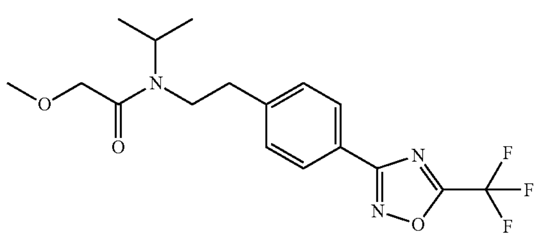 [SMILES: COCC(=O)N(CCc1ccc(-c2noc(C(F)(F)F)n2)cc1)C(C)C] | 1.08 | 272 | A | |
| 1.157 | 2,2-difluoro-N-prop-2-ynyl-N-[[4-[5-(trifluoromethyl)-1,2,4-oxadiazol-3-yl]phenyl]methyl]-cyclopropane-carboxamide | 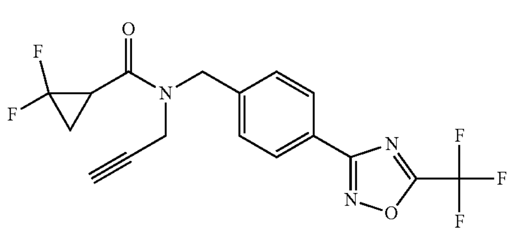 [SMILES: C#CCN(Cc1ccc(-c2noc(C(F)(F)F)n2)cc1)C(=O)C1CC1(F)F] | 1.77 | 386.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.158 | N-prop-2-ynyl-N-[[4-[5-(trifluoromethyl)-1,2,4-oxadiazol-3-yl]phenyl]methyl]-cyclohexane-carboxamide | 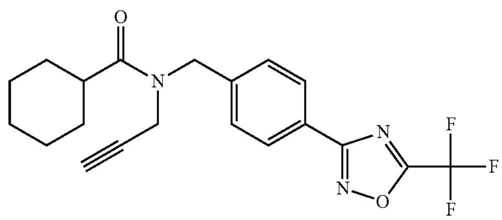 [SMILES: C#CCN(Cc1ccc(-c2noc(C(F)(F)F)n2)cc1)C(=O)C1CCCCC1] | 1.99 | 392.2 | B | |
| 1.159 | N-prop-2-ynyl-N-[[4-[5-(trifluoromethyl)-1,2,4-oxadiazol-3-yl]phenyl]methyl]-pent-4-enamide | 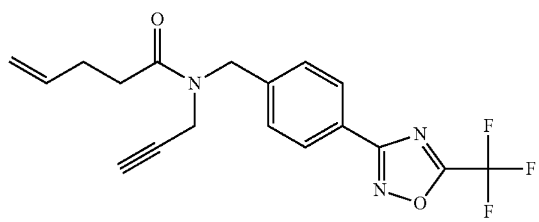 [SMILES: C#CCN(Cc1ccc(-c2noc(C(F)(F)F)n2)cc1)C(=O)CCC=C] | 1.83 | 364.2 | B | |
| 1.160 | 3-(4-chlorophenyl)-N-prop-2-ynyl-N-[[4-[5-(trifluoromethyl)-1,2,4-oxadiazol-3-yl]phenyl]methyl]-propanamide | 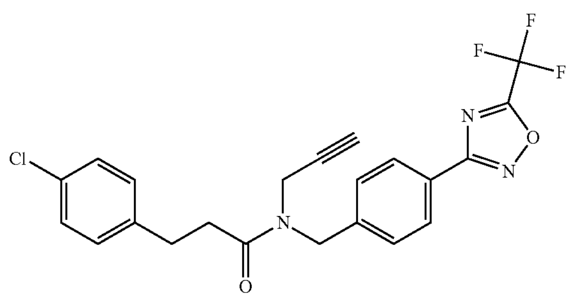 [SMILES: C#CCN(Cc1ccc(-c2noc(C(F)(F)F)n2)cc1)C(=O)CCc1ccc(Cl)cc1] | 2.04 | 448.2 | B | |
| 1.161 | N-prop-2-ynyl-1-(trifluoromethyl)-N-[[4-[5-(trifluoromethyl)-1,2,4-oxadiazol-3-yl]phenyl]methyl]-cyclobutane-carboxamide | 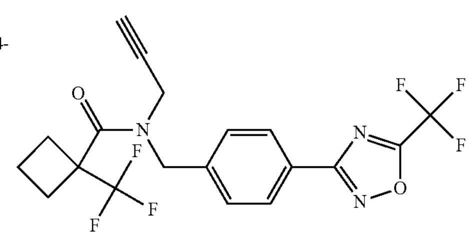 | 2.01 | 432.2 | B | |
| 1.162 | N-prop-2-ynyl-N-[[4-[5-(trifluoromethyl)-1,2,4-oxadiazol-3-yl]phenyl]methyl]-hexanamide | 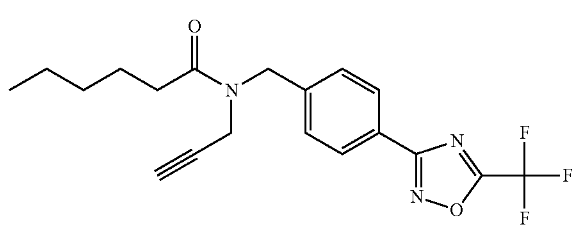 [SMILES: C#CCN(Cc1ccc(-c2noc(C(F)(F)F)n2)cc1)C(=O)CCCCC] | 2 | 380.2 | B | |
| 1.163 | 2-(2-chlorophenyl)-N-prop-2-ynyl-N-[[4-[5-(trifluoromethyl)-1,2,4-oxadiazol-3-yl]phenyl]methyl]-acetamide | 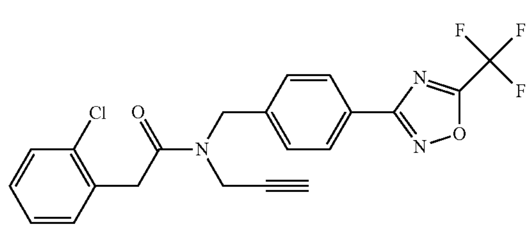 [SMILES: C#CCN(Cc1ccc(-c2noc(C(F)(F)F)n2)cc1)C(=O)Cc1ccccc1Cl] | 1.96 | 434.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.164 | 2-methyl-4-oxo-N-prop-2-ynyl-N-[[4-[5-(trifluoromethyl)-1,2,4-oxadiazol-3-yl]phenyl]methyl]-pentanamide | 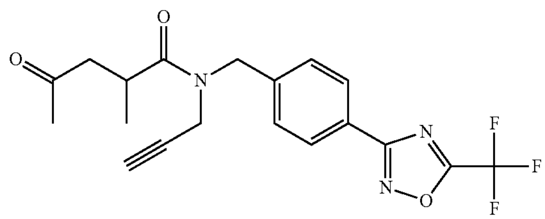 [SMILES: C#CCN(Cc1ccc(-c2noc(C(F)(F)F)n2)cc1)C(=O)C(C)CC(C)=O] | 1.7 | 394.2 | B | |
| 1.165 | N-prop-2-ynyl-N-[[4-[5-(trifluoromethyl)-1,2,4-oxadiazol-3-yl]phenyl]methyl]-butanamide | 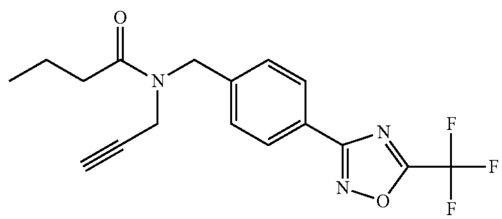 [SMILES: C#CCN(Cc1ccc(-c2noc(C(F)(F)F)n2)cc1)C(=O)CCC] | 1.8 | 352.2 | B | |
| 1.166 | 2-phenyl-N-prop-2-ynyl-N-[[4-[5-(trifluoromethyl)-1,2,4-oxadiazol-3-yl]phenyl]methyl]-cyclopropane-carboxamide | 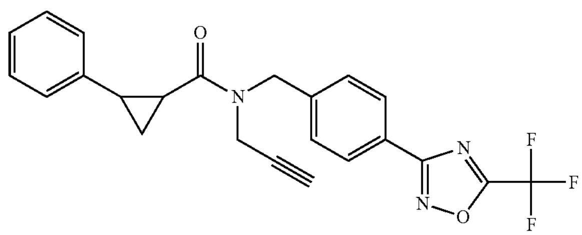 [SMILES: C#CCN(Cc1ccc(-c2noc(C(F)(F)F)n2)cc1)C(=O)C1CC1c1ccccc1] | 1.98 | 426.2 | B | |
| 1.167 | 2-cyclopropyl-N-prop-2-ynyl-N-[[4-[5-(trifluoromethyl)-1,2,4-oxadiazol-3-yl]phenyl]methyl]-acetamide | 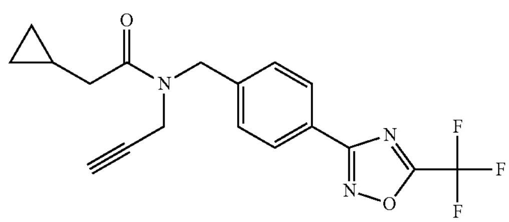 [SMILES: C#CCN(Cc1ccc(-c2noc(C(F)(F)F)n2)cc1)C(=O)CC1CC1] | 1.79 | 364.2 | B | |
| 1.168 | N-prop-2-ynyl-N-[[4-[5-(trifluoromethyl)-1,2,4-oxadiazol-3-yl]phenyl]methyl]-cyclopentane-carboxamide | 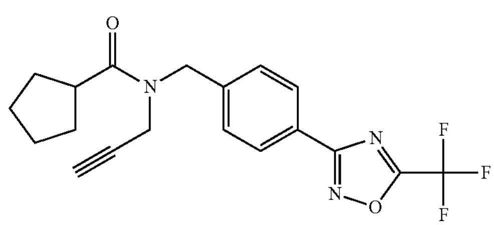 [SMILES: C#CCN(Cc1ccc(-c2noc(C(F)(F)F)n2)cc1)C(=O)C1CCCC1] | 1.93 | 378.2 | B | |
| 1.169 | 4,4,4-trifluoro-N-prop-2-ynyl-N-[[4-[5-(trifluoromethyl)-1,2,4-oxadiazol-3-yl]phenyl]methyl]-butanamide | 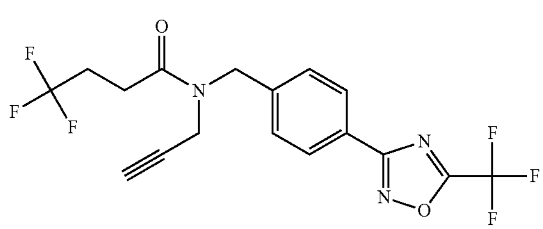 [SMILES: C#CCN(Cc1ccc(-c2noc(C(F)(F)F)n2)cc1)C(=O)CCC(F)(F)F] | 1.85 | 406.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.170 | N-prop-2-ynyl-2-(3-pyridyl)-N-[[4-[5-(trifluoromethyl)-1,2,4-oxadiazol-3-yl]phenyl]methyl]-acetamide | 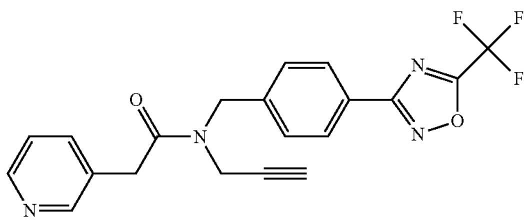 [SMILES: C#CCN(Cc1ccc(-c2noc(C(F)(F)F)n2)cc1)C(=O)Cc1cccnc1] | 1.26 | 401.2 | B | |
| 1.171 | N-prop-2-ynyl-N-[[4-[5-(trifluoromethyl)-1,2,4-oxadiazol-3-yl]phenyl]methyl]-tetrahydrofuran-3-carboxamide | 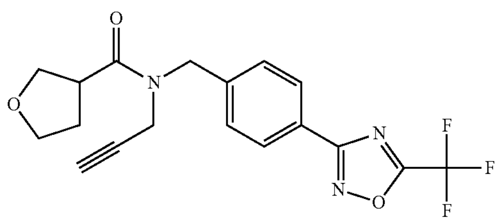 [SMILES: C#CCN(Cc1ccc(-c2noc(C(F)(F)F)n2)cc1)C(=O)C1CCOC1] | 1.61 | 380.2 | B | |
| 1.172 | N-prop-2-ynyl-N-[[4-[5-(trifluoromethyl)-1,2,4-oxadiazol-3-yl]phenyl]methyl]-thietane-3-carboxamide | 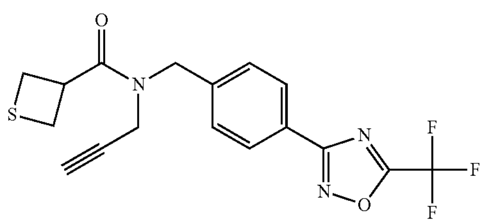 [SMILES: C#CCN(Cc1ccc(-c2noc(C(F)(F)F)n2)cc1)C(=O)C1CSC1] | 1.78 | 382.2 | B | |
| 1.173 | 3-methoxy-N-prop-2-ynyl-N-[[4-[5-(trifluoromethyl)-1,2,4-oxadiazol-3-yl]phenyl]methyl]-propanamide | 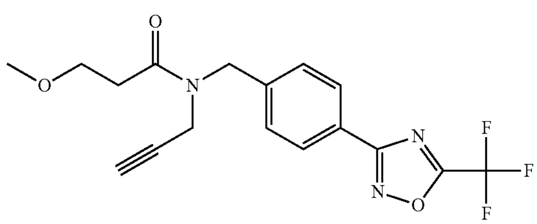 [SMILES: C#CCN(Cc1ccc(-c2noc(C(F)(F)F)n2)cc1)C(=O)CCOC] | 1.64 | 368.2 | B | |
| 1.174 | 2,2-dichloro-1-methyl-N-prop-2-ynyl-N-[[4-[5-(trifluoromethyl)-1,2,4-oxadiazol-3-yl]phenyl]methyl]-cyclopropane-carboxamide | 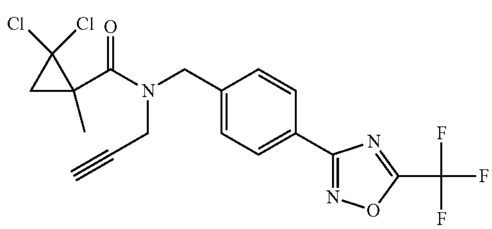 [SMILES: C#CCN(Cc1ccc(-c2noc(C(F)(F)F)n2)cc1)C(=O)C1(C)CC1(Cl)Cl] | 2.02 | 432.1 | B | |
| 1.175 | 3-methyl-N-prop-2-ynyl-N-[[4-[5-(trifluoromethyl)-1,2,4-oxadiazol-3-yl]phenyl]methyl]-butanamide | 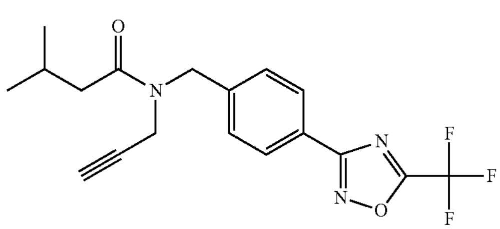 [SMILES: C#CCN(Cc1ccc(-c2noc(C(F)(F)F)n2)cc1)C(=O)CC(C)C] | 1.89 | 366.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.176 | 3-chloro-2,2-dimethyl-N-prop-2-ynyl-N-[[4-[5-(trifluoromethyl)-1,2,4-oxadiazol-3-yl]phenyl]methyl]-propanamide | 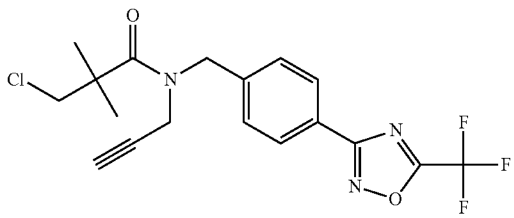 [SMILES: C#CCN(Cc1ccc(-c2noc(C(F)(F)F)n2)cc1)C(=O)C(C)(C)CCl] | 1.93 | 400.2 | B | |
| 1.177 | 3,3,3-trifluoro-N-prop-2-ynyl-N-[[4-[5-(trifluoromethyl)-1,2,4-oxadiazol-3-yl]phenyl]methyl]-propanamide | 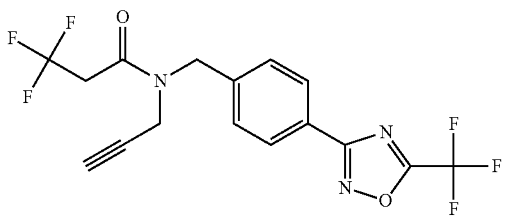 [SMILES: C#CCN(Cc1ccc(-c2noc(C(F)(F)F)n2)cc1)C(=O)CC(F)(F)F] | 1.76 | 392.2 | B | |
| 1.178 | N-prop-2-ynyl-N-[[4-[5-(trifluoromethyl)-1,2,4-oxadiazol-3-yl]phenyl]methyl]-cyclobutane-carboxamide | 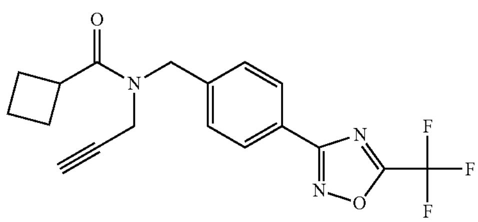 [SMILES: C#CCN(Cc1ccc(-c2noc(C(F)(F)F)n2)cc1)C(=O)C1CCC1] | 1.85 | 364.2 | B | |
| 1.179 | 2-(2-methoxyphenyl)-N-prop-2-ynyl-N-[[4-[5-(trifluoromethyl)-1,2,4-oxadiazol-3-yl]phenyl]methyl]-acetamide | 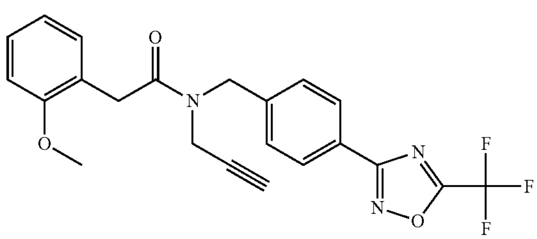 [SMILES: C#CCN(Cc1ccc(-c2noc(C(F)(F)F)n2)cc1)C(=O)Cc1ccccc1OC] | 1.91 | 430.2 | B | |
| 1.180 | N-prop-2-ynyl-N-[[4-[5-(trifluoromethyl)-1,2,4-oxadiazol-3-yl]phenyl]methyl]-pent-3-enamide | 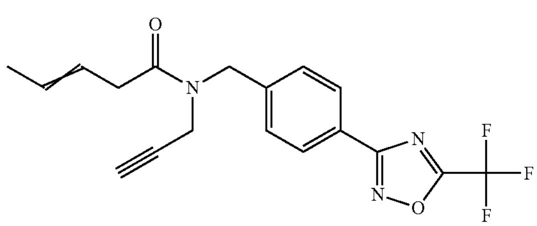 [SMILES: C#CCN(Cc1ccc(-c2noc(C(F)(F)F)n2)cc1)C(=O)CC=CC] | 1.83 | 364.2 | B | |
| 1.181 | 2-methyl-N-prop-2-ynyl-N-[[4-[5-(trifluoromethyl)-1,2,4-oxadiazol-3-yl]phenyl]methyl]-cyclopropane-carboxamide | 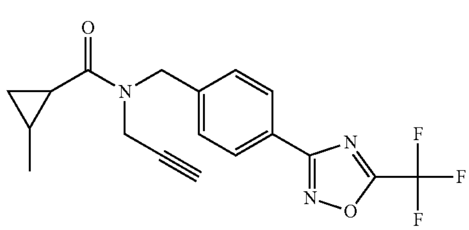 [SMILES: C#CCN(Cc1ccc(-c2noc(C(F)(F)F)n2)cc1)C(=O)C1CC1C] | 1.82 | 364.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.182 | 2,2-dimethyl-N-prop-2-ynyl-N-[[4-[5-(trifluoromethyl)-1,2,4-oxadiazol-3-yl]phenyl]methyl]-propanamide | 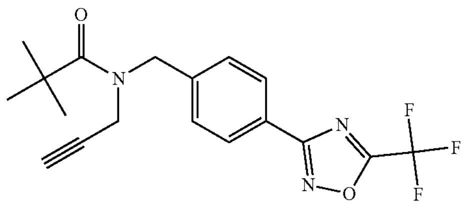 [SMILES: C#CCN(Cc1ccc(-c2noc(C(F)(F)F)n2)cc1)C(=O)C(C)(C)C] | 1.92 | 366.2 | B | |
| 1.183 | 1-methyl-N-prop-2-ynyl-N-[[4-[5-(trifluoromethyl)-1,2,4-oxadiazol-3-yl]phenyl]methyl]-cyclopropane-carboxamide | 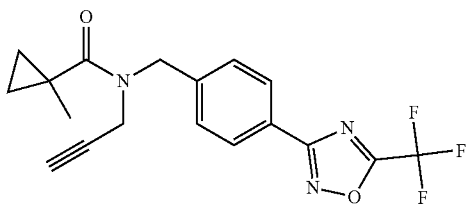 [SMILES: C#CCN(Cc1ccc(-c2noc(C(F)(F)F)n2)cc1)C(=O)C1(C)CC1] | 1.8 | 364.2 | B | |
| 1.184 | 5-chloro-2-hydroxy-N-prop-2-ynyl-N-[[4-(5-(trifluoromethyl)-1,2,4-oxadiazol-3-yl]phenyl]methyl]-benzamide | 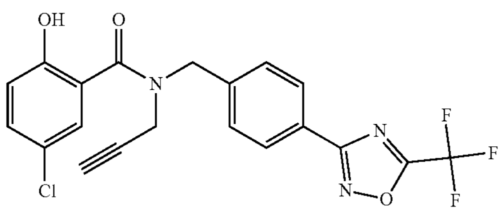 [SMILES: C#CCN(Cc1ccc(-c2noc(C(F)(F)F)n2)cc1)C(=O)c1cc(Cl)ccc1O] | 1.8 | 436.2 | B | |
| 1.185 | N-prop-2-ynyl-N-[[4-[5-(trifluoromethyl)-1,2,4-oxadiazol-3-yl]phenyl]methyl]-propanamide | 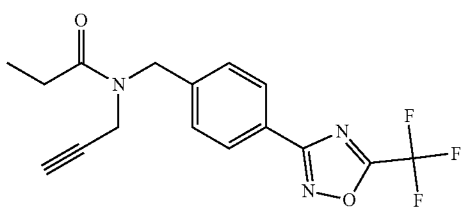 [SMILES: C#CCN(Cc1ccc(-c2noc(C(F)(F)F)n2)cc1)C(=O)CC] | 1.7 | 338.2 | B | |
| 1.186 | 2-phenyl-N-prop-2-ynyl-N-[[4-[5-(trifluoromethyl)-1,2,4-oxadiazol-3-yl]phenyl]methyl]-acetamide | 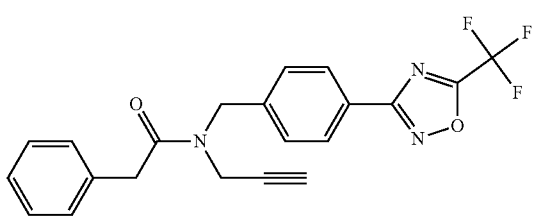 [SMILES: C#CCN(Cc1ccc(-c2noc(C(F)(F)F)n2)cc1)C(=O)Cc1ccccc1] | 1.88 | 400.2 | B | |
| 1.187 | 2-methyl-N-prop-2-ynyl-N-[[4-[5-(trifluoromethyl)-1,2,4-oxadiazol-3-yl]phenyl]methyl]-prop-2-enamide | 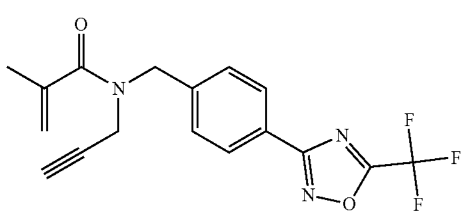 [SMILES: C#CCN(Cc1ccc(-c2noc(C(F)(F)F)n2)cc1)C(=O)C(=C)C] | 1.76 | 350.2 | B | |
| 1.188 | N-prop-2-ynyl-N-[[4-[5-(trifluoromethyl)-1,2,4-oxadiazol-3-yl]phenyl]methyl]-tetrahydrothiopyran-4-carboxamide | 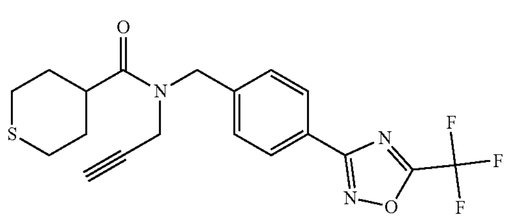 [SMILES: C#CCN(Cc1ccc(-c2noc(C(F)(F)F)n2)cc1)C(=O)C1CCSCC1] | 1.82 | 410.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.189 | 2,2-dimethyl-N-prop-2-ynyl-N-[[4-[5-(trifluoromethyl)-1,2,4-oxadiazol-3-yl]phenyl]methyl]-cyclopropane-carboxamide | 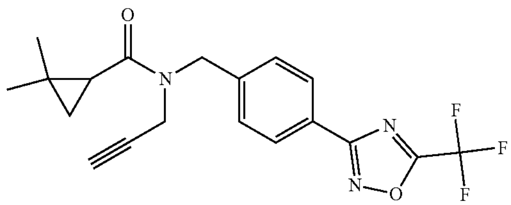 [SMILES: C#CCN(Cc1ccc(-c2noc(C(F)(F)F)n2)cc1)C(=O)C1CC1(C)C] | 1.93 | 378.2 | B | |
| 1.190 | 2,2-dichloro-N-prop-2-ynyl-N-[[4-[5-(trifluoromethyl)-1,2,4-oxadiazol-3-yl]phenyl]methyl]-cyclopropane-carboxamide | 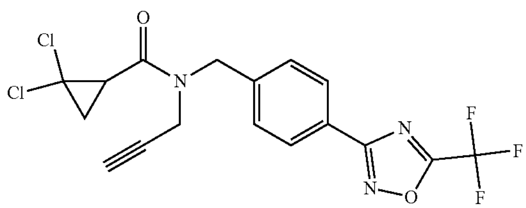 [SMILES: C#CCN(Cc1ccc(-c2noc(C(F)(F)F)n2)cc1)C(=O)C1CC1(Cl)Cl] | 1.92 | 418.1 | B | |
| 1.191 | 2-methyl-N-prop-2-ynyl-N-[[4-[5-(trifluoromethyl)-1,2,4-oxadiazol-3-yl]phenyl]methy]-butanamide | 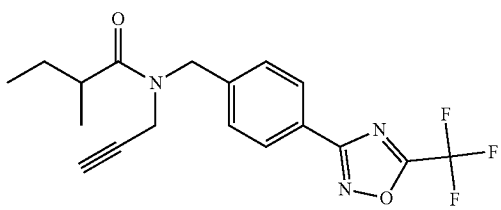 [SMILES: C#CCN(Cc1ccc(-c2noc(C(F)(F)F)n2)cc1)C(=O)C(C)CC] | 1.88 | 366.3 | B | |
| 1.192 | 3-methyl-N-prop-2-ynyl-N-[[4-[5-(trifluoromethyl)-1,2,4-oxadiazol-3-yl]phenyl]methyl]-oxetane-3-carboxamide | 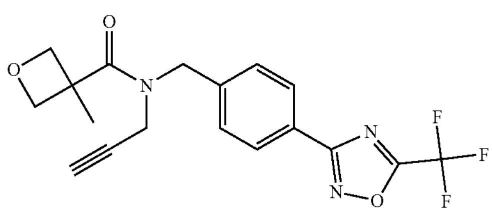 [SMILES: C#CCN(Cc1ccc(-c2noc(C(F)(F)F)n2)cc1)C(=O)C1(C)COC1] | 1.63 | 380.2 | B | |
| 1.193 | 2-(4-cyanophenyl)-N-prop-2-ynyl-N-[[4-[5-(trifluoromethyl)-1,2,4-oxadiazol-3-yl]phenyl]methyl]-acetamide | 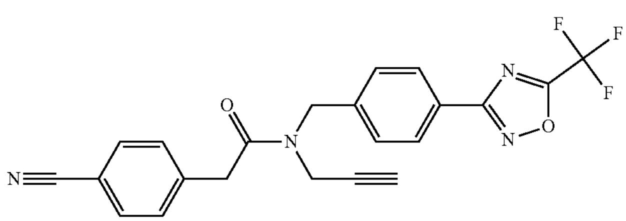 [SMILES: C#CCN(Cc1ccc(-c2noc(C(F)(F)F)n2)cc1)C(=O)Cc1ccc(C#N)cc1] | 1.79 | 425.2 | B | |
| 1.194 | 2-(methoxymethyl)-N-prop-2-ynyl-N-[[4-[5-(trifluoromethyl)-1,2,4-oxadiazol-3-yl]phenyl]methyl]-butanamide | 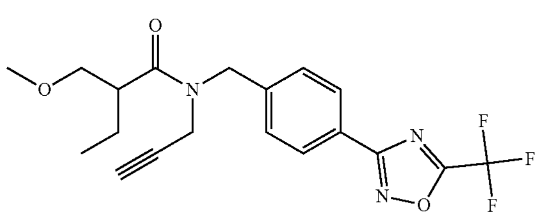 [SMILES: C#CCN(Cc1ccc(-c2noc(C(F)(F)F)n2)cc1)C(=O)C(CC)COC] | 1.86 | 396.3 | B | |
| 1.195 | 2-ethyl-2-methyl-N-prop-2-ynyl-N-[[4-[5-(trifluoromethyl)-1,2,4-oxadiazol-3-yl]phenyl]methyl]-butanamide | 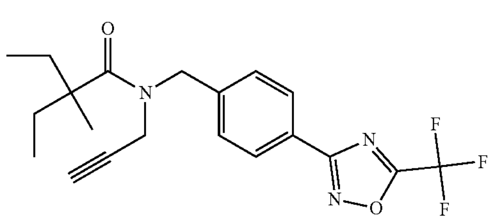 [SMILES: C#CCN(Cc1ccc(-c2noc(C(F)(F)F)n2)cc1)C(=O)C(C)(CC)CC] | 2.1 | 394.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.196 | 4-methoxy-N-prop-2-ynyl-N-[[4-[5-(trifluoromethyl)-1,2,4-oxadiazol-3-yl]phenyl]methyl]-butanamide | 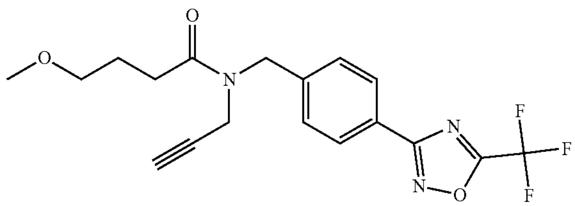 [SMILES: C#CCN(Cc1ccc(-c2noc(C(F)(F)F)n2)cc1)C(=O)CCCOC] | 1.69 | 382.2 | B | |
| 1.197 | 2-(2,2-difluorocyclopropyl)-N-prop-2-ynyl-N-[[4-[5-(trifluoromethyl)-1,2,4-oxadiazol-3-yl]phenyl]methyl]-acetamide | 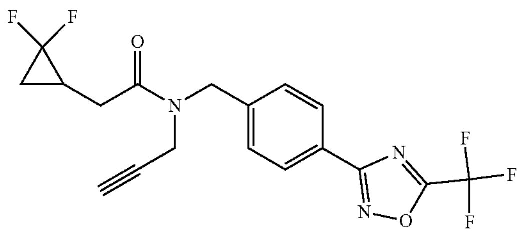 [SMILES: C#CCN(Cc1ccc(-c2noc(C(F)(F)F)n2)cc1)C(=O)CC1CC1(F)F] | 1.79 | 400.2 | B | |
| 1.198 | prop-2-ynyl N-[2-methyl-1-[prop-2-ynyl-[[4-[5-(trifluoromethyl)-1,2,4-oxadiazol-3-yl]phenyl]methyl]-carbamoyl]propyl]-carbamate | 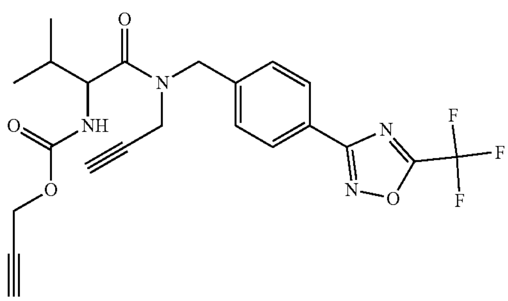 [SMILES: C#CCOC(=O)NC(C(=O)N(CC#C)Cc1ccc(-c2noc(C(F)(F)F)n2)cc1)C(C)C] | 1.84 | 463.3 | B | |
| 1.199 | 2-cyano-N-prop-2-ynyl-N-[[4-[5-(trifluoromethyl)-1,2,4-oxadiazol-3-yl]phenyl]methyl]-acetamide | 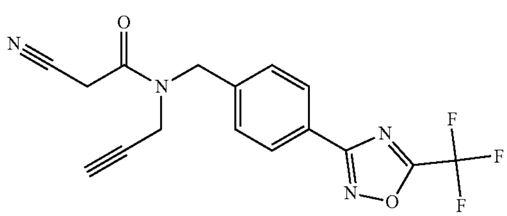 [SMILES: C#CCN(Cc1ccc(-c2noc(C(F)(F)F)n2)cc1)C(=O)CC#N] | 1.55 | 349.2 | B | |
| 1.200 | 2-methoxy-N-prop-2-ynyl-N-[[4-[5-(trifluoromethyl)-1,2,4-oxadiazol-3-yl]phenyl]methyl]-propanamide | 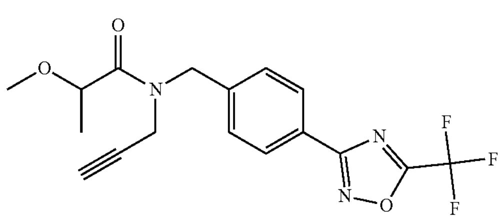 [SMILES: C#CCN(Cc1ccc(-c2noc(C(F)(F)F)n2)cc1)C(=O)C(C)OC] | 1.67 | 368.2 | B | |
| 1.201 | N-prop-2-ynyl-N-[[4-[5-(trifluoromethyl)-1,2,4-oxadiazol-3-yl]phenyl]methyl]-cyclopropane-carboxamide | 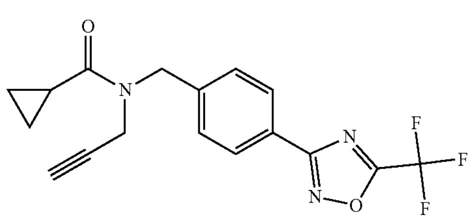 [SMILES: C#CCN(Cc1ccc(-c2noc(C(F)(F)F)n2)cc1)C(=O)C1CC1] | 1.73 | 350.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.202 | N-prop-2-ynyl-N-[[4-[5-(trifluoromethyl)-1,2,4-oxadiazol-3-yl]phenyl]methyl]-benzamide | 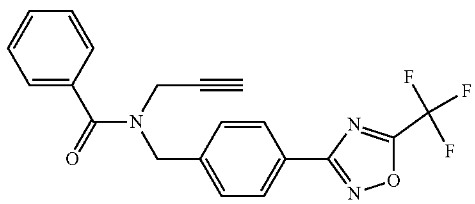 [SMILES: C#CCN(Cc1ccc(-c2noc(C(F)(F)F)n2)cc1)C(=O)c1ccccc1] | 1.85 | 386.2 | B | |
| 1.203 | N-(cyclopropylmethyl)-1-(trifluoromethyl)-N-[[4-[5-(trifluoromethyl)-1,2,4-oxadiazol-3-yl]phenyl]methyl]-cyclopropane-carboxamide | 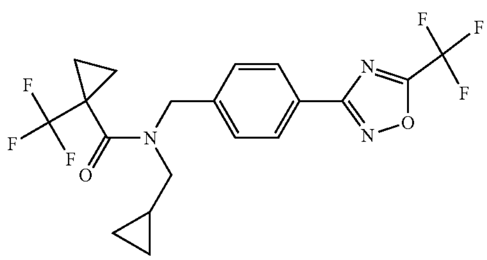 [SMILES: O=C(N(Cc1ccc(-c2noc(C(F)(F)F)n2)cc1)CC1CC1)C1(C(F)(F)F)CC1] | 2.03 | 434.2 | B | |
| 1.204 | N-(cyclopropylmethyl)-2,2-dimethyl-N-[[4-[5-(trifluoromethyl)-1,2,4-oxadiazol-3-yl]phenyl]methyl]-pentanamide | 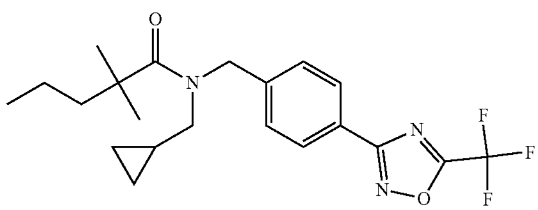 [SMILES: CCCC(C)(C)C(=O)N(Cc1ccc(-c2noc(C(F)(F)F)n2)cc1)CC1CC1] | 2.26 | 410.3 | B | |
| 1.205 | N-(cyclopropylmethyl)-N-[[4-[5-(trifluoromethyl)-1,2,4-oxadiazol-3-yl]phenyl]methyl]pent-4-ynamide | 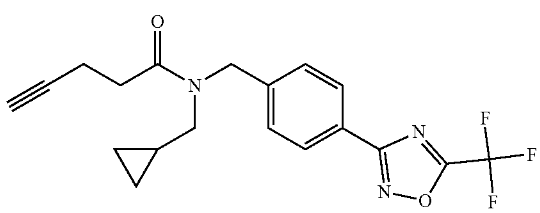 [SMILES: C#CCCC(=O)N(Cc1ccc(-c2noc(C(F)(F)F)n2)cc1)CC1CC1] | 1.86 | 378.2 | B | |
| 1.206 | N-(cyclopropylmethyl)-2-methyl-N-[[4-[5-(trifluoromethyl)-1,2,4-oxadiazol-3-yl]phenyl]methyl]-propanamide | 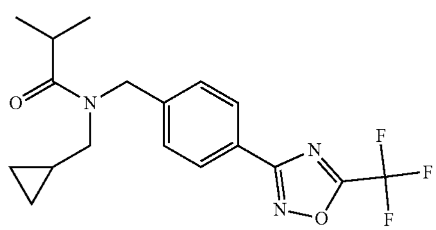 [SMILES: CC(C)C(=O)N(Cc1ccc(-c2noc(C(F)(F)F)n2)cc1)CC1CC1] | 1.94 | 368.3 | B | |
| 1.207 | N-(cyclopropylmethyl)-2,2-difluoroN-[[4-[5-(trifluoromethyl)-1,2,4-oxadiazol-3-yl]phenyl]methyl]-cyclopropane-carboxamide | 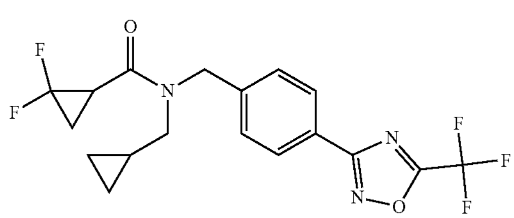 [SMILES: O=C(C1CC1(F)F)N(Cc1ccc(-c2noc(C(F)(F)F)n2)cc1)CC1CC1] | 1.91 | 402.2 | B | |
| 1.208 | N-(cyclopropylmethyl)-N-[[4-[5-(trifluoromethyl)-1,2,4-oxadiazol-3-yl]phenyl]methyl]-pent-4-enamide | 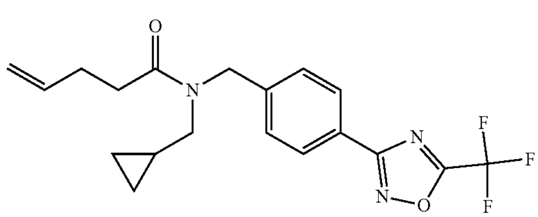 [SMILES: C=CCCC(=O)N(Cc1ccc(-c2noc(C(F)(F)F)n2)cc1)CC1CC1] | 1.97 | 380.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.209 | N-(cyclopropylmethyl)-2-methyl-4-oxo-N-[[4-[5-(trifluoromethyl)-1,2,4-oxadiazol-3-yl]phenyl]methyl]-pentanamide | 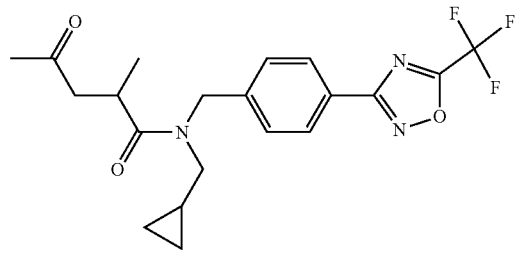 [SMILES: CC(=O)CC(C)C(=O)N(Cc1ccc(-c2noc(C(F)(F)F)n2)cc1)CC1CC1] | 1.84 | 410.2 | B | |
| 1.210 | N-(cyclopropylmethyl)-N-[[4-[5-(trifluoromethyl)-1,2,4-oxadiazol-3-yl]phenyl]methyl]-butanamide | 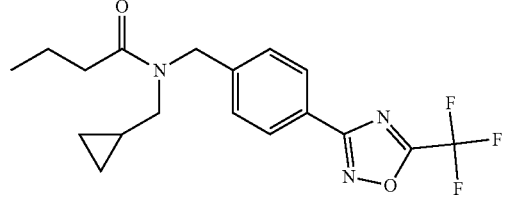 [SMILES: CCCC(=O)N(Cc1ccc(-c2noc(C(F)(F)F)n2)cc1)CC1CC1] | 1.94 | 368.2 | B | |
| 1.211 | 2-cyclopropyl-N-(cyclopropylmethyl)-N-[[4-[5-(trifluoromethyl)-1,2,4-oxadiazol-3-yl]phenyl]methyl]-acetamide | 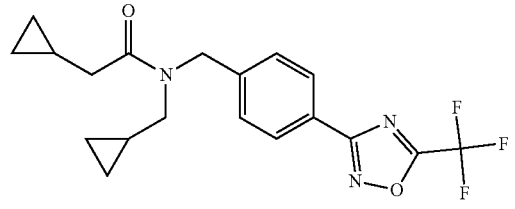 [SMILES: O=C(CC1CC1)N(Cc1ccc(-c2noc(C(F)(F)F)n2)cc1)CC1CC1] | 1.93 | 380.2 | B | |
| 1.212 | N-(cyclopropylmethyl)-N-[[4-[5-(trifluoromethyl)-1,2,4-oxadiazol-3-yl]phenyl]methyl]-cyclopentane-carboxamide | 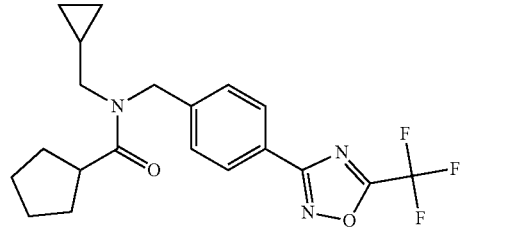 [SMILES: O=C(C1CCCC1)N(Cc1ccc(-c2noc(C(F)(F)F)n2)cc1)CC1CC1] | 2.08 | 394.3 | B | |
| 1.213 | N-(cyclopropylmethyl)-4,4,4-trifluoro-N-[[4-[5-(trifluoromethyl)-1,2,4-oxadiazol-3-yl]phenyl]methyl]-butanamide | 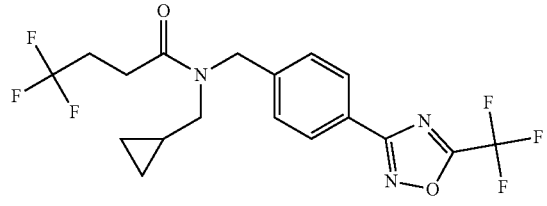 [SMILES: O=C(CCC(F)(F)F)N(Cc1ccc(-c2noc(C(F)(F)F)n2)cc1)CC1CC1] | 1.99 | 422.2 | B | |
| 1.214 | N-(cyclopropylmethyl)-2-(3-pyridyl)-N-[[4-[5-(trifluoromethyl)-1,2,4-oxadiazol-3-yl]phenyl]methyl]-acetamide | 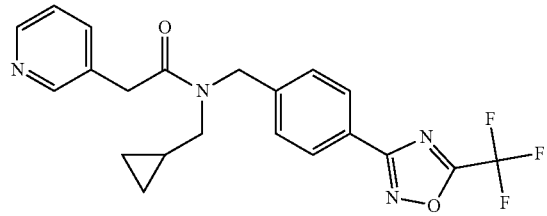 [SMILES: O=C(Cc1cccnc1)N(Cc1ccc(-c2noc(C(F)(F)F)n2)cc1)CC1CC1] | 1.41 | 417.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.215 | N-(cyclopropylmethyl)-N-[[4-[5-(trifluoromethyl)-1,2,4-oxadiazol-3-yl]phenyl]methyl]-tetrahydrofuran-3-carboxamide | 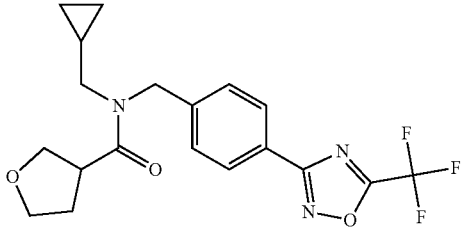 [SMILES: O=C(C1CCOC1)N(Cc1ccc(-c2noc(C(F)(F)F)n2)cc1)CC1CC1] | 1.75 | 396.2 | B | |
| 1.216 | N-(cyclopropylmethyl)-N-[[4-[5-(trifluoromethyl)-1,2,4-oxadiazol-3-yl]phenyl]methyl]-thietane-3-carboxamide | 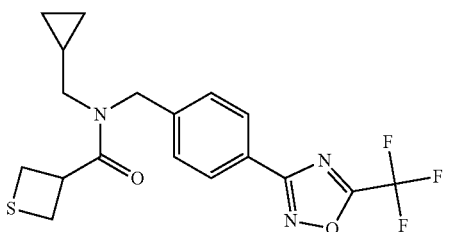 | 1.92 | 398.2 | B | |
| 1.217 | N-(cyclopropylmethyl)-3-methoxy-N-[[4-[5-(trifluoromethyl)-1,2,4-oxadiazol-3-yl]phenyl]methyl]-propanamide | 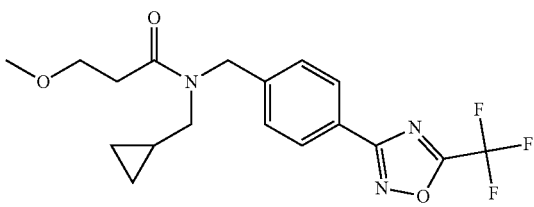 [SMILES: COCCC(=O)N(Cc1ccc(-c2noc(C(F)(F)F)n2)cc1)CC1CC1] | 1.78 | 384.2 | B | |
| 1.218 | N-(cyclopropylmethyl)-3-methyl-N-[[4-[5-(trifluoromethyl)-1,2,4-oxadiazol-3-yl]phenyl]methyl]-butanamide | 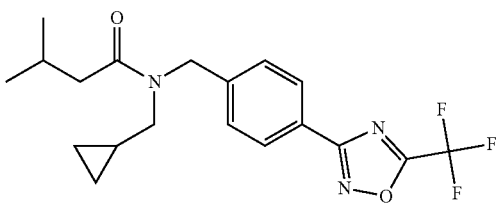 [SMILES: CC(C)CC(=O)N(Cc1ccc(-c2noc(C(F)(F)F)n2)cc1)CC1CC1] | 2.04 | 382.3 | B | |
| 1.219 | 3-chloro-N-(cyclopropylmethyl)-2,2-dimethyl-N-[[4-[5-(trifluoromethyl)-1,2,4-oxadiazol-3-yl]phenyl]methyl]-propanamide | 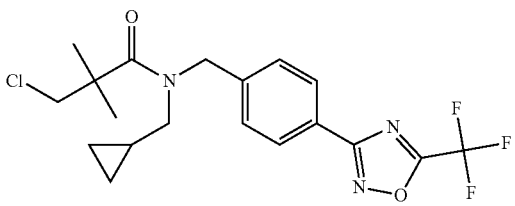 [SMILES: CC(C)(CCl)C(=O)N(Cc1ccc(-c2noc(C(F)(F)F)n2)cc1)CC1CC1] | 2.08 | 416.2 | B | |
| 1.220 | N-(cyclopropylmethyl)-3,3,3-trifluoro-N-[[4-[5-(trifluoromethyl)-1,2,4-oxadiazol-3-yl]phenyl]methyl]-propanamide | 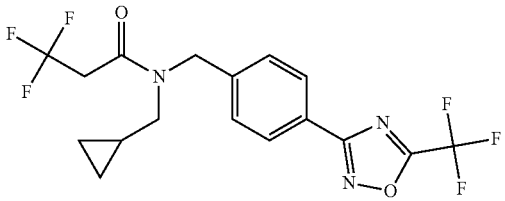 [SMILES: O=C(CC(F)(F)F)N(Cc1ccc(-c2noc(C(F)(F)F)n2)cc1)CC1CC1] | 1.89 | 408.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.221 | N-(cyclopropylmethyl)-N-[[4-[5-(trifluoromethyl)-1,2,4-oxadiazol-3-yl]phenyl]methyl]-cyclobutane-carboxamide | 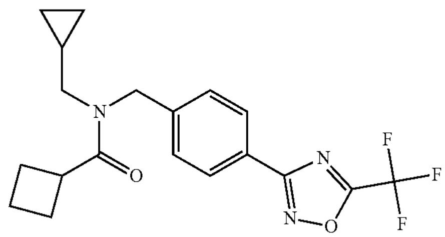 [SMILES: O=C(C1CCC1)N(Cc1ccc(-c2noc(C(F)(F)F)n2)cc1)CC1CC1] | 2 | 380.2 | B | |
| 1.222 | N-(cyclopropylmethyl)-N-[[4-[5-(trifluoromethyl)-1,2,4-oxadiazol-3-yl]phenyl]methyl]-pent-3-enamide | 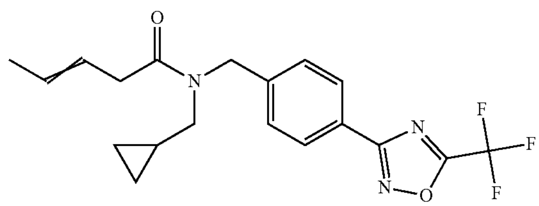 [SMILES: CC=CCC(=O)N(Cc1ccc(-c2noc(C(F)(F)F)n2)cc1)CC1CC1] | 2 | 380.2 | B | |
| 1.223 | N-(cyclopropylmethyl)-2-methyl-N-[[4-[5-(trifluoromethyl)-1,2,4-oxadiazol-3-yl]phenyl]methyl]-cyclopropane-carboxamide | 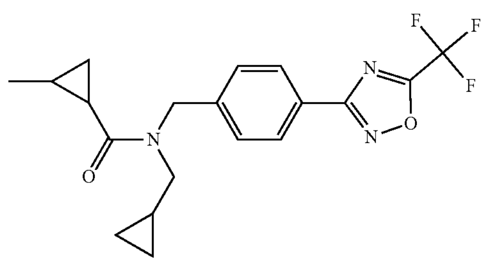 [SMILES: CC1CC1C(=O)N(Cc1ccc(-c2noc(C(F)(F)F)n2)cc1)CC1CC1] | 2 | 380.2 | B | |
| 1.224 | N-(cyclopropylmethyl)-3,3-dimethyl-N-[[4-[5-(trifluoromethyl)-1,2,4-oxadiazol-3-yl]phenyl]methyl]-butanamide | 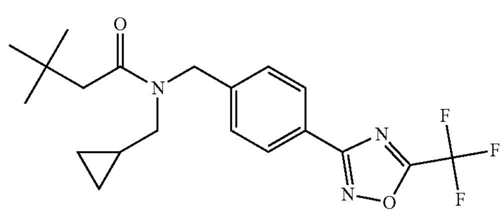 [SMILES: CC(C)(C)CC(=O)N(Cc1ccc(-c2noc(C(F)(F)F)n2)cc1)CC1CC1] | 2 | 380.2 | B | |
| 1.225 | N-(cyclopropylmethyl)-2,2-dimethyl-N-[[4-[5-(trifluoromethyl)-1,2,4-oxadiazol-3-yl]phenyl]methyl]-propanamide | 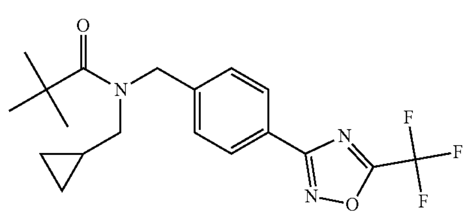 [SMILES: CC(C)(C)C(=O)N(Cc1ccc(-c2noc(C(F)(F)F)n2)cc1)CC1CC1] | 2 | 380.2 | B | |
| 1.226 | N-(cyclopropylmethyl)-1-methyl-N-[[4-[5-(trifluoromethyl)-1,2,4-oxadiazol-3-yl]phenyl]methyl]-cyclopropane-carboxamide | 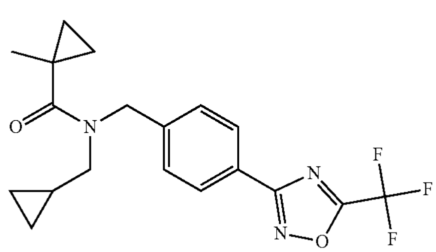 [SMILES: CC1(C(=O)N(Cc2ccc(-c3noc(C(F)(F)F)n3)cc2)CC2CC2)CC1] | 2 | 380.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.227 | N-(cyclopropylmethyl)-N-[[4-[5-(trifluoromethyl)-1,2,4-oxadiazol-3-yl]phenyl]methyl]-propanamide | 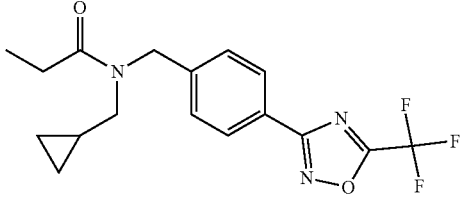 [SMILES: CCC(=O)N(Cc1ccc(-c2noc(C(F)(F)F)n2)cc1)CC1CC1] | 1.84 | 354.2 | B | |
| 1.228 | N-(cyclopropylmethyl)-2-phenyl-N-[[4-[5-(trifluoromethyl)-1,2,4-oxadiazol-3-yl]phenyl]methyl]-acetamide | 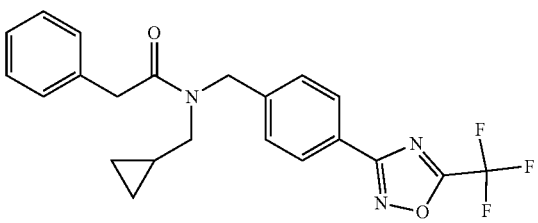 [SMILES: O=C(Cc1ccccc1)N(Cc1ccc(-c2noc(C(F)(F)F)n2)cc1)CC1CC1] | 2.02 | 416.3 | B | |
| 1.229 | N-(cyclopropylmethyl)-2-methyl-N-[[4-[5-(trifluoromethyl)-1,2,4-oxadiazol-3-yl]phenyl]methyl]-prop-2-enamide | 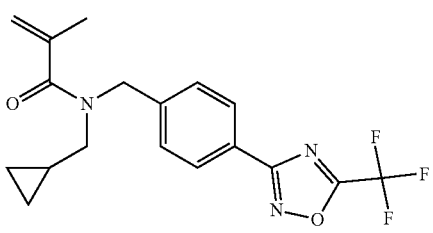 [SMILES: C=C(C)C(=O)N(Cc1ccc(-c2noc(C(F)(F)F)n2)cc1)CC1CC1] | 1.9 | 366.2 | B | |
| 1.230 | N-(cyclopropylmethyl)-N-[[4-[5-(trifluoromethyl)-1,2,4-oxadiazol-3-yl]phenyl]methyl]-tetrahydrothiopyran-4-carboxamide | 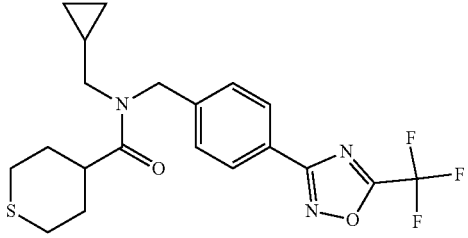 [SMILES: O=C(C1CCSCC1)N(Cc1ccc(-c2noc(C(F)(F)F)n2)cc1)CC1CC1] | 1.95 | 426.2 | B | |
| 1.231 | N-(cyclopropylmethyl)-2,2-dimethyl-N-[[4-[5-(trifluoromethyl)-1,2,4-oxadiazol-3-yl]phenyl]methyl]-cyclopropane-carboxamide | 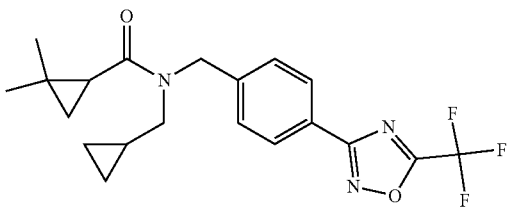 [SMILES: CC1(C)CC1C(=O)N(Cc1ccc(-c2noc(C(F)(F)F)n2)cc1)CC1CC1] | 2.07 | 394.3 | B | |
| 1.232 | 2,2-dichloro-N-(cyclopropylmethyl)-N-[[4-[5-(trifluoromethyl)-1,2,4-oxadiazol-3-yl]phenyl]methyl]-cyclopropane-carboxamide | 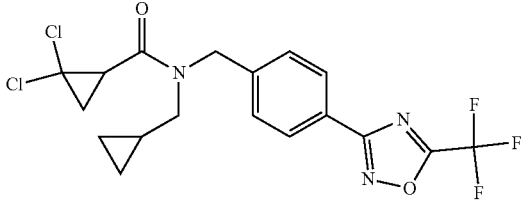 [SMILES: O=C(C1CC1(Cl)Cl)N(Cc1ccc(-c2noc(C(F)(F)F)n2)cc1)CC1CC1] | 2.07 | 434.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.233 | N-(cyclopropylmethyl)-2-methyl-N-[[4-[5-(trifluoromethyl)-1,2,4-oxadiazol-3-yl]phenyl]methyl]-butanamide | 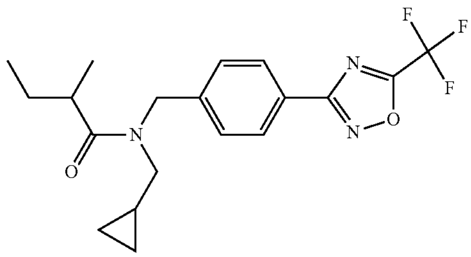 [SMILES: CCC(C)C(=O)N(Cc1ccc(-c2noc(C(F)(F)F)n2)cc1)CC1CC1] | 2.03 | 382.3 | B | |
| 1.234 | 2-(4-chlorophenyl)-N-(cyclopropylmethyl)-N-[[4-[5-(trifluoromethyl)-1,2,4-oxadiazol-3-yl]phenyl]methyl]-acetamide | 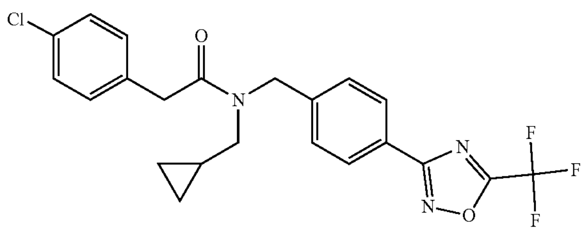 [SMILES: O=C(Cc1ccc(Cl)cc1)N(Cc1ccc(-c2noc(C(F)(F)F)n2)cc1)CC1CC1] | 2.11 | 450.2 | B | |
| 1.235 | N-(cyclopropylmethyl)-3-methyl-N-[[4-[5-(trifluoromethyl)-1,2,4-oxadiazol-3-yl]phenyl]methyl]-oxetane-3-carboxamide | 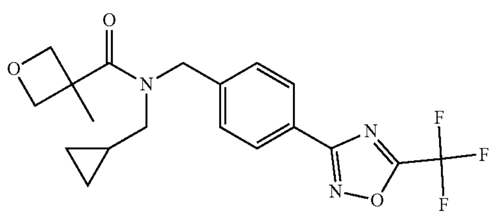 [SMILES: CC1(C(=O)N(Cc2ccc(-c3noc(C(F)(F)F)n3)cc2)CC2CC2)COC1] | 1.76 | 396.2 | B | |
| 1.236 | 2-(4-cyanophenyl)-N-(cyclopropylmethyl)-N-[[4-[5-(trifluoromethyl)-1,2,4-oxadiazol-3-yl]phenyl]methyl]-acetamide | 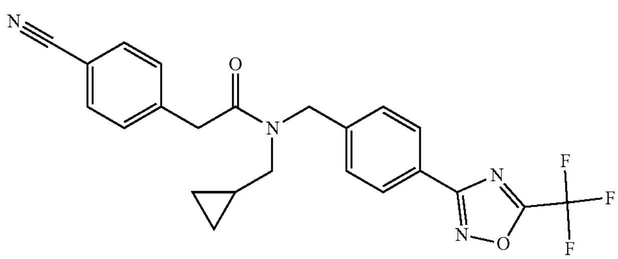 [SMILES: N#Cc1ccc(CC(=O)N(Cc2ccc(-c3noc(C(F)(F)F)n3)cc2)CC2CC2)cc1] | 1.91 | 441.2 | B | |
| 1.237 | N-(cyclopropylmethyl)-2-(methoxymethyl)-N-[[4-[5-(trifluoromethyl)-1,2,4-oxadiazol-3-yl]phenyl]methyl]-butanamide | 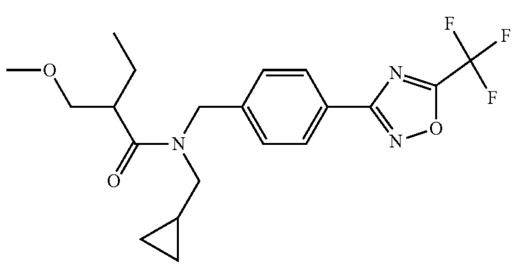 [SMILES: CCC(COC)C(=O)N(Cc1ccc(-c2noc(C(F)(F)F)n2)cc1)CC1CC1] | 2 | 412.3 | B | |
| 1.238 | N-(cyclopropylmethyl)-4-methoxy-N-[[4-[5-(trifluoromethyl)-1,2,4-oxadiazol-3-yl]phenyl]methyl]-butanamide | 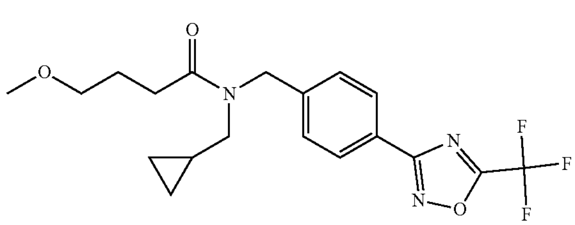 [SMILES: COCCCC(=O)N(Cc1ccc(-c2noc(C(F)(F)F)n2)cc1)CC1CC1] | 1.83 | 398.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.239 | N-(cyclopropylmethyl)-2-(ethylsulfonylamino)-N-[[4-[5-(trifluoromethyl)-1,2,4-oxadiazol-3-yl]phenyl]methyl]-pent-4-ynamide | 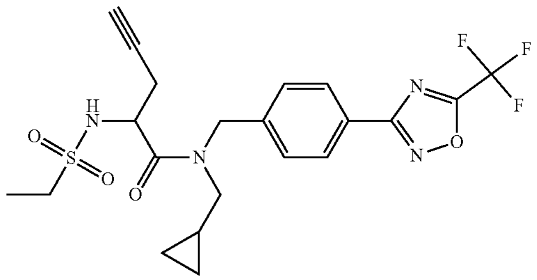 [SMILES: C#CCC(NS(=O)(=O)CC)C(=O)N(Cc1ccc(-c2noc(C(F)(F)F)n2)cc1)CC1CC1] | 1.79 | 485.2 | B | |
| 1.240 | N-(cyclopropylmethyl)-2-(2,2-difluorocyclopropyl)-N-[[4-[5-(trifluoromethyl)-1,2,4-oxadiazol-3-yl]phenyl]methyl]-acetamide | 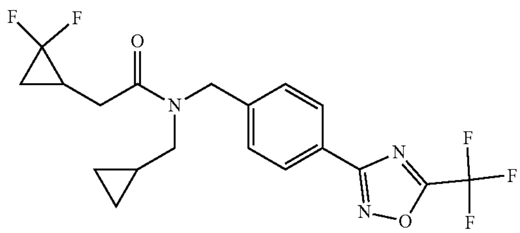 [SMILES: O=C(CC1CC1(F)F)N(Cc1ccc(-c2noc(C(F)(F)F)n2)cc1)CC1CC1] | 1.93 | 416.2 | B | |
| 1.241 | prop-2-ynyl N-[1-(cyclopropylmethyl-[[4-[5-(trifluoromethyl)-1,2,4-oxadiazol-3-yl]phenyl]methyl]-carbamoyl]-2-methyl-propyl]carbamate | 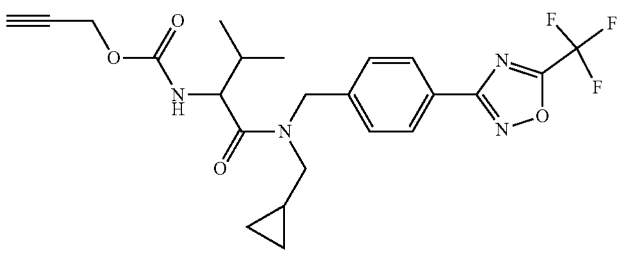 [SMILES: C#CCOC(=O)NC(C(=O)N(Cc1ccc(-c2noc(C(F)(F)F)n2)cc1)CC1CC1)C(C)C] | 1.97 | 479.3 | B | |
| 1.242 | N-(cyclopropylmethyl)-N-[[4-[5-(trifluoromethyl)-1,2,4-oxadiazol-3-yl]phenyl]methyl]-tetrahydrofuran-2-carboxamide | 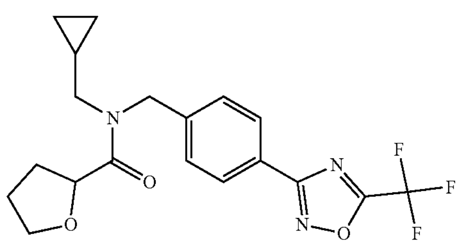 [SMILES: O=C(C1CCCO1)N(Cc1ccc(-c2noc(C(F)(F)F)n2)cc1)CC1CC1] | 1.82 | 396.2 | B | |
| 1.243 | 2-cyano-N-(cyclopropylmethyl)-N-[[4-[5-(trifluoromethyl)-1,2,4-oxadiazol-3-yl]phenyl]methyl]-acetamide | 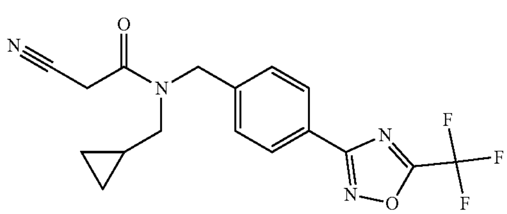 [SMILES: N#CCC(=O)N(Cc1ccc(-c2noc(C(F)(F)F)n2)cc1)CC1CC1] | 1.69 | 365.2 | B | |
| 1.244 | 1-cyano-N-(cyclopropylmethyl)-N-[[4-[5-(trifluoromethyl)-1,2,4-oxadiazol-3-yl]phenyl]methyl]-cyclopropane-carboxamide | 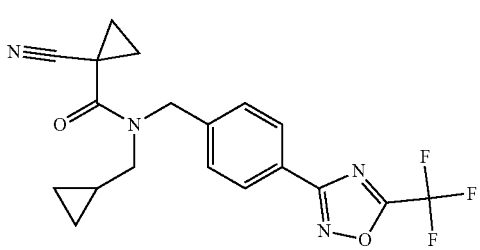 [SMILES: N#CC1(C(=O)N(Cc2ccc(-c3noc(C(F)(F)F)n3)cc2)CC2CC2)CC1] | 1.86 | 391.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.245 | N-(cyclopropylmethyl)-2-methoxy-N-[[4-[5-(trifluoromethyl)-1,2,4-oxadiazol-3-yl]phenyl]methyl]-propanamide | 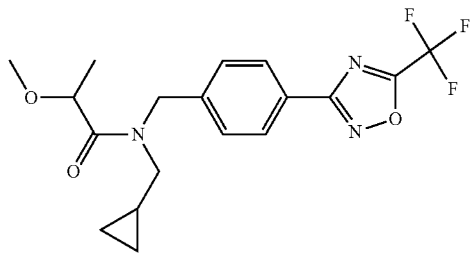 [SMILES: COC(C)C(=O)N(Cc1ccc(-c2noc(C(F)(F)F)n2)cc1)CC1CC1] | 1.79 | 384.2 | B | |
| 1.246 | N-(cyclopropylmethyl)-N-[[4-[5-(trifluoromethyl)-1,2,4-oxadiazol-3-yl]phenyl]methyl]-cyclopropane-carboxamide | 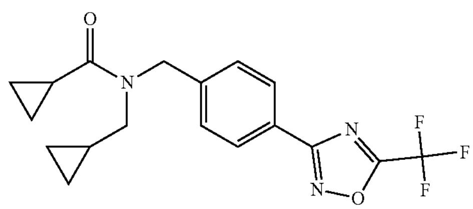 [SMILES: O=C(C1CC1)N(Cc1ccc(-c2noc(C(F)(F)F)n2)cc1)CC1CC1] | 1.88 | 366.2 | B | |
| 1.247 | N-(cyclopropylmethyl)-N-[[4-[5-(trifluoromethyl)-1,2,4-oxadiazol-3-yl]phenyl]methyl]-benzamide | 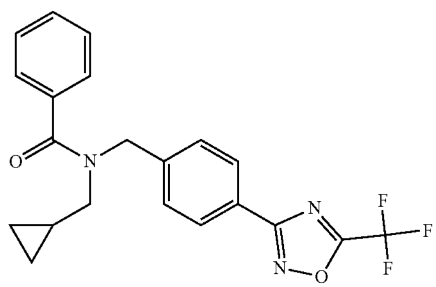 [SMILES: O=C(c1ccccc1)N(Cc1ccc(-c2noc(C(F)(F)F)n2)cc1)CC1CC1] | 1.98 | 402.2 | B | |
| 1.248 | N-methoxy-N-[1-[4-[5-(trifluoromethyl)-1,2,4-oxadiazol-3-yl]phenyl]ethyl]but-2-ynamide | 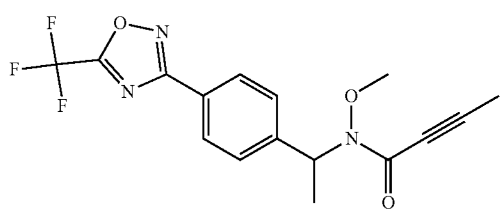 [SMILES: CC#CC(=O)N(OC)C(C)c1ccc(-c2noc(C(F)(F)F)n2)cc1] | 1.75 | 353.1 | B | |
| 1.249 | N-methoxy-N-[1-[4-[5-(trifluoromethyl)-1,2,4-oxadiazol-3-yl]phenyl]ethyl]-tetrahydropyran-2-carboxamide | 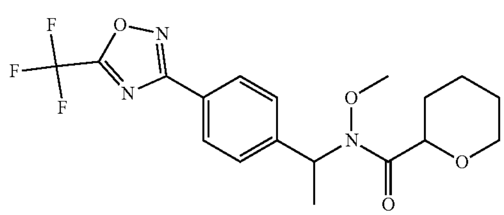 [SMILES: CON(C(=O)C1CCCCO1)C(C)c1ccc(-c2noc(C(F)(F)F)n2)cc1] | 1.80 | 399.1 | B | |
| 1.250 | N-methoxy-N-[1-[4-[5-(trifluoromethyl)-1,2,4-oxadiazol-3-yl]phenyl]ethyl]but-2-enamide | 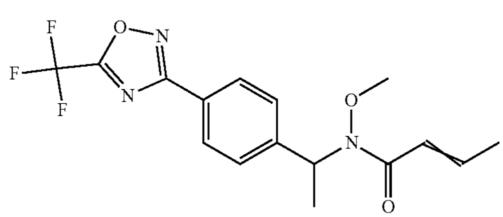 [SMILES: CC=CC(=O)N(OC)C(C)c1ccc(-c2noc(C(F)(F)F)n2)cc1] | 1.83 | 355.1 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.251 | 2,2-difluoro-N-methoxy-N-[1-[4-[5-(trifluoromethyl)-1,2,4-oxadiazol-3-yl]phenyl]ethyl]-cyclopropane-carboxamide | 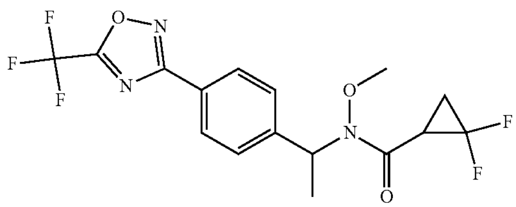 [SMILES: CON(C(=O)C1CC1(F)F)C(C)c1ccc(-c2noc(C(F)(F)F)n2)cc1] | 1.86 | 391.1 | B | |
| 1.252 | 4-chloro-3-fluoro-N-methoxy-N-[1-[4-[5-(trifluoromethyl)-1,2,4-oxadiazol-3-yl]phenyl]ethyl]but-2-enamide | 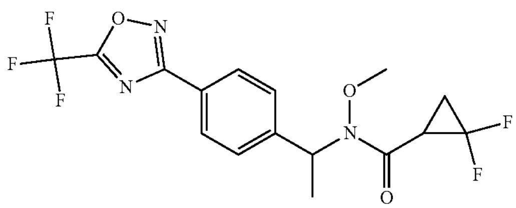 [SMILES: CON(C(=O)C1CC1(F)F)C(C)c1ccc(-c2noc(C(F)(F)F)n2)cc1] | 1.98 | 407.1 | B | |
| 1.253 | N,2-dimethoxy-N-(1-[4-[5-(trifluoromethyl)-1,2,4-oxadiazol-3-yl]phenyl]ethyl]-acetamide | 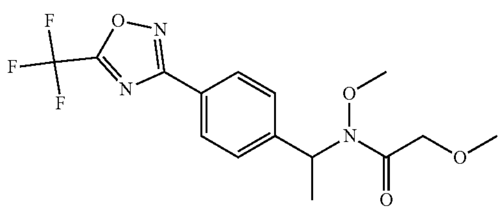 [SMILES: COCC(=O)N(OC)C(C)c1ccc(-c2noc(C(F)(F)F)n2)cc1] | 1.63 | 359.1 | B | |
| 1.254 | N-methoxy-N-[1-[4-[5-(trifluoromethyl)-1,2,4-oxadiazol-3-yl]phenyl]ethyl]-butanamide | 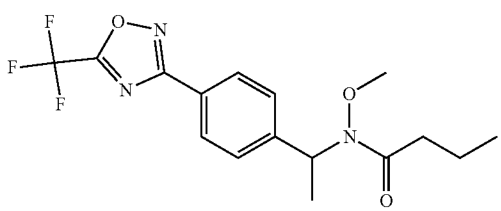 | 1.90 | 357.1 | B | |
| 1.255 | N-methoxy-2-methyl-N-[1-[4-[5-(trifluoromethyl)-1,2,4-oxadiazol-3-yl]phenyl]ethyl]but-2-enamide | 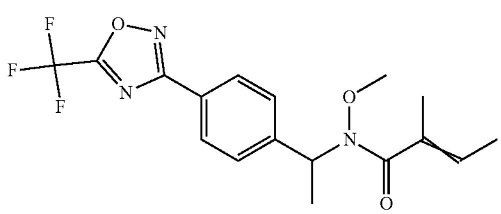 [SMILES: CC=C(C)C(=O)N(OC)C(C)c1ccc(-c2noc(C(F)(F)F)n2)cc1] | 1.86 | 369.1 | B | |
| 1.256 | 2-cyclopropyl-N-methoxy-N-[1-[4-[5-(trifluoromethyl)-1,2,4-oxadiazol-3-yl]phenyl]ethyl]-acetamide | 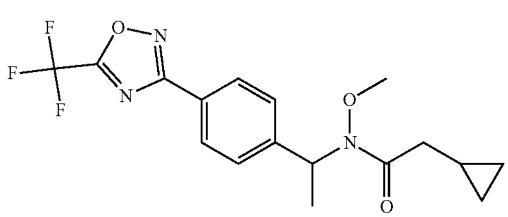 [SMILES: CON(C(=O)CC1CC1)C(C)c1ccc(-c2noc(C(F)(F)F)n2)cc1] | 1.89 | 369.1 | B | |
| 1.257 | N-methoxy-N-[1(trifluoromethyl)-1,2,4-oxadiazol-3-yl]phenyl]ethyl]-cyclopentane-carboxamide | 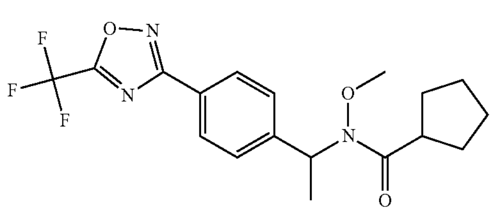 [SMILES: CON(C(=O)C1CCCC1)C(C)c1ccc(-c2noc(C(F)(F)F)n2)cc1] | 2.05 | 383.1 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.258 | N-methoxy-N-[1-[4-[5-(trifluoromethyl)-1,2,4-oxadiazol-3-yl]phenyl]ethyl]-cyclopentene-1-carboxamide | 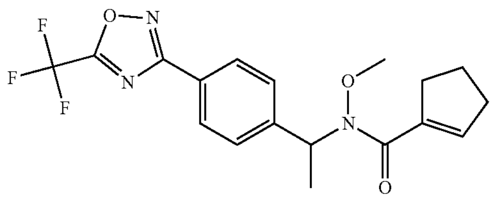 [SMILES: CON(C(=O)C1=CCCC1)C(C)c1ccc(-c2noc(C(F)(F)F)n2)cc1] | 1.94 | 381.1 | B | |
| 1.259 | N-methoxy-N-[1-[4-[5-(trifluoromethyl)-1,2,4-oxadiazol-3-yl]phenyl]ethyl]-thietane-3-carboxamide | 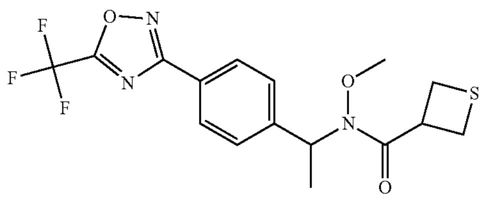 [SMILES: CON(C(=O)C1CSC1)C(C)c1ccc(-c2noc(C(F)(F)F)n2)cc1] | 1.87 | 387.1 | B | |
| 1.260 | N,3-dimethoxy-N-[1-[4-[5-(trifluoromethyl)-1,2,4-oxadiazol-3-yl]phenyl]ethyl]-propanamide | 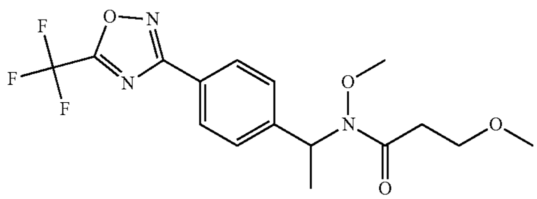 [SMILES: COCCC(=O)N(OC)C(C)c1ccc(-c2noc(C(F)(F)F)n2)cc1] | 1.71 | 373.1 | B | |
| 1.261 | N-methoxy-3-methyl-N-[1-[4-[5-(trifluoromethyl)-1,2,4-oxadiazol-3-yl]phenyl]ethyl]-butanamide | 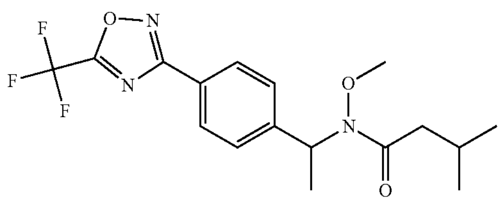 [SMILES: CON(C(=O)CC(C)C)C(C)c1ccc(-c2noc(C(F)(F)F)n2)cc1] | 2.00 | 371.1 | B | |
| 1.262 | N-methoxy-N-[1-[4-[5-(trifluoromethyl)-1,2,4-oxadiazol-3-yl]phenyl]ethyl]-cyclobutane-carboxamide | 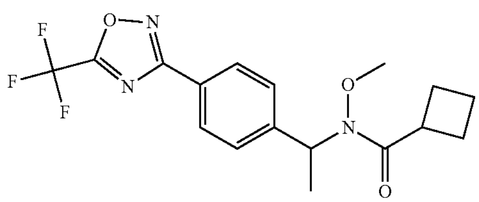 [SMILES: CON(C(=O)C1CCC1)C(C)c1ccc(-c2noc(C(F)(F)F)n2)cc1] | 1.94 | 369.1 | B | |
| 1.263 | 4,4,4-trifluoro-N-methoxy-N-[1-[4-[5-(trifluoromethyl)-1,2,4-oxadiazol-3-yl]phenyl]ethyl]but-2-enamide | 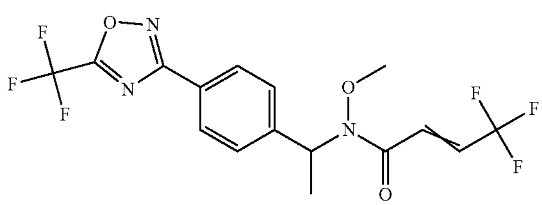 [SMILES: CON(C(=O)C=CC(F)(F)F)C(C)c1ccc(-c2noc(C(F)(F)F)n2)cc1] | 1.97 | 409.1 | B | |
| 1.264 | 2-ethoxy-N-methoxy-N-[1-[4-[5-(trifluoromethyl)-1,2,4-oxadiazol-3-yl]phenyl]ethyl]-acetamide | 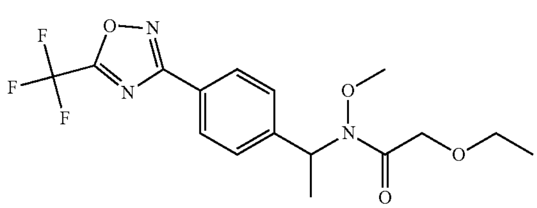 [SMILES: CCOCC(=O)N(OC)C(C)c1ccc(-c2noc(C(F)(F)F)n2)cc1] | 1.73 | 373.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.265 | N-methoxy-2-methyl-N-[1-[4-[5-(trifluoromethyl)-1,2,4-oxadiazol-3-yl]phenyl]ethyl]-cyclopropane-carboxamide | 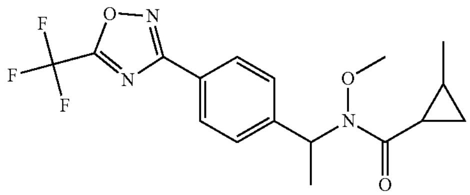 [SMILES: CON(C(=O)C1CC1C)C(C)c1ccc(-c2noc(C(F)(F)F)n2)cc1] | 1.91 | 369.1 | B | |
| 1.266 | N-methoxy-2-(2-methoxyethoxy)-N-[1-[4-[5-(trifluoromethyl)-1,2,4-oxadiazol-3-yl]phenyl]ethyl]-acetamide | 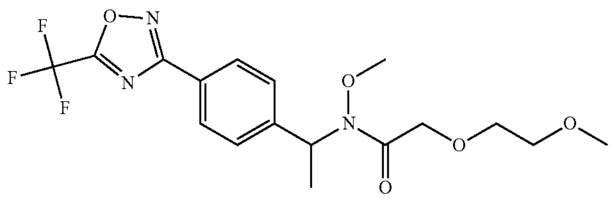 [SMILES: COCCOCC(=O)N(OC)C(C)c1ccc(-c2noc(C(F)(F)F)n2)cc1] | 1.64 | 403.1 | B | |
| 1.267 | N-methoxy-3,3-dimethyl-N-[1-[4-[5-(trifluoromethyl)-1,2,4-oxadiazol-3-yl]phenyl]ethyl]-butanamide | 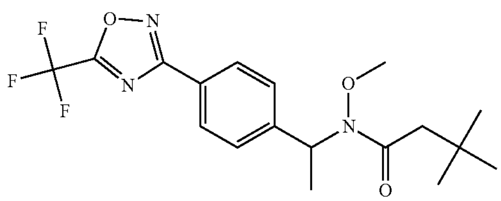 [SMILES: CON(C(=O)CC(C)(C)C)C(C)c1ccc(-c2noc(C(F)(F)F)n2)cc1] | 2.12 | 385.2 | B | |
| 1.268 | N-methoxy-1-methyl-N-[1-[4-[5-(trifluoromethyl)-1,2,4-oxadiazol-3-yl]phenyl]ethyl]-cyclopropane-carboxamide | 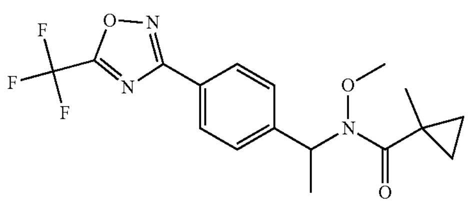 [SMILES: CON(C(=O)C1(C)CC1)C(C)c1ccc(-c2noc(C(F)(F)F)n2)cc1] | 1.87 | 369.1 | B | |
| 1.269 | N-methoxy-N-[1-[4-[5-(trifluoromethyl)-1,2,4-oxadiazol-3-yl]phenyl]ethyl]prop-2-ynamide | 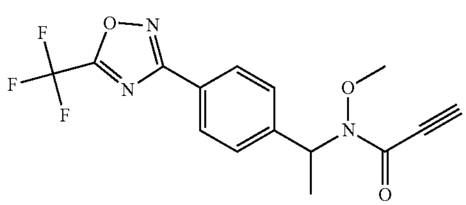 [SMILES: C#CC(=O)N(OC)C(C)c1ccc(-c2noc(C(F)(F)F)n2)cc1] | 2.31 | 339.1 | B | |
| 1.270 | [2-[methoxy-[1-[4-[5-(trifluoromethyl)-1,2,4-oxadiazol-3-yl]phenyl]ethyl]-amino]-2-oxo-ethyl] acetate | 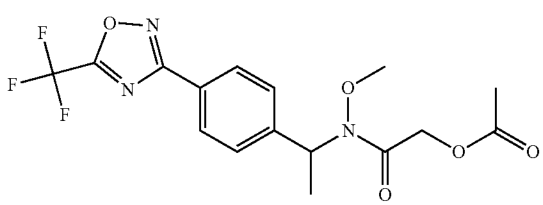 [SMILES: CON(C(=O)COC(C)=O)C(C)c1ccc(-c2noc(C(F)(F)F)n2)cc1] | 1.68 | 387.1 | B | |
| 1.271 | 1-fluoro-N-methoxy-N-[1-[4-[5-(trifluoromethyl)-1,2,4-oxadiazol-3-yl]phenyl]ethyl]-cyclopropane-carboxamide | 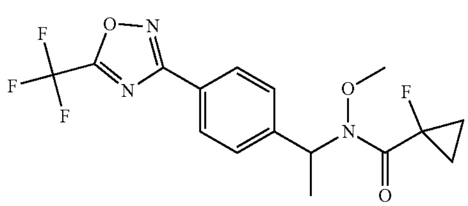 [SMILES: CON(C(=O)C1(F)CC1)C(C)c1ccc(-c2noc(C(F)(F)F)n2)cc1] | 1.87 | 373.1 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.272 | N-methoxy-4-oxo-N-[1-[4-[5-(trifluoromethyl)-1,2,4-oxadiazol-3-yl]phenyl]ethyl]pent-2-enamide | 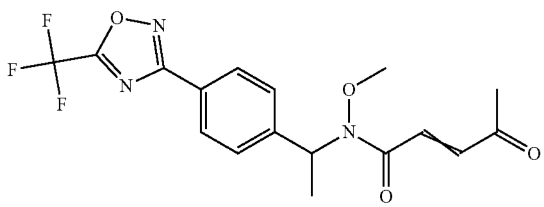 [SMILES: CON(C(=O)C=CC(C)=O)C(C)c1ccc(-c2noc(C(F)(F)F)n2)cc1] | 1.70 | 383.1 | B | |
| 1.273 | N-methoxy-N-[1-[4-[5-(trifluoromethyl)-1,2,4-oxadiazol-3-yl]phenyl]ethyl]-tetrahydrofuran-2-carboxamide | 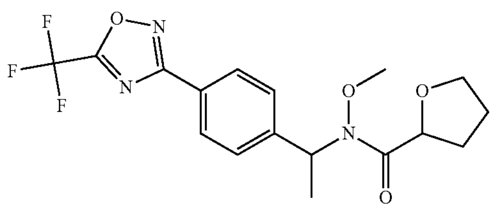 [SMILES: CON(C(=O)C1CCCO1)C(C)c1ccc(-c2noc(C(F)(F)F)n2)cc1] | 1.73 | 385.1 | B | |
| 1.274 | 1-cyano-N-methoxy-N-[1-[4-[5-(trifluoromethyl)-1,2,4-oxadiazol-3-yl]phenyl]ethyl]-cyclopropane-carboxamide | 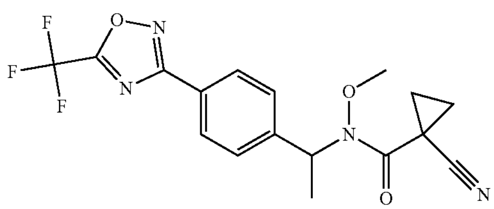 [SMILES: CON(C(=O)C1(C#N)CC1)C(C)c1ccc(-c2noc(C(F)(F)F)n2)cc1] | 1.76 | 380.1 | B | |
| 1.275 | 2-fluoroN-methoxy-N-[1-[4-[5-(trifluoromethyl)-1,2,4-oxadiazol-3-yl]phenyl]ethyl]-cyclopropane-carboxamide | 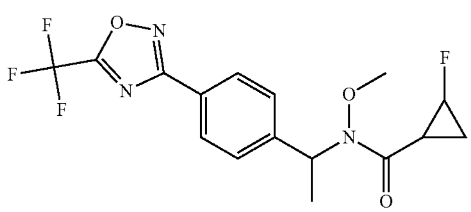 [SMILES: CON(C(=O)C1CC1F)C(C)c1ccc(-c2noc(C(F)(F)F)n2)cc1] | 1.73 | 373.1 | B | |
| 1.276 | N-methoxy-N-[1-[4-[5-(trifluoromethyl)-1,2,4-oxadiazol-3-yl]phenyl]ethyl]-1,3-dioxolane-2-carboxamide | 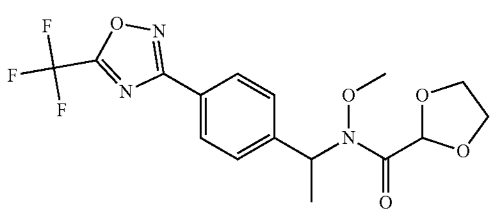 [SMILES: CON(C(=O)C1OCCO1)C(C)c1ccc(-c2noc(C(F)(F)F)n2)cc1] | 1.65 | 387.1 | B | |
| 1.277 | 3,3,3-trifluoro-N-methoxy-N-[1-[4-[5-(trifluoromethyl)-1,2,4-oxadiazol-3-yl]phenyl]ethyl]-propanamide | 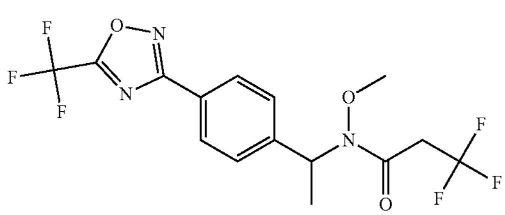 [SMILES: CON(C(=O)CC(F)(F)F)C(C)c1ccc(-c2noc(C(F)(F)F)n2)cc1] | 1.85 | 397.1 | B | |
| 1.278 | N-methoxy-N-[1-[4-[5-(trifluoromethyl)-1,2,4-oxadiazol-3-yl]phenyl]ethyl]furan-3-carboxamide | 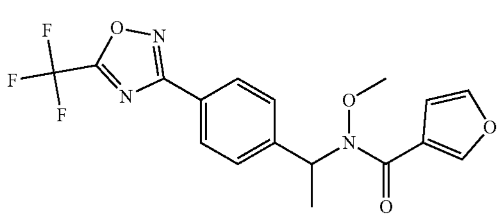 [SMILES: CON(C(=O)c1ccoc1)C(C)c1ccc(-c2noc(C(F)(F)F)n2)cc1] | 1.82 | 381.1 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.279 | N-methoxy-N-[1-[4-[5-(trifluoromethyl)-1,2,4-oxadiazol-3-yl]phenyl]ethyl]-cyclopropane-carboxamide | 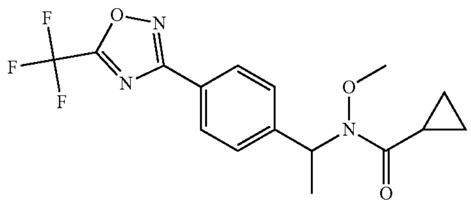 [SMILES: CON(C(=O)C1CC1)C(C)c1ccc(-c2noc(C(F)(F)F)n2)cc1] | 1.82 | 355.1 | B | |
| 1.280 | N,4-dimethoxy-N-[1-[4-[5-(trifluoromethyl)-1,2,4-oxadiazol-3-yl]phenyl]ethyl]-butanamide | 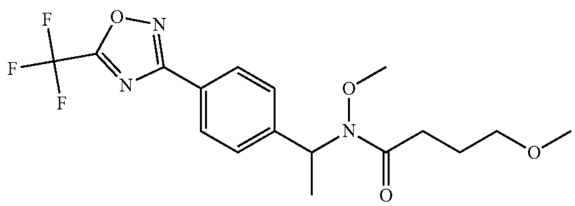 [SMILES: COCCCC(=O)N(OC)C(C)c1ccc(-c2noc(C(F)(F)F)n2)cc1] | 1.77 | 387.1 | B | |
| 1.281 | N-methoxy-N-[1-[4-[5-(trifluoromethyl)-1,2,4-oxadiazol-3-yl]phenyl]ethyl]-pentanamide | 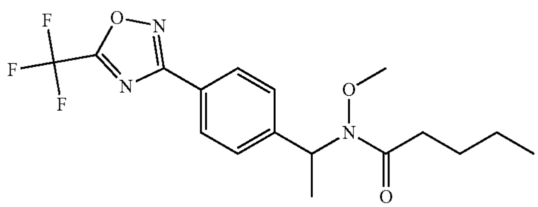 [SMILES: CCCCC(=O)N(OC)C(C)c1ccc(-c2noc(C(F)(F)F)n2)cc1] | 2.01 | 371.1 | B | |
| 1.282 | N-propoxy-N-[[4-[5-(trifluoromethyl)-1,2,4-oxadiazol-3-yl]phenyl]methyl]but-2-ynamide | 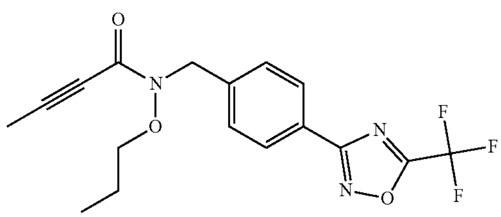 | 1.85 | 367.1 | B | |
| 1.283 | N-propoxy-N-[[4-[5-(trifluoromethyl)-1,2,4-oxadiazol-3-yl]phenyl]methyl]-tetrahydropyran-2-carboxamide | 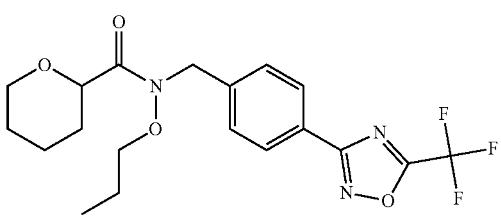 [SMILES: CCCON(Cc1ccc(-c2noc(C(F)(F)F)n2)cc1)C(=O)C1CCCCO1] | 1.91 | 413.2 | B | |
| 1.284 | 2-methyl-N-propoxy-N-[[4-[5-(trifluoromethyl)-1,2,4-oxadiazol-3-yl]phenyl]methyl]-propanamide | 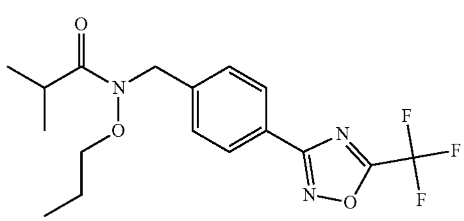 [SMILES: CCCON(Cc1ccc(-c2noc(C(F)(F)F)n2)cc1)C(=O)C(C)C] | 1.99 | 371.1 | B | |
| 1.285 | N-propoxy-N-[[4-[5-(trifluoromethyl)-1,2,4-oxadiazol-3-yl]phenyl]methyl]but-2-enamide | 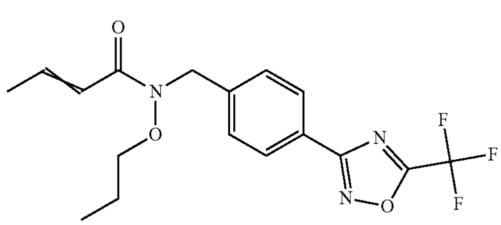 [SMILES: CC=CC(=O)N(Cc1ccc(-c2noc(C(F)(F)F)n2)cc1)OCCC] | 1.92 | 369.1 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.286 | 2,2-difluoro-N-propoxy-N-[[4-[5-(trifluoromethyl)-1,2,4-oxadiazol-3-yl]phenyl]methyl]-cyclopropane-carboxamide | 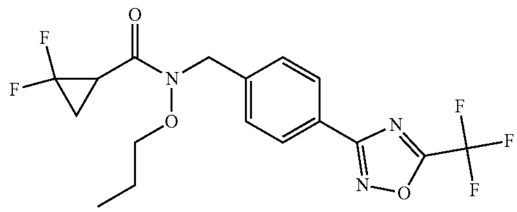 [SMILES: CCCON(Cc1ccc(-c2noc(C(F)(F)F)n2)cc1)C(=O)C1CC1(F)F] | 1.94 | 405.1 | B | |
| 1.287 | 2-methoxy-N-propoxy-N-[[4-[5-(trifluoromethyl)-1,2,4-oxadiazol-3-yl]phenyl]methyl]-acetamide | 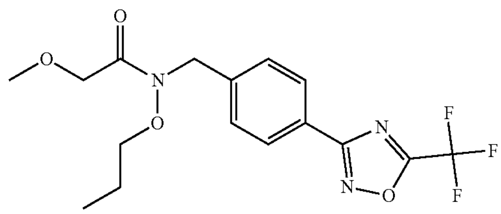 | 1.73 | 373.1 | B | |
| 1.288 | N-propoxy-N-[[4-[5-(trifluoromethyl)-1,2,4-oxadiazol-3-yl]phenyl]methyl]-butanamide | 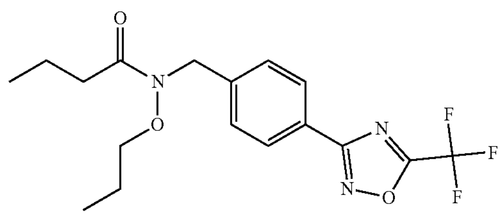 [SMILES: CCCON(Cc1ccc(-c2noc(C(F)(F)F)n2)cc1)C(=O)CCC] | 1.99 | 371.1 | B | |
| 1.289 | 2-cyclopropyl-N-propoxy-N-[[4-[5-(trifluoromethyl)-1,2,4-oxadiazol-3-yl]phenyl]methyl]-acetamide | 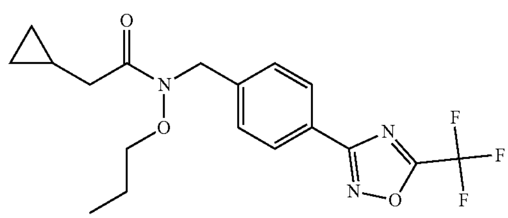 [SMILES: CCCON(Cc1ccc(-c2noc(C(F)(F)F)n2)cc1)C(=O)CC1CC1] | 1.98 | 383.1 | B | |
| 1.290 | N-propoxy-N-[[4-[5-(trifluoromethyl)-1,2,4-oxadiazol-3-yl]phenyl]methyl]-cyclopentane-carboxamide | 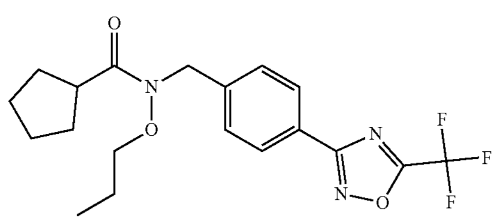 [SMILES: CCCON(Cc1ccc(-c2noc(C(F)(F)F)n2)cc1)C(=O)C1CCCC1] | 2.13 | 397.2 | B | |
| 1.291 | N-propoxy-N-[[4-[5-(trifluoromethyl)-1,2,4-oxadiazol-3-yl]phenyl]methyl]-cyclopentene-1-carboxamide | 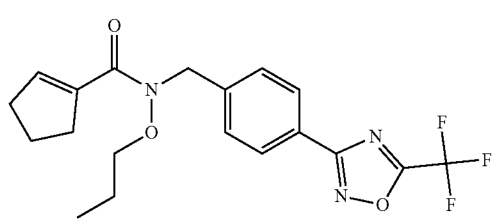 [SMILES: CCCON(Cc1ccc(-c2noc(C(F)(F)F)n2)cc1)C(=O)C1=CCCC1] | 2.04 | 395.1 | B | |
| 1.292 | N-propoxy-N-[[4-[5-(trifluoromethyl)-1,2,4-oxadiazol-3-yl]phenyl]methyl]-thietane-3-carboxamide | 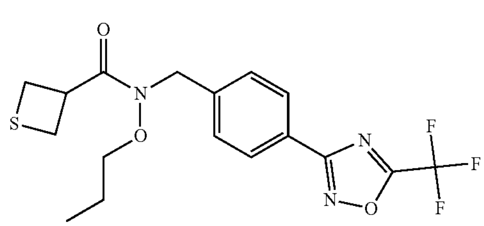 [SMILES: CCCON(Cc1ccc(-c2noc(C(F)(F)F)n2)cc1)C(=O)C1CSC1] | 1.96 | 401.1 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.293 | 3-methoxy-N-propoxy-N-[[4-[5-(trifluoromethyl)-1,2,4-oxadiazol-3-yl]phenyl]methyl]-propanamide | 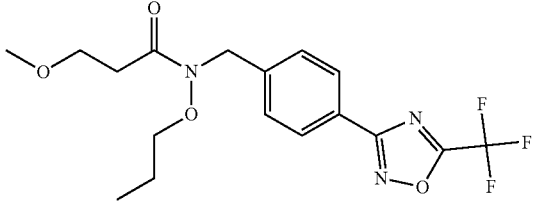 [SMILES: CCCON(Cc1ccc(-c2noc(C(F)(F)F)n2)cc1)C(=O)CCOC] | 1.81 | 387.1 | B | |
| 1.294 | 3-methyl-N-propoxy-N-[[4-[5-(trifluoromethyl)-1,2,4-oxadiazol-3-yl]phenyl]methyl]-butanamide | 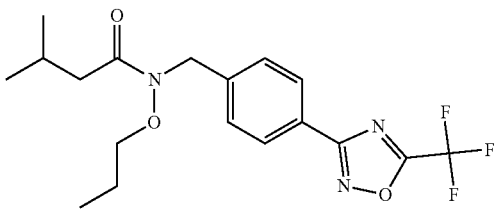 [SMILES: CCCON(Cc1ccc(-c2noc(C(F)(F)F)n2)cc1)C(=O)CC(C)C] | 2.08 | 385.2 | B | |
| 1.295 | N-propoxy-N-[[4-[5-(trifluoromethyl)-1,2,4-oxadiazol-3-yl]phenyl]methyl]-cyclobutane-carboxamide | 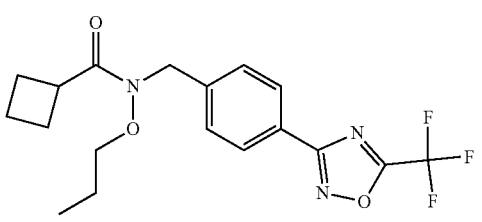 [SMILES: CCCON(Cc1ccc(-c2noc(C(F)(F)F)n2)cc1)C(=O)C1CCC1] | 2.04 | 383.1 | B | |
| 1.296 | 4,4,4-trifluoro-N-propoxy-N-[[4-[5-(trifluoromethyl)-1,2,4-oxadiazol-3-yl]phenyl]methyl]but-2-enamide | 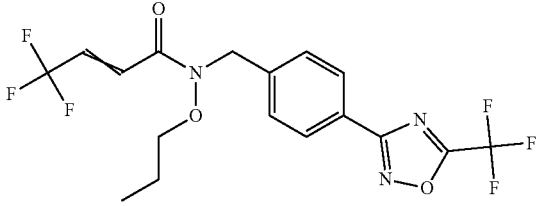 | 2.06 | 423.1 | B | |
| 1.297 | 2-ethoxy-N-propoxy-N-[[4-[5-(trifluoromethyl)-1,2,4-oxadiazol-3-yl]phenyl]methyl]-acetamide | 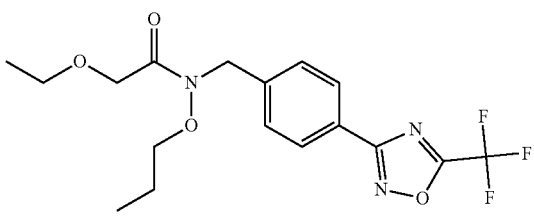 [SMILES: CCCON(Cc1ccc(-c2noc(C(F)(F)F)n2)cc1)C(=O)COCC] | 1.83 | 387.1 | B | |
| 1.298 | 2-(2-methoxyethoxy)-N-propoxy-N-[[4-[5-(trifluoromethyl)-1,2,4-oxadiazol-3-yl]phenyl]methyl]-acetamide | 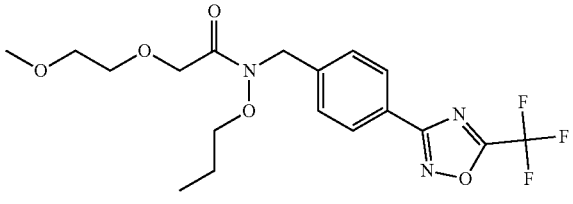 [SMILES: CCCON(Cc1ccc(-c2noc(C(F)(F)F)n2)cc1)C(=O)COCCOC] | 1.75 | 417.2 | B | |
| 1.299 | 2-methyl-N-propoxy-N-[[4-[5-(trifluoromethyl)-1,2,4-oxadiazol-3-yl]phenyl]methyl]-cyclopropane-carboxamide | 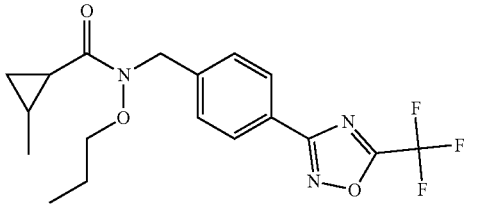 [SMILES: CCCON(Cc1ccc(-c2noc(C(F)(F)F)n2)cc1)C(=O)C1CC1C] | 2.01 | 383.1 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.300 | 3,3-dimethyl-N-propoxy-N-[[4-[5-(trifluoromethyl)-1,2,4-oxadiazol-3-yl]phenyl]methyl]-butanamide | 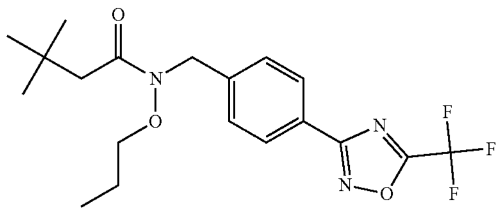 [SMILES: CCCON(Cc1ccc(-c2noc(C(F)(F)F)n2)cc1)C(=O)CC(C)(C)C] | 2.19 | 399.2 | B | |
| 1.301 | N-propoxy-N-[[4-[5-(trifluoromethyl)-1,2,4-oxadiazol-3-yl]phenyl]methyl]-prop-2-enamide | 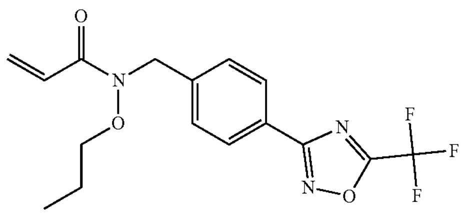 [SMILES: C=CC(=O)N(Cc1ccc(-c2noc(C(F)(F)F)n2)cc1)OCCC] | 1.85 | 355.1 | B | |
| 1.302 | 1-methyl-N-propoxy-N-[[4-[5-(trifluoromethyl)-1,2,4-oxadiazol-3-yl]phenyl]methyl]-cyclopropane-carboxamide | 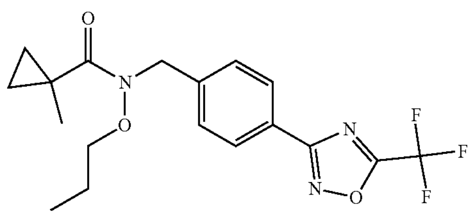 [SMILES: CCCON(Cc1ccc(-c2noc(C(F)(F)F)n2)cc1)C(=O)C1(C)CC1] | 1.98 | 383.1 | B | |
| 1.303 | N-propoxy-N-[[4-[5-(trifluoromethyl)-1,2,4-oxadiazol-3-yl]phenyl]methyl]-propanamide | 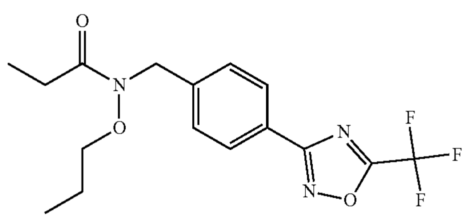 [SMILES: CCCON(Cc1ccc(-c2noc(C(F)(F)F)n2)cc1)C(=O)CC] | 1.90 | 357.1 | B | |
| 1.304 | 2-methyl-N-propoxy-N-[[4-[5-(trifluoromethyl)-1,2,4-oxadiazol-3-yl]phenyl]methyl]-prop-2-enamide | 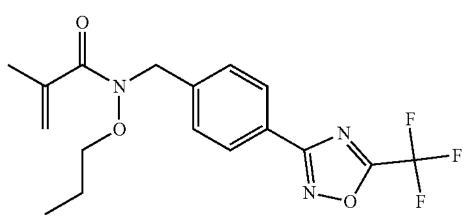 [SMILES: C=C(C)C(=O)N(Cc1ccc(-c2noc(C(F)(F)F)n2)cc1)OCCC] | 1.91 | 369.1 | B | |
| 1.305 | N-propoxy-N-[[4-[5-(trifluoromethyl)-1,2,4-oxadiazol-3-yl]phenyl]methyl]-prop-2-ynamide | 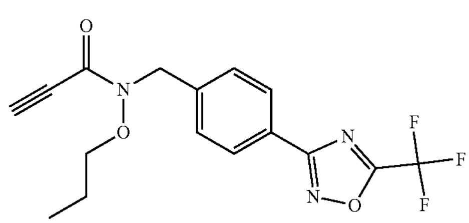 [SMILES: C#CC(=O)N(Cc1ccc(-c2noc(C(F)(F)F)n2)cc1)OCCC] | 1.79 | 353.1 | B | |
| 1.306 | [2-oxo-2-[propoxy-[[4-[5-(trifluoromethyl)-1,2,4-oxadiazol-3-yl]phenyl]methyl]-amino]ethyl] acetate | 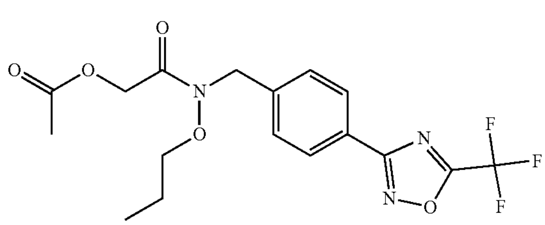 [SMILES: CCCON(Cc1ccc(-c2noc(C(F)(F)F)n2)cc1)C(=O)COC(C)=O] | 1.77 | 401.1 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.307 | 1-fluoro-N-propoxy-N-[[4-[5-(trifluoromethyl)-1,2,4-oxadiazol-3-yl]phenyl]methyl]-cyclopropane-carboxamide | 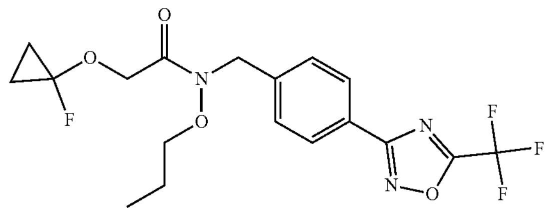 [SMILES: CCCON(Cc1ccc(-c2noc(C(F)(F)F)n2)cc1)C(=O)COC1(F)CC1] | 1.97 | 387.1 | B | |
| 1.308 | 2-methyl-N-propoxy-N-[[4-[5-(trifluoromethyl)-1,2,4-oxadiazol-3-yl]phenyl]methyl]-butanamide | 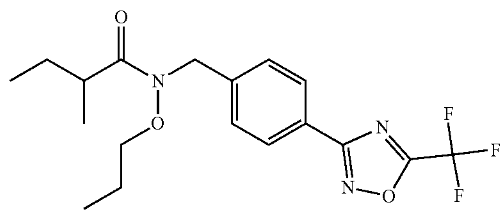 [SMILES: CCCON(Cc1ccc(-c2noc(C(F)(F)F)n2)cc1)C(=O)C(C)CC] | 2.08 | 385.2 | B | |
| 1.309 | 3-methyl-N-propoxy-N-[[4-[5-(trifluoromethyl)-1,2,4-oxadiazol-3-yl]phenyl]methyl]-oxetane-3-carboxamide | 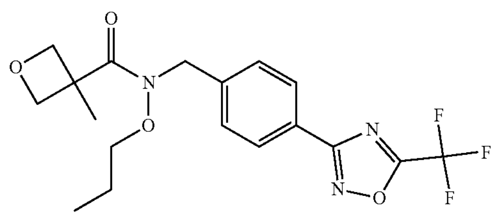 [SMILES: CCCON(Cc1ccc(-c2noc(C(F)(F)F)n2)cc1)C(=O)C1(C)COC1] | 1.79 | 399.1 | B | |
| 1.310 | 4-oxo-N-propoxy-N-[[4-[5-(trifluoromethyl)-1,2,4-oxadiazol-3-yl]phenyl]methyl]-pent-2-enamide | 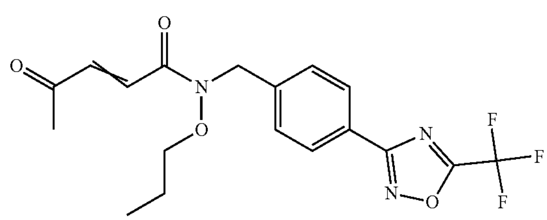 [SMILES: CCCON(Cc1ccc(-c2noc(C(F)(F)F)n2)cc1)C(=O)C=CC(C)=O] | 1.80 | 397.1 | B | |
| 1.311 | 2-(methoxymethyl)-N-propoxy-N-[[4-[5-(trifluoromethyl)-1,2,4-oxadiazol-3-yl]phenyl]methyl]-butanamide | 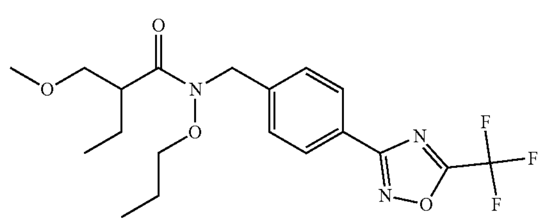 [SMILES: CCCON(Cc1ccc(-c2noc(C(F)(F)F)n2)cc1)C(=O)C(CC)COC] | 2.01 | 415.2 | B | |
| 1.312 | N-propoxy-N-[[4-[5-(trifluoromethyl)-1,2,4-oxadiazol-3-yl]phenyl]methyl]-tetrahydrofuran-2-carboxamide | 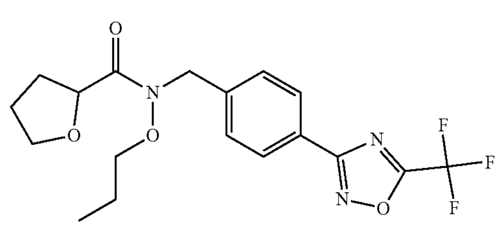 [SMILES: CCCON(Cc1ccc(-c2noc(C(F)(F)F)n2)cc1)C(=O)C1CCCO1] | 1.81 | 399.1 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.313 | 1-cyano-N-propoxy-N-[[4-[5-(trifluoromethyl)-1,2,4-oxadiazol-3-yl]phenyl]methyl]-cyclopropane-carboxamide | 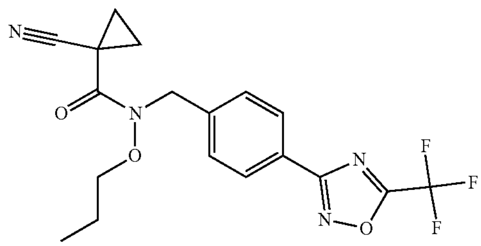 [SMILES: CCCON(Cc1ccc(-c2noc(C(F)(F)F)n2)cc1)C(=O)C1(C#N)CC1] | 1.84 | 394.1 | B | |
| 1.314 | 1-acetyl-N-propoxy-N-[[4-[5-(trifluoromethyl)-1,2,4-oxadiazol-3-yl]phenyl]methyl]-pyrrolidine-2-carboxamide | 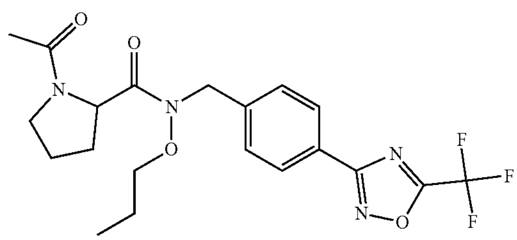 [SMILES: CCCON(Cc1ccc(-c2noc(C(F)(F)F)n2)cc1)C(=O)C1CCCN1C(C)=O] | 1.69 | 440.2 | B | |
| 1.315 | 2-fluoro-N-propoxy-N-[[4-[5-(trifluoromethyl)-1,2,4-oxadiazol-3-yl]phenyl]methyl]-cyclopropane-carboxamide | 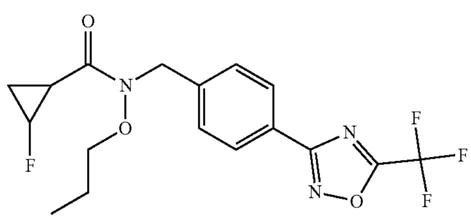 [SMILES: CCCON(Cc1ccc(-c2noc(C(F)(F)F)n2)cc1)C(=O)C1CC1F] | 1.83 | 387.1 | B | |
| 1.316 | 2-methoxy-N-propoxy-N-[[4-[5-(trifluoromethyl)-1,2,4-oxadiazol-3-yl]phenyl]methyl]-propanamide | 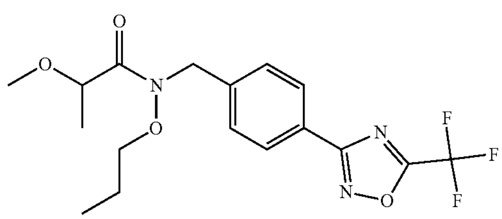 | 1.80 | 387.1 | B | |
| 1.317 | N-propoxy-N-[[4-[5-(trifluoromethyl)-1,2,4-oxadiazol-3-yl]phenyl]methyl]-1,3-dioxolane-2-carboxamide | 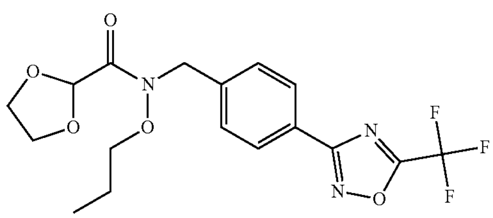 | 1.76 | 401.1 | B | |
| 1.318 | 3,3,3-trifluoro-N-propoxy-N-[[4-[5-(trifluoromethyl)-1,2,4-oxadiazol-3-yl]phenyl]methyl]-propanamide | 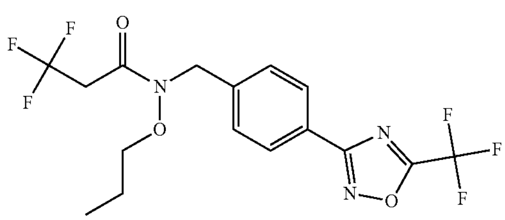 [SMILES: CCCON(Cc1ccc(-c2noc(C(F)(F)F)n2)cc1)C(=O)CC(F)(F)F] | 1.93 | 411.1 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.319 | N-propoxy-N-[[4-[5-(trifluoromethyl)-1,2,4-oxadiazol-3-yl]phenyl]methyl]-cyclopropane-carboxamide | 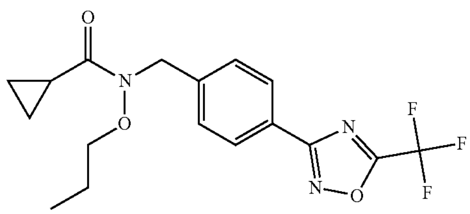 [SMILES: CCCON(Cc1ccc(-c2noc(C(F)(F)F)n2)cc1)C(=O)C1CC1] | 1.92 | 369.1 | B | |
| 1.320 | N-propoxy-N-[[4-[5-(trifluoromethyl)-1,2,4-oxadiazol-3-yl]phenyl]methyl]-acetamide | 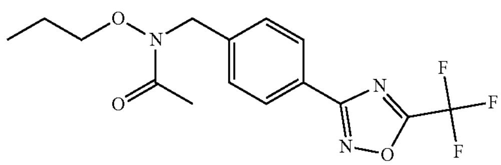 [SMILES: CCCON(Cc1ccc(-c2noc(C(F)(F)F)n2)cc1)C(C)=O] | 1.77 | 343.1 | B | |
| 1.321 | 4-methoxy-N-propoxy-N-[[4-[5-(trifluoromethyl)-1,2,4-oxadiazol-3-yl]phenyl]methyl]-butanamide | 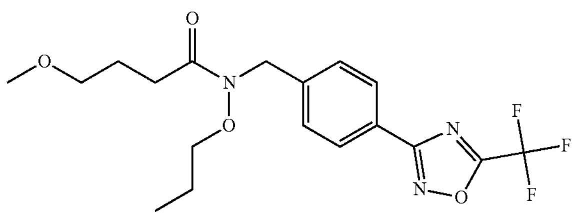 [SMILES: CCCON(Cc1ccc(-c2noc(C(F)(F)F)n2)cc1)C(=O)CCCOC] | 1.87 | 401.2 | B | |
| 1.322 | N-propoxy-N-[[4-[5-(trifluoromethyl)-1,2,4-oxadiazol-3-yl]phenyl]methyl]-pentanamide | 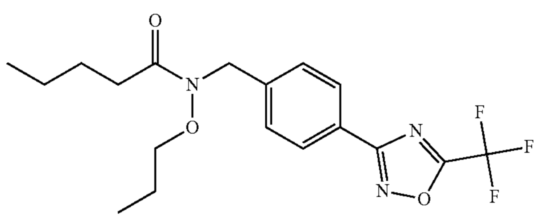 [SMILES: CCCCC(=O)N(Cc1ccc(-c2noc(C(F)(F)F)n2)cc1)OCCC] | 2.09 | 385.2 | B | |
| 1.323 | N-(2-methoxyethyl)-N-[[4-[5-(trifluoromethyl)-1,2,4-oxadiazol-3-yl]phenyl]methyl]but-2-ynamide | 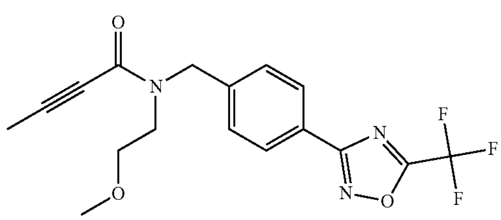 [SMILES: CC#CC(=O)N(CCOC)Cc1ccc(-c2noc(C(F)(F)F)n2)cc1] | 1.65 | 368.3 | B | |
| 1.324 | N-(2-methoxyethyl)-N-[[4-[5-(trifluoromethyl)-1,2,4-oxadiazol-3-yl]phenyl]methyl]-tetrahydropyran-2-carboxamide | 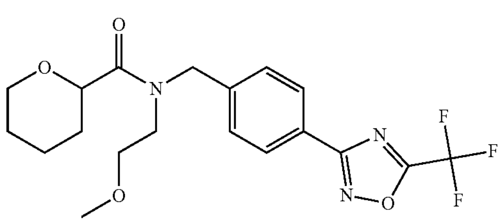 [SMILES: COCCN(Cc1ccc(-c2noc(C(F)(F)F)n2)cc1)C(=O)C1CCCCO1] | 1.73 | 413.2 | B | |
| 1.325 | N-(2-methoxyethyl)-2-methyl-N-[[4-[5-(trifluoromethyl)-1,2,4-oxadiazol-3-yl]phenyl]methyl]-propanamide | 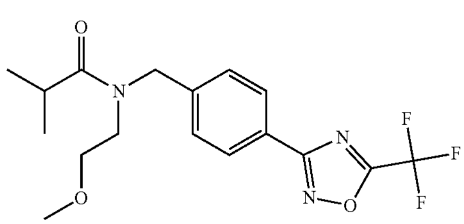 [SMILES: COCCN(Cc1ccc(-c2noc(C(F)(F)F)n2)cc1)C(=O)C(C)C] | 1.73 | 372.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.326 | N-(2-methoxyethyl)-N-[[4-[5-(trifluoromethyl)-1,2,4-oxadiazol-3-yl]phenyl]methyl]but-2-enamide | 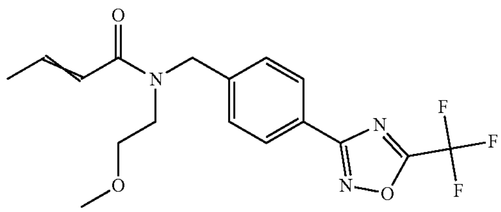 [SMILES: CC=CC(=O)N(CCOC)Cc1ccc(-c2noc(C(F)(F)F)n2)cc1] | 1.66 | 370.3 | B | |
| 1.327 | 2,2-difluoro-N-(2-methoxyethyl)-N-[[4-[5-(trifluoromethyl)-1,2,4-oxadiazol-3-yl]phenyl]methyl]-cyclopropane-carboxamide | 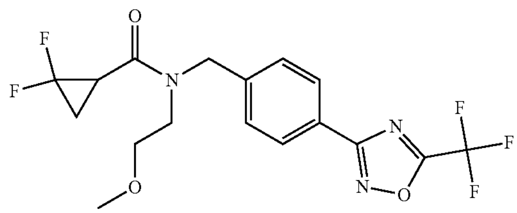 [SMILES: COCCN(Cc1ccc(-c2noc(C(F)(F)F)n2)cc1)C(=O)C1CC1(F)F] | 1.73 | 406.3 | B | |
| 1.328 | 2-methoxy-N-(2-methoxyethyl)-N-[[4-[5-(trifluoromethyl)-1,2,4-oxadiazol-3-yl]phenyl]methyl]-acetamide | 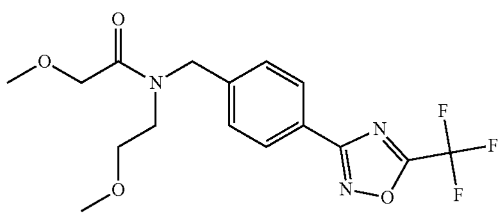 [SMILES: COCCN(Cc1ccc(-c2noc(C(F)(F)F)n2)cc1)C(=O)COC] | 1.51 | 374.3 | B | |
| 1.329 | N-(2-methoxyethyl)-N-[[4-[5-(trifluoromethyl)-1,2,4-oxadiazol-3-yl]phenyl]methyl]-butanamide | 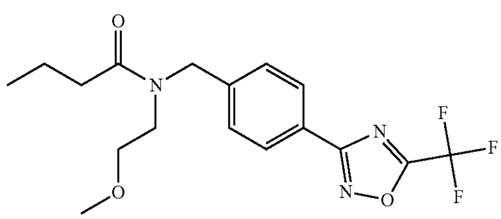 [SMILES: CCCC(=O)N(CCOC)Cc1ccc(-c2noc(C(F)(F)F)n2)cc1] | 1.74 | 372.3 | B | |
| 1.330 | N-(2-methoxyethyl)-2-methyl-N-[[4-[5-(trifluoromethyl)-1,2,4-oxadiazol-3-yl]phenyl]methyl]-but-2-enamide | 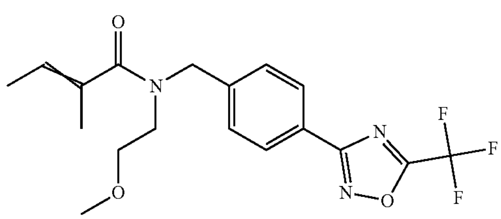 [SMILES: CC=C(C)C(=O)N(CCOC)Cc1ccc(-c2noc(C(F)(F)F)n2)cc1] | 1.75 | 384.4 | B | |
| 1.331 | 2-cyclopropyl-N-(2-methoxyethyl)-N-[[4-[5-(trifluoromethyl)-1,2,4-oxadiazol-3-yl]phenyl]methyl]-acetamide | 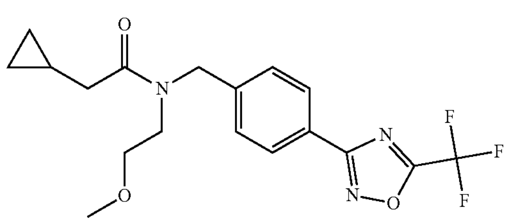 [SMILES: COCCN(Cc1ccc(-c2noc(C(F)(F)F)n2)cc1)C(=O)CC1CC1] | 1.73 | 384.4 | B | |
| 1.332 | N-(2-methoxyethyl)-N-[[4-[5-(trifluoromethyl)-1,2,4-oxadiazol-3-yl]phenyl]methyl]-cyclopentane-carboxamide | 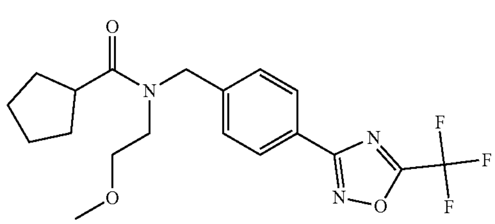 [SMILES: COCCN(Cc1ccc(-c2noc(C(F)(F)F)n2)cc1)C(=O)C1CCCC1] | 1.88 | 398.4 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.333 | N-(2-methoxyethyl)-N-[[4-[5-(trifluoromethyl)-1,2,4-oxadiazol-3-yl]phenyl]methyl]-cyclopentene-1-carboxamide | 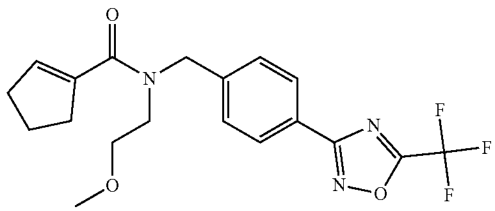 [SMILES: COCCN(Cc1ccc(-c2noc(C(F)(F)F)n2)cc1)C(=O)C1=CCCC1] | 1.8 | 396.4 | B | |
| 1.334 | N-(2-methoxyethyl)-N-[[4-[5-(trifluoromethyl)-1,2,4-oxadiazol-3-yl]phenyl]methyl]-thietane-3-carboxamide | 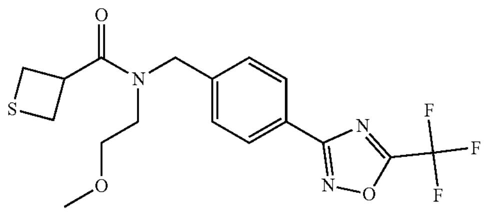 [SMILES: COCCN(Cc1ccc(-c2noc(C(F)(F)F)n2)cc1)C(=O)C1CSC1] | 1.73 | 402.3 | B | |
| 1.335 | 3-methoxy-N-(2-methoxyethyl)-N-[[4-[5-(trifluoromethyl)-1,2,4-oxadiazol-3-yl]phenyl]methyl]-propanamide | 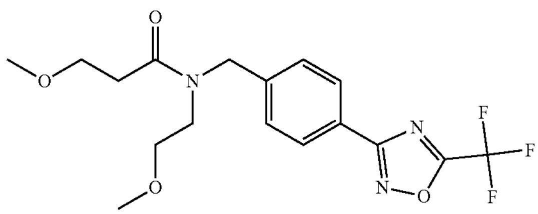 [SMILES: COCCC(=O)N(CCOC)Cc1ccc(-c2noc(C(F)(F)F)n2)cc1] | 1.57 | 388.4 | B | |
| 1.336 | N-(2-methoxyethyl)-3-methyl-N-[[4-[5-(trifluoromethyl)-1,2,4-oxadiazol-3-yl]phenyl]methyl]-butanamide | 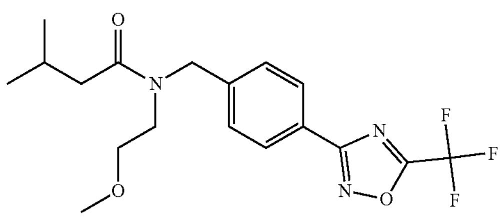 [SMILES: COCCN(Cc1ccc(-c2noc(C(F)(F)F)n2)cc1)C(=O)CC(C)C] | 1.84 | 386.4 | B | |
| 1.337 | N-(2-methoxyethyl)-N-[[4-[5-(trifluoromethyl)-1,2,4-oxadiazol-3-yl]phenyl]methyl]-cyclobutane-carboxamide | 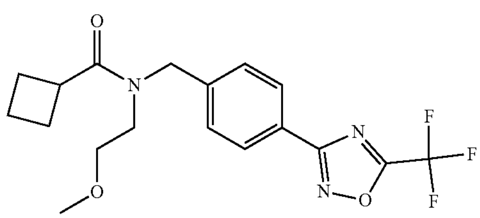 [SMILES: COCCN(Cc1ccc(-c2noc(C(F)(F)F)n2)cc1)C(=O)C1CCC1] | 1.79 | 384.4 | B | |
| 1.338 | 4,4,4-trifluoro-N-(2-methoxyethyl)-N-[[4-[5-(trifluoromethyl)-1,2,4-oxadiazol-3-yl]phenyl]methyl]but-2-enamide | 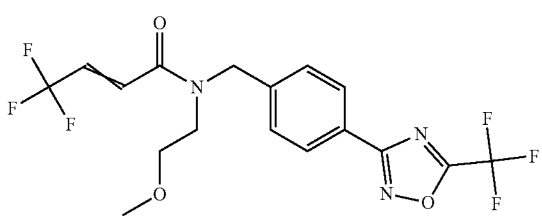 [SMILES: COCCN(Cc1ccc(-c2noc(C(F)(F)F)n2)cc1)C(=O)C=CC(F)(F)F] | 1.83 | 424.3 | B | |
| 1.339 | 2-ethoxy-N-(2-methoxyethyl)-N-[[4-[5-(trifluoromethyl)-1,2,4-oxadiazol-3-yl]phenyl]methyl]-acetamide | 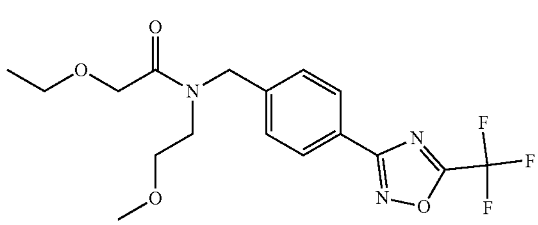 [SMILES: CCOCC(=O)N(CCOC)Cc1ccc(-c2noc(C(F)(F)F)n2)cc1] | 1.61 | 388.4 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.340 | 2-(2-methoxyethoxy)-N-(2-methoxyethyl)-N-[[4-[5-(trifluoromethyl)-1,2,4-oxadiazol-3-yl]phenyl]methyl]-acetamide | 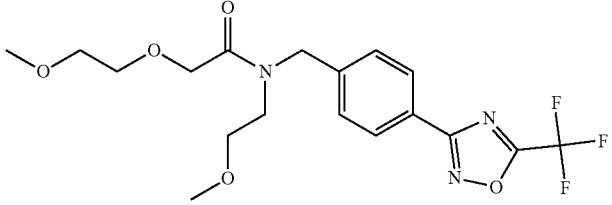 [SMILES: COCCOCC(=O)N(CCOC)Cc1ccc(-c2noc(C(F)(F)F)n2)cc1] | 1.53 | 418.4 | B | |
| 1.341 | N-(2-methoxyethyl)-2-methyl-N-[[4-[5-(trifluoromethyl)-1,2,4-oxadiazol-3-yl]phenyl]methyl]-cyclopropane-carboxamide | 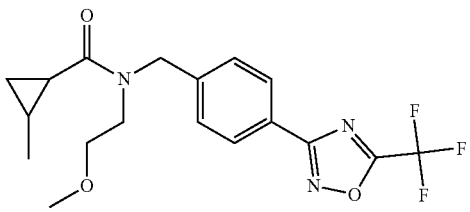 [SMILES: COCCN(Cc1ccc(-c2noc(C(F)(F)F)n2)cc1)C(=O)C1CC1C] | 1.76 | 384.4 | B | |
| 1.342 | N-(2-methoxyethyl)-3,3-dimethyl-N-[[4-[5-(trifluoromethyl)-1,2,4-oxadiazol-3-yl]phenyl]methyl]-butanamide | 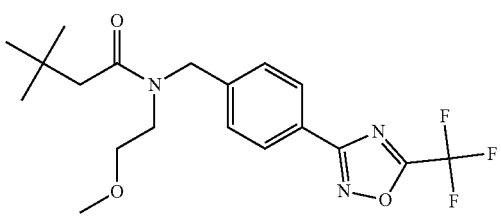 [SMILES: COCCN(Cc1ccc(-c2noc(C(F)(F)F)n2)cc1)C(=O)CC(C)(C)C] | 1.95 | 400.4 | B | |
| 1.343 | N-(2-methoxyethyl)-N-[[4-[5-(trifluoromethyl)-1,2,4-oxadiazol-3-yl]phenyl]methyl]prop-2-enamide | 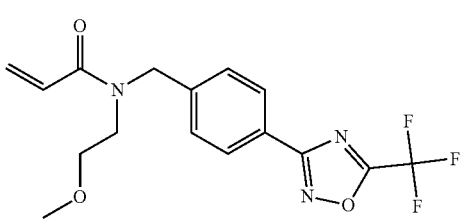 [SMILES: C=CC(=O)N(CCOC)Cc1ccc(-c2noc(C(F)(F)F)n2)cc1] | 1.59 | 356.3 | B | |
| 1.344 | N-(2-methoxyethyl)-1-methyl-N-[[4-[5-(trifluoromethyl)-1,2,4-oxadiazol-3-yl]phenyl]methyl]-cyclopropane-carboxamide | 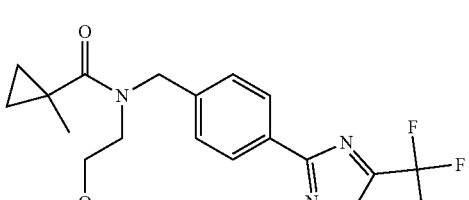 | 1.73 | 384.3 | B | |
| 1.345 | N-(2-methoxyethyl)-N-[[4-[5-(trifluoromethyl)-1,2,4-oxadiazol-3-yl]phenyl]methyl]-propanamide | 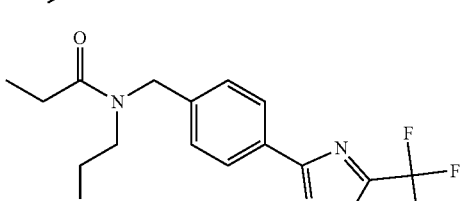 | 1.62 | 358.3 | B | |
| 1.346 | N-(2-methoxyethyl)-2-methyl-N-[[4-[5-(trifluoromethyl)-1,2,4-oxadiazol-3-yl]phenyl]methyl]prop-2-enamide | 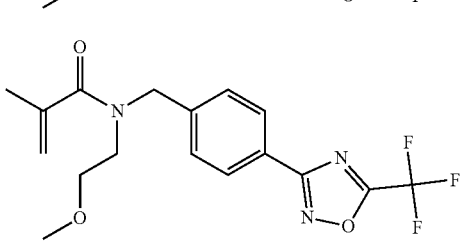 | 1.69 | 370.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.347 | N-(2-methoxyethyl)-N-[[4-[5-(trifluoromethyl)-1,2,4-oxadiazol-3-yl]phenyl]methyl]prop-2-ynamide | 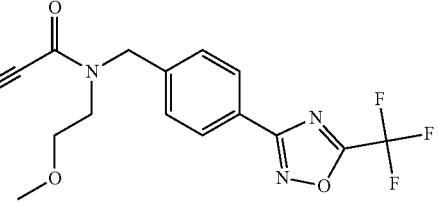 | 1.59 | 354.3 | B | |
| 1.348 | [2-[2-methoxyethyl-[[4-[5-(trifluoromethyl)-1,2,4-oxadiazol-3-yl]phenyl]methyl]-amino]-2-oxo-ethyl] acetate | 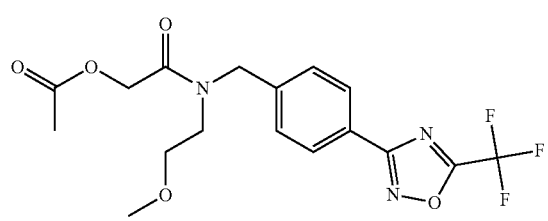 [SMILES: COCCN(Cc1ccc(-c2noc(C(F)(F)F)n2)cc1)C(=O)COC(C)=O] | 1.54 | 402.3 | B | |
| 1.349 | 1-fluoro-N-(2-methoxyethyl)-N-[[4-[5-(trifluoromethyl)-1,2,4-oxadiazol-3-yl]phenyl]methyl]-cyclopropane-carboxamide | 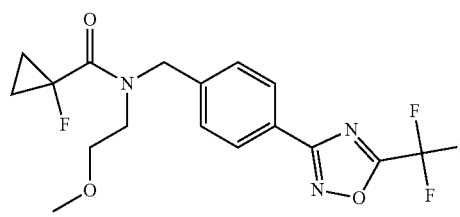 | 1.79 | 388.3 | B | |
| 1.350 | N-(2-methoxyethyl)-2-methyl-N-[[4-[5-(trifluoromethyl)-1,2,4-oxadiazol-3-yl]phenyl]methyl]-butanamide | 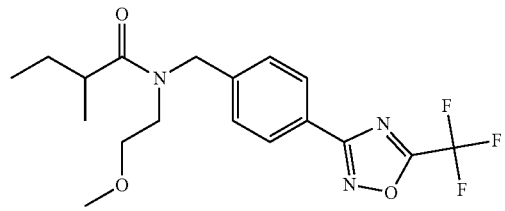 [SMILES: CCC(C)C(=O)N(CCOC)Cc1ccc(-c2noc(C(F)(F)F)n2)cc1] | 1.83 | 386.4 | B | |
| 1.351 | N-(2-methoxyethyl)-3-methyl-N-[[4-[5-(trifluoromethyl)-1,2,4-oxadiazol-3-yl]phenyl]methyl]-oxetane-3-carboxamide | 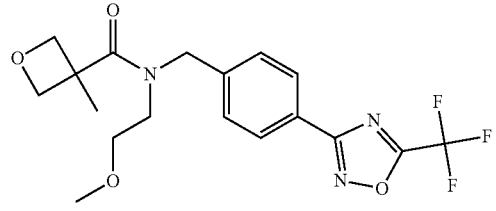 [SMILES: COCCN(Cc1ccc(-c2noc(C(F)(F)F)n2)cc1)C(=O)C1(C)COC1] | 1.56 | 400.4 | B | |
| 1.352 | N-(2-methoxyethyl)-4-oxo-N-[[4-[5-(trifluoromethyl)-1,2,4-oxadiazol-3-yl]phenyl]methyl]-pent-2-enamide | 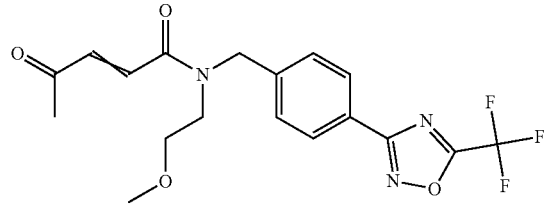 [SMILES: COCCN(Cc1ccc(-c2noc(C(F)(F)F)n2)cc1)C(=O)C=CC(C)=O] | 1.56 | 398.3 | B | |
| 1.353 | N-(2-methoxyethyl)-2-(methoxymethyl)-N-[[4-[5-(trifluoromethyl)-1,2,4-oxadiazol-3-yl]phenyl]methyl]-butanamide | 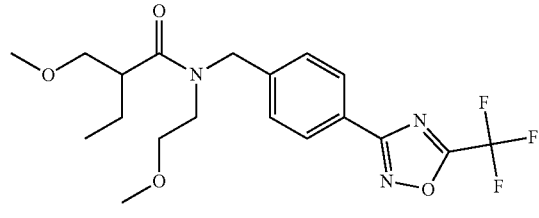 [SMILES: CCC(COC)C(=O)N(CCOC)Cc1ccc(-c2noc(C(F)(F)F)n2)cc1] | 1.81 | 416.4 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.354 | 1-formamido-N-(2-methoxyethyl)-N-[[4-[5-(trifluoromethyl)-1,2,4-oxadiazol-3-yl]phenyl]methyl]-cyclopropane-carboxamide | 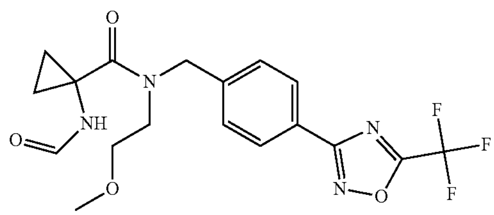 [SMILES: COCCN(Cc1ccc(-c2noc(C(F)(F)F)n2)cc1)C(=O)C1(NC=O)CC1] | 1.36 | 413.4 | B | |
| 1.355 | N-(2-methoxyethyl)-N-[[4-[5-(trifluoromethyl)-1,2,4-oxadiazol-3-yl]phenyl]methyl]-tetrahydrofuran-2-carboxamide | 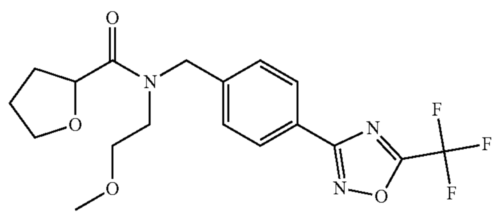 [SMILES: COCCN(Cc1ccc(-c2noc(C(F)(F)F)n2)cc1)C(=O)C1CCCO1] | 1.61 | 400.4 | B | |
| 1.356 | 1-cyano-N-(2-methoxyethyl)-N-[[4-[5-(trifluoromethyl)-1,2,4-oxadiazol-3-yl]phenyl]methyl]-cyclopropane-carboxamide | 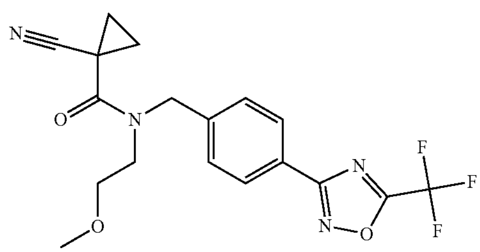 [SMILES: COCCN(Cc1ccc(-c2noc(C(F)(F)F)n2)cc1)C(=O)C1(C#N)CC1] | 1.68 | 395.3 | B | |
| 1.357 | 1-acetyl-N-(2-methoxyethyl)-N-[[4-[5-(trifluoromethyl)-1,2,4-oxadiazol-3-yl]phenyl]methyl]-pyrrolidine-2-carboxamide | 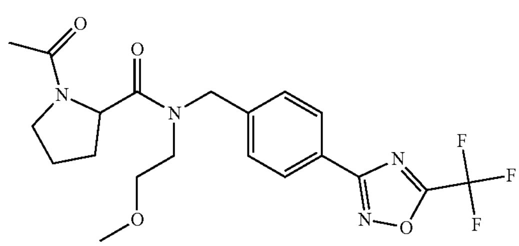 [SMILES: COCCN(Cc1ccc(-c2noc(C(F)(F)F)n2)cc1)C(=O)C1CCCN1C(C)=O] | 1.47 | 441.4 | B | |
| 1.358 | 2-fluoro-N-(2-methoxyethyl)-N-[[4-[5-(trifluoromethyl)-1,2,4-oxadiazol-3-yl]phenyl]methyl]-cyclopropane-carboxamide | 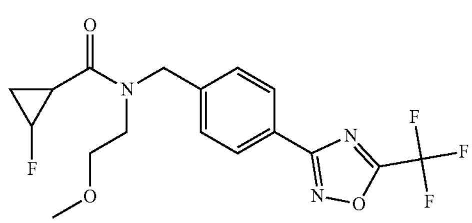 [SMILES: COCCN(Cc1ccc(-c2noc(C(F)(F)F)n2)cc1)C(=O)C1CC1F] | 1.61 | 388.3 | B | |
| 1.359 | 2-methoxy-N-(2-methoxyethyl)-N-[[4-[5-(trifluoromethyl)-1,2,4-oxadiazol-3-yl]phenyl]methyl]-propanamide | 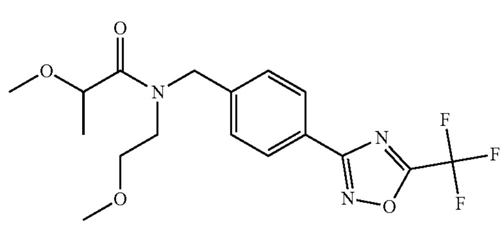 [SMILES: COCCN(Cc1ccc(-c2noc(C(F)(F)F)n2)cc1)C(=O)C(C)OC] | 1.58 | 388.4 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.360 | N-(2-methoxyethyl)-N-[[4-[5-(trifluoromethyl)-1,2,4-oxadiazol-3-yl]phenyl]methyl]-1,3-dioxolane-2-carboxamide | 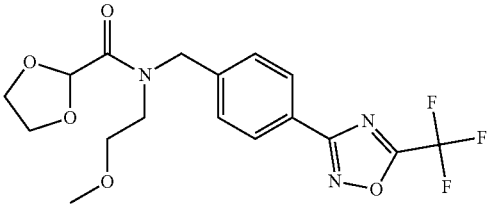 [SMILES: COCCN(Cc1ccc(-c2noc(C(F)(F)F)n2)cc1)C(=O)C1OCCO1] | 1.55 | 402.3 | B | |
| 1.361 | 3,3,3-trifluoro-N-(2-methoxyethyl)-N-[[4-[5-(trifluoromethyl)-1,2,4-oxadiazol-3-yl]phenyl]methyl]-propanamide | 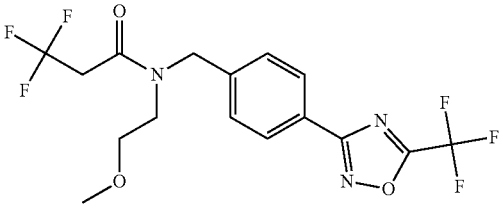 | 1.73 | 412.3 | B | |
| 1.362 | N-(2-methoxyethyl)-N-[[4-[5-(trifluoromethyl)-1,2,4-oxadiazol-3-yl]phenyl]methyl]-furan-3-carboxamide | 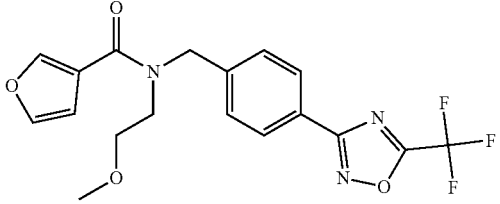 [SMILES: COCCN(Cc1ccc(-c2noc(C(F)(F)F)n2)cc1)C(=O)c1ccoc1] | 1.67 | 396.3 | B | |
| 1.363 | N-(2-methoxyethyl)-N-[[4-[5-(trifluoromethyl)-1,2,4-oxadiazol-3-yl]phenyl]methyl]-cyclopropane-carboxamide | 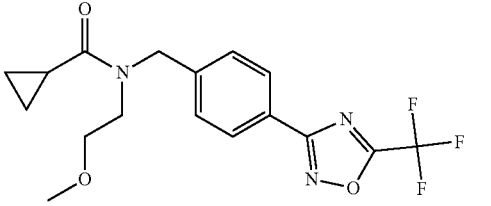 [SMILES: COCCN(Cc1ccc(-c2noc(C(F)(F)F)n2)cc1)C(=O)C1CC1] | 1.66 | 370.3 | B | |
| 1.364 | N-(2-methoxyethyl)-N-[[4-[5-(trifluoromethyl)-1,2,4-oxadiazol-3-yl]phenyl]methyl]-acetamide | 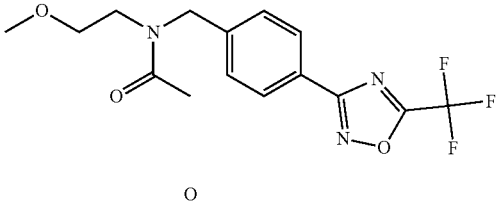 | 1.5 | 344.3 | B | |
| 1.365 | 4-methoxy-N-(2-methoxyethyl)-N-[[4-[5-(trifluoromethyl)-1,2,4-oxadiazol-3-yl]phenyl]methyl]-butanamide | 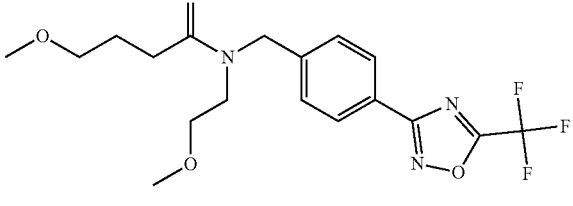 | 1.62 | 402.4 | B | |
| 1.366 | N-(2-methoxyethyl)-N-[[4-[5-(trifluoromethyl)-1,2,4-oxadiazol-3-yl]phenyl]methyl]-pentanamide | 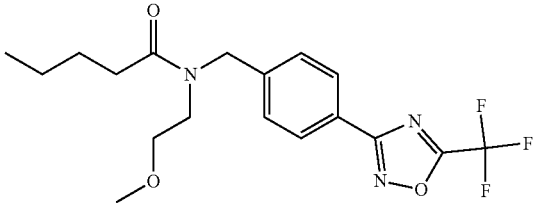 [SMILES: CCCCC(=O)N(CCOC)Cc1ccc(-c2noc(C(F)(F)F)n2)cc1] | 1.84 | 386.4 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.367 | N-sec-butyl-N-[[4-[5-(trifluoromethyl)-1,2,4-oxadiazol-3-yl]phenyl]methyl]-but-2-ynamide | 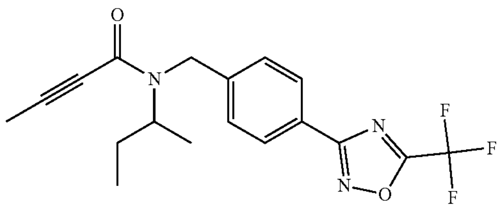 [SMILES: CC#CC(=O)N(Cc1ccc(-c2noc(C(F)(F)F)n2)cc1)C(C)CC] | 1.87 | 365.1 | B | |
| 1.368 | N-sec-butyl-N-[[4-[5-(trifluoromethyl)-1,2,4-oxadiazol-3-yl]phenyl]methyl]-tetrahydropyran-2-carboxamide | 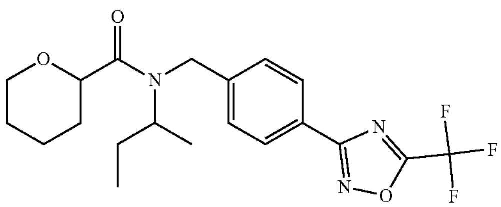 [SMILES: CCC(C)N(Cc1ccc(-c2noc(C(F)(F)F)n2)cc1)C(=O)C1CCCCO1] | 1.97 | 411.2 | B | |
| 1.369 | 2-methyl-N-sec-butyl-N-[[4-[5-(trifluoromethyl)-1,2,4-oxadiazol-3-yl]phenyl]methyl]-propanamide | 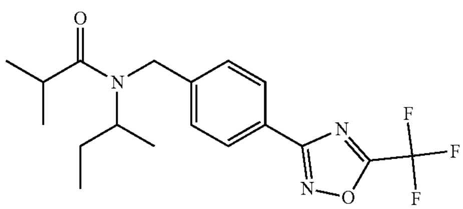 [SMILES: CCC(C)N(Cc1ccc(-c2noc(C(F)(F)F)n2)cc1)C(=O)C(C)C] | 1.95 | 369.2 | B | |
| 1.370 | N-sec-butyl-N-[[4-[5-(trifluoromethyl)-1,2,4-oxadiazol-3-yl]phenyl]methyl]but-2-enamide | 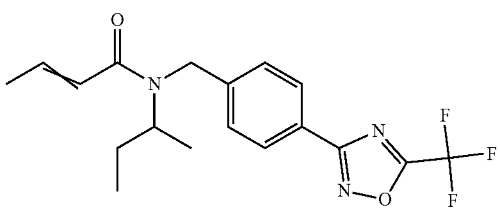 [SMILES: CC=CC(=O)N(Cc1ccc(-c2noc(C(F)(F)F)n2)cc1)C(C)CC] | 1.88 | 367.2 | B | |
| 1.371 | 2,2-difluoro-N-sec-butyl-N-[[4-[5-(trifluoromethyl)-1,2,4-oxadiazol-3-yl]phenyl]methyl]-cyclopropane-carboxamide | 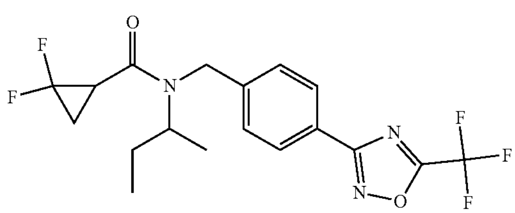 [SMILES: CCC(C)N(Cc1ccc(-c2noc(C(F)(F)F)n2)cc1)C(=O)C1CC1(F)F] | 1.92 | 403.1 | B | |
| 1.372 | 2-methoxy-N-sec-butyl-N-[[4-[5-(trifluoromethyl)-1,2,4-oxadiazol-3-yl]phenyl]methyl]-acetamide | 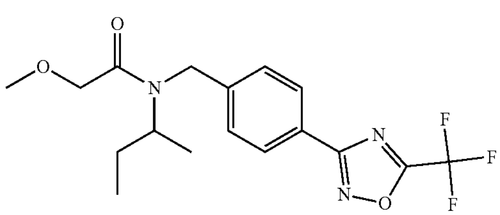 [SMILES: CCC(C)N(Cc1ccc(-c2noc(C(F)(F)F)n2)cc1)C(=O)COC] | 1.73 | 371.1 | B | |
| 1.373 | N-sec-butyl-N-[[4-[5-(trifluoromethyl)-1,2,4-oxadiazol-3-yl]phenyl]methyl]-butanamide | 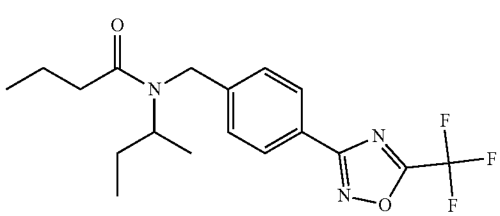 [SMILES: CCCC(=O)N(Cc1ccc(-c2noc(C(F)(F)F)n2)cc1)C(C)CC] | 1.96 | 369.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.374 | 2-methyl-N-sec-butyl-N-[[4-[5-(trifluoromethyl)-1,2,4-oxadiazol-3-yl]phenyl]methyl]but-2-enamide | 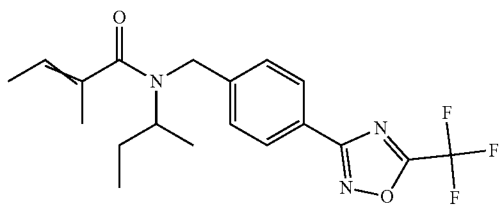 [SMILES: CC=C(C)C(=O)N(Cc1ccc(-c2noc(C(F)(F)F)n2)cc1)C(C)CC] | 1.97 | 381.2 | B | |
| 1.375 | 2-cyclopropyl-N-sec-butyl-N-[[4-(5-(trifluoromethyl)-1,2,4-oxadiazol-3-yl]phenyl]methyl]-acetamide | 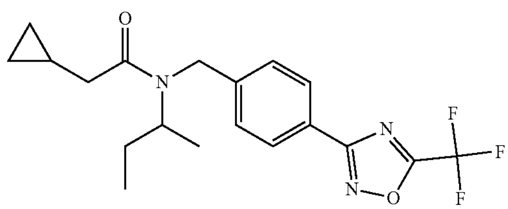 [SMILES: CCC(C)N(Cc1ccc(-c2noc(C(F)(F)F)n2)cc1)C(=O)CC1CC1] | 1.94 | 381.2 | B | |
| 1.376 | N-sec-butyl-N-[[4-[5-(trifluoromethyl)-1,2,4-oxadiazol-3-yl]phenyl]methyl]-cyclopentane-carboxamide | 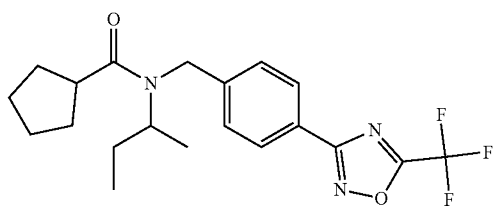 [SMILES: CCC(C)N(Cc1ccc(-c2noc(C(F)(F)F)n2)cc1)C(=O)C1CCCC1] | 2.10 | 395.2 | B | |
| 1.377 | N-sec-butyl-N-[[4-[5-(trifluoromethyl)-1,2,4-oxadiazol-3-yl]phenyl]methyl]-cyclopentene-1-carboxamide | 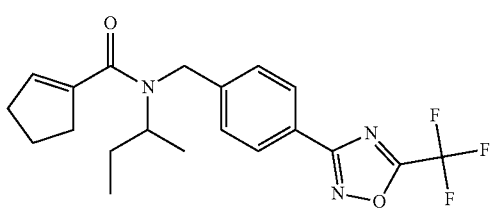 [SMILES: CCC(C)N(Cc1ccc(-c2noc(C(F)(F)F)n2)cc1)C(=O)C1=CCCC1] | 2.01 | 393.2 | B | |
| 1.378 | N-sec-butyl-N-[[4-[5-(trifluoromethyl)-1,2,4-oxadiazol-3-yl]phenyl]methyl]-thietane-3-carboxamide | 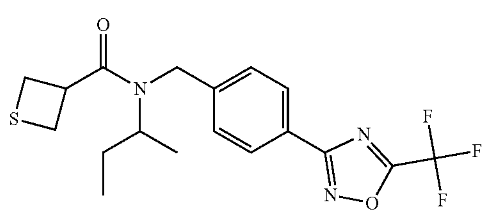 [SMILES: CCC(C)N(Cc1ccc(-c2noc(C(F)(F)F)n2)cc1)C(=O)C1CSC1] | 1.93 | 399.1 | B | |
| 1.379 | 3-methoxy-N-sec-butyl-N-[[4-[5-(trifluoromethyl)-1,2,4-oxadiazol-3-yl]phenyl]methyl]-propanamide | 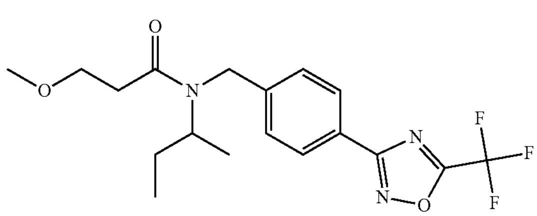 [SMILES: CCC(C)N(Cc1ccc(-c2noc(C(F)(F)F)n2)cc1)C(=O)CCOC] | 1.80 | 385.2 | B | |
| 1.380 | 3-methyl-N-sec-butyl-N-[[4-[5-(trifluoromethyl)-1,2,4-oxadiazol-3-yl]phenyl]methyl]-butanamide | 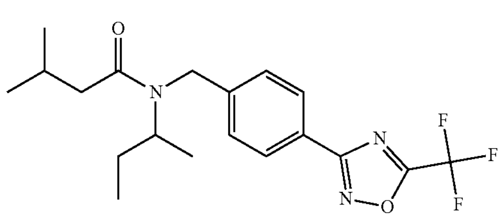 [SMILES: CCC(C)N(Cc1ccc(-c2noc(C(F)(F)F)n2)cc1)C(=O)CC(C)C] | 2.05 | 383.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.381 | N-sec-butyl-N-[[4-[5-(trifluoromethyl)-1,2,4-oxadiazol-3-yl]phenyl]methyl]-cyclobutane-carboxamide | 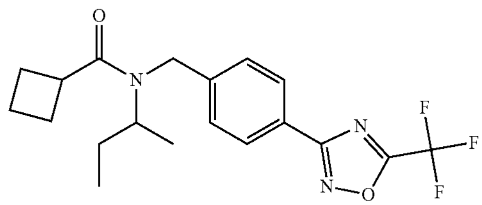 [SMILES: CCC(C)N(Cc1ccc(-c2noc(C(F)(F)F)n2)cc1)C(=O)C1CCC1] | 2.01 | 381.2 | B | |
| 1.382 | 4,4,4-trifluoro-N-sec-butyl-N-[[4-[5-(trifluoromethyl)-1,2,4-oxadiazol-3-yl]phenyl]methyl]but-2-enamide | 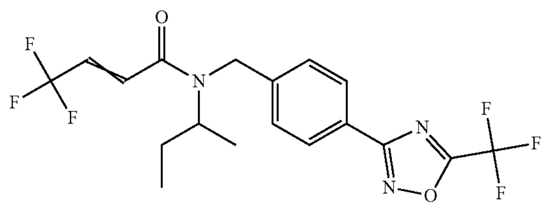 [SMILES: CCC(C)N(Cc1ccc(-c2noc(C(F)(F)F)n2)cc1)C(=O)C=CC(F)(F)F] | 2.00 | 421.1 | B | |
| 1.383 | 2-ethoxy-N-sec-butyl-N-[[4-[5-(trifluoromethyl)-1,2,4-oxadiazol-3-yl]phenyl]methyl]-acetamide | 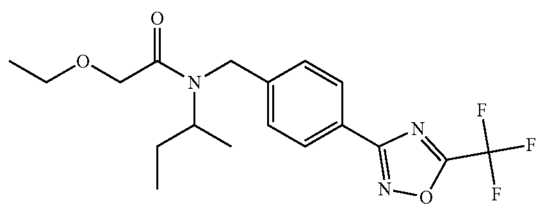 [SMILES: CCOCC(=O)N(Cc1ccc(-c2noc(C(F)(F)F)n2)cc1)C(C)CC] | 1.83 | 385.2 | B | |
| 1.384 | 2-(2-methoxyethoxy)-N-sec-butyl-N-[[4-[5-(trifluoromethyl)-1,2,4-oxadiazol-3-yl]phenyl]methyl]-acetamide | 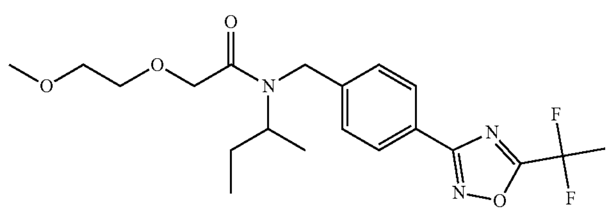 [SMILES: CCC(C)N(Cc1ccc(-c2noc(C(C)(F)F)n2)cc1)C(=O)COCCOC] | 1.74 | 415.2 | B | |
| 1.385 | 2-methyl-N-sec-butyl-N-[[4-[5-(trifluoromethyl)-1,2,4-oxadiazol-3-yl]phenyl]methyl]-cyclopropane-carboxamide | 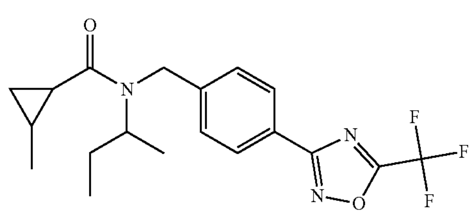 [SMILES: CCC(C)N(Cc1ccc(-c2noc(C(F)(F)F)n2)cc1)C(=O)C1CC1C] | 1.98 | 381.2 | B | |
| 1.386 | 3,3-dimethyl-N-sec-butyl-N-[[4-[5-(trifluoromethyl)-1,2,4-oxadiazol-3-yl]phenyl]methyl]-butanamide | 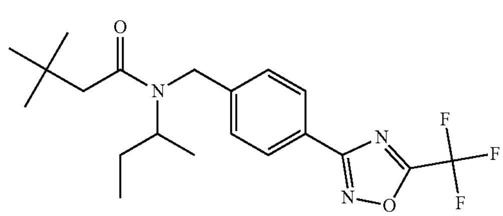 [SMILES: CCC(C)N(Cc1ccc(-c2noc(C(F)(F)F)n2)cc1)C(=O)CC(C)(C)C] | 2.16 | 397.2 | B | |
| 1.387 | N-sec-butyl-N-[[4-[5-(trifluoromethyl)-1,2,4-oxadiazol-3-yl]phenyl]methyl]-prop-2-enamide | 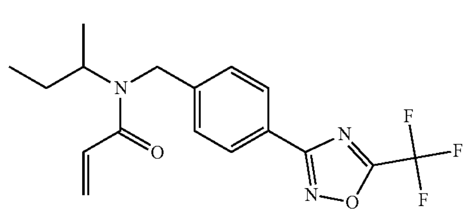 [SMILES: C=CC(=O)N(Cc1ccc(-c2noc(C(F)(F)F)n2)cc1)C(C)CC] | 1.81 | 353.1 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.388 | 1-methyl-N-sec-butyl-N-[[4-[5-(trifluoromethyl)-1,2,4-oxadiazol-3-yl]phenyl]methyl]-cyclopropane-carboxamide | 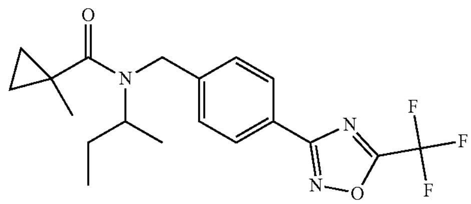 [SMILES: CCC(C)N(Cc1ccc(-c2noc(C(F)(F)F)n2)cc1)C(=O)C1(C)CC1] | 1.95 | 381.2 | B | |
| 1.389 | N-sec-butyl-N-[[4-[5-(trifluoromethyl)-1,2,4-oxadiazol-3-yl]phenyl]methyl]-propanamide | 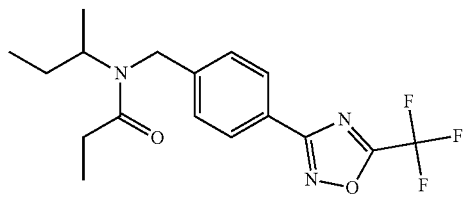 [SMILES: CCC(=O)N(Cc1ccc(-c2noc(C(F)(F)F)n2)cc1)C(C)CC] | 1.85 | 355.2 | B | |
| 1.390 | 2-methyl-N-sec-butyl-N-[[4-[5-(trifluoromethyl)-1,2,4-oxadiazol-3-yl]phenyl]methyl]-prop-2-enamide | 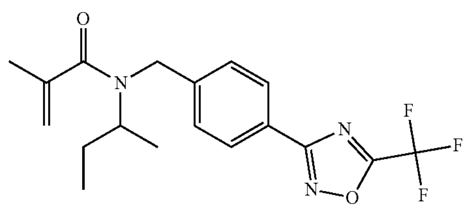 [SMILES: C=C(C)C(=O)N(Cc1ccc(-c2noc(C(F)(F)F)n2)cc1)C(C)CC] | 1.90 | 367.2 | B | |
| 1.391 | N-sec-butyl-N-[[4-[5-(trifluoromethyl)-1,2,4-oxadiazol-3-yl]phenyl]methyl]-prop-2-ynamide | 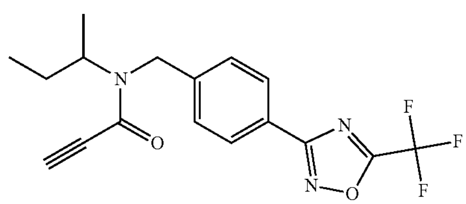 [SMILES: C#CC(=O)N(Cc1ccc(-c2noc(C(F)(F)F)n2)cc1)C(C)CC] | 1.81 | 351.1 | B | |
| 1.392 | [2-oxo-2-[sec-butyl-[[4-[5-(trifluoromethyl)-1,2,4-oxadiazol-3-yl]phenyl]methyl]-amino]ethyl] acetate | 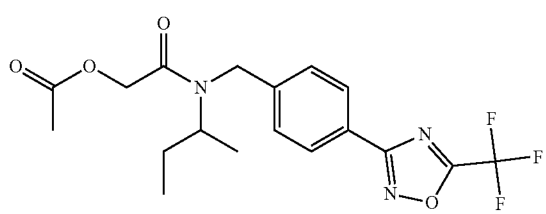 [SMILES: CCC(C)N(Cc1ccc(-c2noc(C(F)(F)F)n2)cc1)C(=O)COC(C)=O] | 1.74 | 399.1 | B | |
| 1.393 | 1-fluoro-N-sec-butyl-N-[[4-[5-(trifluoromethyl)-1,2,4-oxadiazol-3-yl]phenyl]methyl]-cyclopropane-carboxamide | 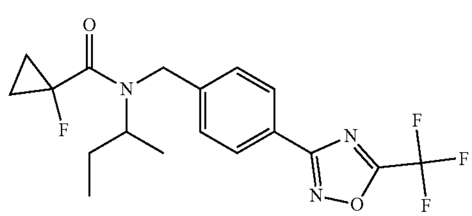 [SMILES: CCC(C)N(Cc1ccc(-c2noc(C(F)(F)F)n2)cc1)C(=O)C1(F)CC1] | 2.00 | 385.1 | B | |
| 1.394 | 2-methyl-N-sec-butyl-N-[[4-[5-(trifluoromethyl)-1,2,4-oxadiazol-3-yl]phenyl]methyl]-butanamide | 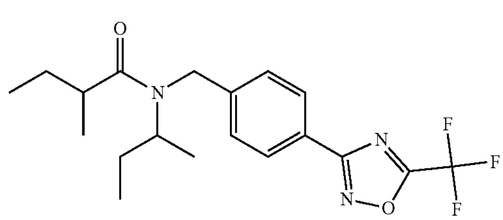 [SMILES: CCC(C)C(=O)N(Cc1ccc(-c2noc(C(F)(F)F)n2)cc1)C(C)CC] | 2.05 | 383.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.395 | 3-methyl-N-sec-butyl-N-[[4-[5-(trifluoromethyl)-1,2,4-oxadiazol-3-yl]phenyl]methyl]-oxetane-3-carboxamide | 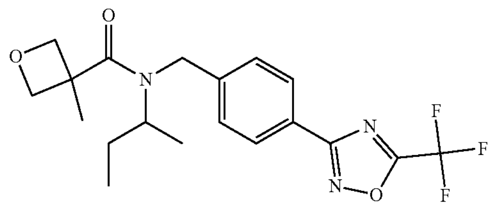 [SMILES: CCC(C)N(Cc1ccc(-c2noc(C(F)(F)F)n2)cc1)C(=O)C1(C)COC1] | 1.76 | 397.2 | B | |
| 1.396 | 4-oxo-N-sec-butyl-N-[[4-[5-(trifluoromethyl)-1,2,4-oxadiazol-3-yl]phenyl]methyl]-pent-2-enamide | 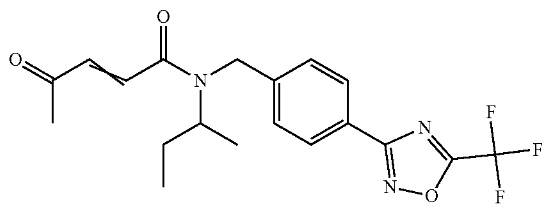 [SMILES: CCC(C)N(Cc1ccc(-c2noc(C(F)(F)F)n2)cc1)C(=O)C=CC(C)=O] | 1.76 | 395.1 | B | |
| 1.397 | 2-(methoxymethyl)-N-sec-butyl-N-[[4-[5-(trifluoromethyl)-1,2,4-oxadiazol-3-yl]phenyl]methyl]-butanamide | 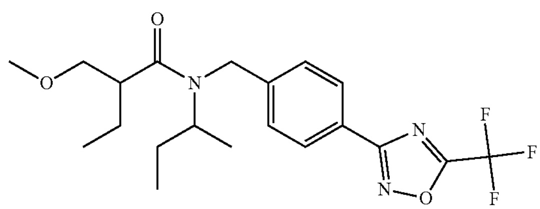 [SMILES: CCC(COC)C(=O)N(Cc1ccc(-c2noc(C(F)(F)F)n2)cc1)C(C)CC] | 2.02 | 413.2 | B | |
| 1.398 | N-sec-butyl-N-[[4-[5-(trifluoromethyl)-1,2,4-oxadiazol-3-yl]phenyl]methyl]-tetrahydrofuran-2-carboxamide | 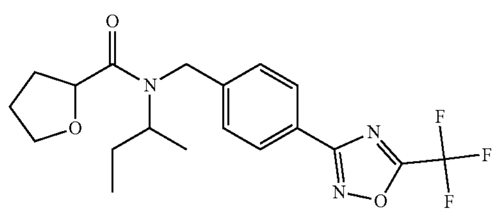 [SMILES: CCC(C)N(Cc1ccc(-c2noc(C(F)(F)F)n2)cc1)C(=O)C1CCCO1] | 1.85 | 397.2 | B | |
| 1.399 | 1-cyano-N-sec-butyl-N-[[4-[5-(trifluoromethyl)-1,2,4-oxadiazol-3-yl]phenyl]methyl]-cyclopropane-carboxamide | 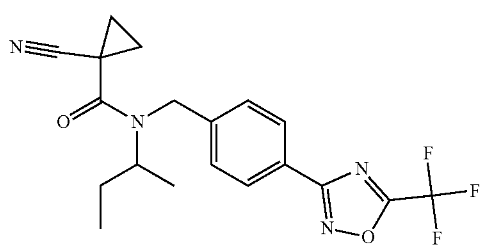 [SMILES: CCC(C)N(Cc1ccc(-c2noc(C(F)(F)F)n2)cc1)C(=O)C1(C#N)CC1] | 1.86 | 392.1 | B | |
| 1.400 | 1-acetyl-N-sec-butyl-N-[[4-[5-(trifluoromethyl)-1,2,4-oxadiazol-3-yl]phenyl]methyl]-pyrrolidine-2-carboxamide | 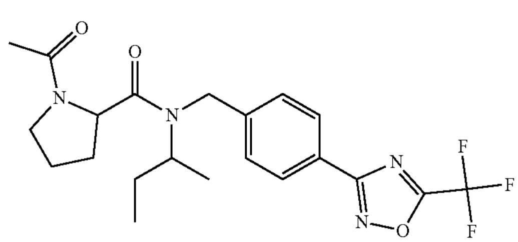 [SMILES: CCC(C)N(Cc1ccc(-c2noc(C(F)(F)F)n2)cc1)C(=O)C1CCCN1C(C)=O] | 1.66 | 438.2 | B | |
| 1.401 | 2-fluoro-N-sec-butyl-N-[[4-[5-(trifluoromethyl)-1,2,4-oxadiazol-3-yl]phenyl]methyl]-cyclopropane-carboxamide | 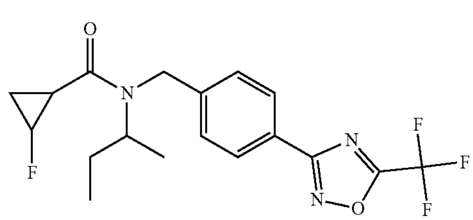 [SMILES: CCC(C)N(Cc1ccc(-c2noc(C(F)(F)F)n2)cc1)C(=O)C1CC1F] | 1.82 | 385.1 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.402 | 2-methoxy-N-sec-butyl-N-[[4-(5-(trifluoromethyl)-1,2,4-oxadiazol-3-yl]phenyl]methyl]-propanamide | 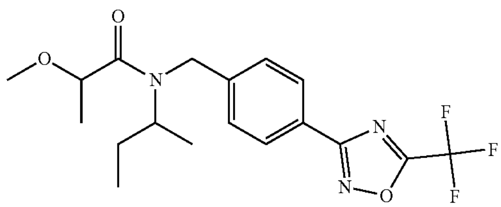 [SMILES: CCC(C)N(Cc1ccc(-c2noc(C(F)(F)F)n2)cc1)C(=O)C(C)OC] | 1.78 | 385.2 | B | |
| 1.403 | N-sec-butyl-N-[[4-[5-(trifluoromethyl)-1,2,4-oxadiazol-3-yl]phenyl]methyl]-1,3-dioxolane-2-carboxamide | 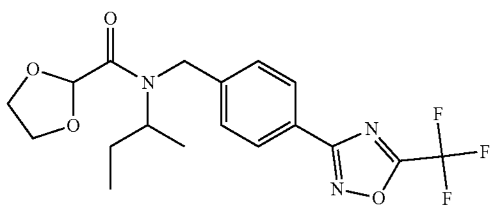 | 1.76 | 399.1 | B | |
| 1.404 | 3,3,3-trifluoro-N-sec-butyl-N-[[4-(5-(trifluoromethyl)-1,2,4-oxadiazol-3-yl]phenylmethyl]-propanamide | 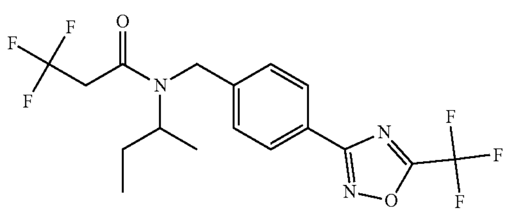 [SMILES: CCC(C)N(Cc1ccc(-c2noc(C(F)(F)F)n2)cc1)C(=O)CC(F)(F)F] | 1.90 | 409.1 | B | |
| 1.405 | N-sec-butyl-N-[[4-[5-(trifluoromethyl)-1,2,4-oxadiazol-3-yl]phenyl]methyl]-furan-3-carboxamide | 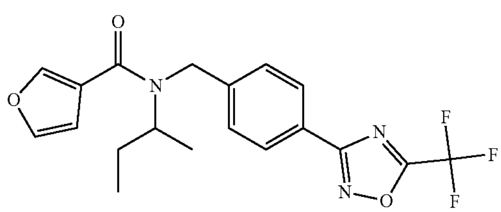 [SMILES: CCC(C)N(Cc1ccc(-c2noc(C(F)(F)F)n2)cc1)C(=O)c1ccoc1] | 1.87 | 393.1 | B | |
| 1.406 | N-sec-butyl-N-[[4-[5-(trifluoromethyl)-1,2,4-oxadiazol-3-yl]phenyl]methyl]-cyclopropane-carboxamide | 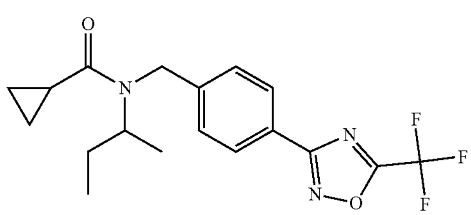 [SMILES: CCC(C)N(Cc1ccc(-c2noc(C(F)(F)F)n2)cc1)C(=O)C1CC1] | 1.90 | 367.2 | B | |
| 1.407 | N-sec-butyl-N-[[4-[5-(trifluoromethyl)-1,2,4-oxadiazol-3-yl]phenyl]methyl]-acetamide | 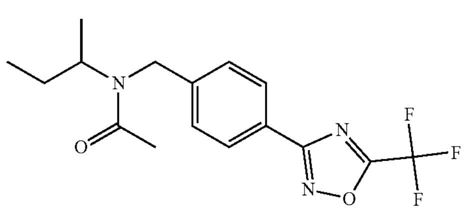 [SMILES: CCC(C)N(Cc1ccc(-c2noc(C(F)(F)F)n2)cc1)C(C)=O] | 1.73 | 341.1 | B | |
| 1.408 | 4-methoxy-N-sec-butyl-N-[[4-[5-(trifluoromethyl)-1,2,4-oxadiazol-3-yl]phenyl]methyl]-butanamide | 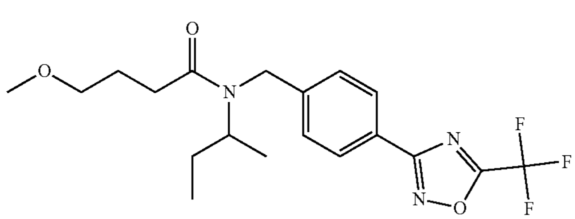 [SMILES: CCC(C)N(Cc1ccc(-c2noc(C(F)(F)F)n2)cc1)C(=O)CCCOC] | 1.85 | 399.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.409 | N-sec-butyl-N-[[4-[5-(trifluoromethyl)-1,2,4-oxadiazol-3-yl]phenyl]methyl]-pentanamide | 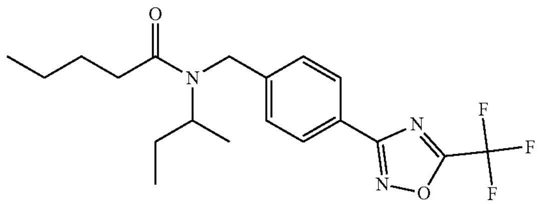 [SMILES: CCCCC(=O)N(Cc1ccc(-c2noc(C(F)(F)F)n2)cc1)C(C)CC] | 2.05 | 383.2 | B | |
| 1.410 | N-(tetrahydrofuran-2-ylmethyl)-N-[[4-[5-(trifluoromethyl)-1,2,4-oxadiazol-3-yl]phenyl]methyl]-2-ynamide | 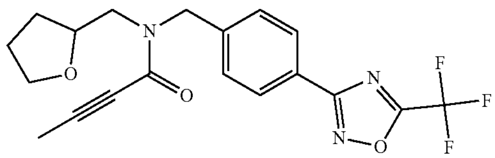 [SMILES: CC#CC(=O)N(Cc1ccc(-c2noc(C(F)(F)F)n2)cc1)CC1CCCO1] | 1.73 | 394.3 | B | |
| 1.411 | N-(tetrahydrofuran-2-ylmethyl)-N-[[4-[5-(trifluoromethyl)-1,2,4-oxadiazol-3-yl]phenyl]methyl]-tetrahydropyran-2-carboxamide | 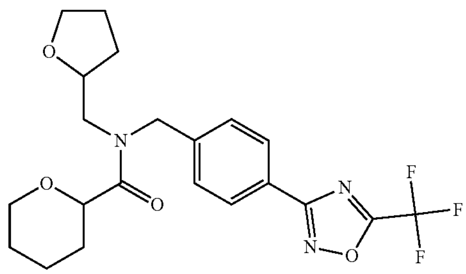 [SMILES: O=C(C1CCCCO1)N(Cc1ccc(-c2noc(C(F)(F)F)n2)cc1)CC1CCCO1] | 1.8 | 440.4 | B | |
| 1.412 | 2-methyl-N-(tetrahydrofuran-2-ylmethyl)-N-[[4-[5-(trifluoromethyl)-1,2,4-oxadiazol-3-yl]phenyl]methyl]-propanamide | 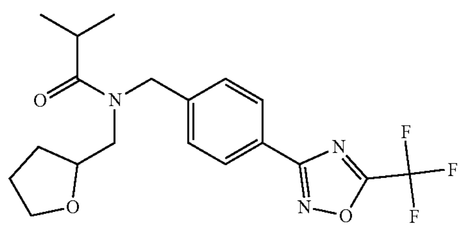 [SMILES: CC(C)C(=O)N(Cc1ccc(-c2noc(C(F)(F)F)n2)cc1)CC1CCCO1] | 1.8 | 398.4 | B | |
| 1.413 | N-(tetrahydrofuran-2-ylmethyl)-N-[[4-[5-(trifluoromethyl)-1,2,4-oxadiazol-3-yl]phenyl]methyl]but-2-enamide | 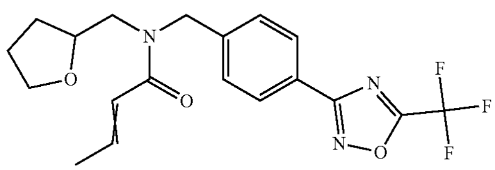 [SMILES: CC=CC(=O)N(Cc1ccc(-c2noc(C(F)(F)F)n2)cc1)CC1CCCO1] | 1.74 | 396.4 | B | |
| 1.414 | 2,2-difluoro-N-(tetrahydrofuran-2-ylmethyl)-N-[[4-[5-(trifluoromethyl)-1,2,4-oxadiazol-3-yl]phenyl]methyl]-cyclopropane-carboxamide | 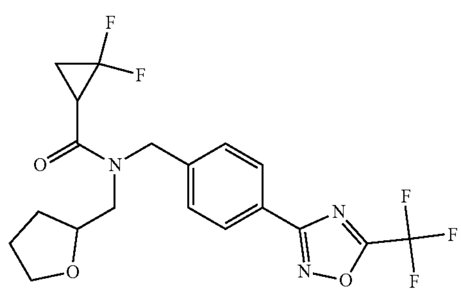 [SMILES: O=C(C1CC1(F)F)N(Cc1ccc(-c2noc(C(F)(F)F)n2)cc1)CC1CCCO1] | 1.79 | 432.4 | B | |
| 1.415 | 2-methoxy-N-(tetrahydrofuran-2-ylmethyl)-N-[[4-[5-(trifluoromethyl)-1,2,4-oxadiazol-3-yl]phenyl]methyl]-acetamide | 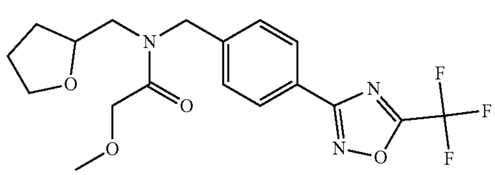 [SMILES: COCC(=O)N(Cc1ccc(-c2noc(C(F)(F)F)n2)cc1)CC1CCCO1] | 1.59 | 400.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.416 | N-(tetrahydrofuran-2-ylmethyl)-N-[[4-[5-(trifluoromethyl)-1,2,4-oxadiazol-3-yl]phenyl]methyl]-butanamide | 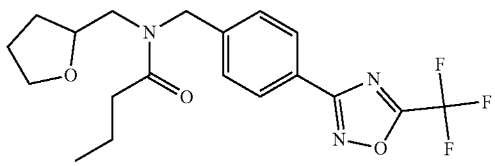 [SMILES: CCCC(=O)N(Cc1ccc(-c2noc(C(F)(F)F)n2)cc1)CC1CCCO1] | 1.81 | 398.4 | B | |
| 1.417 | 2-methyl-N-(tetrahydrofuran-2-ylmethyl)-N-[[4-[5-(trifluoromethyl)-1,2,4-oxadiazol-3-yl]phenyl]methyl]but-2-enamide | 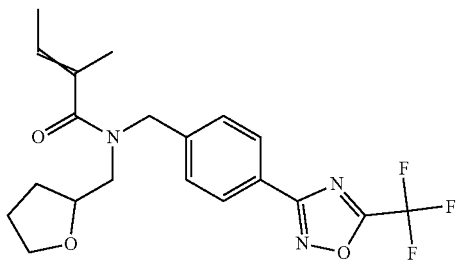 [SMILES: CC=C(C)C(=O)N(Cc1ccc(-c2noc(C(F)(F)F)n2)cc1)CC1CCCO1] | 1.83 | 410.4 | B | |
| 1.418 | 2-cyclopropyl-N-(tetrahydrofuran-2-ylmethyl)-N-[[4-[5-(trifluoromethyl)-1,2,4-oxadiazol-3-yl]phenyl]methyl]-acetamide | 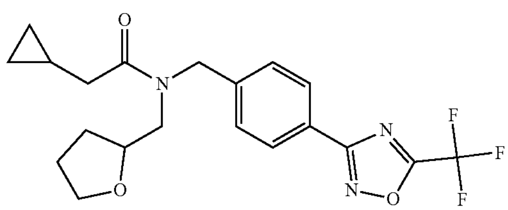 [SMILES: O=C(CC1CC1)N(Cc1ccc(-c2noc(C(F)(F)F)n2)cc1)CC1CCCO1] | 1.8 | 410.4 | B | |
| 1.419 | N-(tetrahydrofuran-2-ylmethyl)-N-[[4-[5-(trifluoromethyl)-1,2,4-oxadiazol-3-yl]phenyl]methyl]-cyclopentane-carboxamide | 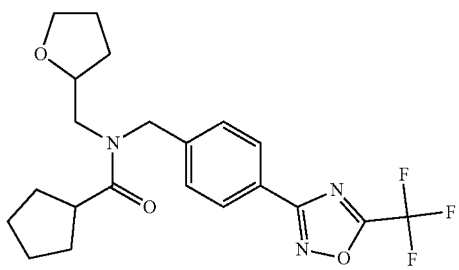 [SMILES: O=C(C1CCCC1)N(Cc1ccc(-c2noc(C(F)(F)F)n2)cc1)CC1CCCO1] | 1.95 | 424.4 | B | |
| 1.420 | N-(tetrahydrofuran-2-ylmethyl)-N-[[4-[5-(trifluoromethyl)-1,2,4-oxadiazol-3-yl]phenyl]methyl]-cyclopentene-1-carboxamide | 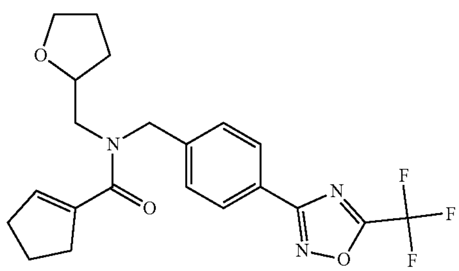 [SMILES: O=C(C1=CCCC1)N(Cc1ccc(-c2noc(C(F)(F)F)n2)cc1)CC1CCCO1] | 1.87 | 422.4 | B | |
| 1.421 | N-(tetrahydrofuran-2-ylmethyl)-N-[[4-[5-(trifluoromethyl)-1,2,4-oxadiazol-3-yl]phenyl]methyl]-thietane-3-carboxamide | 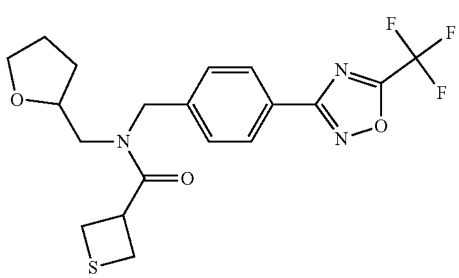 [SMILES: O=C(C1CSC1)N(Cc1ccc(-c2noc(C(F)(F)F)n2)cc1)CC1CCCO1] | 1.8 | 428.4 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.422 | 3-methoxy-N-(tetrahydrofuran-2-ylmethyl)-N-[[4-[5-(trifluoromethyl)-1,2,4-oxadiazol-3-yl]phenyl]methyl]-propanamide | 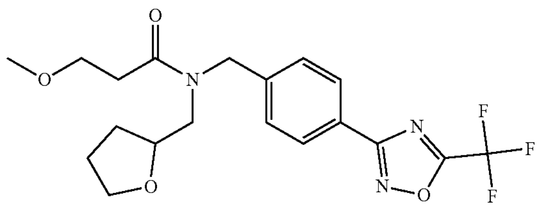 | 1.65 | 414.4 | B | |
| 1.423 | 3-methyl-N-(tetrahydrofuran-2-ylmethyl)-N-[[4-[5-(trifluoromethyl)-1,2,4-oxadiazol-3-yl]phenyl]methyl]-butanamide | 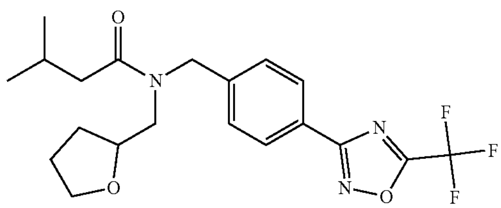 [SMILES: CC(C)CC(=O)N(Cc1ccc(-c2noc(C(F)(F)F)n2)cc1)CC1CCCO1] | 1.91 | 412.4 | B | |
| 1.424 | N-(tetrahydrofuran-2-ylmethyl)-N-[[4-[5-(trifluoromethyl)-1,2,4-oxadiazol-3-yl]phenyl]methyl]-cyclobutane-carboxamide | 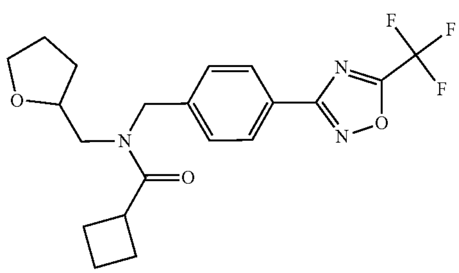 [SMILES: O=C(C1CCC1)N(Cc1ccc(-c2noc(C(F)(F)F)n2)cc1)CC1CCCO1] | 1.86 | 410.4 | B | |
| 1.425 | 4,4,4-trifluoro-N-(tetrahydrofuran-2-ylmethyl)-N-[[4-[5-(trifluoromethyl)-1,2,4-oxadiazol-3-yl]phenyl]methyl]-but-2-enamide | 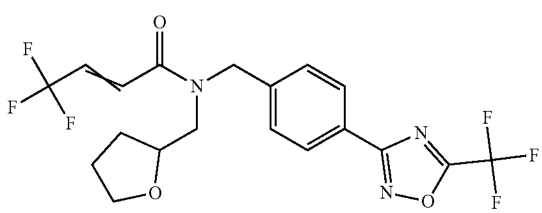 [SMILES: O=C(C=CC(F)(F)F)N(Cc1ccc(-c2noc(C(F)(F)F)n2)cc1)CC1CCCO1] | 1.9 | 450.4 | B | |
| 1.426 | 2-ethoxy-N-(tetrahydrofuran-2-ylmethyl)-N-[[4-[5-(trifluoromethyl)-1,2,4-oxadiazol-3-yl]phenyl]methyl]-acetamide | 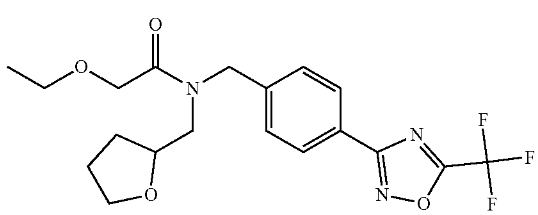 [SMILES: CCOCC(=O)N(Cc1ccc(-c2noc(C(F)(F)F)n2)cc1)CC1CCCO1] | 1.69 | 414.4 | B | |
| 1.427 | 2-(2-methoxyethoxy)-N-(tetrahydrofuran-2-ylmethyl)-N-[[4-[5-(trifluoromethyl)-1,2,4-oxadiazol-3-yl]phenyl]methyl]-acetamide | 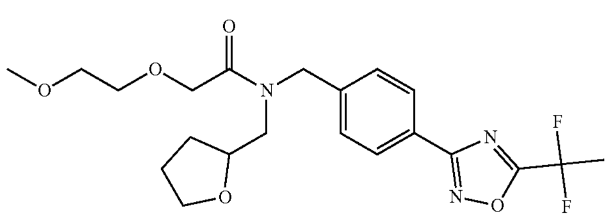 [SMILES: COCCOCC(=O)N(Cc1ccc(-c2noc(C(C)(F)F)n2)cc1)CC1CCCO1] | 1.61 | 444.4 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.428 | 2-methyl-N-(tetrahydrofuran-2-ylmethyl)-N-[[4-[5-(trifluoromethyl)-1,2,4-oxadiazol-3-yl]phenyl]methyl]-cyclopropane-carboxamide | 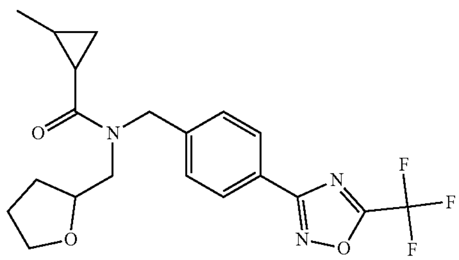 [SMILES: CC1CC1C(=O)N(Cc1ccc(-c2noc(C(F)(F)F)n2)cc1)CC1CCCO1] | 1.84 | 410.4 | B | |
| 1.429 | 3,3-dimethyl-N-(tetrahydrofuran-2-ylmethyl)-N-[[4-[5-(trifluoromethyl)-1,2,4-oxadiazol-3-yl]phenyl]methyl]-butanamide | 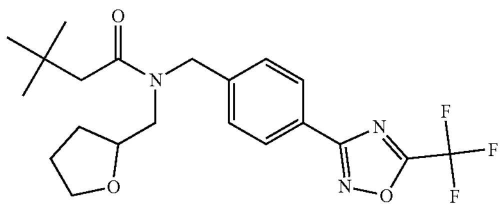 [SMILES: CC(C)(C)CC(=O)N(Cc1ccc(-c2noc(C(F)(F)F)n2)cc1)CC1CCCO1] | 2.02 | 426.4 | B | |
| 1.430 | N-(tetrahydrofuran-2-ylmethyl)-N-[[4-[5-(trifluoromethyl)-1,2,4-oxadiazol-3-yl]phenyl]methyl]-prop-2-enamide | 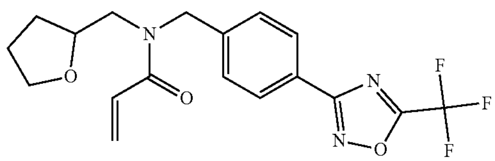 [SMILES: C=CC(=O)N(Cc1ccc(-c2noc(C(F)(F)F)n2)cc1)CC1CCCO1] | 1.67 | 382.3 | B | |
| 1.431 | 1-methyl-N-(tetrahydrofuran-2-ylmethyl)-N-[[4-[5-(trifluoromethyl)-1,2,4-oxadiazol-3-yl]phenyl]methyl]-cyclopropane-carboxamide | 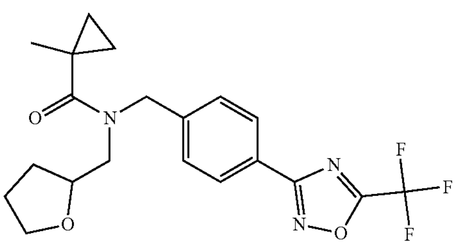 [SMILES: CC1(C(=O)N(Cc2ccc(-c3noc(C(F)(F)F)n3)cc2)CC2CCCO2)CC1] | 1.81 | 410.4 | B | |
| 1.432 | N-(tetrahydrofuran-2-ylmethyl)-N-[[4-[5-(trifluoromethyl)-1,2,4-oxadiazol-3-yl]phenyl]methyl]-propanamide | 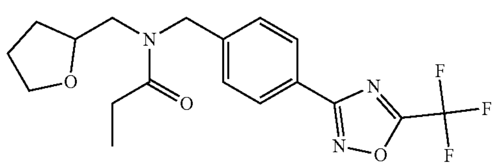 [SMILES: CCC(=O)N(Cc1ccc(-c2noc(C(F)(F)F)n2)cc1)CC1CCCO1] | 1.71 | 384.3 | B | |
| 1.433 | 2-methyl-N-(tetrahydrofuran-2-ylmethyl)-N-[[4-[5-(trifluoromethyl)-1,2,4-oxadiazol-3-yl]phenyl]methyl]-prop-2-enamide | 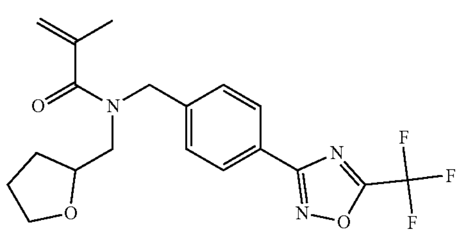 [SMILES: C=C(C)C(=O)N(Cc1ccc(-c2noc(C(F)(F)F)n2)cc1)CC1CCCO1] | 1.77 | 396.4 | B | |
| 1.434 | N-(tetrahydrofuran-2-ylmethyl)-N-[[4-[5-(trifluoromethyl)-1,2,4-oxadiazol-3-yl]phenyl]methyl] prop-2-ynamide | 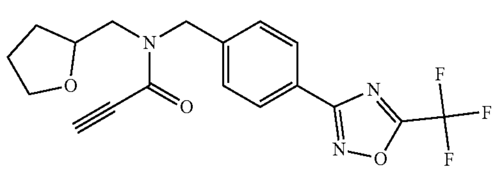 [SMILES: C#CC(=O)N(Cc1ccc(-c2noc(C(F)(F)F)n2)cc1)CC1CCCO1] | 1.67 | 380.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.435 | [2-oxo-2-[tetrahydrofuran-2-ylmethyl-[[4-[5-(trifluoromethyl)-1,2,4-oxadiazol-3-yl]phenyl]methyl]-amino]ethyl] acetate | 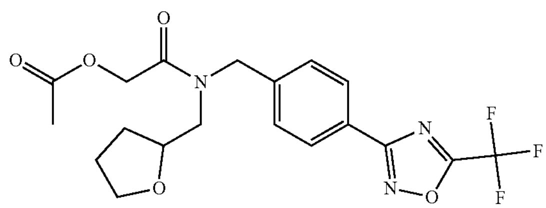 [SMILES: CC(=O)OCC(=O)N(Cc1ccc(-c2noc(C(F)(F)F)n2)cc1)CC1CCCO1] | 1.62 | 428.4 | B | |
| 1.436 | 1-fluoro-N-(tetrahydrofuran-2-ylmethyl)-N-[[4-[5-(trifluoromethyl)-1,2,4-oxadiazol-3-yl]phenyl]methyl]-cyclopropane-carboxamide | 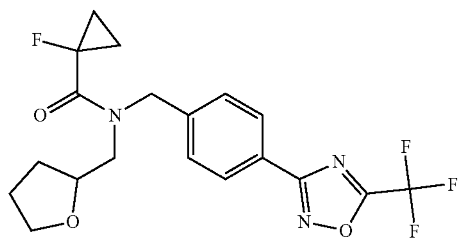 [SMILES: O=C(N(Cc1ccc(-c2noc(C(F)(F)F)n2)cc1)CC1CCCO1)C1(F)CC1] | 1.88 | 414.4 | B | |
| 1.437 | 2-methyl-N-(tetrahydrofuran-2-ylmethyl)-N-[[4-[5-(trifluoromethyl)-1,2,4-oxadiazol-3-yl]phenyl]methyl]-butanamide | 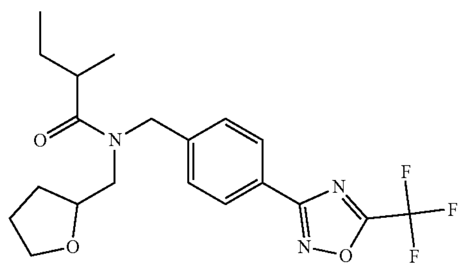 | 1.9 | 412.4 | B | |
| 1.438 | 3-methyl-N-(tetrahydrofuran-2-ylmethyl)-N-[[4-[5-(trifluoromethyl)-1,2,4-oxadiazol-3-yl]phenyl)methyl]-oxetane-3-carboxamide | 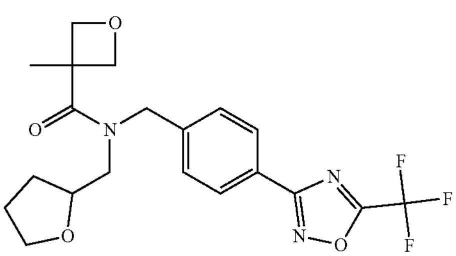 [SMILES: CC1(C(=O)N(Cc2ccc(-c3noc(C(F)(F)F)n3)cc2)CC2CCCO2)COC1] | 1.64 | 426.4 | B | |
| 1.439 | 4-oxo-N-(tetrahydrofuran-2-ylmethyl)-N-[[4-[5-(trifluoromethyl)-1,2,4-oxadiazol-3-yl]phenyl]methyl]-pent-2-enamide | 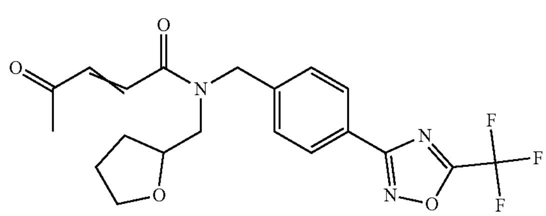 [SMILES: CC(=O)C=CC(=O)N(Cc1ccc(-c2noc(C(F)(F)F)n2)cc1)CC1CCCO1] | 1.64 | 424.4 | B | |
| 1.440 | 2-(methoxymethyl)-N-(tetrahydrofuran-2-ylmethyl)-N-[[4-[5-(trifluoromethyl)-1,2,4-oxadiazol-3-yl]phenyl]methyl]-butanamide | 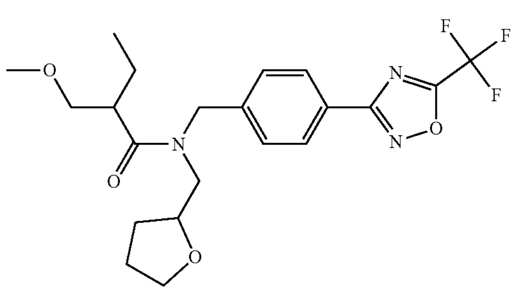 [SMILES: CCC(COC)C(=O)N(Cc1ccc(-c2noc(C(F)(F)F)n2)cc1)CC1CCCO1] | 1.87 | 442.4 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.441 | 1-formamido-N-(tetrahydrofuran-2-ylmethyl)-N-[[4-[5-(trifluoromethyl)-1,2,4-oxadiazol-3-yl]phenyl]methyl]-cyclopropane-carboxamide | 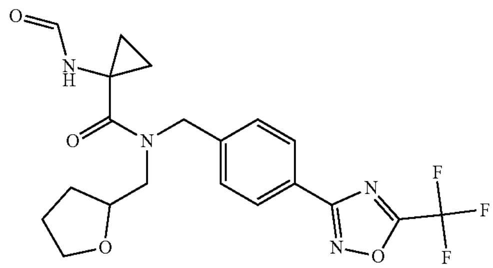 [SMILES: O=CNC1(C(=O)N(Cc2ccc(-c3noc(C(F)(F)F)n3)cc2)CC2CCCO2)CC1] | 1.45 | 439.4 | B | |
| 1.442 | N-(tetrahydrofuran-2-ylmethyl)-N-[[4-[5-(trifluoromethyl)-1,2,4-oxadiazol-3-yl]phenyl]methyl]-tetrahydrofuran-2-carboxamide | 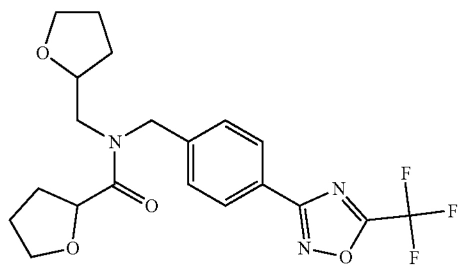 | 1.68 | 426.4 | B | |
| 1.443 | 1-cyano-N-(tetrahydrofuran-2-ylmethyl)-N-[[4-[5-(trifluoromethyl)-1,2,4-oxadiazol-3-yl]phenyl]methyl]-cyclopropane-carboxamide | 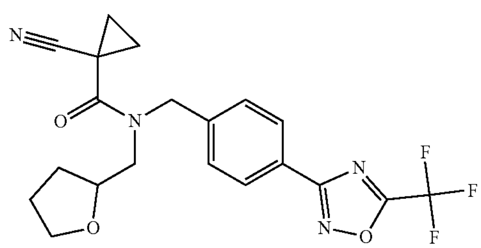 [SMILES: N#CC1(C(=O)N(Cc2ccc(-c3noc(C(F)(F)F)n3)cc2)CC2CCCO2)CC1] | 1.76 | 421.4 | B | |
| 1.444 | 1-acetyl-N-(tetrahydrofuran-2-ylmethyl)-N-[[4-[5-(trifluoromethyl)-1,2,4-oxadiazol-3-yl]phenyl]methyl]-pyrrolidine-2-carboxamide | 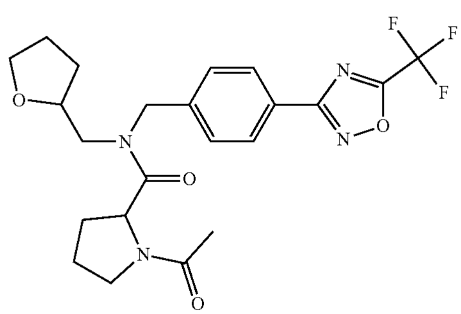 [SMILES: CC(=O)N1CCCC1C(=O)N(Cc1ccc(-c2noc(C(F)(F)F)n2)cc1)CC1CCCO1] | 1.54 | 467.4 | B | |
| 1.445 | 2-fluoro-N-(tetrahydrofuran-2-ylmethyl)-N-[[4-[5-(trifluoromethyl)-1,2,4-oxadiazol-3-yl]phenyl]methyl]-cyclopropane-carboxamide | 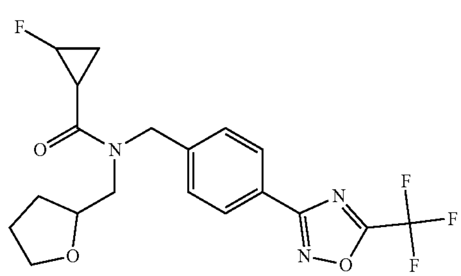 [SMILES: O=C(C1CC1F)N(Cc1ccc(-c2noc(C(F)(F)F)n2)cc1)CC1CCCO1] | 1.69 | 414.4 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.446 | 2-methoxy-N-(tetrahydrofuran-2-ylmethyl)-N-[[4-[5-(trifluoromethyl)-1,2,4-oxadiazol-3-yl]phenyl]methyl]-propanamide | 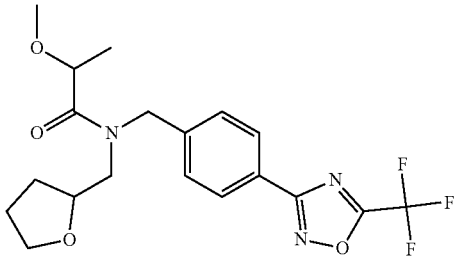 | 1.65 | 414.4 | B | |
| 1.447 | N-(tetrahydrofuran-2-ylmethyl)-N-[[4-[5-(trifluoromethyl)-1,2,4-oxadiazol-3-yl]phenyl]methyl]-1,3-dioxolane-2-carboxamide | 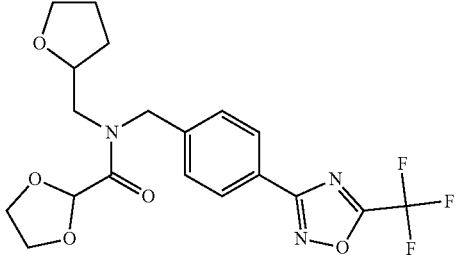 [SMILES: O=C(C1OCCO1)N(Cc1ccc(-c2noc(C(F)(F)F)n2)cc1)CC1CCCO1] | 1.63 | 428.4 | B | |
| 1.448 | 3,3,3-trifluoro-N-(tetrahydrofuran-2-ylmethyl)-N-[[4-[5-(trifluoromethyl)-1,2,4-oxadiazol-3-yl]phenyl]methyl]-propanamide | 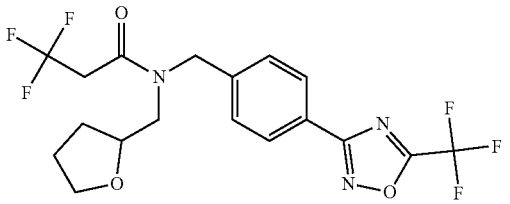 [SMILES: O=C(CC(F)(F)F)N(Cc1ccc(-c2noc(C(F)(F)F)n2)cc1)CC1CCCO1] | 1.8 | 438.4 | B | |
| 1.449 | N-(tetrahydrofuran-2-ylmethyl)-N-[[4-[5-(trifluoromethyl)-1,2,4-oxadiazol-3-yl]phenyl]methyl]-furan-3-carboxamide | 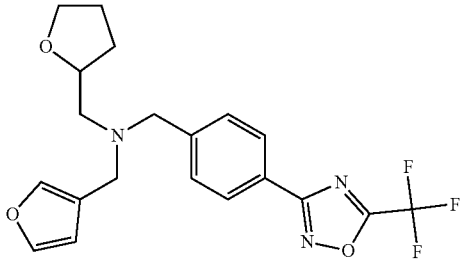 [SMILES: FC(F)(F)c1nc(-c2ccc(CN(Cc3ccoc3)CC3CCCO3)cc2)no1] | 1.75 | 422.3 | B | |
| 1.450 | N-(tetrahydrofuran-2-ylmethyl)-N-[[4-[5-(trifluoromethyl)-1,2,4-oxadiazol-3-yl]phenyl]methyl]-cyclopropane-carboxamide | 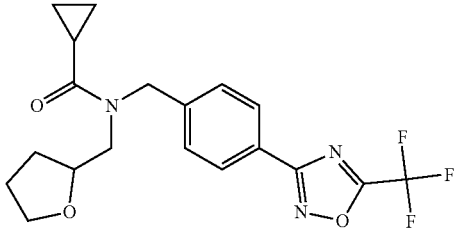 [SMILES: O=C(C1CC1)N(Cc1ccc(-c2noc(C(F)(F)F)n2)cc1)CC1CCCO1] | 1.75 | 396.4 | B | |
| 1.451 | N-(tetrahydrofuran-2-ylmethyl)-N-[[4-[5-(trifluoromethyl)-1,2,4-oxadiazol-3-yl]phenyl]methyl]-acetate | 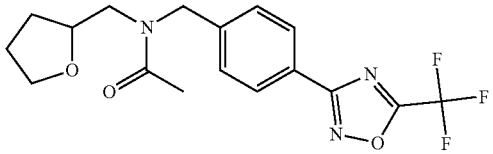 [SMILES: CC(=O)N(Cc1ccc(-c2noc(C(F)(F)F)n2)cc1)CC1CCCO1] | 1.58 | 370.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.452 | 4-methoxy-N-(tetrahydrofuran-2-ylmethyl)-N-[[4-[5-(trifluoromethyl)-1,2,4-oxadiazol-3-yl]phenyl]methyl]-butanamide | 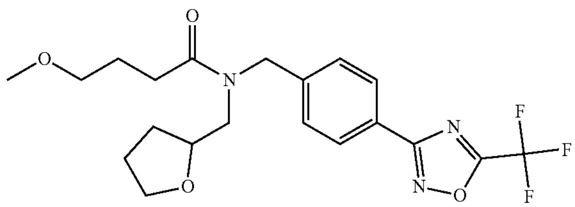 [SMILES: COCCCC(=O)N(Cc1ccc(-c2noc(C(F)(F)F)n2)cc1)CC1CCCO1] | 1.7 | 428.4 | B | |
| 1.453 | N-(tetrahydrofuran-2-ylmethyl)-N-[[4-[5-(trifluoromethyl)-1,2,4-oxadiazol-3-yl]phenyl]methyl]-pentanamide | 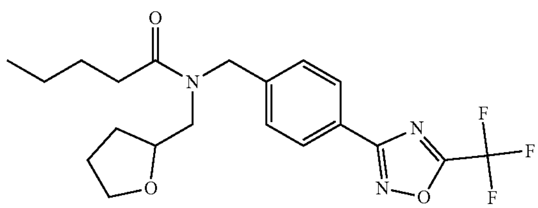 [SMILES: CCCCC(=O)N(Cc1ccc(-c2noc(C(F)(F)F)n2)cc1)CC1CCCO1] | 1.92 | 412.4 | B | |
| 1.454 | N-methoxy-2-(trifluoromethyl)-N-[[4-[5-(trifluoromethyl)-1,2,4-oxadiazol-3-yl]phenyl]methyl]-benzamide | 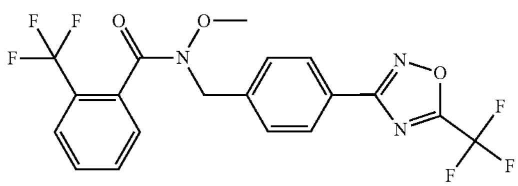 [SMILES: CON(Cc1ccc(-c2noc(C(F)(F)F)n2)cc1)C(=O)c1ccccc1C(F)(F)F] | 1.15 | 446.3 | | |
| 1.455 | N-(2-furylmethyl)-N-[[4-[5-(trifluoromethyl)-1,2,4-oxadiazol-3-yl]phenyl]methyl]-cyclopentane-carboxamide | 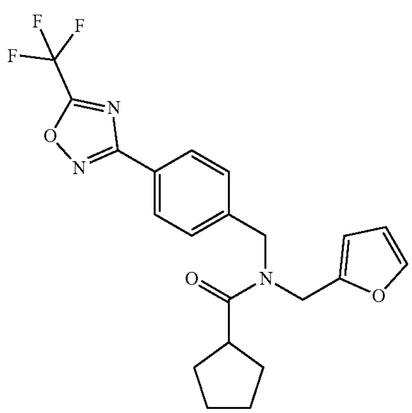 [SMILES: O=C(C1CCCC1)N(Cc1ccc(-c2noc(C(F)(F)F)n2)cc1)Cc1ccco1] | 2.01 | 420.3 | B | |
| 1.456 | N-(2-furylmethyl)-3-methoxy-N-[[4-[5-(trifluoromethyl)-1,2,4-oxadiazol-3-yl]phenyl]methyl]-propanamide | 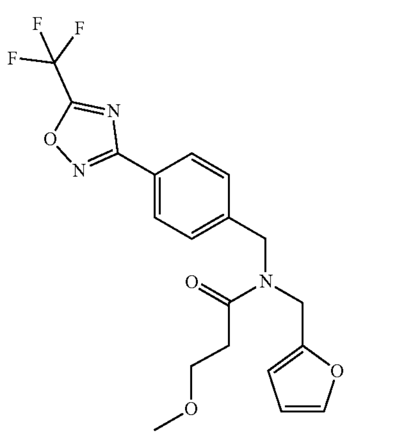 [SMILES: COCCC(=O)N(Cc1ccc(-c2noc(C(F)(F)F)n2)cc1)Cc1ccco1] | 1.73 | 410.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.457 | N-(2-furylmethyl)-N-[[4-[5-(trifluoromethyl)-1,2,4-oxadiazol-3-yl]phenyl]methyl]-propanamide | 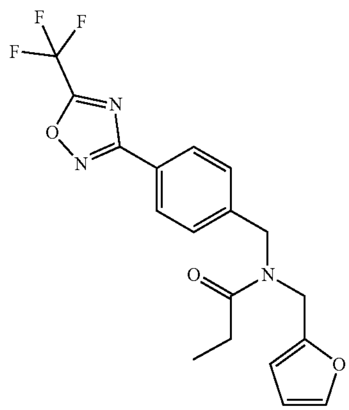 [SMILES: CCC(=O)N(Cc1ccc(-c2noc(C(F)(F)F)n2)cc1)Cc1ccco1] | 1.78 | 380.3 | B | |
| 1.458 | N-(2-furylmethyl)-N-[[4-[5-(trifluoromethyl)-1,2,4-oxadiazol-3-yl]phenyl]methyl]-cyclobutane-carboxamide | 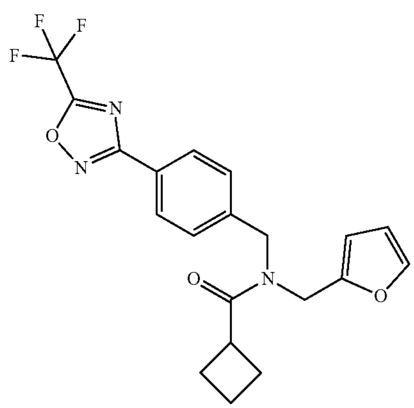 [SMILES: O=C(C1CCC1)N(Cc1ccc(-c2noc(C(F)(F)F)n2)cc1)Cc1ccco1] | 1.93 | 406.3 | B | |
| 1.459 | N-(2-furylmethyl)-2-methoxy-N-[[4-[5-(trifluoromethyl)-1,2,4-oxadiazol-3-yl]phenyl]methyl]-acetamide | 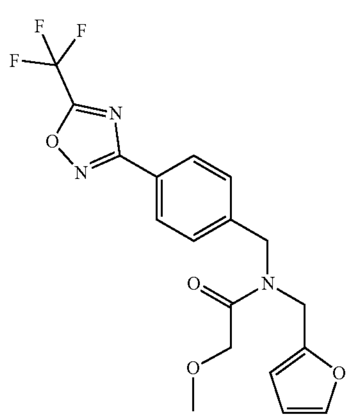 [SMILES: COCC(=O)N(Cc1ccc(-c2noc(C(F)(F)F)n2)cc1)Cc1ccco1] | 1.67 | 396.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.460 | N-(2-furylmethyl)-2-methyl-N-[[4-[5-(trifluoromethyl)-1,2,4-oxadiazol-3-yl]phenyl]methyl]-cyclopropane-carboxamide | 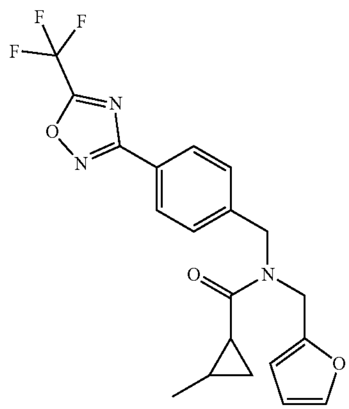 [SMILES: CC1CC1C(=O)N(Cc1ccc(-c2noc(C(F)(F)F)n2)cc1)Cc1ccco1] | 1.9 | 406.3 | B | |
| 1.461 | 2-acetamido-N-(2-furylmethyl)-N-[[4-[5-(trifluoromethyl)-1,2,4-oxadiazol-3-yl]phenyl]methyl]-acetamide | 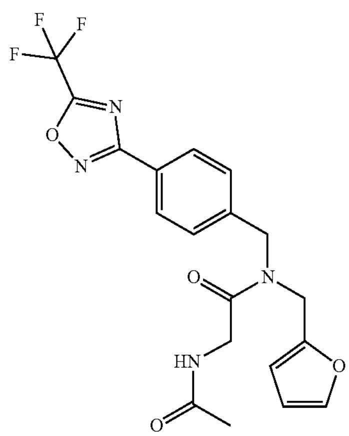 [SMILES: CC(=O)NCC(=O)N(Cc1ccc(-c2noc(C(F)(F)F)n2)cc1)Cc1ccco1] | 1.5 | 423.3 | B | |
| 1.462 | 2-chloro-N-(2-furylmethyl)-N-[[4-[5-(trifluoromethyl)-1,2,4-oxadiazol-3-yl]phenyl]methyl]-acetamide | 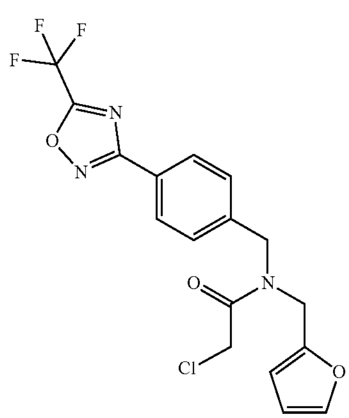 | 1.77 | 400.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.463 | N-(2-furylmethyl)-2-methyl-N-[[4-[5-(trifluoromethyl)-1,2,4-oxadiazol-3-yl]phenyl]methyl]-propanamide | 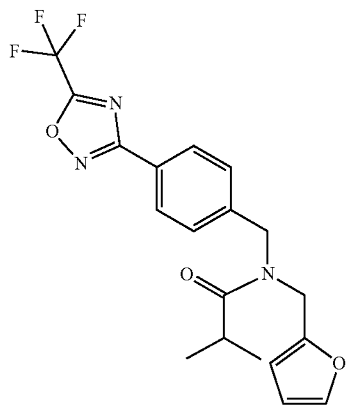 [SMILES: CC(C)C(=O)N(Cc1ccc(-c2noc(C(F)(F)F)n2)cc1)Cc1ccco1] | 1.87 | 394.3 | B | |
| 1.464 | 2,2-difluoro-N-(2-furylmethyl)-N-[[4-[5-(trifluoromethyl)-1,2,4-oxadiazol-3-yl]phenyl]methyl]-cyclopropane-carboxamide | 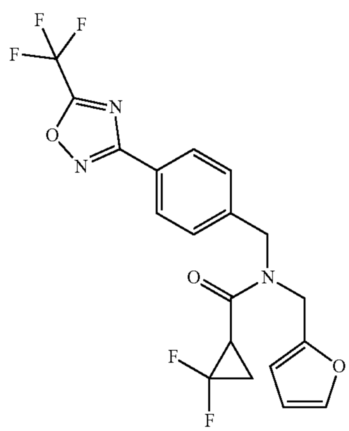 [SMILES: O=C(C1CC1(F)F)N(Cc1ccc(-c2noc(C(F)(F)F)n2)cc1)Cc1ccco1] | 1.85 | 428.3 | B | |
| 1.465 | N-(2-furylmethyl)-N-[[4-[5-(trifluoromethyl)-1,2,4-oxadiazol-3-yl]phenyl]methyl]-butanamide | 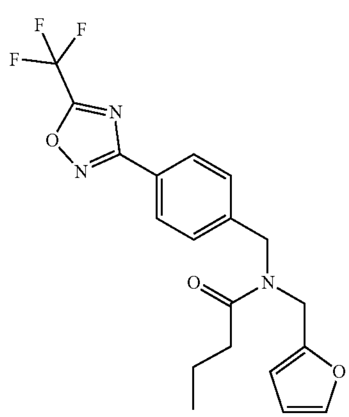 [SMILES: CCCC(=O)N(Cc1ccc(-c2noc(C(F)(F)F)n2)cc1)Cc1ccco1] | 1.88 | 394.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.466 | N-(2-furylmethyl)-2-methyl-N-[[4-[5-(trifluoromethyl)-1,2,4-oxadiazol-3-yl]phenyl]methyl]-butanamide | 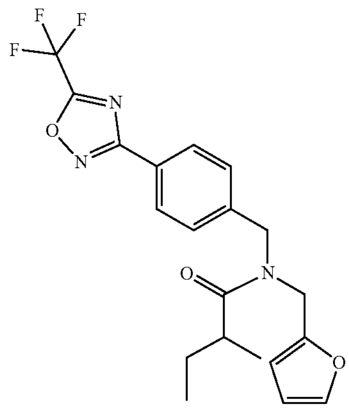 [SMILES: CCC(C)C(=O)N(Cc1ccc(-c2noc(C(F)(F)F)n2)cc1)Cc1ccco1] | 1.96 | 408.3 | B | |
| 1.467 | N-(2-furylmethyl)-4-methoxy-N-[[4-[5-(trifluoromethyl)-1,2,4-oxadiazol-3-yl]phenyl]methyl]-butanamide | 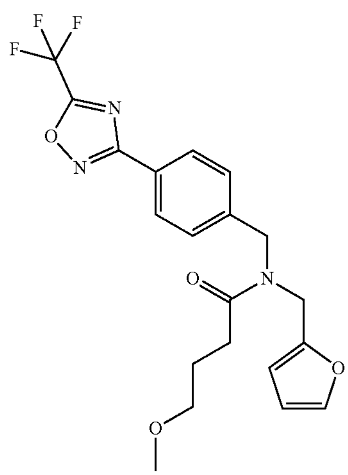 [SMILES: COCCCC(=O)N(Cc1ccc(-c2noc(C(F)(F)F)n2)cc1)Cc1ccco1] | 1.77 | 424.3 | B | |
| 1.468 | N-(2-furylmethyl)-3-methyl-N-[[4-[5-(trifluoromethyl)-1,2,4-oxadiazol-3-yl]phenyl]methyl]-oxetane-3-carboxamide | 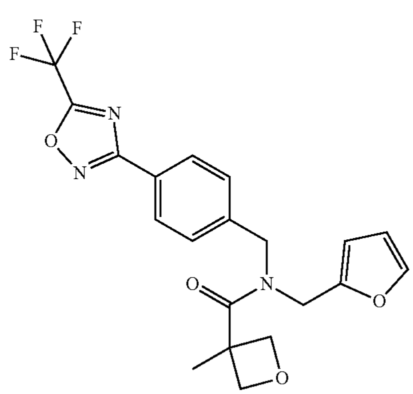 [SMILES: CC1(C(=O)N(Cc2ccc(-c3noc(C(F)(F)F)n3)cc2)Cc2ccco2)COC1] | 1.7 | 422.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.469 | N-(2-furylmethyl)-N-[[4-[5-(trifluoromethyl)-1,2,4-oxadiazol-3-yl]phenyl]methyl]-tetrahydrofuran-2-carboxamide | 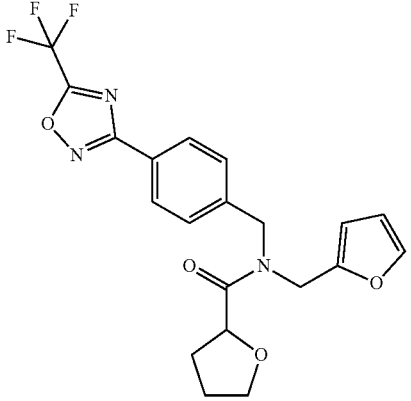 [SMILES: O=C(C1CCCO1)N(Cc1ccc(-c2noc(C(F)(F)F)n2)cc1)Cc1ccco1] | 1.77 | 422.3 | B | |
| 1.470 | 2-cyano-N-(2-furylmethyl)-N-[[4-[5-(trifluoromethyl)-1,2,4-oxadiazol-3-yl]phenyl]methyl]-acetamide | 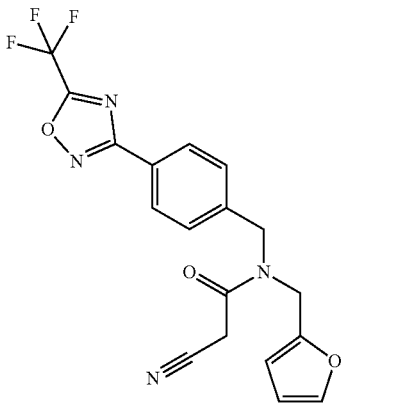 [SMILES: N#CCC(=O)N(Cc1ccc(-c2noc(C(F)(F)F)n2)cc1)Cc1ccco1] | 1.64 | 391.4 | B | |
| 1.471 | 2-fluoro-N-(2-furylmethyl)-N-[[4-(5-(trifluoromethyl)-1,2,4-oxadiazol-3-yl]phenyl]methyl]-cyclopropane-carboxamide | 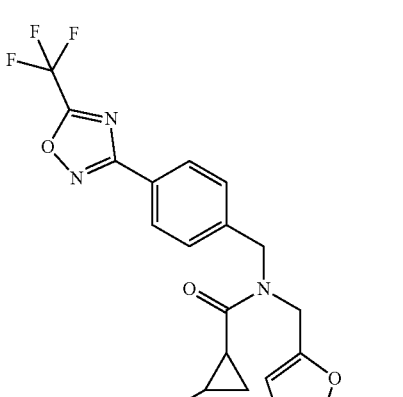 | 1.75 | 410.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.472 | N-(2-furylmethyl)-2-methoxy-N-[[4-[5-(trifluoromethyl)-1,2,4-oxadiazol-3-yl]phenyl]methyl]-propanamide | 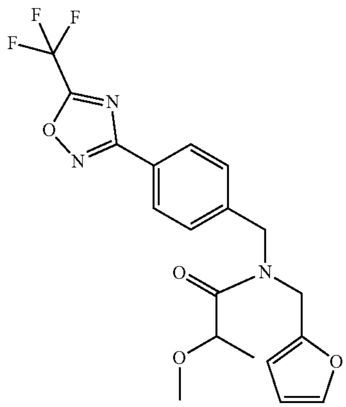 [SMILES: COC(C)C(=O)N(Cc1ccc(-c2noc(C(F)(F)F)n2)cc1)Cc1ccco1] | 1.74 | 410.3 | B | |
| 1.473 | N-(2-furylmethyl)-N-[[4-[5-(trifluoromethyl)-1,2,4-oxadiazol-3-yl]phenyl]methyl]-1,3-dioxolane-2-carboxamide | 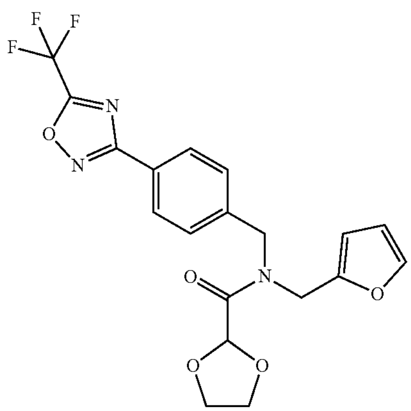 [SMILES: O=C(C1OCCO1)N(Cc1ccc(-c2noc(C(F)(F)F)n2)cc1)Cc1ccco1] | 1.7 | 424.3 | B | |
| 1.474 | N-(2-furylmethyl)-N-[[4-[5-(trifluoromethyl)-1,2,4-oxadiazol-3-yl]phenyl]methyl]-cyclopropane-carboxamide | 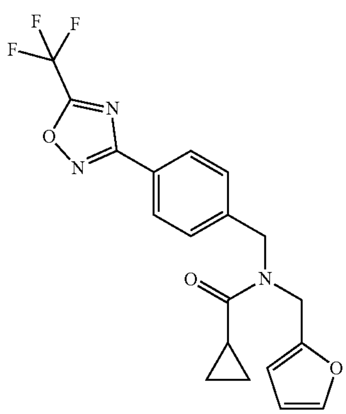 [SMILES: O=C(C1CC1)N(Cc1ccc(-c2noc(C(F)(F)F)n2)cc1)Cc1ccco1] | 1.82 | 392.3 | B | |
| 1.475 | N-allyl-N-[[4-[5-(trifluoromethyl)-1,2,4-oxadiazol-3-yl]phenyl]methyl]-cyclopentane-carboxamide | 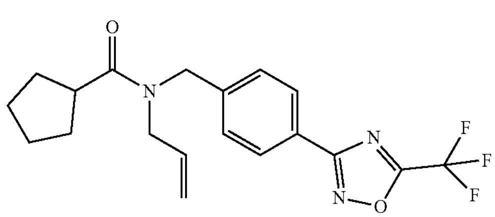 [SMILES: C=CCN(Cc1ccc(-c2noc(C(F)(F)F)n2)cc1)C(=O)C1CCCC1] | 1.99 | 380.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.476 | N-allyl-3-methoxy-N-[[4-[5-(trifluoromethyl)-1,2,4-oxadiazol-3-yl]phenyl]methyl]-propanamide | 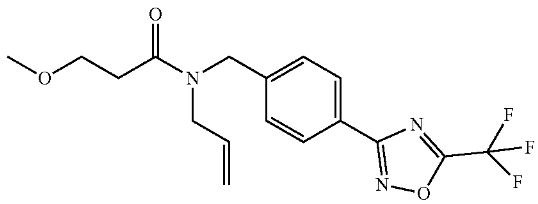 [SMILES: C=CCN(Cc1ccc(-c2noc(C(F)(F)F)n2)cc1)C(=O)CCOC] | 1.68 | 370.3 | B | |
| 1.477 | N-allyl-N-[[4-[5-(trifluoromethyl)-1,2,4-oxadiazol-3-yl]phenyl]methyl]-propanamide | 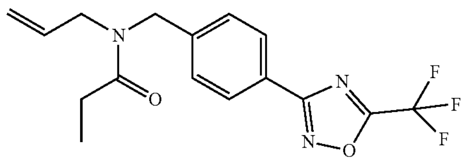 [SMILES: C=CCN(Cc1ccc(-c2noc(C(F)(F)F)n2)cc1)C(=O)CC] | 1.74 | 340.3 | B | |
| 1.478 | N-allyl-N-[[4-[5-(trifluoromethyl)-1,2,4-oxadiazol-3-yl]phenyl]methyl]-cyclobutane-carboxamide | 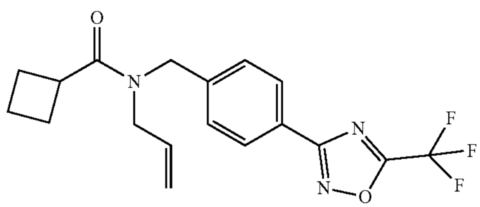 [SMILES: C=CCN(Cc1ccc(-c2noc(C(F)(F)F)n2)cc1)C(=O)C1CCC1] | 1.9 | 366.3 | B | |
| 1.479 | N-allyl-2-methoxy-N-[[4-[5-(trifluoromethyl)-1,2,4-oxadiazol-3-yl]phenyl]methyl]-acetamide | 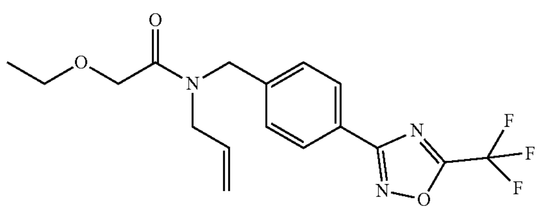 [SMILES: C=CCN(Cc1ccc(-c2noc(C(F)(F)F)n2)cc1)C(=O)COCC] | 1.61 | 356.3 | B | |
| 1.480 | N-allyl-2-methyl-N-[[4-[5-(trifluoromethyl)-1,2,4-oxadiazol-3-yl]phenyl]methyl]-cyclopropane-carboxamide | 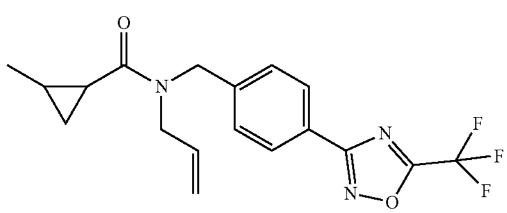 [SMILES: C=CCN(Cc1ccc(-c2noc(C(F)(F)F)n2)cc1)C(=O)C1CC1C] | 1.88 | 366.3 | B | |
| 1.481 | 2-acetamido-N-allyl-N-[[4-[5-(trifluoromethyl)-1,2,4-oxadiazol-3-yl]phenyl]methyl]-acetamide | 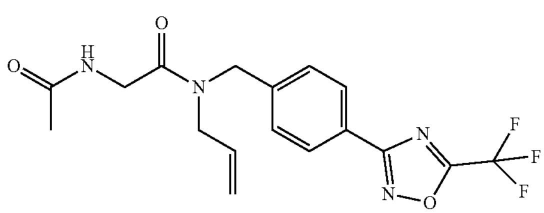 [SMILES: C=CCN(Cc1ccc(-c2noc(C(F)(F)F)n2)cc1)C(=O)CNC(C)=O] | 1.43 | 383.3 | B | |
| 1.482 | N-allyl-2-chloro-N-[[4-[5-(trifluoromethyl)-1,2,4-oxadiazol-3-yl]phenyl]methyl]-acetamide | 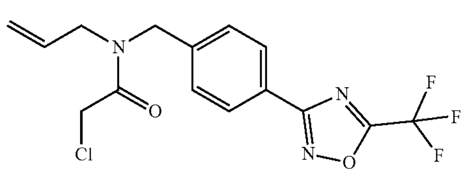 [SMILES: C=CCN(Cc1ccc(-c2noc(C(F)(F)F)n2)cc1)C(=O)CCl] | 1.73 | 360.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.483 | N-allyl-2-methyl-N-[[4-[5-(trifluoromethyl)-1,2,4-oxadiazol-3-yl]phenyl]methyl]-propanamide | 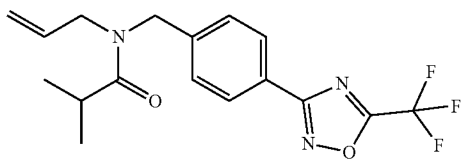 [SMILES: C=CCN(Cc1ccc(-c2noc(C(F)(F)F)n2)cc1)C(=O)C(C)C] | 1.84 | 354.3 | B | |
| 1.484 | N-allyl-2,2-difluoro-N-[[4-[5-(trifluoromethyl)-1,2,4-oxadiazol-3-yl]phenyl]methyl]-cyclopropane-carboxamide | 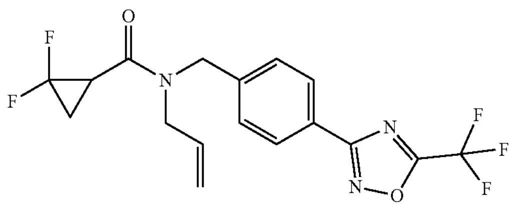 [SMILES: C=CCN(Cc1ccc(-c2noc(C(F)(F)F)n2)cc1)C(=O)C1CC1(F)F] | 1.82 | 388.3 | B | |
| 1.485 | N-allyl-N-[[4-[5-(trifluoromethyl)-1,2,4-oxadiazol-3-yl]phenyl]methyl]-butanamide | 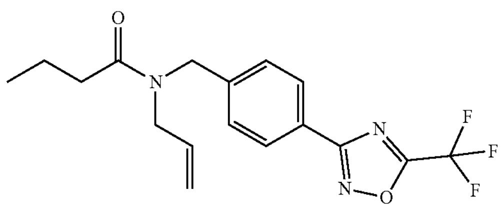 [SMILES: C=CCN(Cc1ccc(-c2noc(C(F)(F)F)n2)cc1)C(=O)CCC] | 1.85 | 354.3 | B | |
| 1.486 | N-allyl-2-methyl-N-[[4-[5-(trifluoromethyl)-1,2,4-oxadiazol-3-yl]phenyl]methyl]-butanamide | 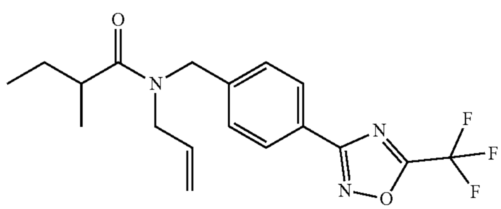 [SMILES: C=CCN(Cc1ccc(-c2noc(C(F)(F)F)n2)cc1)C(=O)C(C)CC] | 1.94 | 368.3 | B | |
| 1.487 | N-allyl-4-methoxy-N-[[4-[5-(trifluoromethyl)-1,2,4-oxadiazol-3-yl]phenyl]methyl]-butanamide | 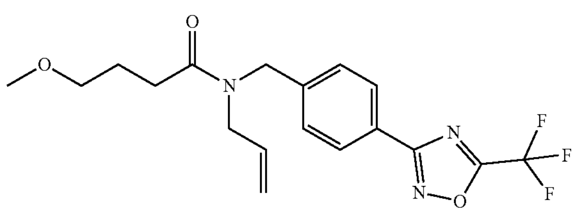 [SMILES: C=CCN(Cc1ccc(-c2noc(C(F)(F)F)n2)cc1)C(=O)CCCOC] | 1.73 | 384.3 | B | |
| 1.488 | N-allyl-3-methyl-N-[[4-[5-(trifluoromethyl)-1,2,4-oxadiazol-3-yl]phenyl]methyl]-oxetane-3-carboxamide | 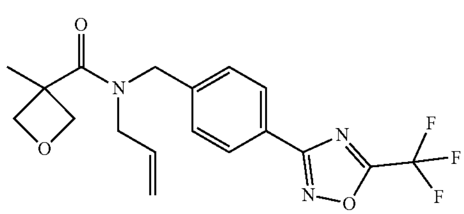 [SMILES: C=CCN(Cc1ccc(-c2noc(C(F)(F)F)n2)cc1)C(=O)C1(C)COC1] | 1.65 | 382.3 | B | |
| 1.489 | N-allyl-N-[[4-[5-(trifluoromethyl)-1,2,4-oxadiazol-3-yl]phenyl]methyl]-tetrahydrofuran-2-carboxamide | 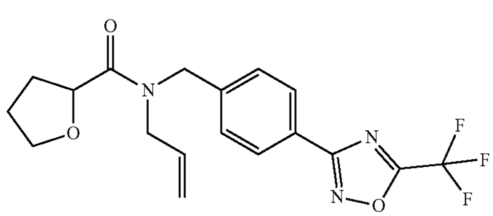 | 1.72 | 382.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.490 | N-allyl-2-cyano-N-[[4-[5-(trifluoromethyl)-1,2,4-oxadiazol-3-yl]phenyl]methyl]-acetamide | 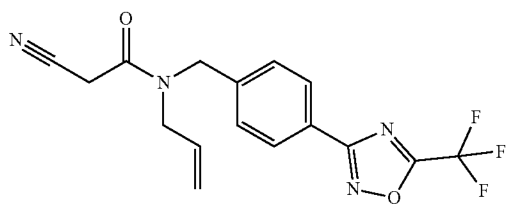 [SMILES: C=CCN(Cc1ccc(-c2noc(C(F)(F)F)n2)cc1)C(=O)CC#N] | 1.58 | 351.3 | B | |
| 1.491 | N-allyl-2-fluoro-N-[[4-[5-(trifluoromethyl)-1,2,4-oxadiazol-3-yl]phenyl]methyl]-cyclopropane-carboxamide | 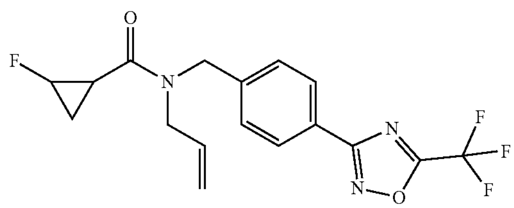 [SMILES: C=CCN(Cc1ccc(-c2noc(C(F)(F)F)n2)cc1)C(=O)C1CC1F] | 1.71 | 370.3 | B | |
| 1.492 | N-allyl-2-methoxy-N-[[4-[5-(trifluoromethyl)-1,2,4-oxadiazol-3-yl]phenyl]methyl]-propanamide | 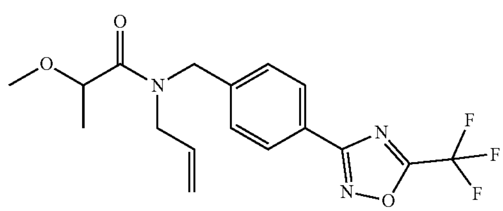 [SMILES: C=CCN(Cc1ccc(-c2noc(C(F)(F)F)n2)cc1)C(=O)C(C)OC] | 1.69 | 370.3 | B | |
| 1.493 | N-allyl-N-[[4-[5-(trifluoromethyl)-1,2,4-oxadiazol-3-yl]phenyl]methyl]-1,3-dioxolane-2-carboxamide | 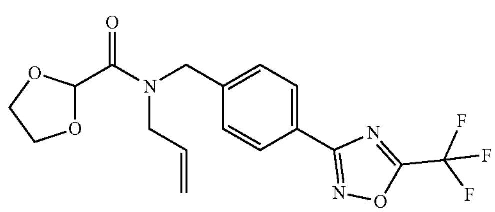 [SMILES: C=CCN(Cc1ccc(-c2noc(C(F)(F)F)n2)cc1)C(=O)C1OCCO1] | 1.65 | 384.3 | B | |
| 1.494 | N-allyl-N-[[4-[5-(trifluoromethyl)-1,2,4-oxadiazol-3-yl]phenyl]methyl]-cyclopropane-carboxamide | 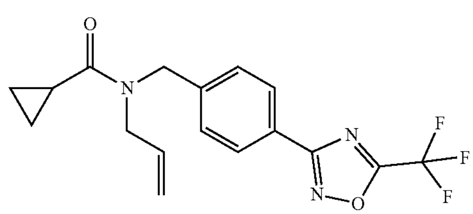 [SMILES: C=CCN(Cc1ccc(-c2noc(C(F)(F)F)n2)cc1)C(=O)C1CC1] | 1.78 | 352.3 | B | |
| 1.495 | N-ethyl-N-[[4-[5-(trifluoromethyl)-1,2,4-oxadiazol-3-yl]phenyl]methyl]-cyclopentane-carboxamide | 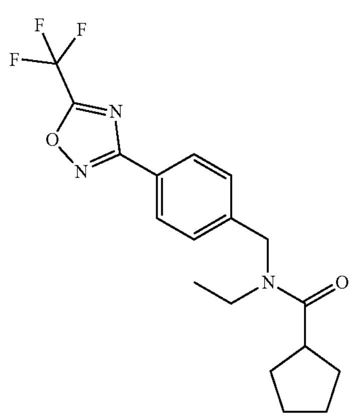 [SMILES: CCN(Cc1ccc(-c2noc(C(F)(F)F)n2)cc1)C(=O)C1CCCC1] | 1.93 | 368.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.496 | N-ethyl-3-methoxy-N-[[4-[5-(trifluoromethyl)-1,2,4-oxadiazol-3-yl]phenyl]methyl]-propanamide | 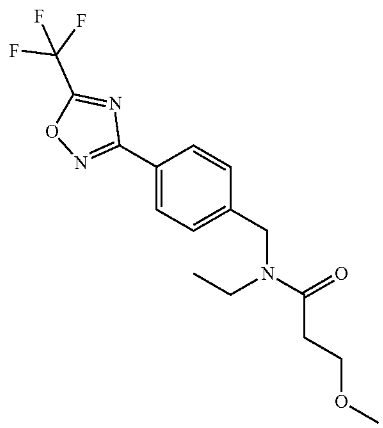 [SMILES: CCN(Cc1ccc(-c2noc(C(F)(F)F)n2)cc1)C(=O)CCOC] | 1.61 | 358.3 | B | |
| 1.497 | N-ethyl-N-[[4-[5-(trifluoromethyl)-1,2,4-oxadiazol-3-yl]phenyl]methyl]-propanamide | 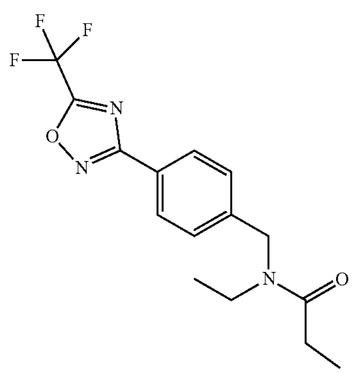 [SMILES: CCC(=O)N(CC)Cc1ccc(-c2noc(C(F)(F)F)n2)cc1] | 1.67 | 328.3 | B | |
| 1.498 | N-ethyl-N-[[4-[5-(trifluoromethyl)-1,2,4-oxadiazol-3-yl]phenyl]methyl]-cyclobulane-carboxamide | 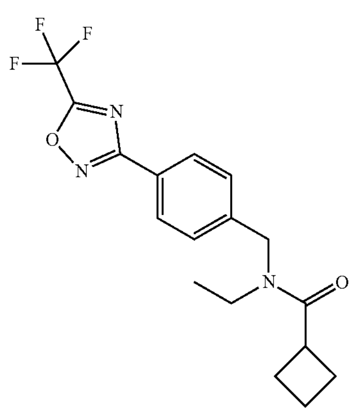 [SMILES: CCN(Cc1ccc(-c2noc(C(F)(F)F)n2)cc1)C(=O)C1CCC1] | 1.84 | 354.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.499 | N-ethyl-2-methoxy-N-[[4-[5-(trifluoromethyl)-1,2,4-oxadiazol-3-yl]phenyl]methyl]-acetamide | 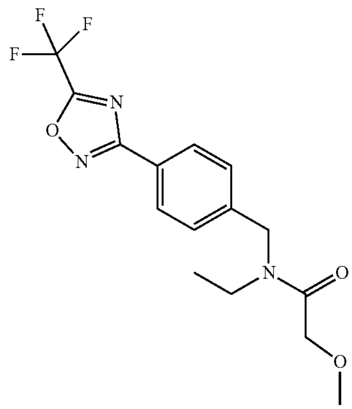 [SMILES: CCN(Cc1ccc(-c2noc(C(F)(F)F)n2)cc1)C(=O)COC] | 1.54 | 344.3 | B | |
| 1.500 | N-ethyl-2-methyl-N-[[4-[5-(trifluoromethyl)-1,2,4-oxadiazol-3-yl]phenyl]methyl]-cyclopropane-carboxamide | 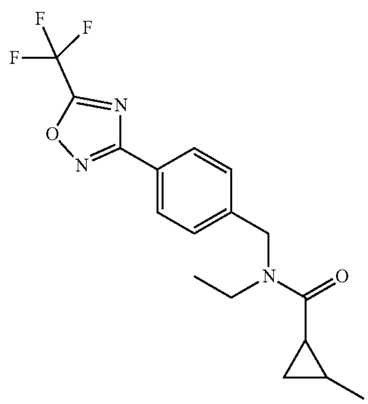 [SMILES: CCN(Cc1ccc(-c2noc(C(F)(F)F)n2)cc1)C(=O)C1CC1C] | 1.82 | 354.3 | B | |
| 1.501 | 2-acetamido-N-ethyl-N-[[4-[5-(trifluoromethyl)-1,2,4-oxadiazol-3-yl]phenyl]methyl]-acetamide | 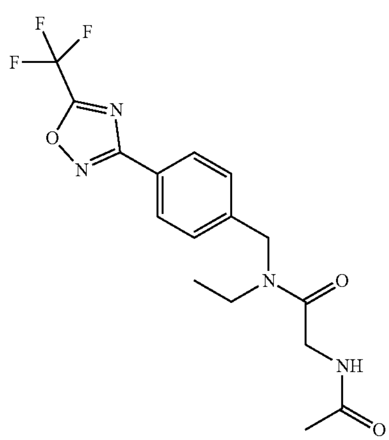 [SMILES: CCN(Cc1ccc(-c2noc(C(F)(F)F)n2)cc1)C(=O)CNC(C)=O] | 1.37 | 371.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.502 | 2-chloro-N-ethyl-N-[[4-[5-(trifluoromethyl)-1,2,4-oxadiazol-3-yl]phenyl]methyl]-acetamide | 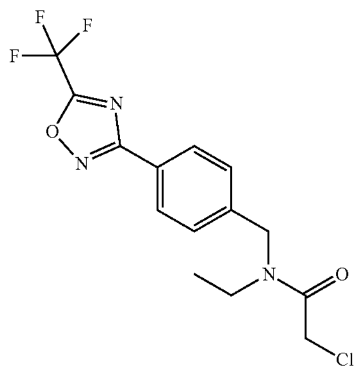 [SMILES: CCN(Cc1ccc(-c2noc(C(F)(F)F)n2)cc1)C(=O)CCl] | 1.66 | 348.2 | B | |
| 1.503 | N-ethyl-2-methyl-N-[4-[5-(trifluoromethyl)-1,2,4-oxadiazol-3-yl]phenyl]methyl]-propanamide | 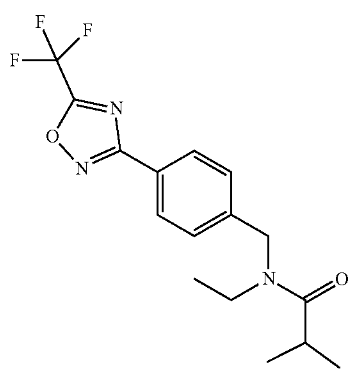 [SMILES: CCN(Cc1ccc(-c2noc(C(F)(F)F)n2)cc1)C(=O)C(C)C] | 1.78 | 342.3 | B | |
| 1.504 | N-ethyl-2,2-difluoro-N-[[4-[5-(trifluoromethyl)-1,2,4-oxadiazol-3-yl]phenyl]methyl]-cyclopropane-carboxamide | 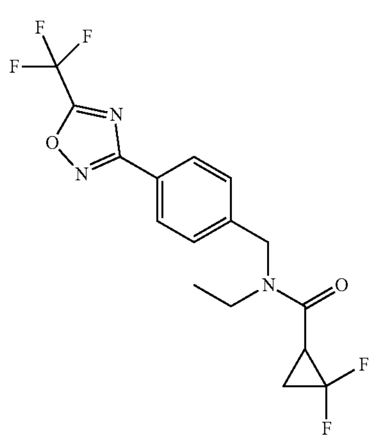 [SMILES: CCN(Cc1ccc(-c2noc(C(F)(F)F)n2)cc1)C(=O)C1CC1(F)F] | 1.76 | 376.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.505 | N-ethyl-N-[[4-[5-(trifluoromethyl)-1,2,4-oxadiazol-3-yl]phenyl]methyl]-butanamide | 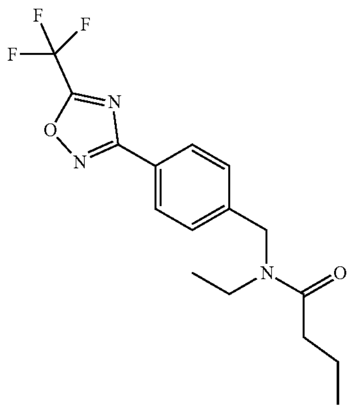 [SMILES: CCCC(=O)N(CC)Cc1ccc(-c2noc(C(F)(F)F)n2)cc1] | 1.78 | 342.3 | B | |
| 1.506 | N-ethyl-2-methyl-N-[[4-[5-(trifluoromethyl)-1,2,4-oxadiazol-3-yl]phenyl]methyl]-butanamide | 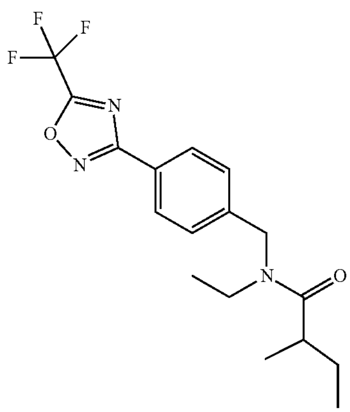 [SMILES: CCC(C)C(=O)N(CC)Cc1ccc(-c2noc(C(F)(F)F)n2)cc1] | 1.88 | 356.3 | B | |
| 1.507 | N-ethyl-4-methoxy-N-[[4-[5-(trifluoromethyl)-1,2,4-oxadiazol-3-yl]phenyl]methyl]-butanamide | 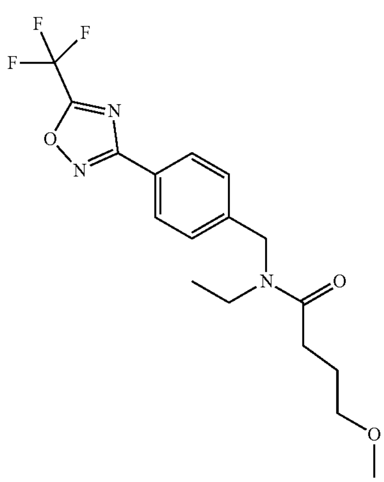 [SMILES: CCN(Cc1ccc(-c2noc(C(F)(F)F)n2)cc1)C(=O)CCCOC] | 1.67 | 372.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.508 | N-ethyl-3-methyl-N-[[4-[5-(trifluoromethyl)-1,2,4-oxadiazol-3-yl]phenyl]methyl]-oxetane-3-carboxamide | 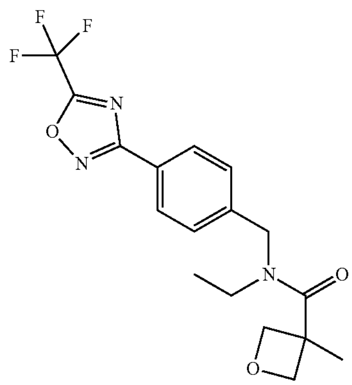 [SMILES: CCN(Cc1ccc(-c2noc(C(F)(F)F)n2)cc1)C(=O)C1(C)COC1] | 1.58 | 370.3 | B | |
| 1.509 | N-ethyl-N-[[4-[5-(trifluoromethyl)-1,2,4-oxadiazol-3-yl]phenyl]methyl]-tetrahydrofuran-2-carboxamide | 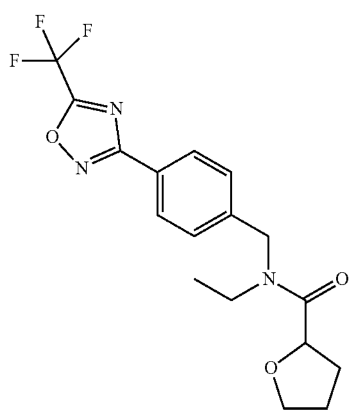 [SMILES: CCN(Cc1ccc(-c2noc(C(F)(F)F)n2)cc1)C(=O)C1CCCO1] | 1.64 | 370.3 | B | |
| 1.510 | 2-cyano-N-ethyl-N-[[4-[5-(trifluoromethyl)-1,2,4-oxadiazol-3-yl]phenyl]methyl]-acetamide | 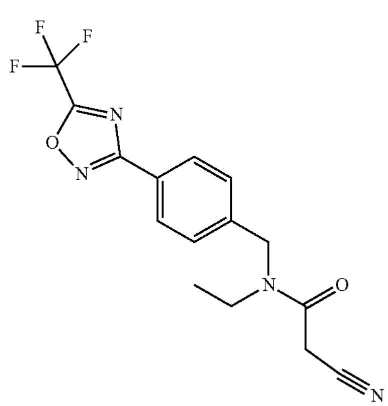 [SMILES: CCN(Cc1ccc(-c2noc(C(F)(F)F)n2)cc1)C(=O)CC#N] | 1.51 | 339.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.511 | N-ethyl-2-fluoro-N-[[4-[5-(trifluoromethyl)-1,2,4-oxadiazol-3-yl]phenyl]methyl]-cyclopropane-carboxamide | 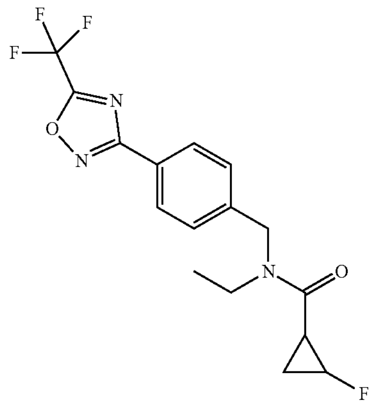 [SMILES: CCN(Cc1ccc(-c2noc(C(F)(F)F)n2)cc1)C(=O)C1CC1F] | 1.64 | 358.3 | B | |
| 1.512 | N-ethyl-2-methoxy-N-[[4-[5-(trifluoromethyl)-1,2,4-oxadiazol-3-yl]phenyl]methyl]-propanamide | 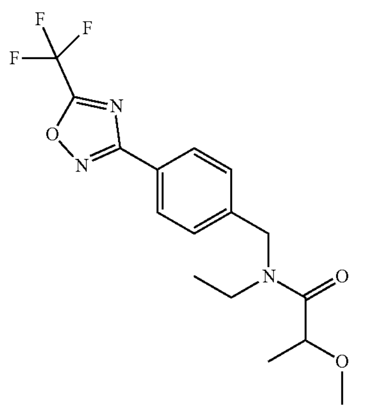 [SMILES: CCN(Cc1ccc(-c2noc(C(F)(F)F)n2)cc1)C(=O)C(C)OC] | 1.61 | 358.3 | B | |
| 1.513 | N-ethyl-N-[[4-[5-(trifluoromethyl)-1,2,4-oxadiazol-3-yl]phenyl]methyl]-1,3-dioxolane-2-carboxamide | 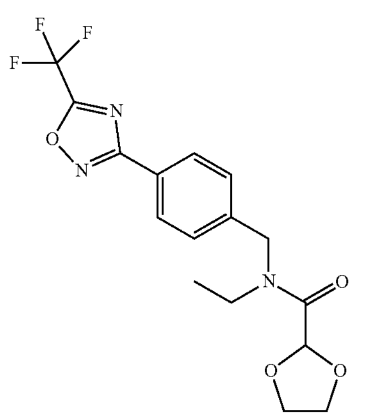 [SMILES: CCN(Cc1ccc(-c2noc(C(F)(F)F)n2)cc1)C(=O)C1OCCO1] | 1.58 | 372.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.514 | N-ethyl-N-[[4-[5-(trifluoromethyl)-1,2,4-oxadiazol-3-yl]phenyl]methyl]-cyclopropane-carboxamide | 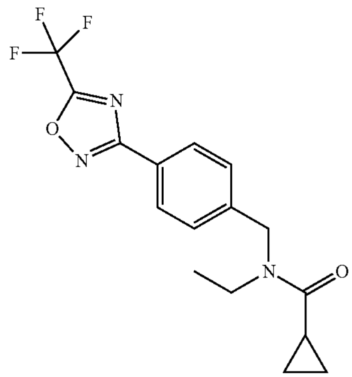 [SMILES: CCN(Cc1ccc(-c2noc(C(F)(F)F)n2)cc1)C(=O)C1CC1] | 1.72 | 340.3 | B | |
| 1.515 | N-methyl-N-[[4-[5-(trifluoromethyl)-1,2,4-oxadiazol-3-yl]phenyl]methyl]-cyclopentane-carboxamide | 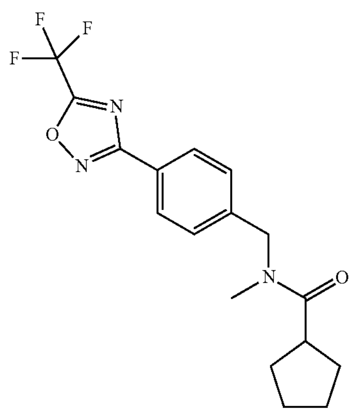 [SMILES: CN(Cc1ccc(-c2noc(C(F)(F)F)n2)cc1)C(=O)C1CCCC1] | 1.83 | 354.3 | B | |
| 1.516 | 3-methoxy-N-methyl-N-[[4-[5-(trifluoromethyl)-1,2,4-oxadiazol-3-yl]phenyl]methyl]-propanamide | 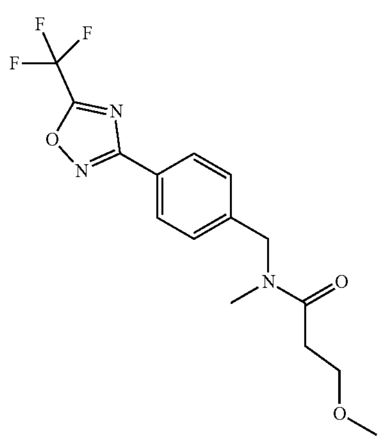 [SMILES: COCCC(=O)N(C)Cc1ccc(-c2noc(C(F)(F)F)n2)cc1] | 1.50 | 344.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.517 | N-methyl-N-[[4-[5-(trifluoromethyl)-1,2,4-oxadiazol-3-yl]phenyl]methyl]-propanamide | 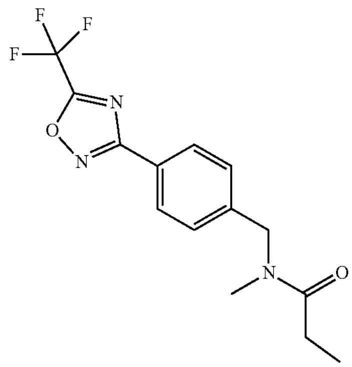 [SMILES: CCC(=O)N(C)Cc1ccc(-c2noc(C(F)(F)F)n2)cc1] | 1.56 | 314.3 | B | |
| 1.518 | N-methyl-N-[[4-[5-(trifluoromethyl)-1,2,4-oxadiazol-3-yl]phenyl]methyl]-cyclobutane-carboxamide | 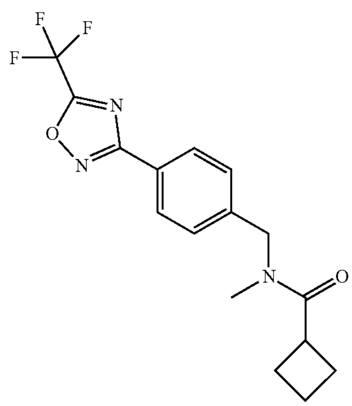 [SMILES: CN(Cc1ccc(-c2noc(C(F)(F)F)n2)cc1)C(=O)C1CCC1] | 1.74 | 340.3 | B | |
| 1.519 | 2-methoxy-N-methyl-N-[[4-[5-(trifluoromethyl)-1,2,4-oxadiazol-3-yl]phenyl]methyl]-acetamide | 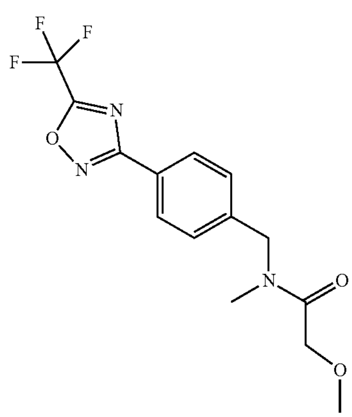 [SMILES: COCC(=O)N(C)Cc1ccc(-c2noc(C(F)(F)F)n2)cc1] | 1.43 | 330.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.520 | N,2-dimethyl-N-[[4-[5-(trifluoromethyl)-1,2,4-oxadiazol-3-yl]phenyl]methyl]-cyclopropane-carboxamide | 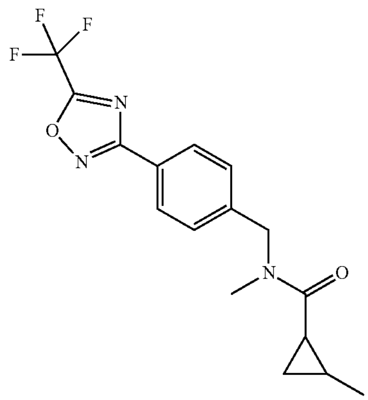 [SMILES: CC1CC1C(=O)N(C)Cc1ccc(-c2noc(C(F)(F)F)n2)cc1] | 1.72 | 340.3 | B | |
| 1.521 | 2-acetamido-N-methyl-N-[[4-[5-(trifluoromethyl)-1,2,4-oxadiazol-3-yl]phenyl]methyl]-acetamide | 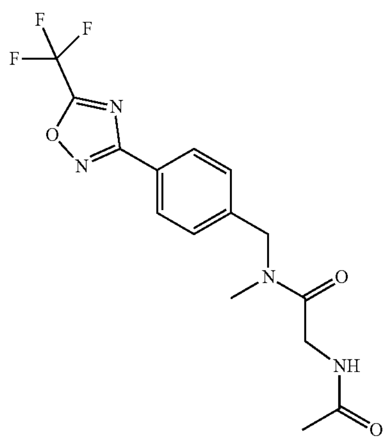 [SMILES: CC(=O)NCC(=O)N(C)Cc1ccc(-c2noc(C(F)(F)F)n2)cc1] | 1.27 | 357.3 | B | |
| 1.522 | 2-chloro-N-methyl-N-[[4-[5-(trifluoromethyl)-1,2,4-oxadiazol-3-yl]phenyl]methyl]-acetamide | 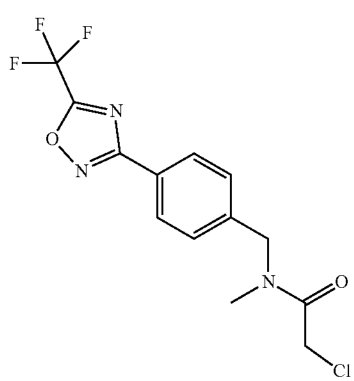 [SMILES: CN(Cc1ccc(-c2noc(C(F)(F)F)n2)cc1)C(=O)CCl] | 1.56 | 334.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.523 | 2,2-difluoro-N-methyl-N-[[4-[5-(trifluoromethyl)-1,2,4-oxadiazol-3-yl]phenyl]methyl]-cyclopropane-carboxamide | 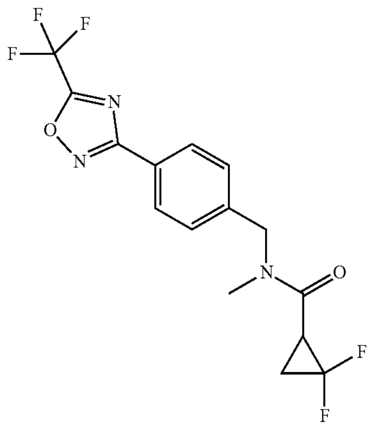 [SMILES: CN(Cc1ccc(-c2noc(C(F)(F)F)n2)cc1)C(=O)C1CC1(F)F] | 1.66 | 362.2 | B | |
| 1.524 | N-methyl-N-[[4-[5-(trifluoromethyl)-1,2,4-oxadiazol-3-yl]phenyl]methyl]-butanamide | 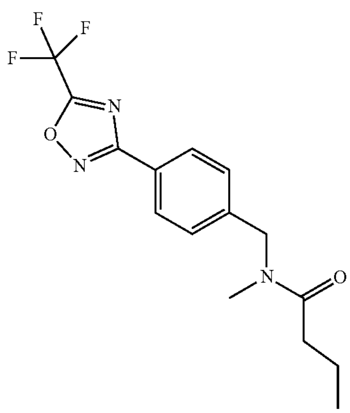 [SMILES: CCCC(=O)N(C)Cc1ccc(-c2noc(C(F)(F)F)n2)cc1] | 1.68 | 328.3 | B | |
| 1.525 | N,2-dimethyl-N-[[4-[5-(trifluoromethyl)-1,2,4-oxadiazol-3-yl]phenyl]methyl]-butanamide | 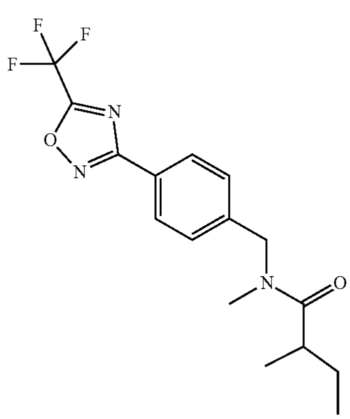 [SMILES: CCC(C)C(=O)N(C)Cc1ccc(-c2noc(C(F)(F)F)n2)cc1] | 1.78 | 342.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.526 | 4-methoxy-N-methyl-N-[[4-[5-(trifluoromethyl)-1,2,4-oxadiazol-3-yl]phenyl]methyl]-butanamide | 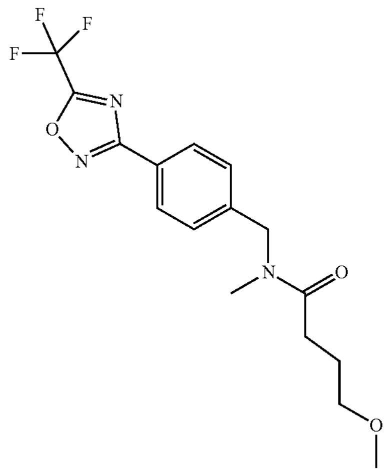 [SMILES: COCCCC(=O)N(C)Cc1ccc(-c2noc(C(F)(F)F)n2)cc1] | 1.56 | 358.3 | B | |
| 1.527 | N,3-dimethyl-N-[[4-[5-(trifluoromethyl)-1,2,4-oxadiazol-3-yl]phenyl]methyl]-oxetane-3-carboxamide | 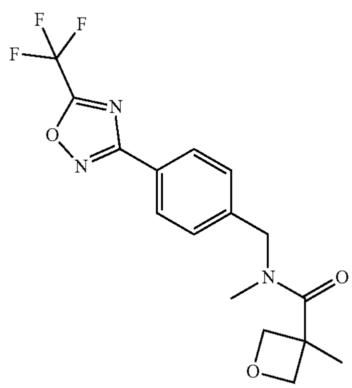 [SMILES: CN(Cc1ccc(-c2noc(C(F)(F)F)n2)cc1)C(=O)C1(C)COC1] | 1.48 | 356.3 | B | |
| 1.528 | N-methyl-N-[[4-[5-(trifluoromethyl)-1,2,4-oxadiazol-3-yl]phenyl]methyl]-tetrahydrofuran-2-carboxamide | 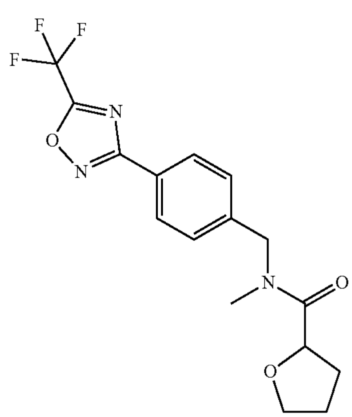 [SMILES: CN(Cc1ccc(-c2noc(C(F)(F)F)n2)cc1)C(=O)C1CCCO1] | 1.53 | 356.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.529 | 2-fluoro-N-methyl-N-[[4-[5-(trifluoromethyl)-1,2,4-oxadiazol-3-yl]phenyl]methyl]-cyclopropane-carboxamide | 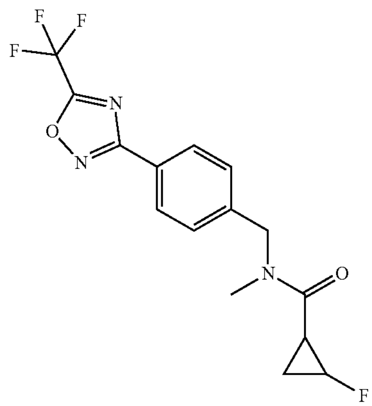 [SMILES: CN(Cc1ccc(-c2noc(C(F)(F)F)n2)cc1)C(=O)C1CC1F] | 1.54 | 344.3 | B | |
| 1.530 | 2-methoxy-N-methyl-N-[[4-[5-(trifluoromethyl)-1,2,4-oxadiazol-3-yl]phenyl]methyl]-propanamide | 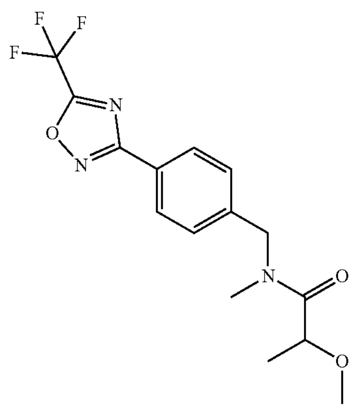 [SMILES: COC(C)C(=O)N(C)Cc1ccc(-c2noc(C(F)(F)F)n2)cc1] | 1.51 | 344.3 | B | |
| 1.531 | N-methyl-N-[[4-[5-(trifluoromethyl)-1,2,4-oxadiazol-3-yl]phenyl]methyl]-1,3-dioxolane-2-carboxamide | 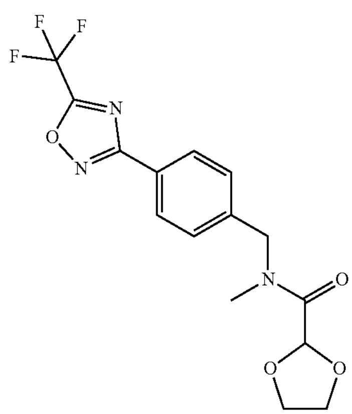 [SMILES: CN(Cc1ccc(-c2noc(C(F)(F)F)n2)cc1)C(=O)C1OCCO1] | 1.47 | 358.3 | B | |
| 1.532 | N-methyl-N-[[4-[5-(trifluoromethyl)-1,2,4-oxadiazol-3-yl]phenyl]methyl]-cyclopropane-carboxamide | 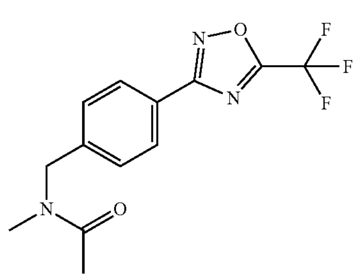 [SMILES: CC(=O)N(C)Cc1ccc(-c2noc(C(F)(F)F)n2)cc1] | 1.61 | 326.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.533 | N-(3,3-dichloroallyloxy)-3-methoxy-N-[[4-[5-(trifluoromethyl)-1,2,4-oxadiazol-3-yl]phenyl]methyl]-propanamide | 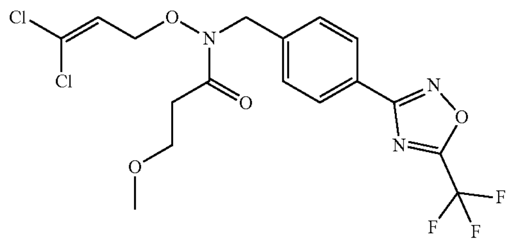 [SMILES: COCCC(=O)N(Cc1ccc(-c2noc(C(F)(F)F)n2)cc1)OCC=C(Cl)Cl] | 1.92 | 454.3 | B | |
| 1.534 | N-(3,3-dichloroallyloxy)-N-[[4-[5-(trifluoromethyl)-1,2,4-oxadiazol-3-yl]phenyl]methyl]-propanamide | 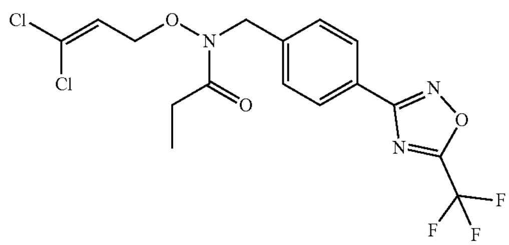 [SMILES: CCC(=O)N(Cc1ccc(-c2noc(C(F)(F)F)n2)cc1)OCC=C(Cl)Cl] | 2 | 424.2 | B | |
| 1.535 | N-(3,3-dichloroallyloxy)-2-methoxy-N-[[4-[5-(trifluoromethyl)-1,2,4-oxadiazol-3-yl]phenyl]methyl]-acetamide | 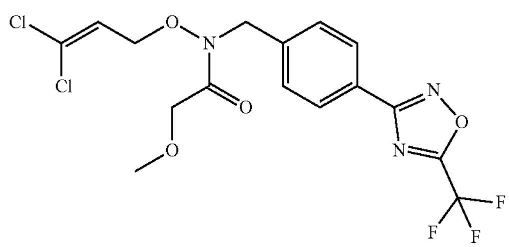 [SMILES: COCC(=O)N(Cc1ccc(-c2noc(C(F)(F)F)n2)cc1)OCC=C(Cl)Cl] | 1.85 | 440.2 | B | |
| 1.536 | N-(3,3-dichloroallyloxy)-2-methyl-N-[[4-[5-(trifluoromethyl)-1,2,4-oxadiazol-3-yl]phenyl]methyl]-cyclopropane-carboxamide | 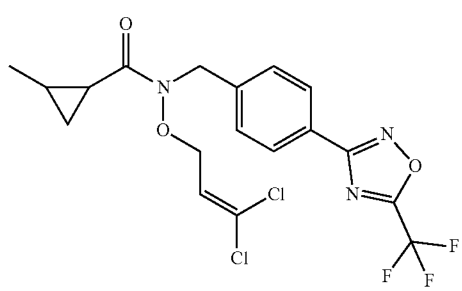 [SMILES: CC1CC1C(=O)N(Cc1ccc(-c2noc(C(F)(F)F)n2)cc1)OCC=C(Cl)Cl] | 2.1 | 450.3 | B | |
| 1.537 | 2-acetamido-N-(3,3-dichloroallyloxy)-N-[[4-[5-(trifluoromethyl)-1,2,4-oxadiazol-3-yl]phenyl]methyl]-acetamide | 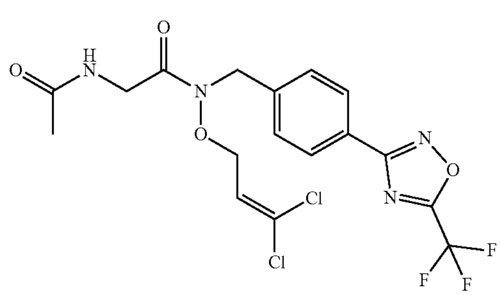 [SMILES: CC(=O)NCC(=O)N(Cc1ccc(-c2noc(C(F)(F)F)n2)cc1)OCC=C(Cl)Cl] | 1.65 | 467.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.538 | 2-chloro-N-(3,3-dichloroallyloxy)-N-[[4-[5-(trifluoromethyl)-1,2,4-oxadiazol-3-yl]phenyl]methyl]-acetamide | 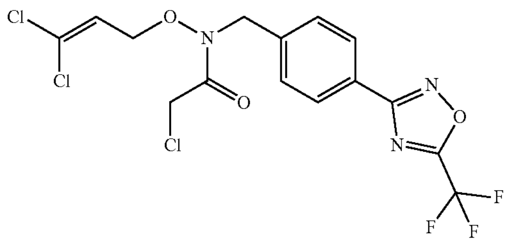 [SMILES: O=C(CCl)N(Cc1ccc(-c2noc(C(F)(F)F)n2)cc1)OCC=C(Cl)Cl] | 1.96 | 444.2 | B | |
| 1.539 | N-(3,3-dichloroallyloxy)-2-methyl-N-[[4-[5-(trifluoromethyl)-1,2,4-oxadiazol-3-yl]phenyl]methyl]-propanamide | 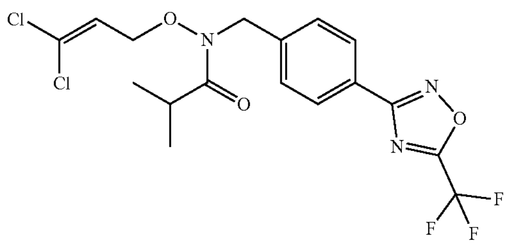 [SMILES: CC(C)C(=O)N(Cc1ccc(-c2noc(C(F)(F)F)n2)cc1)OCC=C(Cl)Cl] | 2.08 | 438.2 | B | |
| 1.540 | N-(3,3-dichloroallyloxy)-2,2-difluoro-N-[[4-[5-(trifluoromethyl)-1,2,4-oxadiazol-3-yl]phenyl]methyl]-cyclopropane-carboxamide | 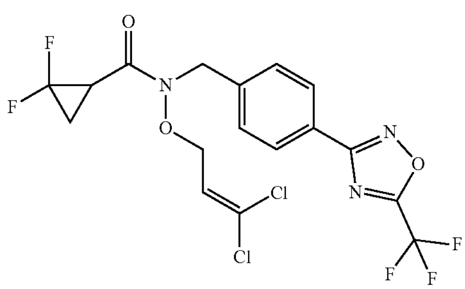 [SMILES: O=C(C1CC1(F)F)N(Cc1ccc(-c2noc(C(F)(F)F)n2)cc1)OCC=C(Cl)Cl] | 2.02 | 472.2 | B | |
| 1.541 | N-(3,3-dichloroallyloxy)-N-[[4-[5-(trifluoromethyl)-1,2,4-oxadiazol-3-yl]phenyl]methyl]-butanamide | 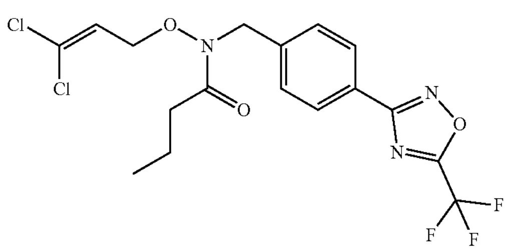 | 2.08 | 438.2 | B | |
| 1.542 | N-(3,3-dichloroallyloxy)-2-methyl-N-[[4-[5-(trifluoromethyl)-1,2,4-oxadiazol-3-yl]phenyl]methyl]-butanamide | 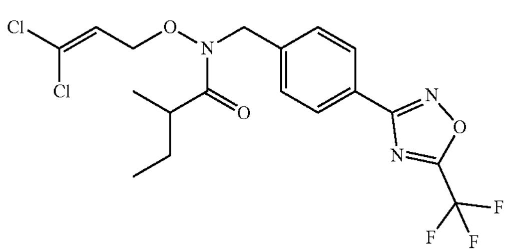 | 2.16 | 452.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.543 | N-(3,3-dichloroallyloxy)-4-methoxy-N-[[4-[5-(trifluoromethyl)-1,2,4-oxadiazol-3-yl]phenyl]methyl]-butanamide | 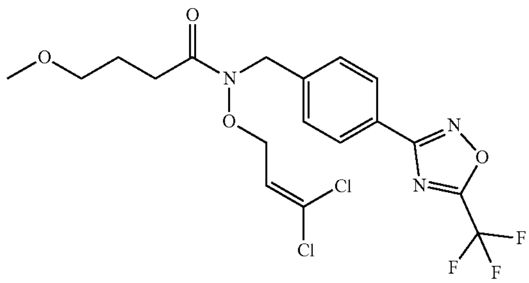 [SMILES: COCCCC(=O)N(Cc1ccc(-c2noc(C(F)(F)F)n2)cc1)OCC=C(Cl)Cl] | 1.97 | 468.3 | B | |
| 1.544 | N-(3,3-dichloroallyloxy)-3-methyl-N-[[4-[5-(trifluoromethyl)-1,2,4-oxadiazol-3-yl]phenyl]methyl]-oxetane-3-carboxamide | 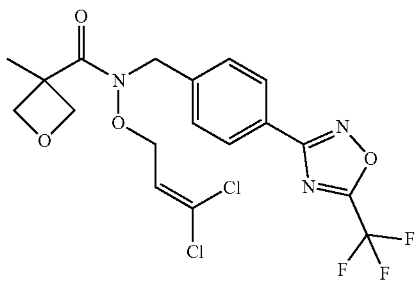 [SMILES: CC1(C(=O)N(Cc2ccc(-c3noc(C(F)(F)F)n3)cc2)OCC=C(Cl)Cl)COC1] | 1.9 | 466.2 | B | |
| 1.545 | N-(3,3-dichloroallyloxy)-2-fluoro-N-[[4-[5-(trifluoromethyl)-1,2,4-oxadiazol-3-yl]phenyl]methyl]-cyclopropane-carboxamide | 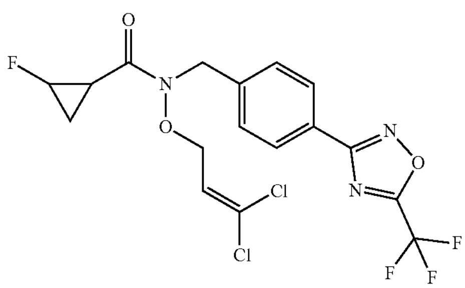 [SMILES: O=C(C1CC1F)N(Cc1ccc(-c2noc(C(F)(F)F)n2)cc1)OCC=C(Cl)Cl] | 1.93 | 454.2 | B | |
| 1.546 | N-(3,3-dichloroallyloxy)-2-methoxy-N-[[4-[5-(trifluoromethyl)-1,2,4-oxadiazol-3-yl]phenyl]methyl]-propanamide | 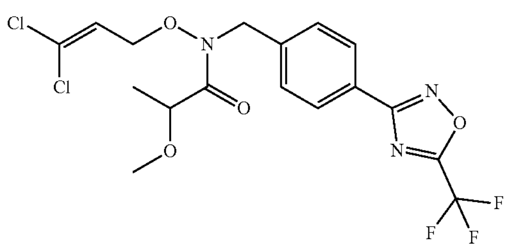 [SMILES: COC(C)C(=O)N(Cc1ccc(-c2noc(C(F)(F)F)n2)cc1)OCC=C(Cl)Cl] | 1.91 | 454.2 | B | |
| 1.547 | N-(3,3-dichloroallyloxy)-N-[[4-[5-(trifluoromethyl)-1,2,4-oxadiazol-3-yl]phenyl]methyl]-1,3-dioxolane-2-carboxamide | 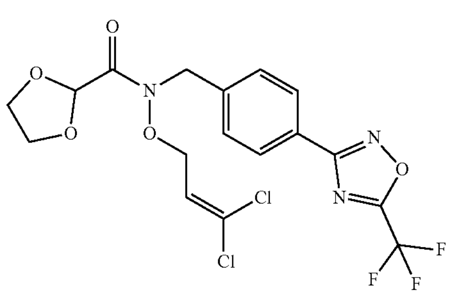 [SMILES: O=C(C1OCCO1)N(Cc1ccc(-c2noc(C(F)(F)F)n2)cc1)OCC=C(Cl)Cl] | 1.88 | 468.2 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.548 | N-(3,3-dichloroallyloxy)-N-[[4-[5-(trifluoromethyl)-1,2,4-oxadiazol-3-yl]phenyl]methyl]-cyclopropane-carboxamide | 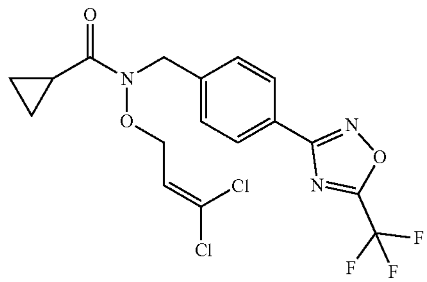 [SMILES: O=C(C1CC1)N(Cc1ccc(-c2noc(C(F)(F)F)n2)cc1)OCC=C(Cl)Cl] | 2.02 | 436.2 | B | |
| 1.549 | N-[(4-chlorophenyl)-methoxy]-3-methoxy-N-[[4-[5-(trifluoromethyl)-1,2,4-oxadiazol-3-yl]phenyl]methyl]-propanamide | 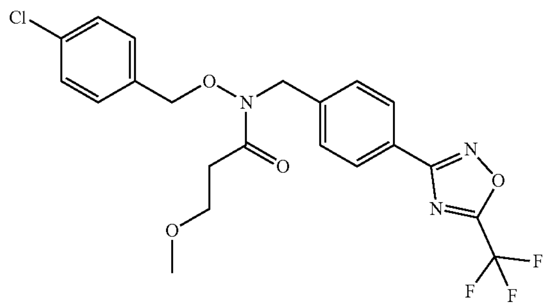 [SMILES: COCCC(=O)N(Cc1ccc(-c2noc(C(F)(F)F)n2)cc1)OCc1ccc(Cl)cc1] | 1.98 | 470.3 | B | |
| 1.550 | N-[(4-chlorophenyl)-methoxy]-N-[[4-[5-(trifluoromethyl)-1,2,4-oxadiazol-3-yl]phenyl]methyl]-propanamide | 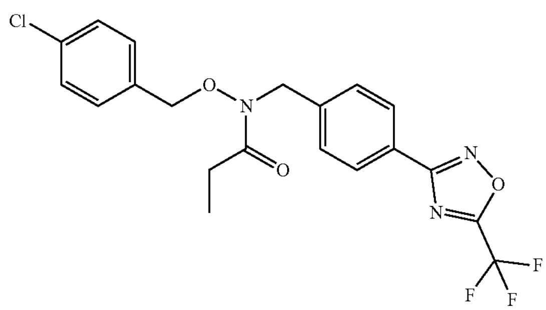 [SMILES: CCC(=O)N(Cc1ccc(-c2noc(C(F)(F)F)n2)cc1)OCc1ccc(Cl)cc1] | 2.05 | 440.3 | B | |
| 1.551 | N-[(4-chlorophenyl)-methoxy]-2-methoxy-N-[[4-[5-(trifluoromethyl)-1,2,4-oxadiazol-3-yl]phenyl]methyl]-acetamide | 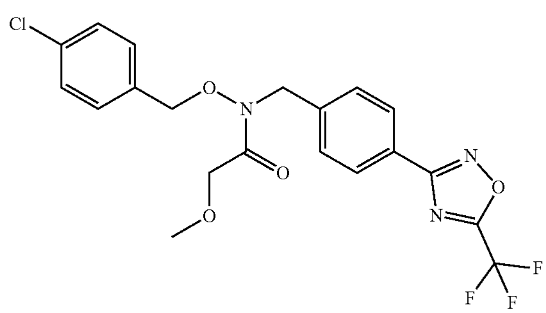 | 1.91 | 456.3 | B | |
| 1.552 | 2-acetamido-N-[(4-chlorophenyl)-methoxy]-N-[[4-[5-(trifluoromethyl)-1,2,4-oxadiazol-3-yl]phenyl]methyl]-acetamide | 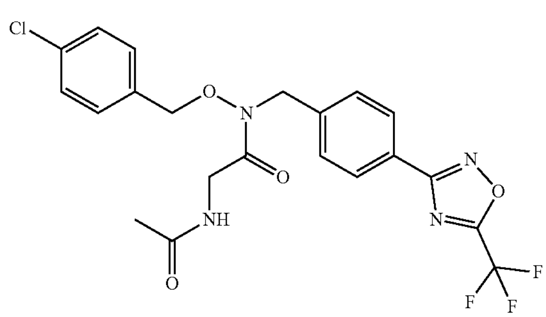 [SMILES: CC(=O)NCC(=O)N(Cc1ccc(-c2noc(C(F)(F)F)n2)cc1)OCc1ccc(Cl)cc1] | 1.73 | 483.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.553 | 2-chloro-N-[(4-chlorophenyl)-methoxy]-N-[[4-[5-(trifluoromethyl)-1,2,4-oxadiazol-3-yl]phenyl]methyl]-acetamide | 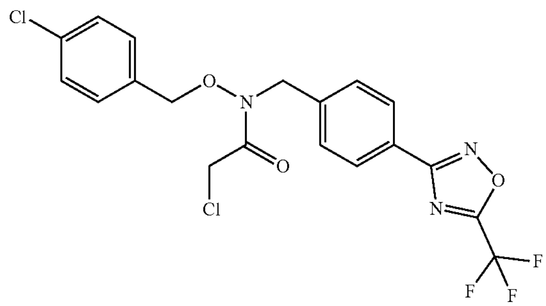 [SMILES: O=C(CCl)N(Cc1ccc(-c2noc(C(F)(F)F)n2)cc1)OCc1ccc(Cl)cc1] | 2.01 | 460.2 | B | |
| 1.554 | N-[(4-chlorophenyl)-methoxy]-N-[[4-[5-(trifluoromethyl)-1,2,4-oxadiazol-3-yl]phenyl]methyl]-butanamide | 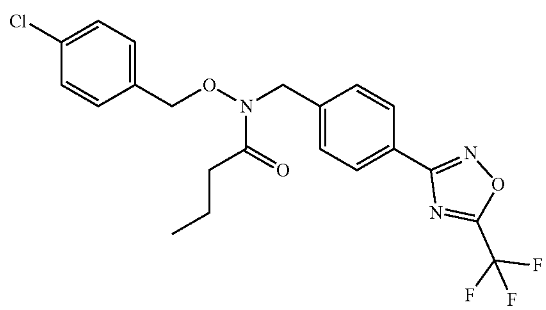 [SMILES: CCCC(=O)N(Cc1ccc(-c2noc(C(F)(F)F)n2)cc1)OCc1ccc(Cl)cc1] | 2.13 | 454.3 | B | |
| 1.555 | N-[(4-chlorophenyl)-methoxy]-4-methoxy-N-[[4-[5-(trifluoromethyl)-1,2,4-oxadiazol-3-yl]phenyl]methyl]-butanamide | 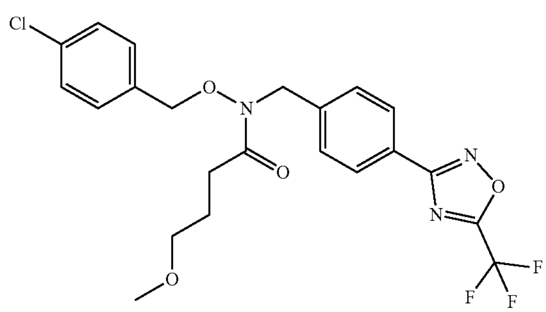 [SMILES: COCCCC(=O)N(Cc1ccc(-c2noc(C(F)(F)F)n2)cc1)OCc1ccc(Cl)cc1] | 2.02 | 484.3 | B | |
| 1.556 | N-[(4-chlorophenyl)-methoxy]-3-methyl-N-[[4-[5-(trifluoromethyl)-1,2,4-oxadiazol-3-yl]phenyl]methyl]-oxetane-3-carboxamide | 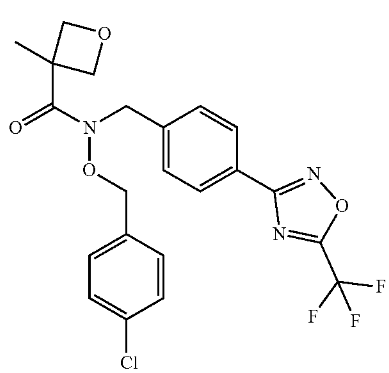 [SMILES: CC1(C(=O)N(Cc2ccc(-c3noc(C(F)(F)F)n3)cc2)OCc2ccc(Cl)cc2)COC1] | 1.96 | 482.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.557 | N-[(4-chlorophenyl)-methoxy]-N-[[4-[5-(trifluoromethyl)-1,2,4-oxadiazol-3-yl]phenyl]methyl]-tetrahydrofuran-2-carboxamide | 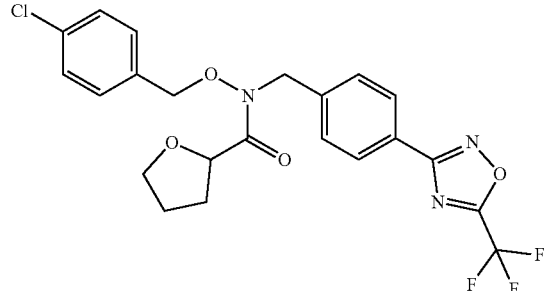 | 1.99 | 482.3 | B | |
| 1.558 | N-[(4-chlorophenyl)-methoxy]-2-fluoro-N-[[4-[5-(trifluoromethyl)-1,2,4-oxadiazol-3-yl]phenyl]methyl]-cyclopropane-carboxamide | 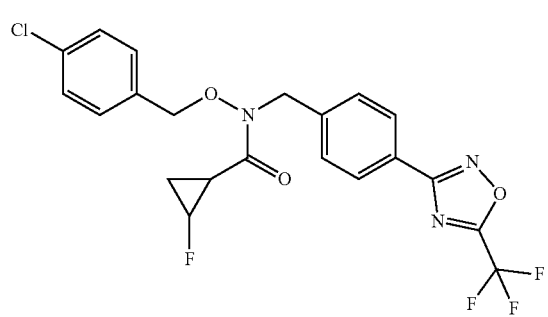 | 1.99 | 470.3 | B | |
| 1.559 | N-[(4-chlorophenyl)-methoxy]-2-methoxy-N-[[4-[5-(trifluoromethyl)-1,2,4-oxadiazol-3-yl]phenyl)methyl]-propanamide | 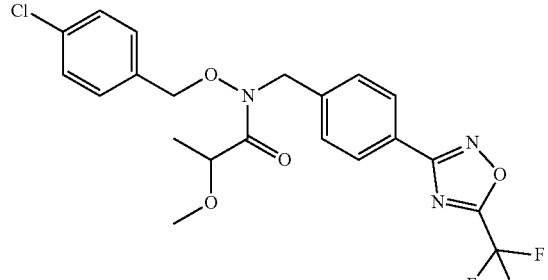 | 1.97 | 470.3 | B | |
| 1.560 | N-[(4-chlorophenyl)-methoxy]-N-[[4-[5-(trifluoromethyl)-1,2,4-oxadiazol-3-yl]phenyl]methyl]-1,3-dioxolane-2-carboxamide | 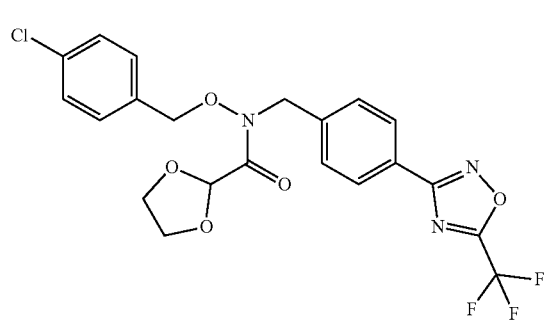 [SMILES: O=C(C1OCCO1)N(Cc1ccc(-c2noc(C(F)(F)F)n2)cc1)OCc1ccc(Cl)cc1] | 1.94 | 484.3 | B | |
| 1.561 | N-[(4-chlorophenyl)-methoxy]-N-[[4-[5-(trifluoromethyl)-1,2,4-oxadiazol-3-yl]phenyl]methyl]-cyclopropane-carboxamide | 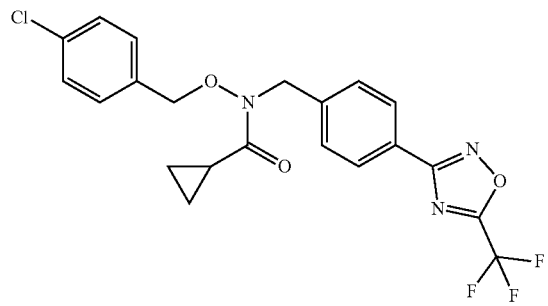 [SMILES: O=C(C1CC1)N(Cc1ccc(-c2noc(C(F)(F)F)n2)cc1)OCc1ccc(Cl)cc1] | 2.05 | 452.3 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.562 | N-ethoxy-N-[[4-[5-(trifluoromethyl)-1,2,4-oxadiazol-3-yl]phenyl]methyl]-propanamide | 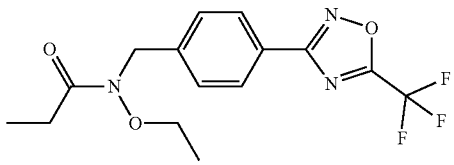 [SMILES: CCON(Cc1ccc(-c2noc(C(F)(F)F)n2)cc1)C(=O)CC] | 1.76 | 344.15 | B | |
| 1.563 | N-[[2-fluoro-4-[5-(trifluoromethyl)-1,2,4-oxadiazol-3-yl]phenyl]methyl]-N-methoxy-tetrahydrofuran-2-carboxamide | 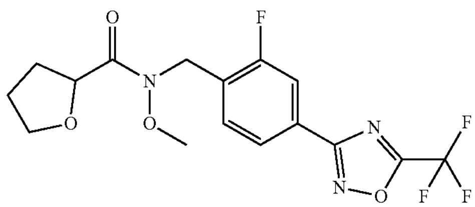 [SMILES: CON(Cc1ccc(-c2noc(C(F)(F)F)n2)cc1F)C(=O)C1CCCO1] | 1.06 | 390 | A | |
| 1.564 | N-ethoxy-N-[[4-[5-(trifluoromethyl)-1,2,4-oxadiazol-3-yl]phenyl]methyl]-cyclopropane-carboxamide | 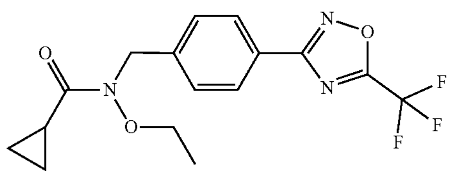 [SMILES: CCON(Cc1ccc(-c2noc(C(F)(F)F)n2)cc1)C(=O)C1CC1] | 1.79 | 356.15 | B | |
| 1.565 | 2-chloro-N-[[2-fluoro-4-[5-(trifluoromethyl)-1,2,4-oxadiazol-3-yl]phenyl]methyl]-N-methoxy-benzamide | 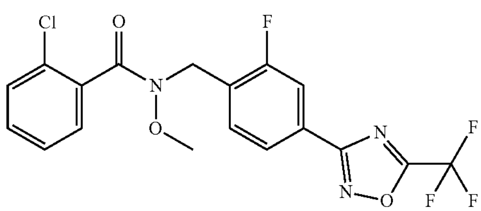 [SMILES: CON(Cc1ccc(-c2noc(C(F)(F)F)n2)cc1F)C(=O)c1ccccc1Cl] | 1.17 | 430 | A | |
| 1.566 | N-[[2-fluoro-4-[5-(trifluoromethyl)-1,2,4-oxadiazol-3-yl]phenyl]methyl]-N-methoxy-cyclopropane-carboxamide | 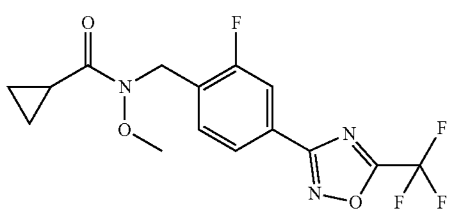 [SMILES: CON(Cc1ccc(-c2noc(C(F)(F)F)n2)cc1F)C(=O)C1CC1] | 1.11 | 360 | A | |
| 1.567 | N-ethoxy-2-methoxy-N-[[4-[5-(trifluoromethyl)-1,2,4-oxadiazol-3-yl]phenyl]methyl]-acetamide | 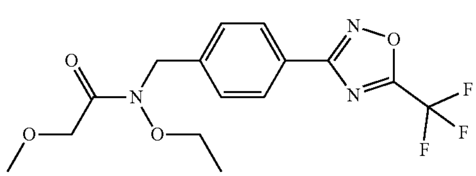 [SMILES: CCON(Cc1ccc(-c2noc(C(F)(F)F)n2)cc1)C(=O)COC] | 1.60 | 360.14 | B | |
| 1.568 | N-[[2-fluoro-4-[5-(trifluoromethyl)-1,2,4-oxadiazol-3-yl]phenyl]methyl]-N-methoxy-propanamide | 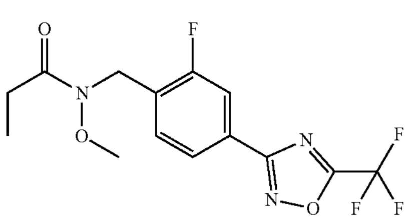 [SMILES: CCC(=O)N(Cc1ccc(-c2noc(C(F)(F)F)n2)cc1F)OC] | 1.1 | 348 | A | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.569 | N-methoxy-N-[[5-[5-(trifluoromethyl)-1,2,4-oxadiazol-3-yl]-2-pyridyl]methyl]-tetrahydrofuran-2-carboxamide | 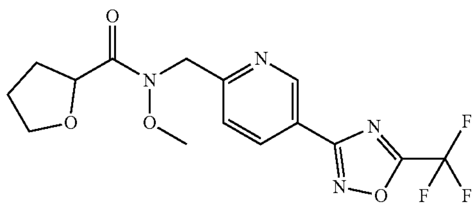 [SMILES: CON(Cc1ccc(-c2noc(C(F)(F)F)n2)cn1)C(=O)C1CCCO1] | 0.94 | 373 | A | |
| 1.570 | N-methoxy-N-[[5-[5-(trifluoromethyl)-1,2,4-oxadiazol-3-yl]-2-pyridyl]methyl]-cyclopropane-carboxamide | 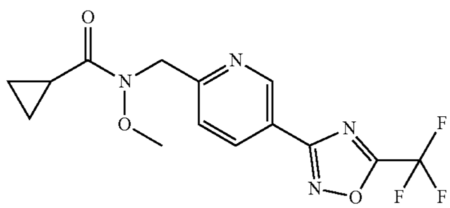 [SMILES: CON(Cc1ccc(-c2noc(C(F)(F)F)n2)cn1)C(=O)C1CC1] | 0.99 | 343 | A | |
| 1.571 | N-methoxy-N-[[5-[5-(trifluoromethyl)-1,2,4-oxadiazol-3-yl]-2-pyridyl]methyl]-propanamide | 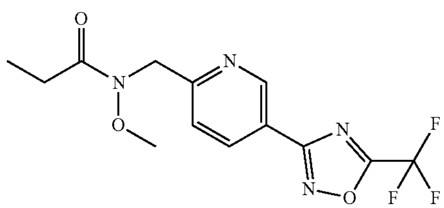 [SMILES: CCC(=O)N(Cc1ccc(-c2noc(C(F)(F)F)n2)cn1)OC] | 0.97 | 331 | A | |
| 1.572 | 2-chloro-N-methoxy-N-[[5-[5-(trifluoromethyl)-1,2,4-oxadiazol-3-yl]-2-pyridyl]methyl]-benzamide | 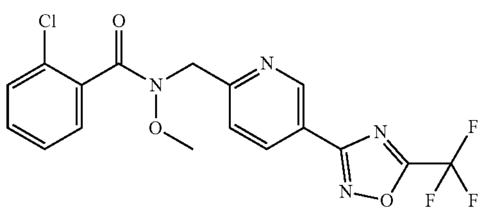 [SMILES: CON(Cc1ccc(-c2noc(C(F)(F)F)n2)cn1)C(=O)c1ccccc1Cl] | | | | 80-89 |
| 1.573 | N-propyl-N-[[4-[5-(trifluoromethyl)-1,2,4-oxadiazol-3-yl]phenyl]methyl]-propanamide | 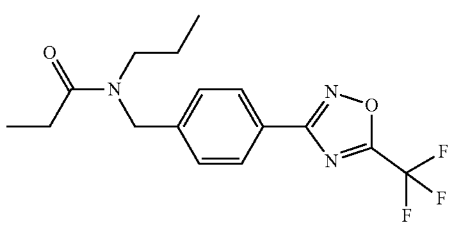 [SMILES: CCCN(Cc1ccc(-c2noc(C(F)(F)F)n2)cc1)C(=O)CC] | 1.77 | 342.19 | B | |
| 1.574 | N-propyl-N-[[4-[5-(trifluoromethyl)-1,2,4-oxadiazol-3-yl]phenyl]methyl]-cyclopropane-carboxamide | 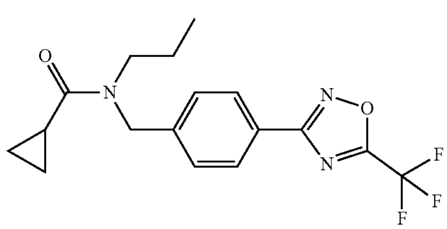 [SMILES: CCCN(Cc1ccc(-c2noc(C(F)(F)F)n2)cc1)C(=O)C1CC1] | 1.82 | 354.18 | B | |
| 1.575 | 2-methoxy-N-propyl-N-[[4-[5-(trifluoromethyl)-1,2,4-oxadiazol-3-yl]phenyl]methyl]-acetamide | 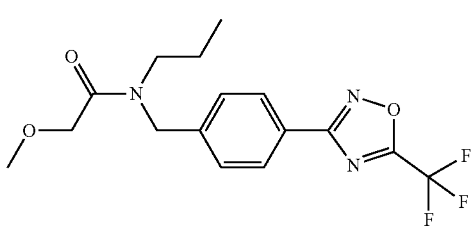 [SMILES: CCCN(Cc1ccc(-c2noc(C(F)(F)F)n2)cc1)C(=O)COC] | 1.63 | 358.18 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.576 | 2-chloro-N-[[2,3-difluoro-4-[5-(trifluoromethyl)-1,2,4-oxadiazol-3-yl]phenyl]methyl]-N-methoxy-benzamide | 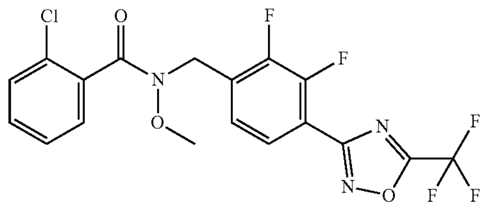 [SMILES: CON(Cc1ccc(-c2noc(C(F)(F)F)n2)c(F)c1F)C(=O)c1ccccc1Cl] | 1.16 | 448 | A | |
| 1.577 | N-[[2,3-difluoro-4-[5-(trifluoromethyl)-1,2,4-oxadiazol-3-yl]phenyl]methyl]-N-methoxy-tetrahydrofuran-2-carboxamide | 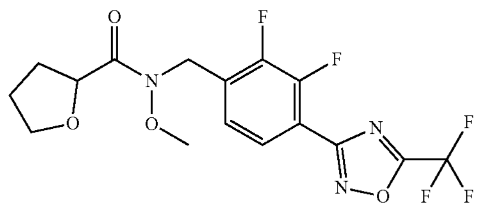 [SMILES: CON(Cc1ccc(-c2noc(C(F)(F)F)n2)c(F)c1F)C(=O)C1CCCO1] | 1.08 | 408 | A | |
| 1.578 | N-[[3-fluoro-4-[5-(trifluoromethyl)-1,2,4-oxadiazol-3-yl]phenyl]methyl]-N-methoxy-tetrahydrofuran-2-carboxamide | 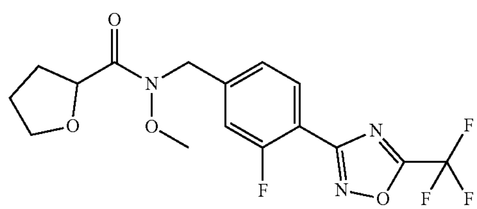 [SMILES: CON(Cc1ccc(-c2noc(C(F)(F)F)n2)c(F)c1)C(=O)C1CCCO1] | 1.04 | 391 | A | |
| 1.579 | N-[[3-fluoro-4-[5-(trifluoromethyl)-1,2,4-oxadiazol-3-yl]phenyl]methyl]-N-methoxy-cyclopropane-carboxamide | 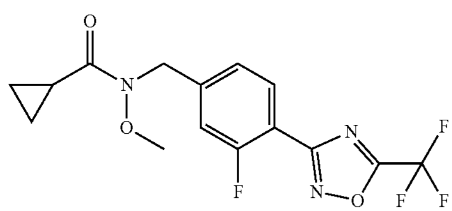 [SMILES: CON(Cc1ccc(-c2noc(C(F)(F)F)n2)c(F)c1)C(=O)C1CC1] | 1.06 | 360 | A | |
| 1.580 | N-[[3-fluoro-4-[5-(trifluoromethyl)-1,2,4-oxadiazol-3-yl]phenyl]methyl]-N-methoxy-propanamide | 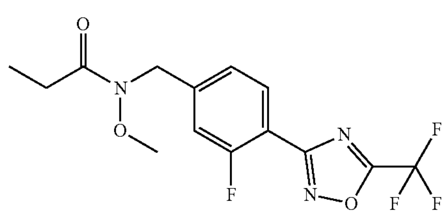 [SMILES: CCC(=O)N(Cc1ccc(-c2noc(C(F)(F)F)n2)c(F)c1)OC] | 1.05 | 348 | A | |
| 1.581 | 2-chloro-N-[[3-fluoro-4-[5-(trifluoromethyl)-1,2,4-oxadiazol-3-yl]phenyl]methyl]-N-methoxy-benzamide | 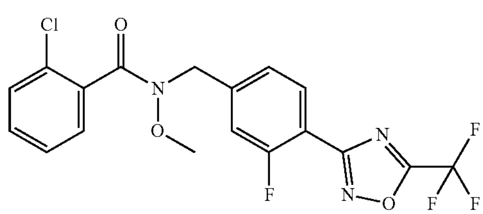 [SMILES: CON(Cc1ccc(-c2noc(C(F)(F)F)n2)c(F)c1)C(=O)c1ccccc1Cl] | | | | 89-95 |
| 1.582 | N-(2,2,2-trifluoroethyl)-N-[[4-[5-(trifluoromethyl)-1,2,4-oxadiazol-3-yl]phenyl]methyl]-propanamide | 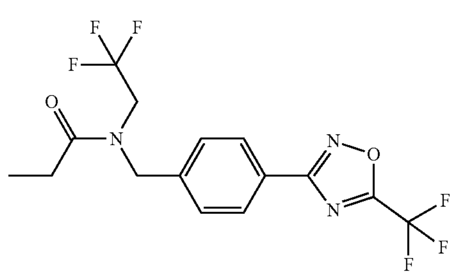 [SMILES: CCC(=O)N(Cc1ccc(-c2noc(C(F)(F)F)n2)cc1)CC(F)(F)F] | 1.78 | 382.15 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.583 | 2-methoxy-N-(2,2,2-trifluoroethyl)-N-[[4-[5-(trifluoromethyl)-1,2,4-oxadiazol-3-yl]phenyl]methyl]-acetamide | 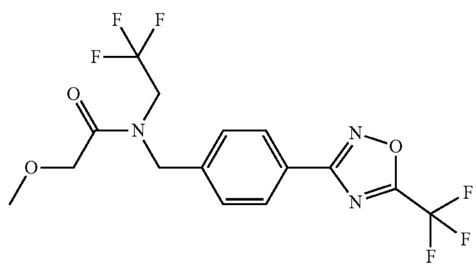 [SMILES: COCC(=O)N(Cc1ccc(-c2noc(C(F)(F)F)n2)cc1)CC(F)(F)F] | | | | 92.6-94.3 |
| 1.584 | N-[[2,3-difluoro-4-[5-(trifluoromethyl)-1,2,4-oxadiazol-3-yl]phenyl]methyl]-N-methoxy-cyclopropane-carboxamide | 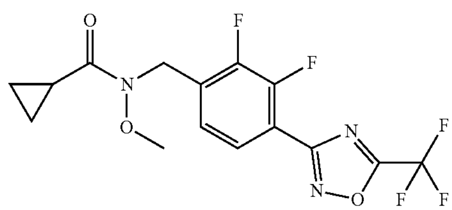 [SMILES: CON(Cc1ccc(-c2noc(C(F)(F)F)n2)c(F)c1F)C(=O)C1CC1] | 1.11 | 378 | A | |
| 1.585 | N-[[2,3-difluoro-4-[5-(trifluoromethyl)-1,2,4-oxadiazol-3-yl)phenyl]methyl]-N-methoxy-propanamide | 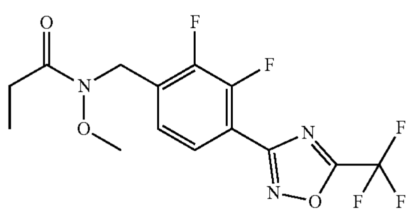 [SMILES: CCC(=O)N(Cc1ccc(-c2noc(C(F)(F)F)n2)c(F)c1F)OC] | 1.09 | 366 | A | |
| 1.586 | N-(2,2,2-trifluoroethyl)-N-[[4-[5-(trifluoromethyl)-1,2,4-oxadiazol-3-yl]phenyl]methyl]-cyclopropane-carboxamide | 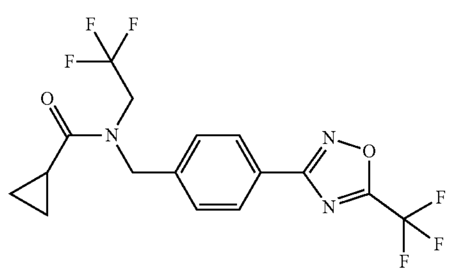 [SMILES: O=C(C1CC1)N(Cc1ccc(-c2noc(C(F)(F)F)n2)cc1)CC(F)(F)F] | 1.81 | 394.14 | B | |
| 1.587 | N-(2,2,2-trifluoroethyl)-N-[[4-[5-(trifluoromethyl)-1,2,4-oxadiazol-3-yl]phenyl]methyl]-tetrahydrofuran-2-carboxamide | 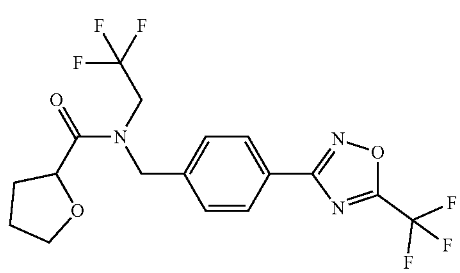 [SMILES: O=C(C1CCCO1)N(Cc1ccc(-c2noc(C(F)(F)F)n2)cc1)CC(F)(F)F] | 1.80 | 424.17 | B | |
| 1.588 | N-butoxy-N-[[4-[5-(trifluoromethyl)-1,2,4-oxadiazol-3-yl]phenyl]methyl]-propanamide | 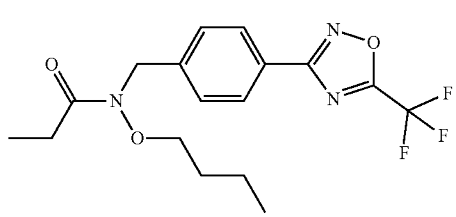 [SMILES: CCCCON(Cc1ccc(-c2noc(C(F)(F)F)n2)cc1)C(=O)CC] | 2.00 | 372.20 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.589 | N-isopropyl-N-[[4-[5-(trifluoromethyl)-1,2,4-oxadiazol-3-yl]phenyl]methyl]-propanamide | 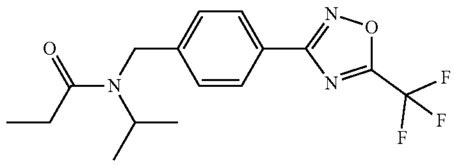 [SMILES: CCC(=O)N(Cc1ccc(-c2noc(C(F)(F)F)n2)cc1)C(C)C] | 1.74 | 342.19 | B | |
| 1.590 | 2-[propanoyl-[[4-[5-(trifluoromethyl)-1,2,4-oxadiazol-3-yl]phenyl]methyl]-amino]ethyl propanoate | 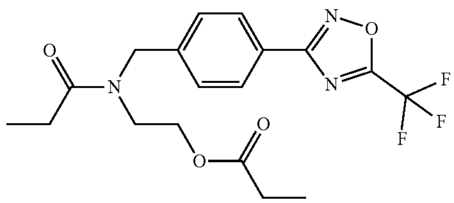 [SMILES: CCC(=O)OCCN(Cc1ccc(-c2noc(C(F)(F)F)n2)cc1)C(=O)CC] | 1.08 | 400 | A | |
| 1.591 | N-(2-hydroxyethyl)-N-[[4-[5-(trifluoromethyl)-1,2,4-oxadiazol-3-yl]phenyl]methyl]-propanamide | 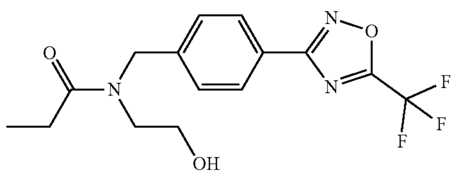 [SMILES: CCC(=O)N(CCO)Cc1ccc(-c2noc(C(F)(F)F)n2)cc1] | 1.34 | 344.15 | B | |
| 1.592 | N-allyl-N-[cyano-[4-[5-(trifluoromethyl)-1,2,4-oxadiazol-3-yl]phenyl]methyl]-propanamide | 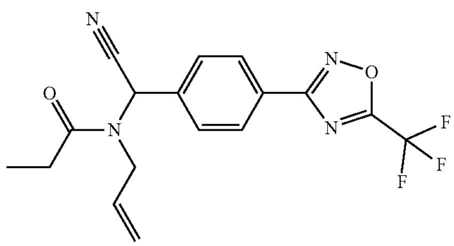 [SMILES: C=CCN(C(=O)CC)C(C#N)c1ccc(-c2noc(C(F)(F)F)n2)cc1] | 1.11 | 365.3 | A | |
| 1.593 | 2-hydroxy-N-methyl-N-[[4-[5-(trifluoromethyl)-1,2,4-oxadiazol-3-yl]phenyl]methyl]-acetamide | 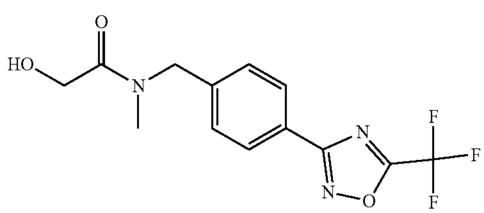 [SMILES: CN(Cc1ccc(-c2noc(C(F)(F)F)n2)cc1)C(=O)CO] | | | | 54-60 |
| 1.594 | N-[[2,6-difluoro-4-[5-(trifluoromethyl)-1,2,4-oxadiazol-3-yl]phenyl]methyl]-N-methoxy-propanamide | 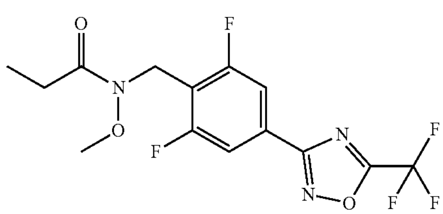 [SMILES: CCC(=O)N(Cc1c(F)cc(-c2noc(C(F)(F)F)n2)cc1F)OC] | 1.12 | 366 | A | |
| 1.595 | 2-(difluoromethoxy)-N-methyl-N-[[4-[5-(trifluoromethyl)-1,2,4-oxadiazol-3-yl]phenyl]methyl]-acetamide | 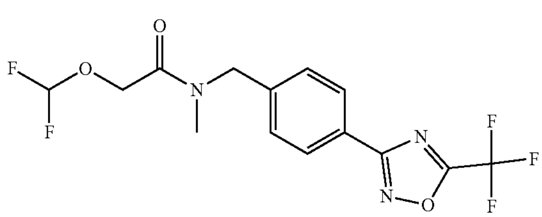 [SMILES: CN(Cc1ccc(-c2noc(C(F)(F)F)n2)cc1)C(=O)COC(F)F] | 1.02 | 366 | A | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.596 | N-[[2,6-difluoro-4-[5-(trifluoromethyl)-1,2,4-oxadiazol-3-yl]phenyl]methyl]-N-methoxy-cyclopropane-carboxamide | 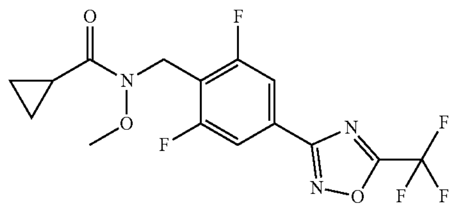 [SMILES: CON(Cc1c(F)cc(-c2noc(C(F)(F)F)n2)cc1F)C(=O)C1CC1] | 1.13 | 378 | A | |
| 1.597 | N-[[2,6-difluoro-4-[5-(trifluoromethyl)-1,2,4-oxadiazol-3-yl]phenyl]methyl]-N-methoxy-tetrahydrofuran-2-carboxamide | 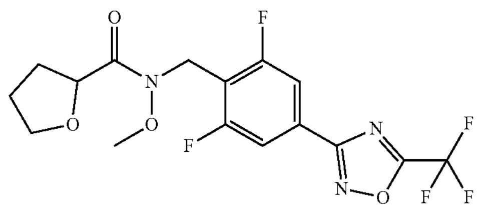 [SMILES: CON(Cc1c(F)cc(-c2noc(C(F)(F)F)n2)cc1F)C(=O)C1CCCO1] | 1.08 | 408 | A | |
| 1.598 | 2-chloro-N-[[2,6-difluoro-4-[5-(trifluoromethyl)-1,2,4-oxadiazol-3-yl]phenyl]methyl]-N-methoxy-benzamide | 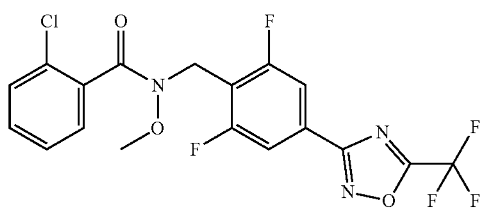 [SMILES: CON(Cc1c(F)cc(-c2noc(C(F)(F)F)n2)cc1F)C(=O)c1ccccc1Cl] | 1.19 | 448 | A | |
| 1.599 | N-isopropyl-N-[[4-[5-(trifluoromethyl)-1,2,4-oxadiazol-3-yl]phenyl]methyl]-cyclopropane-carboxamide | 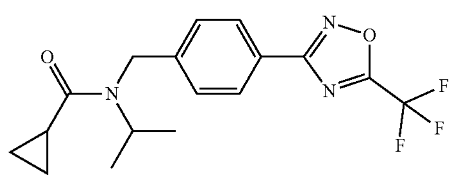 [SMILES: CC(C)N(Cc1ccc(-c2noc(C(F)(F)F)n2)cc1)C(=O)C1CC1] | 1.79 | 354.18 | B | |
| 1.600 | N-isopropyl-2-methoxy-N-[[4-[5-(trifluoromethyl)-1,2,4-oxadiazol-3-yl]phenyl]methyl]-acetamide | 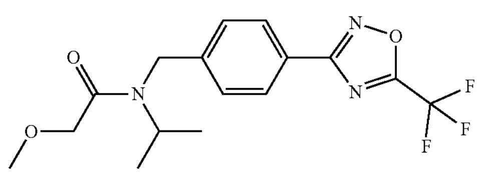 [SMILES: COCC(=O)N(Cc1ccc(-c2noc(C(F)(F)F)n2)cc1)C(C)C] | 1.60 | 358.18 | B | |
| 1.601 | N-butoxy-N-[[4-[5-(trifluoromethyl)-1,2,4-oxadiazol-3-yl]phenyl]methyl]-cyclopropane-carboxamide | 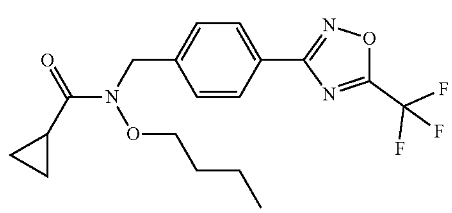 [SMILES: CCCCON(Cc1ccc(-c2noc(C(F)(F)F)n2)cc1)C(=O)C1CC1] | 2.02 | 384.20 | B | |
| 1.602 | N-butoxy-2-methoxy-N-[[4-[5-(trifluoromethyl)-1,2,4-oxadiazol-3-yl]phenyl]methyl]-acetamide | 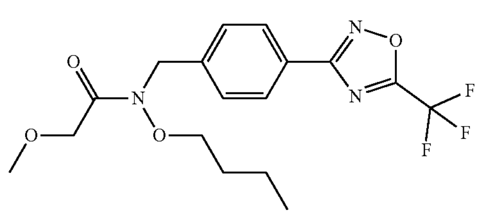 [SMILES: CCCCON(Cc1ccc(-c2noc(C(F)(F)F)n2)cc1)C(=O)COC] | 1.83 | 388.18 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.603 | N-hydroxy-N-[[4-[5-(trifluoromethyl)-1,2,4-oxadiazol-3-yl]phenyl]methyl]-propanamide | 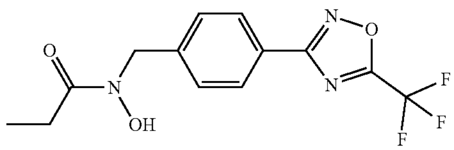 [SMILES: CCC(=O)N(O)Cc1ccc(-c2noc(C(F)(F)F)n2)cc1] | 1.39 | 316.12 | B | 141.2-143.5 |
| 1.604 | N-(oxetan-3-yl)-N-[[4-[5-(trifluoromethyl)-1,2,4-oxadiazol-3-yl]phenyl]methyl]-propanamide | 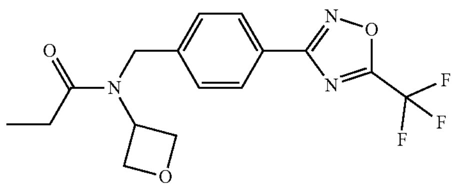 [SMILES: CCC(=O)N(Cc1ccc(-c2noc(C(F)(F)F)n2)cc1)C1COC1] | | | | 88.8-93.5 |
| 1.605 | N-(oxetan-3-yl)-N-[[4-[5-(trifluoromethyl)-1,2,4-oxadiazol-3-yl]phenyl]methyl]-cyclopropane-carboxamide | 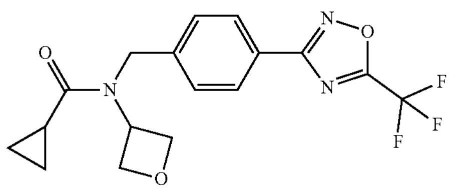 [SMILES: O=C(C1CC1)N(Cc1ccc(-c2noc(C(F)(F)F)n2)cc1)C1COC1] | | | | 89.5-94 |
| 1.606 | N-hydroxy-2-methoxy-N-[[4-[5-(trifluoromethyl)-1,2,4-oxadiazol-3-yl]phenyl]methyl]-acetamide | 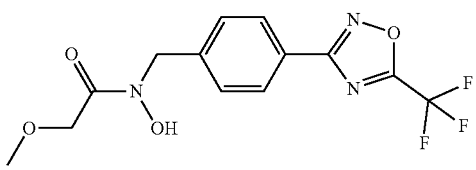 [SMILES: COCC(=O)N(O)Cc1ccc(-c2noc(C(F)(F)F)n2)cc1] | | | | 144.4-147.8 |
| 1.607 | N-hydroxy-N-[[4-[5-(trifluoromethyl)-1,2,4-oxadiazol-3-yl]phenyl]methyl]-cyclopropane-carboxamide | 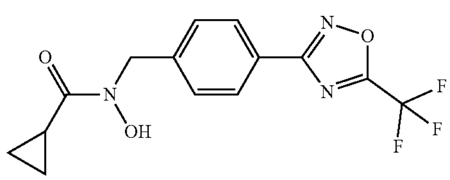 [SMILES: O=C(C1CC1)N(O)Cc1ccc(-c2noc(C(F)(F)F)n2)cc1] | | | | 141.2-143.5 |
| 1.608 | [cyclopropanecarbonyl-[[4-[5-(trifluoromethyl)-1,2,4-oxadiazol-3-yl]phenyl]methyl]-amino]-cyclopropane-carboxylate | 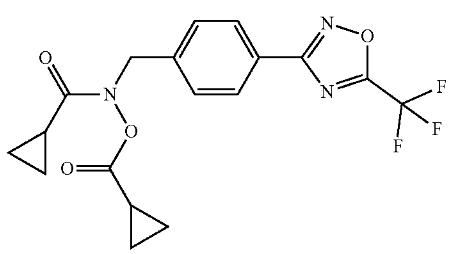 [SMILES: O=C(ON(Cc1ccc(-c2noc(C(F)(F)F)n2)cc1)C(=O)C1CC1)C1CC1] | 1.79 | 396.16 | B | |
| 1.609 | N-(2-hydroxyethyl)-N-[[4-[5-(trifluoromethyl)-1,2,4-oxadiazol-3-yl]phenyl]methyl]-cyclopropane-carboxamide | 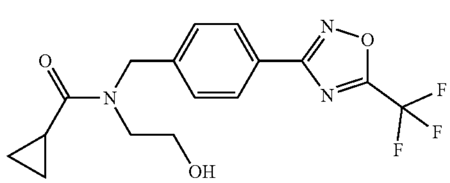 [SMILES: O=C(C1CC1)N(CCO)Cc1ccc(-c2noc(C(F)(F)F)n2)cc1] | 1.38 | 356.16 | B | |
| 1.610 | N-(2-hydroxyethyl)-2-methoxy-N-[[4-[5-(trifluoromethyl)-1,2,4-oxadiazol-3-yl]phenyl]methyl]-acetamide | 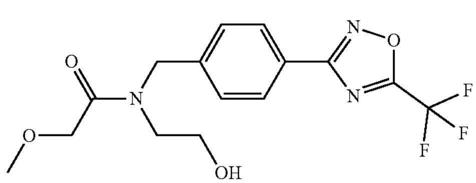 [SMILES: COCC(=O)N(CCO)Cc1ccc(-c2noc(C(F)(F)F)n2)cc1] | 1.24 | 360.16 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.611 | N-[cyano-[4-[5-(trifluoromethyl)-1,2,4-oxadiazol-3-yl]phenyl]methyl]-N-methyl-propanamide | 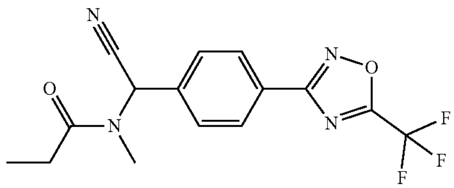 [SMILES: CCC(=O)N(C)C(C#N)c1ccc(-c2noc(C(F)(F)F)n2)cc1] | | | | 75-76 |
| 1.612 | N-[cyano-[4-[5-(trifluoromethyl)-1,2,4-oxadiazol-3-yl]phenyl]methyl)-N-methyl-cyclopropane-carboxamide | 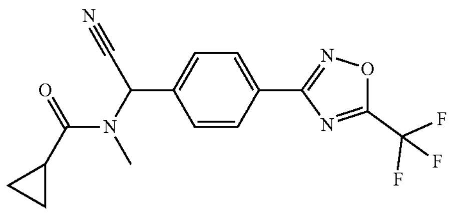 [SMILES: CN(C(=O)C1CC1)C(C#N)c1ccc(-c2noc(C(F)(F)F)n2)cc1] | 1.08 | 351 | A | |
| 1.613 | 2-methoxy-N-(oxetan-3-yl)-N-[[4-[5-(trifluoromelhyl)-1,2,4-oxadiazol-3-yl]phenyl]methyl]-acetamide | 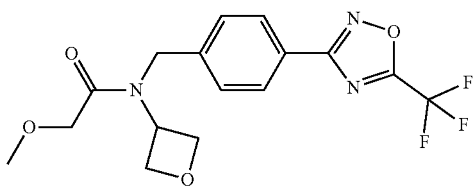 [SMILES: COCC(=O)N(Cc1ccc(-c2noc(C(F)(F)F)n2)cc1)C1COC1] | 1.28 | 372.15 | B | |
| 1.614 | N-ethoxy-2-methyl-N-[[4-[5-(trifluoromethyl)-1,2,4-oxadiazol-3-yl]phenyl]methyl]-propanamide | 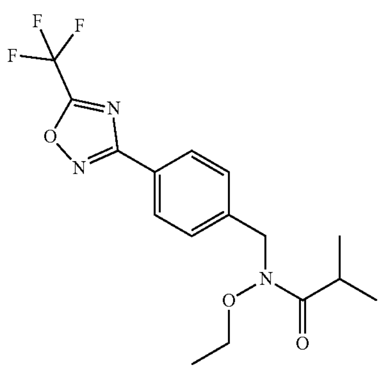 [SMILES: CCON(Cc1ccc(-c2noc(C(F)(F)F)n2)cc1)C(=O)C(C)C] | 1.87 | 358.17 | B | |
| 1.615 | N-ethoxy-2,2-difluoro-N-[[4-[5-(trifluoromethyl)-1,2,4-oxadiazol-3-yl]phenyl]methyl]-cyclopropane-carboxamide | 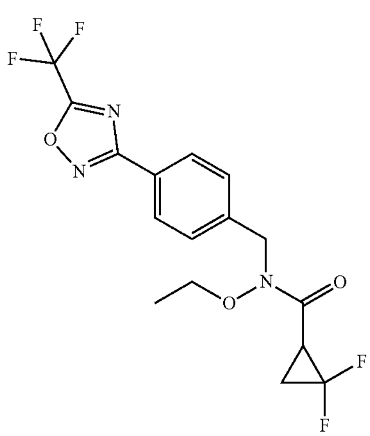 [SMILES: CCON(Cc1ccc(-c2noc(C(F)(F)F)n2)cc1)C(=O)C1CC1(F)F] | 1.83 | 392.14 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.616 | 2-chloro-N-ethoxy-N-[[4-[5-(trifluoromethyl)-1,2,4-oxadiazol-3-yl]phenyl]methyl]-benzamide | 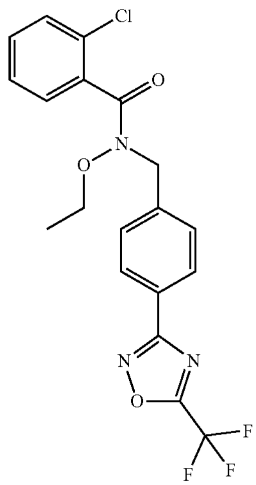 [SMILES: CCON(Cc1ccc(-c2noc(C(F)(F)F)n2)cc1)C(=O)c1ccccc1Cl] | 1.92 | 426.13 | B | |
| 1.617 | N-ethoxy-N-[[4-[5-(trifluoromethyl)-1,2,4-oxadiazol-3-yl]phenyl]methyl]-tetrahydrofuran-3-carboxamide | 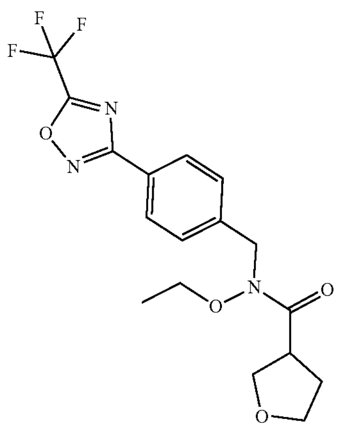 [SMILES: CCON(Cc1ccc(-c2noc(C(F)(F)F)n2)cc1)C(=O)C1CCOC1] | 1.66 | 386.17 | B | |
| 1.618 | N-ethoxy-3-methoxy-N-[[4-[5-(trifluoromethyl)-1,2,4-oxadiazol-3-yl]phenyl]methyl]-propanamide | 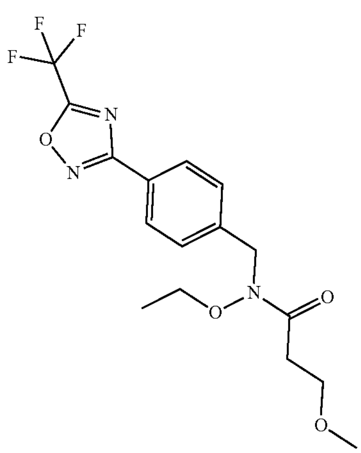 [SMILES: CCON(Cc1ccc(-c2noc(C(F)(F)F)n2)cc1)C(=O)CCOC] | 1.67 | 374.17 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.619 | N-ethoxy-N-[[4-[5-(trifluoromethyl)-1,2,4-oxadiazol-3-yl]phenyl]methyl]-cyclobutane-carboxamide | 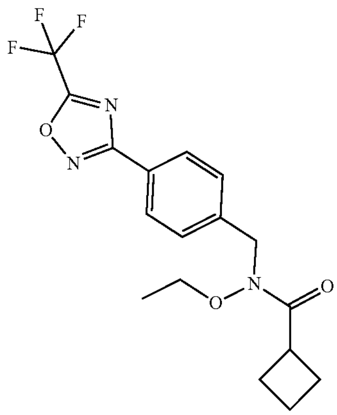 [SMILES: CCON(Cc1ccc(-c2noc(C(F)(F)F)n2)cc1)C(=O)C1CCC1] | 1.91 | 370.17 | B | |
| 1.620 | N-ethoxy-N-[[4-[5-(trifluoromethyl)-1,2,4-oxadiazol-3-yl]phenyl]methyl]-cyctobutane-carboxamide | 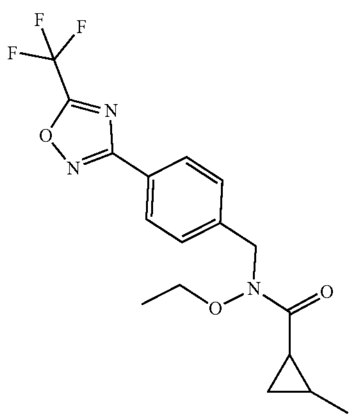 [SMILES: CCON(Cc1ccc(-c2noc(C(F)(F)F)n2)cc1)C(=O)C1CC1C] | 1.90 | 370.17 | B | |
| 1.621 | N-ethoxy-1-methyl-N-[[4-[5-(trifluoromethyl)-1,2,4-oxadiazol-3-yl]phenyl]methyl]-cyclopropane-carboxamide | 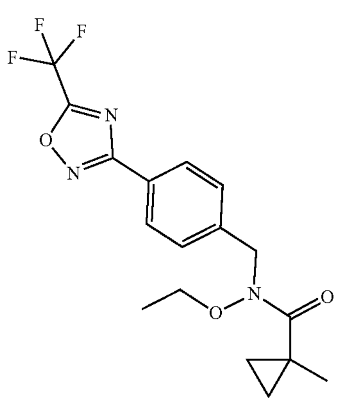 [SMILES: CCON(Cc1ccc(-c2noc(C(F)(F)F)n2)cc1)C(=O)C1(C)CC1] | 1.86 | 370.17 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.622 | N-ethoxy-2-methyl-N-[[4-[5-(trifluoromethyl)-1,2,4-oxadiazol-3-yl]phenyl]methyl]-butanamide | 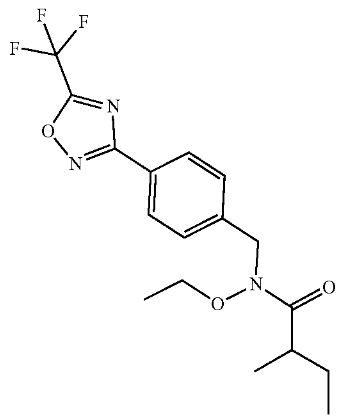 [SMILES: CCON(Cc1ccc(-c2noc(C(F)(F)F)n2)cc1)C(=O)C(C)CC] | 1.97 | 372.19 | B | |
| 1.623 | N-ethoxy-3-methyl-N-[[4-[5-(trifluoromethyl)-1,2,4-oxadiazol-3-yl]phenyl]methyl]-oxetane-3-carboxamide | 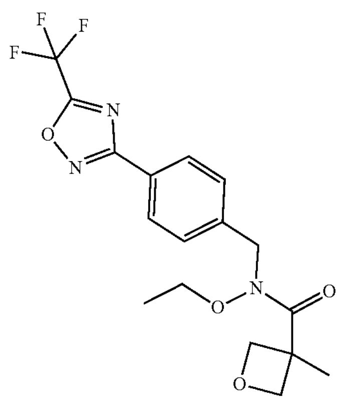 [SMILES: CCON(Cc1ccc(-c2noc(C(F)(F)F)n2)cc1)C(=O)C1(C)COC1] | 1.66 | 386.16 | B | |
| 1.624 | N-ethoxy-2-(methoxymethyl)-N-[[4-[5-(trifluoromethyl)-1,2,4-oxadiazol-3-yl]phenyl]methyl]-butanamide | 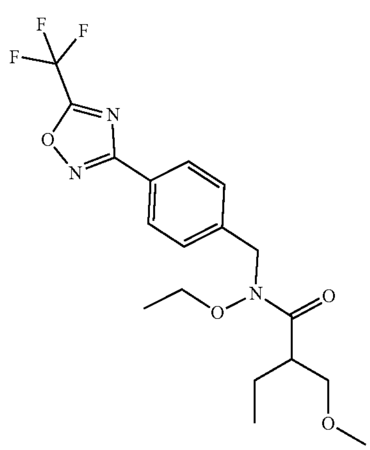 [SMILES: CCON(Cc1ccc(-c2noc(C(F)(F)F)n2)cc1)C(=O)C(CC)COC] | 1.89 | 402.21 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.625 | N-ethoxy-4-methoxy-N-[[4-[5-(trifluoromethyl)-1,2,4-oxadiazol-3-yl]phenyl]methyl]-butanamide | 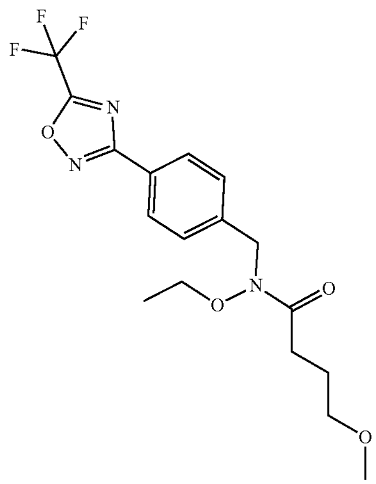 [SMILES: CCON(Cc1ccc(-c2noc(C(F)(F)F)n2)cc1)C(=O)CCCOC] | 1.74 | 388.19 | B | |
| 1.626 | N-ethoxy-N-[[4-[5-(trifluoromethyl)-1,2,4-oxadiazol-3-yl]phenyl]methyl]-tetrahydrofuran-2-carboxamide | 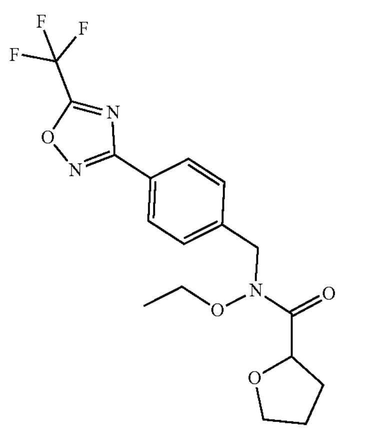 [SMILES: CCON(Cc1ccc(-c2noc(C(F)(F)F)n2)cc1)C(=O)C1CCCO1] | 1.68 | 386.17 | B | |
| 1.627 | 2-cyano-N-ethoxy-N-[[4-[5-(trifluoromethyl)-1,2,4-oxadiazol-3-yl)phenyl]methyl]-acetamide | 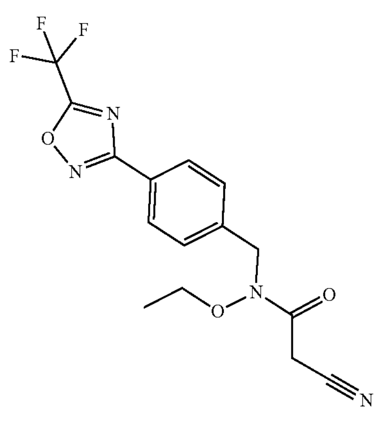 [SMILES: CCON(Cc1ccc(-c2noc(C(F)(F)F)n2)cc1)C(=O)CC#N] | 1.59 | 355.14 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.628 | 1-cyano-N-ethoxy-N-[[4-[5-(trifluoromethyl)-1,2,4-oxadiazol-3-yl]phenyl]methyl]-cyclopropane-carboxamide | 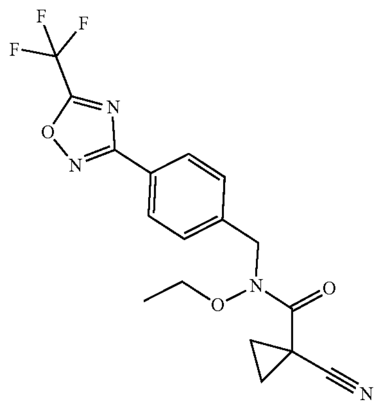 [SMILES: CCON(Cc1ccc(-c2noc(C(F)(F)F)n2)cc1)C(=O)C1(C#N)CC1] | 1.73 | 381.15 | B | |
| 1.629 | N-ethoxy-2-methoxy-N-[[4-[5-(trifluoromethyl)-1,2,4-oxadiazol-3-yl]phenyl]methyl]-propanamide | 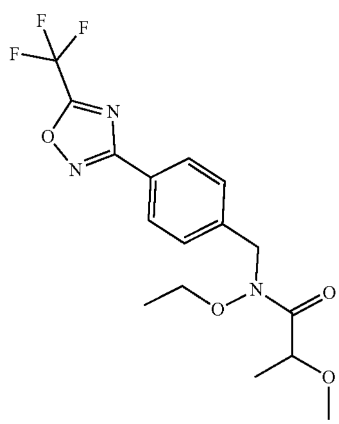 [SMILES: CCON(Cc1ccc(-c2noc(C(F)(F)F)n2)cc1)C(=O)C(C)OC] | 1.67 | 374.17 | B | |
| 1.630 | N-ethoxy-3,3,3-trifluoro-N-[[4-[5-(trifluoromethyl)-1,2,4-oxadiazol-3-yl]phenyl]methyl]-propanamide | 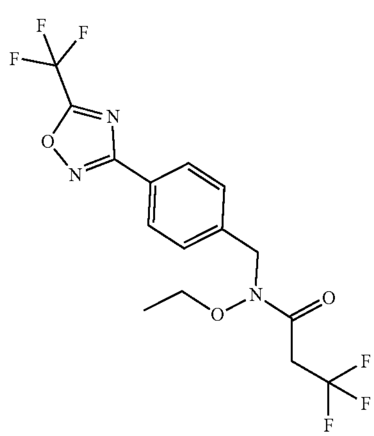 [SMILES: CCON(Cc1ccc(-c2noc(C(F)(F)F)n2)cc1)C(=O)CC(F)(F)F] | 1.82 | 398.16 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.631 | N-ethoxy-N-[[4-[5-(trifluoromethyl)-1,2,4-oxadiazol-3-yl]phenyl]methyl]-acetamide | 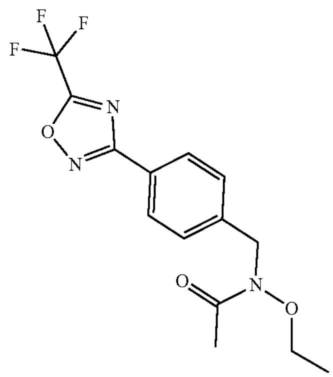 [SMILES: CCON(Cc1ccc(-c2noc(C(F)(F)F)n2)cc1)C(C)=O] | 1.62 | 330.13 | B | |
| 1.632 | 2-cyclopropyl-N-ethoxy-N-[[4-[5-(trifluoromethyl)-1,2,4-oxadiazol-3-yl]phenyl]methyl]-acetamide | 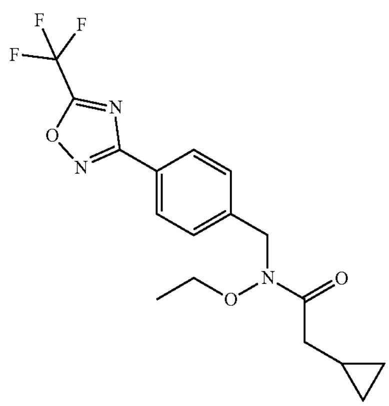 [SMILES: CCON(Cc1ccc(-c2noc(C(F)(F)F)n2)cc1)C(=O)CC1CC1] | 1.86 | 370.18 | B | |
| 1.633 | N-butoxy-2-methyl-N-[[4-[5-(trifluoromethyl)-1,2,4-oxadiazol-3-yl]phenyl]methyl]-propanamide | 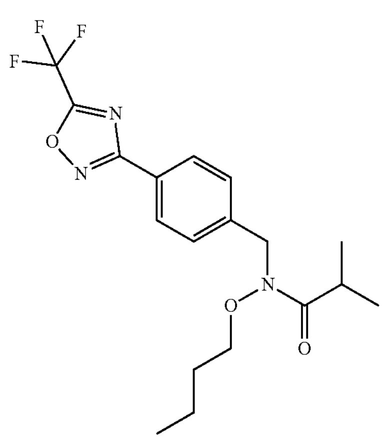 [SMILES: CCCCON(Cc1ccc(-c2noc(C(F)(F)F)n2)cc1)C(=O)C(C)C] | 2.09 | 386.22 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.634 | N-butoxy-2,2-difluoro-N-[[4-[5-(trifluoromethyl)-1,2,4-oxadiazol-3-yl]phenyl]methyl]-cyclopropane-carboxamide | 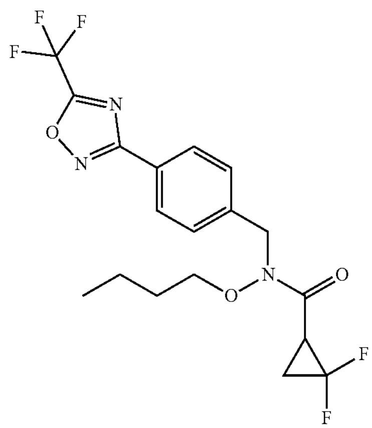 [SMILES: CCCCON(Cc1ccc(-c2noc(C(F)(F)F)n2)cc1)C(=O)C1CC1(F)F] | 2.03 | 420.19 | B | |
| 1.635 | N-butoxy-2-chloro-N-[[4-[5-(trifluoromethyl)-1,2,4-oxadiazol-3-yl]phenyl]methyl]-benzamide | 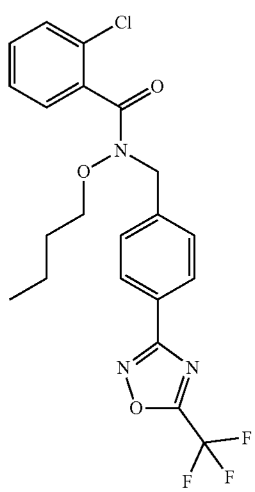 [SMILES: CCCCON(Cc1ccc(-c2noc(C(F)(F)F)n2)cc1)C(=O)c1ccccc1Cl] | 2.11 | 454.18 | B | |
| 1.636 | N-butoxy-N-[[4-[5-(trifluoromethyl)-1,2,4-oxadiazol-3-yl]phenyl]methyl]-tetrahydrofuran-3-carboxamide | 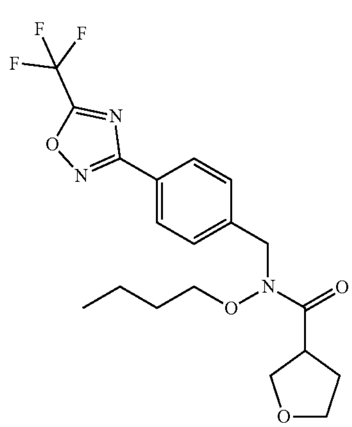 [SMILES: CCCCON(Cc1ccc(-c2noc(C(F)(F)F)n2)cc1)C(=O)C1CCOC1] | 1.89 | 414.22 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.637 | N-butoxy-3-methoxy-N-[[4-[5-(trifluoromethyl)-1,2,4-oxadiazol-3-yl]phenyl]methyl]-propanamide | 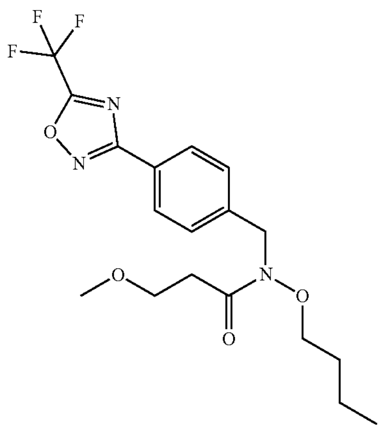 [SMILES: CCCCON(Cc1ccc(-c2noc(C(F)(F)F)n2)cc1)C(=O)CCOC] | 1.91 | 402.21 | B | |
| 1.638 | N-butoxy-N-[[4-[5-(trifluoromethyl)-1,2,4-oxadiazol-3-yl]phenyl]methyl]-cyclobutane-carboxamide | 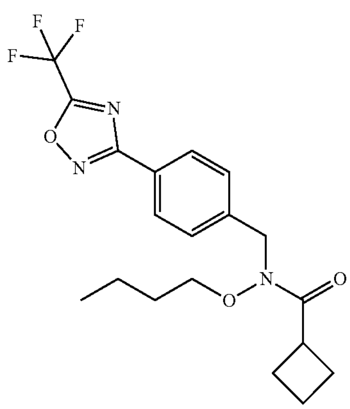 [SMILES: CCCCON(Cc1ccc(-c2noc(C(F)(F)F)n2)cc1)C(=O)C1CCC1] | 2.13 | 398.22 | B | |
| 1.639 | N-butoxy-1-methyl-N-[[4-[5-(trifluoromethyl)-1,2,4-oxadiazol-3-yl]phenyl]methyl]-cyclopropane-carboxamide | 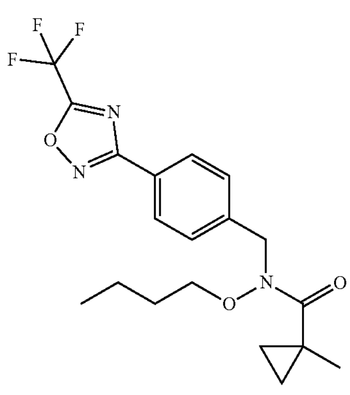 [SMILES: CCCCON(Cc1ccc(-c2noc(C(F)(F)F)n2)cc1)C(=O)C1(C)CC1] | 2.08 | 398.23 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.640 | N-butoxy-2-methyl-N-[[4-[5-(trifluoromethyl)-1,2,4-oxadiazol-3-yl]phenyl]methyl]-butanamide | 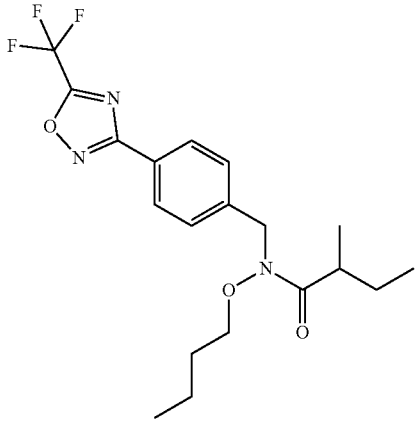 | 2.18 | 400.24 | B | |
| 1.641 | N-butoxy-3-methyl-N-[[4-[5-(trifluoromethyl)-1,2,4-oxadiazol-3-yl]phenyl]methyl]-oxetane-3-carboxamide | 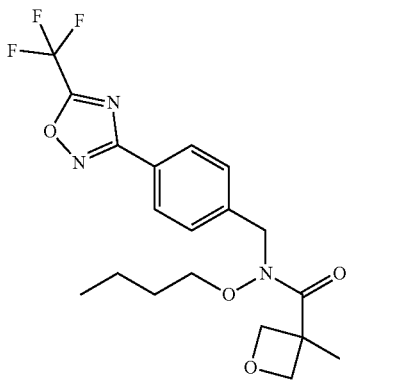 [SMILES: CCCCON(Cc1ccc(-c2noc(C(F)(F)F)n2)cc1)C(=O)C1(C)COC1] | 1.88 | 414.22 | B | |
| 1.642 | N-butoxy-2-(methoxymethyl)-N-[[4-[5-(trifluoromethyl)-1,2,4-oxadiazol-3-yl]phenyl]methyl]-butanamide | 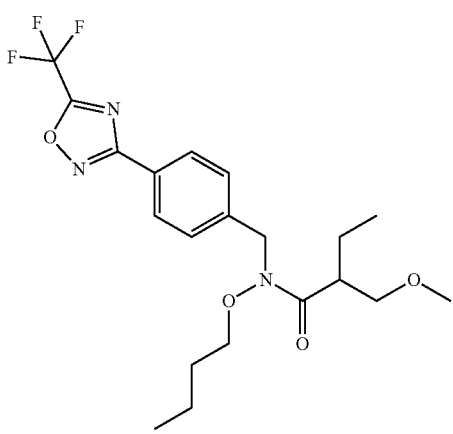 [SMILES: CCCCON(Cc1ccc(-c2noc(C(F)(F)F)n2)cc1)C(=O)C(CC)COC] | 2.10 | 430.26 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.643 | N-butoxy-4-methoxy-N-[[4-[5-(trifluoromethyl)-1,2,4-oxadiazol-3-yl]phenyl]methyl]-butanamide | 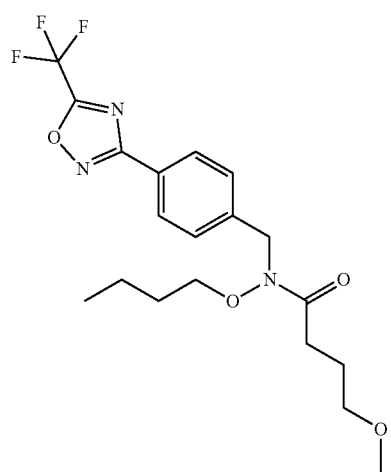 [SMILES: CCCCON(Cc1ccc(-c2noc(C(F)(F)F)n2)cc1)C(=O)CCCOC] | 1.96 | 416.24 | B | |
| 1.644 | N-butoxy-N-[[4-[5-(trifluoromethyl)-1,2,4-oxadiazol-3-yl]phenyl]methyl]-tetrahydrofuran-2-carboxamide | 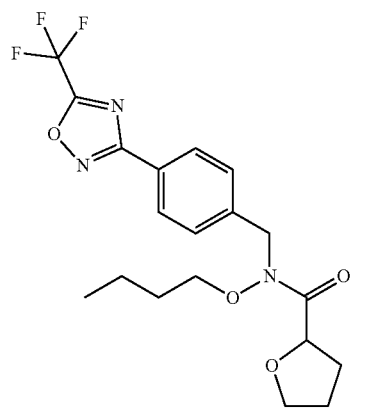 [SMILES: CCCCON(Cc1ccc(-c2noc(C(F)(F)F)n2)cc1)C(=O)C1CCCO1] | 1.91 | 414.22 | B | |
| 1.645 | N-butoxy-2-cyano-N-[[4-[5-(trifluoromethyl)-1,2,4-oxadiazol-3-yl]phenyl]methyl]-acetamide | 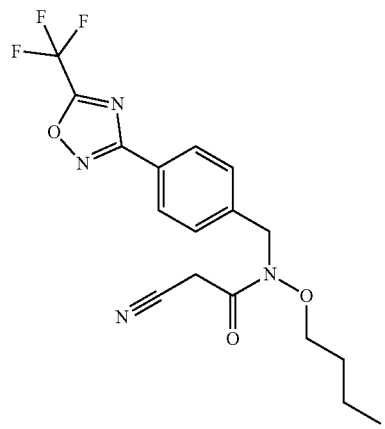 [SMILES: CCCCON(Cc1ccc(-c2noc(C(F)(F)F)n2)cc1)C(=O)CC#N] | 1.81 | 383.18 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.646 | N-butoxy-1-cyano-N-[[4-[5-(trifluoromethyl)-1,2,4-oxadiazol-3-yl]phenyl]methyl]-cyclopropane-carboxamide | 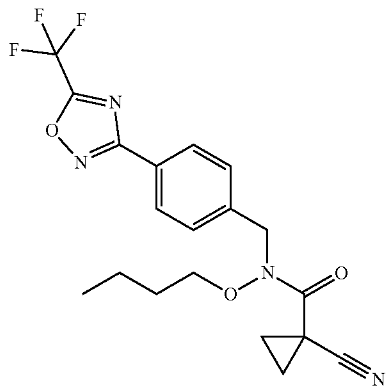 [SMILES: CCCCON(Cc1ccc(-c2noc(C(F)(F)F)n2)cc1)C(=O)C1(C#N)CC1] | 1.93 | 409.20 | B | |
| 1.647 | N-butoxy-2-methoxy-N-[[4-[5-(trifluoromethyl)-1,2,4-oxadiazol-3-yl]phenyl]methyl]-propanamide | 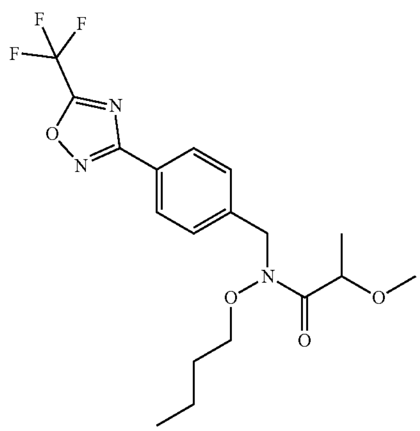 [SMILES: CCCCON(Cc1ccc(-c2noc(C(F)(F)F)n2)cc1)C(=O)C(C)OC] | 1.90 | 402.23 | B | |
| 1.648 | N-butoxy-3,3,3-trifluoro-N-[[4-[5-(trifluoromethyl)-1,2,4-oxadiazol-3-yl]phenyl]methyl]-propanamide | 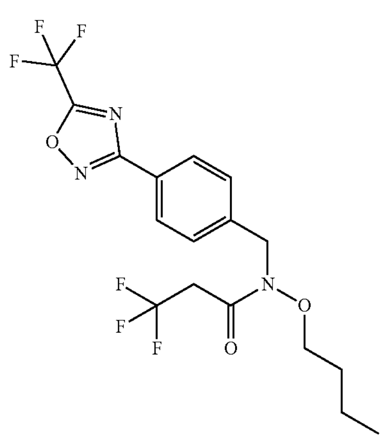 [SMILES: CCCCON(Cc1ccc(-c2noc(C(F)(F)F)n2)cc1)C(=O)CC(F)(F)F] | 2.02 | 426.19 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.649 | N-butoxy-N-[[4-[5-(trifluoromethyl)-1,2,4-oxadiazol-3-yl]phenyl]methyl]-acetamide | 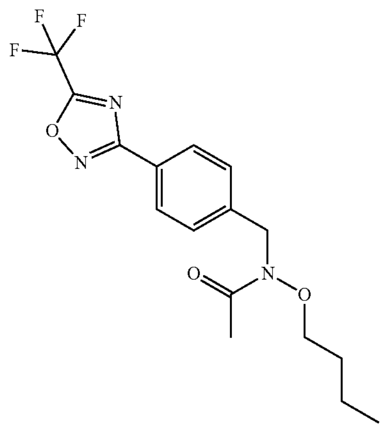 [SMILES: CCCCON(Cc1ccc(-c2noc(C(F)(F)F)n2)cc1)C(C)=O] | 1.87 | 358.18 | B | |
| 1.650 | N-butoxy-2-cyclopropyl-N-[[4-[5-(trifluoromethyl)-1,2,4-oxadiazol-3-yl]phenyl]methyl]-acetamide | 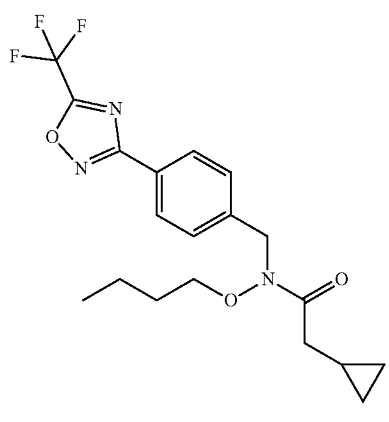 [SMILES: CCCCON(Cc1ccc(-c2noc(C(F)(F)F)n2)cc1)C(=O)CC1CC1] | 2.07 | 398.22 | B | |
| 1.651 | 2-methyl-N-propyl-N-[[4-[5-(trifluoromethyl)-1,2,4-oxadiazol-3-yl]phenyl]methyl]-propanamide | 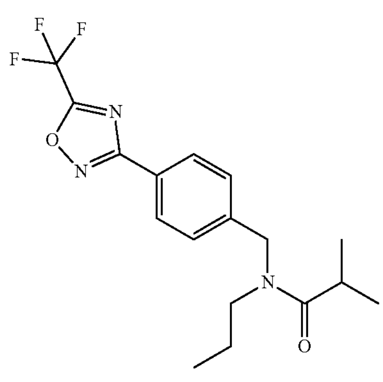 | 1.88 | 356.23 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.652 | 2,2-difluoro-N-propyl-N-[[4-[5-(trifluoromethyl)-1,2,4-oxadiazol-3-yl]phenyl]methyl]-cyclopropane-carboxamide | 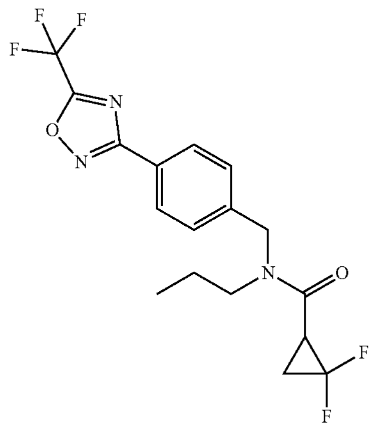 [SMILES: CCCN(Cc1ccc(-c2noc(C(F)(F)F)n2)cc1)C(=O)C1CC1(F)F] | 1.85 | 390.18 | B | |
| 1.653 | 2-chloro-N-propyl-N-[[4-[5-(trifluoromethyl)-1,2,4-oxadiazol-3-yl]phenyl]methyl]-benzamide | 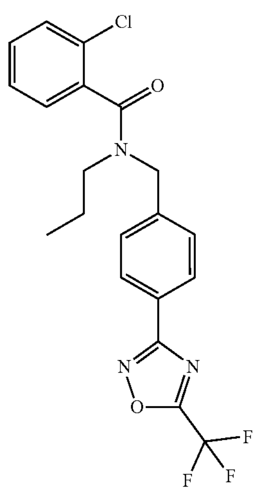 [SMILES: CCCN(Cc1ccc(-c2noc(C(F)(F)F)n2)cc1)C(=O)c1ccccc1Cl] | 1.99 | 424.17 | B | |
| 1.654 | N-propyl-N-[[4-[5-(trifluoromethyl)-1,2,4-oxadiazol-3-yl]phenyl]methyl]-tetrahydrofuran-3-carboxamide | 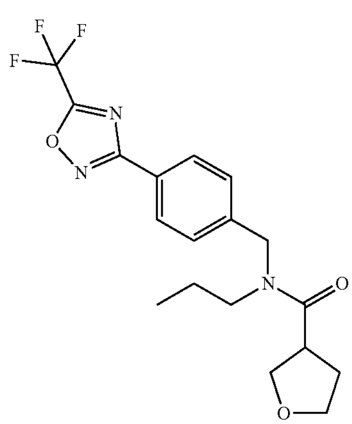 [SMILES: CCCN(Cc1ccc(-c2noc(C(F)(F)F)n2)cc1)C(=O)C1CCOC1] | 1.68 | 384.20 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.655 | 3-methoxy-N-propyl-N-[[4-[5-(trifluoromethyl)-1,2,4-oxadiazol-3-yl]phenyl]methyl]-propanamide | 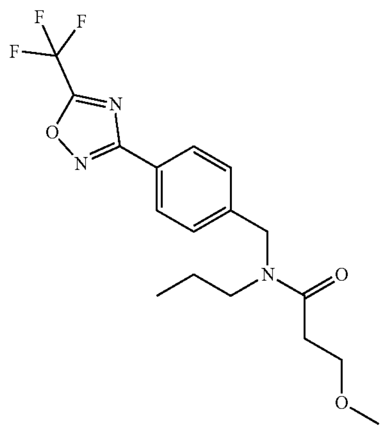 [SMILES: CCCN(Cc1ccc(-c2noc(C(F)(F)F)n2)cc1)C(=O)CCOC] | 1.71 | 372.20 | B | |
| 1.656 | N-propyl-N-[[4-[5-(trifluoromethyl)-1,2,4-oxadiazol-3-yl]phenyl]methyl]-cyclobutane-carboxamide | 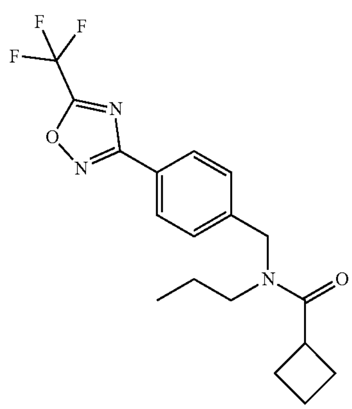 [SMILES: CCCN(Cc1ccc(-c2noc(C(F)(F)F)n2)cc1)C(=O)C1CCC1] | 1.94 | 368.20 | B | |
| 1.657 | 2-methyl-N-propyl-N-[[4-[5-(trifluoromethyl)-1,2,4-oxadiazol-3-yl]phenyl]methyl]-cyclopropane-carboxamide | 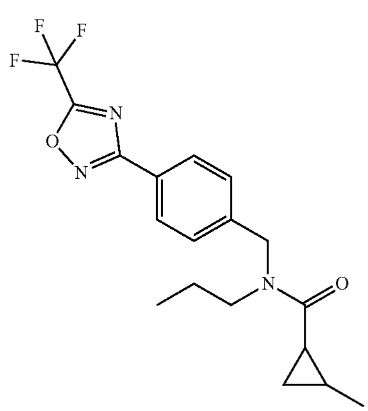 [SMILES: CCCN(Cc1ccc(-c2noc(C(F)(F)F)n2)cc1)C(=O)C1CC1C] | 1.91 | 368.21 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.658 | 1-methyl-N-propyl-N-[[4-[5-(trifluoromethyl)-1,2,4-oxadiazol-3-yl]phenyl]methyl]-cyclopropane-carboxamide | 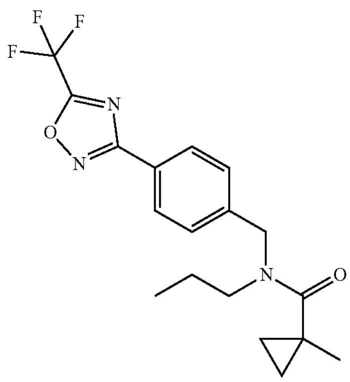 [SMILES: CCCN(Cc1ccc(-c2noc(C(F)(F)F)n2)cc1)C(=O)C1(C)CC1] | 1.87 | 368.20 | B | |
| 1.659 | 2-methyl-N-propyl-N-[[4-[5-(trifluoromethyl)-1,2,4-oxadiazol-3-yl]phenyl]methyl]-butanamide | 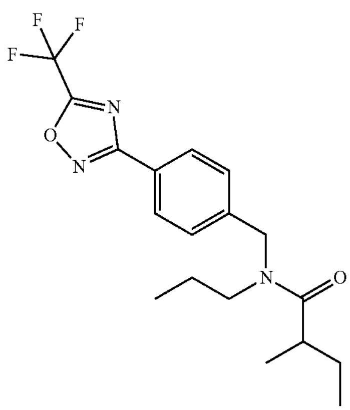 [SMILES: CCCN(Cc1ccc(-c2noc(C(F)(F)F)n2)cc1)C(=O)C(C)CC] | 1.97 | 370.23 | B | |
| 1.660 | 3-methyl-N-propyl-N-[[4-[5-(trifluoromethyl)-1,2,4-oxadiazol-3-yl]phenyl]methyl]-oxetane-3-carboxamide | 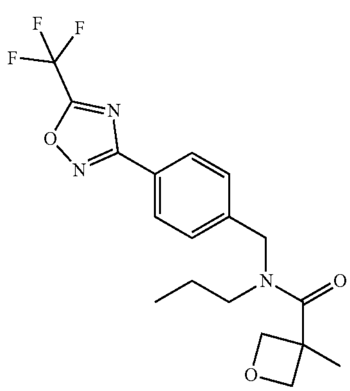 [SMILES: CCCN(Cc1ccc(-c2noc(C(F)(F)F)n2)cc1)C(=O)C1(C)COC1] | 1.67 | 384.20 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.661 | 2-(methoxymethyl)-N-propyl-N-[[4-[5-(trifluoromethyl)-1,2,4-oxadiazol-3-yl]phenyl]methyl]-butanamide | 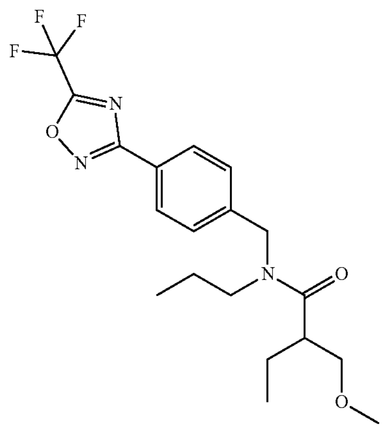 [SMILES: CCCN(Cc1ccc(-c2noc(C(F)(F)F)n2)cc1)C(=O)C(CC)COC] | 1.94 | 400.24 | B | |
| 1.662 | 4-methoxy-N-propyl-N-[[4-[5-(trifluoromethyl)-1,2,4-oxadiazol-3-yl]phenyl]methyl]-butanamide | 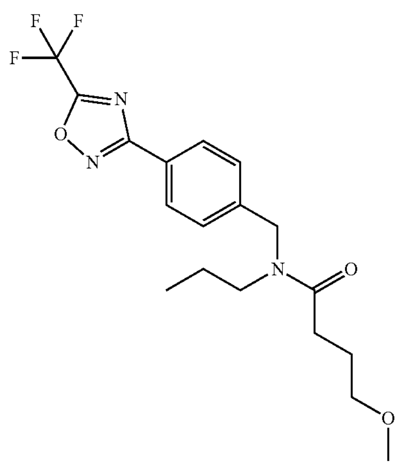 [SMILES: CCCN(Cc1ccc(-c2noc(C(F)(F)F)n2)cc1)C(=O)CCCOC] | 1.76 | 386.22 | B | |
| 1.663 | N-propyl-N-[[4-[5-(trifluoromethyl)-1,2,4-oxadiazol-3-yl]phenyl]methyl]-tetrahydrofuran-2-carboxamide | 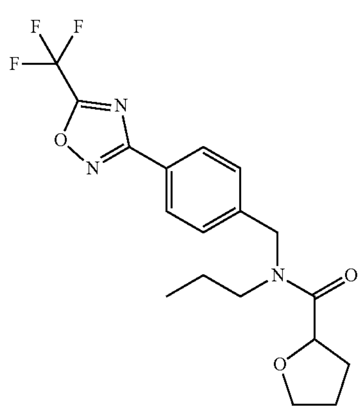 [SMILES: CCCN(Cc1ccc(-c2noc(C(F)(F)F)n2)cc1)C(=O)C1CCCO1] | 1.74 | 384.20 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.664 | 2-cyano-N-propyl-N-[[4-[5-(trifluoromethyl)-1,2,4-oxadiazol-3-yl]phenyl]methyl]-acetamide | 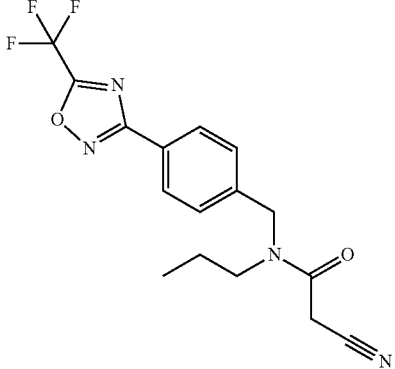 [SMILES: CCCN(Cc1ccc(-c2noc(C(F)(F)F)n2)cc1)C(=O)CC#N] | 1.61 | 353.16 | B | |
| 1.665 | 1-cyano-N-propyl-N-[[4-[5-(trifluoromethyl)-1,2,4-oxadiazol-3-yl]phenyl]methyl]-cyclopropane-carboxamide | 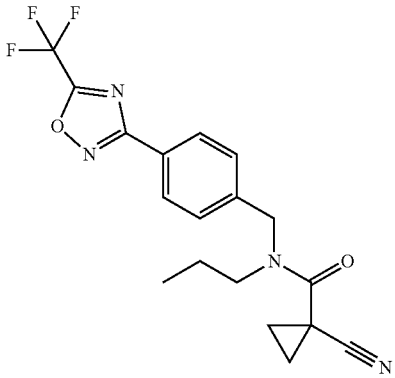 [SMILES: CCCN(Cc1ccc(-c2noc(C(F)(F)F)n2)cc1)C(=O)C1(C#N)CC1] | 1.79 | 379.18 | B | |
| 1.666 | 2-methoxy-N-propyl-N-[[4-[5-(trifluoromethyl)-1,2,4-oxadiazol-3-yl]phenyl]methyl]-propanamide | 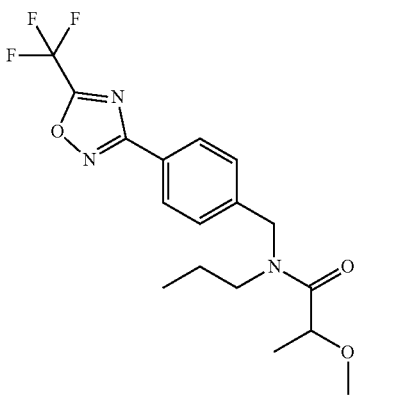 [SMILES: CCCN(Cc1ccc(-c2noc(C(F)(F)F)n2)cc1)C(=O)C(C)OC] | 1.71 | 372.19 | B | |
| 1.667 | 3,3,3-trifluoroN-propyl-N-[[4-[5-(trifluoromethyl)-1,2,4-oxadiazol-3-yl]phenyl]methyl]-propanamide | 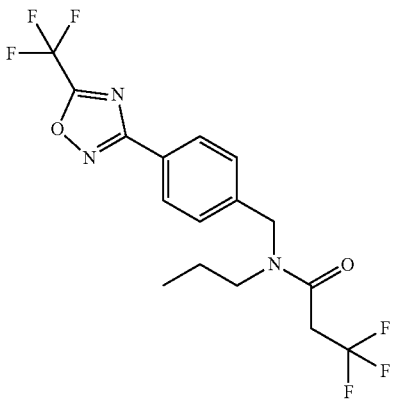 [SMILES: CCCN(Cc1ccc(-c2noc(C(F)(F)F)n2)cc1)C(=O)CC(F)(F)F] | 1.82 | 396.18 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.668 | N-propyl-N-[[4-[5-(trifluoromethyl)-1,2,4-oxadiazol-3-yl]phenyl]methyl]-acetamide | 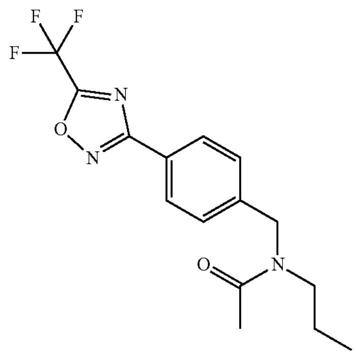 [SMILES: CCCN(Cc1ccc(-c2noc(C(F)(F)F)n2)cc1)C(C)=O] | 1.63 | 328.17 | B | |
| 1.669 | 2-cyclopropyl-N-propyl-N-[[4-[5-(trifluoromethyl)-1,2,4-oxadiazol-3-yl]phenyl]methyl]-acetamide | 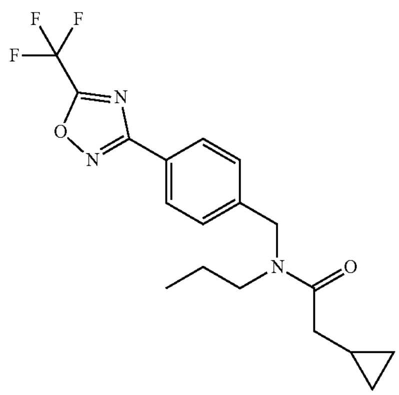 [SMILES: CCCN(Cc1ccc(-c2noc(C(F)(F)F)n2)cc1)C(=O)CC1CC1] | 1.87 | 368.21 | B | |
| 1.670 | N-isopropyl-2-methyl-N-[[4-[5-(trifluoromethyl)-1,2,4-oxadiazol-3-yl]phenyl]methyl]-propanamide | 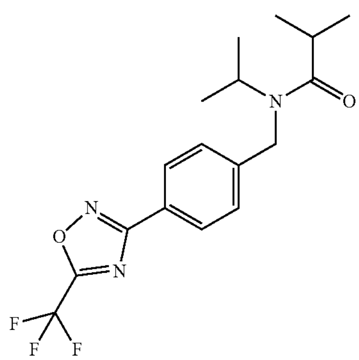 [SMILES: CC(C)C(=O)N(Cc1ccc(-c2noc(C(F)(F)F)n2)cc1)C(C)C] | 1.84 | 356.21 | B | |
| 1.671 | 2,2-difluoro-N-isopropyl-N-[[4-[5-(trifluoromethyl)-1,2,4-oxadiazol-3-yl]phenyl]methyl]-cyclopropane-carboxamide | 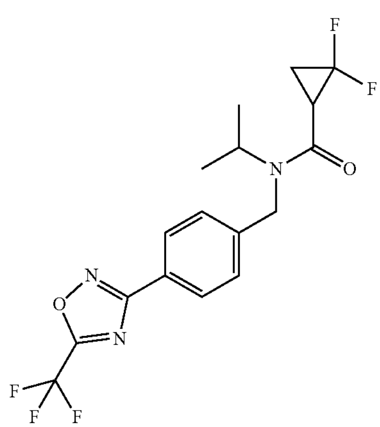 [SMILES: CC(C)N(Cc1ccc(-c2noc(C(F)(F)F)n2)cc1)C(=O)C1CC1(F)F] | 1.82 | 390.18 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.672 | 2-chloro-N-isopropyl-N-[[4-[5-(trifluoromethyl)-1,2,4-oxadiazol-3-yl]phenyl]methyl]-benzamide | 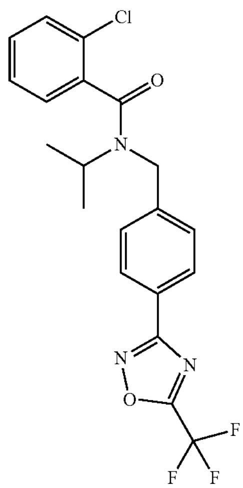 [SMILES: CC(C)N(Cc1ccc(-c2noc(C(F)(F)F)n2)cc1)C(=O)c1ccccc1Cl] | 1.97 | 424.17 | B | |
| 1.673 | N-isopropyl-N-[[4-[5-(trifluoromethyl)-1,2,4-oxadiazol-3-yl]phenyl]methyl]-tetrahydrofuran-3-carboxamide | 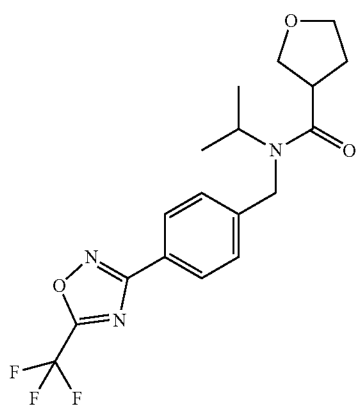 [SMILES: CC(C)N(Cc1ccc(-c2noc(C(F)(F)F)n2)cc1)C(=O)C1CCOC1] | 1.65 | 384.21 | B | |
| 1.674 | N-isopropyl-3-methoxy-N-[[4-[5-(trifluoromethyl)-1,2,4-oxadiazol-3-yl]phenyl]methyl]-propanamide | 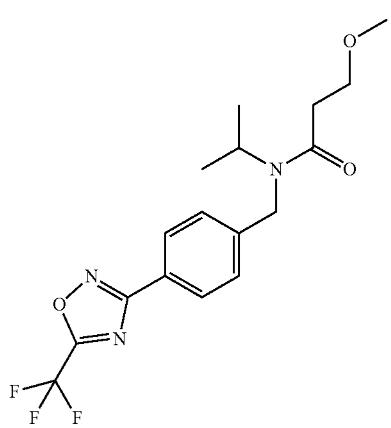 [SMILES: COCCC(=O)N(Cc1ccc(-c2noc(C(F)(F)F)n2)cc1)C(C)C] | 1.68 | 372.20 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.675 | N-isopropyl-N-[[4-[5-(trifluoromethyl)-1,2,4-oxadiazol-3-yl]phenyl]methyl]-cyclobutane-carboxamide | 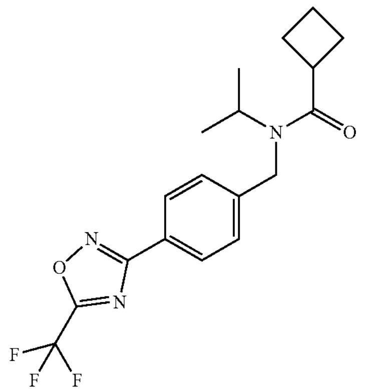 [SMILES: CC(C)N(Cc1ccc(-c2noc(C(F)(F)F)n2)cc1)C(=O)C1CCC1] | 1.91 | 368.21 | B | |
| 1.676 | N-isopropyl-2-methyl-N-[[4-[5-(trifluoromethyl)-1,2,4-oxadiazol-3-yl]phenyl]methyl]-cyclopropane-carboxamide | 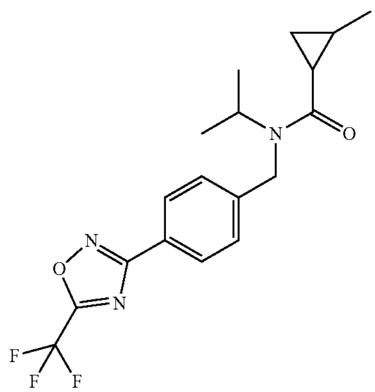 [SMILES: CC1CC1C(=O)N(Cc1ccc(-c2noc(C(F)(F)F)n2)cc1)C(C)C] | 1.88 | 368.21 | B | |
| 1.677 | N-isopropyl-1-methyl-N-[[4-[5-(trifluoromethyl)-1,2,4-oxadiazol-3-yl]phenyl]methyl]-cyclopropane-carboxamide | 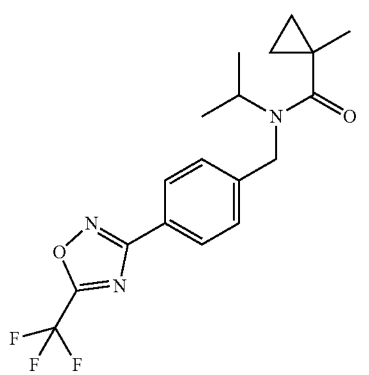 [SMILES: CC(C)N(Cc1ccc(-c2noc(C(F)(F)F)n2)cc1)C(=O)C1(C)CC1] | 1.84 | 368.21 | B | |
| 1.678 | N-isopropyl-2-methyl-N-[[4-[5-(trifluoromethyl)-1,2,4-oxadiazol-3-yl]phenyl]methyl]-butanamide | 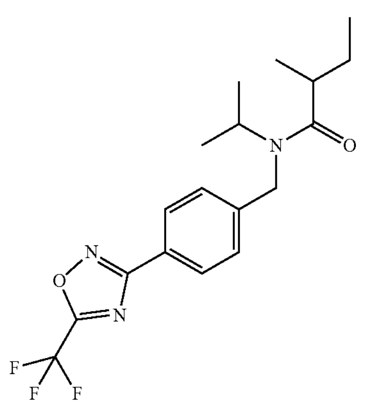 [SMILES: CCC(C)C(=O)N(Cc1ccc(-c2noc(C(F)(F)F)n2)cc1)C(C)C] | 1.94 | 370.22 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.679 | N-isopropyl-3-methyl-N-[[4-[5-(trifluoromethyl)-1,2,4-oxadiazol-3-yl]phenyl]methyl]-oxetane-3-carboxamide | 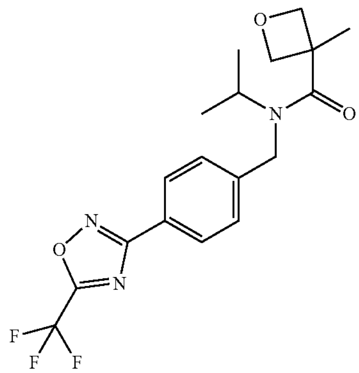 [SMILES: CC(C)N(Cc1ccc(-c2noc(C(F)(F)F)n2)cc1)C(=O)C1(C)COC1] | 1.63 | 384.21 | B | |
| 1.680 | N-isopropyl-2-(methoxymethyl)-N-[[4-[5-(trifluoromethyl)-1,2,4-oxadiazol-3-yl]phenyl]methyl]-butanamide | 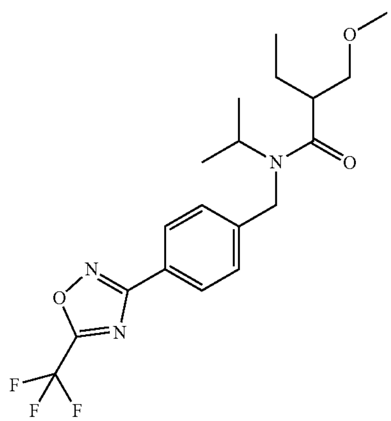 [SMILES: CCC(COC)C(=O)N(Cc1ccc(-c2noc(C(F)(F)F)n2)cc1)C(C)C] | 1.92 | 400.24 | B | |
| 1.681 | N-isopropyl-4-methoxy-N-[[4-[5-(trifluoromethyl)-1,2,4-oxadiazol-3-yl]phenyl]methyl]-butanamide | 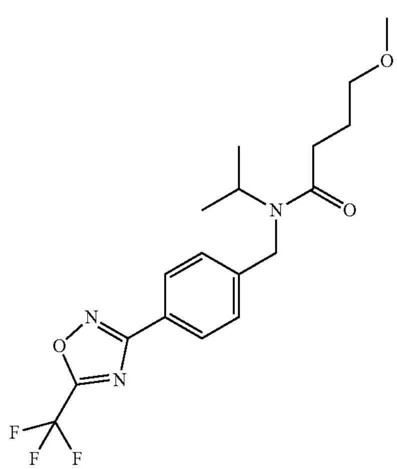 [SMILES: COCCCC(=O)N(Cc1ccc(-c2noc(C(F)(F)F)n2)cc1)C(C)C] | 1.73 | 386.22 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.682 | N-isopropyl-N-[[4-[5-(trifluoromethyl)-1,2,4-oxadiazol-3-yl]phenyl]methyl]-tetrahydrofuran-2-carboxamide | 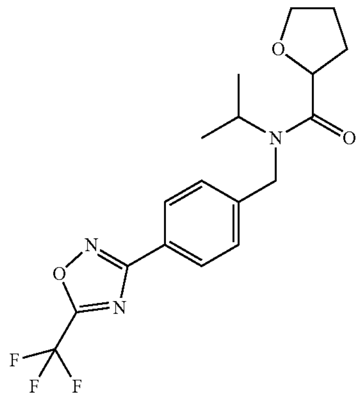 [SMILES: CC(C)N(Cc1ccc(-c2noc(C(F)(F)F)n2)cc1)C(=O)C1CCCO1] | 1.71 | 384.20 | B | |
| 1.683 | 2-cyano-N-isopropyl-N-[[4-[5-(trifluoromethyl)-1,2,4-oxadiazol-3-yl]phenyl]methyl]-acetamide | 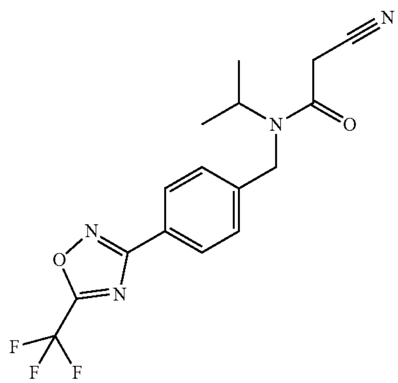 [SMILES: CC(C)N(Cc1ccc(-c2noc(C(F)(F)F)n2)cc1)C(=O)CC#N] | 1.58 | 353.17 | B | |
| 1.684 | 1 cyano-N-isopropyl-N-[[4-[5-(trifluoromethyl)-1,2,4-oxadiazol-3-yl]phenyl]methyl]-cyclopropane-carboxamide | 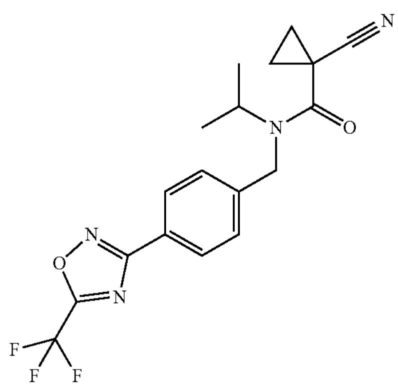 [SMILES: CC(C)N(Cc1ccc(-c2noc(C(F)(F)F)n2)cc1)C(=O)C1(C#N)CC1] | 1.75 | 379.18 | B | |
| 1.685 | N-isopropyl-2-methoxy-N-[[4-[5-(trifluoromethyl)-1,2,4-oxadiazol-3-yl]phenyl]methyl]-propanamide | 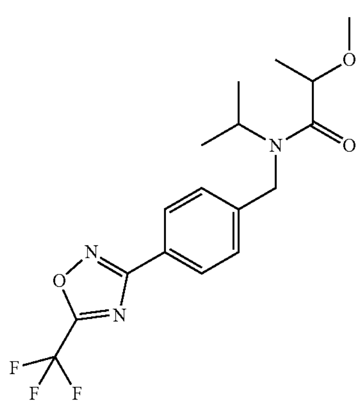 [SMILES: COC(C)C(=O)N(Cc1ccc(-c2noc(C(F)(F)F)n2)cc1)C(C)C] | 1.68 | 372.20 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.686 | 3,3,3-trifluoro-N-isopropyl-N-[[4-[5-(trifluoromethyl)-1,2,4-oxadiazol-3-yl]phenyl]methyl]-propanamide | 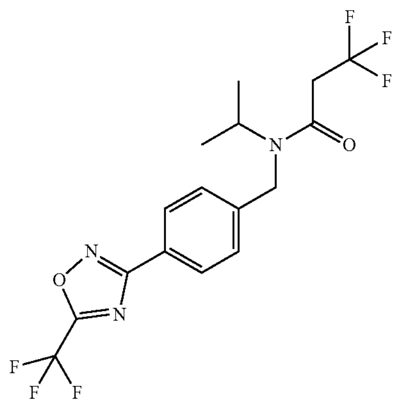 [SMILES: CC(C)N(Cc1ccc(-c2noc(C(F)(F)F)n2)cc1)C(=O)CC(F)(F)F] | 1.80 | 396.18 | B | |
| 1.687 | N-isopropyl-N-[[4-[5-(trifluoromethyl)-1,2,4-oxadiazol-3-yl]phenyl]methyl]-acetamide | 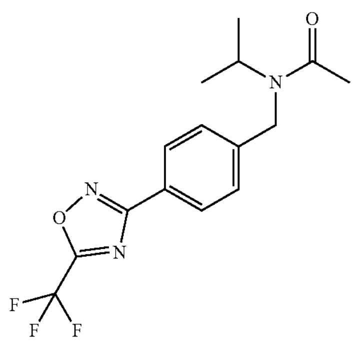 [SMILES: CC(=O)N(Cc1ccc(-c2noc(C(F)(F)F)n2)cc1)C(C)C] | 1.60 | 328.16 | B | |
| 1.688 | 2-cyclopropyl-N-isopropyl-N-[[4-[5-(trifluoromethyl)-1,2,4-oxadiazol-3-yl]phenyl]methyl]-acetamide | 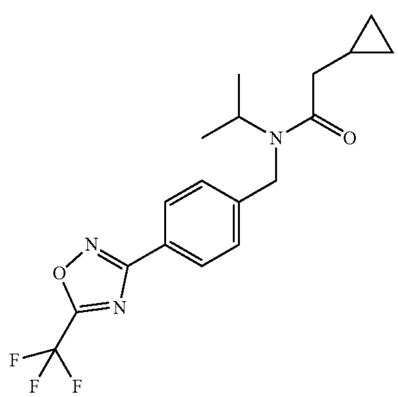 [SMILES: CC(C)N(Cc1ccc(-c2noc(C(F)(F)F)n2)cc1)C(=O)CC1CC1] | 1.84 | 368.20 | B | |
| 1.689 | 2-methyl-N-(2,2,2-trifluoroethyl)-N-[[4-[5-(trifluoromethyl)-1,2,4-oxadiazol-3-yl]phenyl]methyl]-propanamide | 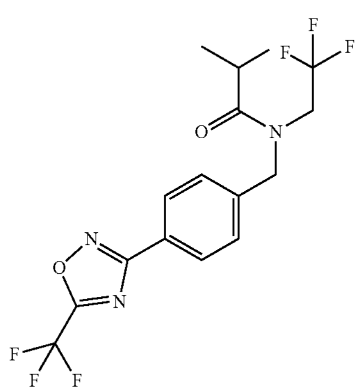 [SMILES: CC(C)C(=O)N(Cc1ccc(-c2noc(C(F)(F)F)n2)cc1)CC(F)(F)F] | 1.87 | 396.18 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.690 | 2,2-difluoro-N-(2,2,2-trifluoroethyl)-N-[[4-[5-(trifluoromethyl)-1,2,4-oxadiazol-3-yl]phenyl]methyl]-cyclopropane-carboxamide | 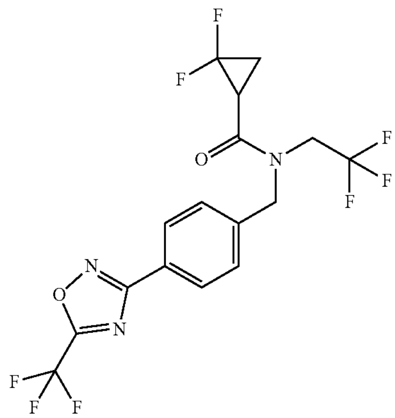 [SMILES: O=C(C1CC1(F)F)N(Cc1ccc(-c2noc(C(F)(F)F)n2)cc1)CC(F)(F)F] | 1.83 | 430.20 | B | |
| 1.691 | 2-chloro-N-(2,2,2-trifluoroethyl)-N-[[4-[5-(trifluoromethyl)-1,2,4-oxadiazol-3-yl]phenyl]methyl]-benzamide | 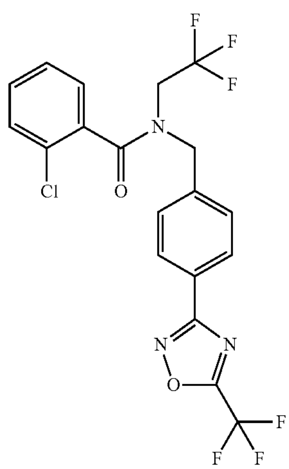 [SMILES: O=C(c1ccccc1Cl)N(Cc1ccc(-c2noc(C(F)(F)F)n2)cc1)CC(F)(F)F] | 1.98 | 464.13 | B | |
| 1.692 | N-(2,2,2-trifluoroethyl)-N-[[4-[5-(trifluoromethyl)-1,2,4-oxadiazol-3-yl]phenyl]methyl]-tetrahydrofuran-3-carboxamide | 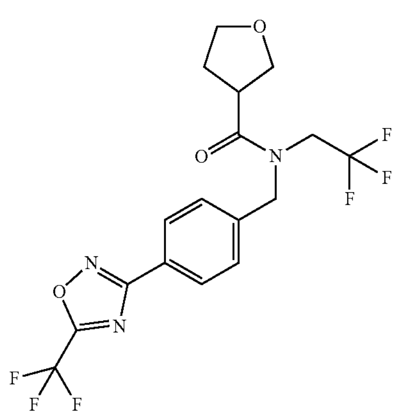 [SMILES: O=C(C1CCOC1)N(Cc1ccc(-c2noc(C(F)(F)F)n2)cc1)CC(F)(F)F] | 1.69 | 424.17 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.693 | 3-methoxy-N-(2,2,2-trifluoroethyl)-N-[[4-[5-(trifluoromethyl)-1,2,4-oxadiazol-3-yl]phenyl]methyl]-propanamide | 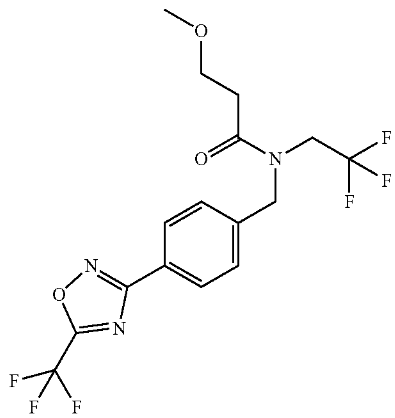 [SMILES: COCCC(=O)N(Cc1ccc(-c2noc(C(F)(F)F)n2)cc1)CC(F)(F)F] | 1.73 | 412.16 | B | |
| 1.694 | N-(2,2,2-trifluoroethyl)-N-[[4-[5-(trifluoromethyl)-1,2,4-oxadiazol-3-yl]phenyl]methyl]-cyclobutane-carboxamide | 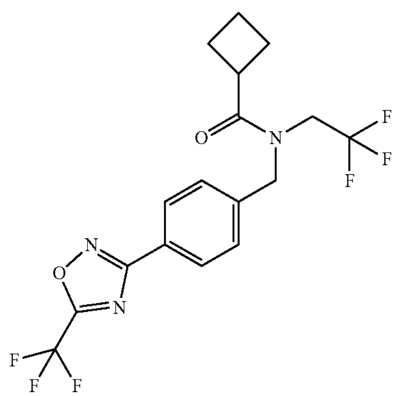 [SMILES: O=C(C1CCC1)N(Cc1ccc(-c2noc(C(F)(F)F)n2)cc1)CC(F)(F)F] | 1.93 | 408.17 | B | |
| 1.695 | 2-methyl-N-(2,2,2-trifluoroethyl)-N-[[4-[5-(trifluoromethyl)-1,2,4-oxadiazol-3-yl]phenyl]methyl]-cyclopropane-carboxamide | 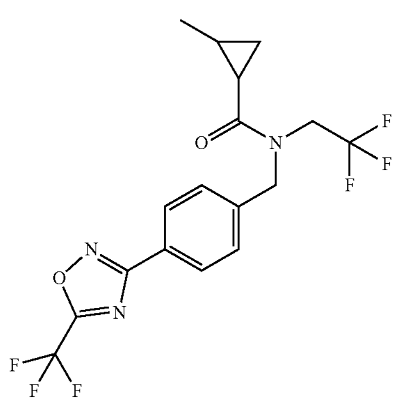 [SMILES: CC1CC1C(=O)N(Cc1ccc(-c2noc(C(F)(F)F)n2)cc1)CC(F)(F)F] | 1.90 | 408.18 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.696 | 1-methyl-N-(2,2,2-trifluoroethyl)-N-[[4-[5-(trifluoromethyl)-1,2,4-oxadiazol-3-yl]phenyl]methyl]-cyclopropane-carboxamide | 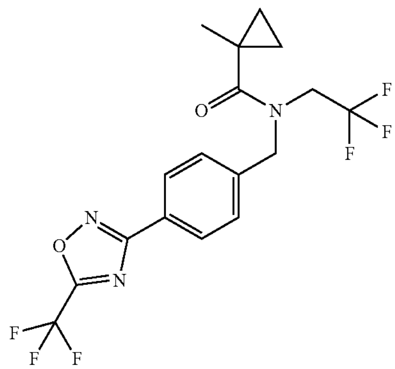 [SMILES: CC1(C(=O)N(Cc2ccc(-c3noc(C(F)(F)F)n3)cc2)CC(F)(F)F)CC1] | 1.90 | 408.12 | B | |
| 1.697 | 2-methyl-N-(2,2,2-trifluoroethyl)-N-[[4-[5-(trifluoromethyl)-1,2,4-oxadiazol-3-yl]phenyl]methyl]-butanamide | 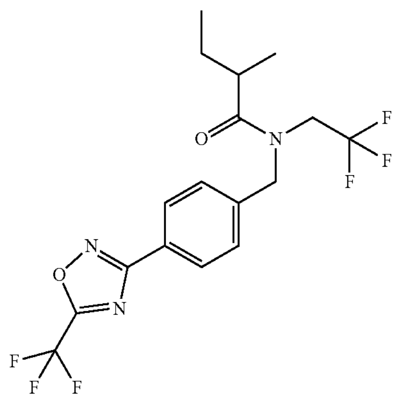 [SMILES: CCC(C)C(=O)N(Cc1ccc(-c2noc(C(F)(F)F)n2)cc1)CC(F)(F)F] | 1.96 | 410.19 | B | |
| 1.698 | 3-methyl-N-(2,2,2-trifluoroethyl)-N-[[4-[5-(trifluoromethyl)-1,2,4-oxadiazol-3-yl]phenyl]methyl]-oxetane-3-carboxamide | 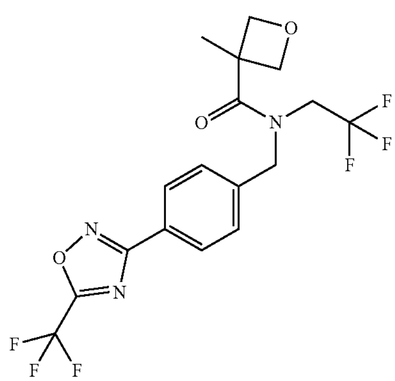 [SMILES: CC1(C(=O)N(Cc2ccc(-c3noc(C(F)(F)F)n3)cc2)CC(F)(F)F)COC1] | 1.71 | 424.33 | B | |
| 1.699 | 2-(methoxymethyl)-N-(2,2,2-trifluoroethyl)-N-[[4-[5-(trifluoromethyl)-1,2,4-oxadiazol-3-yl]phenyl]methyl]-butanamide | 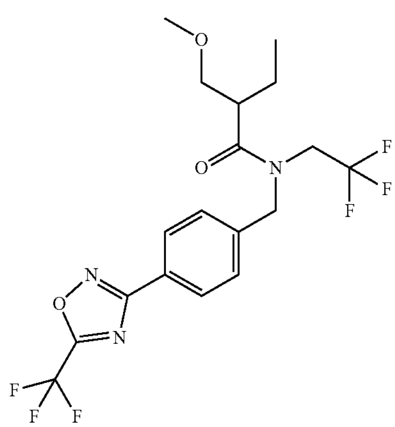 [SMILES: CCC(COC)C(=O)N(Cc1ccc(-c2noc(C(F)(F)F)n2)cc1)CC(F)(F)F] | 1.96 | 440.20 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.700 | 4-methoxy-N-(2,2,2-trifluoroethyl)-N-[[4-[5-(trifluoromethyl)-1,2,4-oxadiazol-3-yl]phenyl]methyl]-butanamide | 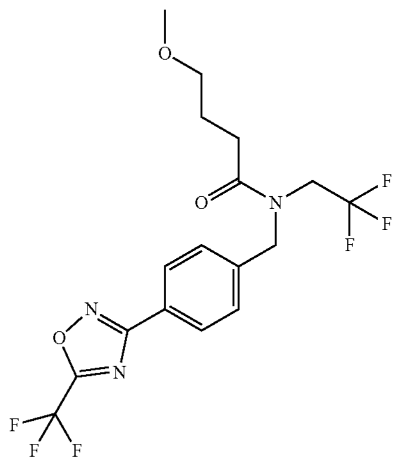 [SMILES: COCCCC(=O)N(Cc1ccc(-c2noc(C(F)(F)F)n2)cc1)CC(F)(F)F] | 1.78 | 426.20 | B | |
| 1.701 | 2-cyano-N-(2,2,2-trifluoroethyl)-N-[[4-[5-(trifluoromethyl)-1,2,4-oxadiazol-3-yl]phenyl]methyl]-acetamide | 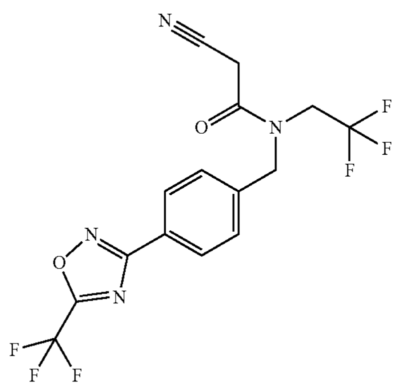 [SMILES: N#CCC(=O)N(Cc1ccc(-c2noc(C(F)(F)F)n2)cc1)CC(F)(F)F] | 1.62 | 393.46 | B | |
| 1.702 | 1-cyano-N-(2,2,2-trrfluoroethyl)-N-[[4-[5-(trifluoromethyl)-1,2,4-oxadiazol-3-yl]phenyl]methyl]-cyclopropane-carboxamide | 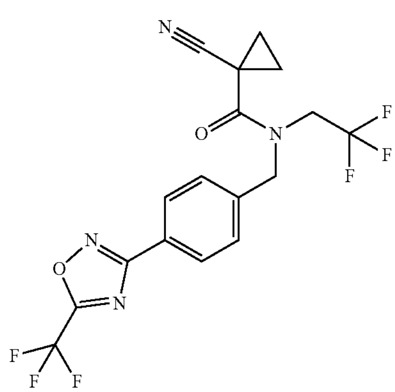 [SMILES: N#CC1(C(=O)N(Cc2ccc(-c3noc(C(F)(F)F)n3)cc2)CC(F)(F)F)CC1] | 1.79 | 419.26 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.703 | 2-methoxy-N-(2,2,2-trifluoroethyl)-N-[[4-[5-(trifluoromethyl)-1,2,4-oxadiazol-3-yl]phenyl]methyl]-propanamide | 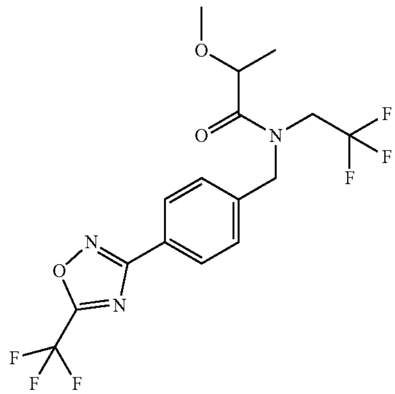 [SMILES: COC(C)C(=O)N(Cc1ccc(-c2noc(C(F)(F)F)n2)cc1)CC(F)(F)F] | 1.75 | 412.16 | B | |
| 1.704 | 3,3,3-trifluoro-N-(2,2,2-trifluoroethyl)-N-[[4-[5-(trifluoromethyl)-1,2,4-oxadiazol-3-yl]phenyl]methyl]-propanamide | 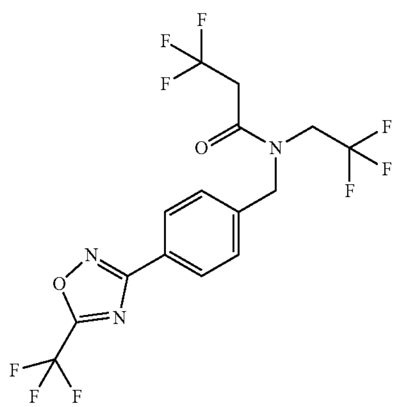 [SMILES: O=C(CC(F)(F)F)N(Cc1ccc(-c2noc(C(F)(F)F)n2)cc1)CC(F)(F)F] | 1.82 | 436.13 | B | |
| 1.705 | N-(2,2,2-trifluoroethyl)-N-[[4-[5-(trifluoromethyl)-1,2,4-oxadiazol-3-yl]phenyl]methyl]-acetamide | 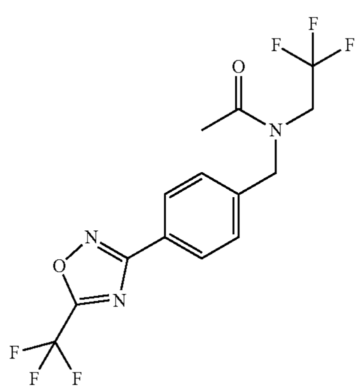 [SMILES: CC(=O)N(Cc1ccc(-c2noc(C(F)(F)F)n2)cc1)CC(F)(F)F] | 1.65 | 368.12 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.706 | 2-cyclopropyl-N-(2,2,2-trifluoroethyl)-N-[[4-[5-(trifluoromethyl)-1,2,4-oxadiazol-3-yl]phenyl]methyl]-acetamide | 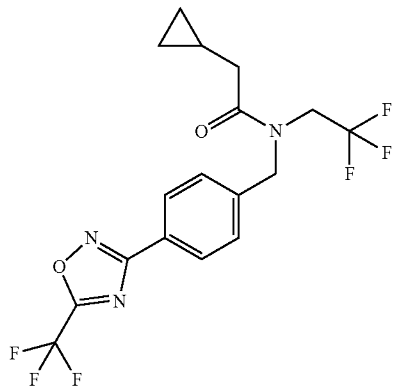 [SMILES: O=C(CC1CC1)N(Cc1ccc(-c2noc(C(F)(F)F)n2)cc1)CC(F)(F)F] | 1.87 | 408.16 | B | |
| 1.707 | N-(2-hydroxyethyl)-2-methyl-N-[[4-[5-(trifluoromethyl)-1,2,4-oxadiazol-3-yl]phenyl]methyl]-propanamide | 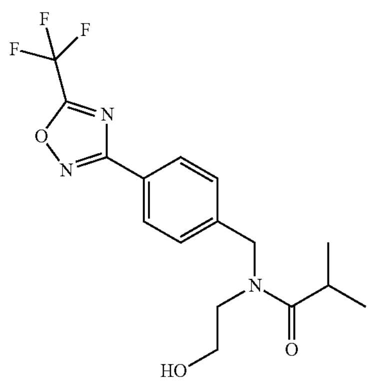 [SMILES: CC(C)C(=O)N(CCO)Cc1ccc(-c2noc(C(F)(F)F)n2)cc1] | 1.44 | 358.17 | B | |
| 1.708 | 2,2-difluoro-N-(2-hydroxyethyl)-N-[[4-[5-(trifluoromethyl)-1,2,4-oxadiazol-3-yl]phenyl]methyl]-cyclopropane-carboxamide | 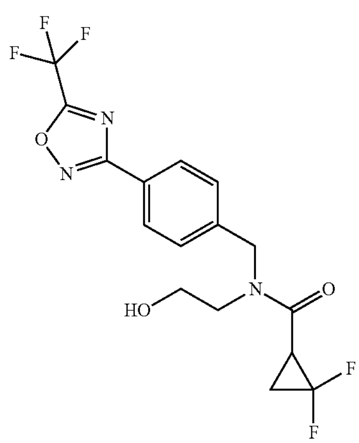 [SMILES: O=C(C1CC1(F)F)N(CCO)Cc1ccc(-c2noc(C(F)(F)F)n2)cc1] | 1.46 | 392.14 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.709 | 2-chloro-N-(2-hydroxyethyl)-N-[[4-[5-(trifluoromethyl)-1,2,4-oxadiazol-3-yl]phenyl]methyl]-benzamide | 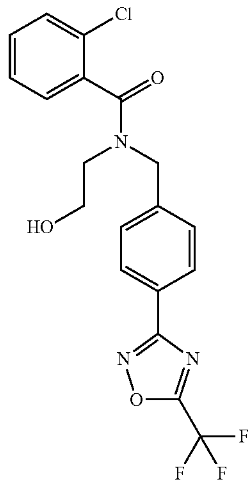 [SMILES: O=C(c1ccccc1Cl)N(CCO)Cc1ccc(-c2noc(C(F)(F)F)n2)cc1] | 1.59 | 426.14 | B | |
| 1.710 | 2-[(2-chlorobenzoyl)-[[4-[5-(trifluoromethyl)-1,2,4-oxadiazol-3-yl]phenyl]methyl]-amino]ethyl 2-chlorobonzoato | 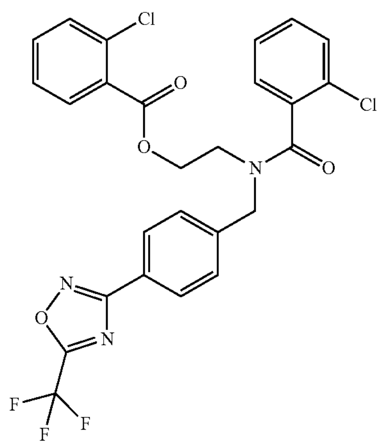 [SMILES: O=C(OCCN(Cc1ccc(-c2noc(C(F)(F)F)n2)cc1)C(=O)c1ccccc1Cl)c1ccccc1Cl] | 2.07 | 564.15 | B | |
| 1.711 | N-(2-hydroxyethyl)-N-[[4-[5-(trifluoromethyl)-1,2,4-oxadiazol-3-yl]phenyl]methyl]-tetrahydrofuran-3-carboxamide | 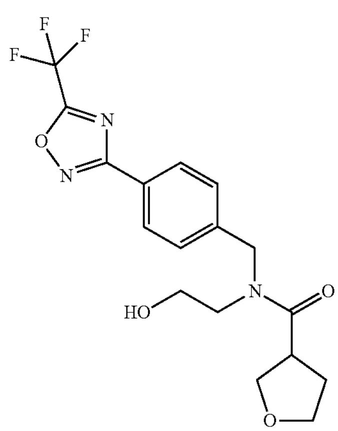 [SMILES: O=C(C1CCOC1)N(CCO)Cc1ccc(-c2noc(C(F)(F)F)n2)cc1] | 1.28 | 386.17 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.712 | 2-(tetrahydrofuran-3-carbonyl-[[4-[5-(trifluoromethyl)-1,2,4-oxadiazol-3-yl]phenyl]methyl]-amino]ethyl tetrahydrofuran-3-carboxylate | 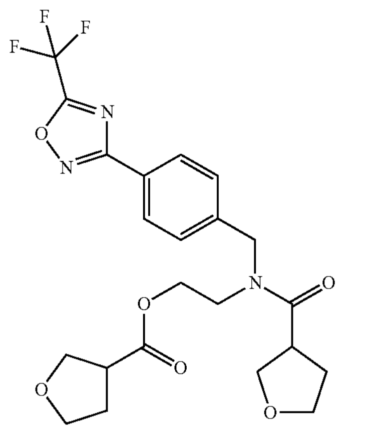 [SMILES: O=C(OCCN(Cc1ccc(-c2noc(C(F)(F)F)n2)cc1)C(=O)C1CCOC1)C1CCOC1] | 1.50 | 484.24 | B | |
| 1.713 | N-(2-hydroxyethyl)-3-methoxy-N-[[4-[5-(trifluoromethyl)-1,2,4-oxadiazol-3-yl]phenyl]methyl]-propanamide | 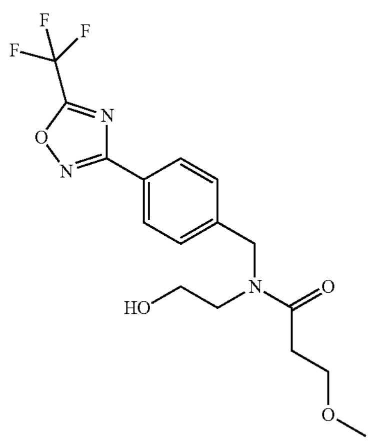 [SMILES: COCCC(=O)N(CCO)Cc1ccc(-c2noc(C(F)(F)F)n2)cc1] | 1.30 | 374.17 | B | |
| 1.714 | N-(2-hydroxyethyl)-N-[[4-[5-(trifluoromethyl)-1,2,4-oxadiazol-3-yl]phenyl]methyl]-cyclobutane-carboxamide | 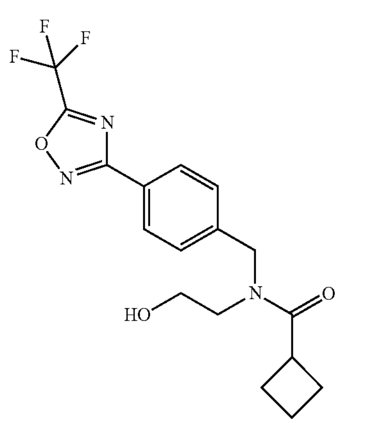 [SMILES: O=C(C1CCC1)N(CCO)Cc1ccc(-c2noc(C(F)(F)F)n2)cc1] | 1.50 | 370.17 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.715 | 2-[cyclobutanecarbonyl-[[4-[5-(trifluoromethyl)-1,2,4-oxadiazol-3-yl]phenyl]methyl]-amino]ethyl cyclobutane-carboxylate | 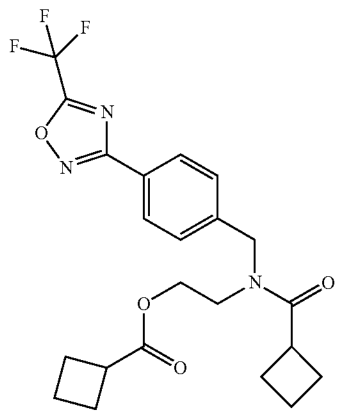 [SMILES: O=C(OCCN(Cc1ccc(-c2noc(C(F)(F)F)n2)cc1)C(=O)C1CCC1)C1CCC1] | 1.97 | 452.23 | B | |
| 1.716 | 2-[(2-methoxy-acetyl)-[[4-[5-(trifluoromethyl)-1,2,4-oxadiazol-3-yl]phenyl]methyl]-amino]ethyl 2-methoxyacetate | 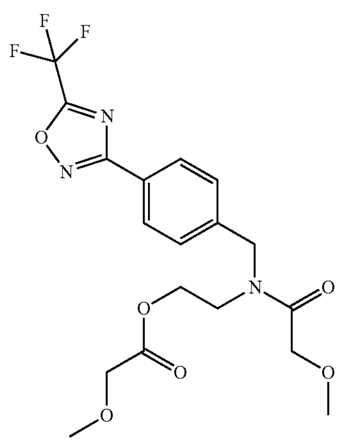 [SMILES: COCC(=O)OCCN(Cc1ccc(-c2noc(C(F)(F)F)n2)cc1)C(=O)COC] | 1.42 | 432.20 | B | |
| 1.717 | N-(2-hydroxyethyl)-2-methyl-N-[[4-[5-(trifluoromethyl)-1,2,4-oxadiazol-3-yl]phenyl]methyl]-cyclopropane-carboxamide | 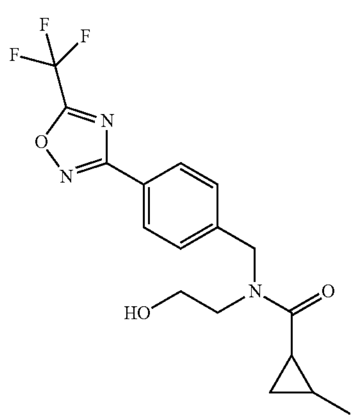 [SMILES: CC1CC1C(=O)N(CCO)Cc1ccc(-c2noc(C(F)(F)F)n2)cc1] | 1.49 | 370.18 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.718 | N-(2-hydroxyethyl)-1-methyl-N-[[4-[5-(trifluoromethyl)-1,2,4-oxadiazol-3-yl]phenyl]methyl]-cyclopropane-carboxamide | 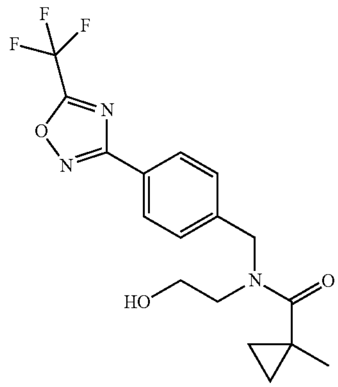 [SMILES: CC1(C(=O)N(CCO)Cc2ccc(-c3noc(C(F)(F)F)n3)cc2)CC1] | 1.45 | 370.17 | B | |
| 1.719 | N,2-dimethoxy-N-[[6-[5-(trifluoromethyl)-1,2,4-oxadiazol-3-yl]-3-pyridyl]methyl]-propanamide | 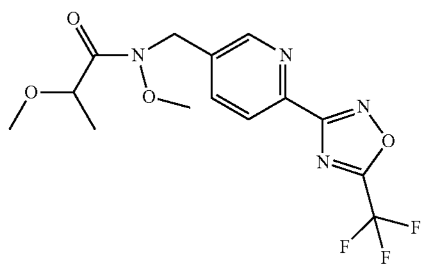 [SMILES: COC(C)C(=O)N(Cc1ccc(-c2noc(C(F)(F)F)n2)nc1)OC] | 0.88 | 361.5 | A | |
| 1.720 | N-(2-hydroxyethyl)-2-methyl-N-[[4-[5-(trifluoromethyl)-1,2,4-oxadiazol-3-yl]phenyl]methyl]-butanamide | 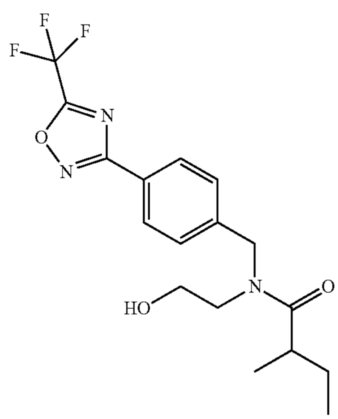 [SMILES: CCC(C)C(=O)N(CCO)Cc1ccc(-c2noc(C(F)(F)F)n2)cc1] | 1.54 | 372.20 | B | |
| 1.721 | N-(2-hydroxyethyl)-3-methyl-N-[[4-[5-(trifluoromethyl)-1,2,4-oxadiazol-3-yl]phenyl]methyl]-oxetane-3-carboxamide | 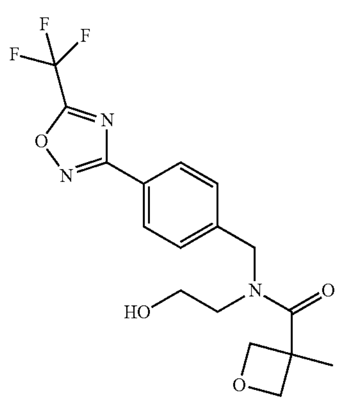 [SMILES: CC1(C(=O)N(CCO)Cc2ccc(-c3noc(C(F)(F)F)n3)cc2)COC1] | 1.28 | 386.17 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.722 | 2-[(3-methyloxetane-3-carbonyl)-[[4-[5-(trifluoromethyl)-1,2,4-oxadiazol-3-yl]phenyl]methyl]-amino]ethyl 3-methyloxetane-3-carboxylate | 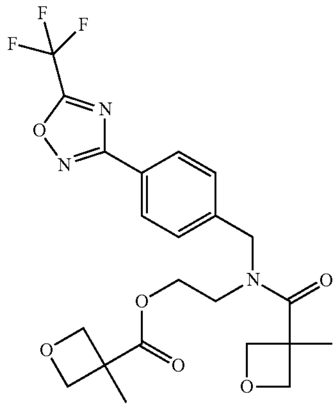 [SMILES: CC1(C(=O)OCCN(Cc2ccc(-c3noc(C(F)(F)F)n3)cc2)C(=O)C2(C)COC2)COC1] | 1.51 | 484.23 | B | |
| 1.723 | N-(2-hydroxyethyl)-2-(methoxymethyl)-N-[[4-[5-(trifluoromethyl)-1,2,4-oxadiazol-3-yl]phenyl]methyl]-butanamide | 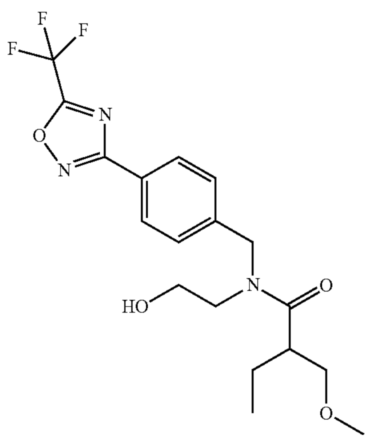 [SMILES: CCC(COC)C(=O)N(CCO)Cc1ccc(-c2noc(C(F)(F)F)n2)cc1] | 1.51 | 402.21 | B | |
| 1.724 | N-(2-hydroxyethyl)-4-methoxy-N-[[4-[5-(trifluoromethyl)-1,2,4-oxadiazol-3-yl]phenyl]methyl]-butanamide | 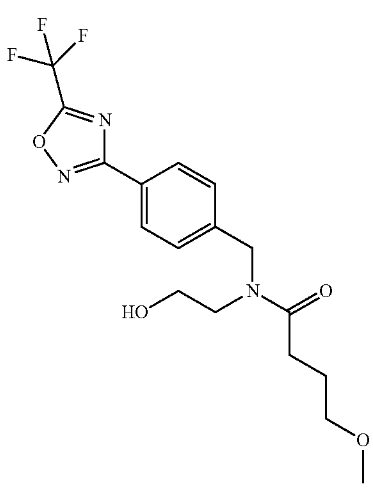 [SMILES: COCCCC(=O)N(CCO)Cc1ccc(-c2noc(C(F)(F)F)n2)cc1] | 1.35 | 388.19 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.725 | 2-[4-methoxybutanoyl-[[4-[5-(trifluoromethyl)-1,2,4-oxadiazol-3-yl]phenyl]methyl]-amino]ethyl 4-methoxybutanoate | 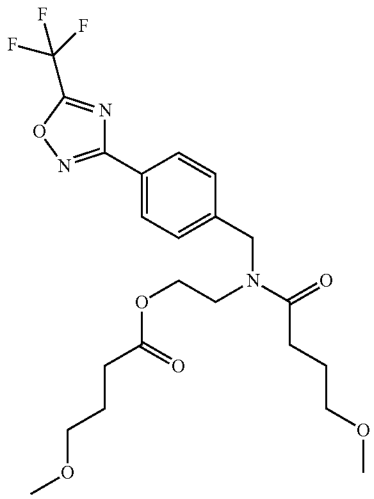 [SMILES: COCCCC(=O)OCCN(Cc1ccc(-c2noc(C(F)(F)F)n2)cc1)C(=O)CCCOC] | 1.66 | 488.28 | B | |
| 1.726 | N-(2-hydroxyethyl)-N-[[4-[5-(trifluoromethyl)-1,2,4-oxadiazol-3-yl]phenyl]methyl]-tetrahydrofuran-2-carboxamido | 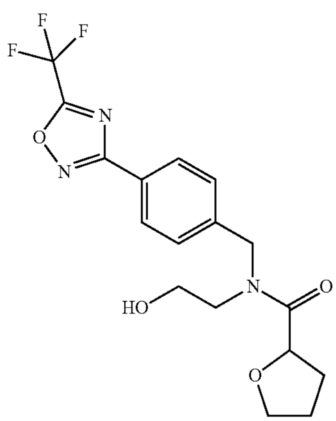 [SMILES: O=C(C1CCCO1)N(CCO)Cc1ccc(-c2noc(C(F)(F)F)n2)cc1] | 1.34 | 386.18 | B | |
| 1.727 | 2-[tetrahydrofuran-2-carbonyl-[[4-[5-(trifluoromethyl)-1,2,4-oxadiazol-3-yl]phenyl]methyl]-amino]ethyl tetrahydrofuran-2-carboxylate | 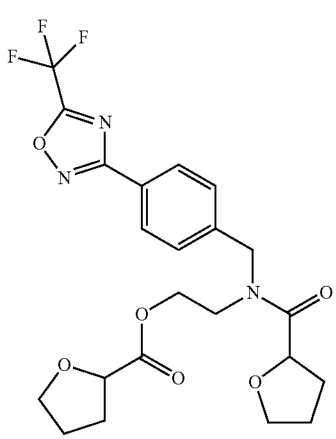 [SMILES: O=C(OCCN(Cc1ccc(-c2noc(C(F)(F)F)n2)cc1)C(=O)C1CCCO1)C1CCCO1] | 1.60 | 484.23 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.728 | 2-cyano-N-(2-hydroxyethyl)-N-[[4-[5-(trifluoromethyl)-1,2,4-oxadiazol-3-yl]phenyl]methyl]-acetamide | 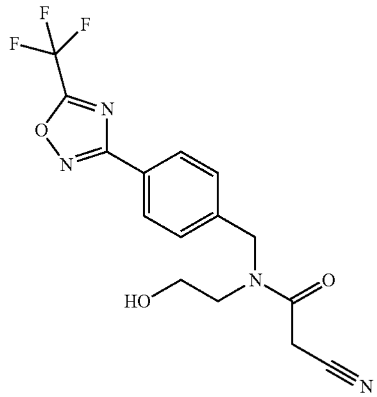 [SMILES: N#CCC(=O)N(CCO)Cc1ccc(-c2noc(C(F)(F)F)n2)cc1] | 1.25 | 355.14 | B | |
| 1.729 | 1-cyano-N-(2-hydroxyethyl)-N-[[4-[5-(trifluoromethyl)-1,2,4-oxadiazol-3-yl]phenyl]methyl]-cyclopropane-carboxamide | 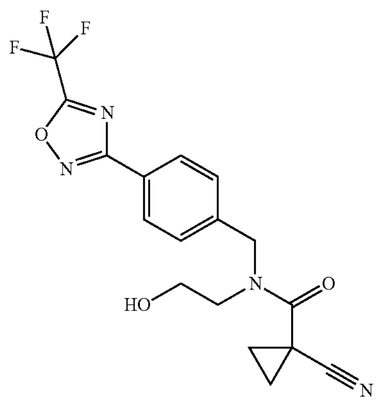 [SMILES: N#CC1(C(=O)N(CCO)Cc2ccc(-c3noc(C(F)(F)F)n3)cc2)CC1] | 1.40 | 381.16 | B | |
| 1.730 | 2-[(1-cyanocyclopropane-carbonyl)-[[4-[5-(trifluoromethyl)-1,2,4-oxadiazol-3-yl]phenyl]methyl]-amino]ethyl 1-cyanocyclopropane-carboxylate | 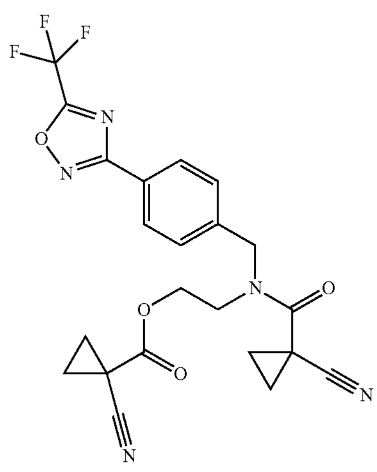 [SMILES: N#CC1(C(=O)OCCN(Cc2ccc(-c3noc(C(F)(F)F)n3)cc2)C(=O)C2(C#N)CC2)CC1] | 1.66 | 474.21 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.731 | N-(2-hydroxyethyl)-2-methoxy-N-[[4-[5-(trifluoromethyl)-1,2,4-oxadiazol-3-yl]phenyl]methyl]-propanamide | 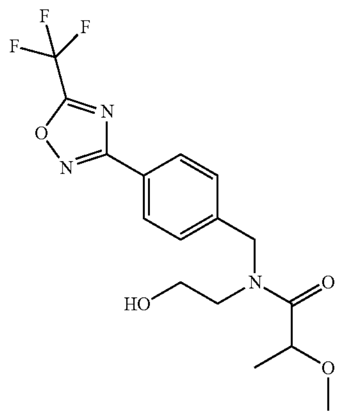 [SMILES: COC(C)C(=O)N(CCO)Cc1ccc(-c2noc(C(F)(F)F)n2)cc1] | 1.30 | 374.18 | B | |
| 1.732 | 2-[2-methoxypropanoyl-[[4-[5-(trifluoromethyl)-1,2,4-oxadiazol-3-yl]phenyl]methyl]-amino]ethyl 2-methoxypropanoate | 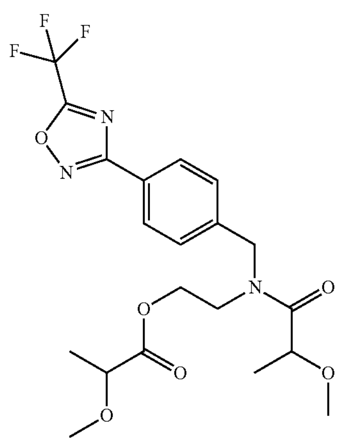 [SMILES: COC(C)C(=O)OCCN(Cc1ccc(-c2noc(C(F)(F)F)n2)cc1)C(=O)C(C)OC] | 1.59 | 460.24 | B | |
| 1.733 | 3,3,3-trifluoro-N-(2-hydroxyethyl)-N-[[4-[5-(trifluoromethyl)-1,2,4-oxadiazol-3-yl]phenyl]methyl]-propanamide | 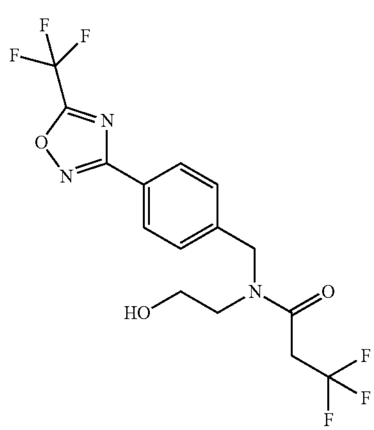 [SMILES: O=C(CC(F)(F)F)N(CCO)Cc1ccc(-c2noc(C(F)(F)F)n2)cc1] | 1.47 | 398.15 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.734 | 2-[[4-[5-(trifluoromethyl)-1,2,4-oxadiazol-3-yl]phenyl]methyl-(3,3,3-trifluoropropanoyl)-amino]ethyl 3,3,3-trifluoropropanoate | 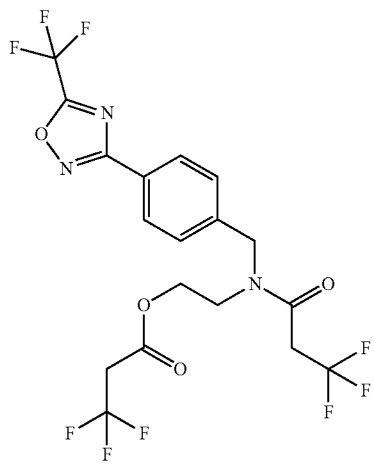 [SMILES: O=C(CC(F)(F)F)OCCN(Cc1ccc(-c2noc(C(F)(F)F)n2)cc1)C(=O)CC(F)(F)F] | 1.47 | 508.16 | B | |
| 1.735 | N-(2-hydroxyethyl)-N-[[4-[5-(trifluoromethyl)-1,2,4-oxadiazol-3-yl]phenyl]methyl]-acetamide | 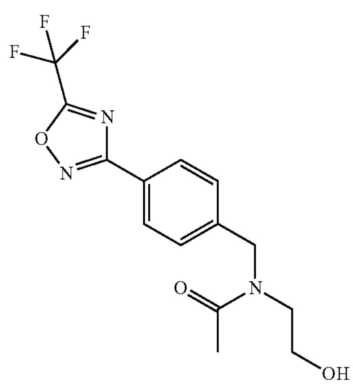 [SMILES: CC(=O)N(CCO)Cc1ccc(-c2noc(C(F)(F)F)n2)cc1] | 1.23 | 330.14 | B | |
| 1.736 | 2-cyclopropyl-N-(2-hydroxyethyl)-N-[[4-[5-(trifluoromethyl)-1,2,4-oxadiazol-3-yl]phenyl]methyl]-acetamide | 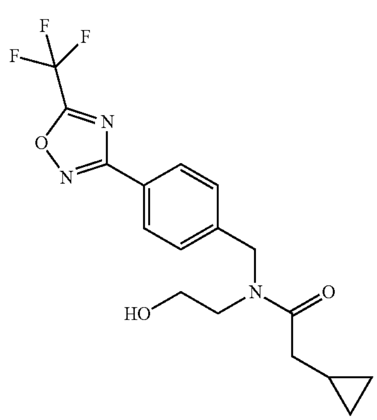 [SMILES: O=C(CC1CC1)N(CCO)Cc1ccc(-c2noc(C(F)(F)F)n2)cc1] | 1.46 | 370.17 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.737 | 2-[(2-cyclopropylacetyl)-[[4-[5-(trifluoromethyl)-1,2,4-oxadiazol-3-yl]phenyl]methyl]-amino]ethyl 2-cyclopropylacetate | 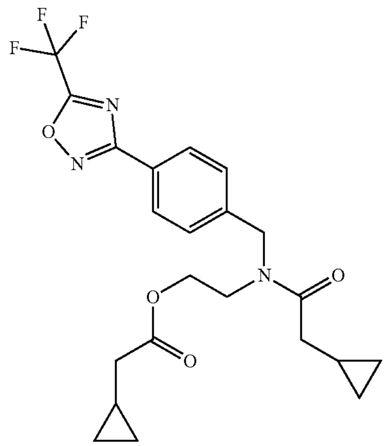 [SMILES: O=C(CC1CC1)OCCN(Cc1ccc(-c2noc(C(F)(F)F)n2)cc1)C(=O)CC1CC1] | 1.87 | 452.23 | B | |
| 1.738 | 2-methyl-N-(oxetan-3-yl)-N-[[4-[5-(trifluoromethyl)-1,2,4-oxadiazol-3-yl]phenyl]methyl]-propanamide | 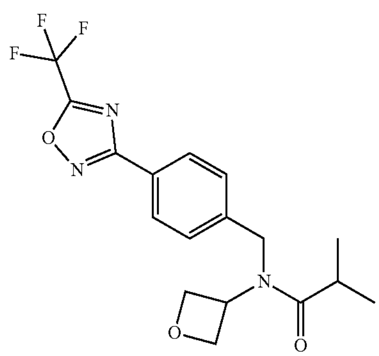 [SMILES: CC(C)C(=O)N(Cc1ccc(-c2noc(C(F)(F)F)n2)cc1)C1COC1] | 1.56 | 370.16 | B | |
| 1.739 | 2,2-difluoro-N-(oxetan-3-yl)-N-[[4-[5-(trifluoromethyl)-1,2,4-oxadiazol-3-yl]phenyl]methyl]-cyclopropane-carboxamide | 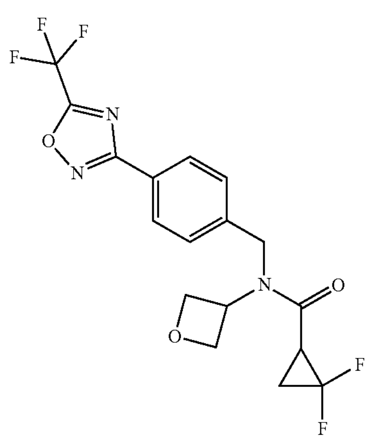 [SMILES: O=C(C1CC1(F)F)N(Cc1ccc(-c2noc(C(F)(F)F)n2)cc1)C1COC1] | 1.56 | 404.15 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.740 | 2-chloro-N-(oxetan-3-yl)-N-[[4-[5-(trifluoromethyl)-1,2,4-oxadiazol-3-yl]phenyl]methyl]-benzamide | 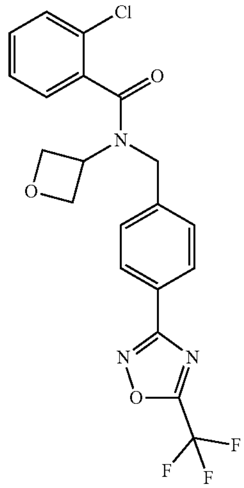 [SMILES: O=C(c1ccccc1Cl)N(Cc1ccc(-c2noc(C(F)(F)F)n2)cc1)C1COC1] | 1.71 | 438.14 | B | |
| 1.741 | 3-methoxy-N-(oxetan-3-yl)-N-[[4-[5-(trifluoromethyl)-1,2,4-oxadiazol-3-yl]phenyl]methyl]-propanamide | 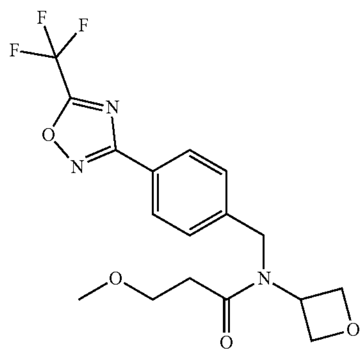 [SMILES: COCCC(=O)N(Cc1ccc(-c2noc(C(F)(F)F)n2)cc1)C1COC1] | 1.40 | 386.18 | B | |
| 1.742 | N-(oxetan-3-yl)-N-[[4-[5-(trifluoromethyl)-1,2,4-oxadiazol-3-yl]phenyl]methyl]-cyclobutane-carboxamide | 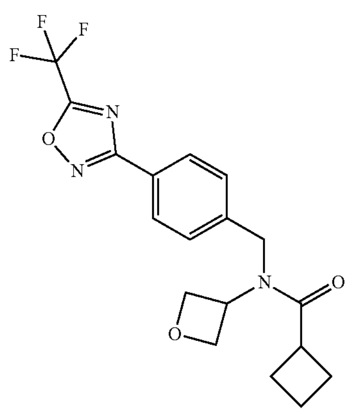 [SMILES: O=C(C1CCC1)N(Cc1ccc(-c2noc(C(F)(F)F)n2)cc1)C1COC1] | 1.62 | 382.18 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.743 | 1-methyl-N-(oxetan-3-yl)-N-[[4-[5-(trifluoromethyl)-1,2,4-oxadiazol-3-yl]phenyl]methyl]-cyclopropane-carboxamide | 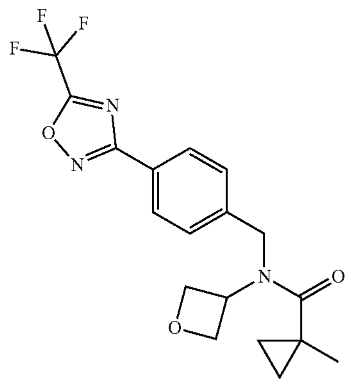 [SMILES: CC1(C(=O)N(Cc2ccc(-c3noc(C(F)(F)F)n3)cc2)C2COC2)CC1] | 1.56 | 382.17 | B | |
| 1.744 | 3-methyl-N-(oxetan-3-yl)-N-[[4-[5-(trifluoromethyl)-1,2,4-oxadiazol-3-yl]phenyl]methyl]-oxetane-3-carboxamide | 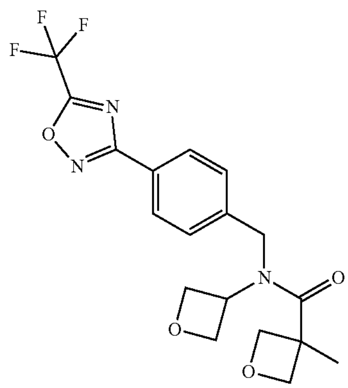 [SMILES: CC1(C(=O)N(Cc2ccc(-c3noc(C(F)(F)F)n3)cc2)C2COC2)COC1] | 1.38 | 398.18 | B | |
| 1.745 | 2-(methoxymethyl)-N-(oxetan-3-yl)-N-[[4-[5-(trifluoromethyl)-1,2,4-oxadiazol-3-yl]phenyl]methyl]-butanamide | 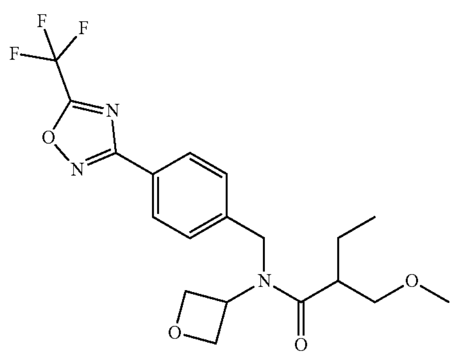 [SMILES: CCC(COC)C(=O)N(Cc1ccc(-c2noc(C(F)(F)F)n2)cc1)C1COC1] | 1.64 | 414.23 | B | |
| 1.746 | 4-methoxy-N-(oxetan-3-yl)-N-[[4-[5-(trifluoromethyl)-1,2,4-oxadiazol-3-yl]phenyl]methyl]-butanamide | 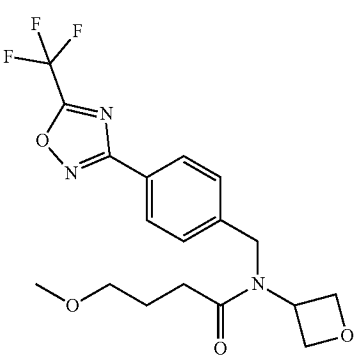 [SMILES: COCCCC(=O)N(Cc1ccc(-c2noc(C(F)(F)F)n2)cc1)C1COC1] | 1.50 | 400.19 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.747 | N-(oxetan-3-yl)-N-[[4-[5-(trifluoromethyl)-1,2,4-oxadiazol-3-yl]phenyl]methyl]-tetrahydrofuran-2-carboxamide | 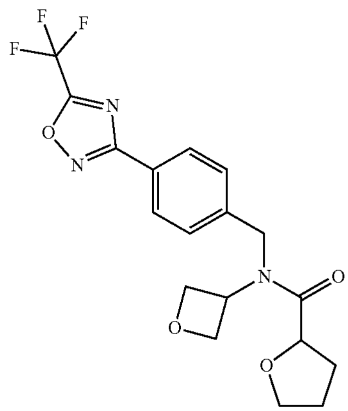 [SMILES: O=C(C1CCCO1)N(Cc1ccc(-c2noc(C(F)(F)F)n2)cc1)C1COC1] | 1.44 | 398.19 | B | |
| 1.748 | 2-cyano-N-(oxetan-3-yl)-N-[[4-[5-(trifluoromethyl)-1,2,4-oxadiazol-3-yl]phenyl]methyl]-acetamide | 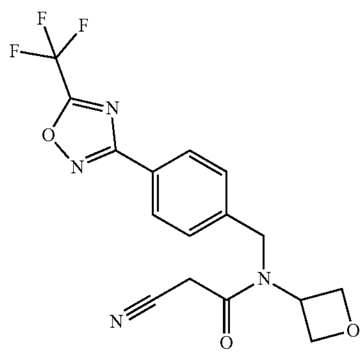 [SMILES: N#CCC(=O)N(Cc1ccc(-c2noc(C(F)(F)F)n2)cc1)C1COC1] | 1.33 | 367.14 | B | |
| 1.749 | 1-cyano-N-(oxetan-3-yl)-N-[[4-[5-(trifluoromethyl)-1,2,4-oxadiazol-3-yl]phenyl]methyl]-cyclopropane-carboxamide | 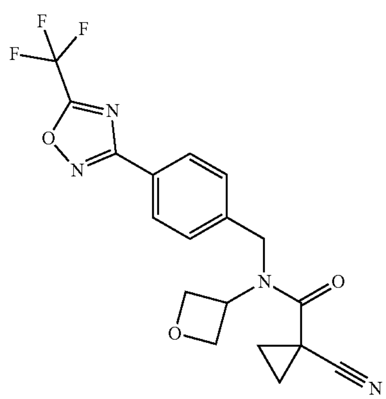 [SMILES: N#CC1(C(=O)N(Cc2ccc(-c3noc(C(F)(F)F)n3)cc2)C2COC2)CC1] | 1.51 | 393.15 | B | |
| 1.750 | 2-methoxy-N-(oxetan-3-yl)-N-[[4-[5-(trifluoromethyl)-1,2,4-oxadiazol-3-yl]phenyl]methyl]-propanamide | 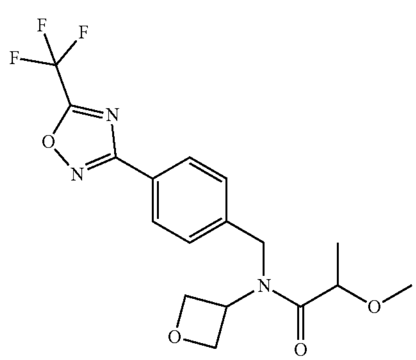 [SMILES: COC(C)C(=O)N(Cc1ccc(-c2noc(C(F)(F)F)n2)cc1)C1COC1] | 1.42 | 386.18 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.751 | 3,3,3-trifluoro-N-(oxetan-3-yl)-N-[[4-[5-(trifluoromethyl)-1,2,4-oxadiazol-3-yl]phenyl]methyl]-propanamide | 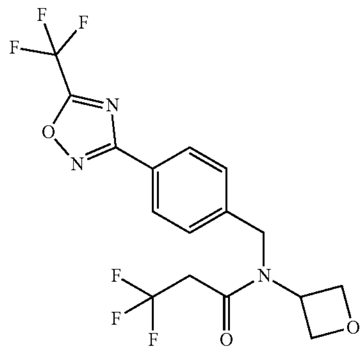 [SMILES: O=C(CC(F)(F)F)N(Cc1ccc(-c2noc(C(F)(F)F)n2)cc1)C1COC1] | 1.56 | 410.15 | B | |
| 1.752 | N-hydroxy-2-methyl-N-[[4-[5-(trifluoromethyl)-1,2,4-oxadiazol-3-yl]phenyl]methyl]-propanamide | 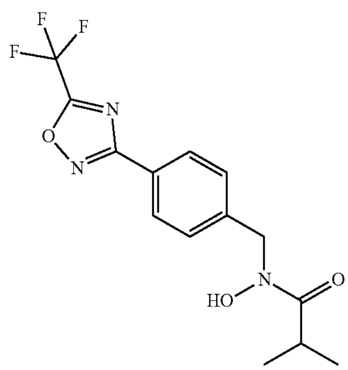 [SMILES: CC(C)C(=O)N(O)Cc1ccc(-c2noc(C(F)(F)F)n2)cc1] | 1.50 | 330.13 | B | |
| 1.753 | 2,2-difluoroN-hydroxy-N-[[4-[5-(trifluoromethyl)-1,2,4-oxadiazol-3-yl]phenyl]methyl]-cyclopropane-carboxamide | 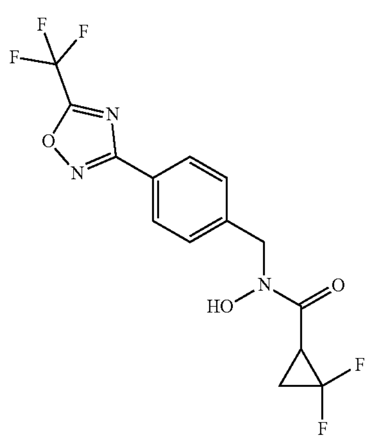 [SMILES: O=C(C1CC1(F)F)N(O)Cc1ccc(-c2noc(C(F)(F)F)n2)cc1] | 1.51 | 364.10 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.754 | 2-chloro-N-hydroxy-N-[[4-[5-(trifluoromethyl)-1,2,4-oxadiazol-3-yl]phenyl]methyl]-benzamide | 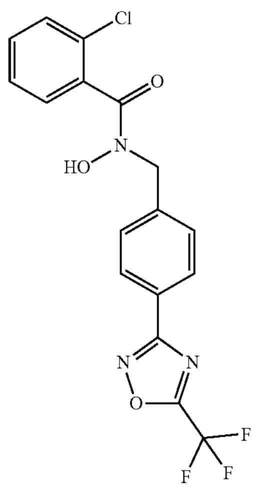 [SMILES: O=C(c1ccccc1Cl)N(O)Cc1ccc(-c2noc(C(F)(F)F)n2)cc1] | 1.60 | 398.09 | B | |
| 1.755 | [(2-chlorobenzoyl)-[[4-[5-(trifluoromethyl)-1,2,4-oxadiazol-3-yl]phenyl]methyl]-amino] 2-chlorobenzoate | 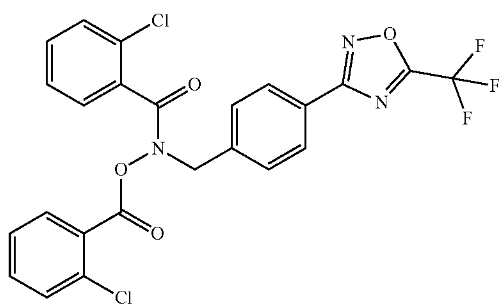 [SMILES: O=C(ON(Cc1ccc(-c2noc(C(F)(F)F)n2)cc1)C(=O)c1ccccc1Cl)c1ccccc1Cl] | 2.11 | 536.12 | B | |
| 1.756 | N-hydroxy-N-[[4-[5-(trifluoromethyl)-1,2,4-oxadiazol-3-yl]phenyl]methyl]-tetrahydrofuran-3-carboxamide | 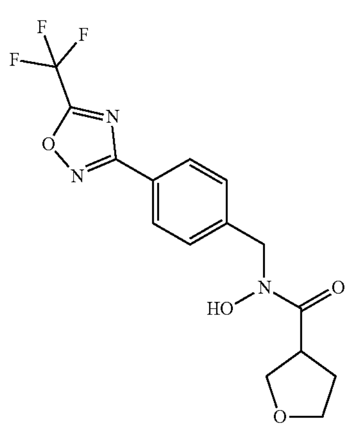 [SMILES: O=C(C1CCOC1)N(O)Cc1ccc(-c2noc(C(F)(F)F)n2)cc1] | 1.34 | 358.13 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.757 | [tetrahydrofuran-3-carbonyl-[[4-[5-(trifluoromethyl)-1,2,4-oxadiazol-3-yl]phenyl]methyl]-amino] tetrahydrofuran-3-carboxylate | 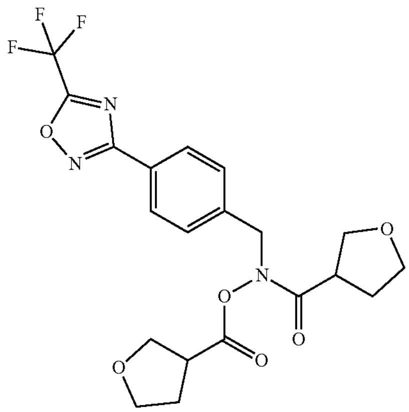 [SMILES: O=C(ON(Cc1ccc(-c2noc(C(F)(F)F)n2)cc1)C(=O)C1CCOC1)C1CCOC1] | 1.57 | 456.20 | B | |
| 1.758 | N-hydroxy-3-methoxy-N-[[4-[5-(trifluoromethyl)-1,2,4-oxadiazol-3-yl]phenyl]methyl]-propanamide | 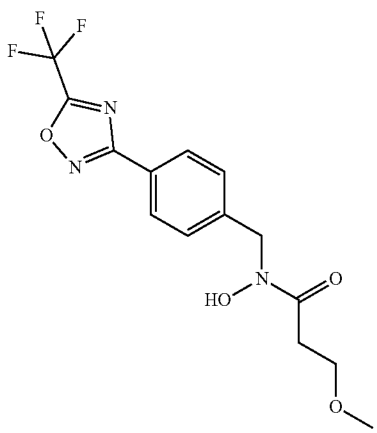 [SMILES: COCCC(=O)N(O)Cc1ccc(-c2noc(C(F)(F)F)n2)cc1] | 1.34 | 346.13 | B | |
| 1.759 | [3-methoxy-propanoyl-[[4-[5-(trifluoromethyl)-1,2,4-oxadiazol-3-yl]phenyl]methyl]-amino] 3-methoxypropanoate | 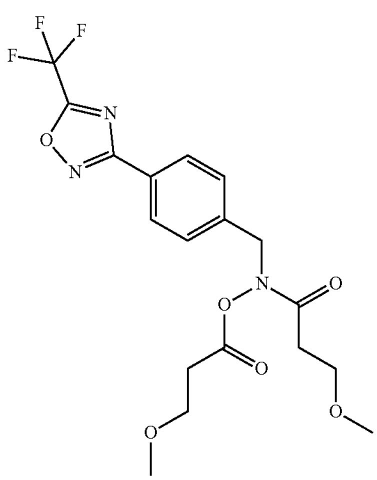 [SMILES: COCCC(=O)ON(Cc1ccc(-c2noc(C(F)(F)F)n2)cc1)C(=O)CCOC] | 1.62 | 432.19 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.760 | [propanoyl-[[4-[5-(trifluoromethyl)-1,2,4-oxadiazol-3-yl]phenyl]methyl]-amino] propanoate | 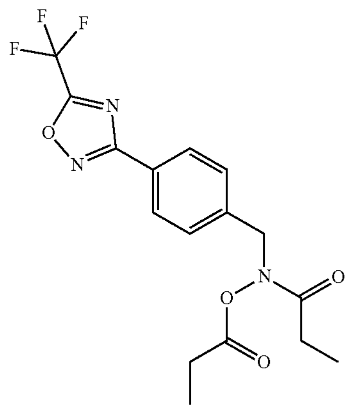 [SMILES: CCC(=O)ON(Cc1ccc(-c2noc(C(F)(F)F)n2)cc1)C(=O)CC] | 1.75 | 372.17 | B | |
| 1.761 | N-hydroxy-N-[[4-[5-(trifluoromethyl)-1,2,4-oxadiazol-3-yl]phenyl]methyl]-cyclobutane-carboxamide | 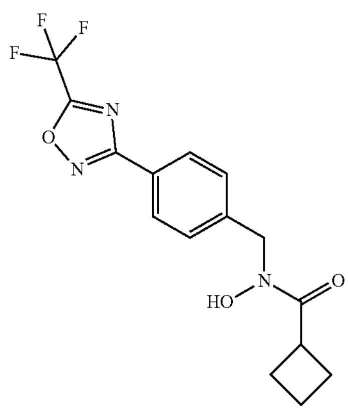 [SMILES: O=C(C1CCC1)N(O)Cc1ccc(-c2noc(C(F)(F)F)n2)cc1] | 1.54 | 342.14 | B | |
| 1.762 | [cyclobutane-carbonyl-[[4-[5-(trifluoromethyl)-1,2,4-oxadiazol-3-yl]phenyl]methyl]-amino] cyclobutane-carboxylate | 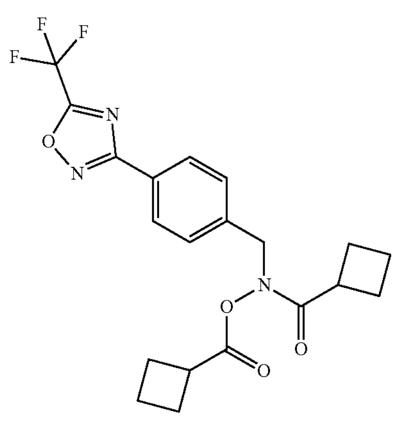 [SMILES: O=C(ON(Cc1ccc(-c2noc(C(F)(F)F)n2)cc1)C(=O)C1CCC1)C1CCC1] | 2.03 | 424.20 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.763 | N-hydroxy-2-methyl-N-[[4-[5-(trifluoromethyl)-1,2,4-oxadiazol-3-yl]phenyl]methyl]-cyclopropane-carboxamide | 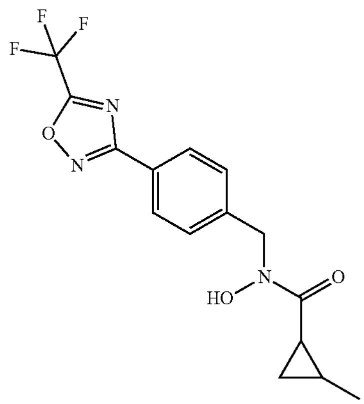 [SMILES: CC1CC1C(=O)N(O)Cc1ccc(-c2noc(C(F)(F)F)n2)cc1] | 1.53 | 342.14 | B | |
| 1.764 | N-hydroxy-1-methyl-N-[[4-[5-(trifluoromethyl)-1,2,4-oxadiazol-3-yl]phenyl]methyl]-cyclopropane-carboxamide | 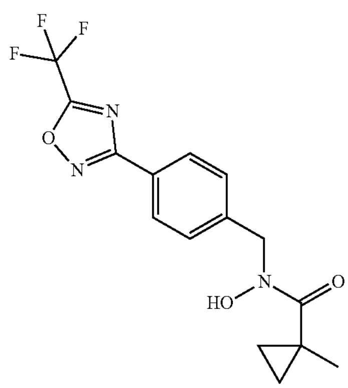 [SMILES: CC1(C(=O)N(O)Cc2ccc(-c3noc(C(F)(F)F)n3)cc2)CC1] | 1.50 | 342.14 | B | |
| 1.765 | N-hydroxy-2-methyl-N-[[4-[5-(trifluoromethyl)-1,2,4-oxadiazol-3-yl]phenyl]methyl]-butanamide | 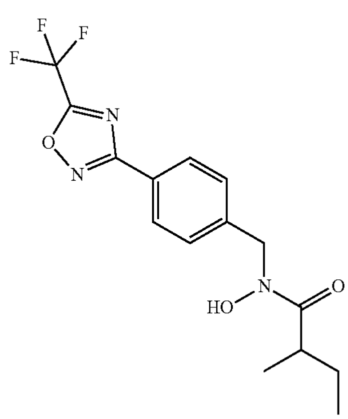 [SMILES: CCC(C)C(=O)N(O)Cc1ccc(-c2noc(C(F)(F)F)n2)cc1] | 1.60 | 344.15 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.766 | N-hydroxy-3-methyl-N-[[4-[5-(trifluoromethyl)-1,2,4-oxadiazol-3-yl]phenyl]methyl]-oxetane-3-carboxamide | 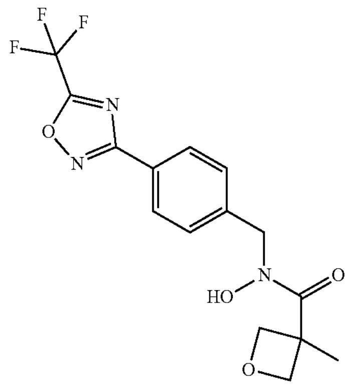 [SMILES: CC1(C(=O)N(O)Cc2ccc(-c3noc(C(F)(F)F)n3)cc2)COC1] | 1.34 | 358.13 | B | |
| 1.767 | [(3-methyloxetane-3-carbonyl)-[[4-[5-(trifluoromethyl)-1,2,4-oxadiazol-3-yl]phenyl]methyl]-amino] 3-methyloxelane-3-carboxylate | 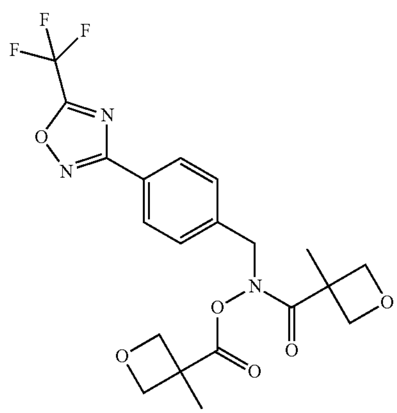 [SMILES: CC1(C(=O)ON(Cc2ccc(-c3noc(C(F)(F)F)n3)cc2)C(=O)C2(C)COC2)COC1] | 1.60 | 456.20 | B | |
| 1.768 | N-hydroxy-2-(methoxymethyl)-N-[[4-[5-(trifluoromethyl)-1,2,4-oxadiazol-3-yl]phenyl]methyl]-butanamide | 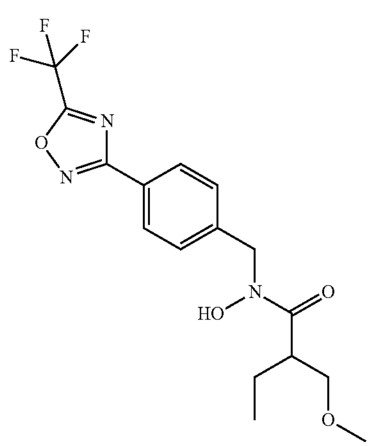 [SMILES: CCC(COC)C(=O)N(O)Cc1ccc(-c2noc(C(F)(F)F)n2)cc1] | 1.55 | 374.16 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.769 | N-hydroxy-4-methoxy-N-[[4-[5-(trifluoromethyl)-1,2,4-oxadiazol-3-yl]phenyl]methyl]-butanamide | 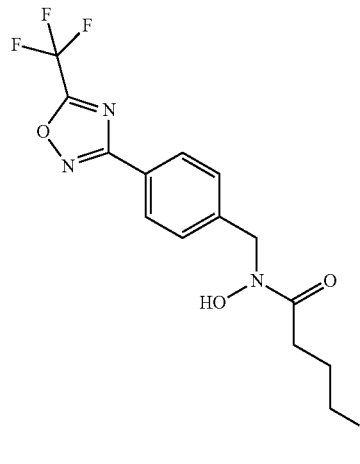 | 1.40 | 360.15 | B | |
| 1.770 | N-hydroxy-N-[[4-[5-(trifluoromethyl)-1,2,4-oxadiazol-3-yl]phenyl]methyl]-tetrahydrofuran-2-carboxamide | 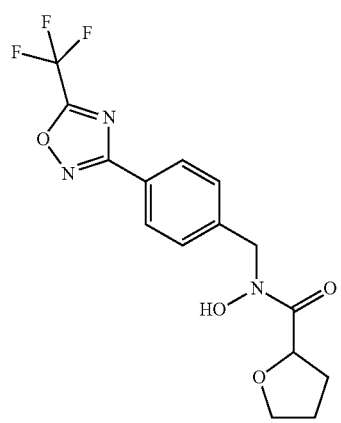 [SMILES: O=C(C1CCCO1)N(O)Cc1ccc(-c2noc(C(F)(F)F)n2)cc1] | 1.35 | 358.13 | B | |
| 1.771 | 2-cyano-N-hydroxy-N-[[4-[5-(trifluoromethyl)-1,2,4-oxadiazol-3-yl]phenyl]methyl]-acetamide | 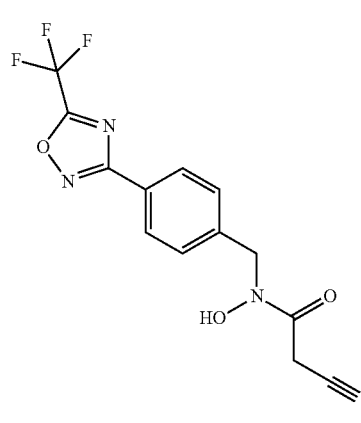 | 1.21 | 327.10 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.772 | N-hydroxy-2-methoxy-N-[[4-[5-(trifluoromethyl)-1,2,4-oxadiazol-3-yl]phenyl]methyl]-propanamide | 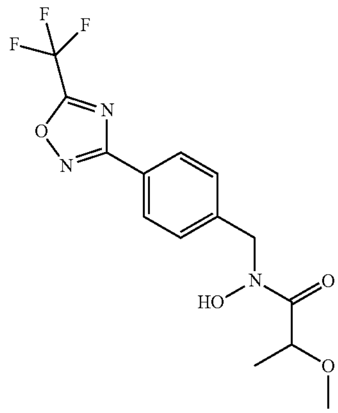 [SMILES: COC(C)C(=O)N(O)Cc1ccc(-c2noc(C(F)(F)F)n2)cc1] | 1.34 | 346.13 | B | |
| 1.773 | N-hydroxy-N-[[4-[5-(trifluoromethyl)-1,2,4-oxadiazol-3-yl]phenyl]methyl]-acetamide | 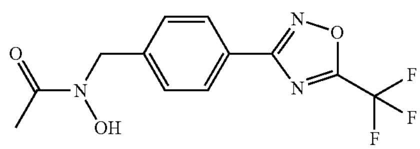 [SMILES: CC(=O)N(O)Cc1ccc(-c2noc(C(F)(F)F)n2)cc1] | 1.27 | 302.11 | B | |
| 1.774 | 2-cyclopropyl-N-hydroxy-N-[[4-[5-(trifluoromethyl)-1,2,4-oxadiazol-3-yl]phenyl]methyl]-acetamide | 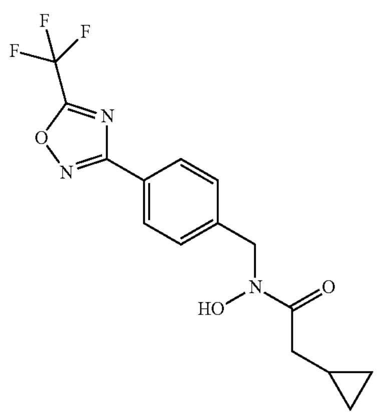 [SMILES: O=C(CC1CC1)N(O)Cc1ccc(-c2noc(C(F)(F)F)n2)cc1] | 1.50 | 342.13 | B | |
| 1.775 | [(2-cyclopropylacetyl)-[[4-[5-(trifluoromethyl)-1,2,4-oxadiazol-3-yl]phenyl]methyl]-amino] 2-cyclopropylacetale | 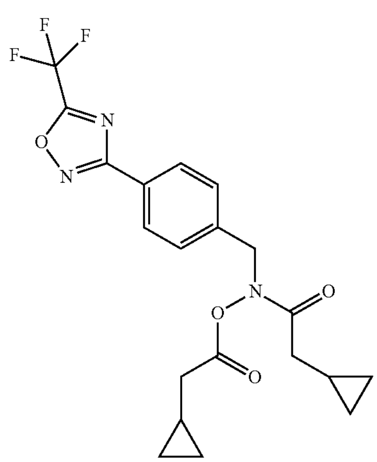 [SMILES: O=C(CC1CC1)ON(Cc1ccc(-c2noc(C(F)(F)F)n2)cc1)C(=O)CC1CC1] | 1.95 | 424.21 | B | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.776 | (acetyl-[[4-[5-(trifluoromethyl)-1,2,4-oxadiazol-3-yl]phenyl]methyl]-amino] acetate | 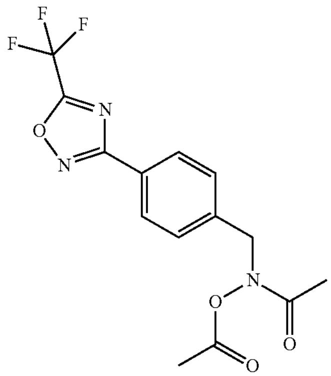 [SMILES: CC(=O)ON(Cc1ccc(-c2noc(C(F)(F)F)n2)cc1)C(C)=O] | 1.51 | 344.12 | B | |
| 1.777 | N-cyclopropyl-2-methoxy-N-[[4-[5-(trifluoromethyl)-1,2,4-oxadiazol-3-yl]phenyl]methyl]-acetamide | 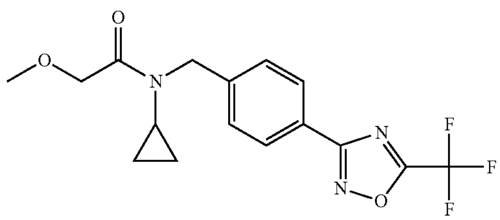 [SMILES: COCC(=O)N(Cc1ccc(-c2noc(C(F)(F)F)n2)cc1)C1CC1] | 1.02 | 356 | A | |
| 1.778 | 2-hydroxy-N-methoxy-N-[[4-[5-(trifluoromethyl)-1,2,4-oxadiazol-3-yl]phenyl]methyl]-acetamide | 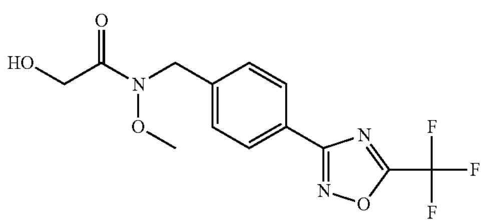 [SMILES: CON(Cc1ccc(-c2noc(C(F)(F)F)n2)cc1)C(=O)CO] | 0.93 | 332 | A | |
| 1.779 | N,2-dimethoxy-2-methyl-N-[[4-[5-(trifluoromethyl)-1,2,4-oxadiazol-3-yl]phenyl]methyl]-propanamide | 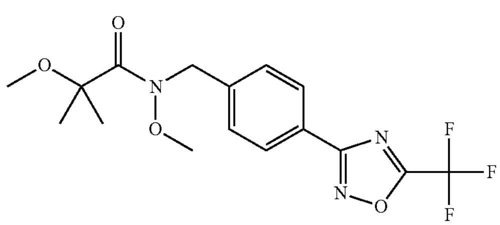 [SMILES: CON(Cc1ccc(-c2noc(C(F)(F)F)n2)cc1)C(=O)C(C)(C)OC] | 1.12 | 374 | A | |
| 1.780 | 2,2,2-trifluoro-N-methoxy-N-[[4-[5-(trifluoromethyl)-1,2,4-oxadiazol-3-yl]phenyl]methyl]-acetamide | 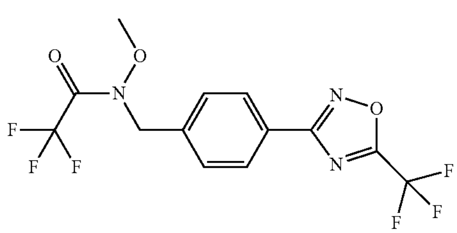 [SMILES: CON(Cc1ccc(-c2noc(C(F)(F)F)n2)cc1)C(=O)C(F)(F)F] | 1.16 | 388 | A | |
| 1.781 | 2-hydroxy-N,2-dimethyl-N-[[4-[5-(trifluoromethyl)-1,2,4-oxadiazol-3-yl]phenyl]methyl]-propanamide | 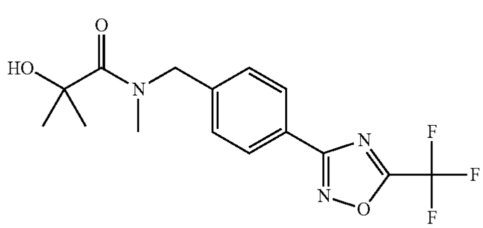 [SMILES: CN(Cc1ccc(-c2noc(C(F)(F)F)n2)cc1)C(=O)C(C)(C)O] | 1.01 | 344 | A | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.782 | 2-methoxy-N,2-dimethyl-N-[[4-[5-(trifluoromethyl)-1,2,4-oxadiazol-3-yl]phenyl]methyl]-propanamide | 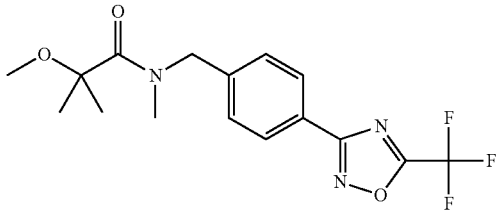 [SMILES: COC(C)(C)C(=O)N(C)Cc1ccc(-c2noc(C(F)(F)F)n2)cc1] | 1.13 | 359 | A | |
| 1.783 | N-((3-fluoro-4-[5-(trifluoromethyl)-1,2,4-oxadiazol-3-yl]phenyl]methyl)-N,2-dimethoxy-propanamide | 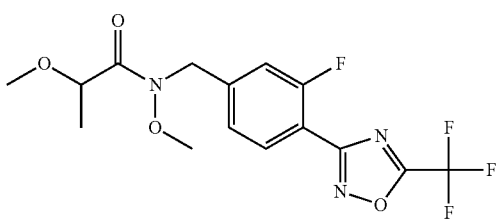 [SMILES: COC(C)C(=O)N(Cc1ccc(-c2noc(C(F)(F)F)n2)c(F)c1)OC] | 1.04 | 378 | A | |
| 1.784 | 2-hydroxy-N-methoxy-2-methyl-N-[[4-[5-(trifluoromethyl)-1,2,4-oxadiazol-3-yl]phenyl]methyl]-propanamide | 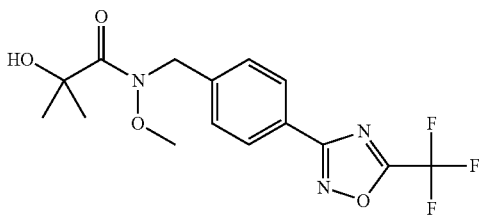 [SMILES: CON(Cc1ccc(-c2noc(C(F)(F)F)n2)cc1)C(=O)C(C)(C)O] | 1.03 | 360 | A | |
| 1.785 | 2-(difuoromethoxy)-N-methoxy-N-[[4-[5-(trifluoromethyl)-1,2,4-oxadiazol-3-yl]phenyl]methyl]-acetamide | 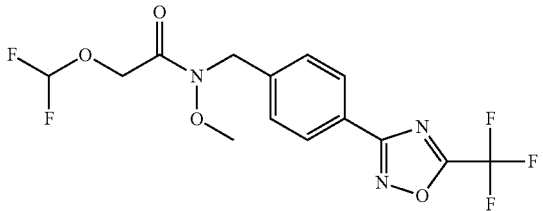 [SMILES: CON(Cc1ccc(-c2noc(C(F)(F)F)n2)cc1)C(=O)COC(F)F] | 0.97 | 382 | A | |
| 1.786 | 2-hydroxy-N-methoxy-N-[[4-[5-(trifluoromethyl)-1,2,4-oxadiazol-3-yl]phenyl]methyl]-propanamide | 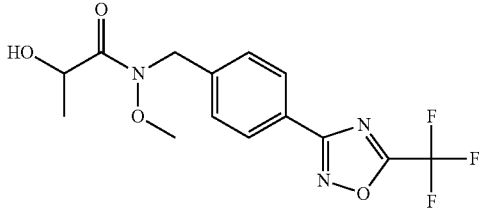 [SMILES: CON(Cc1ccc(-c2noc(C(F)(F)F)n2)cc1)C(=O)C(C)O] | 0.97 | 346 | A | |
| 1.787 | tert-butyl N-[2-(methoxy-[[4-[5-(trifluoromethyl)-1,2,4-oxadiazol-3-yl]phenyl]methyl]-amino]-2-oxo-ethyl]carbamate | 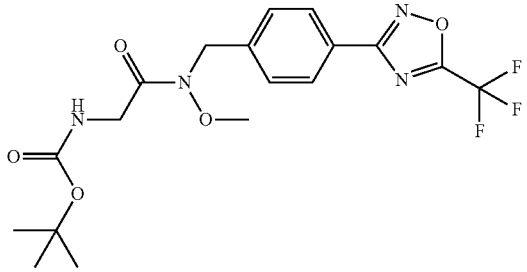 [SMILES: CON(Cc1ccc(-c2noc(C(F)(F)F)n2)cc1)C(=O)CNC(=O)OC(C)(C)C] | | | | 80-83.1 |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.788 | [2-[methoxy-[[4-[5-(trifluoromethyl)-1,2,4-oxadiazol-3-yl]phenyl]methyl]-amino]-2-oxo-ethyl]ammonium; chloride | 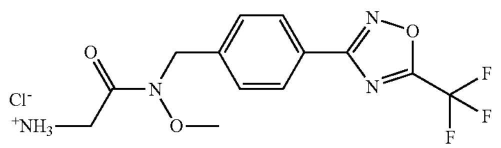 [SMILES: [Cl-] ; CON(Cc1ccc(-c2noc(C(F)(F)F)n2)cc1)C(=O)C[NH3+]] | 0.71 | 331.5 | A | |
| 1.789 | N-methoxy-N-[[6-[5-(trifluoromethyl)-1,2,4-oxadiazol-3-yl]-3-pyridyl]methyl]-tetrahydrofuran-2-carboxamide | 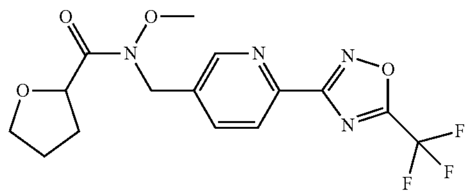 [SMILES: CON(Cc1ccc(-c2noc(C(F)(F)F)n2)nc1)C(=O)C1CCCO1] | 0.9 | 373 | A | |
| 1.790 | N-[2-[methoxy-[[4-[5-(trifluoro-methyl)-1,2,4-oxadiazol-3-yl]phenyl]methyl]-amino]-2-oxo-ethyl]-cyclopropane-carboxamide | 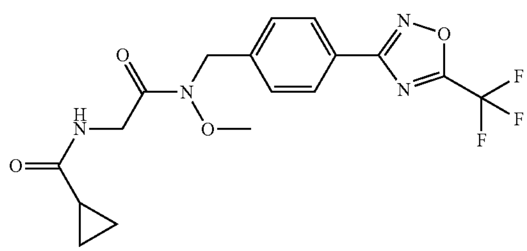 [SMILES: CON(Cc1ccc(-c2noc(C(F)(F)F)n2)cc1)C(=O)CNC(=O)C1CC1] | | | | 135.9-138.5 |
| 1.791 | tert-butyl N-[2-(methoxy-[[4-[5-(trifluoromethyl)-1,2,4-oxadiazol-3-yl]phenyl]methyl]-amino]-1-methyl-2-oxo-ethyl]carbamate | 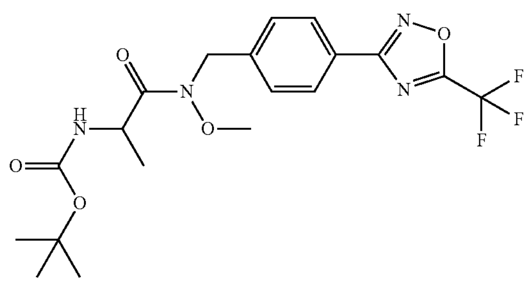 [SMILES: CON(Cc1ccc(-c2noc(C(F)(F)F)n2)cc1)C(=O)C(C)NC(=O)OC(C)(C)C] | | | | 108.8-111.9 |
| 1.792 | [2-[methoxy-[[4-[5-(trifluoromethyl)-1,2,4-oxadiazol-3-yl]phenyl]methyl]-amino]-1-methyl-2-oxo-ethyl]ammonium; chloride | 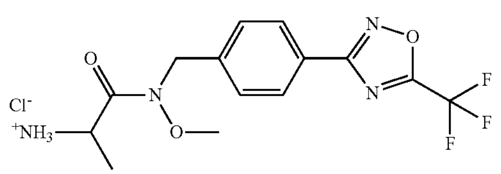 [SMILES: [Cl-] ; CON(Cc1ccc(-c2noc(C(F)(F)F)n2)cc1)C(=O)C(C)[NH3+]] | | | | 200.7-203.2 |
| 1.793 | N-[2-[methoxy-[[4-[5-(trifluoromethyl)-1,2,4-oxadiazol-3-yl]phenyl]methyl]-amino]-2-oxo-ethyl]propanamide | 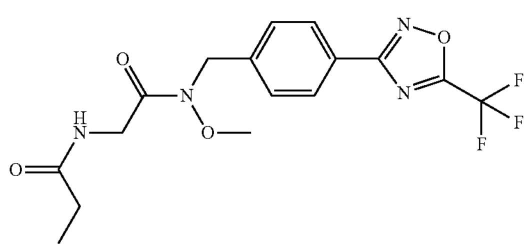 [SMILES: CCC(=O)NCC(=O)N(Cc1ccc(-c2noc(C(F)(F)F)n2)cc1)OC] | | | | 115.3-117.8 |
| 1.794 | 2-acetamido-N-methoxy-N-[[4-[5-(trifluoromethyl)-1,2,4-oxadiazol-3-yl]phenyl]methyl]-acetamide | 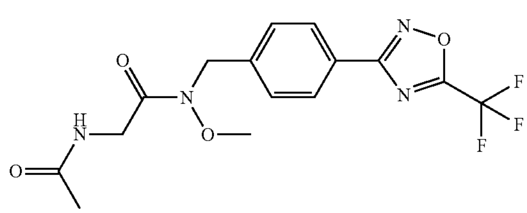 [SMILES: CON(Cc1ccc(-c2noc(C(F)(F)F)n2)cc1)C(=O)CNC(C)=O] | | | | 132.8-134.9 |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.795 | 2-acetamido-N-methoxy-N-[[4-[5-(trifluoromethyl)-1,2,4-oxadiazol-3-yl]phenyl]methyl]-propanamide | 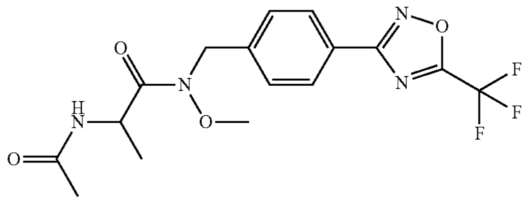 [SMILES: CON(Cc1ccc(-c2noc(C(F)(F)F)n2)cc1)C(=O)C(C)NC(C)=O] | 0.93 | 387.3 | A | |
| 1.796 | N-methoxy-2-methyl-N-[[6-[5-(trifluoromethyl)-1,2,4-oxadiazol-3-yl]-3-pyridyl]methyl]-propanamide | 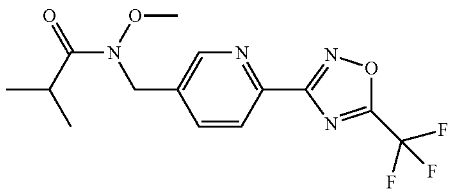 [SMILES: CON(Cc1ccc(-c2noc(C(F)(F)F)n2)nc1)C(=O)C(C)C] | 0.98 | 345 | A | |
| 1.797 | N-methoxy-2-(propanoylamino)-N-[[4-[5-(trifluoromethyl)-1,2,4-oxadiazol-3-yl]phenyl]methyl]-propanamide | 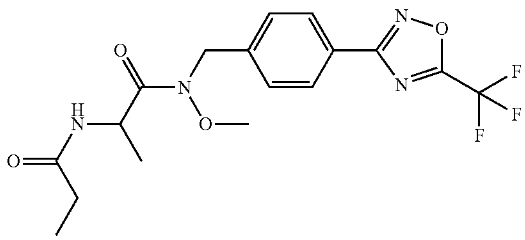 [SMILES: CCC(=O)NC(C)C(=O)N(Cc1ccc(-c2noc(C(F)(F)F)n2)cc1)OC] | | | | 121.7-123.9 |
| 1.798 | N-[2-(methoxy-[[4-[5-(trifluoromethyl)-1,2,4-oxadiazol-3-yl]phenyl]methyl]-amino]-1-methyl-2-oxo-ethyl]-cyclopropane-carboxamide | 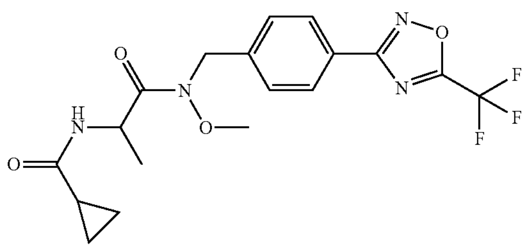 [SMILES: CON(Cc1ccc(-c2noc(C(F)(F)F)n2)cc1)C(=O)C(C)NC(=O)C1CC1] | | | | 129.7-134 |
| 1.799 | tert-butyl 2-[methoxy-[[4-[5-(trifluoromethyl)-1,2,4-oxadiazol-3-yl]phenyl]methyl]-carbamoyl]-pyrrolidine-1-carboxylate | 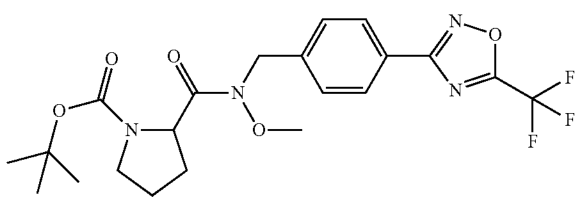 [SMILES: CON(Cc1ccc(-c2noc(C(F)(F)F)n2)cc1)C(=O)C1CCCN1C(=O)OC(C)(C)C] | 1.17 | 471 | A | |
| 1.800 | N-methoxy-N-[[4-[5-(trifluoromethyl)-1,2,4-oxadiazol-3-yl]phenyl]methyl]-pyrrolidin-1-ium-2-carboxamide; chloride | 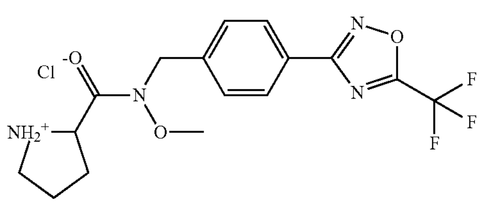 | | | | 185.5-188.5 |
| 1.801 | 2-acetamido-N-methoxy-3-methyl-N-[[4-[5-(trifluoromethyl)-1,2,4-oxadiazol-3-yl]phenyl]methyl]-butanamide | 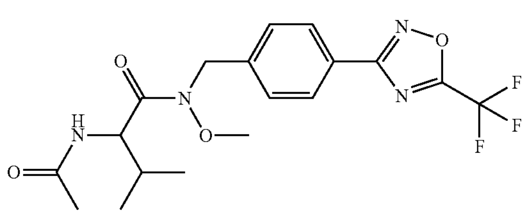 [SMILES: CON(Cc1ccc(-c2noc(C(F)(F)F)n2)cc1)C(=O)C(NC(C)=O)C(C)C] | 1.02 | 415 | A | |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.802 | N-methoxy-3-methyl-2-(propanoylamino)-N-[[4-[5-(trifluoromethyl)-1,2,4-oxadiazol-3-yl]phenyl]methyl]-butanamide | 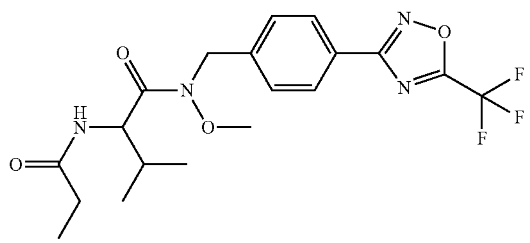 [SMILES: CCC(=O)NC(C(=O)N(Cc1ccc(-c2noc(C(F)(F)F)n2)cc1)OC)C(C)C] | | | | 98.5-100.6 |
| 1.803 | N-methoxy-1-propanoyl-N-[[4-[5-(trifluoromethyl)-1,2,4-oxadiazol-3-yl]phenyl]methyl]-pyrrolidine-2-carboxamide | 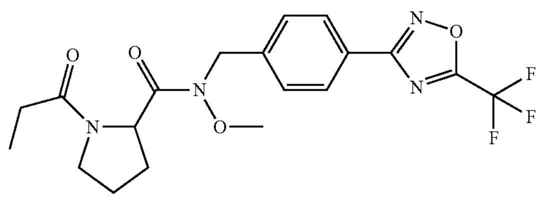 [SMILES: CCC(=O)N1CCCC1C(=O)N(Cc1ccc(-c2noc(C(F)(F)F)n2)cc1)OC] | | | | 148.2-150.6 |
| 1.804 | 1-(cyclopropanecarbonyl)-N-methoxy-N-[[4-[5-(trifluoromethyl)-1,2,4-oxadiazol-3-yl]phenyl]methyl]-pyrrolidine-2-carboxamide | 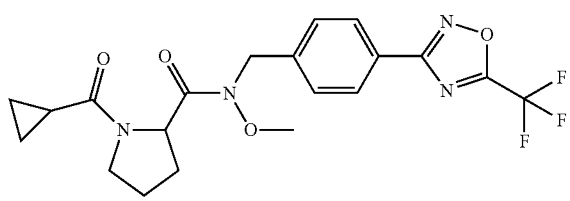 [SMILES: CON(Cc1ccc(-c2noc(C(F)(F)F)n2)cc1)C(=O)C1CCCN1C(=O)C1CC1] | 1.04 | 439 | A | |
| 1.805 | 1-acetyl-N-methoxy-N-[[4-[5-(trifluoromethyl)-1,2,4-oxadiazol-3-yl]phenyl]methyl]-pyrrolidine-2-carboxamide | 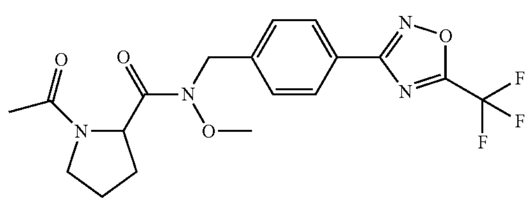 [SMILES: CON(Cc1ccc(-c2noc(C(F)(F)F)n2)cc1)C(=O)C1CCCN1C(C)=O] | | | | 93.9-96.8 |
| 1.806 | 2-bromo-N-methoxy-N-[[4-[5-(trifluoromethyl)-1,2,4-oxadiazol-3-yl]phenyl]methyl]-acetamide | 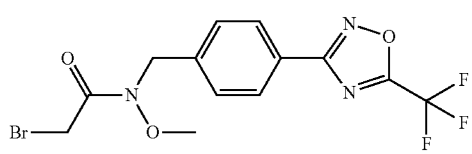 [SMILES: CON(Cc1ccc(-c2noc(C(F)(F)F)n2)cc1)C(=O)CBr] | | | | 81.2-84.9 |
| 1.807 | ethyl 1-[2-[methoxy-[[4-[5-(trifluoromethyl)-1,2,4-oxadiazol-3-yl]phenyl]methyl]-amino]-2-oxo-ethyl]pyrazole-4-carboxylate | 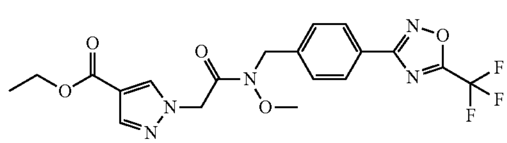 [SMILES: CCOC(=O)c1cnn(CC(=O)N(Cc2ccc(-c3noc(C(F)(F)F)n3)cc2)OC)c1] | | | | 79.1-80.4 |
| 1.808 | N-methoxy-2-(1,2,4-triazol-1-yl)-N-[[4-[5-(trifluoromethyl)-1,2,4-oxadiazol-3-yl]phenyl]methyl]-acetamide | 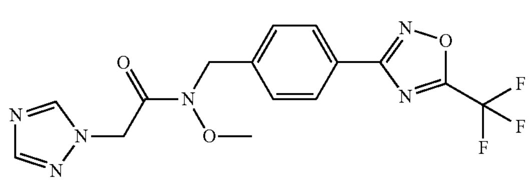 [SMILES: CON(Cc1ccc(-c2noc(C(F)(F)F)n2)cc1)C(=O)Cn1cncn1] | | | | 125.1-127.2 |

TABLE T1-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 1.809 | N-isopropyl-N-[2-[4-[5-(trifluoromethyl)-1,2,4-oxadiazol-3-yl]phenyl]ethyl]-cyclopropane-carboxamide | 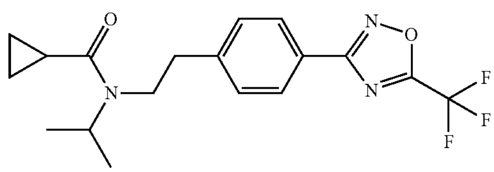 [SMILES: CC(C)N(CCc1ccc(-c2noc(C(F)(F)F)n2)cc1)C(=O)C1CC1] | 1.17 | 368.5 | A | |
| 1.810 | N-cyclopropyl-N-[[4-[5-(trifluoromethyl)-1,2,4-oxadiazol-3-yl]phenyl]methyl]-imidazole-1-carboxamide | 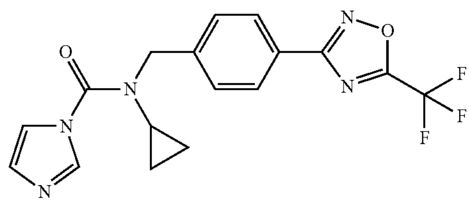 [SMILES: O=C(N(Cc1ccc(-c2noc(C(F)(F)F)n2)cc1)C1CC1)n1ccnc1] | 0.95 | 378.5 | A | |
| 1.811 | N-methoxy-N-[[4-[5-(trifluoromethyl)-1,2,4-oxadiazol-3-yl]phenyl]methyl]-imidazole-1-carboxamide | 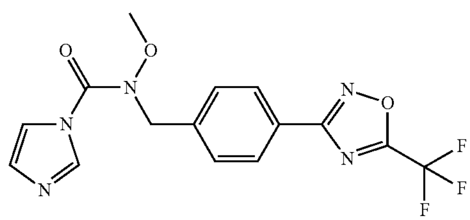 [SMILES: CON(Cc1ccc(-c2noc(C(F)(F)F)n2)cc1)C(=O)n1ccnc1] | 0.97 | 368.4 | A | |

TABLE T2

Melting point (mp) data and/or retention times (RT) for compounds according to Formula (I):

| Entry | Name | Structure | RT (min) | [M + H] | Method | MP (° C.) |
|---|---|---|---|---|---|---|
| 2.1 | ethyl N-methoxy-N-[[4-[5-(trifluoromethyl)-1,2,4-oxadiazol-3-yl]phenyl]methyl]-carbamate | 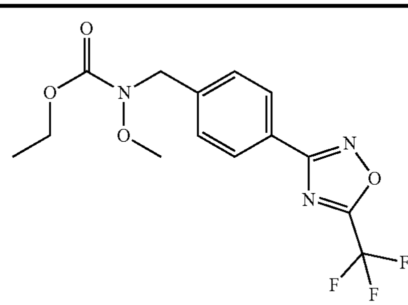 | 1.76 | 346.2 | B | |
| 2.2 | 2-methoxyethyl N-methoxy-N-[[4-[5-(trifluoromethyl)-1,2,4-oxadiazol-3-yl]phenyl]methyl]-carbamate | 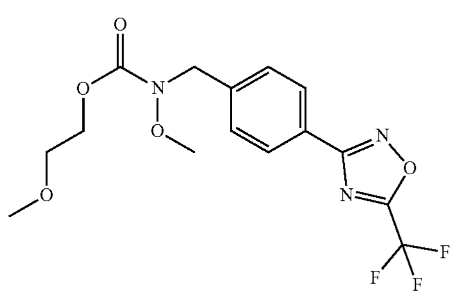 [SMILES: COCCOC(=O)N(Cc1ccc(-c2noc(C(F)(F)F)n2)cc1)OC] | 1.65 | 376.2 | B | |

TABLE T2-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 2.3 | methyl N-methoxy-N-[[4-[5-(trifluoromethyl)-1,2,4-oxadiazol-3-yl]phenyl]methyl]-caramate | 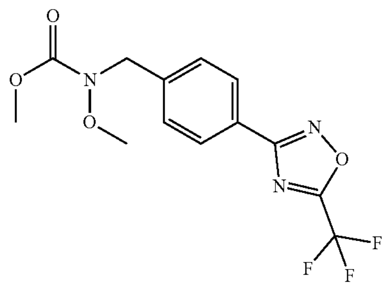 [SMILES: COC(=O)N(Cc1ccc(-c2noc(C(F)(F)F)n2)cc1)OC] | 1.07 | 332 | A | |
| 2.4 | propyl N-methoxy-N-[[4-[5-(trifluoromethyl)-1,2,4-oxadiazol-3-yl]phenyl]methyl]-carbamate | 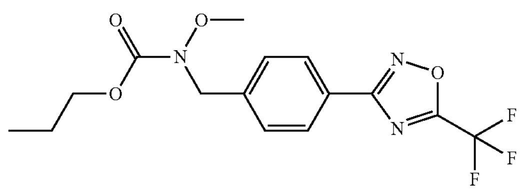 [SMILES: CCCOC(=O)N(Cc1ccc(-c2noc(C(F)(F)F)n2)cc1)OC] | 1.88 | 360.2 | B | |
| 2.5 | methyl N-ethoxy-N-[[4-[5-(trifluoromethyl)-1,2,4-oxadiazol-3-yl]phenyl]methyl]-carbamate | 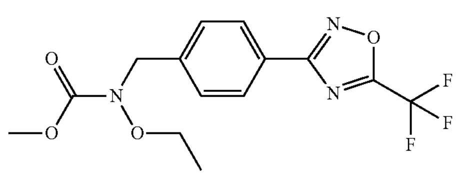 [SMILES: CCON(Cc1ccc(-c2noc(C(F)(F)F)n2)cc1)C(=O)OC] | | | | 50.6-53 |
| 2.6 | phenyl N-methoxy-N-[[4-[5-(trifluoromethyl)-1,2,4-oxadiazol-3-yl]phenyl]methyl]-carbamate | 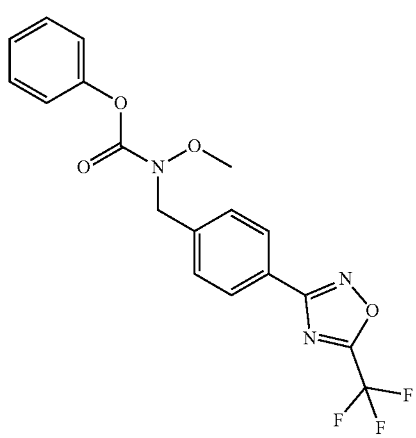 [SMILES: CON(Cc1ccc(-c2noc(C(F)(F)F)n2)cc1)C(=O)Oc1ccccc1] | 1.91 | 394.2 | B | |

TABLE T2-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 2.7 | but-2-ynyl N-methoxy-N-[[4-[5-(trifluoromethyl)-1,2,4-oxadiazol-3-yl]phenyl]methyl]-carbamate | 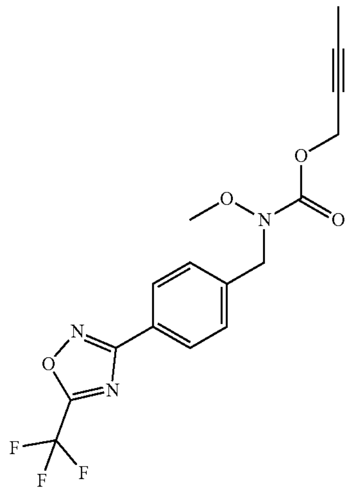 [SMILES: CC#CCOC(=O)N(Cc1ccc(-c2noc(C(F)(F)F)n2)cc1)OC] | 1.80 | 370.2 | B | |
| 2.8 | isobutyl N-methoxy-N-[[4-[5-(trifluoromethyl)-1,2,4-oxadiazol-3-yl]phenyl]methyl]-carbamate | 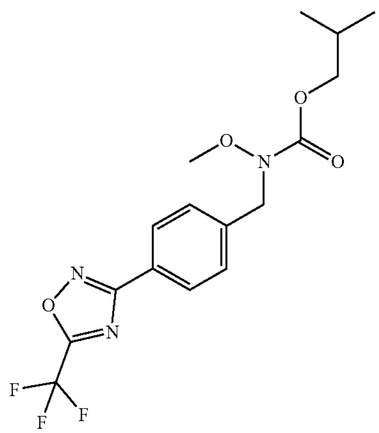 [SMILES: CON(Cc1ccc(-c2noc(C(F)(F)F)n2)cc1)C(=O)OCC(C)C] | 1.98 | 374.2 | B | |
| 2.9 | pentyl N-methoxy-N-[[4-[5-(trifluoromethyl)-1,2,4-oxadiazol-3-yl]phenyl]methyl]-carbamate | 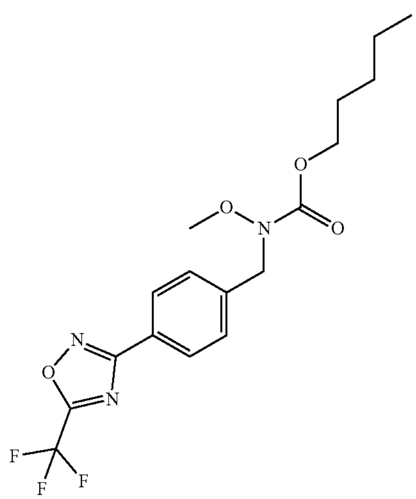 [SMILES: CCCCCOC(=O)N(Cc1ccc(-c2noc(C(F)(F)F)n2)cc1)OC] | 2.09 | 388.2 | B | |

TABLE T2-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 2.10 | benzyl N-methoxy-N-[[4-[5-(trifluoromethyl)-1,2,4-oxadiazol-3-yl]phenyl]methyl]-carbamate | 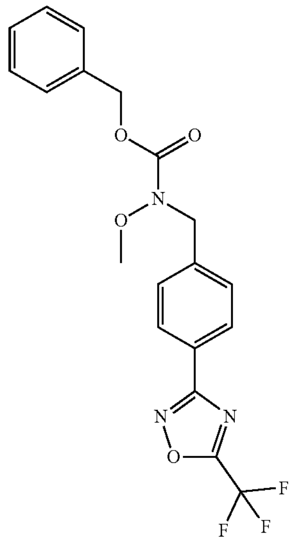 [SMILES: CON(Cc1ccc(-c2noc(C(F)(F)F)n2)cc1)C(=O)OCc1ccccc1] | 1.96 | 408.2 | B | |
| 2.11 | allyl N-methoxy-N-[[4-[5-(trifluoromethyl)-1,2,4-oxadiazol-3-yl]phenyl]methyl]-carbamate | 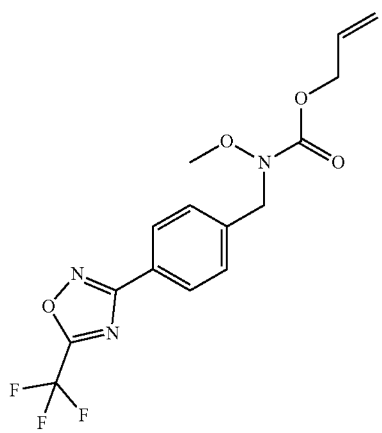 [SMILES: C=CCOC(=O)N(Cc1ccc(-c2noc(C(F)(F)F)n2)cc1)OC] | 1.81 | 358.2 | B | |
| 2.12 | butyl N-methoxy-N-[[4-[5-(trifluoromethyl)-1,2,4-oxadiazol-3-yl]phenyl]methyl]-carbamate | 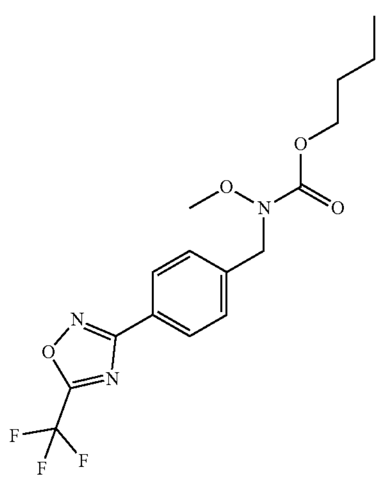 [SMILES: CCCCOC(=O)N(Cc1ccc(-c2noc(C(F)(F)F)n2)cc1)OC] | 1.98 | 374.2 | B | |

TABLE T2-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 2.13 | 4-chlorobutyl N-methoxy-N-[[4-[5-(trifluoromethyl)-1,2,4-oxadiazol-3-yl]phenyl]methyl]-carbamate | 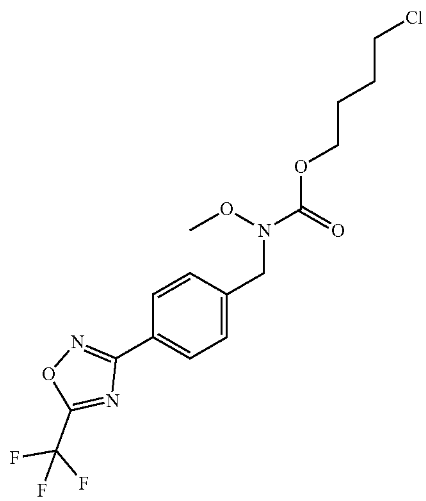 [SMILES: CON(Cc1ccc(-c2noc(C(F)(F)F)n2)cc1)C(=O)OCCCCCl] | 1.92 | 408.2 | B | |
| 2.14 | isopropyl N-methoxy-N-[[4-[5-(trifluoromethyl)-1,2,4-oxadiazol-3-yl]phenyl]methyl]-carbamate | 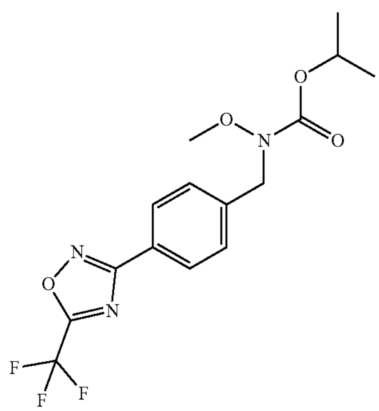 [SMILES: CON(Cc1ccc(-c2noc(C(F)(F)F)n2)cc1)C(=O)OC(C)C] | 1.86 | 360.2 | B | |
| 2.15 | 2-fluoroethyl N-methoxy-N-[[4-[5-(trifluoromethyl)-1,2,4-oxadiazol-3-yl]phenyl]methyl]-carbamate | 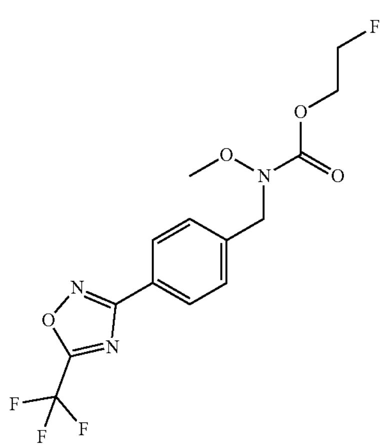 [SMILES: CON(Cc1ccc(-c2noc(C(F)(F)F)n2)cc1)C(=O)OCCF] | 1.66 | 364.2 | B | |

TABLE T2-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 2.16 | 3-chloropropyl N-methoxy-N-[[4-[5-(trifluoromethyl)-1,2,4-oxadiazol-3-yl]phenyl]methyl]-carbamate | 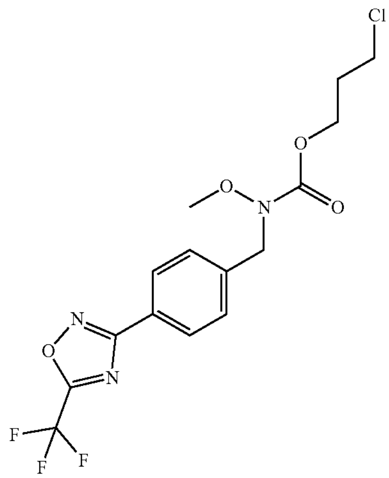 [SMILES: CON(Cc1ccc(-c2noc(C(F)(F)F)n2)cc1)C(=O)OCCCCl] | 1.84 | 394.2 | B | |
| 2.17 | 2-chloroethyl N-methoxy-N-[[4-[5-(trifluoromethyl)-1,2,4-oxadiazol-3-yl]phenyl]methyl]-carbamate | 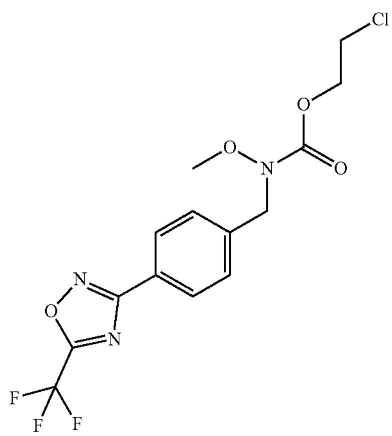 [SMILES: CON(Cc1ccc(-c2noc(C(F)(F)F)n2)cc1)C(=O)OCCCl] | 1.78 | 380.1 | B | |
| 2.18 | 2,2-dimethylpropyl N-methoxy-N-[[4-[5-(trifluoromethyl)-1,2,4-oxadiazol-3-yl]phenyl]methyl]-carbamate | 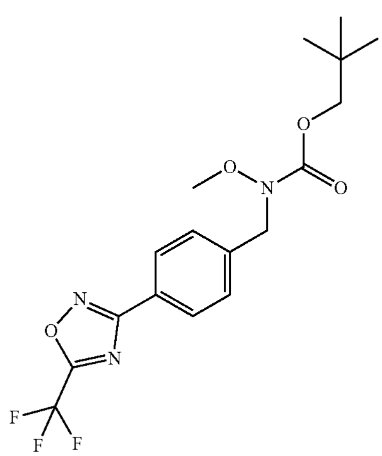 [SMILES: CON(Cc1ccc(-c2noc(C(F)(F)F)n2)cc1)C(=O)OCC(C)(C)C] | 2.07 | 388.2 | B | |

TABLE T2-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 2.19 | (1-chloro-2-methyl-propyl) N-methoxy-N-[[4-[5-(trifluoromethyl)-1,2,4-oxadiazol-3-yl]phenyl]methyl]-carbamate | 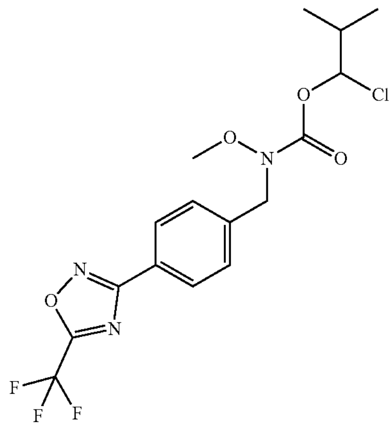 [SMILES: CON(Cc1ccc(-c2noc(C(F)(F)F)n2)cc1)C(=O)OC(Cl)C(C)C] | 2.06 | 408.2 | B | |
| 2.20 | prop-2-ynyl N-methoxy-N-[[4-[5-(trifluoromethyl)-1,2,4-oxadiazol-3-yl]phenyl]methyl]-carbamate | 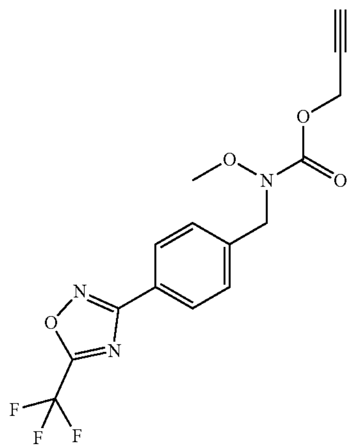 [SMILES: C#CCOC(=O)N(Cc1ccc(-c2noc(C(F)(F)F)n2)cc1)OC] | 1.70 | 356.2 | B | |
| 2.21 | [tert-butoxycarbonyl-[[4-[5-(trifluoromethyl)-1,2,4-oxadiazol-3-yl]phenyl]methyl]-amino]tert-butyl carbonate | 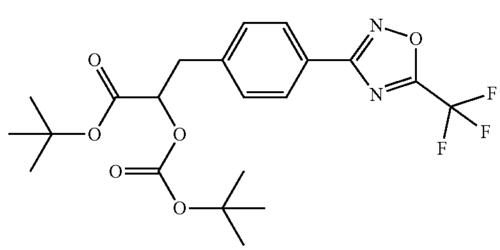 [SMILES: CC(C)(C)OC(=O)OC(Cc1ccc(-c2noc(C(F)(F)F)n2)cc1)C(=O)OC(C)(C)C] | 1.31 | 476 | A | |
| 2.22 | methyl N-(2,2,2-trifluoroethyl)-N-[[4-[5-(trifluoromethyl)-1,2,4-oxadiazol-3-yl]phenyl]methyl]-carbamate | 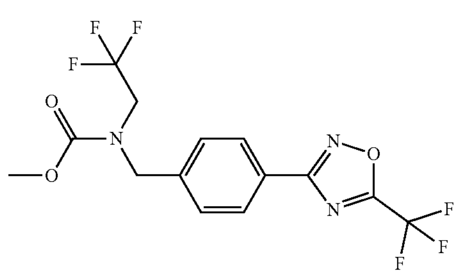 [SMILES: COC(=O)N(Cc1ccc(-c2noc(C(F)(F)F)n2)cc1)CC(F)(F)F] | 1.15 | 400 | A | |

TABLE T2-continued

Melting point (mp) data and/or retention times (RT) for compounds according to Formula (I):

| Entry | Name | Structure | RT (min) | [M + H] | Method | MP (° C.) |
|---|---|---|---|---|---|---|
| 2.23 | methyl N-allyl-N-[cyano-[4-[5-(trifluoromethyl)-1,2,4-oxadiazol-3-yl]phenyl]methyl]-carbamate | 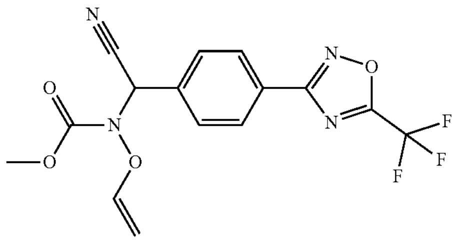 [SMILES: C=CON(C(=O)OC)C(C#N)c1ccc(-c2noc(C(F)(F)F)n2)cc1] | 1.14 | 367 | A | |
| 2.24 | methyl N-hydroxy-N-[[4-[5-(trifluoromethyl)-1,2,4-oxadiazol-3-yl]phenyl]methyl]-carbamate | 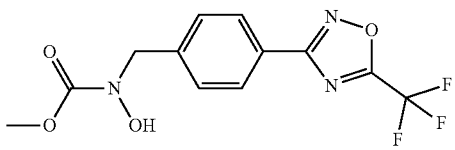 [SMILES: COC(=O)N(O)Cc1ccc(-c2noc(C(F)(F)F)n2)cc1] | | | | 73-75.1 |
| 2.25 | [methoxycarbonyl-[[4-[5-(trifluoromethyl)-1,2,4-oxadiazol-3-yl]phenyl]methyl]-amino]methyl carbonate | 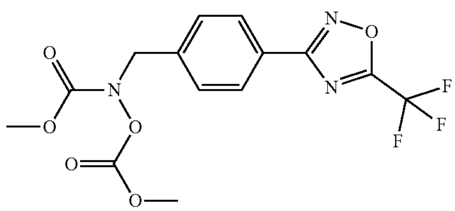 [SMILES: COC(=O)ON(Cc1ccc(-c2noc(C(F)(F)F)n2)cc1)C(=O)OC] | 1.08 | 376 | A | |
| 2.26 | methyl N-isopropyl-N-[2-[4-[5-(trifluoromethyl)-1,2,4-oxadiazol-3-yl]phenyl]ethyl]-carbmate | 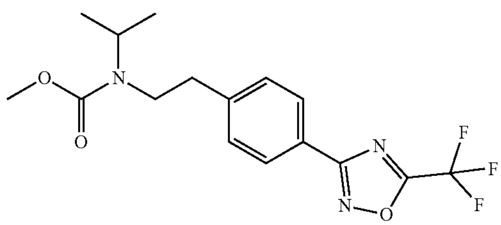 [SMILES: COC(=O)N(CCc1ccc(-c2noc(C(F)(F)F)n2)cc1)C(C)C] | 1.20 | 358 | A | |

TABLE T3

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.1 | N-methoxy-N-[[4-[5-(trifluoromethyl)-1,2,4-oxadiazol-3-yl]phenyl]methyl]-morpholine-4-carboxamide | 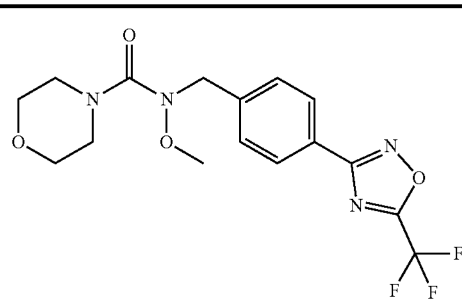 | 1.54 | 387.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.2 | 1-methoxy-3-(2-methoxyethyl)-1-[[4-[5-(trifluoromethyl)-1,2,4-oxadiazol-3-yl]phenyl]methyl]-urea | 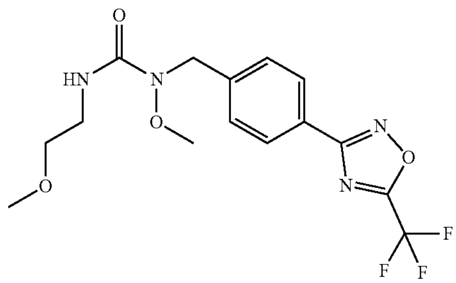 [SMILES: COCCNC(=O)N(Cc1ccc(-c2noc(C(F)(F)F)n2)cc1)OC] | 1.52 | 375.17 | B | |
| 3.3 | 1,3-dimethoxy-1-methyl-3-[[4-[5-(trifluoromethyl)-1,2,4-oxadiazol-3-yl]phenyl]methyl]urea | 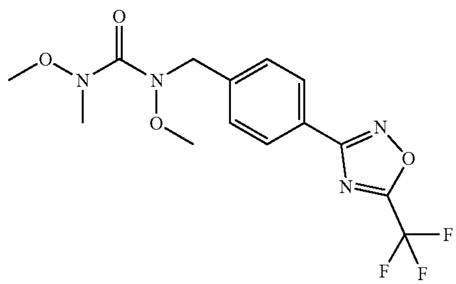 [SMILES: CON(C)C(=O)N(Cc1ccc(-c2noc(C(F)(F)F)n2)cc1)OC] | 1.68 | 361.16 | B | 74-77 |
| 3.4 | 1-methoxy-3-methyl-1-[[4-[5-(trifluoromethyl)-1,2,4-oxadiazol-3-yl]phenyl]methyl]urea | 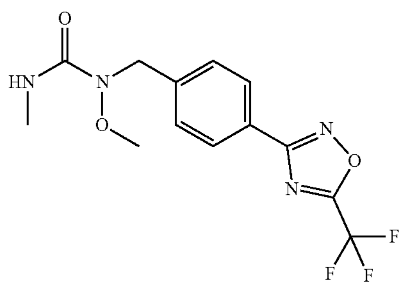 [SMILES: CNC(=O)N(Cc1ccc(-c2noc(C(F)(F)F)n2)cc1)OC] | | | | 75-78 |
| 3.5 | 1-methoxy-3,3-dimethyl-1-[[4-[5-(trifluoromethyl)-1,2,4-oxadiazol-3-yl]phenyl]methyl]urea | 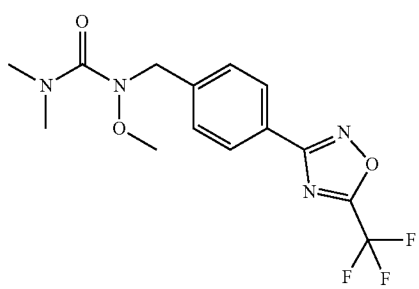 [SMILES: CON(Cc1ccc(-c2noc(C(F)(F)F)n2)cc1)C(=O)N(C)C] | 1.58 | 345.2 | B | |
| 3.6 | 3-(cyclopropylmethyl)-1-methoxy-1-[[4-[5-(trifluoromethyl)-1,2,4-oxadiazol-3-yl]phenyl]methyl]urea | 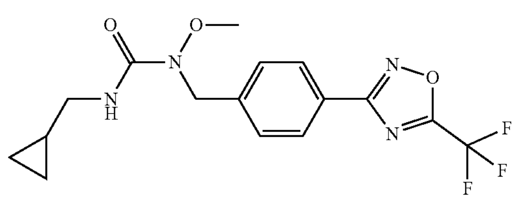 [SMILES: CON(Cc1ccc(-c2noc(C(F)(F)F)n2)cc1)C(=O)NCC1CC1] | | | | 77-81.4 |
| 3.7 | 1-ethoxy-3-methoxy-3-methyl-1-[[4-[5-(trifluoromethyl)-1,2,4-oxadiazol-3-yl]phenyl]methyl]urea | 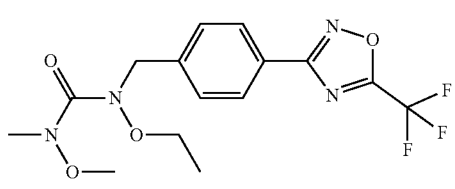 [SMILES: CCON(Cc1ccc(-c2noc(C(F)(F)F)n2)cc1)C(=O)N(C)OC] | 1.12 | 375 | A | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.8 | 1-methoxy-3-phenyl-1-[[4-[5-(trifluoromethyl)-1,2,4-oxadiazol-3-yl]phenyl]methyl]urea | 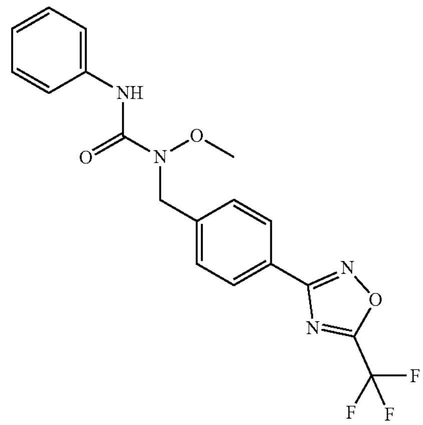 [SMILES: CON(Cc1ccc(-c2noc(C(F)(F)F)n2)cc1)C(=O)Nc1ccccc1] | 1.81 | 393.2 | B | |
| 3.9 | 1-methoxy-3-sec-butyl-1-[[4-[5-(trifluoromethyl)-1,2,4-oxadiazol-3-yl]phenyl]methyl]urea | 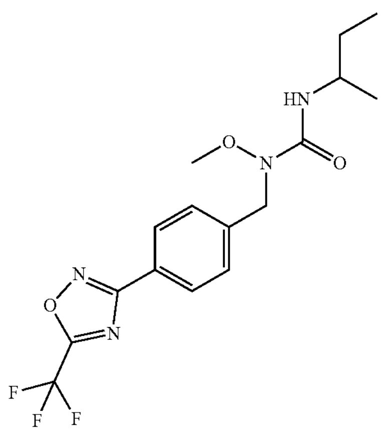 [SMILES: CCC(C)NC(=O)N(Cc1ccc(-c2noc(C(F)(F)F)n2)cc1)OC] | 1.78 | 373.2 | B | |
| 3.10 | 3-(2,2-dimethylpropyl)-1-methoxy-1-[[4-[5-(trifluoromethyl)-1,2,4-oxadiazol-3-yl]phenyl]methyl]urea | 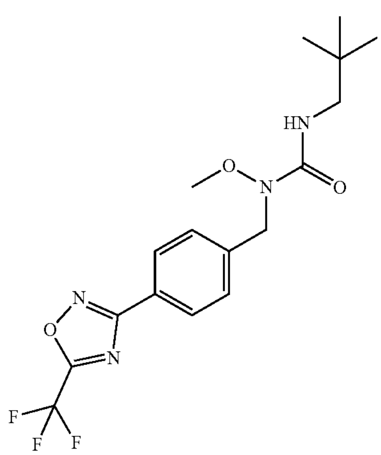 [SMILES: CON(Cc1ccc(-c2noc(C(F)(F)F)n2)cc1)C(=O)NCC(C)(C)C] | 1.88 | 387.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.11 | 3-cyclohexyl-1-methoxy-1-[[4-[5-(trifluoromethyl)-1,2,4-oxadiazol-3-yl]phenyl]methyl]urea | 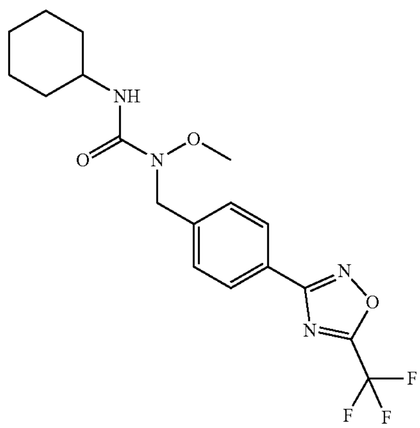 [SMILES: CON(Cc1ccc(-c2noc(C(F)(F)F)n2)cc1)C(=O)NC1CCCCC1] | 1.92 | 399.2 | B | |
| 3.12 | 3-ethyl-1-methoxy-1-[[4-[5-(trifluoromethyl)-1,2,4-oxadiazol-3-yl]phenyl]methyl]urea | 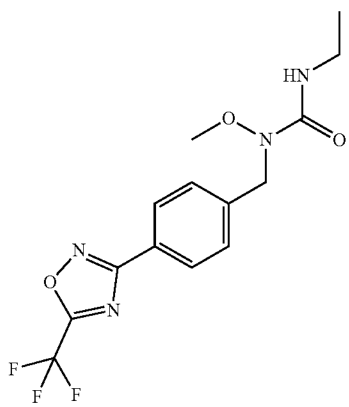 [SMILES: CCNC(=O)N(Cc1ccc(-c2noc(C(F)(F)F)n2)cc1)OC] | 1.56 | 345.2 | B | |
| 3.13 | 3-isobutyl-1-methoxy-1-[[4-[5-(trifluoromethyl)-1,2,4-oxadiazol-3-yl]phenyl]methyl]urea | 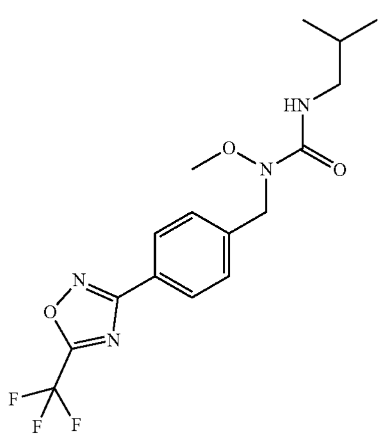 [SMILES: CON(Cc1ccc(-c2noc(C(F)(F)F)n2)cc1)C(=O)NCC(C)C] | 1.78 | 373.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.14 | 3-cyclopropyl-1-methoxy-1-[[4-[5-(trifluoromethyl)-1,2,4-oxadiazol-3-yl]phenyl]methyl]urea | 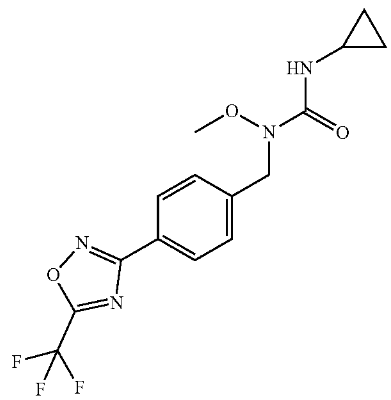 [SMILES: CON(Cc1ccc(-c2noc(C(F)(F)F)n2)cc1)C(=O)NC1CC1] | 1.56 | 357.2 | B | 84-87 |
| 3.15 | 3-benzyl-1-methoxy-1-[[4-[5-(trifluoromethyl)-1,2,4-oxadiazol-3-yl]phenyl]methyl]urea | 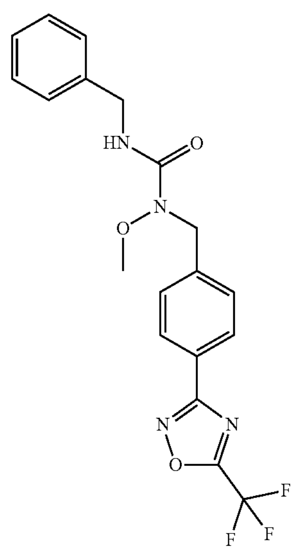 [SMILES: CON(Cc1ccc(-c2noc(C(F)(F)F)n2)cc1)C(=O)NCc1ccccc1] | 1.77 | 407.2 | B | |
| 3.16 | 3-cyclobutyl-1-methoxy-1-[[4-[5-(trifluoromethyl)-1,2,4-oxadiazol-3-yl]phenyl]methyl]urea | 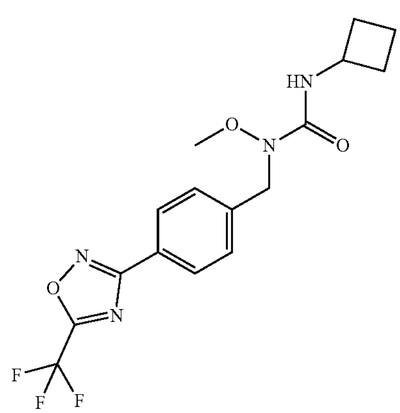 [SMILES: CON(Cc1ccc(-c2noc(C(F)(F)F)n2)cc1)C(=O)NC1CCC1] | 1.72 | 371.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.17 | 1-ethyl-3-methoxy-1-methyl-3-[[4-[5-(trifluoromethyl)-1,2,4-oxadiazol-3-yl]phenyl]methyl]urea | 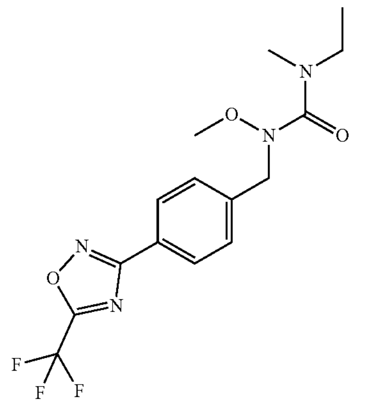 [SMILES: CCN(C)C(=O)N(Cc1ccc(-c2noc(C(F)(F)F)n2)cc1)OC] | 1.70 | 359.2 | B | |
| 3.18 | 3-ethoxy-1-methoxy-1-[[4-[5-(trifluoromethyl)-1,2,4-oxadiazol-3-yl]phenyl]methyl]urea | 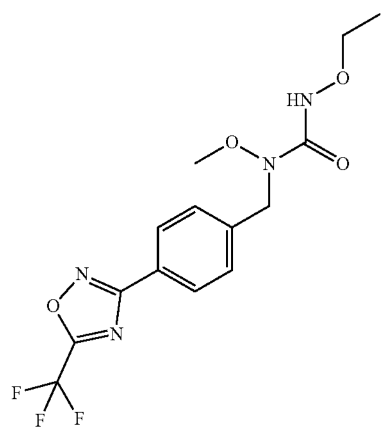 [SMILES: CCONC(=O)N(Cc1ccc(-c2noc(C(F)(F)F)n2)cc1)OC] | 1.50 | 361.2 | B | 107-110 |
| 3.19 | 3-tert-butyl-1-methoxy-1-[[4-[5-(trifluoromethyl)-1,2,4-oxadiazol-3-yl]phenyl]methyl]urea | 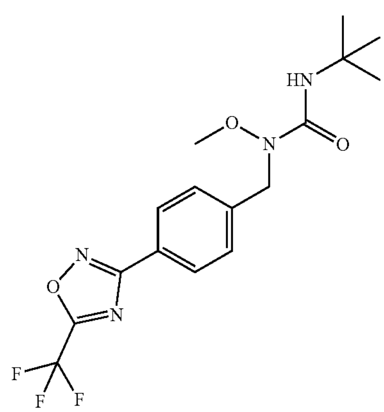 [SMILES: CON(Cc1ccc(-c2noc(C(F)(F)F)n2)cc1)C(=O)NC(C)(C)C] | 1.78 | 373.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.20 | 3-allyl-1-methoxy-1-[[4-[5-(trifluoromethyl)-1,2,4-oxadiazol-3-yl]phenyl]methyl]urea | 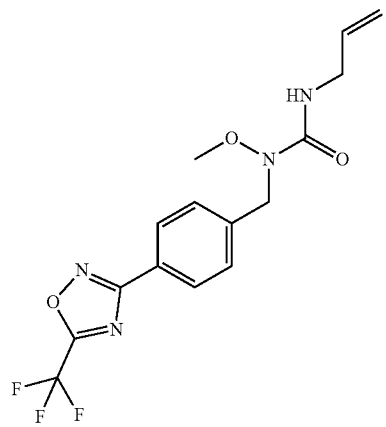 [SMILES: C=CCNC(=O)N(Cc1ccc(-c2noc(C(F)(F)F)n2)cc1)OC] | 1.61 | 357.2 | B | |
| 3.21 | 1-methoxy-3-propyl-1-[[4-[5-(trifluoromethyl)-1,2,4-oxadiazol-3-yl]phenyl]methyl]urea | 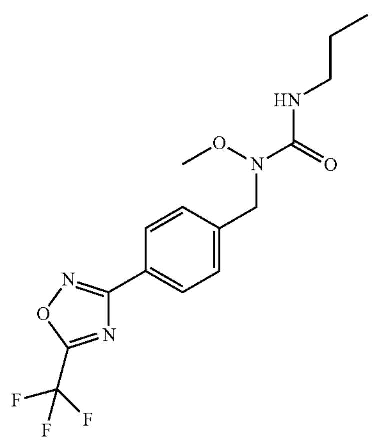 [SMILES: CCCNC(=O)N(Cc1ccc(-c2noc(C(F)(F)F)n2)cc1)OC] | 1.67 | 359.2 | B | |
| 3.22 | 1,3-dimethoxy-1-[[4-[5-(trifluoromethyl)-1,2,4-oxadiazol-3-yl]phenyl]methyl]urea | 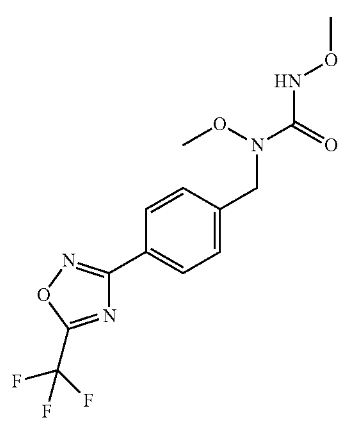 [SMILES: CONC(=O)N(Cc1ccc(-c2noc(C(F)(F)F)n2)cc1)OC] | 1.41 | 347.2 | B | 88-91 |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.23 | 3-cyclopentyl-1-methoxy-1-[[4-[5-(trifluoromethyl)-1,2,4-oxadiazol-3-yl]phenyl]methyl]urea | 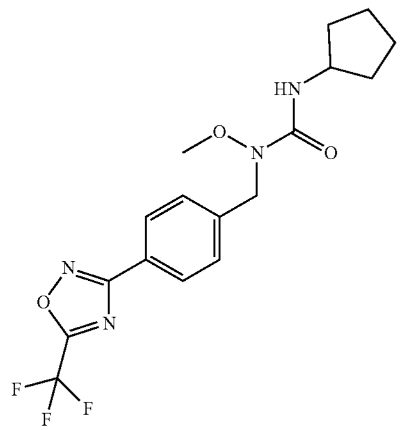 [SMILES: CON(Cc1ccc(-c2noc(C(F)(F)F)n2)cc1)C(=O)NC1CCCC1] | 1.82 | 385.2 | B | |
| 3.24 | 3-(2-furylmethyl)-1-methoxy-1-[[4-[5-(trifluoromethyl)-1,2,4-oxadiazol-3-yl]phenyl]methyl]urea | 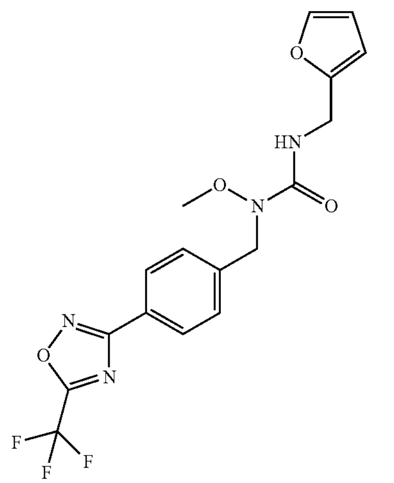 [SMILES: CON(Cc1ccc(-c2noc(C(F)(F)F)n2)cc1)C(=O)NCc1ccco1] | 1.66 | 397.2 | B | |
| 3.25 | 1-methoxy-1-methyl-3-(2,2,2-trifluoroethyl)-3-[[4-[5-(trifluoromethyl)-1,2,4-oxadiazol-3-yl]phenyl]methyl]urea | 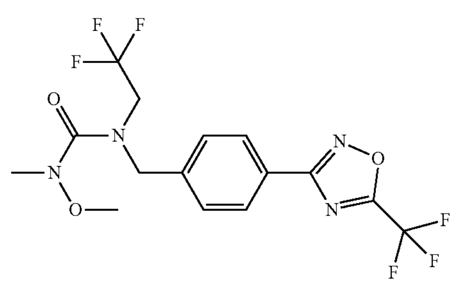 [SMILES: CON(C)C(=O)N(Cc1ccc(-c2noc(C(F)(F)F)n2)cc1)CC(F)(F)F] | 1.16 | 413 | A | |
| 3.26 | 1,1-dimethyl-3-(2,2,2-trifluoroethyl)-3-[[4-[5-(trifluoromethyl)-1,2,4-oxadiazol-3-yl]phenyl]methyl]urea | 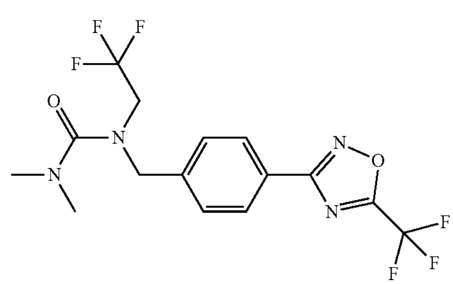 [SMILES: CN(C)C(=O)N(Cc1ccc(-c2noc(C(F)(F)F)n2)cc1)CC(F)(F)F] | 1.12 | 397 | A | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.27 | 1-allyl-1-[cyano-[4-[5-(trifluoromethyl)-1,2,4-oxadiazol-3-yl]phenyl]methyl]-3-methoxy-3-methyl-urea | 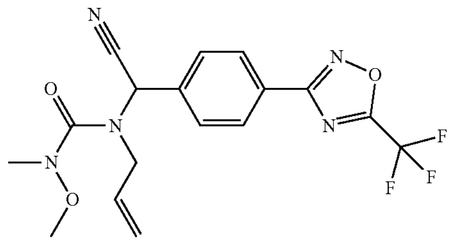 [SMILES: C=CCN(C(=O)N(C)OC)C(C#N)c1ccc(-c2noc(C(F)(F)F)n2)cc1] | 1.12 | 396 | A | |
| 3.28 | 1-ethoxy-3,3-dimethyl-1-[[4-[5-(trifluoromethyl)-1,2,4-oxadiazol-3-yl]phenyl]methyl]urea | 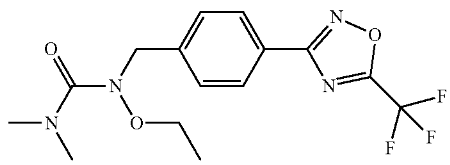 [SMILES: CCON(Cc1ccc(-c2noc(C(F)(F)F)n2)cc1)C(=O)N(C)C] | 1.09 | 359 | A | |
| 3.29 | 1-hydroxy-3-methoxy-3-methyl-1-[[4-[5-(trifluoromethyl)-1,2,4-oxadiazol-3-yl]phenyl]methyl]urea | 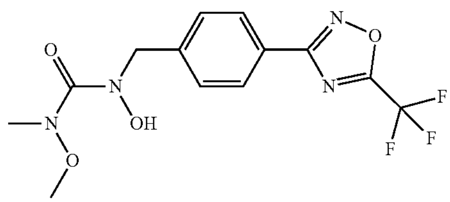 [SMILES: CON(C)C(=O)N(O)Cc1ccc(-c2noc(C(F)(F)F)n2)cc1] | | | | 96.3-100.5 |
| 3.30 | 1-methoxy-1-methyl-3-propyl-3-[[4-[5-(trifluoromethyl)-1,2,4-oxadiazol-3-yl]phenyl]methyl]urea | 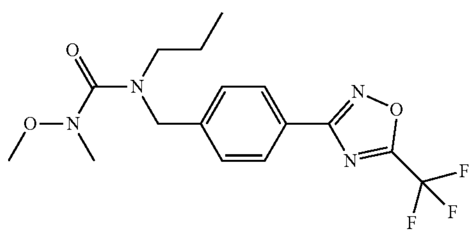 [SMILES: CCCN(Cc1ccc(-c2noc(C(F)(F)F)n2)cc1)C(=O)N(C)OC] | 1.17 | 373.5 | A | |
| 3.31 | 1-[cyano-[4-[5-(trifluoromethyl)-1,2,4-oxadiazol-3-yl]phenyl]methyl]-3-methoxy-1,3-dimethyl-urea | 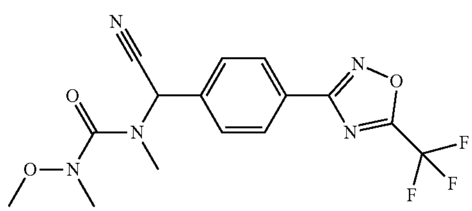 [SMILES: CON(C)C(=O)N(C)C(C#N)c1ccc(-c2noc(C(F)(F)F)n2)cc1] | | | | 106-107 |
| 3.32 | 1-methoxy-1-[[4-[5-(trifluoromethyl)-1,2,4-oxadiazol-3-yl]phenyl]methyl]urea | 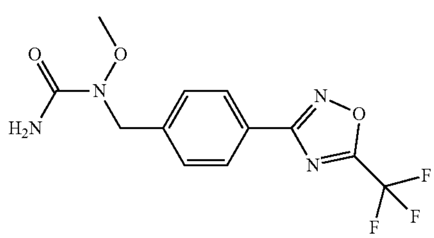 [SMILES: CON(Cc1ccc(-c2noc(C(F)(F)F)n2)cc1)C(N)=O] | | | | 112.2-114.7 |
| 3.33 | 1-cyclopropyl-3-methoxy-3-methyl-1-[[4-[5-(trifluoromethyl)-1,2,4-oxadiazol-3-yl]phenyl]methyl]urea | 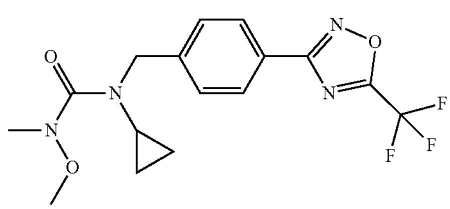 [SMILES: CON(C)C(=O)N(Cc1ccc(-c2noc(C(F)(F)F)n2)cc1)C1CC1] | 1.1 | 371 | A | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.34 | 1-cyclopropyl-3-ethyl-1-[[4-[5-(trifluoromethyl)-1,2,4-oxadiazol-3-yl]phenyl]methyl]urea | 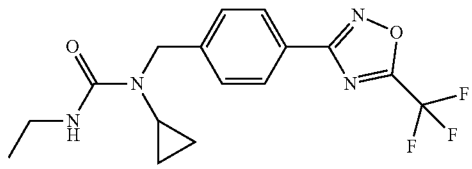 [SMILES: CCNC(=O)N(Cc1ccc(-c2noc(C(F)(F)F)n2)cc1)C1CC1] | 1.05 | 355.4 | A | |
| 3.35 | 1-cyclopropyl-3-methyl-1-[[4-[5-(trifluoromethyl)-1,2,4-oxadiazol-3-yl]phenyl]methyl]urea | 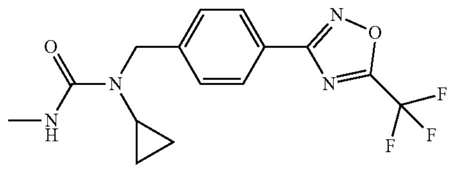 [SMILES: CNC(=O)N(Cc1ccc(-c2noc(C(F)(F)F)n2)cc1)C1CC1] | | | | 113-114 |
| 3.36 | 1,3-dicyclopropyl-1-[[4-[5-(trifluoromethyl)-1,2,4-oxadiazol-3-yl]phenyl]methyl]urea | 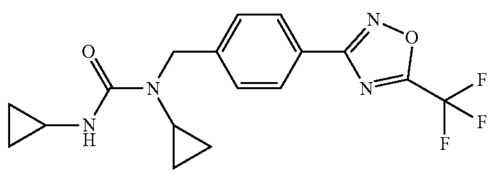 [SMILES: O=C(NC1CC1)N(Cc1ccc(-c2noc(C(F)(F)F)n2)cc1)C1CC1] | 1.07 | 367 | A | |
| 3.37 | 1,3-dimethyl-1-[[4-[5-(trifluoromethyl)-1,2,4-oxadiazol-3-yl]phenyl]methyl]urea | 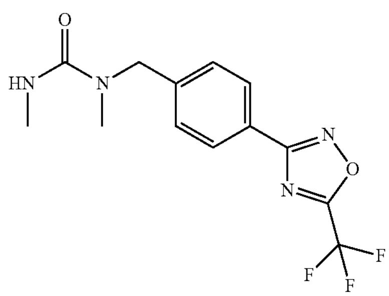 [SMILES: CNC(=O)N(C)Cc1ccc(-c2noc(C(F)(F)F)n2)cc1] | | | | 95-98 |
| 3.38 | 1-methoxy-3-(2,2,2-trifluoroethyl)-1-[[4-[5-(trifluoromethyl)-1,2,4-oxadiazol-3-yl]phenyl]methyl]urea | 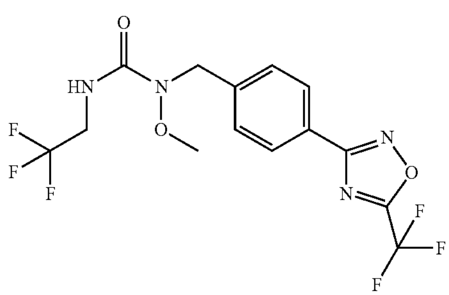 [SMILES: CON(Cc1ccc(-c2noc(C(F)(F)F)n2)cc1)C(=O)NCC(F)(F)F] | | | | 95-98 |
| 3.39 | 3-(cyanomethyl)-1-methoxy-1-[[4-[5-(trifluoromethyl)-1,2,4-oxadiazol-3-yl]phenyl]methyl]urea | 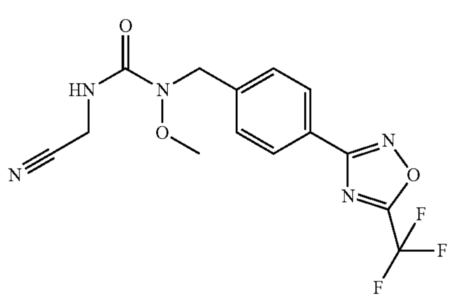 [SMILES: CON(Cc1ccc(-c2noc(C(F)(F)F)n2)cc1)C(=O)NCC#N] | | | | 155-158 |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.40 | 3-[(1-cyanocyclopropyl)-methyl]-1-methoxy-1-[[4-[5-(trifluoromethyl)-1,2,4-oxadiazol-3-yl]phenyl]methyl]urea | 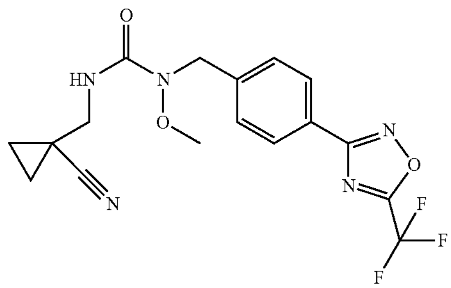 [SMILES: CON(Cc1ccc(-c2noc(C(F)(F)F)n2)cc1)C(=O)NCC1(C#N)CC1] | 1.03 | 396 | A | |
| 3.41 | 3-[(1S)-1-cyclopropylethyl]-1-methoxy-1-[[4-[5-(trifluoromethyl)-1,2,4-oxadiazol-3-yl]phenyl]methyl]urea | 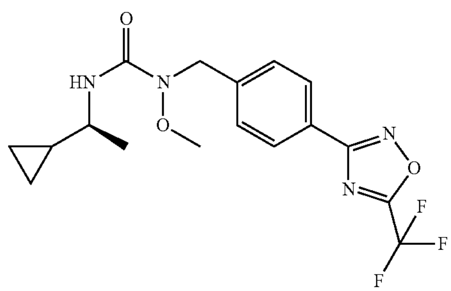 [SMILES: CON(Cc1ccc(-c2noc(C(F)(F)F)n2)cc1)C(=O)N[C@@H](C)C1CC1] | | | | 99-102 |
| 3.42 | 3-isopropyl-1-methoxy-1-[[4-[5-(trifluoromethyl)-1,2,4-oxadiazol-3-yl]phenyl]methyl]urea | 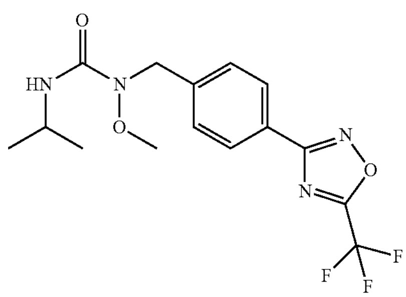 [SMILES: CON(Cc1ccc(-c2noc(C(F)(F)F)n2)cc1)C(=O)NC(C)C] | | | | 106-107.3 |
| 3.43 | 1-methoxy-3-prop-2-ynyl-1-[[4-[5-(trifluoromethyl)-1,2,4-oxadiazol-3-yl]phenyl]methyl]urea | 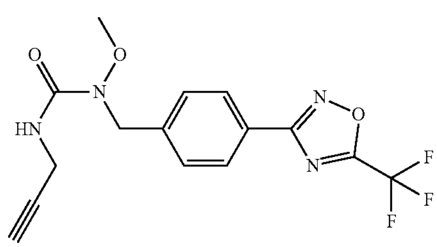 [SMILES: C#CCNC(=O)N(Cc1ccc(-c2noc(C(F)(F)F)n2)cc1)OC] | | | | 88.9-90.6 |
| 3.44 | 1-[[3-fluoro-4-[5-(trifluoromethyl)-1,2,4-oxadiazol-3-yl]phenyl]methyl]-1-methoxy-3-methyl-urea | 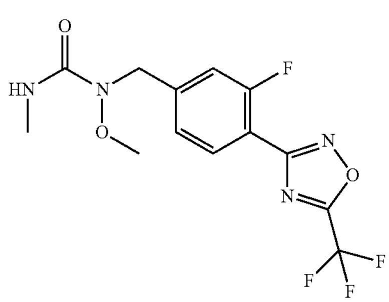 [SMILES: CNC(=O)N(Cc1ccc(-c2noc(C(F)(F)F)n2)c(F)c1)OC] | 0.98 | 349 | A | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.45 | 3-cyclopropyl-1-[[3-fluoro-4-[5-(trifluoromethyl)-1,2,4-oxadiazol-3-yl]phenyl]methyl]-1-methoxy-urea | 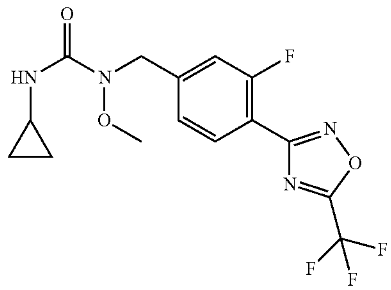 [SMILES: CON(Cc1ccc(-c2noc(C(F)(F)F)n2)c(F)c1)C(=O)NC1CC1] | 1.03 | 375 | A | |
| 3.46 | 1-methoxy-3-(1-methylcyclopropyl)-1-[[4-[5-(trifluoromethyl)-1,2,4-oxadiazol-3-yl]phenyl]methyl]urea | 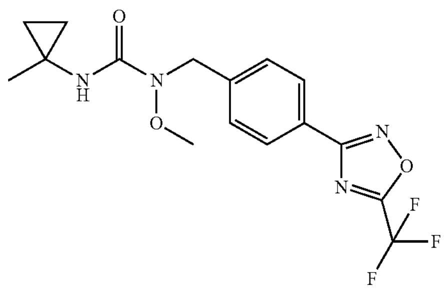 [SMILES: CON(Cc1ccc(-c2noc(C(F)(F)F)n2)cc1)C(=O)NC1(C)CC1] | | | | 93-97 |
| 3.47 | 3-(1-cyanocyclopropyl)-1-methoxy-1-[[4-[5-(trifluoromethyl)-1,2,4-oxadiazol-3-yl]phenyl]methyl]urea | 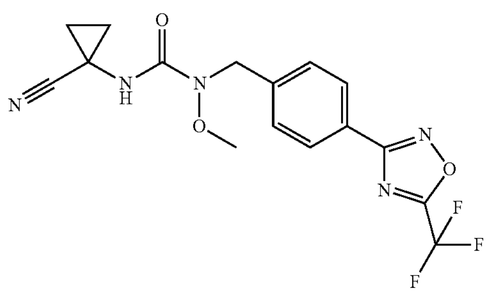 [SMILES: CON(Cc1ccc(-c2noc(C(F)(F)F)n2)cc1)C(=O)NC1(C#N)CC1] | | | | 106-109 |
| 3.48 | ethyl 1-[[methoxy-[[4-[5-(trifluoromethyl)-1,2,4-oxadiazol-3-yl]phenyl]methyl]-carbamoyl]amino]-cyclopropanecarboxylate | 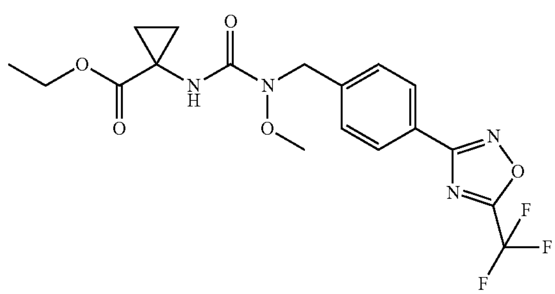 [SMILES: CCOC(=O)C1(NC(=O)N(Cc2ccc(-c3noc(C(F)(F)F)n3)cc2)OC)CC1] | | | | 93-97 |
| 3.49 | ethyl 2-[[methoxy-[[4-[5-(trifluoromethyl)-1,2,4-oxadiazol-3-yl]phenyl]methyl]-carbamoyl]-amino]acetate | 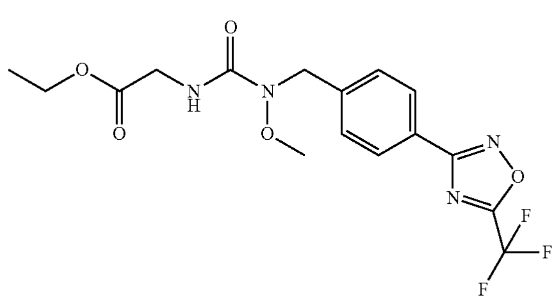 [SMILES: CCOC(=O)CNC(=O)N(Cc1ccc(-c2noc(C(F)(F)F)n2)cc1)OC] | 1.04 | 403 | A | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.50 | 2-[[methoxy-[[4-[5-(trifluoromethyl)-1,2,4-oxadiazol-3-yl]phenyl]methyl]-carbamoyl]amino]-N-methyl-acetamide | 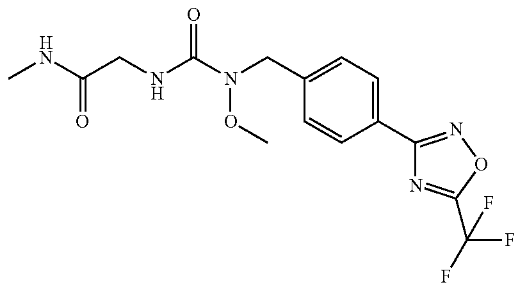 [SMILES: CNC(=O)CNC(=O)N(Cc1ccc(-c2noc(C(F)(F)F)n2)cc1)OC] | | | | 126-130 |
| 3.51 | 2-[[methoxy-[[4-[5-(trifluoromethyl)-1,2,4-oxadiazol-3-yl]phenyl]methyl]-carbamoyl]amino]-N,N-dimethyl-acetamide | 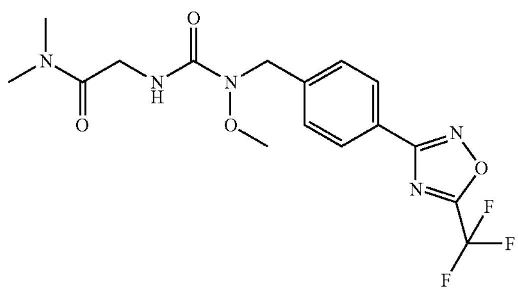 [SMILES: CON(Cc1ccc(-c2noc(C(F)(F)F)n2)cc1)C(=O)NCC(=O)N(C)C] | | | | 98-101 |
| 3.52 | 1-ethyl-3-methyl-1-[[4-[5-(trifluoromethyl)-1,2,4-oxadiazol-3-yl]phenyl]methyl]urea | 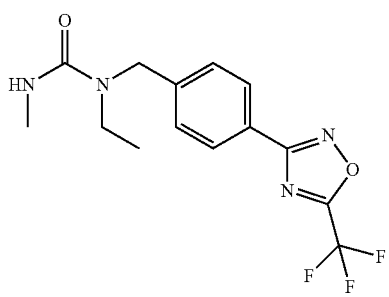 [SMILES: CCN(Cc1ccc(-c2noc(C(F)(F)F)n2)cc1)C(=O)NC] | 0.98 | 329 | A | |
| 3.53 | 3-cyclopropyl-1-ethyl-1-[[4-[5-(trifluoromethyl)-1,2,4-oxadiazol-3-yl]phenyl]methyl]urea | 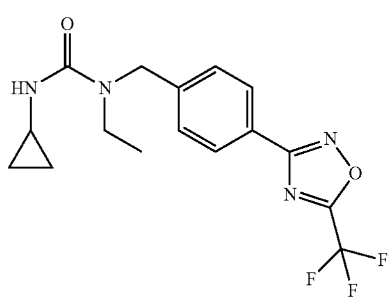 [SMILES: CCN(Cc1ccc(-c2noc(C(F)(F)F)n2)cc1)C(=O)NC1CC1] | 1.02 | 355 | A | |
| 3.54 | 3-[(1-hydroxycyclopropyl)-methyl]-1-methoxy-1-[[4-[5-(trifluoromethyl)-1,2,4-oxadiazol-3-yl]phenyl]methyl]urea | 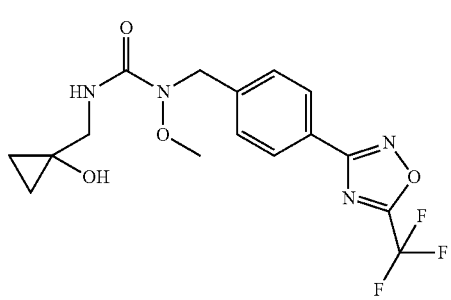 [SMILES: CON(Cc1ccc(-c2noc(C(F)(F)F)n2)cc1)C(=O)NCC1(O)CC1] | | | | 107-110 |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.55 | 1-methoxy-3-(oxetan-3-yl)-1-[[4-[5-(trifluoromethyl)-1,2,4-oxadiazol-3-yl]phenyl]methyl]urea | 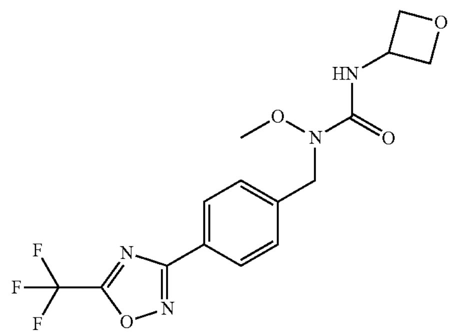 [SMILES: CON(Cc1ccc(-c2noc(C(F)(F)F)n2)cc1)C(=O)NC1COC1] | | | | 97-100 |
| 3.56 | 3-cyclopropyl-1-methyl-1-[[4-[5-(trifluoromethyl)-1,2,4-oxadiazol-3-yl]phenyl]methyl]urea | 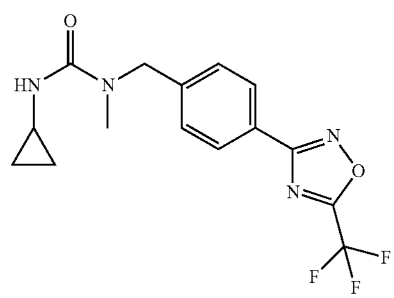 [SMILES: CN(Cc1ccc(-c2noc(C(F)(F)F)n2)cc1)C(=O)NC1CC1] | | | | 113-121 |
| 3.57 | 1-(cyanomethyl)-3-methoxy-1-methyl-3-[[4-[5-(trifluoromethyl)-1,2,4-oxadiazol-3-yl]phenyl]methyl]urea | 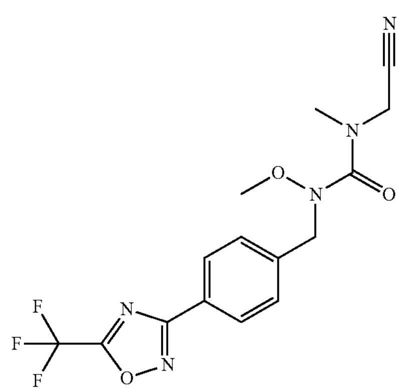 [SMILES: CON(Cc1ccc(-c2noc(C(F)(F)F)n2)cc1)C(=O)N(C)CC#N] | 1.57 | 370.2 | B | |
| 3.58 | 1-cyclopropyl-3-methoxy-1-methyl-3-[[4-[5-(trifluoromethyl)-1,2,4-oxadiazol-3-yl]phenyl]methyl]urea | 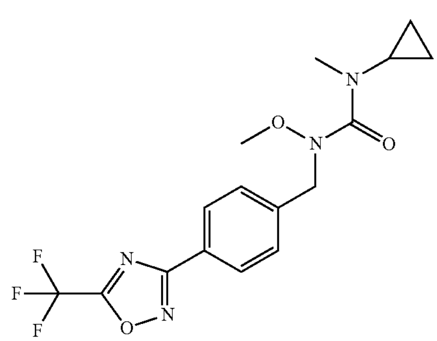 [SMILES: CON(Cc1ccc(-c2noc(C(F)(F)F)n2)cc1)C(=O)N(C)C1CC1] | 1.72 | 371.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.59 | 1-methoxy-3-methyl-3-(oxetan-3-yl)-1-[[4-[5-(trifluoromethyl)-1,2,4-oxadiazol-3-yl]phenyl]methyl]urea | 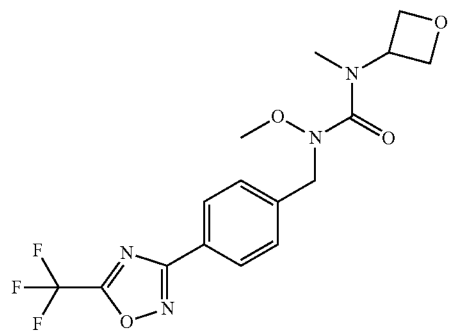 [SMILES: CON(Cc1ccc(-c2noc(C(F)(F)F)n2)cc1)C(=O)N(C)C1COC1] | 1.52 | 387.2 | B | |
| 3.60 | N-methoxy-N-[[4-[5-(trifluoromethyl)-1,2,4-oxadiazol-3-yl]phenyl]methyl]-pyrrolidine-1-carboxamide | 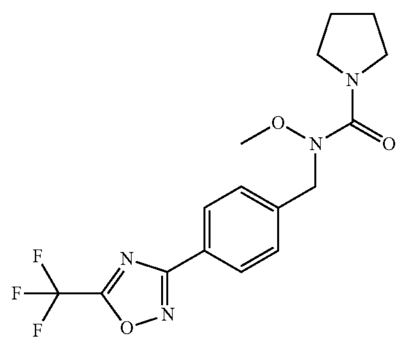 [SMILES: CON(Cc1ccc(-c2noc(C(F)(F)F)n2)cc1)C(=O)N1CCCC1] | 1.72 | 371.2 | B | |
| 3.61 | 1-methoxy-3-methyl-3-prop-2-ynyl-1-[[4-[5-(trifluoromethyl)-1,2,4-oxadiazol-3-yl]phenyl]methyl]urea | 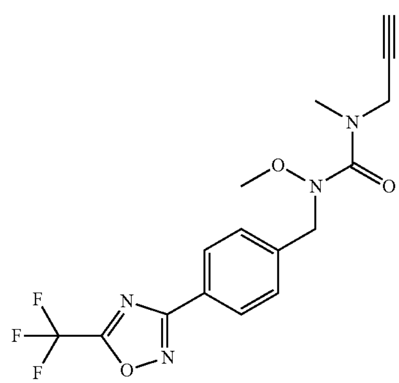 [SMILES: C#CCN(C)C(=O)N(Cc1ccc(-c2noc(C(F)(F)F)n2)cc1)OC] | 1.69 | 369.2 | B | |
| 3.62 | 1-cyano-3-methoxy-1-methyl-3-[[4-[5-(trifluoromethyl)-1,2,4-oxadiazol-3-yl]phenyl]methyl]urea | 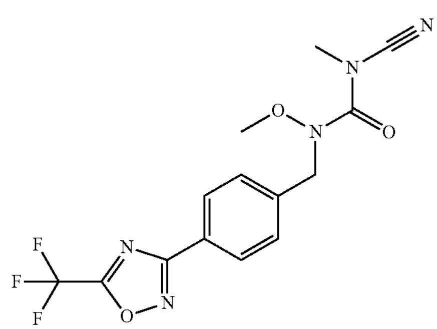 [SMILES: CON(Cc1ccc(-c2noc(C(F)(F)F)n2)cc1)C(=O)N(C)C#N] | 1.61 | 356.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.63 | 1-methoxy-3-(2-methoxyethyl)-3-methyl-1-[[4-[5-(trifluoromethyl)-1,2,4-oxadiazol-3-yl]phenyl]methyl]urea | 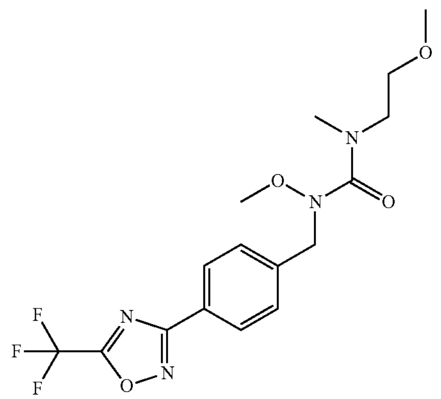 [SMILES: COCCN(C)C(=O)N(Cc1ccc(-c2noc(C(F)(F)F)n2)cc1)OC] | 1.64 | 389.2 | B | |
| 3.64 | 1,1-diethyl-3-methoxy-3-[[4-[5-(trifluoromethyl)-1,2,4-oxadiazol-3-yl]phenyl]methyl]urea | 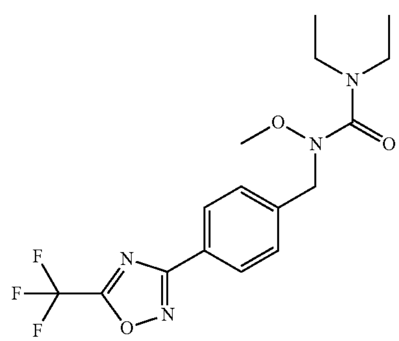 [SMILES: CCN(CC)C(=O)N(Cc1ccc(-c2noc(C(F)(F)F)n2)cc1)OC] | 1.83 | 373.2 | B | |
| 3.65 | 1-cyclobutyl-3-methoxy-1-methyl-3-[[4-[5-(trifluoromethyl)-1,2,4-oxadiazol-3-yl]phenyl]methyl]urea | 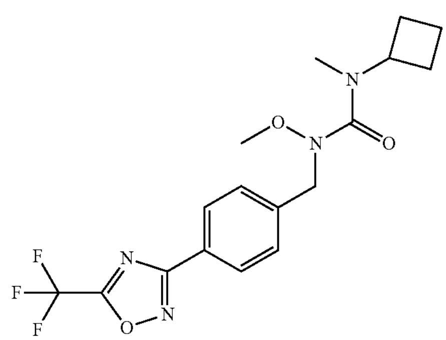 [SMILES: CON(Cc1ccc(-c2noc(C(F)(F)F)n2)cc1)C(=O)N(C)C1CCC1] | 1.87 | 385.2 | B | |
| 3.66 | N-methoxy-N-[[4-[5-(trifluoromethyl)-1,2,4-oxadiazol-3-yl]phenyl]methyl]-isoxazolidine-2-carboxamide | 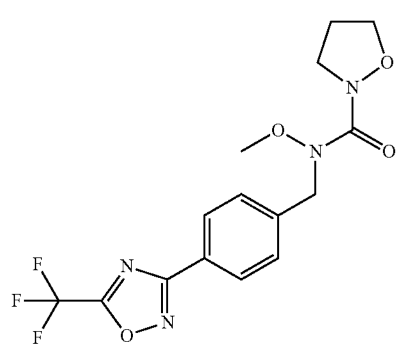 [SMILES: CON(Cc1ccc(-c2noc(C(F)(F)F)n2)cc1)C(=O)N1CCCO1] | 1.61 | 373.1 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.67 | 1-(2-methoxyethyl)-1,3-dimethyl-3-[[4-[5-(trifluoromethyl)-1,2,4-oxadiazol-3-yl]phenyl]methyl]urea | 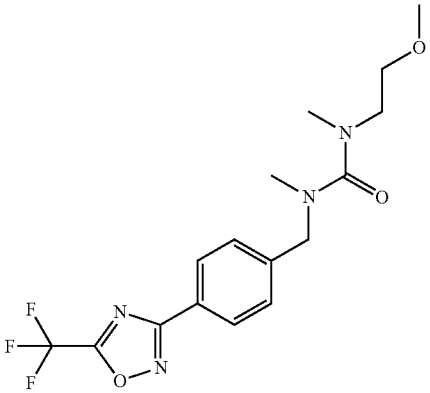 [SMILES: COCCN(C)C(=O)N(C)Cc1ccc(-c2noc(C(F)(F)F)n2)cc1] | 1.61 | 373.2 | B | |
| 3.68 | N-methyl-2-[methyl-[methyl-[[4-[5-(trifluoromethyl)-1,2,4-oxadiazol-3-yl]phenyl]methyl]-carbamoyl]-amino]acetamide | 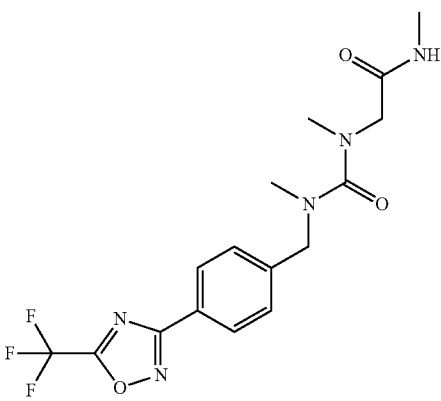 [SMILES: CNC(=O)CN(C)C(=O)N(C)Cc1ccc(-c2noc(C(F)(F)F)n2)cc1] | 1.34 | 386.2 | B | |
| 3.69 | N-methyl-N-[[4-[5-(trifluoromethyl)-1,2,4-oxadiazol-3-yl]phenyl]methyl]-isoxazolidine-2-carboxamide | 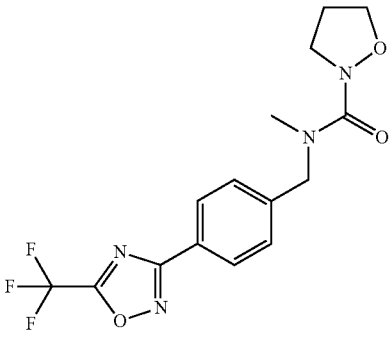 [SMILES: CN(Cc1ccc(-c2noc(C(F)(F)F)n2)cc1)C(=O)N1CCCO1] | 1.63 | 357.2 | B | |
| 3.70 | 1-(cyanomethyl)-1,3-dimethyl-3-[[4-[5-(trifluoromethyl)-1,2,4-oxadiazol-3-yl]phenyl]methyl]urea | 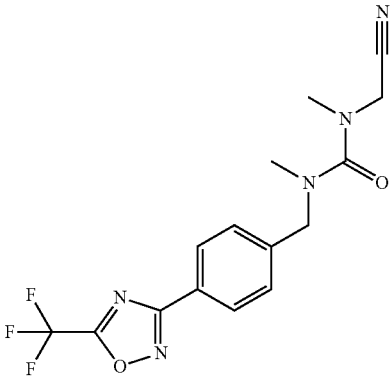 [SMILES: CN(CC#N)C(=O)N(C)Cc1ccc(-c2noc(C(F)(F)F)n2)cc1] | 1.53 | 354.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.71 | 1-cyclopropyl-1-ethyl-3-methyl-3-[[4-[5-(trifluoromethyl)-1,2,4-oxadiazol-3-yl]phenyl]methyl]urea | 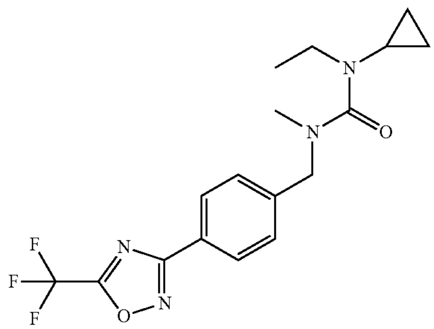 | 1.81 | 369.2 | B | |
| 3.72 | 1-cyclopropyl-1,3-dimethyl-3-[[4-[5-(trifluoromethyl)-1,2,4-oxadiazol-3-yl]phenyl]methyl]urea | 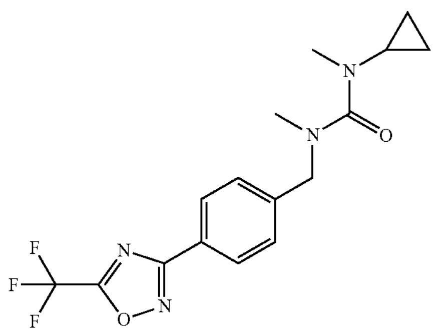 [SMILES: CN(Cc1ccc(-c2noc(C(F)(F)F)n2)cc1)C(=O)N(C)C1CC1] | 1.70 | 355.2 | B | |
| 3.73 | ethyl 2-[methyl-[methyl-[[4-[5-(trifluoromethyl)-1,2,4-oxadiazol-3-yl]phenyl]methyl]-carbamoyl]amino]acetate | 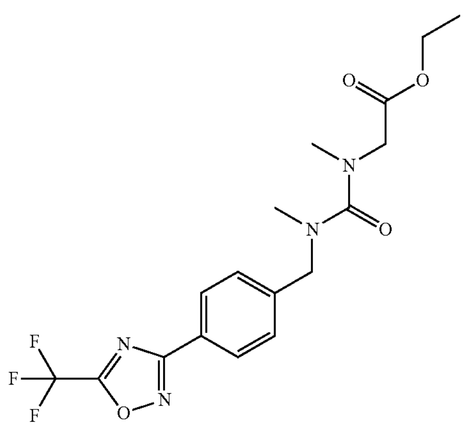 [SMILES: CCOC(=O)CN(C)C(=O)N(C)Cc1ccc(-c2noc(C(F)(F)F)n2)cc1] | 1.68 | 401.2 | B | |
| 3.74 | N-methyl-N-[[4-[5-(trifluoromethyl)-1,2,4-oxadiazol-3-yl]phenyl]methyl]-pyrrolidine-1-carboxamide | 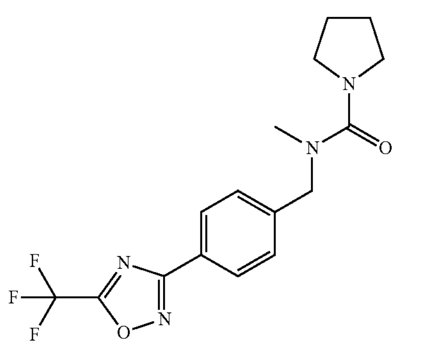 [SMILES: CN(Cc1ccc(-c2noc(C(F)(F)F)n2)cc1)C(=O)N1CCCC1] | 1.70 | 355.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.75 | 1,3-dimethyl-1-propyl-3-[[4-[5-(trifluoromethyl)-1,2,4-oxadiazol-3-yl]phenyl]methyl]urea | 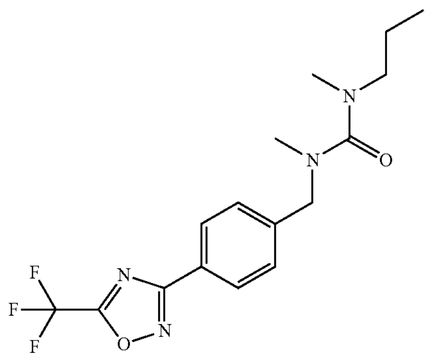 | 1.82 | 357.2 | B | |
| 3.76 | 1-[1-(methoxymethyl)-cyclopropyl]-1,3-dimethyl-3-[[4-[5-(trifluoromethyl)-1,2,4-oxadiazol-3-yl]phenyl]methyl]urea | 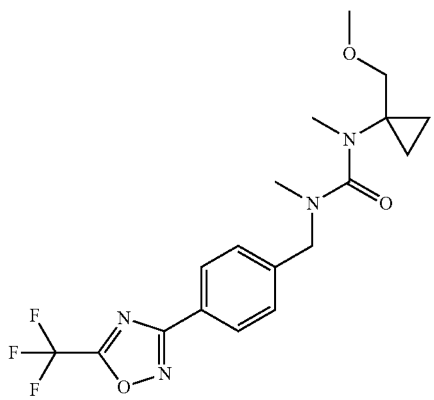 [SMILES: COCC1(N(C)C(=O)N(C)Cc2ccc(-c3noc(C(F)(F)F)n3)cc2)CC1] | 1.76 | 399.2 | B | |
| 3.77 | 1,3-dimethyl-1-prop-2-ynyl-3-[[4-[5-(trifluoromethyl)-1,2,4-oxadiazol-3-yl]phenyl]methyl]urea | 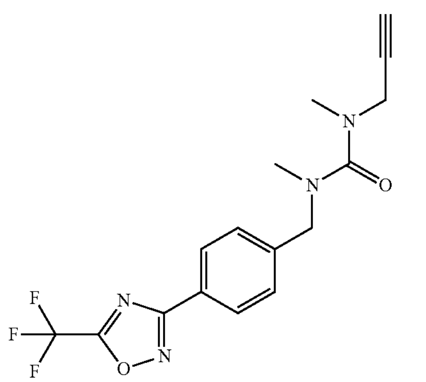 [SMILES: C#CCN(C)C(=O)N(C)Cc1ccc(-c2noc(C(F)(F)F)n2)cc1] | 1.66 | 353.2 | B | |
| 3.78 | 1-allyl-1,3-dimethyl-3-[[4-[5-(trifluoromethyl)-1,2,4-oxadiazol-3-yl]phenyl]methyl]urea | 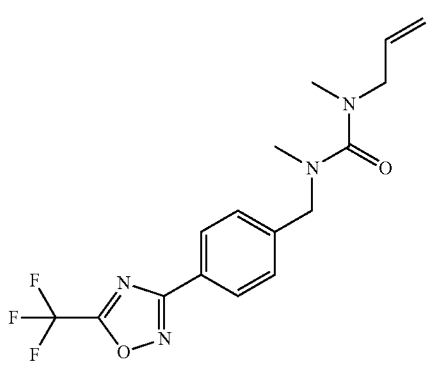 | 1.77 | 355.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.79 | 1-isopropyl-1,3-dimethyl-3-[[4-[5-(trifluoromethyl)-1,2,4-oxadiazol-3-yl]phenyl]methyl]urea | 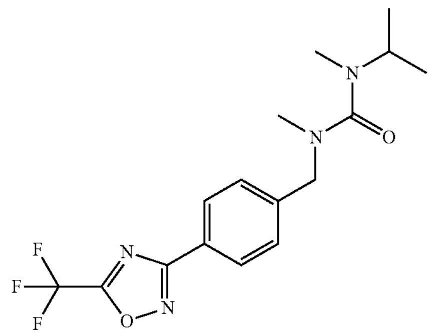 [SMILES: CC(C)N(C)C(=O)N(C)Cc1ccc(-c2noc(C(F)(F)F)n2)cc1] | 1.81 | 357.2 | B | |
| 3.80 | 1-cyclopropyl-3-methyl-1-prop-2-ynyl-3-[[4-[5-(trifluoromethyl)-1,2,4-oxadiazol-3-yl]phenyl]methyl]urea | 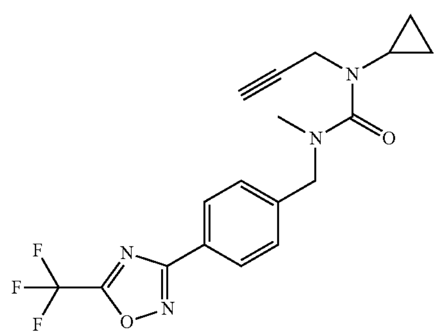 [SMILES: C#CCN(C(=O)N(C)Cc1ccc(-c2noc(C(F)(F)F)n2)cc1)C1CC1] | 1.75 | 379.2 | B | |
| 3.81 | 1-(cyclopropylmethyl)-1-ethyl-3-methyl-3-[[4-[5-(trifluoromethyl)-1,2,4-oxadiazol-3-yl]phenyl]methyl]urea | 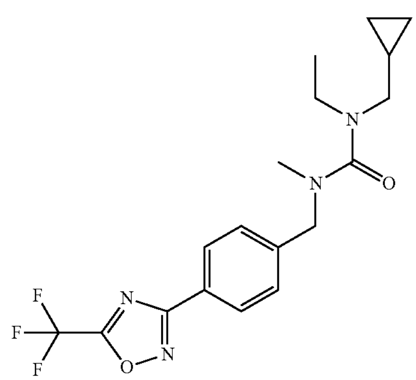 [SMILES: CCN(CC1CC1)C(=O)N(C)Cc1ccc(-c2noc(C(F)(F)F)n2)cc1] | 1.95 | 383.2 | B | |
| 3.82 | 1-cyclobutyl-1,3-dimethyl-3-[[4-[5-(trifluoromethyl)-1,2,4-oxadiazol-3-yl]phenyl]methyl]urea | 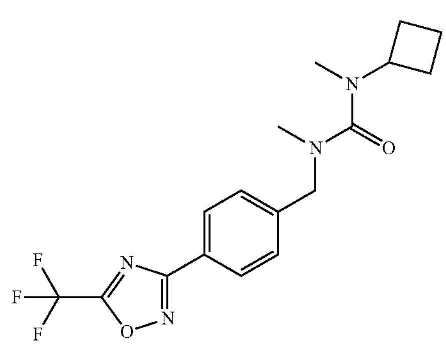 [SMILES: CN(Cc1ccc(-c2noc(C(F)(F)F)n2)cc1)C(=O)N(C)C1CCC1] | 1.86 | 369.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.83 | 1-(cyclopropylmethyl)-1,3-dimethyl-3-[[4-[5-(trifluoromethyl)-1,2,4-oxadiazol-3-yl]phenyl]methyl]urea | 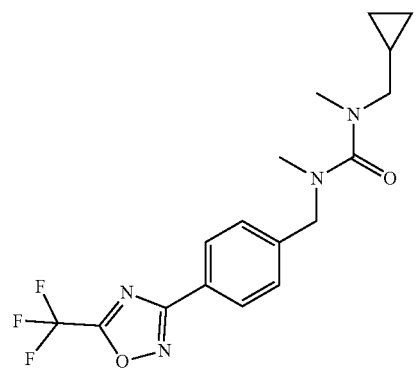 [SMILES: CN(Cc1ccc(-c2noc(C(F)(F)F)n2)cc1)C(=O)N(C)CC1CC1] | 1.84 | 369.2 | B | |
| 3.84 | 1,1-bis(2-methoxyethyl)-3-methyl-3-[[4-[5-(trifluoromethyl)-1,2,4-oxadiazol-3-yl]phenyl]methyl]urea | 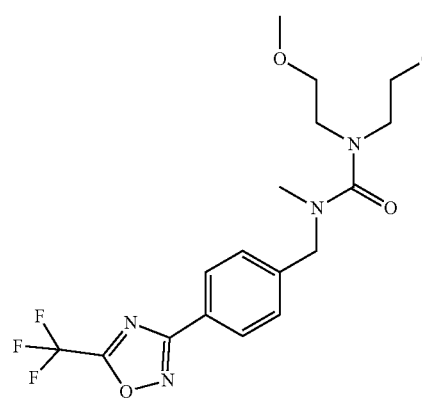 | 1.65 | 417.2 | B | |
| 3.85 | 1-ethyl-3-(2-methoxyethyl)-3-methyl-1-[[4-[5-(trifluoromethyl)-1,2,4-oxadiazol-3-yl]phenyl]methyl]urea | 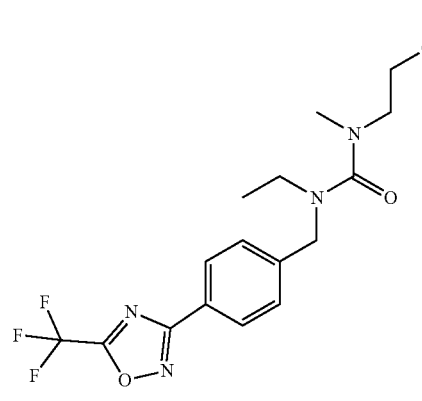 | 1.73 | 387.2 | B | |
| 3.86 | 2-[[ethyl-[[4-[5-(trifluoromethyl)-1,2,4-oxadiazol-3-yl]phenyl]methyl]-carbamoyl]-methyl-amino]-N-methyl-acetamide | 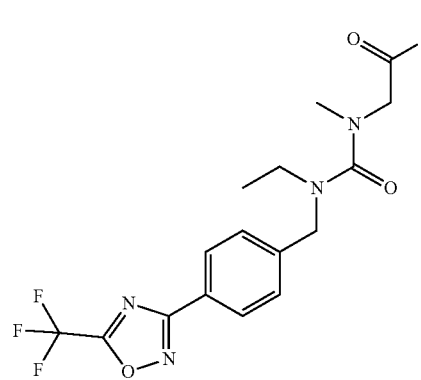 | 1.44 | 400.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.87 | N-ethyl-N-[[4-[5-(trifluoromethyl)-1,2,4-oxadiazol-3-yl]phenyl]methyl]-isoxazolidine-2-carboxamide | 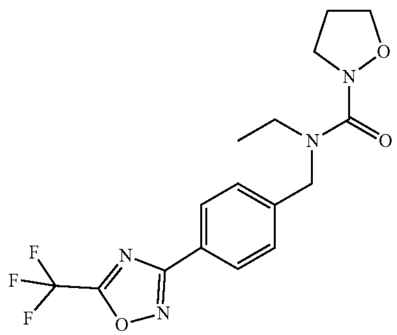 [SMILES: CCN(Cc1ccc(-c2noc(C(F)(F)F)n2)cc1)C(=O)N1CCCO1] | 1.77 | 371.2 | B | |
| 3.88 | 1-(cyanomethyl)-3-ethyl-1-methyl-3-[[4-[5-(trifluoromethyl)-1,2,4-oxadiazol-3-yl]phenyl]methyl]urea | 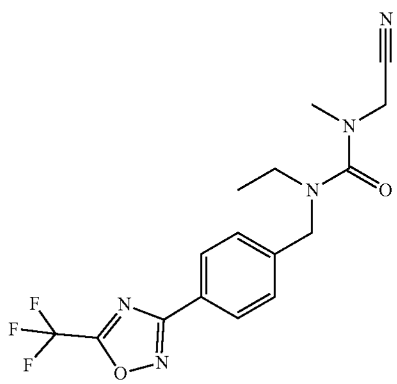 [SMILES: CCN(Cc1ccc(-c2noc(C(F)(F)F)n2)cc1)C(=O)N(C)CC#N] | 1.64 | 368.2 | B | |
| 3.89 | 1-cyclopropyl-1,3-diethyl-3-[[4-[5-(trifluoromethyl)-1,2,4-oxadiazol-3-yl]phenyl]methyl]urea | 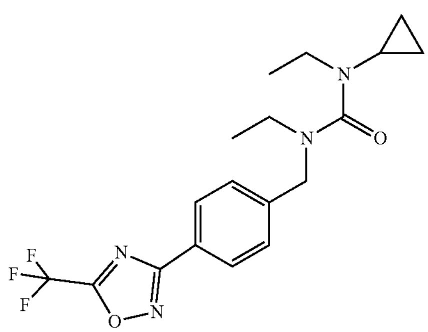 [SMILES: CCN(Cc1ccc(-c2noc(C(F)(F)F)n2)cc1)C(=O)N(CC)C1CC1] | 1.91 | 383.2 | B | |
| 3.90 | 1-cyclopropyl-3-ethyl-1-methyl-3-[[4-[5-(trifluoromethyl)-1,2,4-oxadiazol-3-yl]phenyl]methyl]urea | 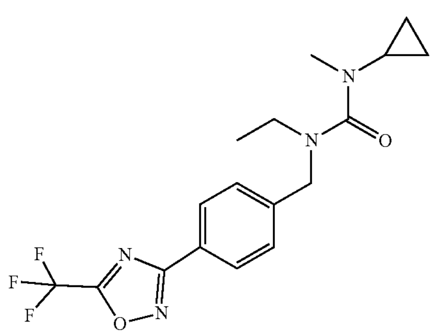 [SMILES: CCN(Cc1ccc(-c2noc(C(F)(F)F)n2)cc1)C(=O)N(C)C1CC1] | 1.81 | 369.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.91 | 1-ethyl-3-methyl-3-(oxetan-3-yl)-1-[[4-[5-(trifluoromethyl)-1,2,4-oxadiazol-3-yl]phenyl]methyl]urea | 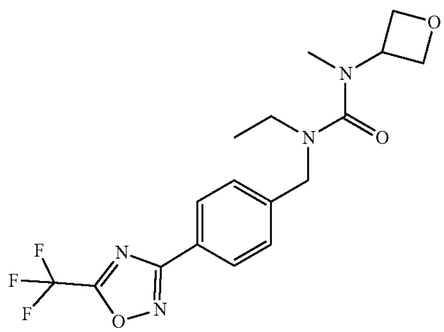 [SMILES: CCN(Cc1ccc(-c2noc(C(F)(F)F)n2)cc1)C(=O)N(C)C1COC1] | 1.59 | 385.2 | B | |
| 3.92 | ethyl 2-[[ethyl-[[4-[5-(trifluoromethyl)-1,2,4-oxadiazol-3-yl]phenyl]methyl]-carbamoyl]-methyl-amino]acetate | 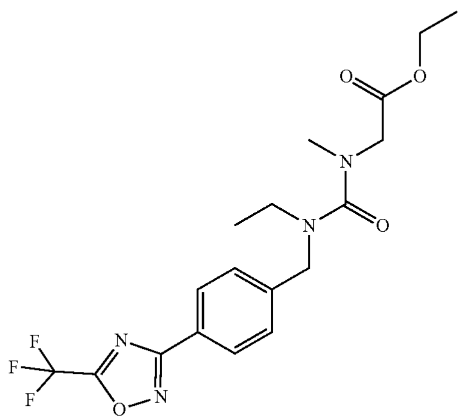 [SMILES: CCOC(=O)CN(C)C(=O)N(CC)Cc1ccc(-c2noc(C(F)(F)F)n2)cc1] | 1.79 | 415.2 | B | |
| 3.93 | N-ethyl-N-[[4-[5-(trifluoromethyl)-1,2,4-oxadiazol-3-yl]phenyl]methyl]-pyrrolidine-1-carboxamide | 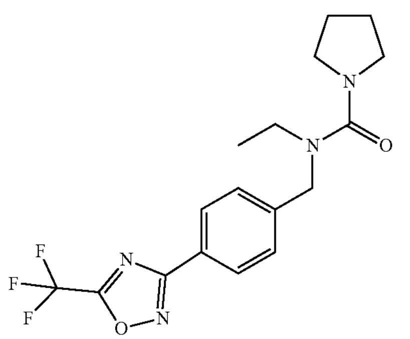 [SMILES: CCN(Cc1ccc(-c2noc(C(F)(F)F)n2)cc1)C(=O)N1CCCC1] | 1.81 | 369.2 | B | |
| 3.94 | 1-ethyl-3-methyl-3-propyl-1-[[4-[5-(trifluoromethyl)-1,2,4-oxadiazol-3-yl]phenyl]methyl]urea | 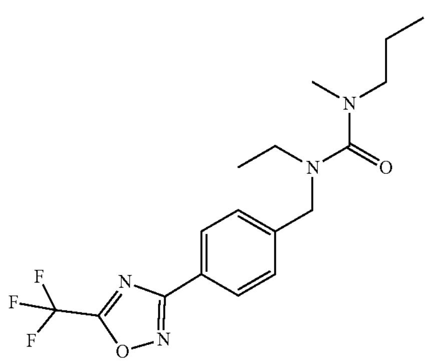 [SMILES: CCCN(C)C(=O)N(CC)Cc1ccc(-c2noc(C(F)(F)F)n2)cc1] | 1.92 | 371.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.95 | 1-ethyl-3-[1-(methoxymethyl)-cyclopropyl]-3-methyl-1-[[4-[5-(trifluoromethyl)-1,2,4-oxadiazol-3-yl]phenyl]methyl]urea | 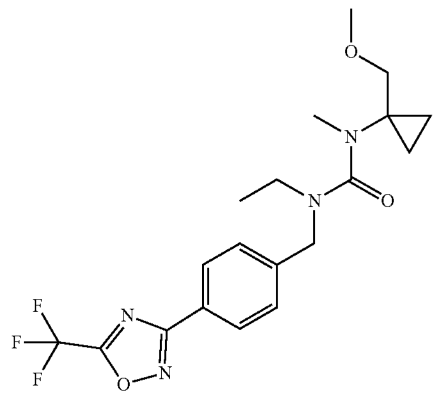 [SMILES: CCN(Cc1ccc(-c2noc(C(F)(F)F)n2)cc1)C(=O)N(C)C1(COC)CC1] | 1.86 | 413.2 | B | |
| 3.96 | 1-ethyl-3-methyl-3-prop-2-ynyl-1-[[4-[5-(trifluoromethyl)-1,2,4-oxadiazol-3-yl]phenyl]methyl]urea | 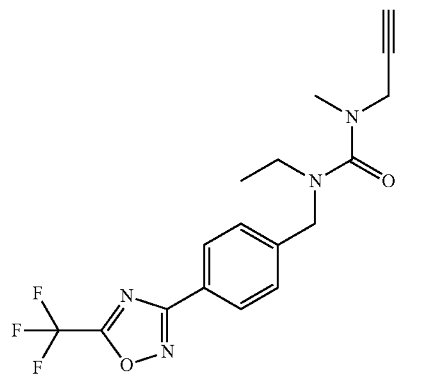 [SMILES: C#CCN(C)C(=O)N(CC)Cc1ccc(-c2noc(C(F)(F)F)n2)cc1] | 1.77 | 367.2 | B | |
| 3.97 | 1-allyl-3-ethyl-1-methyl-3-[[4-[5-(trifluoromethyl)-1,2,4-oxadiazol-3-yl]phenyl]methyl]urea | 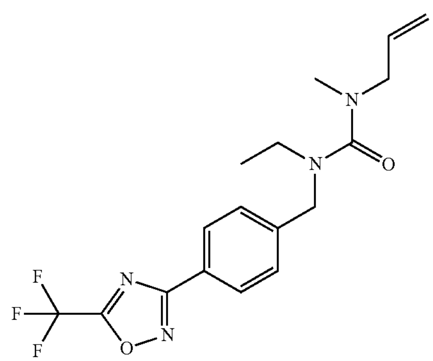 [SMILES: C=CCN(C)C(=O)N(CC)Cc1ccc(-c2noc(C(F)(F)F)n2)cc1] | 1.87 | 369.2 | B | |
| 3.98 | 1-ethyl-3-isopropyl-3-methyl-1-[[4-[5-(trifluoromethyl)-1,2,4-oxadiazol-3-yl]phenyl]methyl]urea | 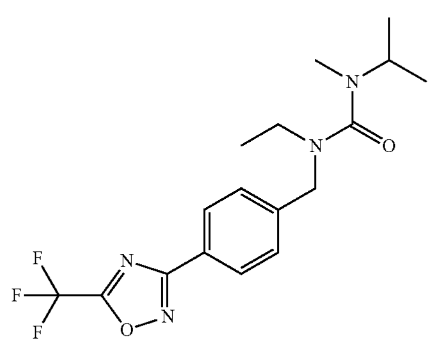 [SMILES: CCN(Cc1ccc(-c2noc(C(F)(F)F)n2)cc1)C(=O)N(C)C(C)C] | 1.91 | 371.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.99 | 1-cyclopropyl-3-ethyl-1-prop-2-ynyl-3-[[4-[5-(trifluoromethyl)-1,2,4-oxadiazol-3-yl]phenyl]methyl]urea | 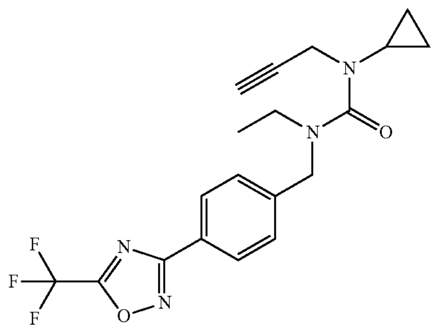 [SMILES: C#CCN(C(=O)N(CC)Cc1ccc(-c2noc(C(F)(F)F)n2)cc1)C1CC1] | 1.85 | 393.2 | B | |
| 3.100 | 1-(cyclopropylmethyl)-1,3-diethyl-3-[[4-[5-(trifluoromethyl)-1,2,4-oxadiazol-3-yl]phenyl]methyl]urea | 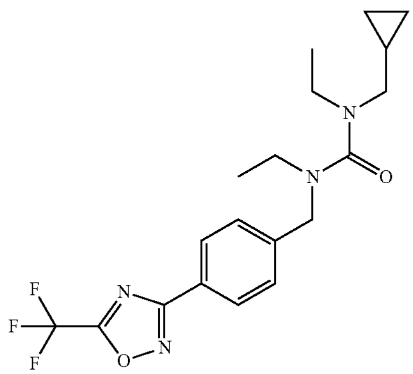 [SMILES: CCN(Cc1ccc(-c2noc(C(F)(F)F)n2)cc1)C(=O)N(CC)CC1CC1] | 2.05 | 397.3 | B | |
| 3.101 | 1-cyclobutyl-3-ethyl-1-methyl-3-[[4-[5-(trifluoromethyl)-1,2,4-oxadiazol-3-yl]phenyl]methyl]urea | 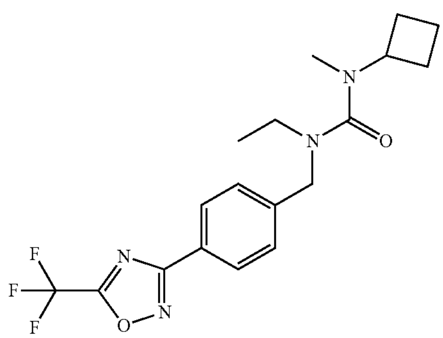 [SMILES: CCN(Cc1ccc(-c2noc(C(F)(F)F)n2)cc1)C(=O)N(C)C1CCC1] | 1.96 | 383.2 | B | |
| 3.102 | 1-ethyl-3,3-bis(2-methoxyethyl)-1-[[4-[5-(trifluoromethyl)-1,2,4-oxadiazol-3-yl]phenyl]methyl]urea | 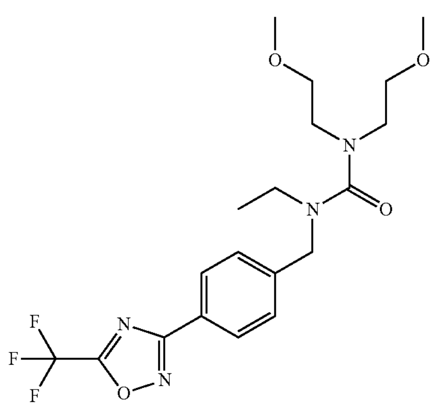 [SMILES: CCN(Cc1ccc(-c2noc(C(F)(F)F)n2)cc1)C(=O)N(CCOC)CCOC] | 1.77 | 431.3 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.103 | 3-[(2,2-difluorocyclopropyl)-methyl]-1-methoxy-1-[[4-[5-(trifluoromethyl)-1,2,4-oxadiazol-3-yl]phenyl]methyl]urea | 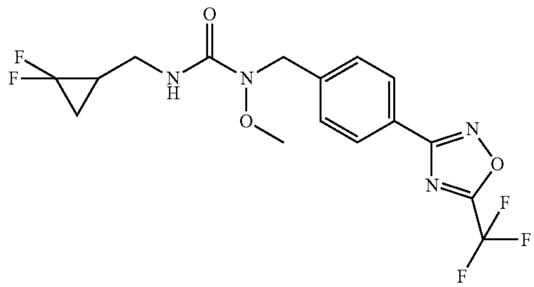 [SMILES: CON(Cc1ccc(-c2noc(C(F)(F)F)n2)cc1)C(=O)NCC1CC1(F)F] | | | | 81-84 |
| 3.104 | 1-methoxy-1,3-dimethyl-3-[[4-[5-(trifluoromethyl)-1,2,4-oxadiazol-3-yl]phenyl]methyl]urea | 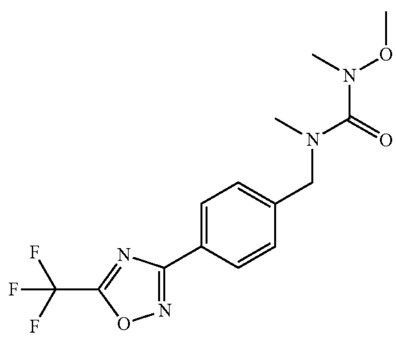 [SMILES: CON(C)C(=O)N(C)Cc1ccc(-c2noc(C(F)(F)F)n2)cc1] | 1.69 | 345.1 | B | |
| 3.105 | 1-methyl-3-prop-2-ynyl-1-[[4-[5-(trifluoromethyl)-1,2,4-oxadiazol-3-yl]phenyl]methyl]urea | 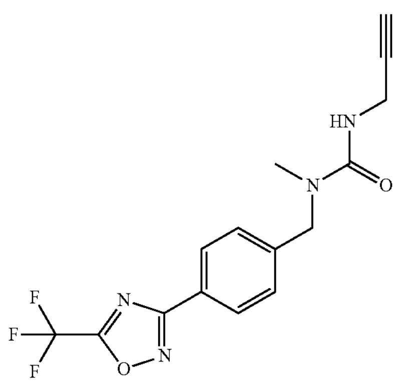 [SMILES: C#CCNC(=O)N(C)Cc1ccc(-c2noc(C(F)(F)F)n2)cc1] | 1.48 | 339.1 | B | |
| 3.106 | 1-methyl-3-(2,2,2-trifluoroethyl)-1-[[4-[5-(trifluoromethyl)-1,2,4-oxadiazol-3-yl]phenyl]methyl]urea | 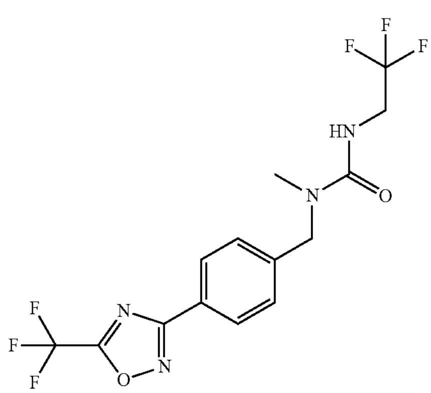 [SMILES: CN(Cc1ccc(-c2noc(C(F)(F)F)n2)cc1)C(=O)NCC(F)(F)F] | 1.65 | 383.1 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.107 | 3-isopropyl-1-methyl-1-[[4-[5-(trifluoromethyl)-1,2,4-oxadiazol-3-yl]phenyl]methyl]urea | 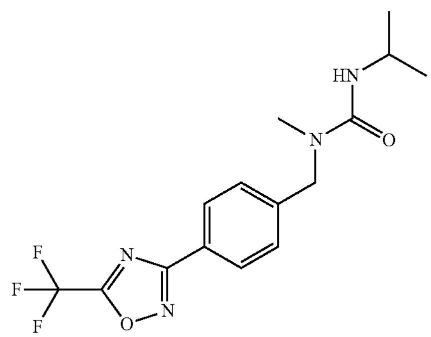 [SMILES: CC(C)NC(=O)N(C)Cc1ccc(-c2noc(C(F)(F)F)n2)cc1] | 1.65 | 343.1 | B | |
| 3.108 | 1-methyl-3-(1-methylcyclopropyl)-1-[[4-[5-(trifluoromethyl)-1,2,4-oxadiazol-3-yl]phenyl]methyl]urea | 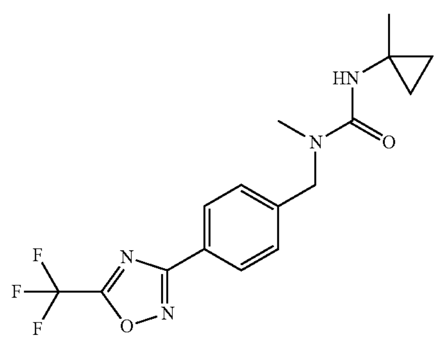 [SMILES: CN(Cc1ccc(-c2noc(C(F)(F)F)n2)cc1)C(=O)NC1(C)CC1] | 1.6 | 355.2 | B | |
| 3.109 | 3-(cyanomethyl)-1-methyl-1-[[4-[5-(trifluoromethyl)-1,2,4-oxadiazol-3-yl]phenyl]methyl]urea | 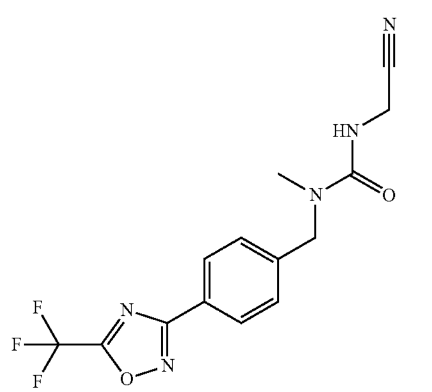 [SMILES: CN(Cc1ccc(-c2noc(C(F)(F)F)n2)cc1)C(=O)NCC#N] | 1.39 | 340.1 | B | |
| 3.110 | 3-(2-methoxyethyl)-1-methyl-1-[[4-[5-(trifluoromethyl)-1,2,4-oxadiazol-3-yl]phenyl]methyl]urea | 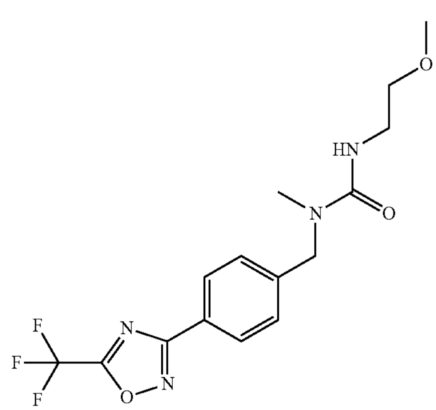 [SMILES: COCCNC(=O)N(C)Cc1ccc(-c2noc(C(F)(F)F)n2)cc1] | 1.44 | 359.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.111 | 3-ethyl-1-methyl-1-[[4-[5-(trifluoromethyl)-1,2,4-oxadiazol-3-yl]phenyl]methyl]urea | 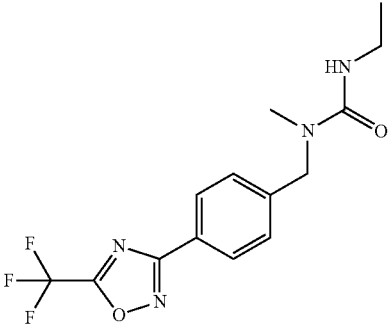 [SMILES: CCNC(=O)N(C)Cc1ccc(-c2noc(C(F)(F)F)n2)cc1] | 1.55 | 329.1 | B | |
| 3.112 | 3-cyclobutyl-1-methyl-1-[[4-[5-(trifluoromethyl)-1,2,4-oxadiazol-3-yl]phenyl]methyl]urea | 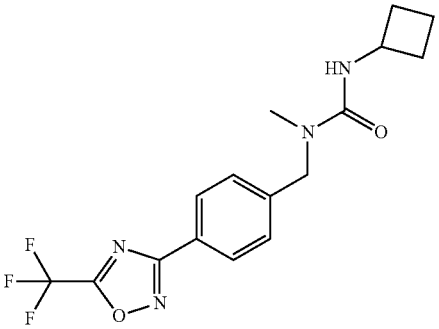 | 1.63 | 355.2 | B | |
| 3.113 | 3-methoxy-1-methyl-1-[[4-[5-(trifluoromethyl)-1,2,4-oxadiazol-3-yl]phenyl]methyl]urea | 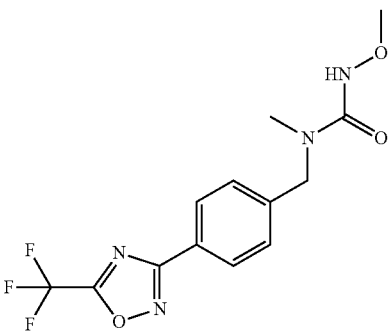 | 1.37 | 331.1 | B | |
| 3.114 | 3-(cyclopropylmethyl)-1-methyl-1-[[4-[5-(trifluoromethyl)-1,2,4-oxadiazol-3-yl]phenyl]methyl]urea | 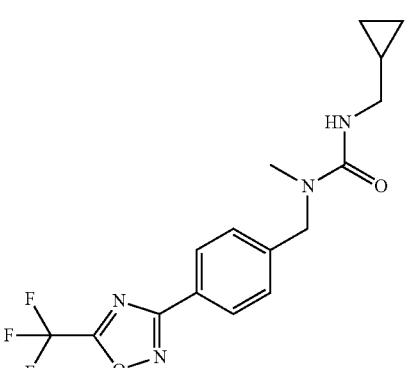 | 1.63 | 355.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.115 | 1,1-diethyl-3-methyl-3-[[4-[5-(trifluoromethyl)-1,2,4-oxadiazol-3-yl]phenyl]methyl]urea | 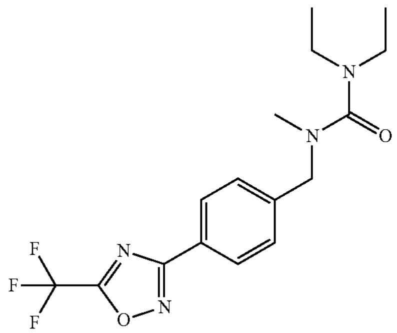 [SMILES: CCN(CC)C(=O)N(C)Cc1ccc(-c2noc(C(F)(F)F)n2)cc1] | 1.89 | 357.2 | B | |
| 3.116 | 1-ethyl-3-methoxy-3-methyl-1-[[4-[5-(trifluoromethyl)-1,2,4-oxadiazol-3-yl]phenyl]methyl]urea | 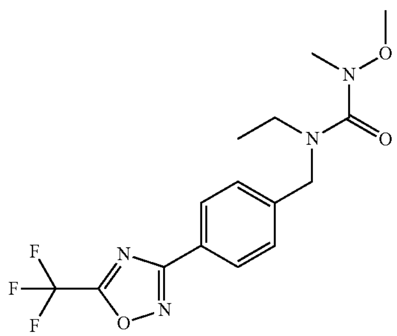 [SMILES: CCN(Cc1ccc(-c2noc(C(F)(F)F)n2)cc1)C(=O)N(C)OC] | 1.79 | 359.2 | B | |
| 3.117 | 1-ethyl-3-prop-2-ynyl-1-[[4-[5-(trifluoromethyl)-1,2,4-oxadiazol-3-yl]phenyl]methyl]urea | 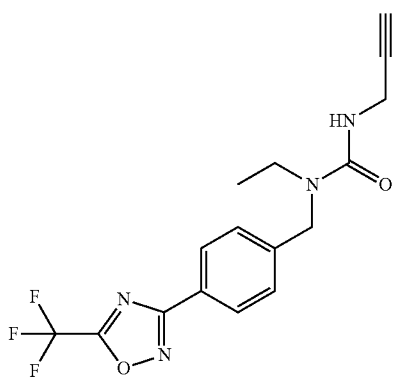 [SMILES: C#CCNC(=O)N(CC)Cc1ccc(-c2noc(C(F)(F)F)n2)cc1] | 1.57 | 353.1 | B | |
| 3.118 | 1-ethyl-3-(2,2,2-trifluoroethyl)-1-[[4-[5-(trifluoromethyl)-1,2,4-oxadiazol-3-yl]phenyl]methyl]urea | 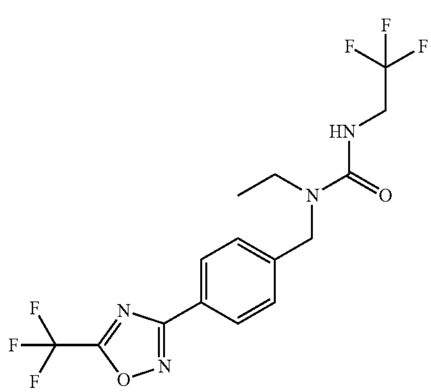 [SMILES: CCN(Cc1ccc(-c2noc(C(F)(F)F)n2)cc1)C(=O)NCC(F)(F)F] | 1.7 | 397.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.119 | 1-ethyl-3-isopropyl-1-[[4-[5-(trifluoromethyl)-1,2,4-oxadiazol-3-yl]phenyl]methyl]urea | 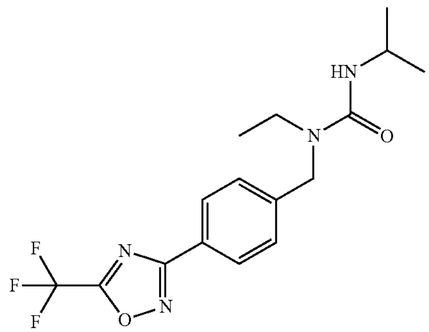 [SMILES: CCN(Cc1ccc(-c2noc(C(F)(F)F)n2)cc1)C(=O)NC(C)C] | 1.7 | 357.2 | B | |
| 3.120 | 1-ethyl-3-(1-methylcyclopropyl)-1-[[4-[5-(trifluoromethyl)-1,2,4-oxadiazol-3-yl]phenyl]methyl]urea | 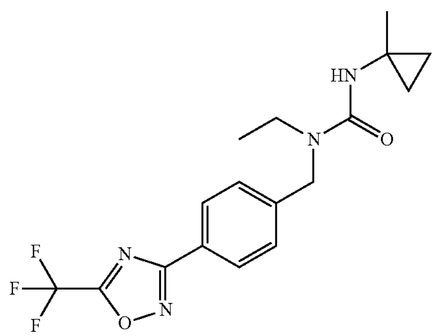 [SMILES: CCN(Cc1ccc(-c2noc(C(F)(F)F)n2)cc1)C(=O)NC1(C)CC1] | 1.7 | 369.2 | B | |
| 3.121 | 3-(cyanomethyl)-1-ethyl-1-[[4-[5-(trifluoromethyl)-1,2,4-oxadiazol-3-yl]phenyl]methyl]urea | 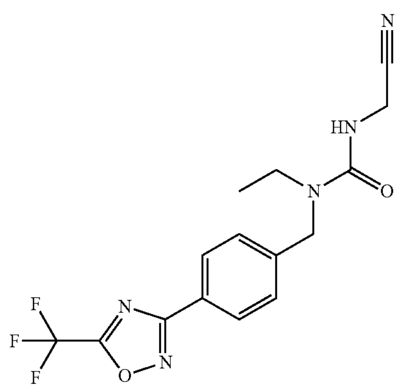 [SMILES: CCN(Cc1ccc(-c2noc(C(F)(F)F)n2)cc1)C(=O)NCC#N] | 1.5 | 354.2 | B | |
| 3.122 | 1-ethyl-3-(2-methoxyethyl)-1-[[4-[5-(trifluoromethyl)-1,2,4-oxadiazol-3-yl]phenyl]methyl]urea | 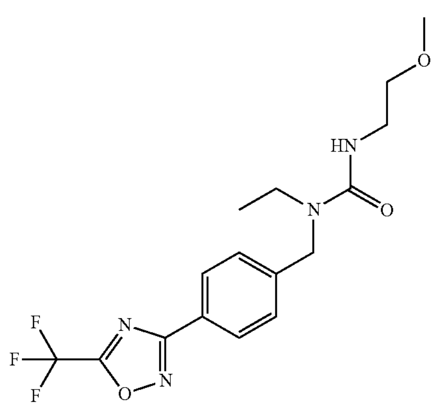 [SMILES: CCN(Cc1ccc(-c2noc(C(F)(F)F)n2)cc1)C(=O)NCCOC] | 1.55 | 373.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.123 | 1,3-diethyl-1-[[4-[5-(trifluoromethyl)-1,2,4-oxadiazol-3-yl]phenyl]methyl]urea | 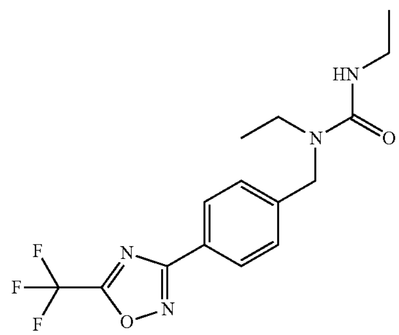 [SMILES: CCNC(=O)N(CC)Cc1ccc(-c2noc(C(F)(F)F)n2)cc1] | 1.6 | 343.1 | B | |
| 3.124 | 3-cyclobutyl-1-ethyl-1-[[4-[5-(trifluoromethyl)-1,2,4-oxadiazol-3-yl]phenyl]methyl]urea | 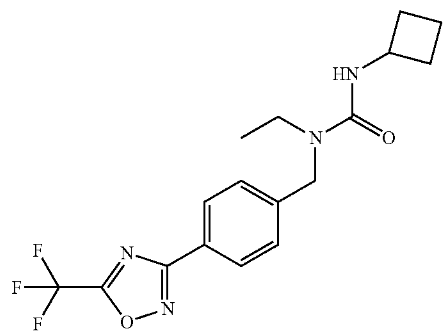 [SMILES: CCN(Cc1ccc(-c2noc(C(F)(F)F)n2)cc1)C(=O)NC1CCC1] | 1.73 | 369.2 | B | |
| 3.125 | 1-ethyl-3-methoxy-1-[[4-[5-(trifluoromethyl)-1,2,4-oxadiazol-3-yl]phenyl]methyl]urea | 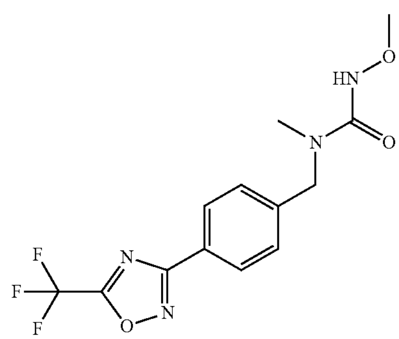 [SMILES: CONC(=O)N(C)Cc1ccc(-c2noc(C(F)(F)F)n2)cc1] | 1.48 | 345.2 | B | |
| 3.126 | 1,1,3-triethyl-3-[[4-[5-(trifluoromethyl)-1,2,4-oxadiazol-3-yl]phenyl]methyl]urea | 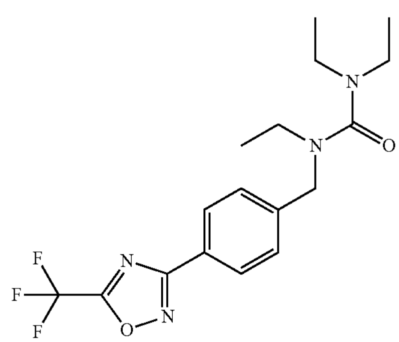 [SMILES: CCN(CC)C(=O)N(CC)Cc1ccc(-c2noc(C(F)(F)F)n2)cc1] | 1.98 | 371.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.127 | 1-methoxy-3-methyl-3-(2,2,2-trifluoroethyl)-1-[[4-[5-(trifluoromethyl)-1,2,4-oxadiazol-3-yl]phenyl]methyl]urea | 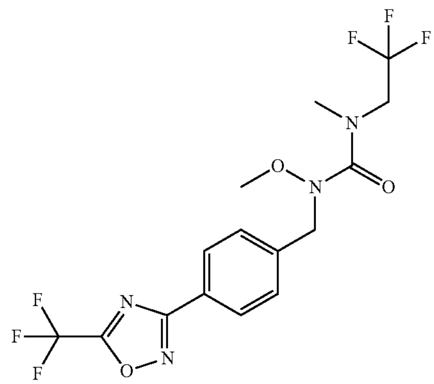 [SMILES: CON(Cc1ccc(-c2noc(C(F)(F)F)n2)cc1)C(=O)N(C)CC(F)(F)F] | 1.9 | 413.2 | B | |
| 3.128 | 1-cyclopropyl-1-ethyl-3-methoxy-3-[[4-[5-(trifluoromethyl)-1,2,4-oxadiazol-3-yl]phenyl]methyl]urea | 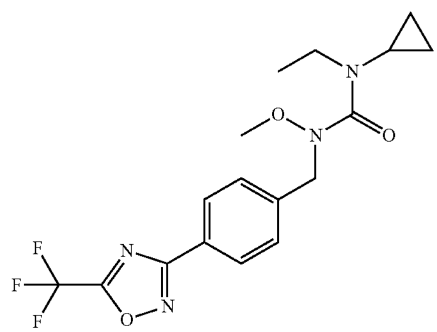 [SMILES: CCN(C(=O)N(Cc1ccc(-c2noc(C(F)(F)F)n2)cc1)OC)C1CC1] | 1.9 | 385.2 | B | |
| 3.129 | 2-[[methoxy-[[4-[5-(trifluoromethyl)-1,2,4-oxadiazol-3-yl]phenyl]methyl]-carbamoyl]-methyl-amino]-N-methyl-acetamide | 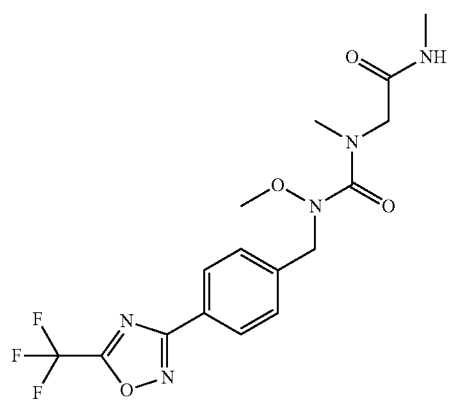 [SMILES: CNC(=O)CN(C)C(=O)N(Cc1ccc(-c2noc(C(F)(F)F)n2)cc1)OC] | 1.4 | 402.2 | B | |
| 3.130 | ethyl 2-[[methoxy-[[4-[5-(trifluoromethyl)-1,2,4-oxadiazol-3-yl]phenyl]methyl]-carbamoyl]-methyl-amino]acetate | 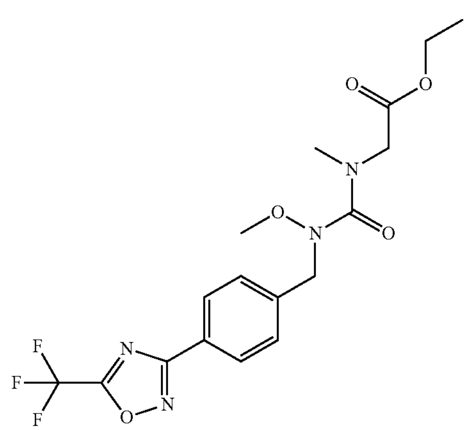 [SMILES: CCOC(=O)CN(C)C(=O)N(Cc1ccc(-c2noc(C(F)(F)F)n2)cc1)OC] | 1.75 | 417.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.131 | 1-methoxy-3-methyl-3-propyl-1-[[4-[5-(trifluoromethyl)-1,2,4-oxadiazol-3-yl]phenyl]methyl]urea | 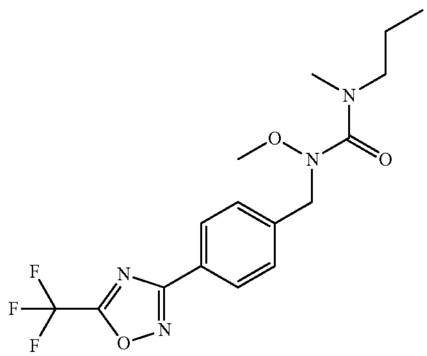 [SMILES: CCCN(C)C(=O)N(Cc1ccc(-c2noc(C(F)(F)F)n2)cc1)OC] | 1.87 | 373.2 | B | |
| 3.132 | 1-isopropyl-3-methoxy-1-methyl-3-[[4-[5-(trifluoromethyl)-1,2,4-oxadiazol-3-yl]phenyl]methyl]urea | 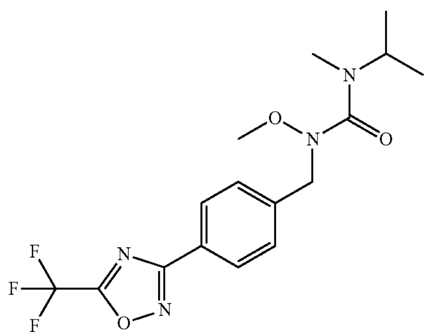 | 1.88 | 373.2 | B | |
| 3.133 | 1-methoxy-3-[1-(methoxymethyl)-cyclopropyl]-3-methyl-1-[[4-[5-(trifluoromethyl)-1,2,4-oxadiazol-3-yl]phenyl]methyl]urea | 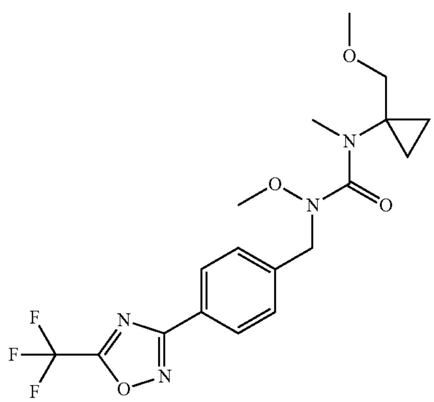 [SMILES: COCC1(N(C)C(=O)N(Cc2ccc(-c3noc(C(F)(F)F)n3)cc2)OC)CC1] | 1.85 | 415.2 | B | |
| 3.134 | 1-methoxy-3,3-bis(2-methoxyethyl)-1-[[4-[5-(trifluoromethyl)-1,2,4-oxadiazol-3-yl]phenyl]methyl]urea | 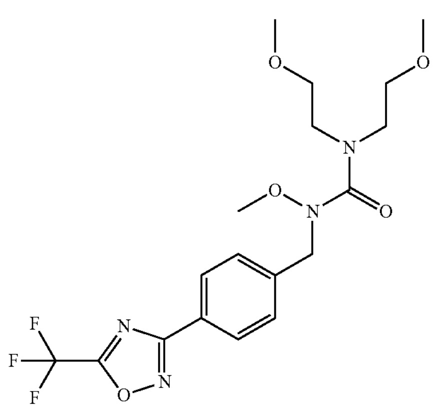 [SMILES: COCCN(CCOC)C(=O)N(Cc1ccc(-c2noc(C(F)(F)F)n2)cc1)OC] | 1.78 | 433.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.135 | 1-allyl-3-methoxy-1-methyl-3-[[4-[5-(trifluoromethyl)-1,2,4-oxadiazol-3-yl]phenyl]methyl]urea | 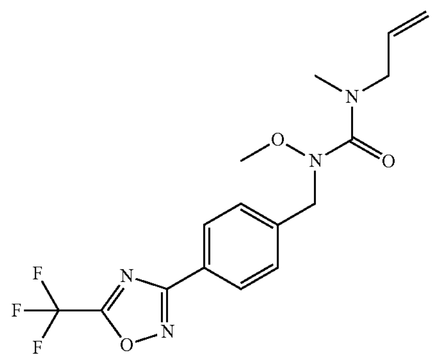 [SMILES: C=CCN(C)C(=O)N(Cc1ccc(-c2noc(C(F)(F)F)n2)cc1)OC] | 1.85 | 371.2 | B | |
| 3.136 | 1-(1-cyanoethyl)-1-cyclopropyl-3-methoxy-3-[[4-[5-(trifluoromethyl)-1,2,4-oxadiazol-3-yl]phenyl]methyl]urea | 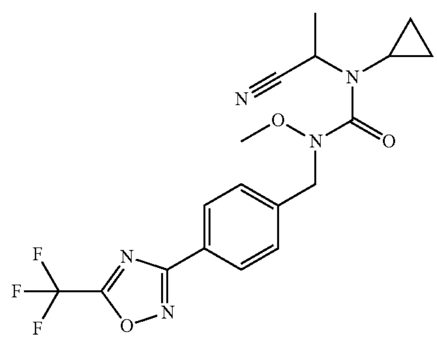 [SMILES: CON(Cc1ccc(-c2noc(C(F)(F)F)n2)cc1)C(=O)N(C(C)C#N)C1CC1] | 1.79 | 410.2 | B | |
| 3.137 | 1-(cyclopropylmethyl)-1-ethyl-3-methoxy-3-[[4-[5-(trifluoromethyl)-1,2,4-oxadiazol-3-yl]phenyl]methyl]urea | 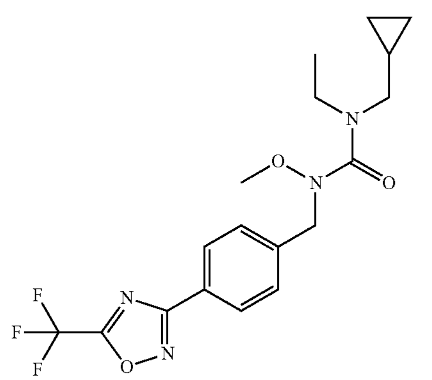 [SMILES: CCN(CC1CC1)C(=O)N(Cc1ccc(-c2noc(C(F)(F)F)n2)cc1)OC] | 2 | 399.2 | B | |
| 3.138 | 1-cyclopropyl-3-methoxy-1-prop-2-ynyl-3-[[4-[5-(trifluoromethyl)-1,2,4-oxadiazol-3-yl]phenyl]methyl]urea | 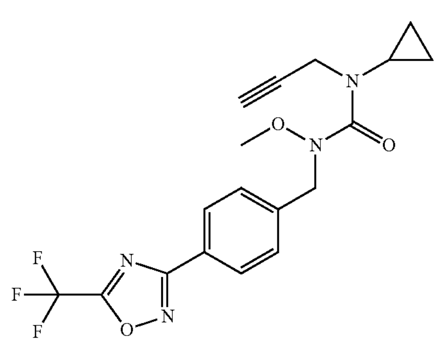 [SMILES: C#CCN(C(=O)N(Cc1ccc(-c2noc(C(F)(F)F)n2)cc1)OC)C1CC1] | 1.86 | 395.2 | B | |

TABLE T3-continued

Melting point (mp) data and/or retention times (RT) for compounds according to Formula (I):

| Entry | Name | Structure | RT +(min) | [M + H] | Method | MP (° C.) |
|---|---|---|---|---|---|---|
| 3.139 | 1-(cyclopropylmethyl)-3-methoxy-1-methyl-3-[[4-[5-(trifluoromethyl)-1,2,4-oxadiazol-3-yl]phenyl]methyl]urea | 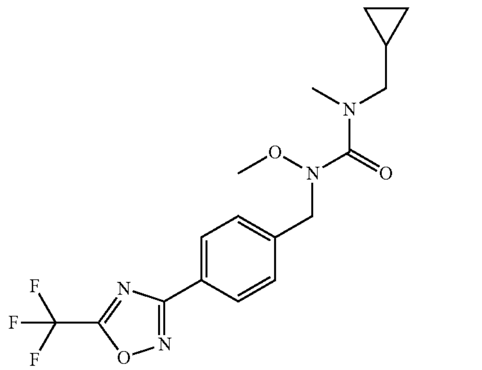 [SMILES: CON(Cc1ccc(-c2noc(C(F)(F)F)n2)cc1)C(=O)N(C)CC1CC1] | 1.92 | 385.2 | B | |
| 3.140 | 1-isopropyl-3-methoxy-3-methyl-1-[2-[4-[5-(trifluoromethyl)-1,2,4-oxadiazol-3-yl]phenyl]ethyl]urea | 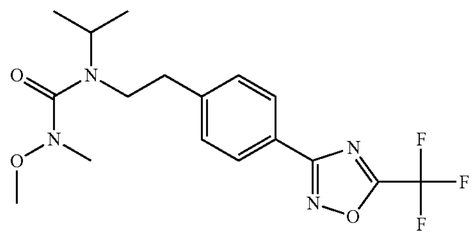 [SMILES: CON(C)C(=O)N(CCc1ccc(-c2noc(C(F)(F)F)n2)cc1)C(C)C] | 1.18 | 387.5 | A | |

BIOLOGICAL EXAMPLES

General Examples of Leaf Disk Tests in Well Plates:

Leaf disks or leaf segments of various plant species are cut from plants grown in a greenhouse. The cut leaf disks or segments are placed in multiwell plates (24-well format) onto water agar. The leaf disks are sprayed with a test solution before (preventative) or after (curative) inoculation. Compounds to be tested are prepared as DMSO solutions (max. 10 mg/ml) which are diluted to the appropriate concentration with 0.025% Tween20 just before spraying. The inoculated leaf disks or segments are incubated under defined conditions (temperature, relative humidity, light, etc.) according to the respective test system. A single evaluation of disease level is carried out 3 to 14 days after inoculation, depending on the pathosystem. Percent disease control relative to the untreated check leaf disks or segments is then calculated.

General Examples of Liquid Culture Tests in Well Plates:

*Mycelia* fragments or conidia suspensions of a fungus prepared either freshly from liquid cultures of the fungus or from cryogenic storage, are directly mixed into nutrient broth. DMSO solutions of the test compound (max. 10 mg/ml) are diluted with 0.025% Tween20 by a factor of 50 and 10 µl of this solution is pipetted into a microtiter plate (96-well format). The nutrient broth containing the fungal spores/mycelia fragments is then added to give an end concentration of the tested compound. The test plates are incubated in the dark at 24° C. and 96% relative humidity. The inhibition of fungal growth is determined photometrically after 2 to 7 days, depending on the pathosystem, and percent antifungal activity relative to the untreated check is calculated.

Fungicidal Activity Against *Puccinia Recondita* f. sp. tritici/wheat/leaf Disc Preventative (Brown Rust)

Wheat leaf segments cv. Kanzler were placed on agar in multiwell plates (24-well format) and sprayed with the formulated test compound diluted in water. The leaf disks were inoculated with a spore suspension of the fungus 1 day after application. The inoculated leaf segments were incubated at 19° C. and 75% relative humidity (rh) under a light regime of 12 hours light/12 hours darkness in a climate cabinet and the activity of a compound was assessed as percent disease control compared to untreated when an appropriate level of disease damage appears in untreated check leaf segments (7 to 9 days after application).

The following compounds at 200 ppm in the applied formulation give at least 80% disease control in this test when compared to untreated control leaf disks under the same conditions, which show extensive disease development.

Compounds (from Table T1) 1.1, 1.2, 1.3, 1.4, 1.6, 1.8, 1.10, 1.11, 1.12, 1.15, 1.16, 1.17, 1.19, 1.20, 1.22, 1.24, 1.25, 1.26, 1.27, 1.28, 1.29, 1.30, 1.31, 1.32, 1.33, 1.34, 1.35, 1.36, 1.38, 1.40, 1.41, 1.42, 1.43, 1.44, 1.45, 1.46, 1.47, 1.48, 1.49, 1.50, 1.51, 1.52, 1.53, 1.54, 1.57, 1.59, 1.60, 1.62, 1.64, 1.67, 1.69, 1.77, 1.81, 1.83, 1.86, 1.87, 1.89, 1.90, 1.91, 1.92, 1.93, 1.95, 1.97, 1.99, 1.100, 1.101, 1.102, 1.103, 1.104, 1.105, 1.106, 1.107, 1.109, 1.110, 1.111, 1.112, 1.113, 1.114, 1.115, 1.117, 1.118, 1.119, 1.120, 1.121, 1.122, 1.123, 1.124, 1.125, 1.126, 1.127, 1.128, 1.129, 1.130, 1.132, 1.133, 1.134, 1.135, 1.136, 1.138, 1.139, 1.140, 1.141, 1.142, 1.143, 1.144, 1.145, 1.146, 1.147, 1.149, 1.150, 1.151, 1.152, 1.154, 1.155, 1.157, 1.158, 1.159, 1.161, 1.162, 1.164, 1.165, 1.167, 1.168, 1.169, 1.170, 1.171, 1.172, 1.173, 1.175, 1.176, 1.177, 1.178, 1.180, 1.181, 1.182, 1.183, 1.184, 1.185, 1.186, 1.187, 1.188, 1.189, 1.190, 1.191, 1.192, 1.193, 1.194, 1.196, 1.198, 1.199, 1.200, 1.201, 1.202, 1.205, 1.206, 1.209, 1.212, 1.214, 1.215, 1.216, 1.217, 1.218, 1.219, 1.221, 1.222, 1.223, 1.225, 1.226, 1.227, 1.229, 1.230, 1.233, 1.234, 1.235, 1.237, 1.238, 1.242, 1.243, 1.244, 1.245, 1.247, 1.248, 1.249, 1.250, 1.251, 1.252, 1.253, 1.258, 1.259, 1.260, 1.264, 1.266, 1.270, 1.273, 1.274, 1.275, 1.276, 1.279, 1.280, 1.283, 1.287, 1.298, 1.305, 1.306, 1.308, 1.309, 1.312, 1.313, 1.314, 1.315, 1.316, 1.320, 1.323, 1.324, 1.325, 1.326, 1.327, 1.328, 1.329, 1.330, 1.331, 1.332, 1.333, 1.334, 1.335, 1.336, 1.337, 1.338, 1.339, 1.340, 1.341, 1.342, 1.344, 1.345, 1.346, 1.347, 1.348, 1.350, 1.351, 1.352, 1.353, 1.354, 1.355, 1.356, 1.357, 1.358, 1.359, 1.360, 1.361, 1.362, 1.363, 1.364, 1.365, 1.366, 1.367, 1.368, 1.369, 1.370, 1.371, 1.372, 1.373, 1.374, 1.375, 1.376, 1.378, 1.379, 1.383, 1.384, 1.387, 1.388, 1.389, 1.390, 1.391, 1.392, 1.395, 1.396, 1.398, 1.399, 1.400, 1.401, 1.402, 1.403, 1.404, 1.405, 1.406, 1.407, 1.408, 1.410, 1.411, 1.412, 1.413, 1.414, 1.415, 1.416, 1.417, 1.418, 1.421, 1.422, 1.423, 1.424, 1.426, 1.427, 1.430, 1.431, 1.432, 1.433, 1.434, 1.435, 1.436, 1.437, 1.438, 1.440, 1.441, 1.442, 1.443, 1.446, 1.447, 1.448, 1.449, 1.450, 1.451, 1.452, 1.453, 1.456, 1.457, 1.458, 1.459, 1.460, 1.461, 1.462, 1.463, 1.464, 1.465, 1.466, 1.467, 1.468, 1.469, 1.471, 1.472, 1.473, 1.474, 1.475, 1.476, 1.477, 1.478, 1.479, 1.480, 1.481, 1.482, 1.483, 1.484, 1.485, 1.486, 1.487, 1.488, 1.489, 1.490, 1.491, 1.492, 1.493, 1.494, 1.495, 1.496, 1.497, 1.498, 1.499, 1.500, 1.501, 1.502, 1.503, 1.504, 1.505, 1.506, 1.507, 1.508, 1.509, 1.510, 1.511, 1.512, 1.513, 1.514, 1.515, 1.516, 1.517, 1.518, 1.519, 1.520, 1.521, 1.522, 1.523, 1.524, 1.525, 1.526, 1.527, 1.528, 1.529, 1.530, 1.531, 1.532, 1.537, 1.550, 1.552, 1.562, 1.563, 1.564, 1.565, 1.566, 1.567, 1.569, 1.570, 1.572, 1.573, 1.574, 1.575, 1.576, 1.577, 1.578, 1.579, 1.580, 1.581, 1.582, 1.583, 1.584, 1.585, 1.587, 1.589, 1.590, 1.591, 1.592, 1.593, 1.594, 1.595, 1.596, 1.597, 1.598, 1.599, 1.600, 1.602, 1.603, 1.604, 1.605, 1.606, 1.607, 1.608, 1.609, 1.610, 1.611, 1.612, 1.613, 1.614, 1.615, 1.617, 1.618, 1.619, 1.620, 1.621, 1.622, 1.623, 1.624, 1.625, 1.626, 1.627, 1.628, 1.629, 1.631, 1.636, 1.640, 1.647, 1.651, 1.652, 1.654, 1.655, 1.656, 1.658, 1.659, 1.660, 1.661, 1.662, 1.663, 1.664, 1.665, 1.666, 1.668, 1.669, 1.670, 1.671, 1.672, 1.673, 1.674, 1.675, 1.676, 1.677, 1.678, 1.679, 1.680, 1.681, 1.682, 1.683, 1.684, 1.685, 1.686, 1.687, 1.688, 1.689, 1.690, 1.692, 1.696, 1.698, 1.701, 1.702, 1.703, 1.704, 1.705, 1.707, 1.708, 1.709, 1.711, 1.712, 1.713, 1.714, 1.715, 1.716, 1.717, 1.718, 1.720, 1.721, 1.722, 1.723, 1.724, 1.725, 1.726, 1.727, 1.728, 1.729, 1.731, 1.732, 1.733, 1.734, 1.735, 1.736, 1.737, 1.738, 1.739, 1.740, 1.741, 1.742, 1.743, 1.744, 1.745, 1.747, 1.748, 1.749, 1.751, 1.752, 1.753, 1.754, 1.756, 1.757, 1.758, 1.759, 1.760, 1.761, 1.762, 1.763, 1.764, 1.765, 1.766, 1.767, 1.768, 1.769, 1.770, 1.771, 1.772, 1.773, 1.774, 1.775, 1.776, 1.777, 1.778, 1.779, 1.781, 1.782, 1.783, 1.784, 1.785, 1.786, 1.787, 1.788, 1.789, 1.790, 1.791, 1.792, 1.793, 1.794, 1.795 and 1.810.

Compounds (from Table T2) 2.1, 2.4, 2.6, 2.7, 2.14, 2.16, 2.21, 2.22, 2.24, and 2.25.

Compounds (from Table T3) 3.11, 3.2, 3.3, 3.4, 3.5, 3.6, 3.7, 3.8, 3.9, 3.10, 3.11, 3.12, 3.13, 3.14, 3.15, 3.16, 3.17, 3.18, 3.19, 3.20, 3.21, 3.22, 3.23, 3.24, 3.25, 3.26, 3.28, 3.29, 3.30, 3.31, 3.32, 3.33, 3.34, 3.35, 3.36, 3.37, 3.38, 3.39, 3.40, 3.41, 3.42, 3.43, 3.44, 3.45, 3.46, 3.47, 3.48, 3.49, 3.50, 3.51, 3.52, 3.53, 3.54, 3.55, 3.56, 3.57, 3.58, 3.59, 3.60, 3.61, 3.62, 3.63, 3.64, 3.65, 3.66, 3.67, 3.68, 3.69, 3.70, 3.71, 3.72, 3.73, 3.74, 3.75, 3.76, 3.77, 3.78, 3.79, 3.80, 3.81, 3.82, 3.83, 3.84, 3.85, 3.86, 3.87, 3.88, 3.89, 3.90, 3.91, 3.92, 3.93, 3.94, 3.95, 3.96, 3.97, 3.98, 3.99, 3.101, 3.102, and 3.103.

Fungicidal activity against *Puccinia recondita* f. sp. tritici/wheat/leaf disc curative (Brown rust Wheat leaf segments cv. Kanzler are placed on agar in multiwell plates (24-well format). The leaf segments are then inoculated with a spore suspension of the fungus. Plates were stored in darkness at 19° C. and 75% relative humidity. The formulated test compound diluted in water was applied 1 day after inoculation. The leaf segments were incubated at 19° C. and 75% relative humidity under a light regime of 12 hours light/12 hours darkness in a climate cabinet and the activity of a compound was assessed as percent disease control compared to untreated when an appropriate level of disease damage appears in untreated check leaf segments (6 to 8 days after application).

The following compounds at 200 ppm in the applied formulation give at least 80% disease control in this test when compared to untreated control leaf disks under the same conditions, which show extensive disease development.

Compounds (from Table T1) 1.1, 1.2, 1.3, 1.4, 1.6, 1.8, 1.10, 1.11, 1.12, 1.13, 1.14, 1.15, 1.16, 1.17, 1.19, 1.20, 1.22, 1.23, 1.24, 1.25, 1.26, 1.27, 1.28, 1.29, 1.30, 1.31, 1.32, 1.34, 1.35, 1.36, 1.37, 1.38, 1.40, 1.41, 1.42, 1.43, 1.44, 1.45, 1.46, 1.47, 1.48, 1.49, 1.50, 1.52, 1.53, 1.54, 1.57, 1.59, 1.64, 1.71, 1.77, 1.81, 1.83, 1.86, 1.87, 1.89, 1.91, 1.92, 1.95, 1.97, 1.99, 1.100, 1.101, 1.102, 1.103, 1.104, 1.106, 1.109, 1.110, 1.111, 1.112, 1.114, 1.115, 1.117, 1.118, 1.119, 1.121, 1.122, 1.123, 1.124, 1.125, 1.126, 1.127, 1.128, 1.129, 1.130, 1.131, 1.132, 1.134, 1.136, 1.137, 1.138, 1.139, 1.145, 1.146, 1.147, 1.149, 1.150, 1.151, 1.153, 1.154, 1.155, 1.157, 1.159, 1.160, 1.161, 1.162, 1.164, 1.165, 1.167, 1.168, 1.169, 1.170, 1.171, 1.172, 1.173, 1.175, 1.176, 1.177, 1.178, 1.180, 1.181, 1.182, 1.183, 1.185, 1.187, 1.188, 1.189, 1.191, 1.192, 1.194, 1.196, 1.199, 1.200, 1.201, 1.202, 1.204, 1.206, 1.207, 1.210, 1.215, 1.216, 1.217, 1.223, 1.225, 1.226, 1.227, 1.229, 1.230, 1.233, 1.235, 1.237, 1.242, 1.243, 1.244, 1.245, 1.248, 1.249, 1.253, 1.259, 1.260, 1.264, 1.266, 1.270, 1.273, 1.275, 1.276, 1.279, 1.280, 1.308, 1.309, 1.314, 1.315, 1.316, 1.317, 1.323, 1.324, 1.325, 1.326, 1.327, 1.328, 1.329, 1.330, 1.331, 1.332, 1.333, 1.334, 1.335, 1.336, 1.337, 1.339, 1.340, 1.341, 1.344, 1.345, 1.346, 1.347, 1.348, 1.349, 1.350, 1.351, 1.353, 1.355, 1.356, 1.357, 1.358, 1.359, 1.360, 1.361, 1.362, 1.363, 1.364, 1.365, 1.366, 1.368, 1.369, 1.370, 1.371, 1.372, 1.373, 1.374, 1.375, 1.377, 1.378, 1.379, 1.383, 1.384, 1.387, 1.388, 1.389, 1.390, 1.391, 1.392, 1.395, 1.396, 1.398, 1.399, 1.400, 1.401, 1.402, 1.403, 1.404, 1.406, 1.407, 1.408, 1.411, 1.412, 1.415, 1.417, 1.421, 1.422, 1.426, 1.427, 1.431, 1.432, 1.433, 1.434, 1.435, 1.438, 1.442, 1.443, 1.444, 1.445, 1.446, 1.447, 1.448, 1.450, 1.451, 1.452, 1.455, 1.456, 1.457, 1.458, 1.459, 1.460, 1.463, 1.465, 1.466, 1.467, 1.468, 1.469, 1.472, 1.473, 1.474, 1.476, 1.477, 1.478, 1.479, 1.480, 1.481, 1.483, 1.484, 1.485, 1.486, 1.487, 1.488, 1.489, 1.490, 1.491, 1.492, 1.493, 1.494, 1.495, 1.496, 1.497, 1.498, 1.499, 1.500, 1.501, 1.502, 1.503, 1.504, 1.505, 1.506, 1.507, 1.508, 1.509, 1.510, 1.511, 1.512, 1.513, 1.514, 1.515, 1.516, 1.517, 1.518, 1.519, 1.520, 1.521, 1.522, 1.523, 1.524, 1.525, 1.526, 1.527, 1.528, 1.529, 1.530, 1.531, 1.532, 1.563, 1.564, 1.566, 1.567, 1.568, 1.569, 1.570, 1.571, 1.573, 1.574, 1.575, 1.577, 1.578, 1.579, 1.580, 1.582, 1.583, 1.584, 1.585, 1.586, 1.587, 1.589, 1.590, 1.591, 1.592, 1.593, 1.594, 1.595, 1.596, 1.597, 1.599, 1.600, 1.603, 1.604, 1.605, 1.606, 1.607, 1.608, 1.609, 1.610, 1.611, 1.612, 1.613, 1.614, 1.615, 1.617, 1.618, 1.620, 1.621, 1.622, 1.623, 1.624, 1.625, 1.626, 1.629, 1.631, 1.640, 1.651, 1.652, 1.654, 1.655, 1.656, 1.658, 1.659, 1.660, 1.661, 1.662, 1.663, 1.664, 1.665, 1.666, 1.667, 1.668, 1.669, 1.670, 1.671, 1.673, 1.674, 1.675, 1.676, 1.677, 1.678, 1.679, 1.680, 1.681, 1.682, 1.683, 1.684, 1.685, 1.686, 1.687, 1.688, 1.689, 1.690, 1.692, 1.693, 1.696, 1.698, 1.701, 1.702, 1.703, 1.705, 1.707, 1.711, 1.712, 1.713, 1.714, 1.717, 1.718, 1.721, 1.722, 1.723, 1.724, 1.725, 1.726, 1.727, 1.731, 1.732, 1.738, 1.739, 1.740, 1.741, 1.742, 1.743, 1.744, 1.745, 1.747, 1.748, 1.749, 1.750, 1.751, 1.752, 1.753, 1.756, 1.757, 1.758, 1.759, 1.760, 1.761, 1.762, 1.763, 1.764, 1.765, 1.766, 1.767, 1.768, 1.769, 1.770, 1.771, 1.772, 1.773, 1.774, 1.775, 1.776, 1.777, 1.778, 1.779, 1.781, 1.782, 1.783, 1.784, 1.785, 1.786, 1.787, 1.788, 1.789, 1.790, 1.791, 1.792, 1.793, 1.794, 1.795 and 1.810.

Compounds (from Table T2) 2.1, 2.2, 2.3, 2.4, 2.5, 2.6, 2.11, 2.14, 2.15, 2.16, 2.17, 2.20, 2.22, 2.24, and 2.25.

Compounds (from Table T3) 3.1, 3.2, 3.3, 3.4, 3.5, 3.6, 3.7, 3.8, 3.9, 3.10, 3.12, 3.13, 3.14, 3.15, 3.16, 3.17, 3.18, 3.19, 3.20, 3.21, 3.22, 3.23, 3.24, 3.25, 3.26, 3.28, 3.29, 3.30, 3.31, 3.32, 3.33, 3.34, 3.36, 3.37, 3.38, 3.39, 3.40, 3.41, 3.42, 3.43, 3.44, 3.45, 3.46, 3.47, 3.48, 3.49, 3.50, 3.51, 3.52, 3.53, 3.54, 3.55, 3.56, 3.57, 3.58, 3.59, 3.60, 3.61, 3.63, 3.64, 3.65, 3.67, 3.68, 3.69, 3.70, 3.71, 3.72, 3.73, 3.74, 3.75, 3.76, 3.77, 3.78, 3.79, 3.80, 3.81, 3.82, 3.83, 3.84, 3.85, 3.86, 3.87, 3.88, 3.89, 3.90, 3.91, 3.92, 3.93, 3.94, 3.95, 3.97, 3.98, 3.99, 3.100, 3.101, 3.102, and 3.103.

Fungicidal Activity Against *Phakopsora pachyrhizi*/Soybean/Leaf Disc Preventative (Asian Soybean Rust)

Soybean leaf disks are placed on water agar in multiwell plates (24-well format) and sprayed with the formulated test compound diluted in water. One day after application leaf discs are inoculated by spraying a spore suspension on the lower leaf surface. After an incubation period in a climate cabinet of 24-36 hours in darkness at 20° C. and 75% rh leaf disc are kept at 20° C. with 12 h light/day and 75% rh. The activity of a compound is assessed as percent disease control compared to untreated when an appropriate level of disease damage appears in untreated check leaf disks (12 to 14 days after application).

The following compounds at 200 ppm in the applied formulation give at least 80% disease control in this test when compared to untreated control leaf disks under the same conditions, which show extensive disease development.

Compounds (from Table T1) 1.1, 1.2, 1.3, 1.4, 1.5, 1.6, 1.8, 1.11, 1.12, 1.14, 1.15, 1.16, 1.17, 1.19, 1.20, 1.22, 1.23, 1.24, 1.26, 1.27, 1.28, 1.29, 1.30, 1.31, 1.32, 1.33, 1.34, 1.35, 1.36, 1.38, 1.40, 1.41, 1.42, 1.43, 1.44, 1.45, 1.46, 1.47, 1.48, 1.49, 1.50, 1.51, 1.53, 1.54, 1.57, 1.58, 1.59, 1.60, 1.64, 1.71, 1.77, 1.81, 1.82, 1.83, 1.84, 1.86, 1.87, 1.89, 1.90, 1.91, 1.92, 1.93, 1.95, 1.97, 1.99, 1.100, 1.101, 1.102, 1.103, 1.104, 1.106, 1.109, 1.110, 1.111, 1.112, 1.114, 1.115, 1.117, 1.118, 1.119, 1.121, 1.122, 1.123, 1.124, 1.125, 1.126, 1.128, 1.130, 1.132, 1.134, 1.135, 1.136, 1.138, 1.144, 1.145, 1.146, 1.147, 1.149, 1.150, 1.151, 1.154, 1.155, 1.157, 1.158, 1.159, 1.164, 1.165, 1.166, 1.167, 1.168, 1.169, 1.170, 1.171, 1.172, 1.173, 1.175, 1.176, 1.177, 1.178, 1.180, 1.181, 1.182, 1.183, 1.185, 1.187, 1.189, 1.190, 1.191, 1.192, 1.193, 1.194, 1.195, 1.196, 1.197, 1.199, 1.200, 1.201, 1.202, 1.206, 1.207, 1.209, 1.210, 1.212, 1.215, 1.216, 1.217, 1.218, 1.220, 1.221, 1.222, 1.223, 1.224, 1.226, 1.227, 1.229, 1.230, 1.233, 1.235, 1.238, 1.241, 1.242, 1.243, 1.244, 1.245, 1.246, 1.253, 1.264, 1.273, 1.274, 1.275, 1.309, 1.312, 1.314, 1.315, 1.316, 1.324, 1.325, 1.327, 1.329, 1.331, 1.335, 1.337, 1.339, 1.341, 1.342, 1.344, 1.345, 1.346, 1.350, 1.351, 1.355, 1.356, 1.358, 1.359, 1.360, 1.361, 1.363, 1.365, 1.368, 1.369, 1.372, 1.379, 1.383, 1.384, 1.387, 1.389, 1.390, 1.392, 1.395, 1.398, 1.399, 1.401, 1.402, 1.403, 1.404, 1.407, 1.408, 1.412, 1.416, 1.418, 1.432, 1.457, 1.466, 1.471, 1.472, 1.475, 1.476, 1.477, 1.478, 1.479, 1.480, 1.483, 1.484, 1.485, 1.486, 1.487, 1.488, 1.489, 1.491, 1.492, 1.493, 1.494, 1.495, 1.496, 1.497, 1.498, 1.499, 1.500, 1.503, 1.504, 1.505, 1.506, 1.507, 1.508, 1.509, 1.510, 1.511, 1.512, 1.513, 1.514, 1.515, 1.516, 1.517, 1.518, 1.519, 1.520, 1.521, 1.523, 1.524, 1.525, 1.526, 1.527, 1.528, 1.529, 1.531, 1.532, 1.562, 1.563, 1.564, 1.566, 1.567, 1.568, 1.569, 1.570, 1.571, 1.573, 1.574, 1.575, 1.576, 1.577, 1.578, 1.579, 1.580, 1.581, 1.582, 1.583, 1.584, 1.585, 1.586, 1.587, 1.589, 1.590, 1.591, 1.592, 1.594, 1.595, 1.596, 1.597, 1.599, 1.600, 1.603, 1.604, 1.605, 1.606, 1.607, 1.608, 1.610, 1.611, 1.612, 1.613, 1.614, 1.615, 1.616, 1.617, 1.618, 1.619, 1.620, 1.621, 1.622, 1.623, 1.624, 1.625, 1.626, 1.627, 1.628, 1.629, 1.630, 1.631, 1.632, 1.634, 1.636, 1.637, 1.639, 1.640, 1.641, 1.642, 1.643, 1.644, 1.645, 1.646, 1.647, 1.648, 1.649, 1.651, 1.652, 1.653, 1.654, 1.655, 1.656, 1.657, 1.658, 1.659, 1.660, 1.661, 1.662, 1.663, 1.664, 1.665, 1.666, 1.667, 1.668, 1.669, 1.670, 1.671, 1.672, 1.673, 1.674, 1.675, 1.676, 1.677, 1.678, 1.679, 1.680, 1.681, 1.682, 1.683, 1.684, 1.685, 1.686, 1.687, 1.688, 1.689, 1.690, 1.691, 1.692, 1.693, 1.694, 1.695, 1.696, 1.697, 1.698, 1.699, 1.700, 1.701, 1.702, 1.703, 1.704, 1.705, 1.706, 1.707, 1.708, 1.709, 1.710, 1.711, 1.712, 1.714, 1.715, 1.716, 1.717, 1.718, 1.720, 1.721, 1.722, 1.723, 1.724, 1.725, 1.726, 1.727, 1.728, 1.729, 1.730, 1.731, 1.732, 1.733, 1.734, 1.735, 1.736, 1.737, 1.738, 1.739, 1.740, 1.741, 1.742, 1.743, 1.744, 1.745, 1.746, 1.747, 1.748, 1.749, 1.750, 1.751, 1.752, 1.753, 1.754, 1.755, 1.756, 1.757, 1.758, 1.759, 1.760, 1.761, 1.762, 1.763, 1.764, 1.765, 1.766, 1.767, 1.768, 1.769, 1.770, 1.771, 1.772, 1.773, 1.774, 1.775, 1.776, 1.777, 1.778, 1.779, 1.781, 1.782, 1.783, 1.784, 1.786 and 1.810.

Compounds (from Table T2) 2.2, 2.3, 2.4, 2.5, 2.21, 2.24, and 2.25.

Compounds (from Table T3) 3.1, 3.2, 3.3, 3.4, 3.5, 3.6, 3.7, 3.8, 3.9, 3.11, 3.12, 3.13, 3.14, 3.15, 3.16, 3.17, 3.18, 3.19, 3.20, 3.21, 3.22, 3.23, 3.24, 3.25, 3.26, 3.28, 3.29, 3.30, 3.31, 3.32, 3.33, 3.34, 3.36, 3.37, 3.38, 3.39, 3.40, 3.41, 3.42, 3.43, 3.44, 3.45, 3.46, 3.47, 3.48, 3.51, 3.52, 3.53, 3.55, 3.56, 3.57, 3.58, 3.59, 3.60, 3.61, and 3.62.

Fungicidal Activity Against *Glomerella lagenarium* (*Colletotrichum lagenarium*) Liquid Culture/Cucumber/Preventative (Anthracnose)

Conidia of the fungus from cryogenic storage are directly mixed into nutrient broth (PDB-potato dextrose broth). After placing a (DMSO) solution of test compound into a microtiter plate (96-well format), the nutrient broth containing the fungal spores is added. The test plates are incubated at 24° C. and the inhibition of growth is measured photometrically 3 to 4 days after application.

The following compounds at 20 ppm in the applied formulation give at least 80% disease control in this test when compared to untreated control under the same conditions, which show extensive disease development.

Compounds (from Table T1) 1.1, 1.2, 1.3, 1.4, 1.5, 1.6, 1.7, 1.8, 1.9, 1.10, 1.11, 1.12, 1.13, 1.15, 1.16, 1.17, 1.18, 1.19, 1.20, 1.22, 1.23, 1.24, 1.25, 1.26, 1.27, 1.28, 1.29, 1.30, 1.31, 1.32, 1.33, 1.34, 1.35, 1.36, 1.37, 1.38, 1.40, 1.41, 1.42, 1.43, 1.44, 1.45, 1.46, 1.47, 1.48, 1.49, 1.50, 1.51, 1.53, 1.54, 1.55, 1.57, 1.58, 1.59, 1.61, 1.64, 1.67, 1.68, 1.69, 1.71, 1.72, 1.74, 1.77, 1.81, 1.82, 1.83, 1.84, 1.85, 1.86, 1.87, 1.88, 1.89, 1.90, 1.91, 1.92, 1.93, 1.94, 1.95, 1.96, 1.97, 1.98, 1.99, 1.100, 1.101, 1.102, 1.103, 1.104, 1.105, 1.106, 1.107, 1.108, 1.109, 1.110, 1.111, 1.112, 1.113, 1.114, 1.115, 1.116, 1.117, 1.118, 1.119, 1.120, 1.121, 1.122, 1.123, 1.124, 1.125, 1.126, 1.127, 1.128, 1.129, 1.130, 1.131, 1.132, 1.133, 1.134, 1.135, 1.136, 1.138, 1.139, 1.142, 1.144, 1.145, 1.146, 1.147, 1.148, 1.149, 1.150, 1.151, 1.152, 1.153, 1.154, 1.155, 1.157, 1.158, 1.159, 1.161, 1.162, 1.163, 1.164, 1.165, 1.166, 1.167, 1.168, 1.169, 1.170, 1.171, 1.173, 1.174, 1.175, 1.176, 1.177, 1.178, 1.179, 1.180, 1.181, 1.182, 1.183, 1.184, 1.185, 1.187, 1.189, 1.190, 1.191, 1.192, 1.193, 1.194, 1.195, 1.196, 1.199, 1.201, 1.202, 1.203, 1.205, 1.206, 1.207, 1.208, 1.209, 1.210, 1.211, 1.212, 1.213, 1.214, 1.215, 1.216, 1.217, 1.218, 1.219, 1.220, 1.221, 1.222, 1.223, 1.224, 1.225, 1.226, 1.227, 1.228, 1.229, 1.230, 1.231, 1.232, 1.233, 1.235, 1.236, 1.237, 1.238, 1.239, 1.240, 1.242, 1.243, 1.244, 1.245, 1.246, 1.247, 1.248, 1.249, 1.250, 1.251, 1.252, 1.253, 1.254, 1.255, 1.256, 1.257, 1.258, 1.259, 1.260, 1.261, 1.262, 1.264, 1.265, 1.266, 1.268, 1.269, 1.270, 1.271, 1.272, 1.273, 1.274, 1.275, 1.276, 1.277, 1.278, 1.279, 1.280, 1.281, 1.282, 1.283, 1.284, 1.285, 1.286, 1.287, 1.288, 1.289, 1.290, 1.291, 1.292, 1.293, 1.294, 1.295, 1.297, 1.298, 1.299, 1.301, 1.302, 1.303, 1.304, 1.305, 1.306, 1.307, 1.308, 1.309, 1.310, 1.311, 1.312, 1.313, 1.314, 1.315, 1.316, 1.317, 1.318, 1.319, 1.320, 1.321, 1.322, 1.323, 1.324, 1.325, 1.326, 1.327, 1.328, 1.329, 1.330, 1.331, 1.332, 1.333, 1.334, 1.335, 1.336, 1.337, 1.338, 1.339, 1.340, 1.341, 1.342, 1.343, 1.344, 1.345, 1.346, 1.347, 1.348, 1.349, 1.350, 1.351, 1.352, 1.355, 1.356, 1.358, 1.359, 1.360, 1.361, 1.362, 1.363, 1.364, 1.365, 1.366, 1.367, 1.368, 1.369, 1.370, 1.371, 1.372, 1.373, 1.374, 1.375, 1.376, 1.377, 1.378, 1.379, 1.380, 1.381, 1.382, 1.384, 1.385, 1.387, 1.388, 1.389, 1.390, 1.391, 1.392, 1.393, 1.394, 1.395, 1.396, 1.397, 1.398, 1.399, 1.400, 1.401, 1.402, 1.403, 1.404, 1.405, 1.406, 1.407, 1.408, 1.409, 1.410, 1.411, 1.412, 1.413, 1.414, 1.415, 1.416, 1.417, 1.418, 1.419, 1.420, 1.421, 1.422, 1.423, 1.424, 1.425, 1.426, 1.427, 1.428, 1.429, 1.430, 1.431, 1.432, 1.433, 1.434, 1.435, 1.436, 1.437, 1.438, 1.439, 1.440, 1.442, 1.443, 1.445, 1.446, 1.447, 1.448, 1.449, 1.450, 1.451, 1.452, 1.453, 1.455, 1.456, 1.457, 1.458, 1.459, 1.460, 1.461, 1.462, 1.463, 1.464, 1.465, 1.466, 1.467, 1.468, 1.469, 1.470, 1.471, 1.472, 1.473, 1.474, 1.475, 1.476, 1.477, 1.478, 1.479, 1.480, 1.481, 1.482, 1.483, 1.484, 1.485, 1.486, 1.487, 1.488, 1.489, 1.490, 1.491, 1.492, 1.493, 1.494, 1.495, 1.496, 1.497, 1.498, 1.499, 1.500, 1.501, 1.502, 1.503, 1.504, 1.505, 1.506, 1.507, 1.508, 1.509, 1.510, 1.511, 1.512, 1.513, 1.514, 1.515, 1.516, 1.517, 1.518, 1.519, 1.520, 1.521, 1.522, 1.523, 1.524, 1.525, 1.526, 1.527, 1.528, 1.529, 1.530, 1.531, 1.532, 1.533, 1.534, 1.535, 1.536, 1.537, 1.538, 1.539, 1.540, 1.541, 1.542, 1.543, 1.544, 1.545, 1.546, 1.547, 1.548, 1.549, 1.550, 1.551, 1.553, 1.554, 1.555, 1.556, 1.557, 1.558, 1.559, 1.560, 1.561, 1.562, 1.563, 1.564, 1.565, 1.566, 1.567, 1.568, 1.569, 1.570, 1.571, 1.572, 1.573, 1.574, 1.575, 1.576, 1.577, 1.578, 1.579, 1.580, 1.581, 1.582, 1.583, 1.584, 1.585, 1.586, 1.587, 1.588, 1.589, 1.590, 1.591, 1.592, 1.593, 1.594, 1.595, 1.596, 1.597, 1.598, 1.599, 1.600, 1.601, 1.602, 1.603, 1.604, 1.605, 1.606, 1.607, 1.608, 1.609, 1.610, 1.611, 1.612, 1.613, 1.614, 1.615, 1.616, 1.617, 1.618, 1.619, 1.620, 1.621, 1.622, 1.623, 1.624, 1.625, 1.626, 1.627, 1.628, 1.629, 1.630, 1.631, 1.632, 1.633, 1.634, 1.636, 1.637, 1.638, 1.639, 1.641, 1.642, 1.643, 1.644, 1.645, 1.646, 1.647, 1.648, 1.649, 1.650, 1.651, 1.652, 1.653, 1.654, 1.655, 1.656, 1.657, 1.658, 1.659, 1.660, 1.661, 1.662, 1.663, 1.664, 1.665, 1.666, 1.667, 1.668, 1.669, 1.670, 1.671, 1.672, 1.673, 1.674, 1.675, 1.676, 1.677, 1.678, 1.679, 1.680, 1.681, 1.682, 1.683, 1.684, 1.685, 1.686, 1.687, 1.688, 1.689, 1.690, 1.691, 1.692, 1.693, 1.694, 1.695, 1.696, 1.697, 1.698, 1.699, 1.700, 1.701, 1.702, 1.703, 1.704, 1.705, 1.706, 1.707, 1.708, 1.709, 1.713, 1.714, 1.715, 1.716, 1.717, 1.718, 1.720, 1.723, 1.724, 1.725, 1.726, 1.727, 1.729, 1.730, 1.733, 1.734, 1.735, 1.736, 1.737, 1.738, 1.739, 1.740, 1.741, 1.742, 1.743, 1.745, 1.749, 1.751, 1.752, 1.753, 1.754, 1.755, 1.756, 1.757, 1.758, 1.759, 1.760, 1.761, 1.762, 1.763, 1.764, 1.765, 1.766, 1.768, 1.769, 1.770, 1.771, 1.772, 1.773, 1.774, 1.775, 1.776, 1.777, 1.778, 1.779, 1.780, 1.781, 1.782, 1.783, 1.784, 1.785, 1.786, 1.787, 1.790, 1.791, 1.793, 1.794, 1.795, 1.810 and 1.811.

Compounds (from Table T2) 2.1, 2.2, 2.3, 2.4, 2.5, 2.6, 2.7, 2.8, 2.9, 2.10, 2.11, 2.12, 2.13, 2.14, 2.15, 2.16, 2.17, 2.18, 2.19, 2.20, 2.21, 2.22, 2.24, and 2.25.

Compounds (from Table T3) 3.1, 3.2, 3.3, 3.4, 3.5, 3.6, 3.7, 3.8, 3.9, 3.10, 3.11, 3.12, 3.13, 3.14, 3.15, 3.16, 3.17, 3.18, 3.19, 3.20, 3.21, 3.22, 3.23, 3.24, 3.25, 3.26, 3.28, 3.29, 3.30, 3.31, 3.32, 3.33, 3.34, 3.35, 3.36, 3.37, 3.38, 3.39, 3.40, 3.41, 3.42, 3.43, 3.44, 3.45, 3.46, 3.47, 3.48, 3.49, 3.51, 3.52, 3.53, 3.54, 3.55, 3.56, 3.57, 3.58, 3.59, 3.60, 3.61, 3.62, 3.63, 3.64, 3.65, 3.66, 3.67, 3.69, 3.70, 3.71, 3.72, 3.73, 3.74, 3.75, 3.76, 3.77, 3.78, 3.79, 3.80, 3.81, 3.82, 3.83, 3.84, 3.85, 3.87, 3.88, 3.89, 3.90, 3.91, 3.92, 3.93, 3.94, 3.95, 3.96, 3.97, 3.98, 3.99, 3.100, 3.101, 3.102, and 3.103.

The invention claimed is:

1. A compound of formula (I):

wherein $R^1$ and $R^2$ are independently selected from hydrogen, chloro, fluoro, methyl, methoxy and trifluoromethyl; and $R^3$ and $R^4$ are independently selected from hydrogen and halogen;

wherein at least two of $R^1$, $R^2$, $R^3$ and $R^4$ are hydrogen;

$R^5$ and $R^6$ are independently selected from hydrogen and $C_{1-4}$alkyl;

$R^7$ is $C_{1-4}$alkyl or $C_{1-4}$alkoxy; and $R^8$ is hydrogen, $C_{1-6}$alkyl, $C_{2-6}$alkenyl, $C_{2-6}$alkynyl, cyanoC$_{1-6}$alkyl, $C_{1-6}$haloalkyl, $C_{1-6}$haloalkenyl, hydroxyC$_{1-6}$alkyl, $C_{1-4}$alkoxyC$_{1-6}$alkyl, $C_{1-4}$haloalkoxyC$_{1-6}$alkyl, $C_{1-4}$alkoxyC$_{1-4}$alkoxyC$_{1-6}$alkyl, $C_{2-4}$alkynyloxyC$_{1-6}$alkyl, aminoC$_{1-6}$alkyl, N—C$_{1-4}$alkylaminoC$_{1-6}$alkyl, N,N-diC$_{1-4}$alkylaminoC$_{1-6}$alkyl, $C_{1-6}$alkylcarbonylC$_{1-6}$alkyl, $C_{1-6}$alkylcarbonylC$_{2-6}$alkenyl, $C_{1-6}$alkoxycarbonylC$_{1-6}$alkyl, $C_{1-6}$alkylcarbonyloxyC$_{1-6}$alkyl, N—C$_{1-4}$alkylaminocarbonylC$_{1-6}$alkyl, N,N-diC$_{1-4}$alkylaminocarbonylC$_{1-6}$alkyl, $C_{1-6}$alkylsulfanylC$_{1-6}$alkyl, $C_{1-6}$alkylsulfonylC$_{1-6}$alkyl, $C_{1-6}$alkylsulfonylaminoC$_{1-6}$alkyl, $C_{1-6}$ alkylsulfonylaminoC$_{2-6}$alkynyl, or $C_{2-6}$alkynyloxycarbonylaminoC$_{1-6}$ alkyl; or $R^8$ is $C_{3-8}$cycloalkylC$_{0-6}$alkyl, wherein the cycloalkyl moiety is optionally partially unsaturated, phenylC$_{0-6}$ alkyl, phenylC$_{2-6}$alkenyl, naphthylC$_{0-6}$alkyl, heteroarylC$_{0-6}$alkyl wherein the heteroaryl moiety is a 5- or 6-membered monocyclic aromatic ring which comprises 1, 2, 3 or 4 heteroatoms individually selected from N, O and S, heterodiarylC$_{0-6}$alkyl wherein the heterodiaryl moiety is a 9- or 10-membered bicyclic aromatic system which comprises 1, 2, 3 or 4 heteroatoms individually selected from N, O and S, heterocyclylC$_{0-6}$alkyl wherein the heterocyclyl moiety is a 4-to 6-membered non-aromatic ring which comprises 1, 2 or 3 heteroatoms individually selected from N, O and S, or C$_{3-6}$cycloalkylcarbonylaminoC$_{1-6}$alkyl, wherein for R$^8$, any of C$_{3-8}$cycloalkylC$_{0-6}$alkyl, phenylC$_{0-6}$alkyl, phenylC$_{2-6}$alkenyl, naphthylC$_{0-6}$alkyl, heteroarylC$_{0-6}$alkyl, heterodiarylC$_{0-6}$alkyl, heterocyclylC$_{0-6}$alkyl and C$_{3-6}$cycloalkylcarbonylaminoC$_{1-6}$alkyl moieties are optionally substituted by 1, 2 or 3 substituents, which may be the same or different, selected from R$^9$; wherein R$^9$ represents cyano, halogen, hydroxy, C$_{1-4}$alkyl, C$_{2-4}$alkenyl, C$_{2-4}$alkynyl, C$_{1-4}$haloalkyl, C$_{2-4}$haloalkenyl, C$_{1-4}$alkoxy, C$_{1-4}$haloalkoxy, C$_{3-4}$alkynyloxy, N—C$_{1-4}$alkylamino, N,N-diC$_{1-4}$alkylamino, C$_{1-4}$alkylcarbonyl, C$_{1-4}$alkoxycarbonyl, carbonylamino, N—C$_{1-4}$ alkylaminocarbonyl, N,N-diC$_{1-4}$alkylaminocarbonyl or C$_{1-4}$alkoxycarbonylamino, and wherein when R$_8$ is substituted C$_{3-8}$cycloalkylC$_{0-6}$alkyl or heterocyclylC$_{0-6}$alkyl, R$^9$ may also represent oxo on the C$_{3-8}$cycloalkyl or heterocyclyl moiety; or wherein for R$^8$, any of C$_{3-8}$cycloalkylC$_{0-6}$alkyl, phenylC$_{0-6}$alkyl, phenylC$_{2-6}$alkenyl, naphthylC$_{0-6}$alkyl, heteroarylC$_{0-6}$alkyl, heterodiarylC$_{0-6}$alkyl, heterocyclylC$_{0-6}$alkyl and C$_{3-6}$cycloalkylcarbonylaminoC$_{1-6}$alkyl moieties are optionally substituted by 1 substituent selected from R$^{10}$; wherein R$^{10}$ represents C$_{3-8}$cycloalkylC$_{0-2}$alkyl, phenylC$_{0-2}$alkyl, heteroarylC$_{0-2}$alkyl wherein the heteroaryl moiety is a 5- or 6-membered monocyclic aromatic ring which comprises 1, 2, 3 or 4 heteroatoms individually selected from N, O and S, heterocyclylC$_{0-6}$alkyl wherein the heterocyclyl moiety is a 4- to 6-membered non-aromatic ring which comprises 1, 2 or 3 heteroatoms individually selected from N, O and S, and wherein any of said cycloalkyl, phenyl, heteroaryl and heterocyclyl moieties are optionally substituted by 1, 2 or 3 substituents, which may be the same or different, selected from R$^{11}$; wherein R$^{11}$ represents hydrogen, cyano, fluoro, chloro, bromo, methyl, trifluoromethyl, methoxy and ethoxy; or a salt or an N-oxide thereof.

2. The compound according to claim 1, wherein R$^8$ represents hydrogen, C$_{1-6}$alkyl, C$_{2-6}$alkenyl, C$_{2-6}$alkynyl, cyanoC$_{1-6}$alkyl, C$_{1-6}$haloalkyl, C$_{1-6}$haloalkenyl, hydroxyC$_{1-6}$ alkyl, C$_{1-4}$alkoxyC$_{1-6}$alkyl, C$_{1-4}$haloalkoxyC$_{1-6}$ alkyl, C$_{1-4}$alkoxyC$_{1-4}$alkoxyC$_{1-6}$alkyl, C$_{2-4}$alkynyloxyC$_{1-6}$alkyl, C$_{1-6}$alkylcarbonylC$_{2-6}$alkenyl, C$_{1-6}$alkylcarbonyloxyC$_{1-6}$alkyl, C$_{1-6}$ alkylsulfonylaminoC$_{2-6}$ alkynyl, C$_{2-6}$alkynyloxycarbonylaminoC$_{1-6}$alkyl; or C$_{3-8}$cycloalkylC$_{0-2}$alkyl, wherein the cycloalkyl moiety is optionally partially unsaturated, phenylC$_{0-2}$alkyl, heteroarylC$_{0-2}$alkyl wherein the heteroaryl moiety is a 5- or 6-membered monocyclic aromatic ring which comprises 1, 2, 3 or 4 heteroatoms individually selected from N, O and S, or heterocyclylC$_{0-2}$alkyl wherein the heterocyclyl moiety is a 4- to 6-membered non-aromatic ring which comprises 1, 2 or 3 heteroatoms individually selected from N, O and S; wherein any of said C$_{3-8}$cycloalkylC$_{0-2}$alkyl, phenylC$_{0-2}$alkyl, heteroarylC$_{0-2}$alkyl and heterocyclylC$_{0-2}$alkyl moieties are optionally substituted by 1, 2 or 3 substituents, which may be the same or different, selected from R$^9$; and R$^9$ represents cyano, halogen, hydroxy, C$_{1-4}$alkyl, C$_{1-4}$haloalkyl, C$_{1-4}$alkoxy, C$_{2-4}$haloalkenyl, C$_{3-4}$alkynyloxy, C$_{1-4}$alkylcarbonyl and C$_{1-4}$alkoxycarbonyl.

3. The compound according to claim 1, wherein R$^8$ represents C$_{1-6}$alkyl, C$_{2-6}$alkenyl, C$_{2-6}$alkynyl, C$_{1-6}$fluoroalkyl, C$_{1-6}$chloroalkyl, C$_{1-4}$alkoxyC$_{1-6}$alkyl, C$_{1-4}$alkoxyC$_{1-4}$alkoxyC$_{1-6}$alkyl, C$_{1-6}$alkylcarbonylC$_{2-6}$alkenyl, C$_{1-6}$alkylcarbonyloxyC$_{1-6}$alkyl, C$_{1-6}$ alkylsulfonylaminoC$_{2-6}$alkynyl or C$_{2-6}$alkynyloxycarbonylaminoC$_{1-6}$alkyl.

4. The compound according to claim 1, wherein R$^8$ represents C$_{3-8}$cycloalkylC$_{0-6}$alkyl, phenylC$_{0-6}$alkyl, or heterocyclylC$_{0-6}$alkyl, wherein any of said cycloalkyl, phenyl, and heterocyclyl moieties are optionally substituted by 1, 2 or 3 substituents which may be the same or different, selected from R$^9$, wherein R$^9$ is cyano, halogen, hydroxy, C$_{1-4}$alkyl, C$_{1-4}$haloalkyl, C$_{2-4}$haloalkenyl, C$_{3-4}$alkynyloxy, C$_{1-4}$alkylcarbonyl, C$_{1-4}$alkoxycarbonyl; or wherein any of said cycloalkyl, phenyl, and heterocyclyl moieties are optionally substituted by 1 substituent selected from R$^{10}$ which is a phenyl.

5. The compound according to claim 4, wherein R$^8$ represents C$_{3-6}$cycloalkylC$_{0-1}$alkyl, phenylC$_{0-1}$alkyl or heterocyclylC$_{0-1}$alkyl, wherein any of said cycloalkyl, phenyl, and heterocyclyl moieties are optionally substituted by 1, 2 or 3 substituents which may be the same or different, selected from R$^9$, wherein R$^9$ is cyano, fluoro, chloro, hydroxy, methyl, ethyl, trifluoromethyl, 2,2-dichloroethenyl, propynyloxy, acetyl, methoxycarbonyl; or wherein any of said cycloalkyl, phenyl, and heterocyclyl moieties are optionally substituted by 1 substituent selected from R$^{10}$ which is a phenyl.

6. The compound according to claim 1, wherein R$^1$ and R$^2$ are independently selected from hydrogen and fluorine.

7. The compound according to claim 1, wherein R$^3$ and R$^4$ are independently selected from hydrogen and fluorine.

8. The compound according to claim 1, wherein R$^5$ and R$^6$ are hydrogen, or R$^5$ is hydrogen and R$^6$ is methyl.

9. The compound according to claim 1, wherein R$^7$ represents methoxy, propoxy or sec-butyl.

10. The compound according to claim 1, said compound being selected from:

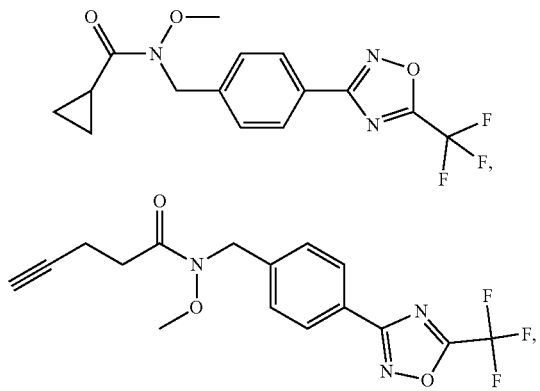

501
-continued

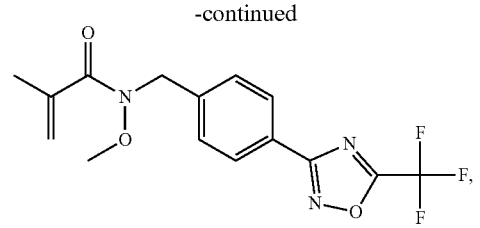

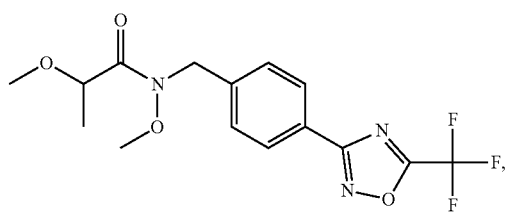

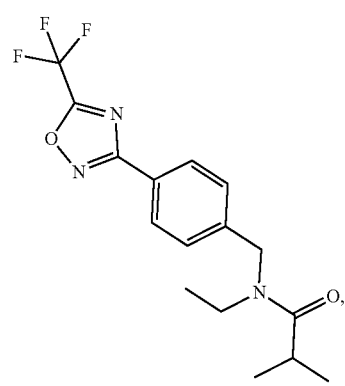

502
-continued

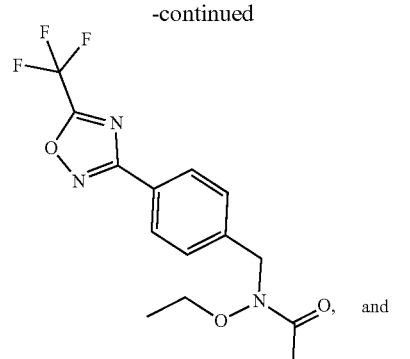

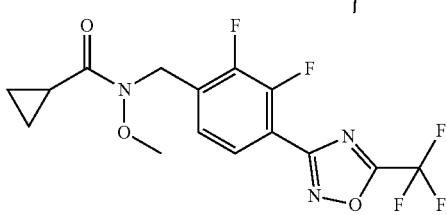

11. An agrochemical composition comprising a fungicidally effective amount of a compound of formula (I) according to claim 1.

12. A composition according to claim 11, further comprising at least one additional active ingredient and/or an agrochemically-acceptable diluent or carrier.

13. A method of controlling or preventing infestation of useful plants by phytopathogenic microorganisms, wherein a fungicidally effective amount of a compound of formula (I) according to claim 1, or a composition comprising this compound as active ingredient, is applied to the plants, to parts thereof or the locus thereof.

* * * * *